(12) United States Patent
Ahmad et al.

(10) Patent No.: US 11,993,625 B2
(45) Date of Patent: May 28, 2024

(54) CALICHEAMICIN DERIVATIVES AND ANTIBODY DRUG CONJUGATES THEREOF

(71) Applicant: PFIZER INC., New York, NY (US)

(72) Inventors: Omar Khaled Ahmad, Providence, RI (US); Stephen Paul Brown, Mystic, CT (US); Kenneth John Dirico, Gales Ferry, CT (US); Russell Dushin, Old Lyme, CT (US); Gary Frederick Filzen, Schwenksville, PA (US); Sujiet Puthenveetil, Franklin, MA (US); Pavel Strop, San Mateo, CA (US); Chakrapani Subramanyam, South Glastonbury, CT (US); Lawrence N. Tumey, Pawcatuck, CT (US)

(73) Assignee: Pfizer, Inc., New York, NY (US)

( * ) Notice: Subject to any disclaimer, the term of this patent is extended or adjusted under 35 U.S.C. 154(b) by 1100 days.

(21) Appl. No.: 16/477,290

(22) PCT Filed: Jan. 10, 2018

(86) PCT No.: PCT/IB2018/050153
§ 371 (c)(1),
(2) Date: Jul. 11, 2019

(87) PCT Pub. No.: WO2018/138591
PCT Pub. Date: Aug. 2, 2018

(65) Prior Publication Data
US 2019/0345186 A1 Nov. 14, 2019

Related U.S. Application Data

(60) Provisional application No. 62/449,839, filed on Jan. 24, 2017.

(51) Int. Cl.
*C07H 15/26* (2006.01)
*A61K 47/68* (2017.01)
*A61P 35/00* (2006.01)
*A61K 45/06* (2006.01)

(52) U.S. Cl.
CPC ......... *C07H 15/26* (2013.01); *A61K 47/6807* (2017.08); *A61P 35/00* (2018.01); *A61K 45/06* (2013.01)

(58) Field of Classification Search
CPC .......... A61P 35/00; C07H 15/00; C07H 15/26
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 4,970,198 A | 11/1990 | Lee et al. | |
| 5,053,394 A | 10/1991 | Ellestad et al. | |
| 5,225,539 A | 7/1993 | Winter | |
| 5,545,806 A | 8/1996 | Lonberg et al. | |
| 5,569,825 A | 10/1996 | Lonberg et al. | |
| 5,585,089 A | 12/1996 | Queen et al. | |
| 5,606,040 A * | 2/1997 | McGahren | C07H 15/203 536/17.6 |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,773,001 A | 6/1998 | Hamann et al. | |
| 6,214,345 B1 | 4/2001 | Firestone et al. | |
| 8,039,273 B2 | 10/2011 | Jeffrey | |
| 8,568,728 B2 | 10/2013 | Jeffrey | |
| 2013/0034559 A1 | 2/2013 | Queva et al. | |
| 2013/0122020 A1 | 5/2013 | Liu et al. | |
| 2013/0230543 A1 | 9/2013 | Pons et al. | |
| 2014/0341917 A1 | 11/2014 | Nastri et al. | |
| 2017/0160268 A1 | 6/2017 | Lee et al. | |
| 2017/0281758 A1 * | 10/2017 | Chen | A61P 35/00 |

FOREIGN PATENT DOCUMENTS

| | | |
|---|---|---|
| EP | 0171496 A2 | 2/1986 |
| EP | 0173494 A2 | 3/1986 |
| EP | 0184187 A2 | 6/1986 |
| EP | 0313873 A1 | 5/1989 |
| EP | 0404097 A2 | 12/1990 |
| EP | 0689845 A2 | 1/1996 |
| WO | 86/01533 A1 | 3/1986 |
| WO | 87/02671 A1 | 5/1987 |
| WO | 93/11161 A1 | 6/1993 |
| WO | 97/34631 A1 | 9/1997 |
| WO | 00/35298 A1 | 6/2000 |
| WO | 2011/066389 A1 | 6/2011 |
| WO | 2012/007896 A1 | 1/2012 |

(Continued)

OTHER PUBLICATIONS

Beidler et al., "Cloning and high level expression of a chimeric antibody with specificity for human carcinoembryonic antigen", The Journal of Immunology, 1988, 141: 4053-4060.
Better et al., "*Escherichia coli* Secretion of an Active Chimeric Antibody Fragment", Science, 240(4855): 1041-1043.
Chari et al., "Antibody-Drug Conjugates: an Emerging Concept in Cancer Therapy", Angewandte Reviews, 2014, 53: 3796-3827.
Chothia et al., "Canonical Structures for the Hypervariable Regions of Immunoglobulins", J. Mol. Biol., 1987: 196:901-917.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., 2002, 13: 855-869.

(Continued)

*Primary Examiner* — Pancham Bakshi
(74) *Attorney, Agent, or Firm* — Saul Ewing LLP; Kathryn Doyle; Domingos J. Silva

(57) ABSTRACT

The present invention is directed to novel calicheamicin derivatives useful as payloads in antibody-drug-conjugates (ADC's), and to payload-linker compounds and ADC compounds comprising the same; to pharmaceutical compositions comprising the same and to methods for using the same to treat pathological conditions such as cancer.

16 Claims, 9 Drawing Sheets

Specification includes a Sequence Listing.

(56) References Cited

FOREIGN PATENT DOCUMENTS

| WO | 2012/059882 A2 | 5/2012 |
|---|---|---|
| WO | 2013/079174 A1 | 6/2013 |
| WO | 2013/093809 A1 | 6/2013 |
| WO | 2014/068443 A1 | 5/2014 |
| WO | 2016/003079 A1 | 1/2016 |
| WO | 2016/030791 A1 | 3/2016 |
| WO | 2017/068511 A1 | 4/2017 |
| WO | 2017/172907 A1 | 10/2017 |
| WO | 2018/069851 A2 | 4/2018 |

OTHER PUBLICATIONS

Farias et al., "Mass Spectrometric Characterization of Transglutaminase Based Site-Specific Antibody-Drug Conjugates", Bioconjugate Chemistry, 2014, 25, 240-250.

Holliger et al., ""Diabodies": Small bivalent and bispecific antibody fragments", Proc. Natl. Acad. Sci. USA, 1993, 90:6444-6448.

Hoogenboom et al., "By-passing Immunisation Human Antibodies from Synthetic Repertoires of Germline VH Gene Segments Rearranged in Vitro", J. Mol. Biol., 1992, 227:391-388.

Jespers et al., "Guiding the Selection of Human Antibodies from Phage Display Repertoires to a Single Epitope of an Antigen", Bio/Technology, 1994, 12:899-903.

Jones et al., "Replacing the complementarity-determining regions in a human antibody with those from a mouse", Nature, 321:522-525.

Kabat, "Origins of antibody complementarity and specificity-hypervariable regions and minigene hypothesis", The Journal of Immunology, 1980, 125: 961-969.

Kozbor et al., "The production of monoclonal antibodies from human lymphocytes", Immunology Today, 1983, 4(3): 72-79.

Laguzza et al., "New Antitumor Monoclonal Antibody—Vinca Conjugates LY203725 and Related Compounds: Design, Preparation, and Representative in Vivo Activity", J. Med. Chem., 1989, 32: 548-555.

Langer, "New Methods of Drug Delivery", Science, 1990: 249(4976): 1527-1533.

Liang et al., "Fast-dissolving intraoral drug delivery systems", Expert Opinion Ther. Patents, 2001, 11(6): 981-986.

Liu et al., "Production of a mouse-human chimeric monoclonal antibody to CD20 with potent Fc-dependent biologic activity", The Journal of Immunology, 1987, 139: 3521-3526.

Li et al., "Chimeric mouse-human IgG1 antibody that can mediate lysis of cancer cells", Proc. Natl. Acad. Sci. USA, 1987, 84: 3439-3443.

Lonberg et al., "Human Antibodies from Transgenic Mice", Intern. Rev. Immunol., 1995, 13: 65-93.

Marks et al., "By-passing Immunization Human Antibodies from V-gene Libraries Displayed on Phage", J. Mol. Biol., 1991, 222: 581-597.

Morrison, "Transfectomas Provide Novel Chimeric Antibodies", Science, 1985, 229(4719): 1202-1207.

Nishimura et al., "Recombinant Human-Mouse Chimeric Monoclonal Antibody Specific for Common Acute Lymphocytic Leukemia Antigen", Cancer Research, 1987, 47: 999-1005.

Oi et al., "Chimeric Antibodies", BioTechniques, 1986, 4(3): 214-221.

Olsson et al., "Human-Human Monoclonal Antibody-Producing Hybridomas: Technical Aspects", Methods in Enzymology, 1982, 92: 3-16.

Presta, "Antibody engineering", Current Opinion in Structural Biology, 1992, 2: 593-596.

Riechmann, et al., "Reshaping human antibodies for therapy", Nature, 1988, 332: 323-327.

Shaw et al., "Mouse/Human Chimeric Antibodies to a Tumor-Associated Antigen: Biologic Activity of the Four Human IgG Subclasses", Journal of the National Cancer Institute, 1988, 80(19): 1553-1559.

Strop et al., "Location Matters: Site of Conjugation Modulates Stability and Pharmacokinetics of Antibody Drug Conjugates", Chemistry and Biology, 2013, 20: 161-167.

Sun et al., "Chimeric antibody with human constant regions and mouse variable regions directed against carcinoma-associated antigen 17-1A", PNAS, 1987: 84: 214-218.

Teng et al., "Construction and testing of mouse-human heteromyelomas for human monoclonal antibody production", PNAS, 1983, 80: 7308-7312.

Verhoeyen et al., "Reshaping Human Antibodies: Grafting an Antilysozyme Activity", Science, 1988, 239(4847): 1534-1536.

Verma et al., "Current Status of Drug Delivery Technologies and Future Directions", Pharmaceutical Technology on-Line, 2001, 25(2): 1-14.

Wood et al., "The Synthesis and in vivo assembly of functional antibodies in yeast", Nature, 1985, 314: 446-449.

Melancon et al., "Glyco-Stripping and Glyco-Swapping", ACS Chemical Biology, 2006, 1(8): 499-504.

Hinman et al., "Preparation and Characterization of Monoclonal Antibody Conjugates of the Calicheamicins: a Novel and Potent Family of Antitumor Antibiotics", Cancer Research, 1993, 53: 3336-3342.

Hollander et al., "Selection of Reaction Additives Used in the Preparation of Monomeric Antibody—Calicheamicin Conjugates", Bioconjugate Chem., 2008, 19: 358-361.

International Search Report and the Written Opinion of the International Searching Authority, PCT/IB2018/050153 dated Jun. 6, 2018.

* cited by examiner

SEQUENCE LISTING

<160> NUMBER OF SEQ ID NOS: 20

<210> SEQ ID NO 1
<211> LENGTH: 449
<212> TYPE: PRT
<213> ORGANISM: Artificial
<220> FEATURE:
<223> OTHER INFORMATION: Synthetic

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
            20                  25                  30

```
Val Thr His Trp Val Arg Gln Ala Pro Gly Lys Gly Leu Glu Trp Ile
        35                  40                  45

Ala Tyr Ile Asn Pro Tyr Asn Asp Gly Thr Lys Tyr Asn Glu Arg Phe
    50                  55                  60

Lys Gly Arg Phe Thr Ile Ser Ser Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Tyr Glu Ile Tyr Gly Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Leu Leu Gln Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly

```
<210> SEQ ID NO 2
<211> LENGTH: 213
<212> TYPE: PRT
<213> ORGANISM: Artificial
<220> FEATURE:
<223> OTHER INFORMATION: Synthetic

<400> SEQUENCE: 2
```

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Ser Gln Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Leu Trp Asn Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

```
<210> SEQ ID NO 3
<211> LENGTH: 449
<212> TYPE: PRT
<213> ORGANISM: Artificial
<220> FEATURE:
<223> OTHER INFORMATION: Synthetic

<400> SEQUENCE: 3
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
            20                  25                  30

Val Thr His Trp Val Arg Gln Ala Pro Gly Lys Gly Leu Glu Trp Ile
        35                  40                  45

Ala Tyr Ile Asn Pro Tyr Asn Ala Gly Thr Lys Tyr Asn Glu Arg Phe
    50                  55                  60

Lys Gly Arg Phe Thr Ile Ser Ser Asp Asn Ala Lys Asn Ser Leu Tyr
65                  70                  75                  80

```
Leu Gln Met Asn Ser Leu Arg Ala Glu Asp Thr Ala Val Tyr Tyr Cys
             85                  90                  95

Ala Arg Asp Tyr Arg Tyr Glu Ile Tyr Gly Met Asp Tyr Trp Gly Gln
         100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
         210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Leu Leu Gln Gly Ser Thr Tyr Arg
         290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
         370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

Gly

<210> SEQ ID NO 4
<211> LENGTH: 213
<212> TYPE: PRT
<213> ORGANISM: Artificial
<220> FEATURE:
<223> OTHER INFORMATION: Synthetic
```

```
<400> SEQUENCE: 4

Asp Ile Gln Leu Thr Gln Ser Pro Ser Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Gln Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Leu Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 5
<211> LENGTH: 449
<212> TYPE: PRT
<213> ORGANISM: Artificial
<220> FEATURE:
<223> OTHER INFORMATION: Synthetic

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Asn Ser Arg Gly Thr Ile Ile His Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

```
                130             135             140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 6
<211> LENGTH: 214
<212> TYPE: PRT
<213> ORGANISM: Artificial
<220> FEATURE:
<223> OTHER INFORMATION: Synthetic

<400> SEQUENCE: 6

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Gly Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
    210

<210> SEQ ID NO 7
<211> LENGTH: 449
<212> TYPE: PRT
<213> ORGANISM: Artificial
<220> FEATURE:
<223> OTHER INFORMATION: Synthetic

<400> SEQUENCE: 7

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ile Phe Thr Asp Tyr
             20                  25                  30

Val Thr His Trp Val Arg Gln Ala Pro Gly Lys Gly Leu Glu Trp Ile
         35                  40                  45

Ala Tyr Ile Asn Pro Tyr Asn Asp Gly Thr Lys Tyr Asn Glu Arg Phe
     50                  55                  60

Lys Gly Arg Phe Thr Ile Ser Ser Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Arg Tyr Glu Ile Tyr Gly Met Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
             180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Leu Gln Gly Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 8
<211> LENGTH: 221
<212> TYPE: PRT
<213> ORGANISM: Artificial
<220> FEATURE:
<223> OTHER INFORMATION: Synthetic

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Gln Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Leu Trp Asn Ser Asn Pro Leu Thr
                85                  90                  95
```

```
Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Leu Leu Gln Gly Pro Pro
    210                 215                 220
```

<210> SEQ ID NO 9
<211> LENGTH: 449
<212> TYPE: PRT
<213> ORGANISM: Artificial
<220> FEATURE:
<223> OTHER INFORMATION: Synthetic

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Arg Thr His Thr Cys Pro Pro Cys Pro Ala Pro Glu Leu Leu Gly Gly
225                 230                 235                 240
```

```
Pro Ser Val Phe Leu Phe Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Leu Leu Gln Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 10
<211> LENGTH: 214
<212> TYPE: PRT
<213> ORGANISM: Artificial
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 11
<211> LENGTH: 453
<212> TYPE: PRT
<213> ORGANISM: Artificial
<220> FEATURE:
<223> OTHER INFORMATION: Synthetic

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
            20                  25                  30

Val Thr His Trp Val Arg Gln Ala Pro Gly Lys Gly Leu Glu Trp Ile
        35                  40                  45

Ala Tyr Ile Asn Pro Tyr Asn Asp Gly Thr Lys Tyr Asn Glu Arg Phe
    50                  55                  60

Lys Gly Arg Phe Thr Ile Ser Ser Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Tyr Glu Ile Tyr Gly Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Leu Leu Gln Gly Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
```

```
               290                 295                 300
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 12
<211> LENGTH: 213
<212> TYPE: PRT
<213> ORGANISM: Artificial
<220> FEATURE:
<223> OTHER INFORMATION: Synthetic

<400> SEQUENCE: 12

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Gln Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Leu Trp Asn Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

195                 200                 205

Asn Arg Gly Glu Cys
    210

<210> SEQ ID NO 13
<211> LENGTH: 463
<212> TYPE: PRT
<213> ORGANISM: Artificial
<220> FEATURE:
<223> OTHER INFORMATION: Synthetic

<400> SEQUENCE: 13

His Glu Ala Val Tyr Cys His Ala Ile Asn Glu Val Gln Leu Val Glu
1               5                   10                  15

Ser Gly Gly Gly Leu Val Gln Pro Gly Gly Ser Leu Arg Leu Ser Cys
            20                  25                  30

Ala Ala Ser Gly Phe Asn Ile Lys Asp Thr Tyr Ile His Trp Val Arg
        35                  40                  45

Gln Ala Pro Gly Lys Gly Leu Glu Trp Val Ala Arg Ile Tyr Pro Thr
    50                  55                  60

Asn Gly Tyr Thr Arg Tyr Ala Asp Ser Val Lys Gly Arg Phe Thr Ile
65                  70                  75                  80

Ser Ala Asp Thr Ser Lys Asn Thr Ala Tyr Leu Gln Met Asn Ser Leu
                85                  90                  95

Arg Ala Glu Asp Thr Ala Val Tyr Tyr Cys Ser Arg Trp Gly Gly Asp
            100                 105                 110

Gly Phe Tyr Ala Met Asp Tyr Trp Gly Gln Gly Thr Leu Val Thr Val
        115                 120                 125

Ser Ser Ala Ser Thr Lys Gly Pro Ser Val Phe Pro Leu Ala Pro Ser
    130                 135                 140

Ser Lys Ser Thr Leu Leu Gln Gly Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Arg Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr

```
                340                 345                 350
Ile Ser Lys Ala Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly
                450                 455                 460

<210> SEQ ID NO 14
<211> LENGTH: 214
<212> TYPE: PRT
<213> ORGANISM: Artificial
<220> FEATURE:
<223> OTHER INFORMATION: Synthetic

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 450
<212> TYPE: PRT
```

<213> ORGANISM: Artificial
<220> FEATURE:
<223> OTHER INFORMATION: Synthetic

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
```

```
                385                 390                 395                 400
Leu Asp Ser Asp Gly Ser Phe Leu Tyr Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 16
<211> LENGTH: 222
<212> TYPE: PRT
<213> ORGANISM: Artificial
<220> FEATURE:
<223> OTHER INFORMATION: Synthetic

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Leu Leu Gln Gly Pro Pro
    210                 215                 220

<210> SEQ ID NO 17
<211> LENGTH: 449
<212> TYPE: PRT
<213> ORGANISM: Artificial
<220> FEATURE:
<223> OTHER INFORMATION: Synthetic

<400> SEQUENCE: 17

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Ile Phe Thr Asp Tyr
            20                  25                  30

Val Thr His Trp Val Arg Gln Ala Pro Gly Lys Gly Leu Glu Trp Ile
            35                  40                  45

Ala Tyr Ile Asn Pro Tyr Asn Asp Gly Thr Lys Tyr Asn Glu Arg Phe
 50                  55                  60

Lys Gly Arg Phe Thr Ile Ser Ser Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg Asp Tyr Arg Tyr Glu Ile Tyr Gly Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
```

Gly

<210> SEQ ID NO 18
<211> LENGTH: 213
<212> TYPE: PRT
<213> ORGANISM: Artificial
<220> FEATURE:
<223> OTHER INFORMATION: Synthetic

<400> SEQUENCE: 18

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Gly Tyr Met
            20                  25                  30

His Trp Tyr Gln Gln Lys Pro Gly Lys Ala Pro Lys Leu Leu Ile Tyr
                35                  40                  45

Asp Thr Ser Gln Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Leu Trp Asn Ser Asn Pro Leu Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Cys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 450
<212> TYPE: PRT
<213> ORGANISM: Artificial
<220> FEATURE:
<223> OTHER INFORMATION: Synthetic

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Cys Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 20
<211> LENGTH: 214
<212> TYPE: PRT
<213> ORGANISM: Artificial
<220> FEATURE:
<223> OTHER INFORMATION: Synthetic

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

CALICHEAMICIN DERIVATIVES AND ANTIBODY DRUG CONJUGATES THEREOF

CROSS-REFERENCE TO RELATED APPLICATIONS

This Application is the national stage filing under 35 U.S.C. 371 of Patent Cooperation Treaty Patent Application No. PCT/IB2018/050153, filed Jan. 10, 2018, which claims the benefit of priority from U.S. Provisional Application No. 62/449,839 filed Jan. 24, 2017, the contents of each of which are hereby incorporated by reference in their entirety.

REFERENCE TO SEQUENCE LISTING

This application is being filed electronically via EFS-Web and includes an electronically submitted sequence listing in .txt format. The .txt file contains a sequence listing entitled "PC72283A_SEQListing_ST25.txt" created on Jul. 10, 2019 and having a size of 58 KB. The sequence listing contained in this .txt file is part of the specification and is herein incorporated by reference in its entirety.

FIELD OF THE INVENTION

The present invention is directed to novel calicheamicin derivatives useful as payloads in antibody-drug-conjugates (ADC's), and to payload-linker compounds and ADC compounds comprising the same. The present invention further relates to compositions comprising the aforementioned payloads, payload-linkers and ADC's, and to methods for using these payloads, payload-linkers and ADC's, to treat pathological conditions such as cancer.

BACKGROUND

Antibody therapy provides targeted therapeutic treatment in patients with various disorders, such as cancers and immunological diseases, and therefore has played an important role in biological research. Different approaches of targeted antibody therapy, including antibody-drug conjugates (ADCs), have been explored. Chari, R. V., Miller, M. L., and Widdison, W. C. (2014) Antibody-drug conjugates: an emerging concept in cancer therapy. Angewandte Chemie 53, 3796-827; Senter, P. D., and Sievers, E. L. (2012) In the case of ADCs (also called immunoconjugates in certain contexts) small molecule "payloads", which are often cytotoxic small molecules (drug moieties), are covalently linked (conjugated) to antibodies for targeted local delivery of the drug moieties to tumors.

Conjugation of drugs to antibodies, either directly or via linkers, involves consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate. The properties of a given antibody drug conjugate, including its payload release profile, may therefore be dependent on factors such as the properties of the payload, the covalent linker, the antibody and the biological system into which the ADC is introduced.

While a number of different drug classes have been tried for delivery via antibodies, only a few drug classes have proved efficacious as antibody drug conjugates, while having a suitable toxicity profile. One such class is the calicheamicins, also known as the LL-E33288 complex, which are a potent family of antibacterial and antitumor agents derived from the bacterium *Micromonospora enchinospora*. Examples of calicheamcin derivatives are disclosed in U.S. Pat. No. 4,970,198. MYLOTARG® (gemtuzumab ozogamicin) is an example of an anti-body drug conjugate comprising a monoclonal antibody against CD33 that is bound to calicheamicin by means of an acid-hydrolyzable linker. The commercial product was marketed as the first antibody-targeted chemotherapeutic agent and was approved for the treatment of acute myeloid leukemia (AML) in elderly patients. Another example of an antibody drug conjugate comprising calicheamicin is inotuzumab ozogamicin, a CD22 antibody linked to a calicheamicin and which is currently in clinical trials for treatment of certain types of cancer. One example of a method to obtain antibody-drug conjugates of calicheamicin is by reacting the calicheamicin methyltrisulphide with appropriate thiols to form disulphides while at the same time introducing a function group such as a hydrazide or similar nucleophile, see for example U.S. Pat. No. 5,053,394.

There remains a need to develop further calicheamicin derivatives. Such derivatives may have properties which differ from those of known calicheamicin derivatives, such as alternative chemical properties, physical properties, payload release profiles and/or may have a different biological activity profile.

SUMMARY

The present invention relates to a compound of Formula (I):

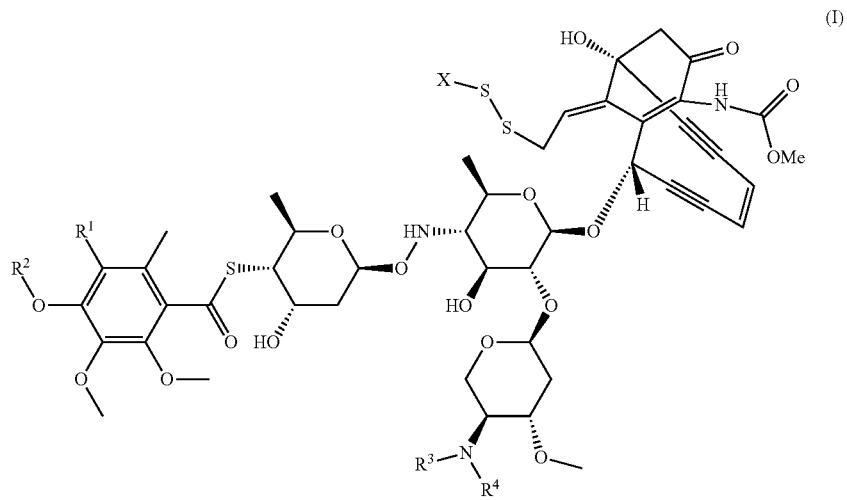

or a pharmaceutically acceptable salt thereof, wherein:
R$^1$ is selected from the group consisting of Br and I;
R$^2$ is selected from the group consisting of H and

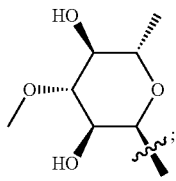

R$^3$ is selected from the group consisting of —CH$_3$, —CH$_2$CH$_3$, and —CH(CH$_3$)$_2$;
R$^4$ is H;
X is selected from the group consisting of:
  (i) —CH$_3$ optionally substituted by one R$^{10}$;
  (ii) —C$_2$-C$_8$alkyl optionally substituted by one R$^{10}$;
  (iii) —(C$_0$-C$_6$alkyl)-C$_3$-C$_{10}$ carbocyclyl, which said C$_3$-C$_{10}$ carbocyclyl is optionally substituted by one R$^{10}$;
  (iv) —(C$_0$-C$_6$alkyl)-3 to 10 membered heterocyclyl, which said 3 to 10 membered heterocyclyl is optionally substituted by one R$^{10}$, and which said 3 to 10 membered heterocyclyl comprises one, two or three heteroatoms independently selected from the group consisting of N, O and S;
  (v) —(C$_0$-C$_6$alkyl)-phenyl, which said phenyl is optionally substituted by one R$^{10}$; and
  (vi) —(C$_0$-C$_6$alkyl)-5 to 10 membered heteroaryl, which said 5 to 10 membered heteroaryl is optionally substituted by one R$^{10}$, and which said 5 to 10 membered heteroaryl comprises one, two or three heteroatoms independently selected from the group consisting of N, O and S;
and which X is optionally further substituted by 1, 2, 3, 4, 5, 6, 7, or 8 G;
R$^{10}$ is —R$^{10a}$-R$^{10b}$, wherein
  R$^{10a}$ is either absent or —(CH$_2$)$_n$—, which R$^{10a}$ is optionally substituted by 1, 2, 3, 4, 5, 6, 7, or 8 G;
  R$^{10b}$ is selected from the group consisting of:
    (i) —OH;
    (ii) —CN;
    (iii) —PO$_3$H;
    (iv) —CO$_2$H;
    (v) —CO$_2$C$_1$-C$_4$alkyl, which said C$_1$-C$_4$alkyl is optionally substituted by 1, 2, 3, 4, 5, or 6 E;
    (vi) —CO—R$^{11}$;
    (vii) —NH—R$^{11}$;
    (viii) —N(C$_1$-C$_4$alkyl)-R$^{11}$, which said C$_1$-C$_4$alkyl is optionally substituted by 1, 2, 3, 4, 5, or 6 E;
    (ix) —CONH—R$^1$;
    (x) —CON(C$_1$-C$_4$alkyl)-R$^{11}$, which said C$_1$-C$_4$alkyl is optionally substituted by 1, 2, 3, 4, 5, or 6 E;
    (xi) —CONHNH—R$^{11}$;
    (xii) —CONHN(C$_1$-C$_4$alkyl)-R$^{11}$, which said C$_1$-C$_4$alkyl is optionally substituted by 1, 2, 3, 4, 5, or 6 E;
    (xiii) —CON(C$_1$-C$_4$alkyl)NH—R$^{11}$, which said C$_1$-C$_4$alkyl is optionally substituted by 1, 2, 3, 40, 5, or 6 E;
    (xiv) —CON(C$_1$-C$_4$alkyl)N(C$_1$-C$_4$alkyl)-R$^1$, wherein each said C$_1$-C$_4$alkyl is independently optionally substituted by 1, 2, 3, 4, 5, or 6 E;
    (xv) —CON(R$^{11}$)NH$_2$;
    (xvi) —CON(R$^{11}$)NH(C$_1$-C$_4$alkyl), which said C$_1$-C$_4$alkyl is optionally substituted by 1, 2, 3, 4, 5, or 6 E;
    (xvii) —CON(R$^1$)N(C$_1$-C$_4$alkyl)$_2$, wherein each said C$_1$-C$_4$alkyl is independently optionally substituted by 1, 2, 3, 4, 5, or 6 E;
    (xviii) —CONHN=C(C$_1$-C$_4$alkyl)-C$_6$H$_4$—OC$_1$-C$_4$alkyl, wherein each said C$_1$-C$_4$alkyl is independently optionally substituted by 1, 2, 3, 4, 5, or 6 E;
    (xix) —CON(C$_1$-C$_4$alkyl)N=C(C$_1$-C$_4$alkyl)-C$_6$H$_4$—OC$_1$-C$_4$alkyl, wherein each said C$_1$-C$_4$alkyl is independently optionally substituted by 1, 2, 3, 4, 5, or 6 E;
    (xx) —N(R$^{11}$)CO(C$_1$-C$_4$alkyl), which said C$_1$-C$_4$alkyl is optionally substituted by 1, 2, 3, 4, 5, or 6 E;
    (xxi) —CH(CO$_2$H)NH—R$^1$;
    (xxii) —CH(CO$_2$C$_1$-C$_4$alkyl)NH—R$^{11}$, which said C$_1$-C$_4$alkyl is optionally substituted by 1, 2, 3, 4, 5, or 6 E;
    (xxiii) —CH(NH$_2$)CO—R$^{11}$;
    (xxiv) —CH(NH(C$_1$-C$_4$alkyl))CO—R$^{11}$, which said C$_1$-C$_4$alkyl is optionally substituted by 1, 2, 3, 4, 5, or 6 E;
    (xxv) —CH(N(C$_1$-C$_4$alkyl)$_2$)CO—R$^{11}$, wherein each said C$_1$-C$_4$alkyl is independently optionally substituted by 1, 2, 3, 4, 5, or 6 E;
    (xxvi) —CH(CO—R$^{11}$)NH—R$^{11}$; and
    (xxvii) —CH(CO—R$^{11}$)N(C$_1$-C$_4$alkyl)-R$^{11}$, which said C$_1$-C$_4$alkyl is optionally substituted by 1, 2, 3, 4, 5, or 6 E;
R$^{11}$ is selected from the group consisting of —R$^{11a}$-R$^{11b}$-R$^{11c}$ and —R$^{11d}$-R$^{11e}$-R$^{11f}$, wherein
  R$^{11a}$ is either absent, or is selected from the group consisting of,

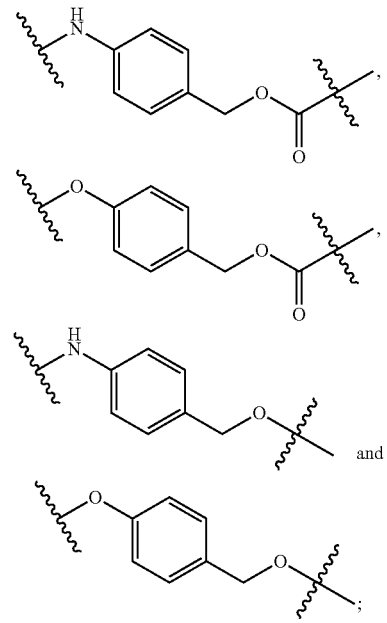

$R^{11b}$ is either absent, or is selected from the group consisting of

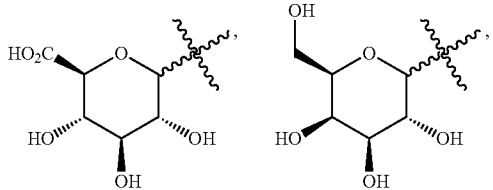

and $AA_r$, wherein AA is independently for each occurrence a natural amino acid or a non-natural amino acid;

$R^{11c}$ is either absent or is selected from the group consisting of —H, —$C_1$-$C_4$alkyl and —CO$C_1$-$C_4$alkyl;

$R^{11d}$ is either absent or —$(CH_2)_r$—, which $R^{11d}$ when present is optionally substituted by 1, 2, 3, 4, 5, 6, 7, or 8 G;

$R^{11e}$ is either absent or selected from the group consisting of —O— and —NH—;

$R^{11f}$ is selected from the group consisting of $C_6$-$C_{12}$ aryl and 5 to 10 membered heteroaryl, which said 5 to 10 membered heteroaryl comprises one, two or three heteroatoms independently selected from the group consisting of N, O and S, and which $R^{11f}$ is optionally substituted by 1, 2, 3, 4, 5, 6, 7, or 8 G;

n is 1, 2, 3, 4, 5, or 6;

r is 1, 2, 3, 4, 5, 6, 7, 8, 9, 10, 11, 12, 13, 14, 15, 16, 17, 18, 19, or 20;

t is 1, 2, 3, 4, 5, or 6;

G is selected, independently for each occurrence, from the group consisting of —F, —Cl, —CN, —OH, —$NH_2$, —NH—$C_1$-$C_4$alkyl, —N($C_1$-$C_4$alkyl)$_2$, —$NO_2$, —$CO_2H$, —$C_1$-$C_4$alkyl, —$C_1$-$C_4$alkylOH, —$C_1$-$C_4$alkylN$H_2$, —$C_1$-$C_4$haloalkyl, —$C_1$-$C_4$alkoxy, =O, —$CO_2C_1$-$C_4$alkyl, —OC(O)$C_1$-$C_4$alkyl, —NHC(O)$C_1$-$C_4$alkyl, —C(O)NH$C_1$-$C_4$alkyl, and —C(O)N($C_1$-$C_4$alkyl)$_2$; and E is selected, independently for each occurrence, from the group consisting of —F, —Cl, —CN, —OH, —$NH_2$, —$NHCH_3$, —N($CH_3$)$_2$, —$NO_2$, —$CO_2H$, —$OCH_3$, —$OCF_3$, and —$CF_3$.

Another aspect of the invention relates to a compound of Formula (II):

or a pharmaceutically acceptable salt thereof, wherein:

$R^1$ is selected from the group consisting of Br and I;

$R^2$ is selected from the group consisting of H and

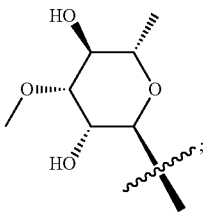

$R^3$ is selected from the group consisting of —$CH_3$, —$CH_2CH_3$, and —CH($CH_3$)$_2$;

X is selected from the group consisting of:
(i) —$CH_3$ optionally substituted by one $R^{10}$;
(ii) —$C_2$-$C_8$alkyl optionally substituted by one $R^{10}$;
(iii) —($C_0$-$C_6$alkyl)-$C_3$-$C_{10}$ carbocyclyl, which said $C_3$-$C_{10}$ carbocyclyl is optionally substituted by one $R^{10}$;
(iv) —($C_0$-$C_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S;
(v) —($C_0$-$C_6$alkyl)-phenyl, which said phenyl is optionally substituted by one $R^{10}$; and
(vi) —($C_0$-$C_6$alkyl)-5 to 10 membered heteroaryl, which said 5 to 10 membered heteroaryl is optionally substituted by one $R^{10}$, and which said 5 to 10 membered heteroaryl comprises one, two or three heteroatoms independently selected from the group consisting of N, O and S;

and which X is optionally further substituted by 1, 2, 3, 4, 5, 6, 7, or 8 G;

$R^{10}$ is —$R^{10a}$-$R^{10b}$, wherein $R^{10a}$ is either absent or —$(CH_2)_n$—, which $R^{10a}$ is optionally substituted by 1, 2, 3, 4, 5, 6, 7, or 8 G;

$R^{10b}$ is selected from the group consisting of:
(i) —OH;
(ii) —CN;

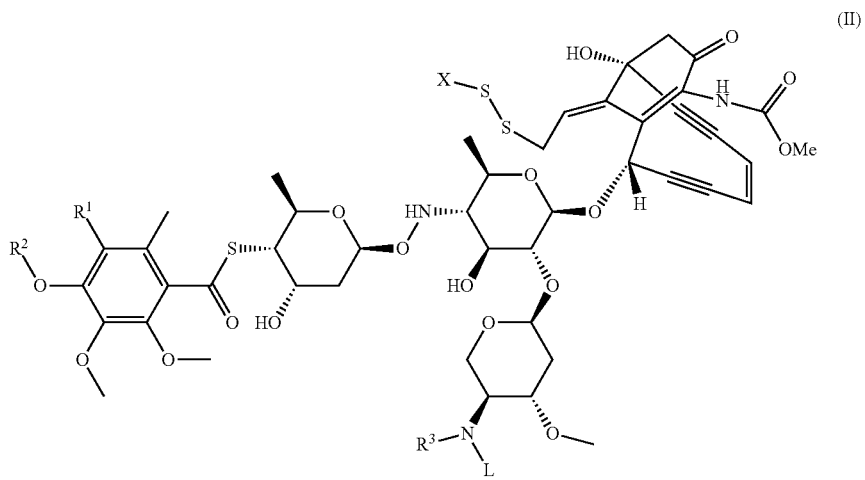

(II)

(iii) —PO₃H;
(iv) —CO₂H;
(v) —CO₂C₁-C₄alkyl, which said C₁-C₄alkyl is optionally substituted by 1, 2, 3, 4, 5, or 6 E;
(vi) —CO—R¹¹;
(vii) —NH—R¹¹;
(viii) —N(C₁-C₄alkyl)-R¹¹, which said C₁-C₄alkyl is optionally substituted by 1, 2, 3, 4, 5, or 6 E;
(ix) —CONH—R¹¹;
(x) —CON(C₁-C₄alkyl)-R¹¹, which said C₁-C₄alkyl is optionally substituted by 1, 2, 3, 4, 5, or 6 E;
(xi) —CONHNH—R¹¹;
(xii) —CONHN(C₁-C₄alkyl)-R¹¹, which said C₁-C₄alkyl is optionally substituted by 1, 2, 3, 4, 5, or 6 E;
(xiii) —CON(C₁-C₄alkyl)NH—R¹¹, which said C₁-C₄alkyl is optionally substituted by 1, 2, 3, 4, 5, or 6 E;
(xiv) —CON(C₁-C₄alkyl)N(C₁-C₄alkyl)-R¹¹, wherein each said C₁-C₄alkyl is independently optionally substituted by 1, 2, 3, 4, 5, or 6 E;
(xv) —CON(R¹¹)NH₂;
(xvi) —CON(R¹¹)NH(C₁-C₄alkyl), which said C₁-C₄alkyl is optionally substituted by 1, 2, 3, 4, 5, or 6 E;
(xvii) —CON(R¹¹)N(C₁-C₄alkyl)₂, wherein each said C₁-C₄alkyl is independently optionally substituted by 1, 2, 3, 4, 5, or 6 E;
(xviii) —CONHN=C(C₁-C₄alkyl)-C₆H₄—OC₁-C₄alkyl, wherein each said C₁-C₄alkyl is independently optionally substituted by 1, 2, 3, 4, 5, or 6 E;
(xix) —CON(C₁-C₄alkyl)N=C(C₁-C₄alkyl)-C₆H₄—OC₁-C₄alkyl, wherein each said C₁-C₄alkyl is independently optionally substituted by 1, 2, 3, 4, 5, or 6 E;
(xx) —N(R¹¹)CO(C₁-C₄alkyl), which said C₁-C₄alkyl is optionally substituted by 1, 2, 3, 4, 5, or 6 E;
(xxi) —CH(CO₂H)NH—R¹¹;
(xxii) —CH(CO₂C₁-C₄alkyl)NH—R¹¹, which said C₁-C₄alkyl is optionally substituted by 1, 2, 3, 4, 5, or 6 E;
(xxiii) —CH(NH₂)CO—R¹¹;
(xxiv) —CH(NH(C₁-C₄alkyl))CO—R¹¹, which said C₁-C₄alkyl is optionally substituted by 1, 2, 3, 4, 5, or 6 E;
(xxv) —CH(N(C₁-C₄alkyl)₂)CO—R¹¹, wherein each said C₁-C₄alkyl is independently optionally substituted by 1, 2, 3, 4, 5, or 6 E;
(xxvi) —CH(CO—R¹¹)NH—R¹¹; and
(xxvii) —CH(CO—R¹¹)N(C₁-C₄alkyl)-R¹¹, which said C₁-C₄alkyl is optionally substituted by 1, 2, 3, 4, 5, or 6 E;

R¹¹ is selected from the group consisting of —R¹¹ᵃ-R¹¹ᵇ-R¹¹ᶜ and —R¹¹ᵈ-R¹¹ᵉ-R¹¹ᶠ, wherein
R¹¹ᵃ is either absent, or is selected from the group consisting of,

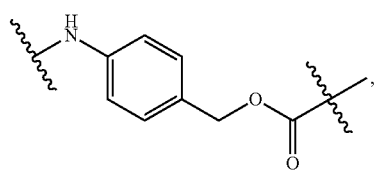

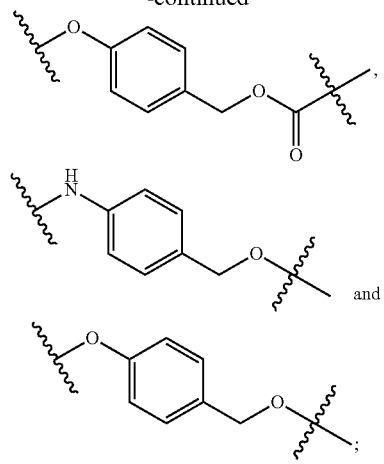

R¹¹ᵇ is either absent, or is selected from the group consisting of

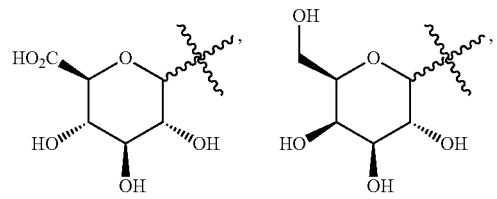

and AAᵣ, wherein AA is independently for each occurrence a natural amino acid or a non-natural amino acid;
R¹¹ᶜ is either absent or is selected from the group consisting of —H, —C₁-C₄alkyl and —COC₁-C₄alkyl;
R¹¹ᵈ is either absent or —(CH₂)ₜ—, which R¹¹ᵈ when present is optionally substituted by 1, 2, 3, 4, 5, 6, 7, or 8 G;
R¹¹ᵉ is either absent or selected from the group consisting of —O— and —NH—;
R¹¹ᶠ is selected from the group consisting of C₆-C₁₂ aryl and 5 to 10 membered heteroaryl, which said 5 to 10 membered heteroaryl comprises one, two or three heteroatoms independently selected from the group consisting of N, O and S, and which
R¹¹ᶠ is optionally substituted by 1, 2, 3, 4, 5, 6, 7, or 8 G;
n is 1, 2, 3, 4, 5, or 6;
r is 1, 2, 3, 4, 5, 6, 7, 8, 9, 10, 11, 12, 13, 14, 15, 16, 17, 18, 19, or 20;
t is 1, 2, 3, 4, 5, or 6;
G is selected, independently for each occurrence, from the group consisting of —F, —Cl, —CN, —OH, —NH₂, —NH—C₁-C₄alkyl, —N(C₁-C₄alkyl)₂, —NO₂, —CO₂H, —C₁-C₄alkyl, —C₁-C₄alkylOH, —C₁-C₄alkylNH₂, —C₁-C₄haloalkyl, —C₁-C₄alkoxy, =O, —CO₂C₁-C₄alkyl, —OC(O)C₁-C₄alkyl, —NHC(O)C₁-C₄alkyl, —C(O)NHC₁-C₄alkyl, and —C(O)N(C₁-C₄alkyl)₂;
E is selected, independently for each occurrence, from the group consisting of —F, —Cl, —CN, —OH, —NH₂, —NHCH₃, —N(CH₃)₂, —NO₂, —CO₂H, —OCH₃, —OCF₃, and —CF₃; and
L is a [LINKER].

Another aspect of the invention relates to a compound of Formula (III),

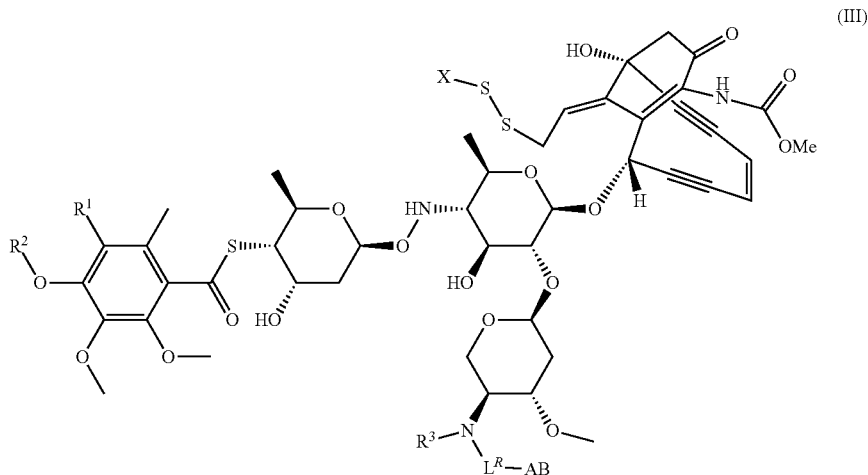

or a pharmaceutically acceptable salt thereof, wherein:
$R^1$ is selected from the group consisting of Br and I;
$R^2$ is selected from the group consisting of H and

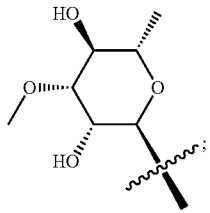

$R^3$ is selected from the group consisting of —$CH_3$, —$CH_2CH_3$, and —$CH(CH_3)_2$;
X is selected from the group consisting of:
(i) —$CH_3$ optionally substituted by one $R^{10}$;
(ii) —$C_2$-$C_8$alkyl optionally substituted by one $R^{10}$;
(iii) —($C_0$-$C_6$alkyl)-$C_3$-$C_{10}$ carbocyclyl, which said $C_3$-$C_{10}$ carbocyclyl is optionally substituted by one $R^{10}$;
(iv) —($C_0$-$C_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S;
(v) —($C_0$-$C_6$alkyl)-phenyl, which said phenyl is optionally substituted by one $R^{10}$; and
(vi) —($C_0$-$C_6$alkyl)-5 to 10 membered heteroaryl, which said 5 to 10 membered heteroaryl is optionally substituted by one $R^{10}$, and which said 5 to 10 membered heteroaryl comprises one, two or three heteroatoms independently selected from the group consisting of N, O and S;
and which X is optionally further substituted by 1, 2, 3, 4, 5, 6, 7, or 8 G;
$R^{10}$ is —$R^{10a}$-$R^{10b}$, wherein
$R^{10a}$ is either absent or —$(CH_2)_n$—, which $R^{10a}$ is optionally substituted by 1, 2, 3, 4, 5, 6, 7, or 8 G;
$R^{10b}$ is selected from the group consisting of:
(i) —OH;
(ii) —CN;
(iii) —$PO_3H$;
(iv) —$CO_2H$;
(v) —$CO_2C_1$-$C_4$alkyl, which said $C_1$-$C_4$alkyl is optionally substituted by 1, 2, 3, 4, 5, or 6 E;
(vi) —CO—$R^{11}$;
(vii) —NH—$R^{11}$;
(viii) —N($C_1$-$C_4$alkyl)-$R^{11}$, which said $C_1$-$C_4$alkyl is optionally substituted by 1, 2, 3, 4, 5, or 6 E;
(ix) —CONH—$R^{11}$;
(x) —CON($C_1$-$C_4$alkyl)-$R^{11}$, which said $C_1$-$C_4$alkyl is optionally substituted by 1, 2, 3, 4, 5, or 6 E;
(xi) —CONHNH—$R^1$;
(xii) —CONHN($C_1$-$C_4$alkyl)-$R^{11}$, which said $C_1$-$C_4$alkyl is optionally substituted by 1, 2, 3, 4, 5, or 6 E;
(xiii) —CON($C_1$-$C_4$alkyl)NH—$R^{11}$, which said $C_1$-$C_4$alkyl is optionally substituted by 1, 2, 3, 4, 5, or 6 E;
(xiv) —CON($C_1$-$C_4$alkyl)N($C_1$-$C_4$alkyl)-$R^{11}$, wherein each said $C_1$-$C_4$alkyl is independently optionally substituted by 1, 2, 3, 4, 5, or 6 E;
(xv) —CON($R^{11}$)$NH_2$;
(xvi) —CON($R^{11}$)NH($C_1$-$C_4$alkyl), which said $C_1$-$C_4$alkyl is optionally substituted by 1, 2, 3, 4, 5, or 6 E;
(xvii) —CON($R^{11}$)N($C_1$-$C_4$alkyl)$_2$, wherein each said $C_1$-$C_4$alkyl is independently optionally substituted by 1, 2, 3, 4, 5, or 6 E;
(xviii) —CONHN=C($C_1$-$C_4$alkyl)-$C_6H_4$—$OC_1$-$C_4$alkyl, wherein each said $C_1$-$C_4$alkyl is independently optionally substituted by 1, 2, 3, 4, 5, or 6 E;
(xix) —CON($C_1$-$C_4$alkyl)N=C($C_1$-$C_4$alkyl)-$C_6H_4$—$OC_1$-$C_4$alkyl, wherein each said $C_1$-$C_4$alkyl is independently optionally substituted by 1, 2, 3, 4, 5, or 6 E;
(xx) —N($R^{11}$)CO($C_1$-$C_4$alkyl), which said $C_1$-$C_4$alkyl is optionally substituted by 1, 2, 3, 4, 5, or 6 E;
(xxi) —CH($CO_2H$)NH—$R^1$;
(xxii) —CH($CO_2C_1$-$C_4$alkyl)NH—$R^{11}$, which said $C_1$-$C_4$alkyl is optionally substituted by 1, 2, 3, 4, 5, or 6 E;
(xxiii) —CH($NH_2$)CO—$R^{11}$;

(xxiv) —CH(NH(C$_1$-C$_4$alkyl))CO—R$^{11}$, which said C$_1$-C$_4$alkyl is optionally substituted by 1, 2, 3, 4, 5, or 6 E;

(xxv) —CH(N(C$_1$-C$_4$alkyl)$_2$)CO—R$^{11}$, wherein each said C$_1$-C$_4$alkyl is independently optionally substituted by 1, 2, 3, 4, 5, or 6 E;

(xxvi) —CH(CO—R$^{11}$)NH—R$^{11}$; and (xxvii) —CH(CO—R$^{11}$)N(C$_1$-C$_4$alkyl)-R$^{11}$, which said C$_1$-C$_4$alkyl is optionally substituted by 1, 2, 3, 4, 5, or 6 E;

R$^{11}$ is selected from the group consisting of —R$^{11a}$-R$^{11b}$-R$^{11c}$ and —R$^{11d}$-R$^{11e}$-R$^{11f}$, wherein R$^{11a}$ is either absent, or is selected from the group consisting of,

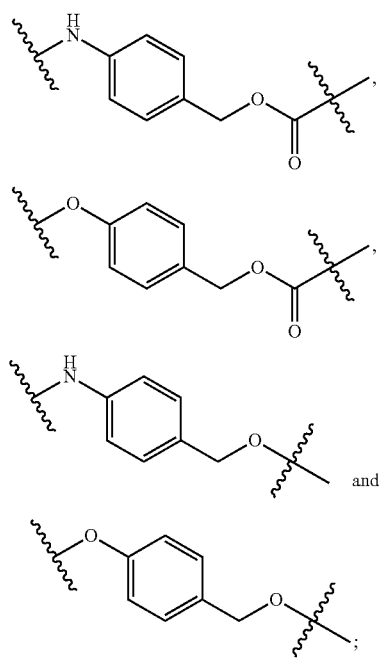

R$^{11b}$ is either absent, or is selected from the group consisting of

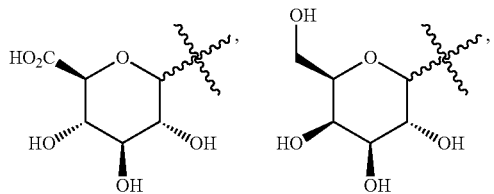

and AA$_r$, wherein AA is independently for each occurrence a natural amino acid or a non-natural amino acid;

R$^{11c}$ is either absent or is selected from the group consisting of —H, —C$_1$-C$_4$alkyl and —COC$_1$-C$_4$alkyl;

R$^{11d}$ is either absent or —(CH$_2$)$_t$—, which R$^{11d}$ when present is optionally substituted by 1, 2, 3, 4, 5, 6, 7, or 8 G;

R$^{11e}$ is either absent or selected from the group consisting of —O— and —NH—;

R$^{11f}$ is selected from the group consisting of C$_6$-C$_{12}$ aryl and 5 to 10 membered heteroaryl, which said 5 to 10 membered heteroaryl comprises one, two or three heteroatoms independently selected from the group consisting of N, O and S, and which R$^{11f}$ is optionally substituted by 1, 2, 3, 4, 5, 6, 7, or 8 G;

n is 1, 2, 3, 4, 5, or 6;

r is 1, 2, 3, 4, 5, 6, 7, 8, 9, 10, 11, 12, 13, 14, 15, 16, 17, 18, 19, or 20;

t is 1, 2, 3, 4, 5, or 6;

G is selected, independently for each occurrence, from the group consisting of —F, —Cl, —CN, —OH, —NH$_2$, —NH—C$_1$-C$_4$alkyl, —N(C$_1$-C$_4$alkyl)$_2$, —NO$_2$, —CO$_2$H, —C$_1$-C$_4$alkyl, —C$_1$-C$_4$alkylOH, —C$_1$-C$_4$alkylNH$_2$, —C$_1$-C$_4$haloalkyl, —C$_1$-C$_4$alkoxy, =O, —CO$_2$C$_1$-C$_4$alkyl, —OC(O)C$_1$-C$_4$alkyl, —NHC(O)C$_1$-C$_4$alkyl, —C(O)NHC$_1$-C$_4$alkyl, and —C(O)N(C$_1$-C$_4$alkyl)$_2$;

E is selected, independently for each occurrence, from the group consisting of —F, —Cl, —CN, —OH, —NH$_2$, —NHCH$_3$, —N(CH$_3$)$_2$, —NO$_2$, —CO$_2$H, —OCH$_3$, —OCF$_3$, and —CF$_3$;

L$^R$ is a [LINKER RADICAL]; and

AB is an antibody.

Another aspect of the invention relates to a compound of Formula (IV),

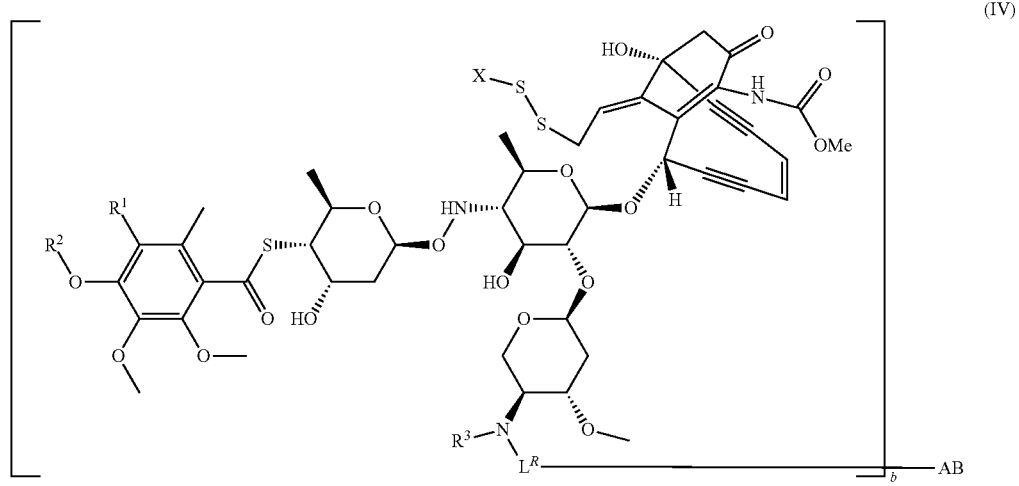

or a pharmaceutically acceptable salt thereof, wherein:
R¹ is selected from the group consisting of Br and I;
R² is selected from the group consisting of H and

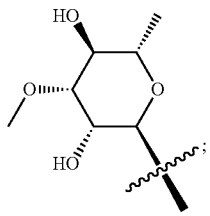

R³ is selected from the group consisting of —CH₃, —CH₂CH₃, and —CH(CH₃)₂;
X is selected from the group consisting of:
(i) —CH₃ optionally substituted by one R¹⁰;
(ii) —C₂-C₈alkyl optionally substituted by one R¹⁰;
(iii) —(C₀-C₆alkyl)-C₃-C₁₀ carbocyclyl, which said C₃-C₁₀ carbocyclyl is optionally substituted by one R¹⁰;
(iv) —(C₀-C₆alkyl)-3 to 10 membered heterocyclyl, which said 3 to 10 membered heterocyclyl is optionally substituted by one R¹⁰, and which said 3 to 10 membered heterocyclyl comprises one, two or three heteroatoms independently selected from the group consisting of N, O and S;
(v) —(C₀-C₆alkyl)-phenyl, which said phenyl is optionally substituted by one R¹⁰; and
(vi) —(C₀-C₆alkyl)-5 to 10 membered heteroaryl, which said 5 to 10 membered heteroaryl is optionally substituted by one R¹⁰, and which said 5 to 10 membered heteroaryl comprises one, two or three heteroatoms independently selected from the group consisting of N, O and S;
and which X is optionally further substituted by 1, 2, 3, 4, 5, 6, 7, or 8 G;
R¹⁰ is —R¹⁰ᵃ-R¹⁰ᵇ, wherein
R¹⁰ᵃ is either absent or —(CH₂)ₙ—, which R¹⁰ᵃ is optionally substituted by 1, 2, 3, 4, 5, 6, 7, or 8 G;
R¹⁰ᵇ is selected from the group consisting of:
(i) —OH;
(ii) —CN;
(iii) —PO₃H;
(iv) —CO₂H;
(v) —CO₂C₁-C₄alkyl, which said C₁-C₄alkyl is optionally substituted by 1, 2, 3, 4, 5, or 6 E;
(vi) —CO—R¹¹;
(vii) —NH—R¹¹;
(viii) —N(C₁-C₄alkyl)-R¹¹, which said C₁-C₄alkyl is optionally substituted by 1, 2, 3, 4, 5, or 6 E;
(ix) —CONH—R¹¹;
(x) —CON(C₁-C₄alkyl)-R¹¹, which said C₁-C₄alkyl is optionally substituted by 1, 2, 3, 4, 5, or 6 E;
(xi) —CONHNH—R¹¹;
(xii) —CONHN(C₁-C₄alkyl)-R¹¹, which said C₁-C₄alkyl is optionally substituted by 1, 2, 3, 4, 5, or 6 E;
(xiii) —CON(C₁-C₄alkyl)NH—R¹¹, which said C₁-C₄alkyl is optionally substituted by 1, 2, 3, 4, 5, or 6 E;
(xiv) —CON(C₁-C₄alkyl)N(C₁-C₄alkyl)-R¹¹, wherein each said C₁-C₄alkyl is independently optionally substituted by 1, 2, 3, 4, 5, or 6 E;
(xv) —CON(R¹¹)NH₂;
(xvi) —CON(R¹¹)NH(C₁-C₄alkyl), which said C₁-C₄alkyl is optionally substituted by 1, 2, 3, 4, 5, or 6 E;
(xvii) —CON(R¹¹)N(C₁-C₄alkyl)₂, wherein each said C₁-C₄alkyl is independently optionally substituted by 1, 2, 3, 4, 5, or 6 E;
(xviii) —CONHN═C(C₁-C₄alkyl)-C₆H₄—OC₁-C₄alkyl, wherein each said C₁-C₄alkyl is independently optionally substituted by 1, 2, 3, 4, 5, or 6 E;
(xix) —CON(C₁-C₄alkyl)N═C(C₁-C₄alkyl)-C₆H₄—OC₁-C₄alkyl, wherein each said C₁-C₄alkyl is independently optionally substituted by 1, 2, 3, 4, 5, or 6 E;
(xx) —N(R¹¹)CO(C₁-C₄alkyl), which said C₁-C₄alkyl is optionally substituted by 1, 2, 3, 4, 5, or 6 E;
(xxi) —CH(CO₂H)NH—R¹¹;
(xxii) —CH(CO₂C₁-C₄alkyl)NH—R¹¹, which said C₁-C₄alkyl is optionally substituted by 1, 2, 3, 4, 5, or 6 E;
(xxiii) —CH(NH₂)CO—R¹¹;
(xxiv) —CH(NH(C₁-C₄alkyl))CO—R¹¹, which said C₁-C₄alkyl is optionally substituted by 1, 2, 3, 4, 5, or 6 E;
(xxv) —CH(N(C₁-C₄alkyl)₂)CO—R¹¹, wherein each said C₁-C₄alkyl is independently optionally substituted by 1, 2, 3, 4, 5, or 6 E;
(xxvi) —CH(CO—R¹¹)NH—R¹¹; and
(xxvii) —CH(CO—R¹¹)N(C₁-C₄alkyl)-R¹¹, which said C₁-C₄alkyl is optionally substituted by 1, 2, 3, 4, 5, or 6 E;
R¹¹ is selected from the group consisting of —R¹¹ᵃ-R¹¹ᵇ-R¹¹ᶜ and —R¹¹ᵈ-R¹¹ᵉ-R¹¹ᶠ, wherein
R¹¹ᵃ is either absent, or is selected from the group consisting of,

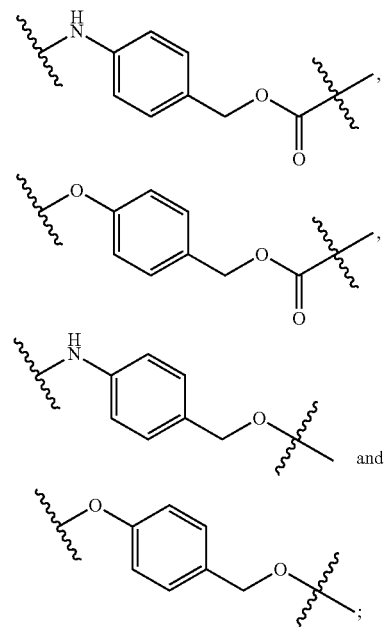

and $R^{11b}$ is either absent, or is selected from the group consisting of

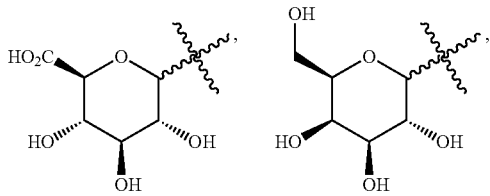

and $AA_r$, wherein AA is independently for each occurrence a natural amino acid or a non-natural amino acid;

$R^{11c}$ is either absent or is selected from the group consisting of —H, —$C_1$-$C_4$alkyl and —$COC_1$-$C_4$alkyl;

$R^{11d}$ is either absent or —$(CH_2)_t$—, which $R^{11d}$ when present is optionally substituted by 1, 2, 3, 4, 5, 6, 7, or 8 G;

$R^{11e}$ is either absent or selected from the group consisting of —O— and —NH—;

$R^{11f}$ is selected from the group consisting of $C_6$-$C_{12}$ aryl and 5 to 10 membered heteroaryl, which said 5 to 10 membered heteroaryl comprises one, two or three heteroatoms independently selected from the group consisting of N, O and S, and which $R^{11f}$ is optionally substituted by 1, 2, 3, 4, 5, 6, 7, or 8 G;

n is 1, 2, 3, 4, 5, or 6;

r is 1, 2, 3, 4, 5, 6, 7, 8, 9, 10, 11, 12, 13, 14, 15, 16, 17, 18, 19, or 20;

t is 1, 2, 3, 4, 5, or 6;

G is selected, independently for each occurrence, from the group consisting of —F, —Cl, —CN, —OH, —$NH_2$, —NH—$C_1$-$C_4$alkyl, —N($C_1$-$C_4$alkyl)$_2$, —$NO_2$, —$CO_2$H, —$C_1$-$C_4$alkyl, —$C_1$-$C_4$alkylOH, —$C_1$-$C_4$alkylNH$_2$, —$C_1$-$C_4$haloalkyl, —$C_1$-$C_4$alkoxy, =O, —$CO_2C_1$-$C_4$alkyl, —OC(O)$C_1$-$C_4$alkyl, —NHC(O)$C_1$-$C_4$alkyl, —C(O)NHC$_1$-$C_4$alkyl, and —C(O)N(C$_1$-$C_4$alkyl)$_2$;

E is selected, independently for each occurrence, from the group consisting of —F, —Cl, —CN, —OH, —$NH_2$, —$NHCH_3$, —$N(CH_3)_2$, —$NO_2$, —$CO_2$H, —$OCH_3$, —$OCF_3$, and —$CF_3$;

$L^R$ is a [LINKER RADICAL];

AB is an antibody; and b is 1-20.

Another aspect of the invention relates to pharmaceutical compositions including an effective amount of any one of the aforementioned compounds and/or any one of the aforementioned antibody drug conjugates and a pharmaceutically acceptable carrier or vehicle.

Another aspect of the invention relates to a method of using an effective amount of any one of the aforementioned compounds and/or any one of the aforementioned antibody drug conjugates to treat cancer by administering to a patient in need thereof an effective amount of said compound and/or conjugate.

Another aspect of the invention relates to a method of treating cancer wherein said cancer includes a tumor, metastasis, or other disease or disorder characterized by uncontrolled cell growth wherein said cancer is selected from the group consisting of carcinomas of the bladder, breast, cervix, colon, gliomas, endometrium, kidney, lung, esophagus, ovary, prostate, pancreas, melanoma, stomach, and testes.

DETAILED DESCRIPTION

Figure 1:
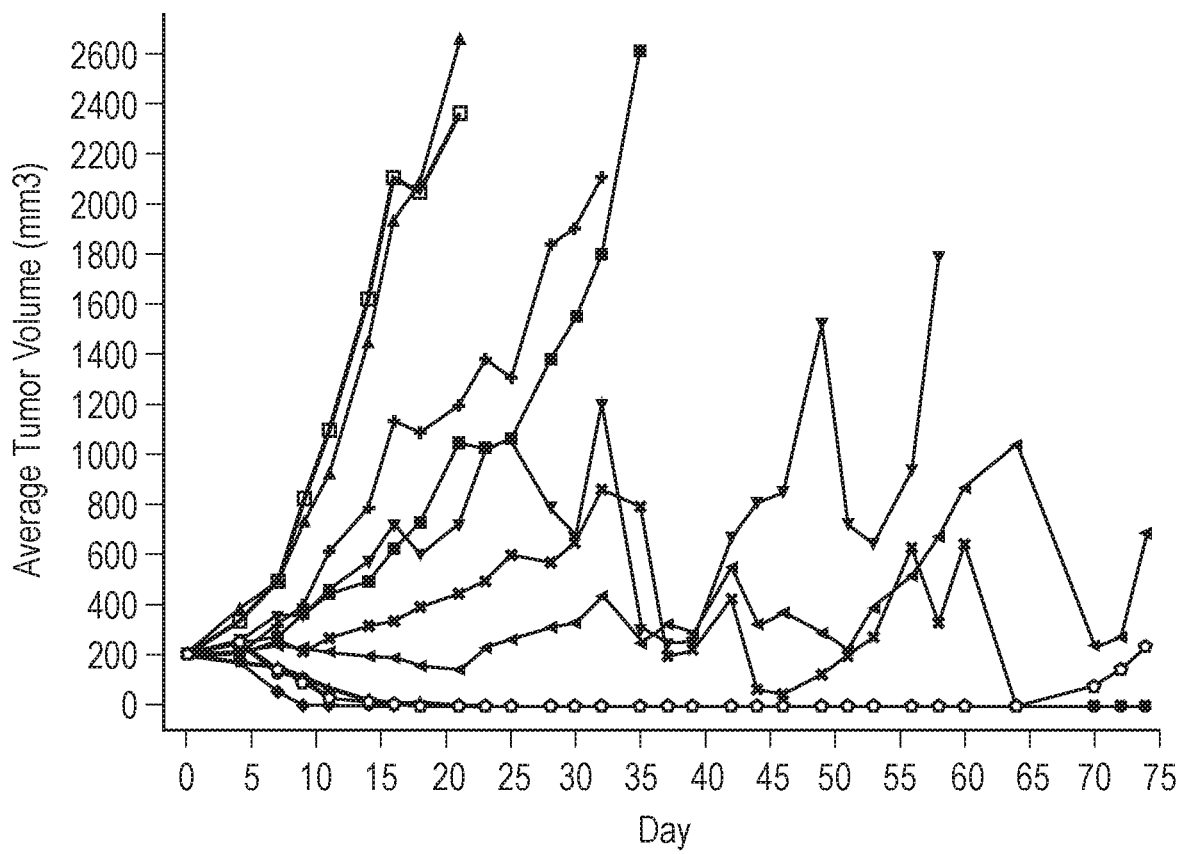
FIG. 1 shows a graph of the data from Table 6 of the calicheamicin ADCs (examples 50, 69, and 84) dosed at 0.01, 0.05 and 0.1 mg/kg doses compared to Mylotarg dosed at 1 mg/kg and PBS vehicle.

The present invention is directed to novel calicheamicin derivatives useful as payloads in antibody-drug-conjugates (ADC's), and to payload-linker compounds and ADC compounds comprising the same. The present invention further relates to compositions comprising the aforementioned payloads, payload-linkers and ADC's, and to methods for using these payloads, payload-linkers and ADC's, to treat pathological conditions such as cancer. The invention also relates to methods of using such compounds and/or conjugates in vitro, in situ, and in vivo for the detection, diagnosis or treatment of mammalian cells, or associated pathological conditions.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

All publications, patents, and patent applications cited herein are hereby incorporated by reference herein in their entirety for all purposes to the same extent as if each individual publication, patent, and patent application were specifically and individually indicated to be so incorporated by reference. In the event that one or more of the incorporated literature and similar materials differs from or contradicts this application, including but not limited to defined terms, term usage, described techniques, or the like, this application controls.

Definitions and Abbreviations

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" (or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, Immuno. Biology, 5th Ed., Garland Publishing, New York). An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

The terms "specifically binds" and "specific binding" refer to antibody binding to a predetermined antigen. Typically, the antibody binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

As used herein, "H(C)-" refers to trastuzumab (trade name HERCEPTIN®) which is a monoclonal antibody that interferes with the HER2/neu receptor, bound through one of its' cysteine to compound of the invention. As used herein, "H(K)-" refers to trastuzumab which is a monoclonal antibody that interferes with the HER2/neu receptor, bound through one of its' lysines to compound of the invention.

An "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof.

An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

The term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (L3) in the heavy chain variable domain; Kabat et al. (Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (142) and 96-101 (H3) in the heavy chain variable domain; Chothia and Lesk, 1987, J. Mol. Biol. 196:901-917). FR residues are those variable domain residues other than the hypervariable region residues as herein defined.

A "single-chain Fv" or "scFv" antibody fragment comprises the V.sub.H and V.sub.L domains of an antibody, wherein these domains are present in a single polypeptide chain. Typically, the Fv polypeptide further comprises a polypeptide linker between the $V_H$ and $V_L$ domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabody" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, Nature 321:522-525; Riechmann et al., 1988, Nature 332:323-329; and Presta, 1992, Curr. Op. Struct. Biol. 2:593-596.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. greater than 50% of a population, of a mixture or a sample.

The term "intracellular metabolite" refers to a compound resulting from a metabolic process or reaction inside a cell on an antibody-drug conjugate (ADC). The metabolic process or reaction may be an enzymatic process such as proteolytic cleavage of a peptide linker of the ADC. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an ADC or the like, whereby the covalent attachment, e.g., the linker, between the drug moiety and the antibody is broken, resulting in the free drug, or other metabolite of the conjugate dissociated from the antibody inside the cell. The cleaved moieties of the ADC are thus intracellular metabolites.

The term "bioavailability" refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a ADC or an intracellular metabolite of said ADC. Cytotoxic activity may be expressed as the $IC_{50}$ value, which is the concentration (molar or mass) per unit volume at which half the cells survive.

A "disorder" is any condition that would benefit from treatment with a drug or antibody-drug conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

The term "package insert" is used to refer to instructions customarily included in commercial packages of therapeutic products, that contain information about the indication(s), usage, dosage, administration, contraindications and/or warnings concerning the use of such therapeutic products.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Unless otherwise indicated, the term "alkyl" by itself or as part of another term refers to a straight chain or branched, saturated hydrocarbon having the indicated number of carbon atoms (e.g., "$C_1$-$C_8$" alkyl refer to an alkyl group having from 1 to 8 carbon atoms; "$C_0$-$C_6$" alkyl refers to an alkyl group having from 0 carbon atoms, meaning that the alkyl group is absent, to 6 carbon atoms). Similarly, when the number of carbon atoms is not indicated, the alkyl group has from 1 to 8 carbon atoms. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tert-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl. Alkyl groups described herein as optionally substituted by may be substituted by one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, preferably from 1 to 4 optional substituents, or more preferably from 1 to 3 optional substituents. In some instances, substituted alkyl groups may be specifically named with reference to the substituent group. For example, "haloalkyl" refers to an alkyl group having the specified number of carbon atoms that is substituted by one or more halo substituents, and typically contain 1-6 carbon atoms and 1, 2 or 3 halo atoms (i.e., "$C_1$-$C_6$ haloalkyl") or sometimes 1-4 carbon atoms and 1, 2 or 3 halo atoms (i.e., "$C_1$-$C_4$ haloalkyl"). Thus, a $C_1$-$C_4$ haloalkyl group includes trifluoromethyl (—$CF_3$) and difluoromethyl (—$CF_2H$). More specifically, fluorinated alkyl groups may be specifically referred to as fluoroalkyl groups, e.g., $C_1$-$C_6$ or $C_1$-$C_4$ fluoroalkyl groups. Similarly, "hydroxyalkyl" refers to an alkyl group having the specified number of carbon atoms that is substituted by one or more hydroxy substituents, and typically contain 1-6 carbon atoms and 1, 2 or 3 hydroxy (i.e., "$C_1$-$C_6$ hydroxyalkyl"). Thus, $C_1$-$C_6$ hydroxyalkyl includes hydroxymethyl (—$CH_2OH$) and 2-hydroxyethyl (—$CH_2CH_2OH$). "Alkoxyalkyl" refers to an alkyl group having the specified number of carbon atoms that is substituted by one or more alkoxy substituents. Alkoxyalkyl groups typically contain 1-6 carbon atoms in the alkyl portion and are substituted by 1, 2 or 3 $C_1$-$C_4$ alkyoxy substituents. Such groups are sometimes described herein as $C_1$-$C_4$ alkyoxy-$C_1$-$C_6$ alkyl. "Aminoalkyl" refers to alkyl group having the specified number of carbon atoms that is substituted by one or more substituted or unsubstituted amino groups, as such groups are further defined herein. Aminoalkyl groups typically contain 1-6 carbon atoms in the alkyl portion and are substituted by 1, 2 or 3 amino substituents. Thus, a $C_1$-$C_6$ aminoalkyl group includes, for example, aminomethyl (—$CH_2NH_2$), N,N-dimethylamino-ethyl (—$CH_2CH_2N(CH_3)_2$), 3-(N-cyclopropylamino)propyl (—$CH_2CH_2CH_2NH$—Pr) and N-pyrrolidinylethyl (—$CH_2CH_2N$-pyrrolidinyl).

Unless otherwise indicated, "alkenyl," by itself or as part of another term, refers to an alkyl group consisting of at least one carbon-carbon double bond. Typically, alkenyl groups have 2 to 20 carbon atoms ("$C_2$-$C_{20}$ alkenyl"), preferably 2 to 12 carbon atoms ("$C_2$-$C_{12}$ alkenyl"), more preferably 2 to 8 carbon atoms ("$C_2$-$C_8$ alkenyl"), or 2 to 6 carbon atoms ("$C_2$-$C_6$ alkenyl"), or 2 to 4 carbon atoms ("$C_2$-$C_4$ alkenyl"). Representative examples include, but are not limited to, ethenyl, 1-propenyl, 2-propenyl, 1-, 2-, 3-butenyl, and the like. Alkenyl groups may be unsubstituted or substituted by the same groups that are described herein as suitable for alkyl.

"Alkynyl" refers to an alkyl groups, as defined herein, consisting of at least two carbon atoms and at least one carbon-carbon triple bond. Alkynyl groups have 2 to 20 carbon atoms ("$C_2$-$C_{20}$alkynyl"), preferably 2 to 12 carbon atoms ("$C_2$-$C_2$ alkynyl"), more preferably 2 to 8 carbon atoms ("$C_2$-$C_8$alkynyl"), or 2 to 6 carbon atoms ("$C_2$-$C_6$alkynyl"), or 2 to 4 carbon atoms ("$C_2$-$C_4$alkynyl"). Representative examples include, but are not limited to, ethynyl, 1-propynyl, 2-propynyl, 1-, 2-, or 3-butynyl, and the like. Akynyl groups may be unsubstituted or substituted.

"Alkoxy" refers to a monovalent —O-alkyl group, wherein the alkyl portion has the specified number of carbon atoms. Alkoxy groups typically contain 1 to 8 carbon atoms ("$C_1$-$C_8$ alkoxy"), or 1 to 6 carbon atoms ("$C_1$-$C_6$ alkoxy"), or 1 to 4 carbon atoms ("$C_1$-$C_4$ alkoxy"). For example, $C_1$-$C_4$ alkoxy includes —$OCH_3$, —$OCH_2CH_3$, —$OCH(CH_3)_2$, —$OC(CH_3)_3$, and the like. Such groups may also be referred to herein as methoxy, ethoxy, isopropoxy, tert-butyloxy, etc. Alkoxy groups may be unsubstituted or substituted on the alkyl portion by the same groups that are described herein as suitable for alkyl. In particular, alkoxy groups may be substituted by one or more halo groups, up to the total number of hydrogen atoms present on the alkyl portion. Thus, $C_1$-$C_4$ alkoxy includes halogenated alkoxy groups, e.g., trifluoromethoxy and 2,2-difluoroethoxy (i.e., —$OCF_3$ and —$OCH_2CHF_2$). In some instances, such groups may be referred to as "haloalkoxy" (or, where fluorinated, more specifically as "fluoroalkoxy") groups having the specified number of carbon atoms and substituted by one or more halo substituents, and typically contain 1-6 carbon atoms and 1, 2 or 3 halo atoms (i.e., "$C_1$-$C_6$ haloalkoxy") or sometimes 1-4 carbon atoms and 1, 2 or 3 halo atoms (i.e., "$C_1$-$C_4$ haloalkoxy"). Thus, a $C_1$-$C_4$ haloalkyoxy group includes trifluoromethoxy (—$OCF_3$) and difluoromethoxy (—$OCF_2H$). More specifically, fluorinated alkyl groups may be specifically referred to as fluoroalkoxy groups, e.g., $C_1$-$C_6$ or $C_1$-$C_4$ fluoroalkoxy groups. Similarly, "alkylthio" refers to a monovalent —S-alkyl group, wherein the alkyl portion has the specified number of carbon atoms, and may be optionally substituted on the alkyl portion by the same groups that are described herein as suitable for alkyl. For example, a $C_1$-$C_4$ alkylthio includes —$SCH_3$ and —$SCH_2CH_3$.

Unless otherwise indicated, "$C_3$-$C_{10}$ carbocyclyl" by itself or as part of another term, is a 3-, 4-, 5-, 6-, 7-, 8-, 9- or 10-membered monovalent, substituted or unsubstituted, saturated or partially unsaturated non-aromatic monocyclic, bicyclic, spirocyclic, bridged, fused or polycyclic carbocyclic ring derived by the removal of one hydrogen atom from a ring atom of a parent ring system. Representative $C_3$-$C_{10}$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(1.1.1.)pentane, and bicyclo(2.2.2.)octane. Carbocyclyl groups may be unsubstituted or substituted by the same groups that are described herein as suitable for alkyl.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive.

Unless otherwise indicated, the term "heteroalkylene" by itself or as part of another substituent means a divalent group derived from heteroalkyl (as discussed above). For heteroalkylene groups, heteroatoms can also occupy either or both of the chain termini.

Unless otherwise indicated, "heterocyclyl" by itself or as part of another term, refers to a monovalent substituted or partially unsubstituted aromatic or non-aromatic monocyclic, bicyclic or tricyclic ring system containing the specified number of ring atoms, including at least one heteroatom selected from N, O and S as a ring member, where ring S atoms may be optionally substituted by one or two oxo groups (i.e., $S(O)_q$, where q is 0, 1 or 2) and where the heterocyclic ring is connected to the base molecule via a ring atom, which may be C or N. Heterocyclic rings may be spirocyclic, bridged, or fused to one or more other heterocyclic or carbocyclic rings, where such spirocyclic, bridged, or fused rings may themselves be saturated, partially unsaturated or aromatic to the extent unsaturation or aromaticity makes chemical sense, provided the point of attachment to the base molecule is an atom of the heterocyclic portion of the ring system. Preferably, heterocyclic rings contain 1 to 4 heteroatoms selected from N, O, and $S(O)_q$ as ring members, and more preferably 1 to 2 ring heteroatoms, provided that such heterocyclic rings do not contain two contiguous oxygen atoms. The ring that includes the heteroatom can be aromatic or nonaromatic. Unless otherwise noted, the heterocyclyl is attached to its pendant group at any heteroatom or carbon atom that results in a stable structure. Representative examples of a "heterocyclyl" include, but are not limited to, tetrahydrofuranyl, oxetanyl, pyranyl, pyrrolidinyl, piperidinyl, piperazinyl, benzofuranyl, benzothiophene, benzothiazolyl, indolyl, benzopyrazolyl, pyrrolyl, thiophenyl (thiopene), furanyl, thiazolyl, imidazolyl, pyrazolyl, triazolyl, quinolinyl including moieties such as 1,2,3,4-tetrshyhro-quinolinyl, pyrimidinyl, pyridinyl, pyridonyl, pyrazinyl, pyridazinyl, isothiazolyl, isoxazolyl, tetrazolyl, epoxide, and oxetane. Heterocyclyl groups may be unsubstituted or substituted by suitable substituent groups, for example the same groups that are described herein as suitable for alkyl, aryl or heteroaryl. Such substituents may be present on the heterocyclic ring attached to the base molecule, or on a spirocyclic, bridged or fused ring attached thereto. In addition, ring N atoms may be optionally substituted by groups suitable for an amine, e.g., alkyl, acyl, carbamoyl, sulfonyl substituents, and the like.

Unless otherwise indicated, "aryl," by itself or an part of another term, means a substituted or unsubstituted monovalent carbocyclic aromatic hydrocarbon radical of 6-20, preferably 6-14, carbon atoms derived by the removal of one hydrogen atom from a single carbon atom of a parent aromatic ring system. The "aryl" group can be monocyclic or fused. Typical aryl groups include, but are not limited to, radicals derived from benzene including phenyl, substituted benzene, naphthalene, anthracene, biphenyl, and the like. "Arylene" is the corresponding divalent moiety. An example of an "arylene" group is —$C_6H4$-, phenylene in which a divalent moiety of benzene has been formed such that it can be disubstituted. The aryl group may be unsubstituted or substituted.

Similarly, "heteroaryl" or "heteroaromatic" refer to monocyclic or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 10 ring atoms ("5-10 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Heteroaryl groups may also be fused to another aryl or heteroaryl ring, or fused to a saturated or partially unsaturated carbocyclic or heterocyclic ring, provided the point of attachment to the base molecule on such fused ring systems is an atom of the heteroaromatic portion of the ring system. Examples of unsubstituted heteroaryl groups often include, but are not limited to, pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthryidine and carbazole. In frequent preferred embodiments, 5- or 6-membered heteroaryl groups are selected from the group consisting of pyrrolyl, furanyl, thiophenyl, pyrazolyl, imidazolyl, isoxazolyl, oxazolyl, isothiazolyl, thiazolyl, triazolyl, pyridinyl and pyrimidinyl, pyrazinyl or pyridazinyl rings. The heteroaryl group may be unsubstituted or substitutent.

Unless otherwise indicated, "aralkyl" by itself or part of another term, means an alkyl group, as defined above, substituted with an aryl group, as defined above.

Unless otherwise indicated, "heteroaralkyl" by itself or part of another term, means an alkyl group, as defined above, substituted with an aromatic heterocyclyl group, as defined above. Heteroaralklo is the corresponding divalent moiety.

Similarly, "arylalkoxy" and "heteroarylalkoxy" refer to aryl and heteroaryl groups, attached to the base molecule through a heteroalkylene linker (i.e., —O-alkylene-), wherein the groups are described according to the total number of non-hydrogen atoms (i.e., C, N, S and O atoms) in the ring and linker combined. Thus, —O—$CH_2$-phenyl and —O—$CH_2$-pyridinyl groups would be referred to as $C_8$-arylalkoxy and $C_8$-heteroarylalkoxy groups, respectively.

Unless otherwise indicated, it is generally understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

"Hydroxy" refers to an —OH group.

"Acyloxy" refers to a monovalent group —OC(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl. Thus, $C_1$-$C_4$ acyloxy includes an —OC(O)$C_1$-$C_4$ alkyl substituent, e.g., —OC(O)$CH_3$.

"Acyl" refers to a monovalent group —C(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl, e.g., by F, OH or alkoxy. Thus, optionally substituted —C(O)$C_1$-$C_4$ alkyl includes unsubstituted acyl groups, such as —C(O)$CH_3$ (i.e., acetyl) and —C(O)$CH_2CH_3$ (i.e., propionyl), as well as substituted acyl groups such as —C(O)$CF_3$ (trifluoroacetyl), —C(O)$CH_2$OH (hydroxyacetyl), —C(O)$CH_2OCH_3$ (methoxyacetyl), —C(O)$CF_2$H (difluoroacetyl), and the like.

"Acylamino" refers to a monovalent group, —NHC(O)alkyl or —NRC(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl. Thus, $C_1$-$C_4$ acylamino includes an —NHC(O)$C_1$-$C_4$ alkyl substituent, e.g., —NHC(O)$CH_3$.

"Aryloxy" or "heteroaryloxy" refer to optionally substituted —O-aryl or —O-heteroaryl, in each case where aryl and heteroaryl are as further defined herein.

"Arylamino" or "heteroarylamino" refer to optionally substituted —NH-aryl, —NR-aryl, —NH-heteroaryl or —NR-heteroaryl, in each case where aryl and heteroaryl are as further defined herein and R represents a substituent suitable for an amine, e.g., an alkyl, acyl, carbamoyl or sulfonyl group, or the like.

"Cyano" refers to a —C≡N group.

"Unsubstituted amino" refers to a group —$NH_2$.

"Halogen" or "halo" refers to fluoro, chloro, bromo and iodo (F, Cl, Br, I). Preferably, halo refers to fluoro or chloro (F or Cl).

"Optional" or "optionally" means that the subsequently described event or circumstance may but need not occur, and the description includes instances where the event or circumstance occurs and instances in which it does not. The terms "optionally substituted" and "substituted or unsubstituted" may be used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that may be included is reduced by two. In the case where optional substituents are selected independently from a list of alternatives, the selected groups may be the same or different. Throughout the disclosure, it will be understood that the number and nature of optional substituent groups will be limited to the extent that such substitutions make chemical sense. Typical substituent include halo, —OH, $C_1$-$C_4$ alkoxy, —O—$C_6$-$C_{12}$ aryl, —CN, —$NO_2$, =O, —COO$R^x$, —OC(O)$R^x$, —C(O)N$R^xR^y$, —N$R^x$C(O)$R^y$, —N$R^xR^y$, —$SO_3$H, —S(=O)$_2R^x$, —OS(=O)$_2OR^x$, —S(=O)$_2NR^x$, —S(=O)$R^x$, —OP(=O)(OR)$_2$, —P(=O)(OR)$_2$, —PO$_{32}$—, PO$_3H_2$, —AsO$_2H_2$, —C(=O)$R^x$, $C_3$-$C_8$ cycloalkyl, $C_6$-$C_{12}$ aryl, 5-12 membered heteroaryl and 3-12 membered heterocyclyl; where each $R^x$ and $R^y$ is independently H or $C_1$-$C_4$ alkyl, or $R^x$ and $R^y$ may be taken together with the N to which they are attached form a 3-12 membered heterocyclyl or 5-12 membered heteroaryl ring, each optionally containing 1, 2 or 3 additional heteroatoms selected from O, N and S(O)$_q$ where q is 0-2; wherein each said $C_3$-$C_8$ cycloalkyl, $C_6$-$C_{12}$ aryl, 5-12 membered heteroaryl and 3-12 membered heterocyclyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl) and —N($C_1$-$C_4$ alkyl)$_2$.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

Stereochemical definitions and conventions used herein generally follow S. P. Parker, Ed., McGraw-Hill Dictionary of Chemical Terms, McGraw-Hill Book Company, New York (1984); and Eliel and Wilen, Stereochemistry of Organic Compounds, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and I or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

An amino acid ("AA") as used herein refers to a compound which contains a central carbon atom to which are bound an amine function group, a carboxyl functional group and side chain. The term amino acid includes natural amino acids, non-natural amino acids, derivatives of natural amino acids or derivatives of non natural amino acids.

A "natural amino acid" refers to an amino acid which is encoded directly by the codons of the universal genetic code and include arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

A "non natural amino acid" refers to an amino acid which is not encoded by the codons of the universal genetic code. One example of a "non natural amino acid" is a "derivative of an amino acid".

A "derivative of an amino acid" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

"Protecting group" refers to a moiety that when attached to a reactive group in a molecule masks, reduces or prevents that reactivity. Examples of protecting groups can be found in T. W. Greene and P. G. M. Wuts, Protective Groups in Organic Synthesis, 3rd edition, John Wiley & Sons, New York, 1999, and Harrison and Harrison et al., Compendium of Synthetic Organic Methods, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, malate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a compound or conjugate of the invention. Examples of solvents that form pharmaceutically acceptable solvates include, but are not limited to, water, isopropanol, ethanol, methanol, DMSO, ethyl acetate, acetic acid, and ethanolamine.

The terms "loading" or "drug loading" or "payload loading" represent or refer to the average number of payloads ("payload" and "payloads" are used interchangeable herein with "drug" and "drugs") per antibody in an ADC molecule. Drug loading may range from 1 to 20 drugs per antibody. This is sometimes referred to as the DAR, or drug to antibody ratio. Compositions of the ADCs described herein typically have DAR's of from 1-20, and in certain embodiments from 1-8, from 2-8, from 2-6, from 2-5 and from 2-4. Typical DAR values are 2, 4, 6 and 8. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis. DAR may be limited by the number of attachment sites on the antibody. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond. Typically, fewer than the theoretical maximum of drug moieties are conjugated to an antibody during a conjugation reaction. An antibody may contain, for example, many lysine residues that do not react with a linker or linker intermediate. Only the most reactive lysine groups may react with a reactive linker reagent.

Generally, antibodies do not contain many, if any, free and reactive cysteine thiol groups which may be linked to a drug via a linker. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (drug/antibody ratio) of an ADC may be controlled in several different manners, including: (i) limiting the molar excess of drug-linker relative to the antibody, (ii) limiting the conjugation reaction time or temperature, and (iii) partial or limiting reductive conditions for cysteine thiol modification. Where more than one nucleophilic group reacts with a drug-linker then the resulting product is a mixture of ADC's with a distribution of one or more drugs moieties per antibody. The average number of drugs per antibody may be calculated from the mixture by, for example, dual ELISA antibody assay, specific for antibody and specific for the drug. Individual ADC's may be identified in the mixture by mass spectroscopy, and separated by HPLC, e. g., hydrophobic interaction chromatography.

Below is a list of abbreviations and definitions that may not otherwise be defined or described in this application: DMSO (refers to dimethyl sulfoxide), DMA (refers to dimethylacetamide), PBS (refers to phosphate buffered saline), DTT (refers to dithiothreitol), DAD (refers to diode array detection), MW (refers to molecular weight), etc. (refers to and so forth), trityl (refers 1,1',1''-ethane-1,1,1-triyltribenzene), THF (refers to tetrahydrofuran), NHS (refers to 1-Hydroxy-2,5-pyrrolidinedione), Cbz (refers to carboxybenzyl), eq. (refers to equivalent), n-BuLi (refers to n-butyllithium), OAc (refers to acetate), MeOH (refers to methanol), i-Pr (refers to isopropyl or propan-2-yl), NMM (refers to 4-methylmorpholine), and "-" (in a table refers to no data available at this time).

Compounds of Formula (I) and Derivatives Thereof

One aspect of the invention relates to a compound of Formula (I):

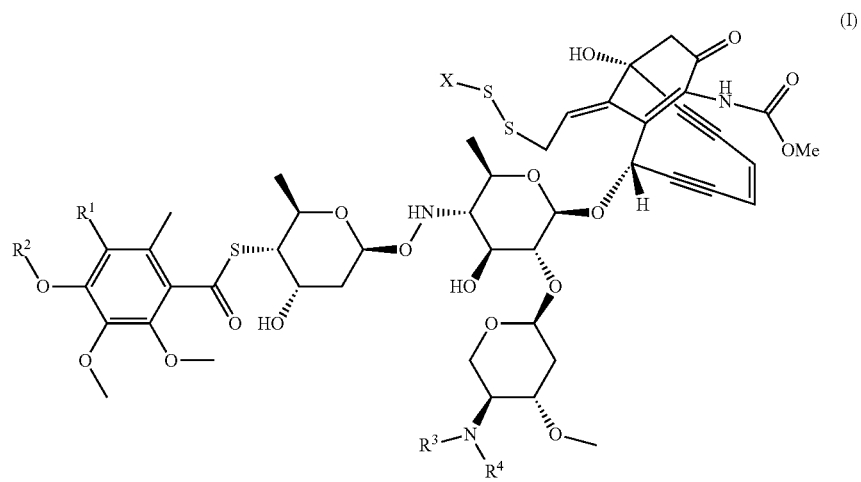

or a pharmaceutically acceptable salt thereof, wherein:

$R^1$ is selected from the group consisting of Br and I;

$R^2$ is selected from the group consisting of H and

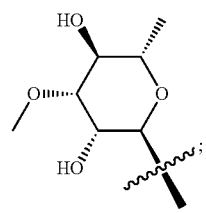

$R^3$ is selected from the group consisting of —$CH_3$, —$CH_2CH_3$, and —$CH(CH_3)_2$;

$R^4$ is H;

X is selected from the group consisting of:
  (i) —$CH_3$ optionally substituted by one $R^{10}$;
  (ii) —$C_2$-$C_8$alkyl optionally substituted by one $R^{10}$;

(iii) —(C$_0$-C$_6$alkyl)-C$_3$-C$_{10}$ carbocyclyl, which said C$_3$-C$_{10}$ carbocyclyl is optionally substituted by one R$^{10}$;
(iv) —(C$_0$-C$_6$alkyl)-3 to 10 membered heterocyclyl, which said 3 to 10 membered heterocyclyl is optionally substituted by one R$^{10}$, and which said 3 to 10 membered heterocyclyl comprises one, two or three heteroatoms independently selected from the group consisting of N, O and S;
(v) —(C$_0$-C$_6$alkyl)-phenyl, which said phenyl is optionally substituted by one R$^{10}$; and
(vi) —(C$_0$-C$_6$alkyl)-5 to 10 membered heteroaryl, which said 5 to 10 membered heteroaryl is optionally substituted by one R$^{10}$, and which said 5 to 10 membered heteroaryl comprises one, two or three heteroatoms independently selected from the group consisting of N, O and S;
and which X is optionally further substituted by 1, 2, 3, 4, 5, 6, 7, or 8 G;
R$^{10}$ is —R$^{10a}$-R$^{10b}$, wherein
R$^{10a}$ is either absent or —(CH$_2$)$_n$—, which R$^{10a}$ is optionally substituted by 1, 2, 3, 4, 5, 6, 7, or 8 G;
R$^{10b}$ is selected from the group consisting of:
(i) —OH;
(ii) —CN;
(iii) —PO$_3$H;
(iv) —CO$_2$H;
(v) —CO$_2$C$_1$-C$_4$alkyl, which said C$_1$-C$_4$alkyl is optionally substituted by 1, 2, 3, 4, 5, or 6 E;
(vi) —CO—R$^{11}$;
(vii) —NH—R$^{11}$;
(viii) —N(C$_1$-C$_4$alkyl)-R$^{11}$, which said C$_1$-C$_4$alkyl is optionally substituted by 1, 2, 3, 4, 5, or 6 E;
(ix) —CONH—R$^{11}$;
(x) —CON(C$_1$-C$_4$alkyl)-R$^{11}$, which said C$_1$-C$_4$alkyl is optionally substituted by 1, 2, 3, 4, 5, or 6 E;
(xi) —CONHNH—R$^{11}$;
(xii) —CONHN(C$_1$-C$_4$alkyl)-R$^{11}$, which said C$_1$-C$_4$alkyl is optionally substituted by 1, 2, 3, 4, 5, or 6 E;
(xiii) —CON(C$_1$-C$_4$alkyl)NH—R$^{11}$, which said C$_1$-C$_4$alkyl is optionally substituted by 1, 2, 3, 4, 5, or 6 E;
(xiv) —CON(C$_1$-C$_4$alkyl)N(C$_1$-C$_4$alkyl)-R$^{11}$, wherein each said C$_1$-C$_4$alkyl is independently optionally substituted by 1, 2, 3, 4, 5, or 6 E;
(xv) —CON(R$^{11}$)NH$_2$;
(xvi) —CON(R$^{11}$)NH(C$_1$-C$_4$alkyl), which said C$_1$-C$_4$alkyl is optionally substituted by 1, 2, 3, 4, 5, or 6 E;
(xvii) —CON(R$^{11}$)N(C$_1$-C$_4$alkyl)$_2$, wherein each said C$_1$-C$_4$alkyl is independently optionally substituted by 1, 2, 3, 4, 5, or 6 E;
(xviii) —CONHN=C(C$_1$-C$_4$alkyl)-C$_6$H4-OC$_1$-C$_4$alkyl, wherein each said C$_1$-C$_4$alkyl is independently optionally substituted by 1, 2, 3, 4, 5, or 6 E;
(xix) —CON(C$_1$-C$_4$alkyl)N=C(C$_1$-C$_4$alkyl)-C$_6$H4-OC$_1$-C$_4$alkyl, wherein each said C$_1$-C$_4$alkyl is independently optionally substituted by 1, 2, 3, 4, 5, or 6 E;
(xx) —N(R$^{11}$)CO(C$_1$-C$_4$alkyl), which said C$_1$-C$_4$alkyl is optionally substituted by 1, 2, 3, 4, 5, or 6 E;
(xxi) —CH(CO$_2$H)NH—R$^{11}$;
(xxii) —CH(CO$_2$C$_1$-C$_4$alkyl)NH—R$^{11}$, which said C$_1$-C$_4$alkyl is optionally substituted by 1, 2, 3, 4, 5, or 6 E;
(xxiii) —CH(NH$_2$)CO—R$^{11}$;
(xxiv) —CH(NH(C$_1$-C$_4$alkyl))CO—R$^{11}$, which said C$_1$-C$_4$alkyl is optionally substituted by 1, 2, 3, 4, 5, or 6 E;
(xxv) —CH(N(C$_1$-C$_4$alkyl)$_2$)CO—R$^{11}$, wherein each said C$_1$-C$_4$alkyl is independently optionally substituted by 1, 2, 3, 4, 5, or 6 E;
(xxvi) —CH(CO—R$^{11}$)NH—R$^{11}$; and
(xxvii) —CH(CO—R$^{11}$)N(C$_1$-C$_4$alkyl)-R$^{11}$, which said C$_1$-C$_4$alkyl is optionally substituted by 1, 2, 3, 4, 5, or 6 E;
R$^{11}$ is selected from the group consisting of —R$^{11a}$-R$^{11b}$-R$^{11c}$ and —R$^{11d}$-R$^{11e}$-R$^{11f}$, wherein
R$^{11a}$ is either absent, or is selected from the group consisting of,

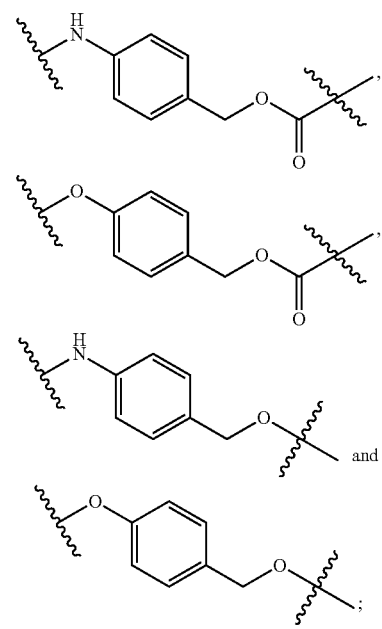

R$^{11b}$ is either absent, or is selected from the group consisting of

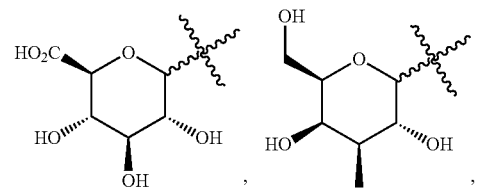

and AA$_r$, wherein AA is independently for each occurrence a natural amino acid or a non-natural amino acid;
R$^{11c}$ is either absent or is selected from the group consisting of —H, —C$_1$-C$_4$alkyl and —COC$_1$-C$_4$alkyl;
R$^{11d}$ is either absent or —(CH$_2$)$_t$—, which R$^{11d}$ when present is optionally substituted by 1, 2, 3, 4, 5, 6, 7, or 8 G;

$R^{11e}$ is either absent or selected from the group consisting of —O— and —NH—;

$R^{11f}$ is selected from the group consisting of $C_6$-$C_{12}$ aryl and 5 to 10 membered heteroaryl, which said 5 to 10 membered heteroaryl comprises one, two or three heteroatoms independently selected from the group consisting of N, O and S, and which $R^{11f}$ is optionally substituted by 1, 2, 3, 4, 5, 6, 7, or 8 G;

n is 1, 2, 3, 4, 5, or 6;

r is 1, 2, 3, 4, 5, 6, 7, 8, 9, 10, 11, 12, 13, 14, 15, 16, 17, 18, 19, or 20;

t is 1, 2, 3, 4, 5, or 6;

G is selected, independently for each occurrence, from the group consisting of —F, —Cl, —CN, —OH, —$NH_2$, —NH—$C_1$-$C_4$alkyl, —N($C_1$-$C_4$alkyl)$_2$, —$NO_2$, —$CO_2H$, —$C_1$-$C_4$alkyl, —$C_1$-$C_4$alkylOH, —$C_1$-$C_4$alkyl$NH_2$, —$C_1$-$C_4$haloalkyl, —$C_1$-$C_4$alkoxy, =O, —$CO_2C_1$-$C_4$alkyl, —OC(O)$C_1$-$C_4$alkyl, —NHC(O)$C_1$-$C_4$alkyl, —C(O)NH$C_1$-$C_4$alkyl, and —C(O)N($C_1$-$C_4$alkyl)$_2$; and E is selected, independently for each occurrence, from the group consisting of —F, —Cl, —CN, —OH, —$NH_2$, —$NHCH_3$, —N($CH_3$)$_2$, —$NO_2$, —$CO_2H$, —$OCH_3$, —$OCF_3$, and —$CF_3$.

In one embodiment, the compound of formula (I) is not (2S)-2-Amino-5-{[(2R)-1-[(carboxymethyl)amino]-3-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy)-3-iodo 5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy)-4-hydroxy-6-methyltetrahydro-2H-pyra n-2-yl]oxy)-1-hydroxy-10-[(methoxycarbonyl)amino]-11-oxobicyclo[7.3.1]trideca-4,9-diene-2,6-diyn-13-ylidene}ethyl]disulfanyl}-1-oxopropan-2-yl]amino)-5-oxopentanoic acid In some embodiments of Formula (I), $R^1$ is I, $R^2$ is H, $R^3$ is $CH_2CH_3$, and $R^4$ is H.

In some embodiments of Formula (I), $R^1$ is Br, $R^2$ is

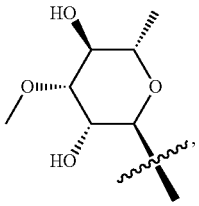

$R^3$ is $CH(CH_3)_2$, and $R^4$ is H.

In some embodiments of Formula (I), $R^1$ is I, $R^2$ is

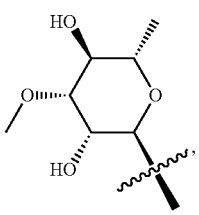

$R^3$ is $CH(CH_3)_2$, and $R^4$ is H.

In some embodiments of Formula (I), $R^1$ is Br, $R^2$ is

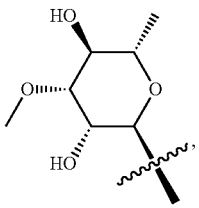

$R^3$ is $CH_2CH_3$, and $R^4$ is H.

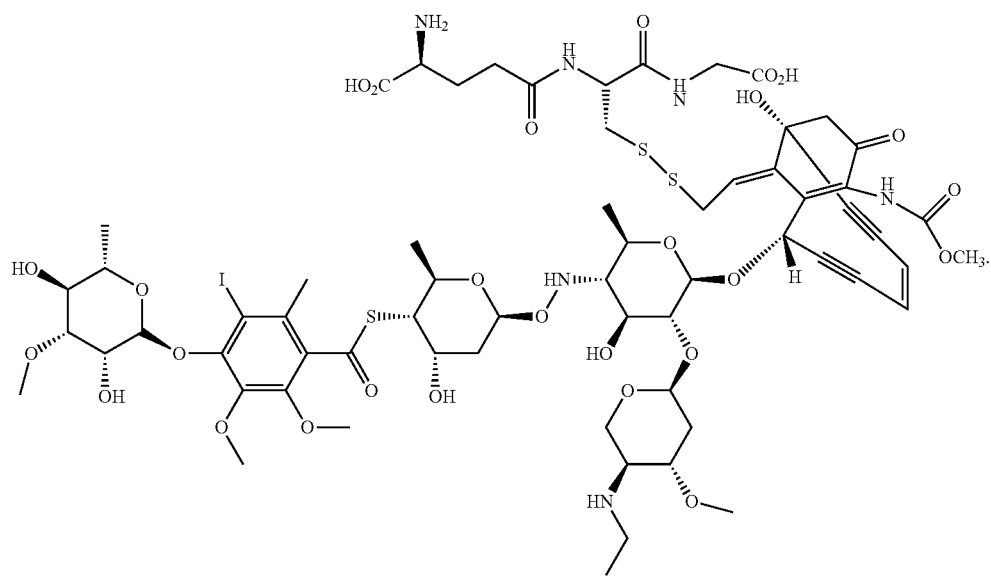

In some embodiments of Formula (I), $R^1$ is I, $R^2$ is


$R^3$ is $CH_2CH_3$, and $R^4$ is H.

In some embodiments of Formula (I), $R^1$ is I, $R^2$ is

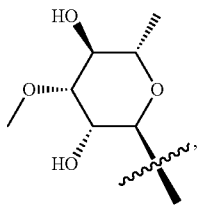

$R^3$ is $CH_3$, and $R^4$ is H.

In some embodiments of Formula (I), $R^3$ is —$CH_2CH_3$.

In some embodiments of Formula (I), X is —$CH_3$, which $CH_3$ is optionally substituted by one $R^{10}$, and which $CH_3$ is optionally substituted by 1, 2, or 3 G. In some embodiments, any optional substituents on X when X is —$CH_3$ are chosen such that there are at least two carbon atoms between the disulphide bond of Formula (I) and any heteroatom present.

In some embodiments of Formula (I), X is —$CH_3$ optionally substituted by one $R^{10}$.

In some embodiments of Formula (I), X is —$CH_3$.

In some embodiments of Formula (I), X is —$C_2$-$C_8$alkyl optionally substituted by one $R^{10}$ which —$C_2$-$C_8$alkyl is optionally substituted by 1, 2, 3, 4, 5, 6, 7, or 8 G.

In some embodiments of Formula (I), X is —$C_2$-$C_8$alkyl, for example —$CH(CH_3)_2$ or —$C(CH_3)_3$.

In some embodiments of Formula (I), X is —$CH(CH_3)_2$.

In some embodiments of Formula (I), X is —$C(CH_3)_3$.

In some embodiments of Formula (I), X is —$C_2$-$C_8$alkyl optionally substituted by one $R^{10}$ which $R^{10}$ is —$R^{10a}$-$R^{10b}$, where $R^{10a}$ is absent and $R^{10b}$ is —OH, to form for example —$CH(CH_3)$—$CH_2OH$.

In some embodiments of Formula (I), X is —$CH(CH_3)$—$CH_2OH$.

In some embodiments of Formula (I), X is —$C_2$-$C_8$alkyl optionally substituted by one $R^{10}$ which $R^{10}$ is —$R^{10a}$-$R^{10b}$, where $R^{10a}$ is absent and $R^{10b}$ is CN, to form, for example —$C(CH_3)_2$—CN.

In some embodiments of Formula (I), X is —$C(CH_3)_2$—CN.

In some embodiments of Formula (I), X is —$C_2$-$C_8$alkyl optionally substituted by one $R^{10}$ which $R^{10}$ is —$R^{10a}$-$R^{10b}$, where $R^{10a}$ is absent and $R^{10b}$ is —$PO_3H$, to form, for example —$CH(CH_3)$—$PO_3H$ or —$CH(CH_2CH_3)$—$PO_3H$.

In some embodiments of Formula (I), X is —$CH(CH_3)$—$PO_3H$.

In some embodiments of Formula (I), X is —$CH(CH_2CH_3)$—$PO_3H$.

In some embodiments of Formula (I), X is —$C_2$-$C_8$alkyl optionally substituted by one $R^{10}$ which $R^{10}$ is —$R^{10a}$-$R^{10b}$, where $R^{10a}$ is absent and $R^{10b}$ is —$CO_2H$, to form, for example —$CH(CH_3)$—$CO_2H$ or —$C(CH_3)_2$—$CO_2H$.

In some embodiments of Formula (I), X is —$CH(CH_3)$—$CO_2H$.

In some embodiments of Formula (I), X is —$C(CH_3)_2$—$CO_2H$.

In some embodiments of Formula (I), X is —$C_2$-$C_8$alkyl optionally substituted by one $R^{10}$ where $R^{10}$ is —$R^{10a}$-$R^{10b}$, which $R^{10a}$ is absent, and $R^{10b}$ is —$CO_2H$, to form, for example —$C(CH_3)_2$—$(CH_2)$—$CO_2H$ or —$C(CH_3)_2$—$(CH_2)_2$—$CO_2H$.

In some embodiments of Formula (I), X is —$C(CH_3)_2$—$(CH_2)$—$CO_2H$.

In some embodiments of Formula (I), X is —$C(CH_3)_2$—$(CH_2)_2$—$CO_2H$.

In some embodiments of Formula (I), X is —$C_2$-$C_8$alkyl optionally substituted by one $R^{10}$ which $R^{10}$ is —$R^{10a}$-$R^{10b}$, where $R^{10a}$ is absent and $R^{10b}$ is —$CO_2H$, and which —$(C_2$-$C_8$alkyl)-$R^{10}$ is optionally substituted by 1 G, for example —$CO_2H$, to form, for example, —$CH(CO_2H)$—$CH_2CO_2H$.

In some embodiments of Formula (I), X is —$CH(CO_2H)$—$CH_2CO_2H$.

In some embodiments of Formula (I), X is —$C_2$-$C_8$alkyl optionally substituted by one $R^{10}$ which $R^{10}$ is —$R^{10a}$-$R^{10b}$, where $R^{10a}$ is absent and $R^{10b}$ is —$CO_2C_1$-$C_4$alkyl, to form, for example —$CH(CH_3)$—$CO_2CH_2CH_3$.

In some embodiments of Formula (I), X is —$CH(CH_3)$—$CO_2CH_2CH_3$.

In some embodiments of Formula (I), X is —$C_2$-$C_8$alkyl optionally substituted by one $R^{10}$ which $R^{10}$ is —$R^{10a}$-$R^{10b}$, where $R^{10a}$ is absent, and $R^{10b}$ is —CO—$R^{11}$, where $R^{11}$ is —$R^{11a}$-$R^{11b}$-$R^{11c}$ where $R^{11a}$ is absent, $R^{11b}$ is $AA_r$ where r is 1 and AA is lysine, and $R^{11c}$ is absent, to form, for example —$C(CH_3)_2$—$(CH_2)_2$—CO—NH—$(CH_2)_4$—$CH(NH_2)$—$CO_2H$.

In some embodiments of Formula (I), X is —$C(CH_3)_2$—$(CH_2)_2$—CO—NH—$(CH_2)_4$—$CH(NH_2)$—$CO_2H$.

In some embodiments of Formula (I), X is —$C_2$-$C_8$alkyl optionally substituted by one $R^{10}$ which $R^{10}$ is —$R^{10a}$-$R^{10b}$, where $R^{10a}$ is absent, and $R^{10b}$ is —NH—$R^{11}$, where $R^{11}$ is —$R^{11a}$-$R^{11b}$-$R^{11c}$, where $R^{11a}$ is, for example, absent, $R^{11b}$ is, for example, absent and $R^{11c}$ is, for example, —H to form, for example —$C(CH_3)_2$—$(CH_2)_2NH_2$.

In some embodiments of Formula (I), X is —$C(CH_3)_2$—$CH_2CH_2NH_2$.

In some embodiments of Formula (I), X is —$C_2$-$C_8$alkyl optionally substituted by one $R^{10}$, which $R^{10}$ is —$R^{10a}$-$R^{10b}$, where $R^{10a}$ is absent, and $R^{10b}$ is —NH—$R^{11}$, where $R^{11}$ is —$R^{11a}$-$R^{11b}$-$R^{11c}$, where $R^{11a}$ is, for example, absent, $R^{11b}$ is, for example, absent and $R^{11c}$ is, for example, —H, and which —$(C_2$-$C_8$alkyl)-$R^{10}$ is optionally substituted by 1 G, for example —$CO_2H$, to form, for example —$C(CH_3)_2$—$CH(CO_2H)$—$NH_2$.

In some embodiments of Formula (I), X is —$C(CH_3)_2$—$CH(CO_2H)$—$NH_2$.

In some embodiments of Formula (I), X is —$C_2$-$C_8$alkyl optionally substituted by one $R^{10}$, which $R^{10}$ is —$R^{10a}$-$R^{10b}$, where $R^{10a}$ is absent, and $R^{10b}$ is —N($C_1$-$C_4$alkyl)-$R^{11}$, which said $C_1$-$C_4$alkyl is optionally substituted by 1, 2, 3, 4, 5, or 6 E, where $R^{11}$ is —$R^{11a}$-$R^{11b}$-$R^{11c}$, where $R^{11a}$ is, for example, absent, $R^{11b}$ is, for example, absent and $R^{11c}$ is, for example, —H to form, for example —$C(CH_3)_2$—$(CH_2)NH$($C_1$-$C_4$alkyl), where E is for example —$CO_2H$.

In some embodiments of Formula (I), X is —$C(CH_3)_2$—$CH_2NH$—$CH_2CH_2CO_2H$.

In some embodiments of Formula (I), X is —C$_2$-C$_8$alkyl optionally substituted by one R$^{10}$, which R$^{10}$ is —R$^{10a}$-R$^{10b}$, where R$^{10a}$ is absent, and R$^{10b}$ is —NH—R$^{11}$, where R$^{11}$ is —R$^{11a}$-R$^{11b}$-R$^{11c}$ where R$^{11a}$ is

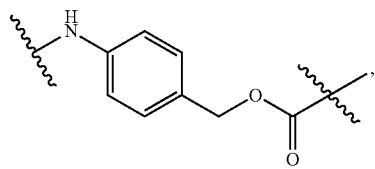 [SMILES: *Nc1ccc(COC(*)=O)cc1]

R$^{11b}$ is AA$_r$ where r is, for example 2, and R$^{11c}$ is —COC$_1$-C$_4$alkyl, for example —COCH$_3$, to form, for example

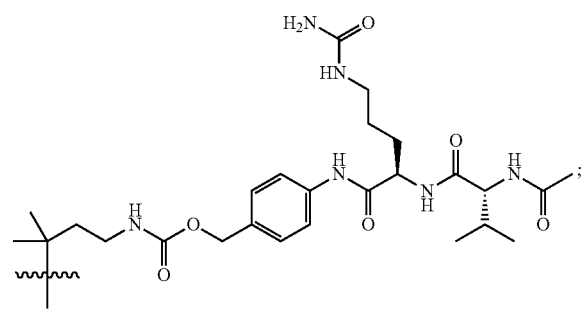 [SMILES: *C(C)(C)CCNC(=O)OCc1ccc(NC(=O)[C@@H](CCCNC(N)=O)NC(=O)[C@H](NC(C)=O)C(C)C)cc1]

or where R$^{11}$ is —R$^{11a}$-R$^{11b}$-R$^{11c}$, where R$^{11a}$ is absent, R$^{11b}$ is AA$_r$ where r is, for example 2, and R$^{11c}$ is —COC$_1$-C$_4$alkyl, for example —COCH$_3$, to form, for example

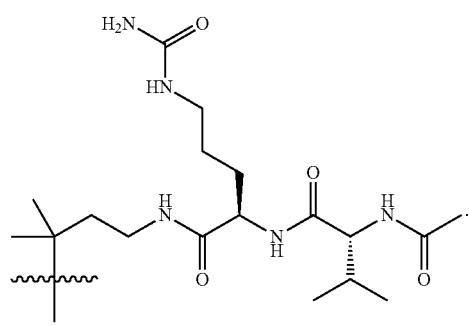 [SMILES: *C(C)(C)CCNC(=O)[C@@H](CCCNC(N)=O)NC(=O)[C@H](NC(C)=O)C(C)C]

In some embodiments of Formula (I), X is

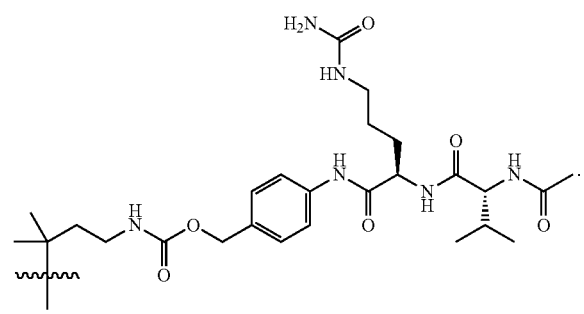 [SMILES: *C(C)(C)CCNC(=O)OCc1ccc(NC(=O)[C@@H](CCCNC(N)=O)NC(=O)[C@H](NC(C)=O)C(C)C)cc1]

In some embodiments of Formula (I), X is

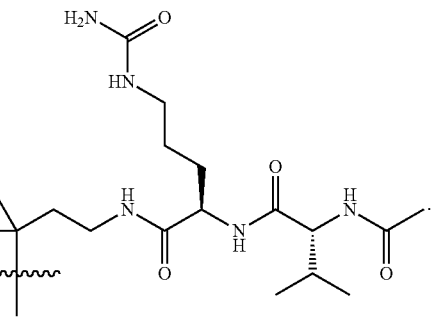

In some embodiments of Formula (I), X is —C$_2$-C$_8$alkyl optionally substituted by one R$^{10}$, which R$^{10}$ is —R$^{10a}$-R$^{10b}$, where R$^{10a}$ is absent, and R$^{10b}$ is —NH—R$^{11}$, where R$^{11}$ is —R$^{11a}$-R$^{11b}$-R$^{11c}$ where R$^{11a}$ is absent, R$^{11b}$ is AA$_r$ where r is, for example 1, and R$^{11c}$ is absent, to form, for example —C(CH$_3$)$_2$—(CH$_2$)$_2$NH—CO—(CH$_2$)$_2$—CH(NH$_2$)—CO$_2$H.

In some embodiments of Formula (I), X is —C(CH$_3$)$_2$—(CH$_2$)$_2$NH—CO—(CH$_2$)$_2$—CH(NH$_2$)—CO$_2$H.

In some embodiments of Formula (I), X is —C$_2$-C$_8$alkyl optionally substituted by one R$^{10}$, R$^{10}$ is —R$^{10a}$-R$^{10b}$, R$^{10a}$ is absent, and R$^{10b}$ is —NH—R$^{11}$, where R$^{11}$ is —R$^{11a}$-R$^{11b}$-R$^{11c}$, where R$^{11a}$ is

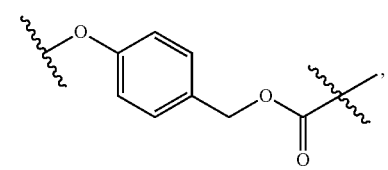 [SMILES: *Oc1ccc(COC(*)=O)cc1]

R$^{11b}$ is

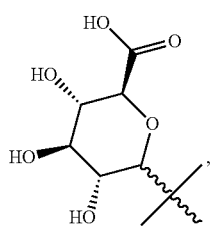

and R$^{11c}$ is absent, to form, for example

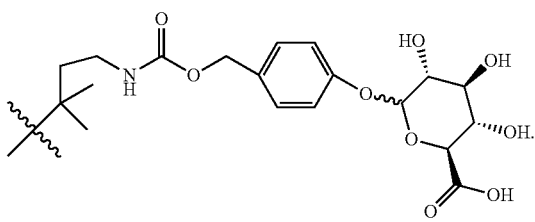 [SMILES: *C(C)(C)CCNC(=O)OCc1ccc(OC2O[C@H](C(=O)O)[C@@H](O)[C@H](O)[C@H]2O)cc1]

In some embodiments of Formula (I), X is

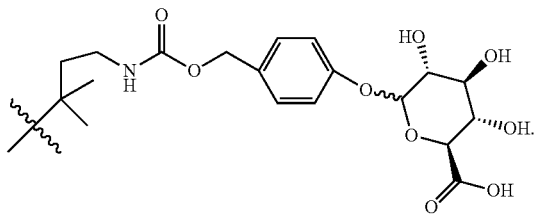 [SMILES: *C(C)(C)CCNC(=O)OCc1ccc(OC2O[C@H](C(=O)O)[C@@H](O)[C@H](O)[C@H]2O)cc1]

In some embodiments of Formula (I), X is —C$_2$-C$_8$alkyl optionally substituted by one R$^{10}$, which R$^{10}$ is —R$^{10a}$-R$^{10b}$, which R$^{10a}$ is absent, and R$^{10b}$ is —NH—R$^{11}$, where R$^{11}$ is —R$^{11d}$-R$^{11e}$-R$^{11f}$, where R$^{11d}$ is —(CH$_2$)$_t$— where t is for example 2 to form, for example —(CH$_2$)$_2$—, R$^{11}$ is —O—, and R$^{11f}$ is -phenyl to form, for example —C(CH$_3$)$_2$—(CH$_2$)—NH—(CH$_2$)$_2$—OPh.

In some embodiments of Formula (I), X is —C(CH$_3$)$_2$—(CH$_2$)—NH—(CH$_2$)$_2$—OPh.

In some embodiments of Formula (I), X is —C$_2$-C$_8$alkyl optionally substituted by one R$^{10}$, which R$^{10}$ is —R$^{10a}$-R$^{10b}$, where R$^{10a}$ is absent, and R$^{10b}$ is —CONH—R$^{11}$, R$^{11}$ is —R$^{11a}$-R$^{11b}$-R$^{11c}$, where R$^{11a}$ is, for example, absent, R$^{11b}$ is, for example, absent and R$^{11c}$ is, for example, —H to form, for example —C(CH$_3$)$_2$—CH$_2$CONH$_2$.

In some embodiments of Formula (I), X is —C(CH$_3$)$_2$—CH$_2$CONH$_2$.

In some embodiments of Formula (I), X is —C$_2$-C$_8$alkyl optionally substituted by one R$^{10}$, which R$^{10}$ is —R$^{10a}$-R$^{10b}$, where R$^{10a}$ is absent, and R$^{10b}$ is —CON(C$_1$-C$_4$alkyl)-R$^{11}$, where R$^{11}$ is —R$^{11a}$-R$^{11b}$-R$^{11c}$ where R$^{11a}$ is, for example, absent, R$^{10b}$ is, for example, absent and R$^{11c}$ is, for example, —C$_1$-C$_4$alkyl, for example CH$_3$, to form, for example —C(CH$_3$)$_2$—CH$_2$CON(CH$_3$)$_2$. In some embodiments of Formula (I), X is —C(CH$_3$)$_2$—CH$_2$CON(CH$_3$)$_2$.

In some embodiments of Formula (I), X is —C$_2$-C$_8$alkyl optionally substituted by one R$^{10}$, which R$^{10}$ is —R$^{10a}$-R$^{10b}$, where R$^{10a}$ is absent, and R$^{10b}$ is —CONHNH—R$^{11}$, R$^{11}$ is —R$^{11a}$-R$^{11b}$-R$^{11c}$ where R$^{11a}$ is, for example, absent, R$^{11b}$ is, for example, absent and R$^{11c}$ is, for example, —H to form, for example —C(CH$_3$)$_2$—CH$_2$CONHNH$_2$.

In some embodiments of Formula (I), X is —C(CH$_3$)$_2$—CH$_2$CONHNH$_2$.

In some embodiments of Formula (I), X is —C$_2$-C$_8$alkyl optionally substituted by one R$^{10}$, which R$^{10}$ is —R$^{10a}$-R$^{10b}$, where R$^{10a}$ is absent, and R$^{10b}$ is —N(R$^{11}$)CO(C$_1$-C$_4$alkyl), R$^{11}$ is —R$^{11a}$-R$^{11b}$-R$^{11c}$, where R$^{11a}$ is, for example, absent, R$^{11b}$ is, for example, absent and R$^{11c}$ is, for example, —H to form, for example —C(CH$_3$)$_2$—(CH$_2$)$_2$—NHCOCH$_3$.

In some embodiments of Formula (I), X is —C(CH$_3$)$_2$—(CH$_2$)$_2$—NHCOCH$_3$.

In some embodiments of Formula (I), X is —C$_2$-C$_8$alkyl optionally substituted by one R$^{10}$ which R$^{10}$ is —R$^{10a}$-R$^{10b}$, where R$^{10a}$ is absent, and R$^{10b}$ is —CH(NH$_2$)CO—R$^{11}$, R$^{11}$ is —R$^{11a}$-R$^{11b}$-R$^{11c}$, where R$^{11a}$ is, for example, absent, R$^{11b}$ is, for example, absent and R$^{11c}$ is, for example, —C$_1$-C$_4$alkyl, for example —CH$_3$, to form, for example —C(CH$_3$)$_2$—CH(NH$_2$)COCH$_3$.

In some embodiments of Formula (I), X is —C(CH$_3$)$_2$—CH(NH$_2$)COCH$_3$.

In some embodiments of Formula (I), X is —C$_2$-C$_8$alkyl optionally substituted by one R$^{10}$, which R$^{10}$ is —R$^{10a}$-R$^{10b}$, where R$^{10a}$ is absent, and R$^{10b}$ is —CH(CO$_2$H)NH—R$^{11}$, where for example R$^{11}$ is —R$^{11a}$-R$^{11b}$-R$^{11c}$, where R$^{11a}$ is

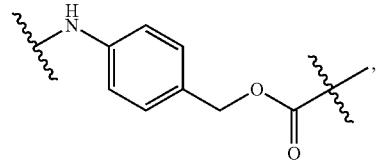 [SMILES: *Nc1ccc(COC(*)=O)cc1]

R$^{11b}$ is AA$_r$, where r is, for example, 2, and R$^{11c}$ is —COC$_1$-C$_4$alkyl, for example —COCH$_3$, to form, for example

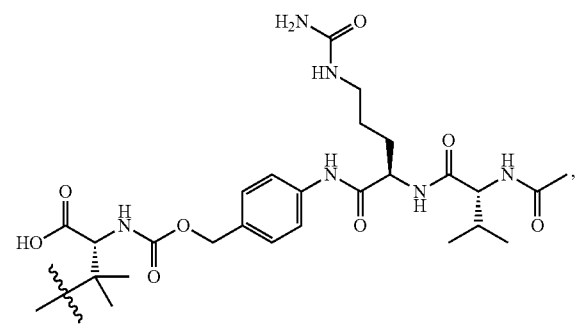 [SMILES: *C(C)(C)[C@@H](NC(=O)OCc1ccc(NC(=O)[C@@H](CCCNC(N)=O)NC(=O)[C@H](NC(C)=O)C(C)C)cc1)C(=O)O]

or where R$^{11}$ is —R$^{11a}$-R$^{11b}$-R$^{11c}$, where R$^{11a}$ is, for example, absent, R$^{11b}$ is AA$_r$, where r is, for example 2, and R$^{11c}$ is —COC$_1$-C$_4$alkyl, for example —COCH$_3$, to form, for example

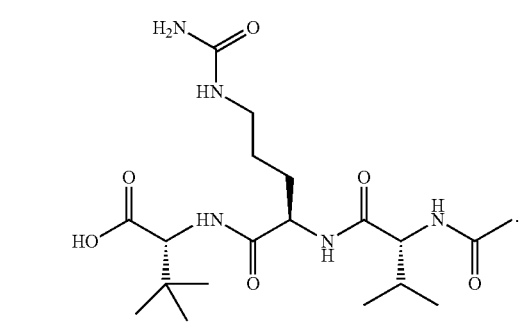 [SMILES: CC(=O)N[C@@H](C(=O)N[C@H](CCCNC(N)=O)C(=O)N[C@@H](C(=O)O)C(C)(C)C)C(C)C]

In some embodiments of Formula (I), X is

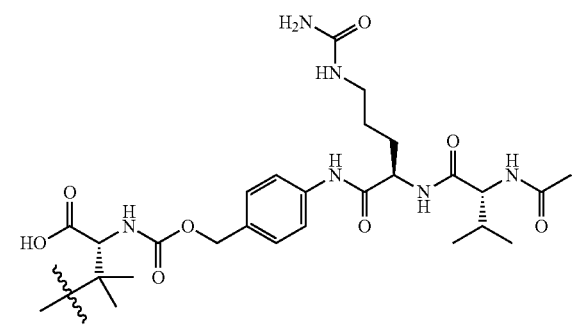 [SMILES: *C(C)(C)[C@@H](NC(=O)OCc1ccc(NC(=O)[C@@H](CCCNC(N)=O)NC(=O)[C@H](NC(C)=O)C(C)C)cc1)C(=O)O]

In some embodiments of Formula (I), X is

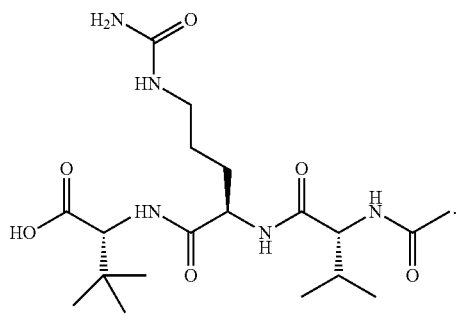 [SMILES: CC(=O)N[C@@H](C(=O)N[C@H](CCCNC(N)=O)C(=O)N[C@@H](C(=O)O)C(C)(C)C)C(C)C]

In some embodiments of Formula (I), X is —$C_2$-$C_8$alkyl optionally substituted by one $R^{10}$, which $R^{10}$ is —$R^{10a}$-$R^{10b}$, where $R^{10a}$ is absent, and $R^{10b}$ is —CONHN=C($C_1$-$C_4$alkyl)-$C_6H_4$—O$C_1$-$C_4$alkyl, for example —CONHN=C(CH$_3$)—$C_6H_4$—OCH$_3$, to form, for example —C(CH$_3$)$_2$—CH$_2$CON H N=C(CH$_3$)—$C_6H_4$—OCH$_3$.

In some embodiments of Formula (I), X is —C(CH$_3$)$_2$—CH$_2$CONHN=C(CH$_3$)—$C_6H_4$—OCH$_3$.

In some embodiments of Formula (I), X is —($C_0$-$C_6$alkyl)-$C_3$-$C_{10}$ carbocyclyl optionally substituted by one $R^{10}$, and which —($C_0$-$C_6$alkyl)-$C_3$-$C_{10}$ carbocyclyl is optionally substituted by 1, 2, 3, 4, 5, 6, 7, or 8 G.

In some embodiments of Formula (I), X is —$C_3$-$C_{10}$ carbocyclyl, which said —$C_3$-$C_{10}$ carbocyclyl is optionally substituted by one $R^{10}$, which —$C_3$-$C_{10}$ carbocyclyl is selected from the group consisting of cyclopropyl, cyclobutyl, cyclopentyl, cyclohexyl, adamantyl.

In some embodiments of Formula (I), X is cyclopropyl.
In some embodiments of Formula (I), X is cyclobutyl.
In some embodiments of Formula (I), X is cyclopentyl.
In some embodiments of Formula (I), X is cyclohexyl.
In some embodiments of Formula (I), X is adamantyl.

In some embodiments of Formula (I), X is —C(CH$_3$)$_2$—$C_3$-$C_{10}$ carbocyclyl, which said —$C_3$-$C_{10}$ carbocyclyl is optionally substituted by one $R^{10}$, and which X is optionally substituted by 1, 2, 3, 4, 5, 6, 7, or 8 G.

In some embodiments of Formula (I), X is —C(CH$_3$)$_2$—$C_3$-$C_{10}$ carbocyclyl, which said —$C_3$-$C_{10}$ carbocyclyl is optionally substituted by one $R^{10}$, which —$C_3$-$C_{10}$ carbocyclyl is selected from the group consisting of example cyclopropyl, cyclobutyl, cyclopentyl, cyclohexyl, adamantyl.

In some embodiments of Formula (I), X is —($C_0$-$C_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S, and which X is optionally substituted by 1, 2, 3, 4, 5, 6, 7, or 8 G. One of ordinary skill would appreciate that for embodiments of the invention which comprise —($C_0$-$C_6$alkyl)-3 to 10 membered heterocyclyl, the heterocycle may be bound through a carbon atom or, where valency allows, through a heteroatom, such as a nitrogen. Similarly one of ordinary skill would appreciate that any optional substitutents may be bound to a carbon atom or, where valency allows, to a heteroatom, such as a nitrogen, it is preferred that there are at least two carbon atoms between the disulphide bond of Formula (I) and any heteroatom in a substituent X.

In some embodiments of Formula (I), X is 3 to 10 membered heterocyclyl, which said 3 to 10 membered heterocyclyl is optionally substituted by one $R^{10}$, for example piperidinyl and the like, and which X is optionally substituted by 1, 2, 3, 4, 5, 6, 7, or 8 G.

In some embodiments of Formula (I), X is piperidinyl which said piperidinyl is optionally substituted by one $R^{10}$, and which X is optionally substituted by 1, 2, 3, 4, 5, 6, 7, or 8 G.

In some embodiments of Formula (I), X is piperidinyl, which said piperidinyl is optionally substituted by 1 G to form, for example, 4-N—CH$_3$ piperidinyl of 4-N—CO$_2$C(CH$_3$)$_3$ piperidinyl.

In some embodiments of Formula (I), X is 4-piperidinyl.
In some embodiments of Formula (I), X is 4-N—CH$_3$piperidinyl.
In some embodiments of Formula (I), X is 4-N—CO$_2$C(CH$_3$)$_3$piperidinyl.

In some embodiments of Formula (I), X is piperidinyl which said piperidinyl is optionally substituted by one $R^{10}$, which $R^{10}$ is —$R^{10a}$-$R^{10b}$, where $R^{10a}$ is, for example, absent, and $R^{10b}$ is, for example, —CO—$R^{11}$, for example where $R^{11}$ is —$R^{11a}$-$R^{11b}$-$R^{11c}$, where $R^{11a}$ is

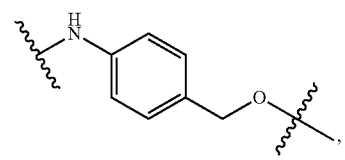 [SMILES: *Nc1ccc(CO*)cc1]

$R^{11b}$ is AA$_r$, where r is, for example 2, and $R^{11c}$ is —CO$C_1$-$C_4$alkyl, for example —COCH$_3$, to form, for example

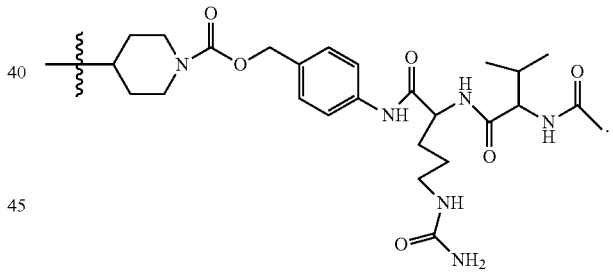

In some embodiments of Formula (I), X is

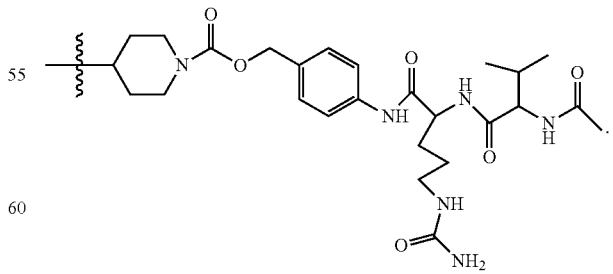

In some embodiments of Formula (I), X is piperidinyl which said piperidinyl is optionally substituted by one $R^{10}$, which $R^{10}$ is —$R^{10a}$-$R^{10b}$, where $R^{10a}$ is, for example, absent, and $R^{10b}$ is, for example, —CO—$R^{11}$, for example where $R^{11}$ is —$R^{11a}$-$R^{11b}$-$R^{11c}$, where $R^{11a}$ is

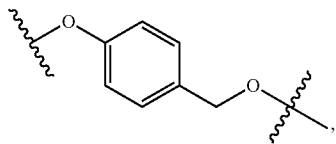 [SMILES: *OCc1ccc(O*)cc1]

$R^{11b}$ is

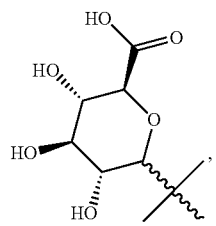

and $R^{11c}$ is absent, to form, for example

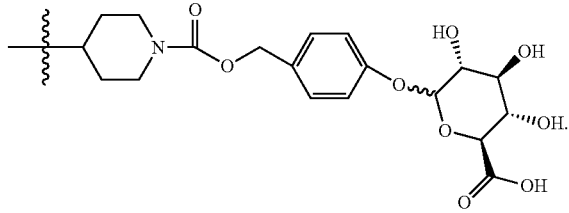 [SMILES: *C1CCN(C(=O)OCc2ccc(OC3O[C@H](C(=O)O)[C@@H](O)[C@H](O)[C@H]3O)cc2)CC1]

In some embodiments of Formula (I), X is

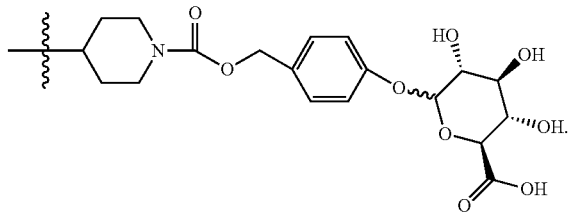 [SMILES: *C1CCN(C(=O)OCc2ccc(OC3O[C@H](C(=O)O)[C@@H](O)[C@H](O)[C@H]3O)cc2)CC1]

In some embodiments of Formula (I), X is —C(CH$_3$)$_2$-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S, and which X is optionally substituted by 1, 2, 3, 4, 5, 6, 7, or 8 G.

In some embodiments of Formula (I), X is —C(CH$_3$)$_2$-piperidinyl, which said piperidinyl is optionally substituted by one $R^{10}$, and which X is optionally substituted by 1, 2, 3, 4, 5, 6, 7, or 8 G.

In some embodiments of Formula (I), X is —C(CH$_3$)$_2$-imidazolinyl, which said imidazolinyl is optionally substituted by one $R^{10}$, and which X is optionally substituted by 1, 2, 3, 4, 5, 6, 7, or 8 G.

In some embodiments of Formula (I), X is —C(CH$_3$)$_2$-imidazolinyl, which said X is optionally substituted by 2 G, which G is for example =O to form, for example,

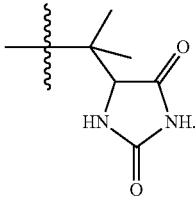

In some embodiments of Formula (I), X is

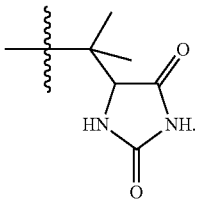 [SMILES: *C(C)(C)C1NC(=O)NC1=O]

In some embodiments of Formula (I), X is —(C$_0$-C$_6$alkyl)-phenyl, which said phenyl is optionally substituted by one $R^{10}$, and which X is optionally substituted by 1, 2, 3, 4, 5, 6, 7, or 8 G.

In some embodiments of Formula (I), X is phenyl optionally substituted by one $R^{10}$, which $R^{10}$ is —$R^{10a}$-$R^{10b}$, where $R^{10a}$ is absent, and $R^{10b}$ is for example —CO$_2$H to form, for example 2-CO$_2$H phenyl, 4-CO$_2$H phenyl, or $R^{10b}$ is for example —NHR$^{11}$, where $R^{11}$ is —$R^{11a}$-$R^{11b}$-$R^{11c}$, where $R^{11a}$ is -absent, $R^{11b}$ is absent, and $R^{11c}$ is —H, to form, for example, 2-NH$_2$-phenyl; and which X is optionally substituted by 1, 2, 3, 4, or 5 G.

In some embodiments of Formula (I), X is phenyl, which X is optionally substituted by 1 G, for example —NO$_2$ to form, for example, 4-NO$_2$-phenyl, or —C$_1$-C$_4$ haloalkyl, for example CF$_3$, to form, for example 4-CF$_3$-phenyl.

In some embodiments of Formula (I), X is phenyl.
In some embodiments of Formula (I), X is 4-NO$_2$-phenyl.
In some embodiments of Formula (I), X is 4-CF$_3$-phenyl.
In some embodiments of Formula (I), X is 2-CO$_2$H phenyl.
In some embodiments of Formula (I), X is 4-CO$_2$H phenyl.
In some embodiments of Formula (I), X is —C(CH$_3$)$_2$-phenyl, which said phenyl is optionally substituted by one $R^{10}$, and which X is optionally substituted by 1, 2, 3, 4, 5, 6, 7, or 8 G.

In some embodiments of Formula (I), X is —C(CH$_3$)$_2$-phenyl, which said phenyl is optionally substituted by one $R^{10}$, $R^{10}$ is —$R^{10a}$-$R^{10b}$, $R^{10a}$ is absent, and $R^{10b}$ is for example —CO$_2$H to form, for example —C(CH$_3$)$_2$-(2-CO$_2$H phenyl), —C(CH$_3$)$_2$-(4-CO$_2$H phenyl), or —NH$_2$ to form, for example, —C(CH$_3$)$_2$-(2-NH$_2$-phenyl) or —C(CH$_3$)$_2$-(4-NH$_2$-phenyl); and which X is optionally substituted by 1, 2, 3, 4, or 5 G.

In some embodiments of Formula (I), X is —C(CH$_3$)$_2$-phenyl, which X is optionally substituted by 1 G to form, for example, —C(CH$_3$)$_2$-(4-NO$_2$ phenyl) or —C(CH$_3$)$_2$-(4-CF$_3$-phenyl).

In some embodiments of Formula (I), X is —C(CH$_3$)$_2$-phenyl.

In some embodiments of Formula (I), X is —C(CH$_3$)$_2$-(4-NO$_2$ phenyl).

In some embodiments of Formula (I), X is —C(CH$_3$)$_2$-(4-CF$_3$-phenyl).

In some embodiments of Formula (I), X is —C(CH$_3$)$_2$-(2-CO$_2$H phenyl).

In some embodiments of Formula (I), X is —C(CH$_3$)$_2$-(4-CO$_2$H phenyl).

In some embodiments of Formula (I), X is —C(CH$_3$)$_2$-(2-NH$_2$-phenyl).

In some embodiments of Formula (I), X is —C(CH$_3$)$_2$-(4-NH$_2$-phenyl).

In some embodiments of Formula (I), X is —(C$_0$-C$_6$alkyl)-5 to 10 membered heteroaryl, which said 5 to 10 membered heteroaryl is optionally substituted by one R$^{10}$, and which said 5 to 10 membered heteroaryl comprises one, two or three heteroatoms independently selected from the group consisting of N, O and S, and which X is optionally substituted by 1, 2, 3, 4, 5, 6, 7, or 8 G. One of ordinary skill would appreciate that for embodiments of the invention which comprise —(C$_0$-C$_6$alkyl)-5 to 10 membered heteroaryl, the heteroaryl may be bound through a carbon atom, or where valency allows through a heteroatom, such as a nitrogen. Similarly one of ordinary skill would appreciate that any optional substitutents may be bound to a carbon atom, or where valency allows, to a heteroatom, such as a nitrogen. It is preferred that there are at least two carbon atoms between the disulphide bond of Formula (I) and any heteroatom in a substituent X.

In some embodiments of Formula (I), X is pyridyl, which said pyridyl is optionally substituted by one R$^{10}$, R$^{10}$ is —R$^{10a}$-R$^{10b}$, R$^{10a}$ is absent, and R$^{10b}$ is for example —CO$_2$H to form, for example 3-CO$_2$H pyridyl, or —NHR$^{11}$, where R$^{11}$ is —R$^{11a}$-R$^{11b}$-R$^{11c}$, where R$^{11a}$ is -absent, R$^{11b}$ is absent, and R$^{11c}$ is —H, to form, for example, 2-NH$_2$pyridyl; and which X is optionally substituted by 1, 2, 3, or 4 G.

In some embodiments of Formula (I), X is pyridyl, which said pyridyl is optionally substituted by one R$^{10}$, and which X is optionally substituted by 1 or 2, G, for example —C$_1$-C$_4$ alkyl, for example CH$_3$, to form, for example, 3,5-(CH$_3$)$_2$ pyridyl.

In some embodiments of Formula (I), X is 2-pyridyl.

In some embodiments of Formula (I), X is 4-pyridyl.

In some embodiments of Formula (I), X is 3-CO$_2$H pyridyl.

In some embodiments of Formula (I), X is 4-(3,5-(CH$_3$)$_2$ pyridyl).

In some embodiments of Formula (I), X is —C(CH$_3$)$_2$-5 to 10 membered heteroaryl, which said 5 to 10 membered heteroaryl is optionally substituted by one R$^{10}$, and which said 5 to 10 membered heteroaryl comprises one, two or three heteroatoms independently selected from the group consisting of N, O and S, for example pyridyl and the like, and which X is optionally substituted by 1, 2, 3, 4, 5, 6, 7, or 8 G.

In some embodiments of Formula (I), X is —C(CH$_3$)$_2$-pyridyl, which pyridyl is optionally substituted by one R$^{10}$, R$^{10}$ is —R$^{10a}$-R$^{10b}$, R$^{10a}$ is absent, and R$^{10b}$ is for example —CO$_2$H to form, for example —C(CH$_3$)$_2$-3-(2-CO$_2$H pyridyl), or —NHR$^{11}$, where R$^{11}$ is —R$^{11a}$-R$^{11b}$-R$^{11c}$, where R$^{11a}$ is -absent, R$^{11b}$ is absent, and R$^{11c}$ is —H, to form, for example, —C(CH$_3$)$_2$-3-(2-NH$_2$ pyridyl); and which X is optionally substituted by 1, 2, 3, or 4 G.

In some embodiments of Formula (I), X is —C(CH$_3$)$_2$-3-(2-NH$_2$pyridyl).

In some embodiments of Formula (I), X is —C(CH$_3$)$_2$-3-(2-CO$_2$H pyridyl).

In some embodiments of Formula (I), R$^{10a}$ is absent.

In some embodiments of Formula (I), R$^{10a}$ is-CH$_2$—.

In some embodiments of Formula (I), R$^{10a}$ is —(CH$_2$)$_2$—.

In some embodiments of Formula (I), R$^{10b}$ is selected from the group consisting of —OH; —CN; —PO$_3$H; —CO$_2$H; —CO$_2$C$_1$-C$_4$alkyl; —CO—R$^{11}$; —NH—R$^{11}$; —CONH—R$^{11}$; —CON(C$_1$-C$_4$alkyl)-R$^{11}$; —CONHNH—R$^{11}$; —N(R$^{11}$)CO(C$_1$-C$_4$alkyl); —CH(CO$_2$H)NH—R$^{11}$; —CH(NH$_2$)CO—R$^{11}$; and —CH(CO—R$^{11}$)NH—R$^{11}$; CONHN=C(C$_1$-C$_4$alkyl)-C$_6$H$_4$—OC$_1$-C$_4$alkyl.

In some embodiments of Formula (I), R$^{11}$ is —R$^{11a}$-R$^{11b}$-R$^{11c}$.

In some embodiments of Formula (I), R$^{11}$ is —R$^{11a}$-R$^{11b}$-R$^{11c}$, where R$^{11a}$ is absent, R$^{11b}$ is absent and R$^{11}$ is —H.

In some embodiments of Formula (I), R$^{11}$ is —R$^{11a}$-R$^{11b}$-R$^{11c}$, where R$^{11a}$ is absent, R$^{11b}$ is absent and R$^{11}$ is CH$_3$.

In some embodiments of Formula (I), R$^{11}$ is —R$^{11a}$-R$^{11b}$-R$^{11c}$, where R$^{11a}$ is absent, R$^{11b}$ is absent and R$^{11}$ is —COCH$_3$.

In some embodiments of Formula (I), R$^{11}$ is —R$^{11a}$-R$^{11b}$-R$^{11c}$, where R$^{11a}$ is absent, R$^{11b}$ is AA$_r$ where r is 1, and R$^{11c}$ is absent.

In some embodiments of Formula (I), R$^{11}$ is —R$^{11a}$-R$^{11b}$-R$^{11c}$, where R$^{11a}$ is absent, R$^{11}$ is —R$^{11a}$-R$^{11b}$-R$^{11c}$ where R$^{11a}$ is absent, R$^{11b}$ is AA$_r$ where r is 2, and R$^{11c}$ is —COCH$_3$.

In some embodiments of Formula (I), R$^{11a}$ is selected from the group consisting of,

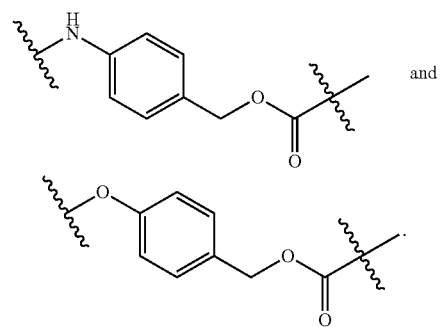

In some embodiments of Formula (I), R$^{11}$ is

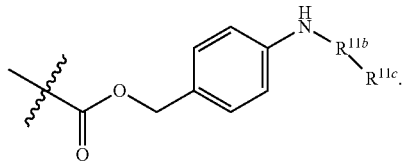

In some embodiments of Formula (I), R$^{11}$ is

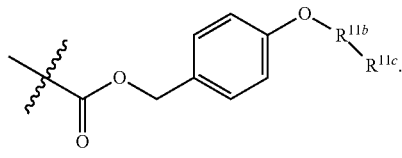

In some embodiments of Formula (I), $R^{11}$ is —$R^{11a}$-$R^{11b}$-$R^{11c}$, where $R^{11a}$ is

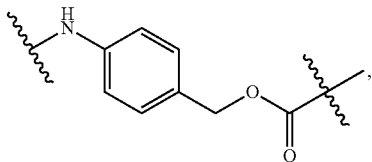 [SMILES: *Nc1ccc(COC(*)=O)cc1]

$R^{11b}$ is $AA_r$ where r is 2, and $R^{11}$ is —$COCH_3$.

In some embodiments of Formula (I), $R^{11}$ is —$R^{11d}$-$R^{11e}$-$R^{11f}$.

In some embodiments of Formula (I), $R^{11}$ is —$R^{11d}$-$R^{11e}$-$R^{11f}$, where $R^{11d}$ is —$(CH_2)_t$— where t is 2, $R^{11e}$ is absent and $R^{11f}$ is phenyl.

In some embodiments of Formula (I), $R^{11}$ is —$R^{11d}$-$R^{11e}$-$R^{11f}$, where $R^{11d}$ is —$(CH_2)_t$— where t is 2, $R^{11e}$ is —O— and $R^{11f}$ is phenyl.

In some embodiments of Formula (I), $R^{11}$ is —$R^{11d}$-$R^{11e}$-$R^{11f}$, where $R^{11d}$ is —$(CH_2)_t$— where t is 2, $R^{11e}$ is absent and $R^{11f}$ is 5 to 10 membered heteroaryl, which said 5 to 10 membered heteroaryl comprises one, two or three heteroatoms independently selected from the group consisting of N, O and S.

In some embodiments of Formula (I), n is 1.
In some embodiments of Formula (I), n is 2.
In some embodiments of Formula (I), r is 1, 2, 3, 4, 5, 6, 7, or 8.
In some embodiments of Formula (I), r is 1, 2, 3, 4, or 5.
In some embodiments of Formula (I), r is 1, 2 or 3.
In some embodiments of Formula (I), r is 2.

One aspect of the invention relates to a compound of Formula (IA)

(iv) —($C_0$-$C_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S;

(v) —($C_0$-$C_6$alkyl)-phenyl, which said phenyl is optionally substituted by one $R^{10}$; and (vi) —($C_0$-$C_6$alkyl)-5 to 10 membered heteroaryl, which said 5 to 10 membered heteroaryl is optionally substituted by one $R^{10}$, and which said 5 to 10 membered heteroaryl comprises one, two or three heteroatoms independently selected from the group consisting of N, O and S;

and which X is optionally further substituted by 1, 2, 3, 4, 5, 6, 7, or 8 G;

$R^{10}$ is —$R^{10a}$-$R^{10b}$ wherein
  $R^{10a}$ is either absent or —$(CH_2)_n$—, which $R^{10a}$ is optionally substituted by 1, 2, 3, 4, 5, 6, 7, or 8 G;
  $R^{10b}$ is selected from the group consisting of:
    (i) —OH;
    (ii) —CN;
    (iii) —$PO_3H$;
    (iv) —$CO_2H$;
    (v) —$CO_2C_1$-$C_4$alkyl, which said $C_1$-$C_4$alkyl is optionally substituted by 1, 2, 3, 4, 5, or 6 E;
    (vi) —CO—$R^{11}$;
    (vii) —NH—$R^{11}$;
    (viii) —N($C_1$-$C_4$alkyl)-$R^{11}$, which said $C_1$-$C_4$alkyl is optionally substituted by 1, 2, 3, 4, 5, or 6 E;
    (ix) —CONH—$R^{11}$;
    (x) —CON($C_1$-$C_4$alkyl)-$R^{11}$, which said $C_1$-$C_4$alkyl is optionally substituted by 1, 2, 3, 4, 5, or 6 E;
    (xi) —CONHNH—$R^{11}$;

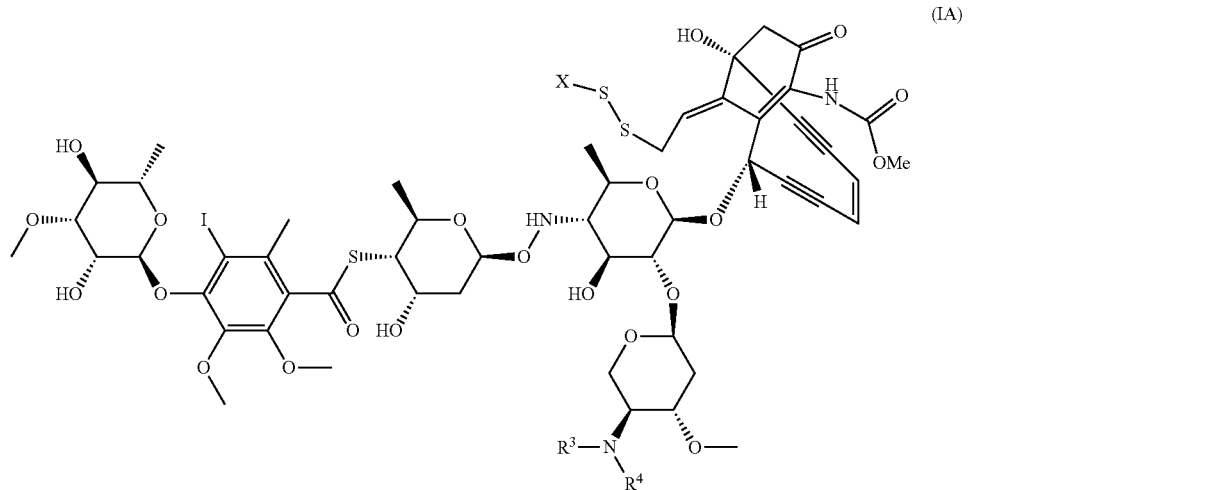

(IA)

or a pharmaceutically acceptable salt thereof, wherein:
  $R^3$ is selected from the group consisting of —$CH_3$, —$CH_2CH_3$, and —$CH(CH_3)_2$;
  $R^4$ is H; and
  X is selected from the group consisting of:
    (i) —$CH_3$ optionally substituted by one $R^{10}$;
    (ii) —$C_2$-$C_8$alkyl optionally substituted by one $R^{10}$;
    (iii) —($C_0$-$C_6$alkyl)-$C_3$-$C_{10}$ carbocyclyl, which said $C_3$-$C_{10}$ carbocyclyl is optionally substituted by one $R^{10}$;

(xii) —CONHN($C_1$-$C_4$alkyl)-$R^{11}$, which said $C_1$-$C_4$alkyl is optionally substituted by 1, 2, 3, 4, 5, or 6 E;
    (xiii) —CON($C_1$-$C_4$alkyl)NH—$R^{11}$, which said $C_1$-$C_4$alkyl is optionally substituted by 1, 2, 3, 4, 5, or 6 E;
    (xiv) —CON($C_1$-$C_4$alkyl)N($C_1$-$C_4$alkyl)-$R^{11}$, wherein each said $C_1$-$C_4$alkyl is independently optionally substituted by 1, 2, 3, 4, 5, or 6 E;
    (xv) —CON($R^{11}$)$NH_2$;

(xvi) —CON($R^{11}$)NH($C_1$-$C_4$alkyl), which said $C_1$-$C_4$alkyl is optionally substituted by 1, 2, 3, 4, 5, or 6 E;

(xvii) —CON($R^{11}$)N($C_1$-$C_4$alkyl)$_2$, wherein each said $C_1$-$C_4$alkyl is independently optionally substituted by 1, 2, 3, 4, 5, or 6 E;

(xviii) —CONHN=C($C_1$-$C_4$alkyl)-$C_6H_4$—O$C_1$-$C_4$alkyl, wherein each said $C_1$-$C_4$alkyl is independently optionally substituted by 1, 2, 3, 4, 5, or 6 E;

(xix) —CON($C_1$-$C_4$alkyl)N=C($C_1$-$C_4$alkyl)-$C_6H_4$—O$C_1$-$C_4$alkyl, wherein each said $C_1$-$C_4$alkyl is independently optionally substituted by 1, 2, 3, 4, 5, or 6 E;

(xx) —N($R^{11}$)CO($C_1$-$C_4$alkyl), which said $C_1$-$C_4$alkyl is optionally substituted by 1, 2, 3, 4, 5, or 6 E;

(xxi) —CH(CO$_2$H)NH—$R^{11}$;

(xxii) —CH(CO$_2$$C_1$-$C_4$alkyl)NH—$R^{11}$, which said $C_1$-$C_4$alkyl is optionally substituted by 1, 2, 3, 4, 5, or 6 E;

(xxiii) —CH(NH$_2$)CO—$R^{11}$;

(xxiv) —CH(NH($C_1$-$C_4$alkyl))CO—$R^{11}$, which said $C_1$-$C_4$alkyl is optionally substituted by 1, 2, 3, 4, 5, or 6 E;

(xxv) —CH(N($C_1$-$C_4$alkyl)$_2$)CO—$R^{11}$, wherein each said $C_1$-$C_4$alkyl is independently optionally substituted by 1, 2, 3, 4, 5, or 6 E;

(xxvi) —CH(CO—$R^{11}$)NH—$R^{11}$; and (xxvii) —CH(CO—$R^{11}$)N($C_1$-$C_4$alkyl)-$R^{11}$, which said $C_1$-$C_4$alkyl is optionally substituted by 1, 2, 3, 4, 5, or 6 E;

$R^{11}$ is selected from the group consisting of —$R^{11a}$-$R^{11b}$-$R^{11c}$ and —$R^{11d}$-$R^{11e}$-$R^{11f}$, wherein $R^{11a}$ is either absent, or is selected from the group consisting of,

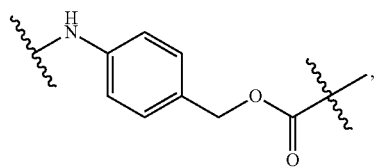

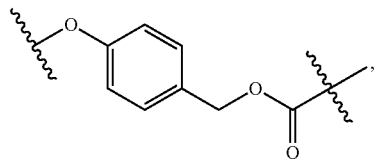

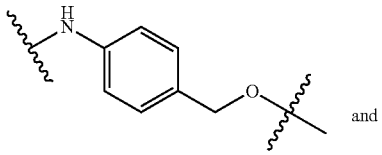

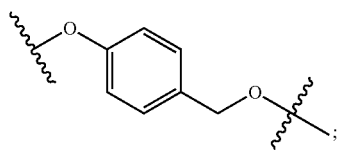

$R^{11b}$ is either absent, or is selected from the group consisting of

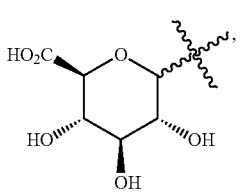

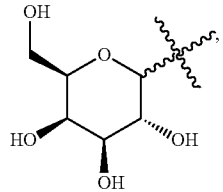

and AA$_r$, wherein AA is independently for each occurrence a natural amino acid or a non-natural amino acid;

$R^{11c}$ is either absent or is selected from the group consisting of —H, —$C_1$-$C_4$alkyl and —CO$C_1$-$C_4$alkyl;

$R^{11d}$ is either absent or —(CH$_2$)$_t$—, which $R^{11d}$ when present is optionally substituted by 1, 2, 3, 4, 5, 6, 7, or 8 G;

$R^{11e}$ is either absent or selected from the group consisting of —O— and —NH—;

$R^{11f}$ is selected from the group consisting of $C_6$-$C_{12}$ aryl and 5 to 10 membered heteroaryl, which said 5 to 10 membered heteroaryl comprises one, two or three heteroatoms independently selected from the group consisting of N, O and S, and which $R^{11f}$ is optionally substituted by 1, 2, 3, 4, 5, 6, 7, or 8 G;

n is 1, 2, 3, 4, 5, or 6;

r is 1, 2, 3, 4, 5, 6, 7, 8, 9, 10, 11, 12, 13, 14, 15, 16, 17, 18, 19, or 20;

t is 1, 2, 3, 4, 5, or 6;

G is selected, independently for each occurrence, from the group consisting of —F, —Cl, —CN, —OH, —NH$_2$, —NH—$C_1$-$C_4$alkyl, —N($C_1$-$C_4$alkyl)$_2$, —NO$_2$, —CO$_2$H, —$C_1$-$C_4$alkyl, —$C_1$-$C_4$alkylOH, —$C_1$-$C_4$alkylNH$_2$, —$C_1$-$C_4$haloalkyl, —$C_1$-$C_4$alkoxy, =O, —CO$_2$$C_1$-$C_4$alkyl, —OC(O)$C_1$-$C_4$alkyl, —NHC(O)$C_1$-$C_4$alkyl, —C(O)NH$C_1$-$C_4$alkyl, and —C(O)N($C_1$-$C_4$alkyl)$_2$; and E is selected, independently for each occurrence, from the group consisting of —F, —Cl, —CN, —OH, —NH$_2$, —NHCH$_3$, —N(CH$_3$)$_2$, —NO$_2$, —CO$_2$H, —OCH$_3$, —OCF$_3$, and —CF$_3$.

In one embodiment, the compound of formula (IA) is not (2S)-2-Amino-5-{[(2R)-1-[(carboxymethyl)amino]-3-{[(2E)-2-{(1R,8S)-8-{[(2R,3R,4S,5S,6R)-5-R{(2S,4S,5S,6R)-5-[(4-{[(2S,3R,4R,5S,6S)-3,5-dihydroxy-4-methoxy-6-methyltetrahydro-2H-pyran-2-yl]oxy)-3-iodo 5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}-1-oxopropan-2-yl]amino}-5-oxopentanoic acid

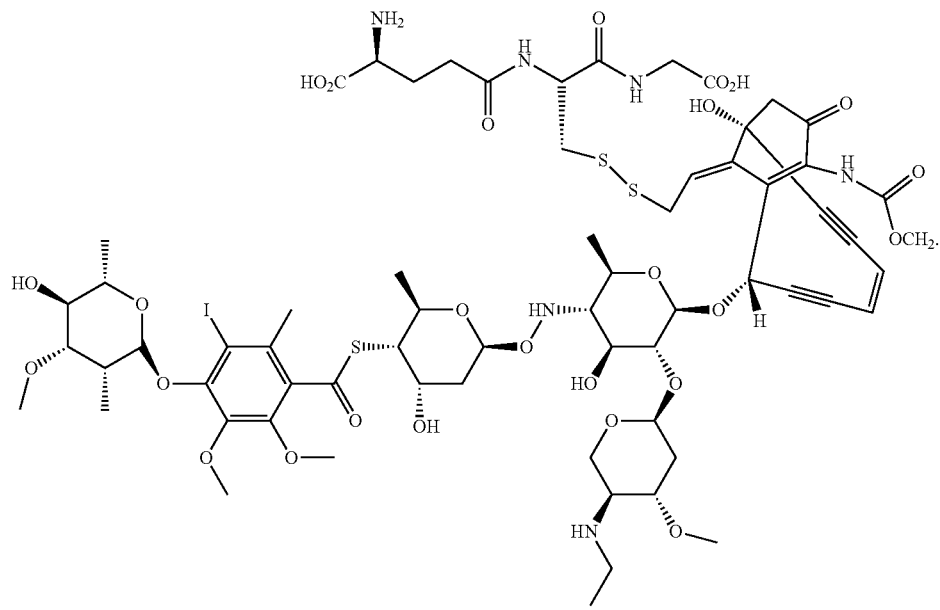

Each of the aspects and embodiments described herein with respect to Formula (I) are, either individually or, where applicable, in combination, also applicable to compounds of Formula (IA), to the extent they are not incompatible with the structure.

In certain embodiments, the present invention relates to any of the aforementioned compounds of Formula (I) or Formula (IA), or a pharmaceutically acceptable salt thereof, and attendant definitions, wherein the compound is selected from the group consisting of:

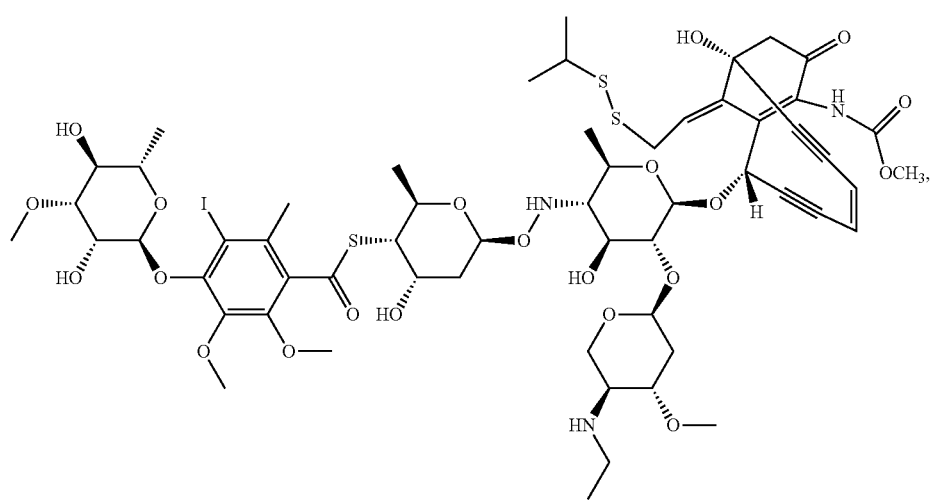

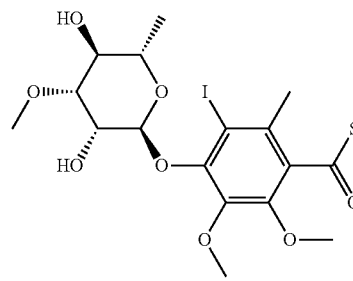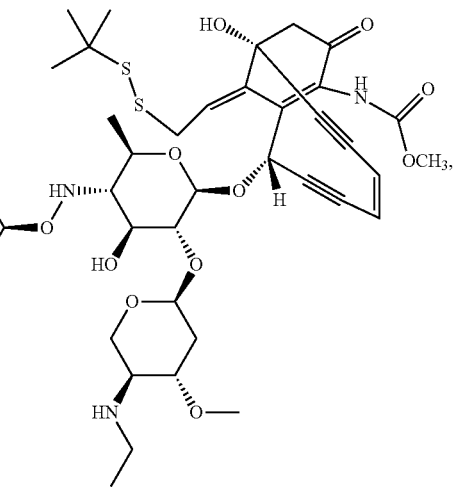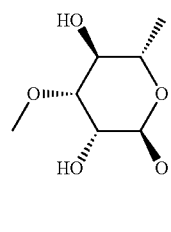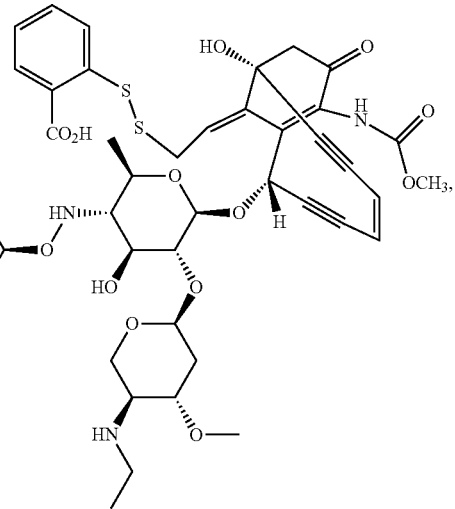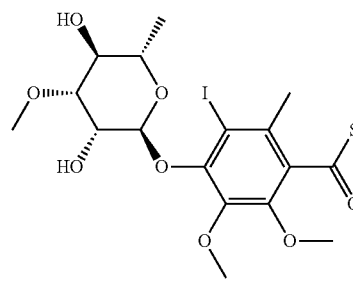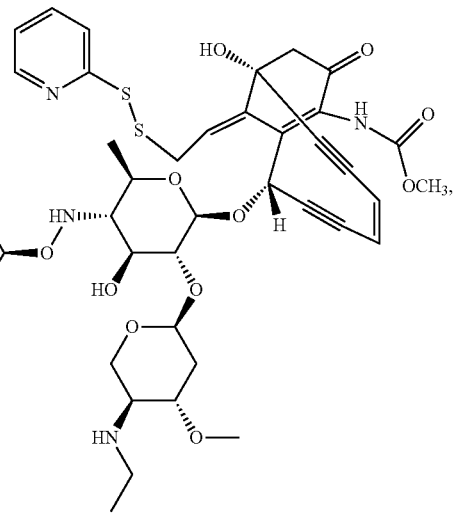

-continued
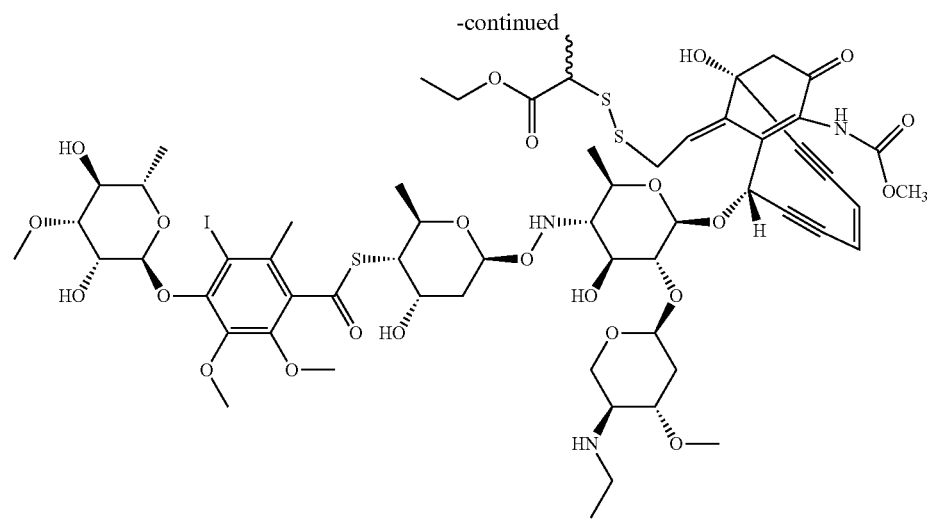
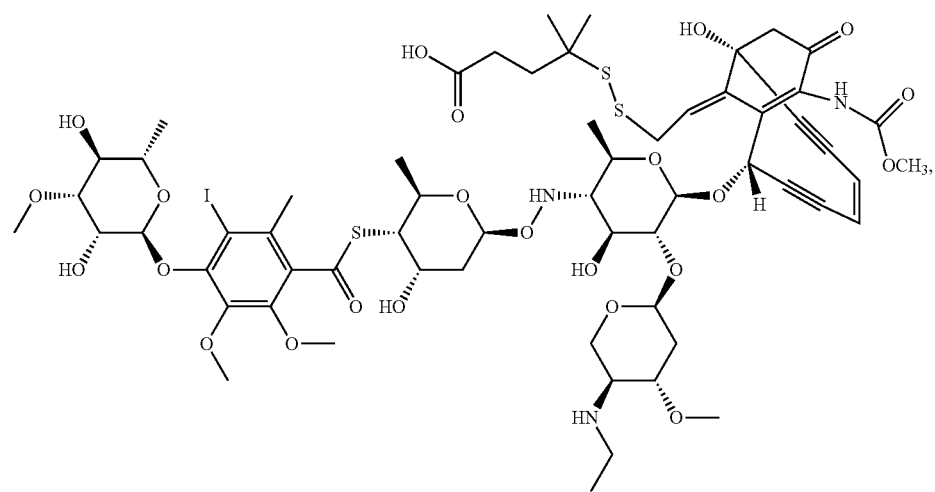
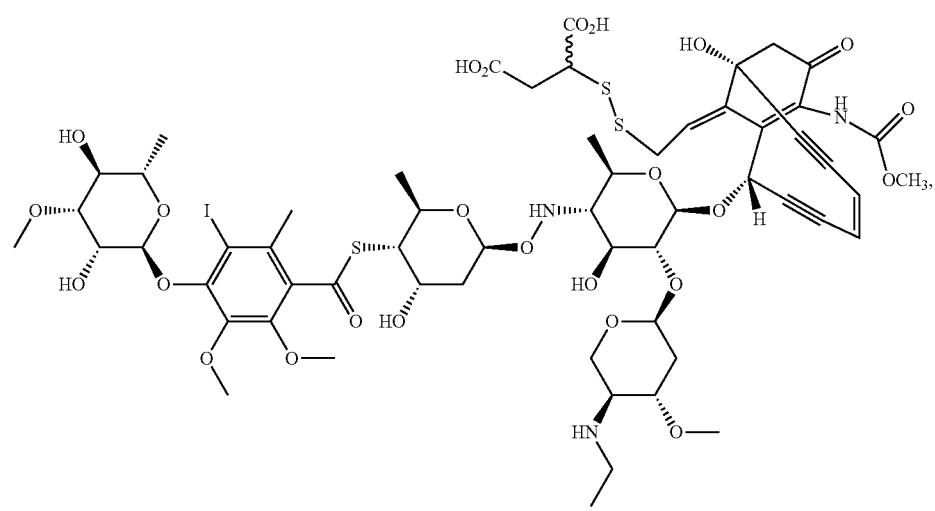

-continued
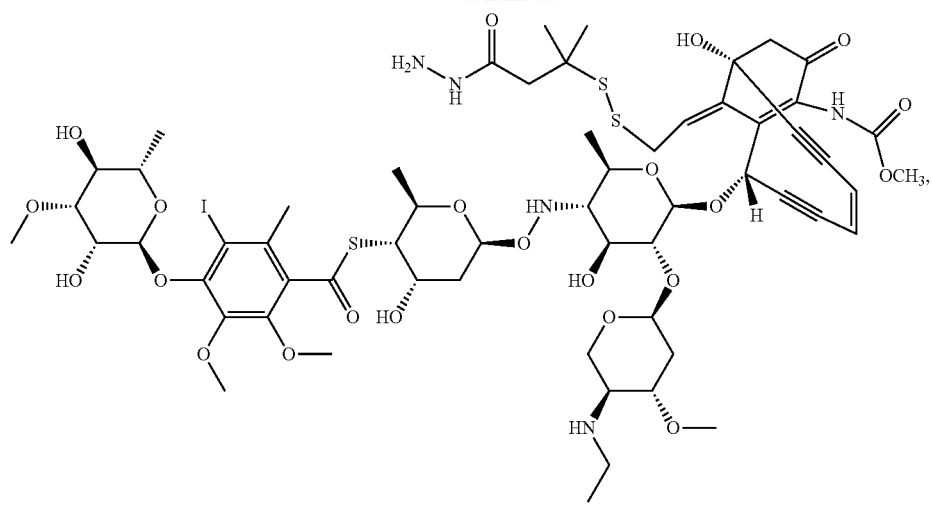
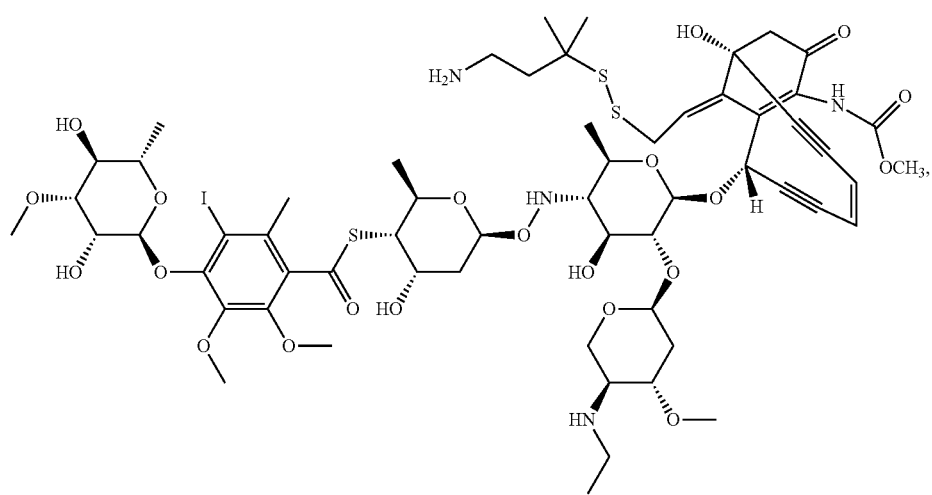
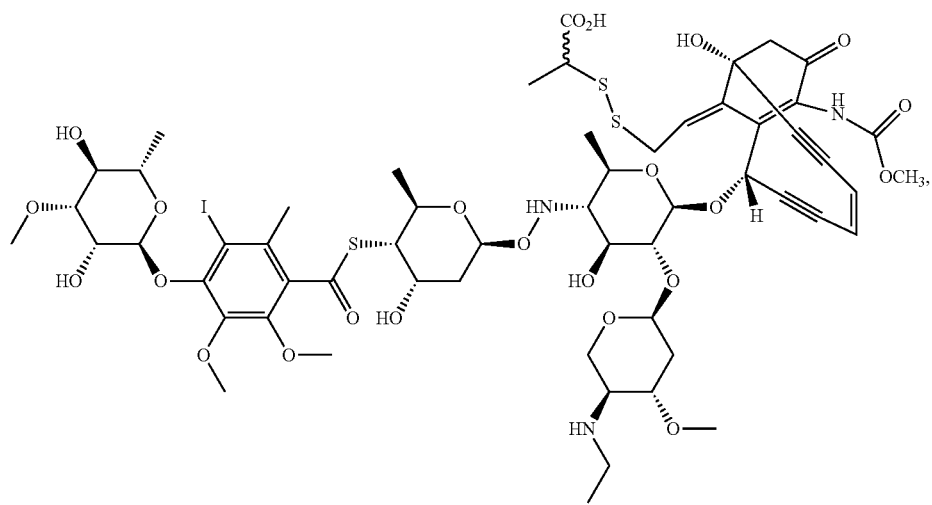

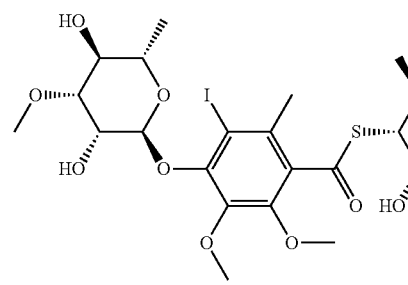
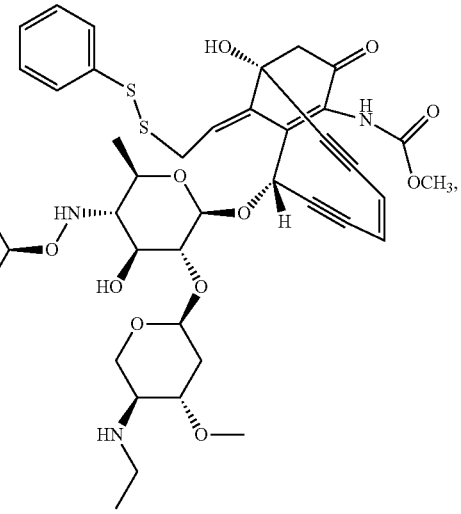
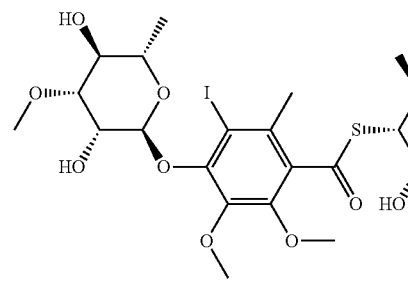
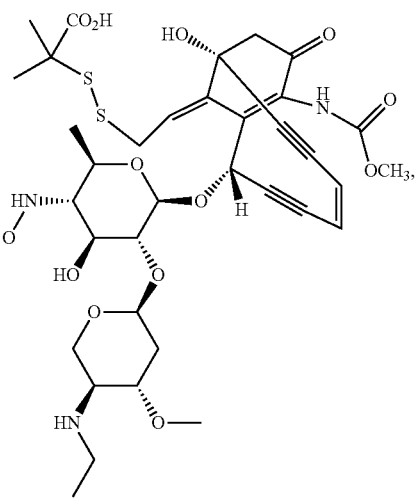
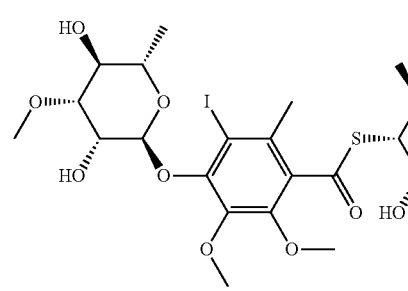
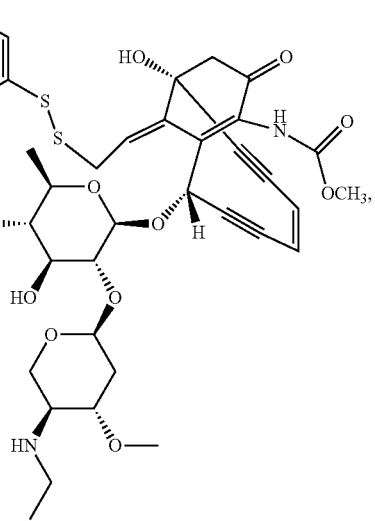

-continued
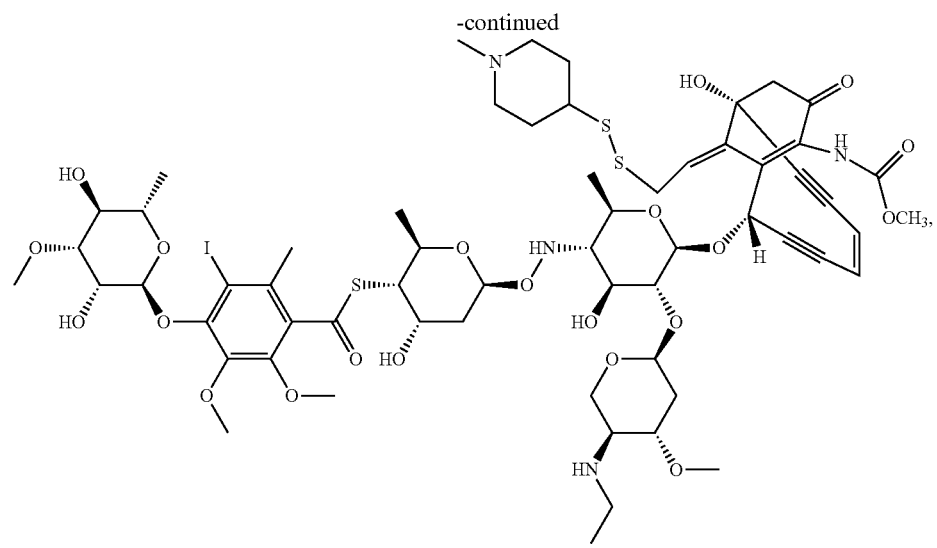
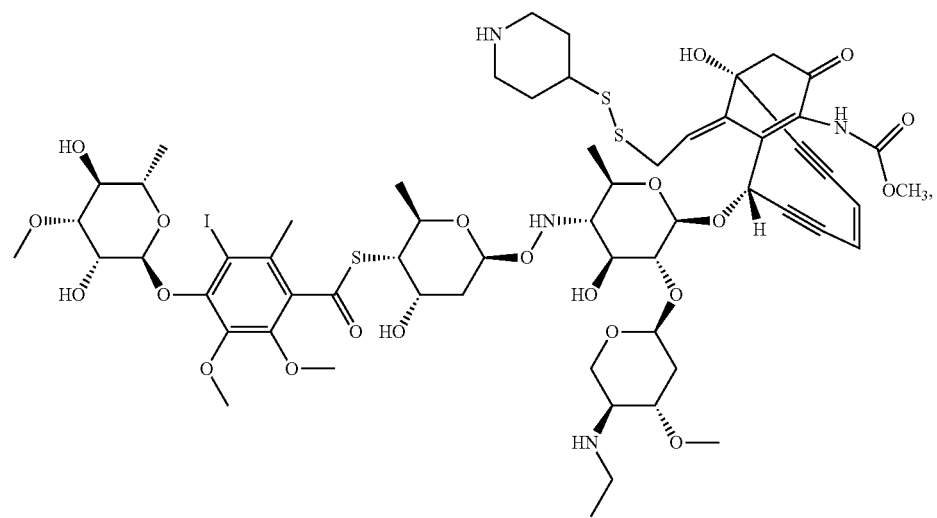
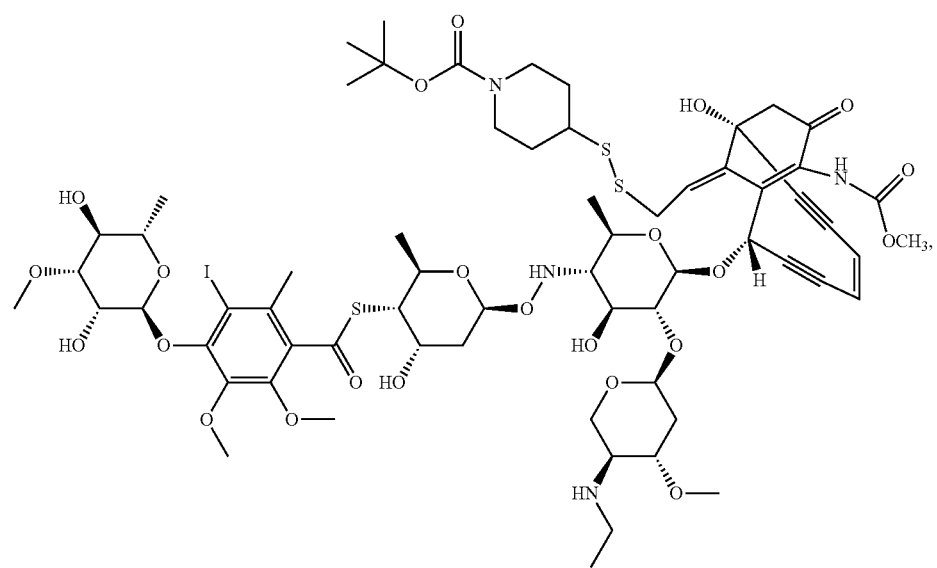

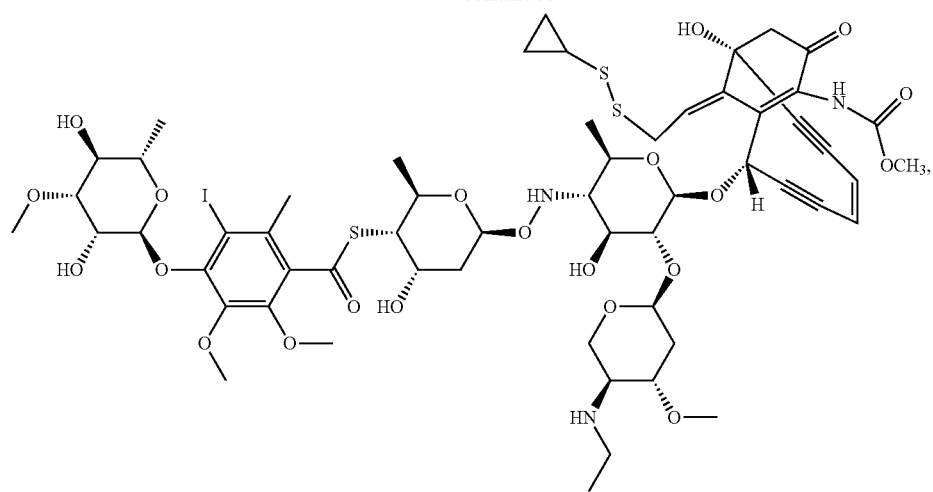
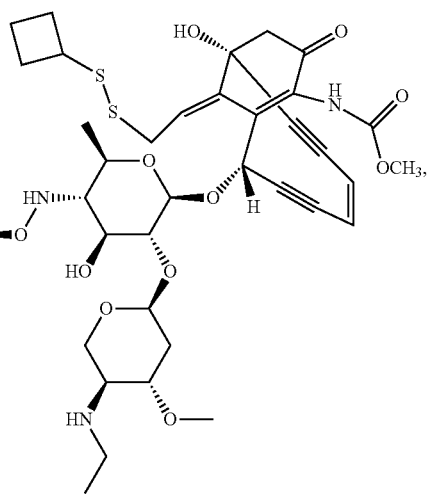
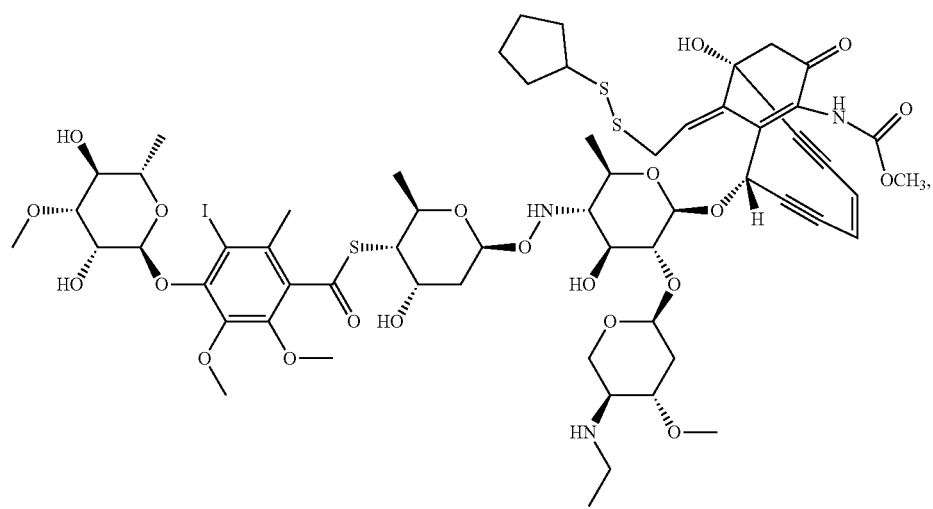

-continued
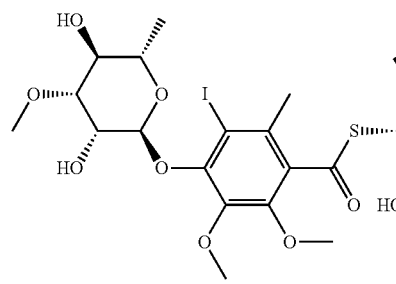
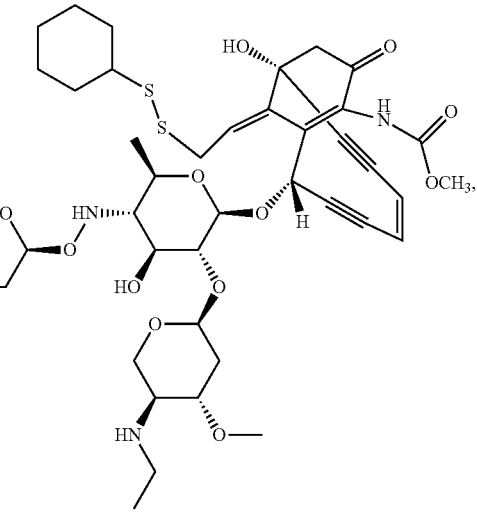
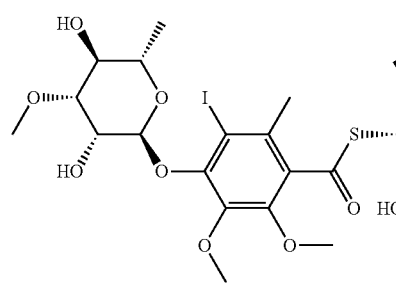
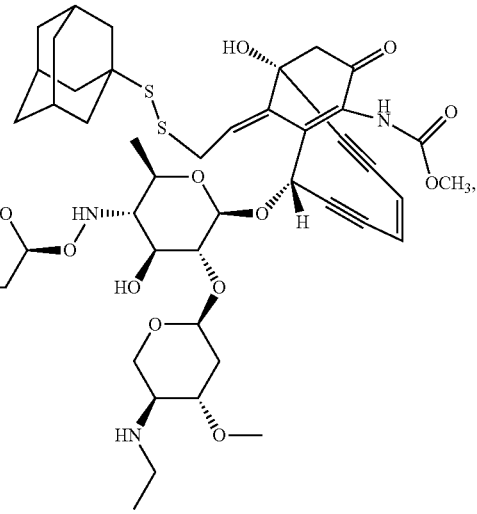
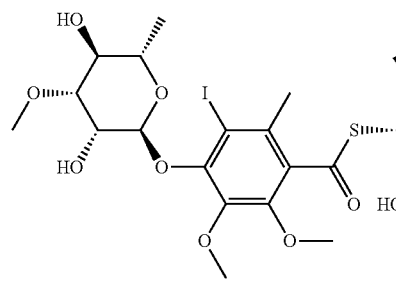
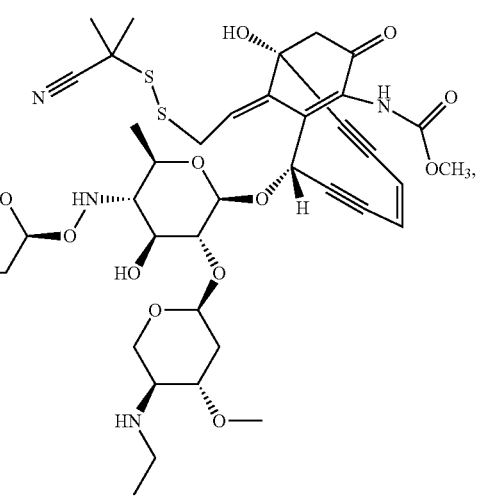

-continued
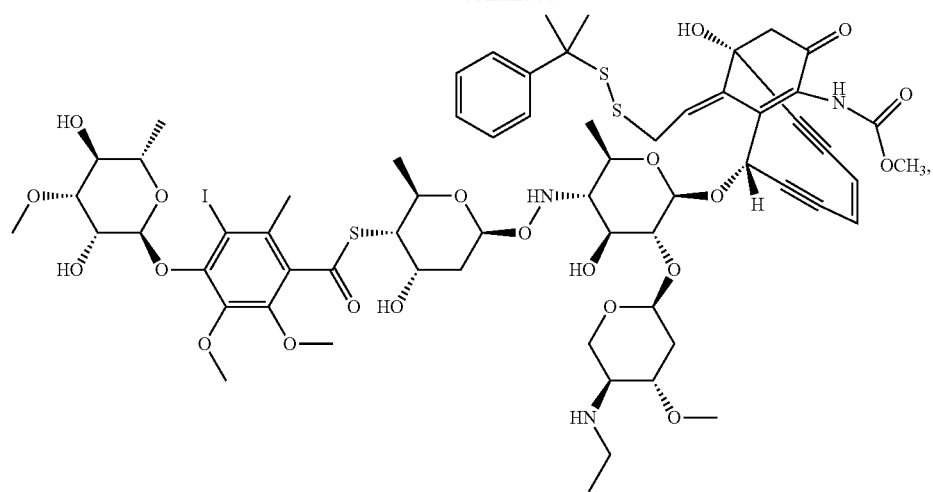
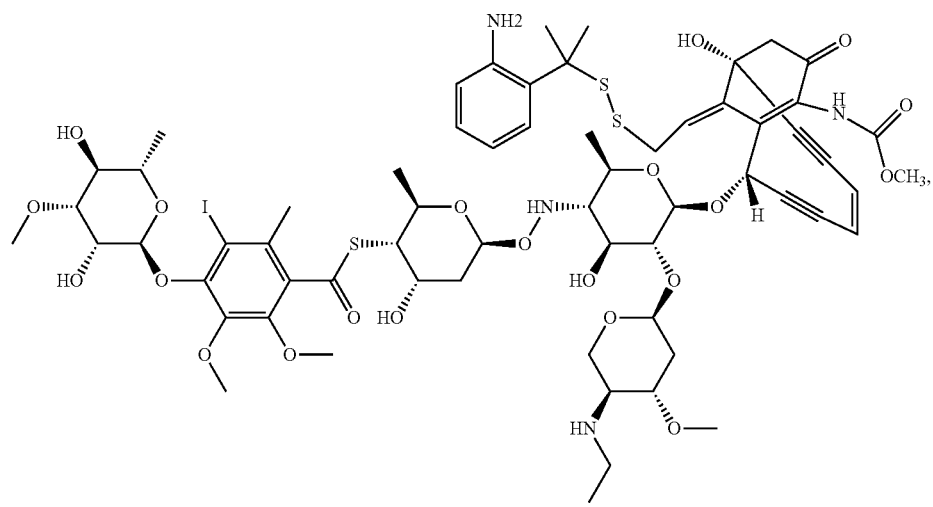
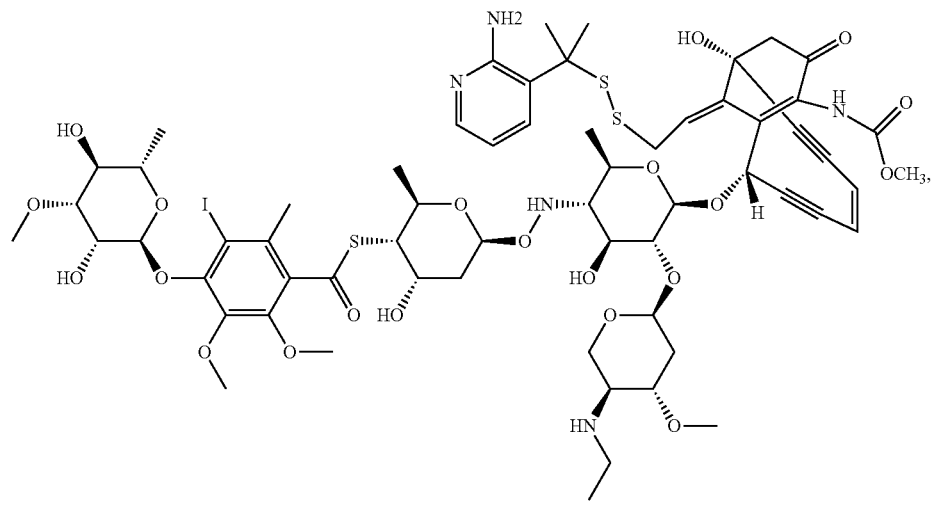

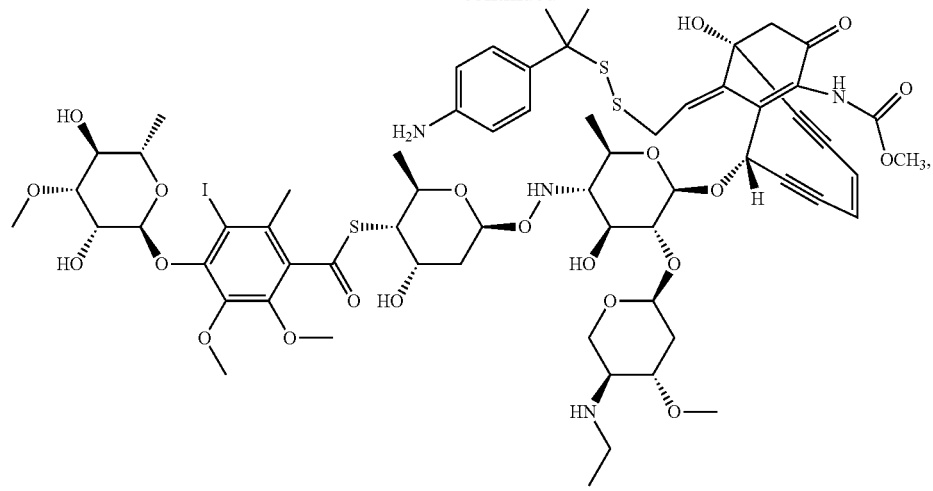
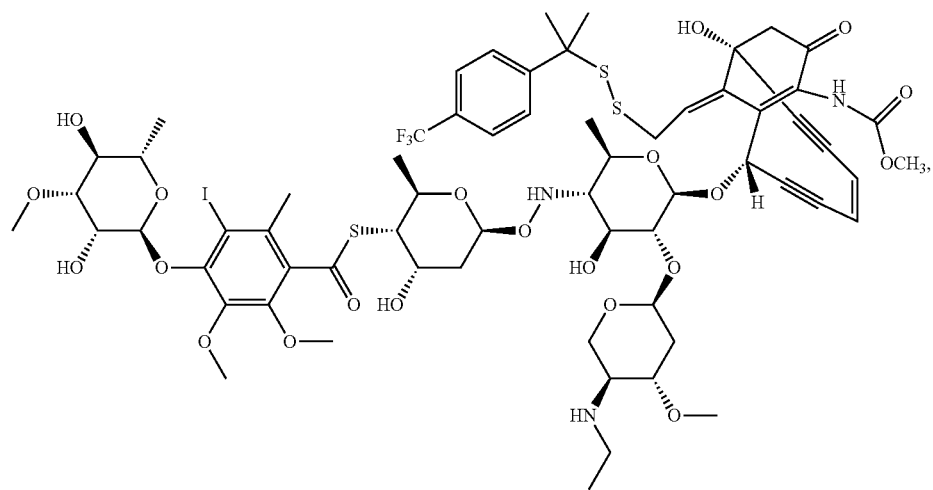
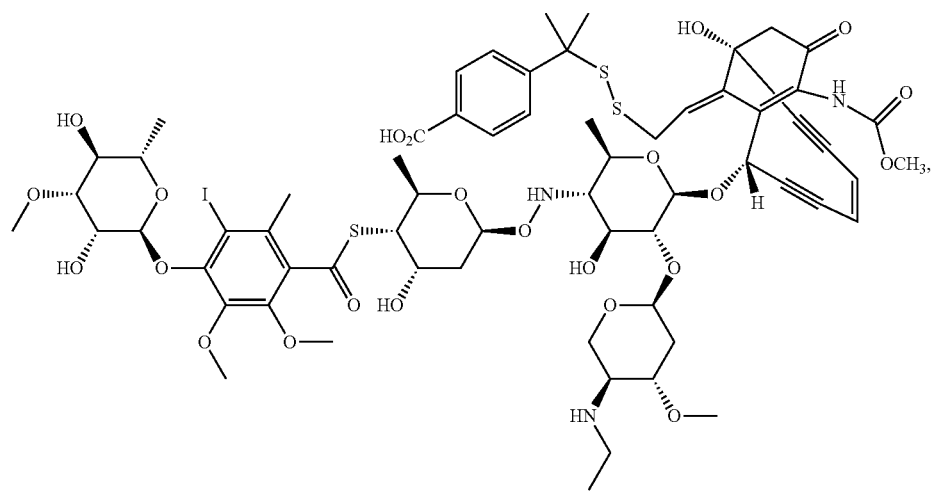

-continued
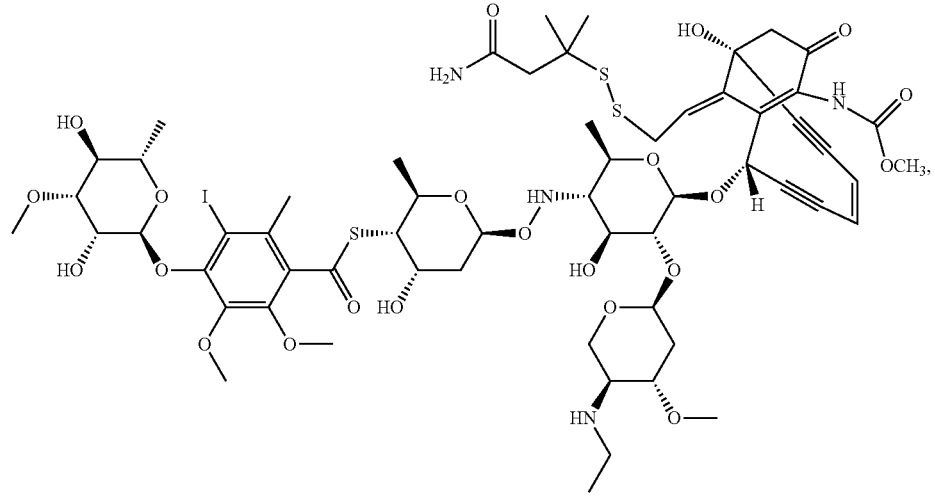
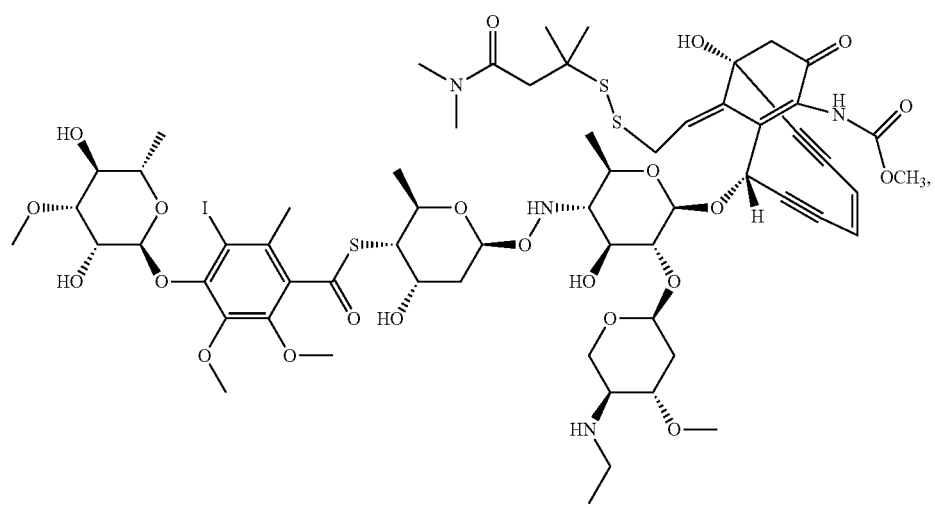
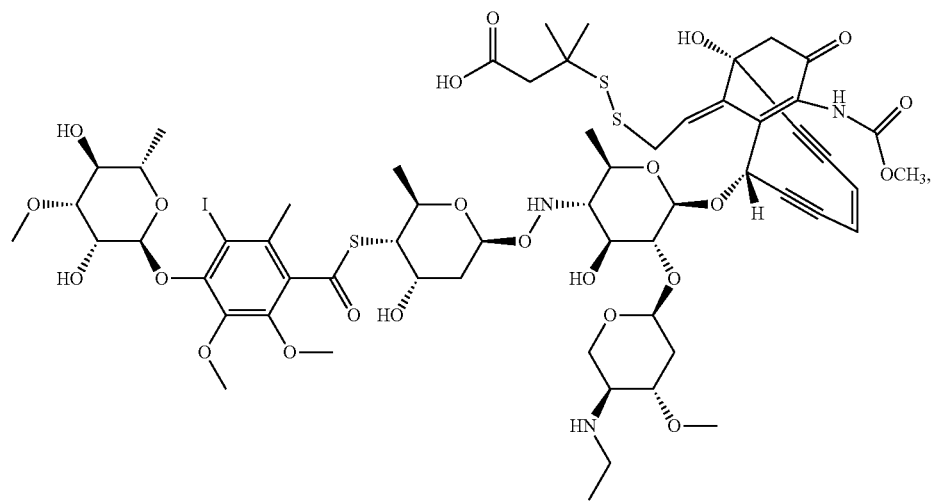

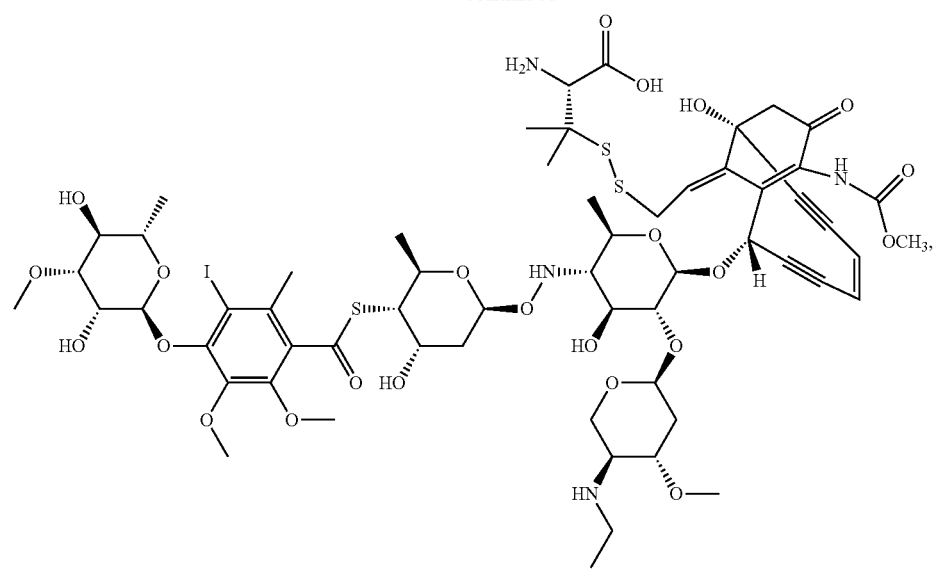
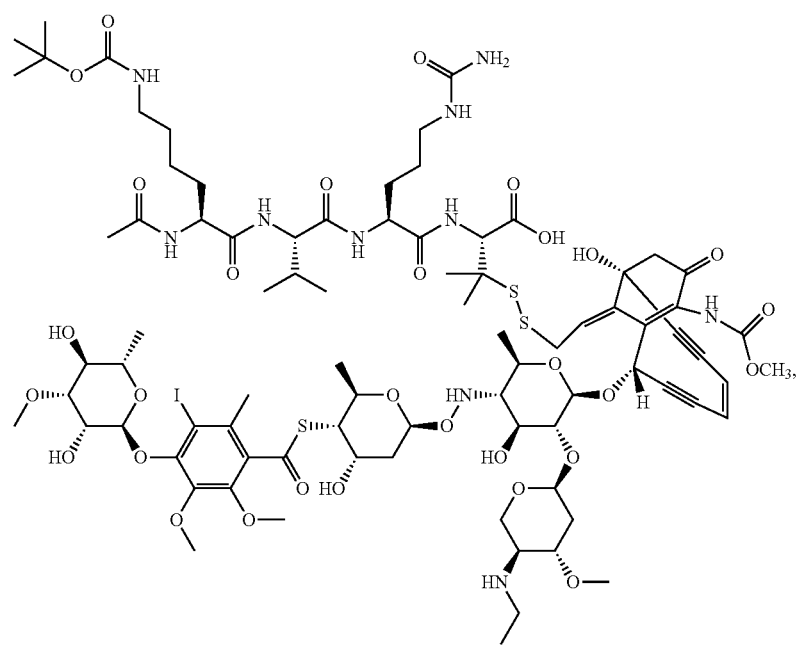

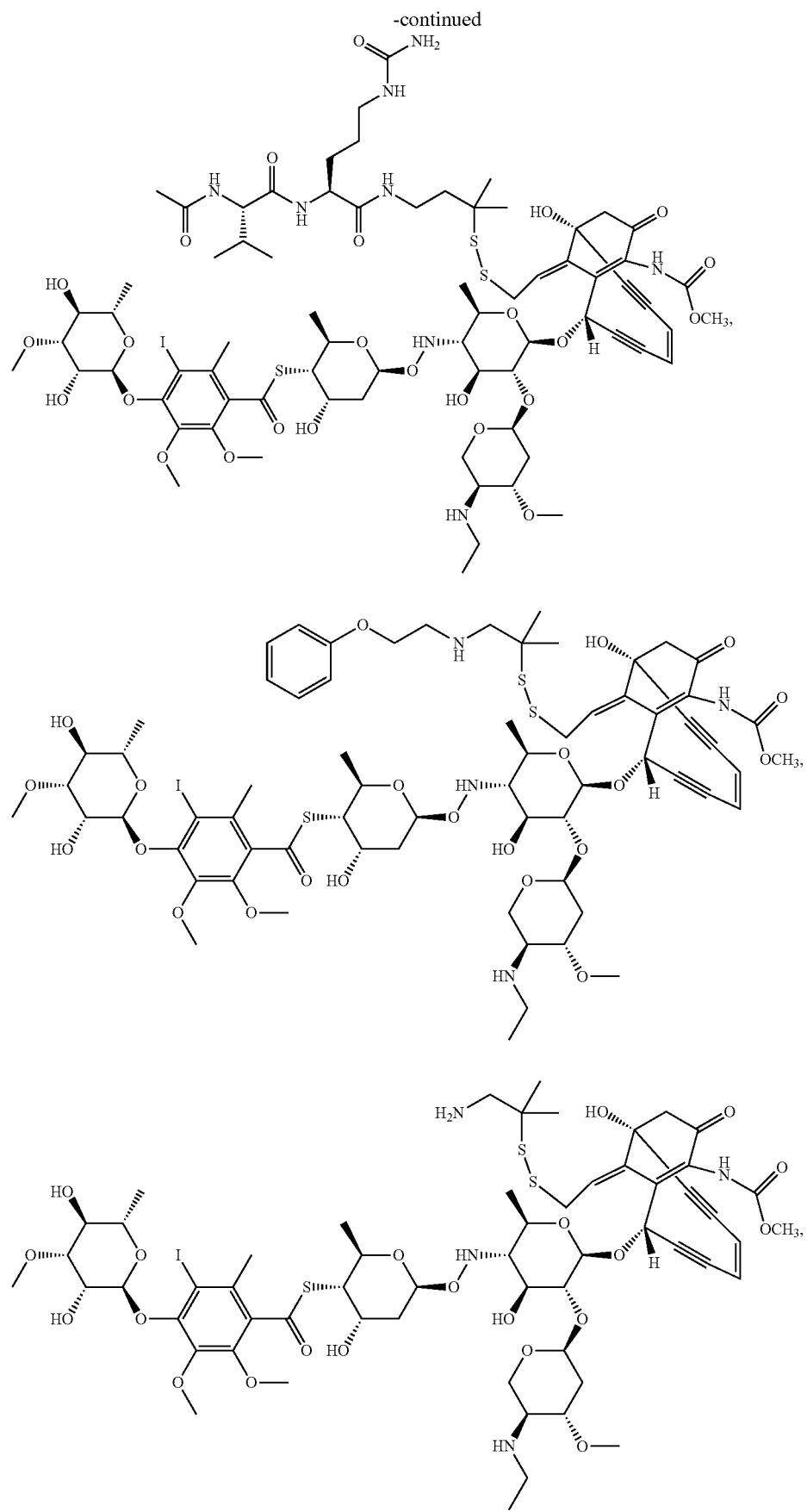

-continued
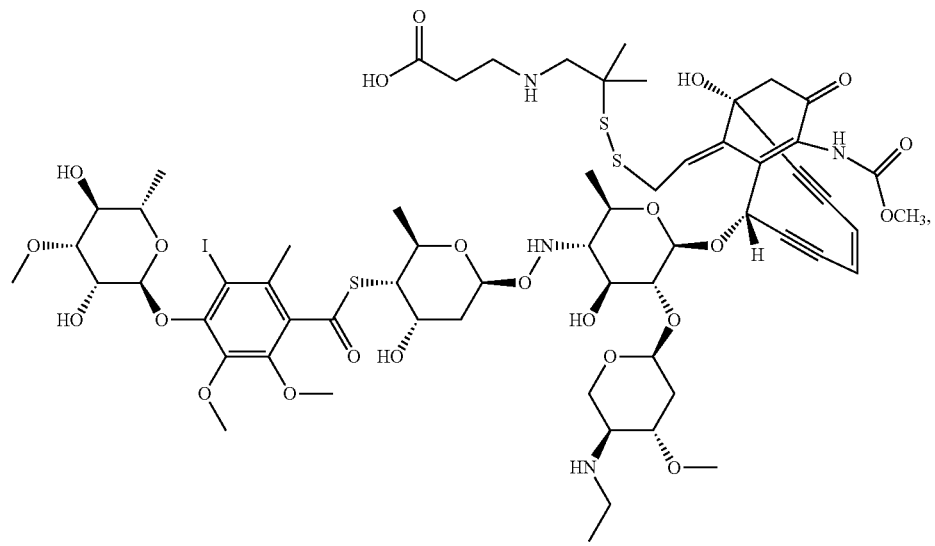
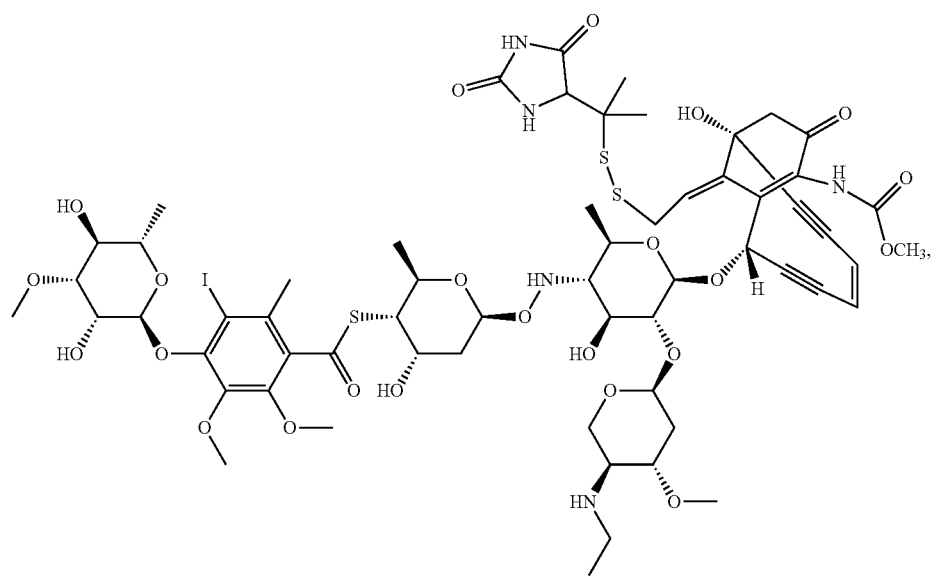
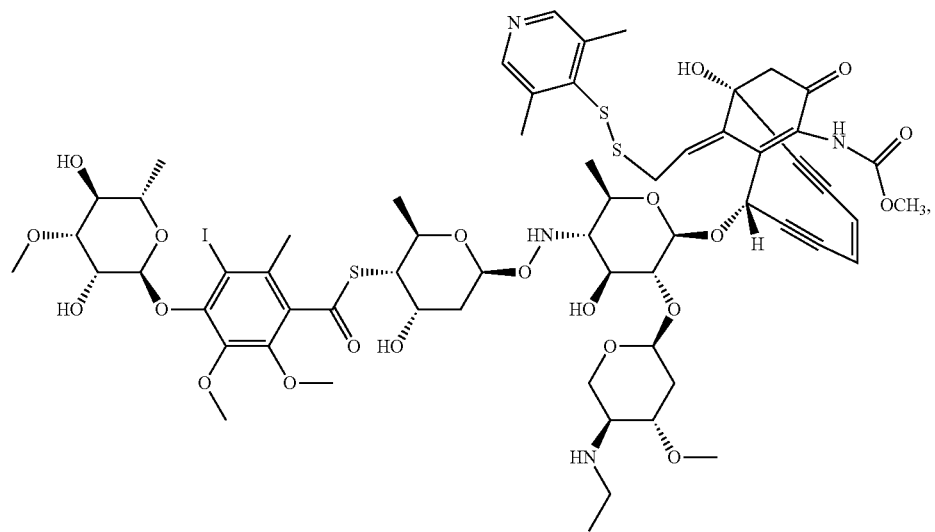

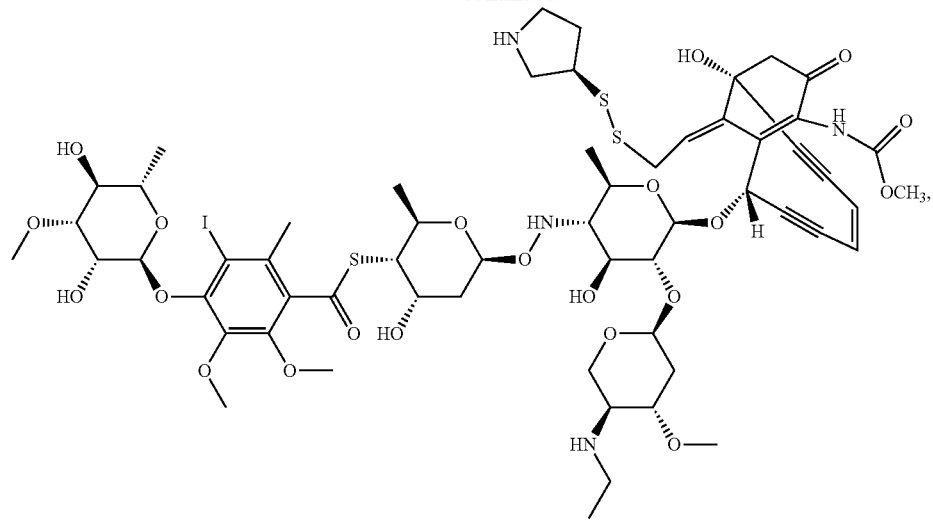
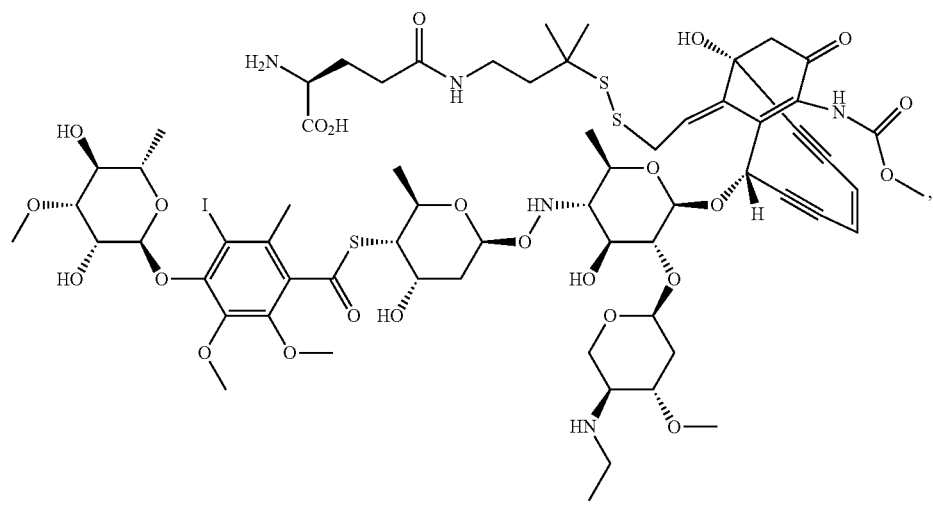
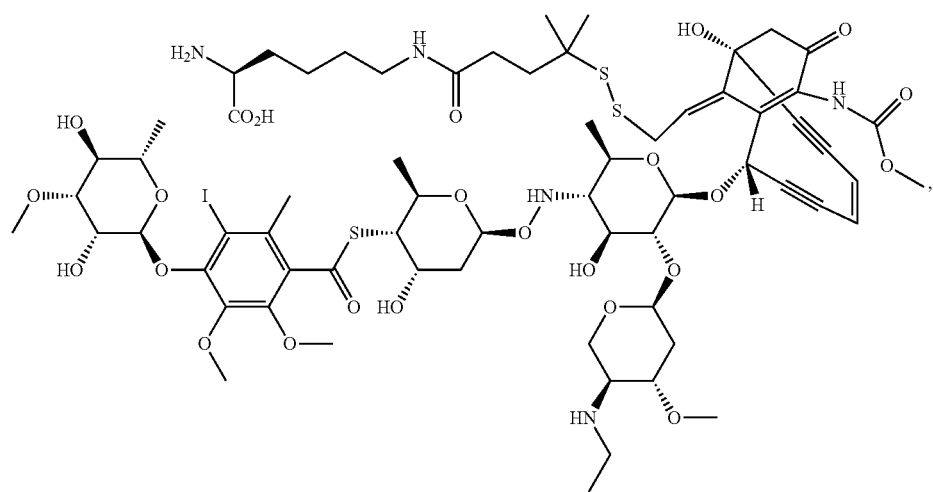

-continued
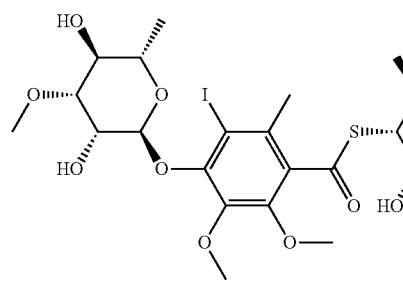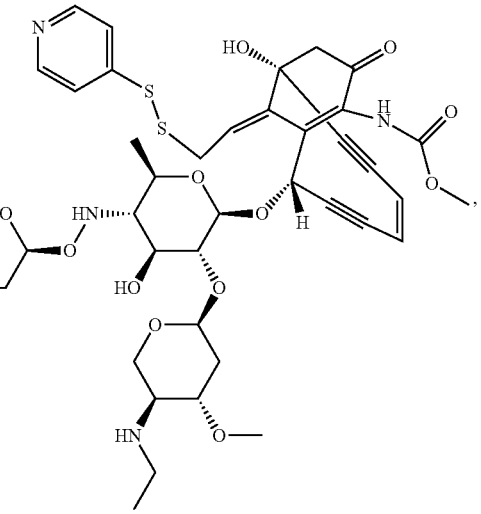
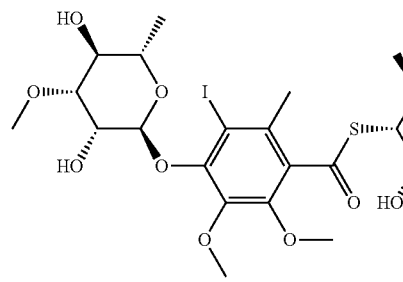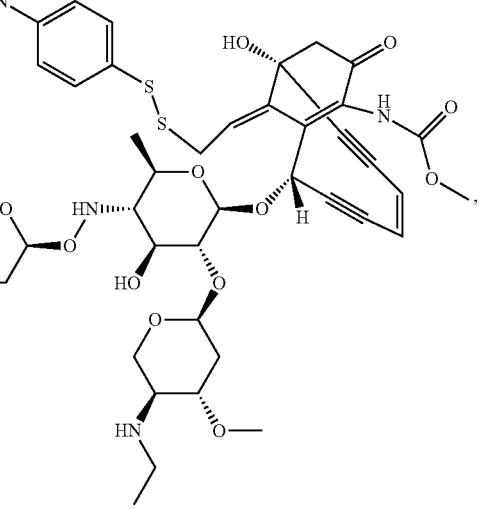
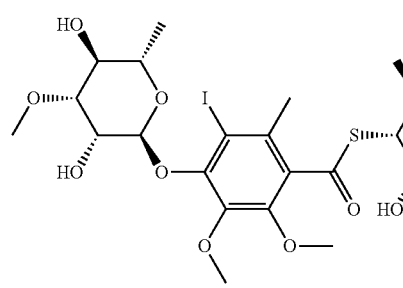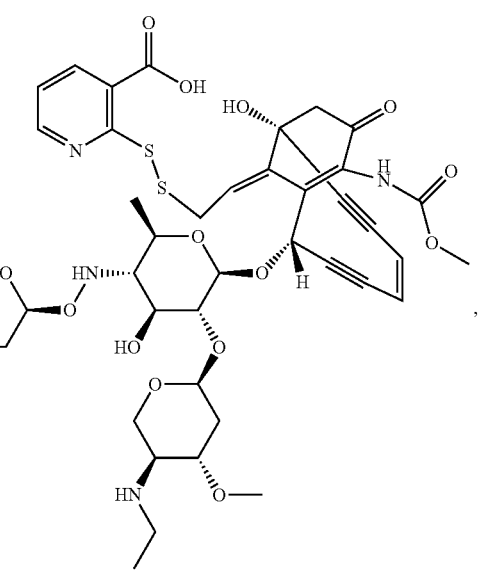

-continued
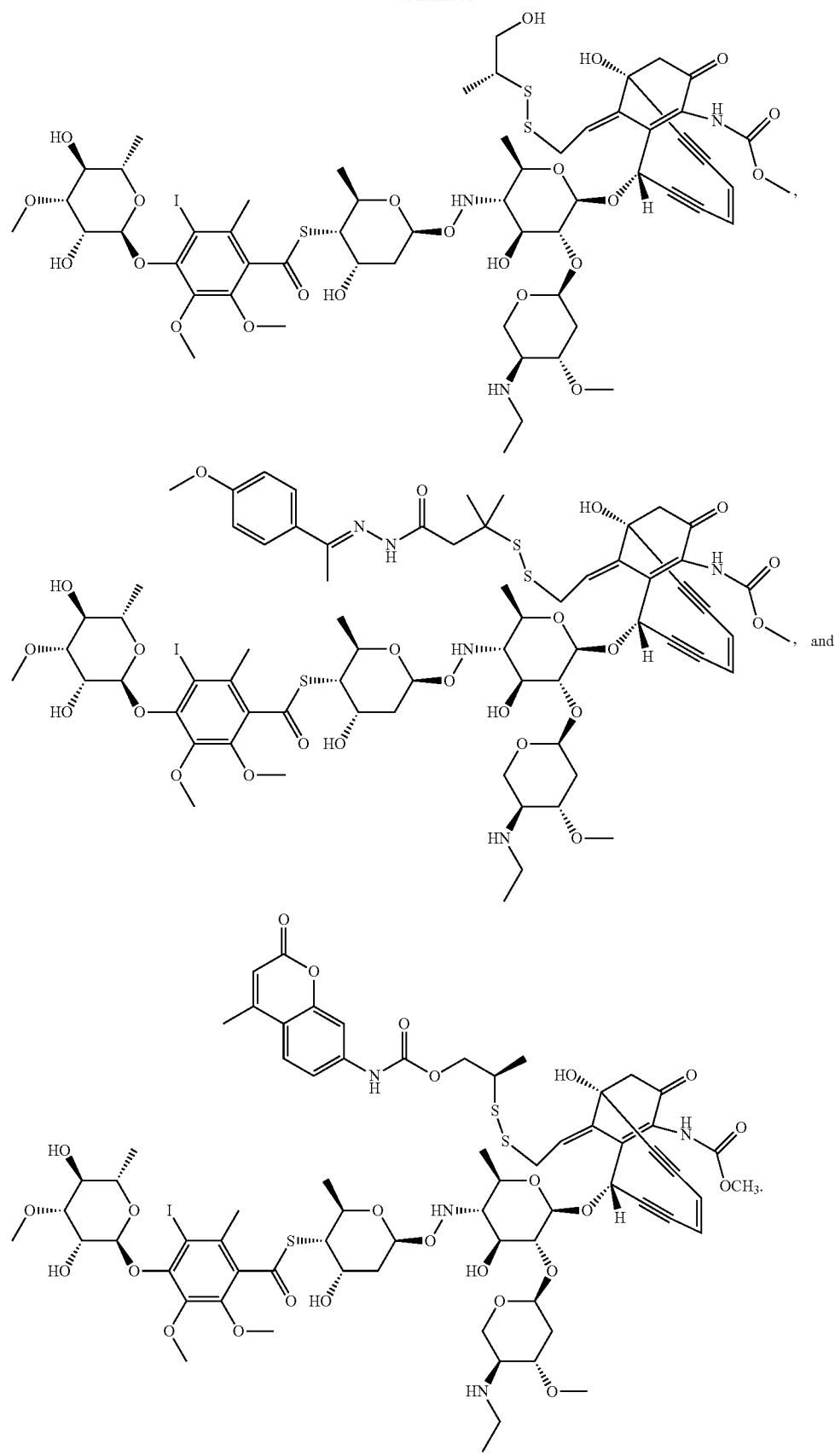

Compounds of Formula (II) and Derivatives Thereof

The present invention also relates to compounds of Formula (II):

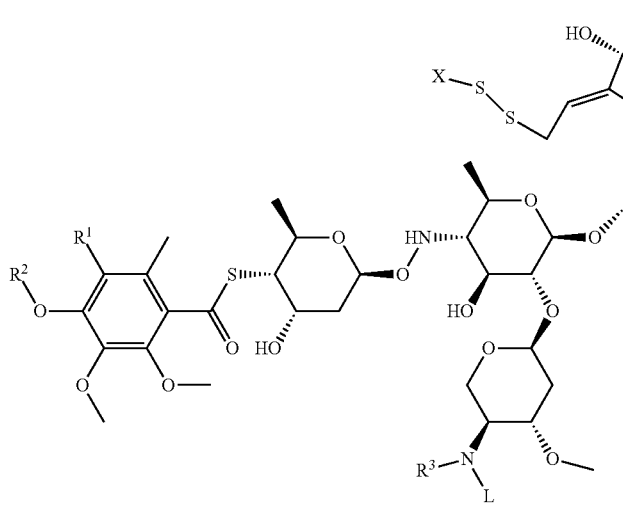

or a pharmaceutically acceptable salt thereof, wherein:
$R^1$ is selected from the group consisting of Br and I;
$R^2$ is selected from the group consisting of H and

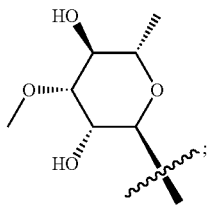

$R^3$ is selected from the group consisting of —$CH_3$, —$CH_2CH_3$, and —$CH(CH_3)_2$;
X is selected from the group consisting of:
(i) —$CH_3$ optionally substituted by one $R^{10}$;
(ii) —$C_2$-$C_8$alkyl optionally substituted by one $R^{10}$;
(iii) —($C_0$-$C_6$alkyl)-$C_3$-$C_{10}$ carbocyclyl, which said $C_3$-$C_{10}$ carbocyclyl is optionally substituted by one $R^{10}$;
(iv) —($C_0$-$C_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S;
(v) —($C_0$-$C_6$alkyl)-phenyl, which said phenyl is optionally substituted by one $R^{10}$; and
(vi) —($C_0$-$C_6$alkyl)-5 to 10 membered heteroaryl, which said 5 to 10 membered heteroaryl is optionally substituted by one $R^{10}$, and which said 5 to 10 membered heteroaryl comprises one, two or three heteroatoms independently selected from the group consisting of N, O and S;
and which X is optionally further substituted by 1, 2, 3, 4, 5, 6, 7, or 8 G;
$R^{10}$ is —$R^{10a}$-$R^{10b}$, wherein
$R^{10a}$ is either absent or —$(CH_2)_n$—, which $R^{10a}$ is optionally substituted by 1, 2, 3, 4, 5, 6, 7, or 8 G;

$R^{10b}$ is selected from the group consisting of:
(i) —OH;
(ii) —CN;
(iii) —$PO_3H$;
(iv) —$CO_2H$;
(v) —$CO_2C_1$-$C_4$alkyl, which said $C_1$-$C_4$alkyl is optionally substituted by 1, 2, 3, 4, 5, or 6 E;
(vi) —CO—$R^{11}$;
(vii) —NH—$R^{11}$;
(viii) —N($C_1$-$C_4$alkyl)-$R^{11}$, which said $C_1$-$C_4$alkyl is optionally substituted by 1, 2, 3, 4, 5, or 6 E;
(ix) —CONH—$R^{11}$;
(x) —CON($C_1$-$C_4$alkyl)-$R^{11}$, which said $C_1$-$C_4$alkyl is optionally substituted by 1, 2, 3, 4, 5, or 6 E;
(xi) —CONHNH—$R^{11}$;
(xii) —CONHN($C_1$-$C_4$alkyl)-$R^{11}$, which said $C_1$-$C_4$alkyl is optionally substituted by 1, 2, 3, 4, 5, or 6 E;
(xiii) —CON($C_1$-$C_4$alkyl)NH—$R^{11}$, which said $C_1$-$C_4$alkyl is optionally substituted by 1, 2, 3, 4, 5, or 6 E;
(xiv) —CON($C_1$-$C_4$alkyl)N($C_1$-$C_4$alkyl)-$R^{11}$, wherein each said $C_1$-$C_4$alkyl is independently optionally substituted by 1, 2, 3, 4, 5, or 6 E;
(xv) —CON($R^{11}$)$NH_2$;
(xvi) —CON($R^{11}$)NH($C_1$-$C_4$alkyl), which said $C_1$-$C_4$alkyl is optionally substituted by 1, 2, 3, 4, 5, or 6 E;
(xvii) —CON($R^{11}$)N($C_1$-$C_4$alkyl)$_2$, wherein each said $C_1$-$C_4$alkyl is independently optionally substituted by 1, 2, 3, 4, 5, or 6 E;
(xviii) —CONHN=C($C_1$-$C_4$alkyl)-$C_6H_4$—$OC_1$-$C_4$alkyl, wherein each said $C_1$-$C_4$alkyl is independently optionally substituted by 1, 2, 3, 4, 5, or 6 E;
(xix) —CON($C_1$-$C_4$alkyl)N=C($C_1$-$C_4$alkyl)-$C_6H_4$—$OC_1$-$C_4$alkyl, wherein each said $C_1$-$C_4$alkyl is independently optionally substituted by 1, 2, 3, 4, 5, or 6 E;
(xx) —N($R^{11}$)CO($C_1$-$C_4$alkyl), which said $C_1$-$C_4$alkyl is optionally substituted by 1, 2, 3, 4, 5, or 6 E;
(xxi) —CH($CO_2H$)NH—$R^{11}$;
(xxii) —CH($CO_2C_1$-$C_4$alkyl)NH—$R^{11}$, which said $C_1$-$C_4$alkyl is optionally substituted by 1, 2, 3, 4, 5, or 6 E;

(xxiii) —CH(NH$_2$)CO—R$^{11}$;
(xxiv) —CH(NH(C$_1$-C$_4$alkyl))CO—R$^{11}$, which said C$_1$-C$_4$alkyl is optionally substituted by 1, 2, 3, 4, 5, or 6 E;
(xxv) —CH(N(C$_1$-C$_4$alkyl)$_2$)CO—R$^{11}$, wherein each said C$_1$-C$_4$alkyl is independently optionally substituted by 1, 2, 3, 4, 5, or 6 E;
(xxvi) —CH(CO—R$^{11}$)NH—R$^{11}$; and
(xxvii) —CH(CO—R$^{11}$)N(C$_1$-C$_4$alkyl)-R$^{11}$, which said C$_1$-C$_4$alkyl is optionally substituted by 1, 2, 3, 4, 5, or 6 E;

R$^{11}$ is selected from the group consisting of —R$^{11a}$-R$^{11b}$-R$^{11c}$ and —R$^{11d}$-R$^{11e}$-R$^{11f}$, wherein R$^{11a}$ is either absent, or is selected from the group consisting of,

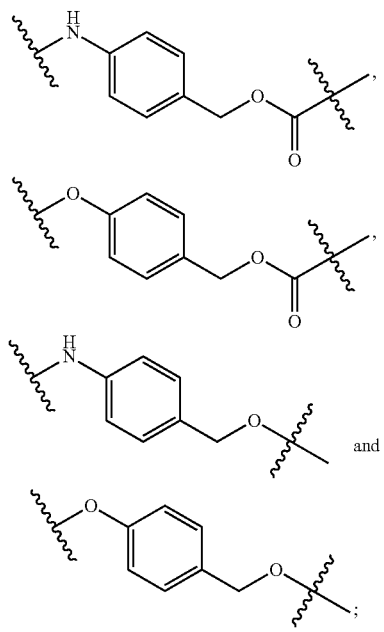

R$^{11b}$ is either absent, or is selected from the group consisting of

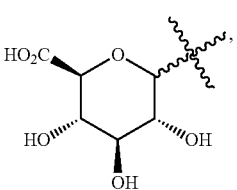 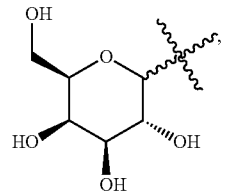

and AA$_r$, wherein AA is independently for each occurrence a natural amino acid or a non-natural amino acid;

R$^{11c}$ is either absent or is selected from the group consisting of —H, —C$_1$-C$_4$alkyl and —COC$_1$-C$_4$alkyl;

R$^{11d}$ is either absent or —(CH$_2$)$_t$—, which R$^{11d}$ when present is optionally substituted by 1, 2, 3, 4, 5, 6, 7, or 8 G;

R$^{11e}$ is either absent or selected from the group consisting of —O— and —NH—;

R$^{11f}$ is selected from the group consisting of C$_6$-C$_{12}$ aryl and 5 to 10 membered heteroaryl, which said 5 to 10 membered heteroaryl comprises one, two or three heteroatoms independently selected from the group consisting of N, O and S, and which R$^{11f}$ is optionally substituted by 1, 2, 3, 4, 5, 6, 7, or 8 G;

n is 1, 2, 3, 4, 5, or 6;
r is 1, 2, 3, 4, 5, 6, 7, 8, 9, 10, 11, 12, 13, 14, 15, 16, 17, 18, 19, or 20;
t is 1, 2, 3, 4, 5, or 6;

G is selected, independently for each occurrence, from the group consisting of —F, —Cl, —CN, —OH, —NH$_2$, —NH—C$_1$-C$_4$alkyl, —N(C$_1$-C$_4$alkyl)$_2$, —NO$_2$, —CO$_2$H, —C$_1$-C$_4$alkyl, —C$_1$-C$_4$alkylOH, —C$_1$-C$_4$alkylNH$_2$, —C$_1$-C$_4$haloalkyl, —C$_1$-C$_4$alkoxy, =O, —CO$_2$C$_1$-C$_4$alkyl, —OC(O)C$_1$-C$_4$alkyl, —NHC(O)C$_1$-C$_4$alkyl, —C(O)NHC$_1$-C$_4$alkyl, and —C(O)N(C$_1$-C$_4$alkyl)$_2$;

E is selected, independently for each occurrence, from the group consisting of —F, —Cl, —CN, —OH, —NH$_2$, —NHCH$_3$, —N(CH$_3$)$_2$, —NO$_2$, —CO$_2$H, —OCH$_3$, —OCF$_3$, and —CF$_3$; and L is a [LINKER].

The present invention also relates to compounds of Formula (IIA)

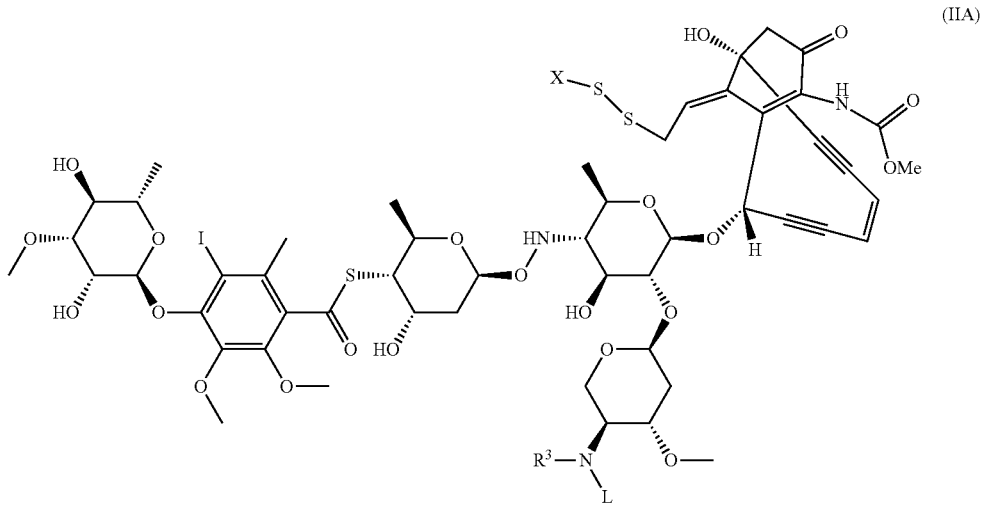

(IIA)

or a pharmaceutically acceptable salt thereof, wherein:

$R^3$ is selected from the group consisting of —CH$_3$, —CH$_2$CH$_3$, and —CH(CH$_3$)$_2$;

X is selected from the group consisting of:
(i) —CH$_3$ optionally substituted by one $R^{10}$;
(ii) —C$_2$-C$_8$alkyl optionally substituted by one $R^{10}$;
(iii) —(C$_0$-C$_6$alkyl)-C$_3$-C$_{10}$ carbocyclyl, which said C$_3$-C$_{10}$ carbocyclyl is optionally substituted by one $R^{10}$;
(iv) —(C$_0$-C$_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S;
(v) —(C$_0$-C$_6$alkyl)-phenyl, which said phenyl is optionally substituted by one $R^{10}$; and
(vi) —(C$_0$-C$_6$alkyl)-5 to 10 membered heteroaryl, which said 5 to 10 membered heteroaryl is optionally substituted by one $R^{10}$, and which said 5 to 10 membered heteroaryl comprises one, two or three heteroatoms independently selected from the group consisting of N, O and S;

and which X is optionally further substituted by 1, 2, 3, 4, 5, 6, 7, or 8 G;

$R^{10}$ is —$R^{10a}$-$R^{10b}$, wherein
$R^{10a}$ is either absent or —(CH$_2$)$_n$—, which $R^{10a}$ is optionally substituted by 1, 2, 3, 4, 5, 6, 7, or 8 G;
$R^{10b}$ is selected from the group consisting of:
(i) —OH;
(ii) —CN;
(iii) —PO$_3$H;
(iv) —CO$_2$H;
(v) —CO$_2$C$_1$-C$_4$alkyl, which said C$_1$-C$_4$alkyl is optionally substituted by 1, 2, 3, 4, 5, or 6 E;
(vi) —CO—$R^{11}$;
(vii) —NH—$R^{11}$;
(viii) —N(C$_1$-C$_4$alkyl)-$R^{11}$, which said C$_1$-C$_4$alkyl is optionally substituted by 1, 2, 3, 4, 5, or 6 E;
(ix) —CONH—$R^{11}$;
(x) —CON(C$_1$-C$_4$alkyl)-$R^{11}$, which said C$_1$-C$_4$alkyl is optionally substituted by 1, 2, 3, 4, 5, or 6 E;
(xi) —CONHNH—$R^{11}$;
(xii) —CONHN(C$_1$-C$_4$alkyl)-$R^{11}$, which said C$_1$-C$_4$alkyl is optionally substituted by 1, 2, 3, 4, 5, or 6 E;
(xiii) —CON(C$_1$-C$_4$alkyl)NH—$R^{11}$, which said C$_1$-C$_4$alkyl is optionally substituted by 1, 2, 3, 4, 5, or 6 E;
(xiv) —CON(C$_1$-C$_4$alkyl)N(C$_1$-C$_4$alkyl)-$R^{11}$, wherein each said C$_1$-C$_4$alkyl is independently optionally substituted by 1, 2, 3, 4, 5, or 6 E;
(xv) —CON($R^{11}$)NH$_2$;
(xvi) —CON($R^{11}$)NH(C$_1$-C$_4$alkyl), which said C$_1$-C$_4$alkyl is optionally substituted by 1, 2, 3, 4, 5, or 6 E;
(xvii) —CON($R^{11}$)N(C$_1$-C$_4$alkyl)$_2$, wherein each said C$_1$-C$_4$alkyl is independently optionally substituted by 1, 2, 3, 4, 5, or 6 E;
(xviii) —CONHN=C(C$_1$-C$_4$alkyl)-C$_6$H$_4$—OC$_1$-C$_4$alkyl, wherein each said C$_1$-C$_4$alkyl is independently optionally substituted by 1, 2, 3, 4, 5, or 6 E;
(xix) —CON(C$_1$-C$_4$alkyl)N=C(C$_1$-C$_4$alkyl)-C$_6$H$_4$—OC$_1$-C$_4$alkyl, wherein each said C$_1$-C$_4$alkyl is independently optionally substituted by 1, 2, 3, 4, 5, or 6 E;
(xx) —N($R^{11}$)CO(C$_1$-C$_4$alkyl), which said C$_1$-C$_4$alkyl is optionally substituted by 1, 2, 3, 4, 5, or 6 E;
(xxi) —CH(CO$_2$H)NH—$R^1$;
(xxii) —CH(CO$_2$C$_1$-C$_4$alkyl)NH—$R^{11}$, which said C$_1$-C$_4$alkyl is optionally substituted by 1, 2, 3, 4, 5, or 6 E;
(xxiii) —CH(NH$_2$)CO—$R^{11}$;
(xxiv) —CH(NH(C$_1$-C$_4$alkyl))CO—$R^{11}$, which said C$_1$-C$_4$alkyl is optionally substituted by 1, 2, 3, 4, 5, or 6 E;
(xxv) —CH(N(C$_1$-C$_4$alkyl)$_2$)CO—$R^{11}$, wherein each said C$_1$-C$_4$alkyl is independently optionally substituted by 1, 2, 3, 4, 5, or 6 E;
(xxvi) —CH(CO—$R^{11}$)NH—$R^{11}$; and
(xxvii) —CH(CO—$R^{11}$)N(C$_1$-C$_4$alkyl)-$R^{11}$, which said C$_1$-C$_4$alkyl is optionally substituted by 1, 2, 3, 4, 5, or 6 E;

$R^{11}$ is selected from the group consisting of —$R^{11a}$-$R^{11b}$-$R^{11c}$ and —$R^{11d}$-$R^{11e}$-$R^{11f}$ wherein P $R^{11a}$ is either absent, or is selected from the group consisting of,

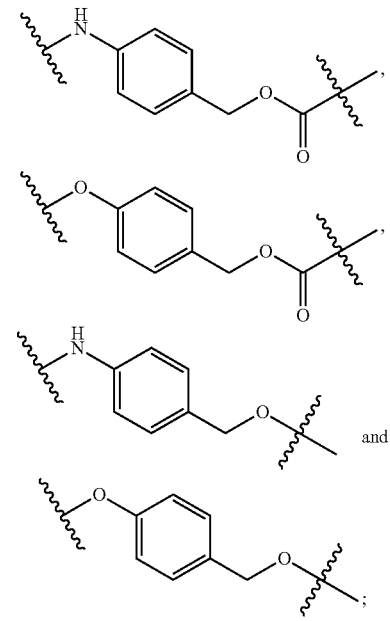

$R^{11b}$ is either absent, or is selected from the group consisting of

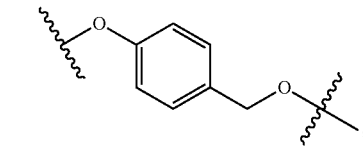

and AA$_p$, wherein AA is independently for each occurrence a natural amino acid or a non-natural amino acid;

$R^{11c}$ is either absent or is selected from the group consisting of —H, —C$_1$-C$_4$alkyl and —COC$_1$-C$_4$alkyl;

$R^{11d}$ is either absent or —$(CH_2)_t$—, which $R^{11d}$ when present is optionally substituted by 1, 2, 3, 4, 5, 6, 7, or 8 G;

$R^{11e}$ is either absent or selected from the group consisting of —O— and —NH—;

$R^{11f}$ is selected from the group consisting of $C_6$-$C_{12}$ aryl and 5 to 10 membered heteroaryl, which said 5 to 10 membered heteroaryl comprises one, two or three heteroatoms independently selected from the group consisting of N, O and S, and which $R^{11f}$ is optionally substituted by 1, 2, 3, 4, 5, 6, 7, or 8 G;

n is 1, 2, 3, 4, 5, or 6;

r is 1, 2, 3, 4, 5, 6, 7, 8, 9, 10, 11, 12, 13, 14, 15, 16, 17, 18, 19, or 20;

t is 1, 2, 3, 4, 5, or 6;

G is selected, independently for each occurrence, from the group consisting of —F, —Cl, —CN, —OH, —$NH_2$, —NH—$C_1$-$C_4$alkyl, —N($C_1$-$C_4$alkyl)$_2$, —$NO_2$, —$CO_2$H, —$C_1$-$C_4$alkyl, —$C_1$-$C_4$alkylOH, —$C_1$-$C_4$alkyl$NH_2$, —$C_1$-$C_4$haloalkyl, —$C_1$-$C_4$alkoxy, =O, —$CO_2C_1$-$C_4$alkyl, —OC(O)$C_1$-$C_4$alkyl, —NHC(O)$C_1$-$C_4$alkyl, —C(O)NH$C_1$-$C_4$alkyl, and —C(O)N($C_1$-$C_4$alkyl)$_2$;

E is selected, independently for each occurrence, from the group consisting of —F, —Cl, —CN, —OH, —$NH_2$, —$NHCH_3$, —N($CH_3$)$_2$, —$NO_2$, —$CO_2$H, —$OCH_3$, —$OCF_3$, and —$CF_3$; and L is a [LINKER].

The payload linker compounds of Formula (II) and Formula (IIA) comprise a linker unit L (sometimes herein referred to as "[LINKER]") bound to a calicheamicin derivative of Formula (I), or a pharmaceutically acceptable salt thereof. The payload linker compound is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells. The skilled person would recognize that the linker unit can comprise any unit suitable of linking the calicheamicin payload compounds of Formula (I) with an antibody.

The payload linker compounds of the present invention are designed such that the linker unit [LINKER] L is bound to the calicheamicin payload through the amino sugar group. Without wishing to be bound by theory it is believed that derivatisation through the amino sugar may enable the release of a more potent form of calicheamicin from the anti-body drug conjugate. Furthermore, without wishing to be bound by theory, it is also believed that derivatised through the amino sugar may increase the therapeutic window for such antibody drug conjugates since if any premature activation of the disulphide bond takes place in vivo prior to cleavage of the antibody drug conjugate, the calicheamicin derivative formed remains bound to the antibody and thus is expected to be less toxic.

Each of the aspects and embodiments described herein with respect to Formula (I) are, either alone or, where applicable, in combination, also applicable to compounds of Formula (II) and Formula (IIA), to the extent they are not incompatible with the structure.

A wide variety of linker units L, or [LINKER], are suitable for use in the present invention. Examples of suitable linker units include, but are not limited to, cleavable linker units, such as proteolytically cleavable linker units, hydrolytically cleavable linker units and glycolytically cleavable linker units; and non-cleavable linker units.

Examples of cleavable linker unit elements include, but are not limited to, chemically cleaved acyl hydrazones, such as those described in U.S. Pat. No. 5,773,001, enzymatically cleaved dipeptide or dipeptide-p-aminobenzylcarbamate sequences, such as those described in U.S. Pat. No. 6,214,345 B1, enzymatically cleaved glucuronide or glycoside moieties, such as those described in U.S. Pat. No. 8,039,273 B2 and in U.S. Pat. No. 8,568,728 B2, and the like. In certain embodiments of the invention additional immolative spacer elements, such as p-aminobenzylcarbamate moieties, substituted or unsubstituted N,N-diaminoethyl or N,N-diaminopropyl moieties, may be incorporated into the linker unit.

In certain embodiments of the invention a linker unit may be "non-cleavable", in which case there are no chemically or enzymatically sensitive bonds within the linker. In these cases, the drug or active agent is envisioned to be released via enzymatic catabolism of the antibody itself, thereby releasing the drug with the linker and one or more amino acids derived from the antibody intact.

In one aspect, a linker unit L has a reactive site which has a nucleophilic group that is reactive to an electrophilic group present on an antibody unit, such as an antibody. The electrophilic group on an antibody provides a convenient site for attachment to a linker unit. Useful electrophilic groups on an antibody include, but are not limited to, aldehyde and ketone carbonyl groups or a carboxylic acid group, for example one which has been activated. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

In another aspect, a linker unit L has a reactive site which has an electrophilic group that is reactive with a nucleophilic group present on an antibody unit, such as an antibody. The electrophilic group on a linker provides a convenient site for linker attachment to an antibody unit. Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups on the linker group include, but are not limited to, maleimide and haloacetamide groups.

Amino functional groups are also useful reactive sites for a linker unit L because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

Proteolytically cleavable peptide-based linkages that employ the p-aminobenzyloxycarbonyl (PABC) immolation element have been widely used in antibody-drug conjugate (ADC) research since their introduction in 2002 (Dubowchik, G. M. et al. Bioconjugate Chem. 2002, 13, 855-869). Such linkages purportedly undergo cleavage upon internalization into antigen-targeted cells and exposure of the ADC to the degradative proteolytic environment found in endosomal and lysosomal organelles. Cysteine-linked variants of these dipeptide-PABC linkers have been patented (U.S. Pat.

No. 6,214,345 B2), and it has been demonstrated that amine-containing versions of these and other linkages are appropriate for site-specific conjugations to glutamine residues using enzymatic conjugations promoted by microbial transglutaminase, as well as the use of aglycosylated antibodies and engineered antibody variants that undergo efficient conjugations using this enzymatic conjugation approach (WO2012/059882 A2).

In another embodiment, the linker unit L for use in the present invention includes linker units such as those disclosed in International Patent application number PCT/IB2011/054899, published on 10 May 2012 as WO 2012/059882, the contents of which are incorporated herein by reference in their entirety. In this embodiment, linker units suitable for use with the payloads of the present invention include those described:

wherein:

M is a stability modulator;

P is a peptide sequence which includes one or more glutamine residues;

Q is a glutamine residue present in P;

each E is independently selected from the group consisting of: —C(R$^1$)$_2$—, —O—C(R$^1$)$_2$—C(R$^1$)$_2$— where r is at least 2, and —C(R$^1$)$_2$—C(R$^1$)$_2$—O— where s is at least 1;

each R$^1$ is independently selected from the group consisting of: H, C$_1$-C$_6$ straight or branched alkyl, C$_2$-C$_6$ straight or branched alkenyl, and C$_2$-C$_6$ straight or branched alkynyl;

each X is independently an amino acid, where each amino acid X is the same or is different;

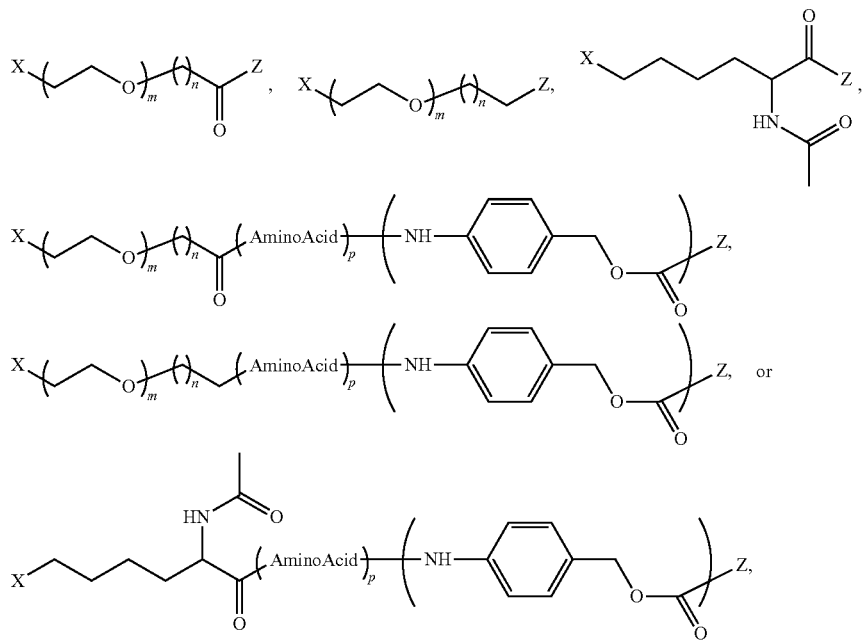

wherein X, m, n, p, q, and amino acid are all defined as disclosed in WO 2012/059882; and Z is a cytotoxic agent, in this case a calicheamicin derivative as described herein.

In another embodiment, linker unit L for use in the present invention include linker units such as those disclosed in International Patent application number PCT/IB2015/056211, published on 3 Mar. 2016 as WO 2016/030791, the contents of which are incorporated herein by reference in their entirety. In this embodiment, linker units suitable for use with the payloads of the present invention include those described in Formula I of WO 2016/030791:

each Y is independently an amino acid, where each amino acid Y is the same or is different;

each Z is independently a spacer element, where each spacer element is the same or is different;

m is 0-5, n is 1-5, p is 0-2, q is 0-10, r is 0-2, and s is 0-2, where q+r+s=2 or more; and wherein M, P, Q, E, R$^1$, X, Y, Z, m, n, p, q, r and s are all defined as disclosed in WO 2016/030791; and D is a cytotoxic agent, in this case a calicheamcin derivative as described herein.

Alternative linker units L suitable for use with the payloads of the present invention are also described in Formula II of WO 2016/030791:

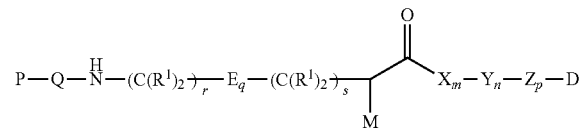

(I)

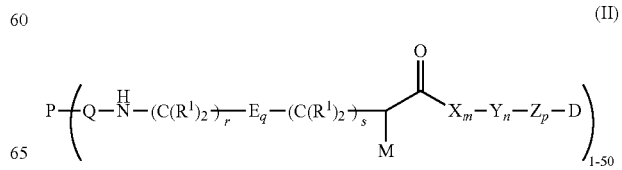

(II)

wherein:
M is a stability modulator;
P is a peptide sequence which includes one or more glutamine residues;
Q is a glutamine residue present in P;
each E is independently selected from the group consisting of: —C(R$^1$)$_2$—, —O—C(R$^1$)$_2$—C(R$^1$)$_2$— where r is at least 2, and —C(R$^1$)$_2$—C(R$^1$)$_2$—O— where s is at least 1;
each R$^1$ is independently selected from the group consisting of: H, C$_1$-C$_6$ straight or branched alkyl, C$_2$-C$_6$ straight or branched alkenyl, and C$_2$-C$_6$ straight or branched alkynyl;
each X is independently an amino acid, where each amino acid X is the same or is different;
each Y is independently an amino acid, where each amino acid Y is the same or is different;
each Z is independently a spacer element, where each spacer element is the same or is different;
m is 0-5, n is 1-5, p is 0-2, q is 0-10, r is 0-2, and s is 0-2, where q+r+s=2 or more; and
wherein M, P, Q, E, R$^1$, X, Y, Z, m, n, p, q, r and s are all defined as disclosed in WO 2016/030791; and D is a cytotoxic agent, in this case a calicheamcin derivative as described herein.

The skilled person will understand that all definitions applicable to the linker units described in WO2016/03079, including all preferred embodiments, will apply equally when such linker units are bound to payloads of the present invention as a [LINKER] L to form payload linker compounds of the present invention.

The skilled person will also recognize that modifications of linker units known in the art are also useful as aspects of linkers to be used in the compounds of the present invention.

In one embodiment of Formula (II), [LINKER] L is -(L$^C$)$_{1-3}$-L$^B$-L$^A$, wherein L$^A$ is selected from the group consisting of -halo; —NHR; —CO—H; —CO$_2$H; —S—S-aryl optionally substituted with —NO$_2$; —S—S-heteroaryl optionally substituted with —NO$_2$; alkyl-SO$_2$-heteroaryl; arylSO$_2$-heteroaryl-;

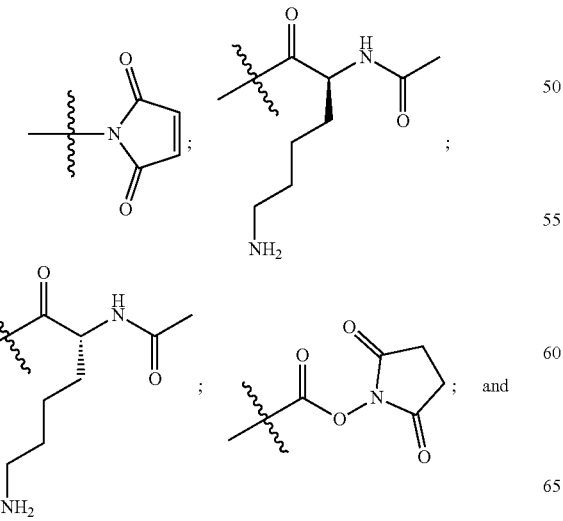

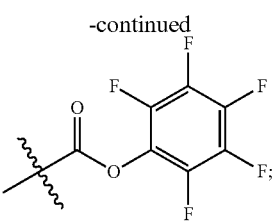

L$^B$ is selected from the group consisting of -L$^{B1}$-L$^{B2}$-L$^{B3}$ and -L$^{B2}$-L$^{B3}$-L$^{B1}$ wherein L$^{B1}$ is either absent or is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$—NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkyl NRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_{1-6}$alkyl-, —N=CR-phenyl-O—C$_1$-C$_6$alkyl-, —N=CR— phenyl-O—C$_1$-C$_6$alkyl-C(O)—, —C(O)—C$_1$-C$_6$alkyl(OCH$_2$CH$_2$)$_{1-8}$NRC(O)—, —C(O)C$_1$-C$_6$alkyl-phenyl(NR—C(O)C$_1$-C$_6$alkyl)$_{1-4}$-, —C(O)C$_1$-C$_6$alkyl(OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1-20}$, —C$_1$-C$_6$alkylene-NR—, and —NRC$_1$-C$_6$alkylene-;

L$^{B2}$ is either absent, or is selected from the group consisting of

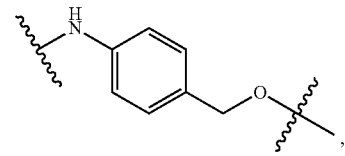

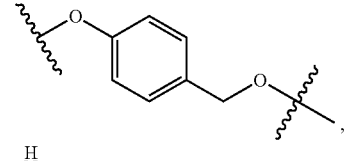

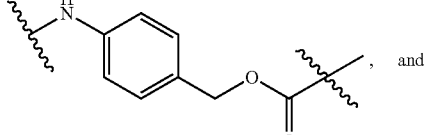

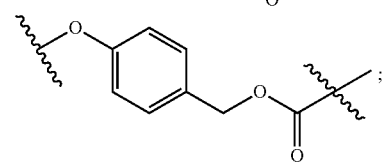

L$^{B3}$ is AA$_{0-12}$, wherein AA is independently for each occurrence a natural amino acid or a non-natural amino acid;

L$^C$ is either absent or is selected, independently for each occurrence, from the group consisting of —CO—, —C$_1$-C$_6$alkylene-, —NRC$_3$-C$_8$-heterocyclylNR—, —NRC$_3$-C$_8$-carbocyclylNR—, —NRC$_1$-C$_6$alkylNR—, —NRC$_1$-C$_6$alkylene-, —S—, —NR—, —NRNR—, —O(CR$_2$)$_{1-4}$S— S(CR$_2$)$_{1-4}$N(R)—, —NRC$_1$-C$_6$-alkylenepheny —NRC$_1$-C$_6$alkylenephenyleneSO$_2$NR—, —OC$_1$-C$_6$alkylS-SC$_1$-C$_6$alkylC(COOR)NR—, —NRC(COOR)C$_1$-C$_6$alkylS-SC$_1$-C$_6$alkylO—,

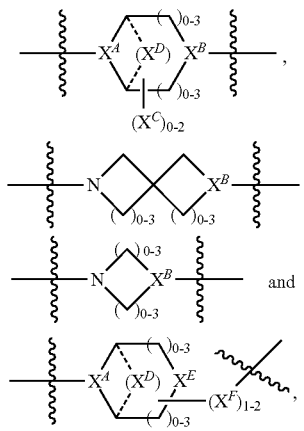

wherein
X$^A$ is selected from the group consisting of CR and N;
X$^B$ is selected from the group consisting of CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) and N;
each X$^C$ is R;
each X$^D$ is either absent or —(CH$_2$)$_{1-5}$—;
X$^E$ is selected from the group consisting of O, S, C(R)$_2$, C(R)(C(R)$_2$)$_{1-3}$—NR$_2$ and NR;
each X$^F$ is selected from the group consisting of (C(R)$_2$)$_{1-3}$—NR and C(R)$_2$—(C(R)$_2$)$_{1-3}$—O; and
each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is -L$^B$-L$^A$, wherein L$^A$ is selected from the group consisting of -halo; —NHR; —CO—H; —CO$_2$H; —S—S-aryl optionally substituted with —NO$_2$; —S—S-heteroaryl optionally substituted with —NO$_2$; alkyl-SO$_2$-heteroaryl; arylSO$_2$-heteroaryl-;

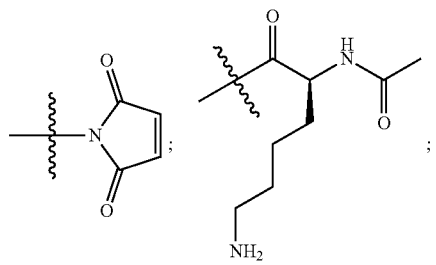

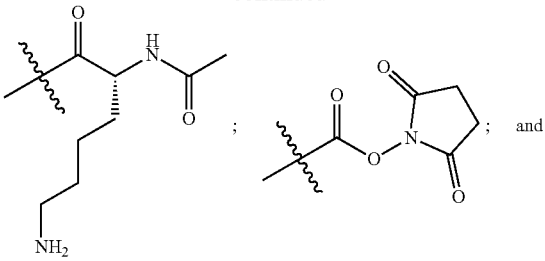

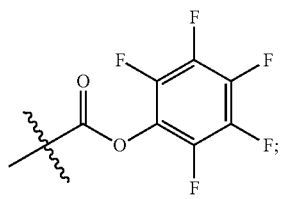

L$^B$ is -L$^{B1}$-L$^{B2}$-L$^{B3}$ wherein
L$^{B1}$ is either absent or is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$—NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_{1-6}$alkyl-, —N=CR-phenyl-O—C$_1$-C$_6$alkyl-, —N=CR— phenyl-O—C$_1$-C$_6$alkyl-C(O)—, —C(O)—C$_1$-C$_6$alkyl(OCH$_2$CH$_2$)$_{1-8}$NRC(O)—, —C(O)C$_1$-C$_6$alkyl-phenyl(NR—C(O)C$_1$-C$_6$alkyl)$_{1-4}$-, —C(O)C$_1$-C$_6$alkyl(OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1-20}$, —C$_1$-C$_6$alkylene-NR—, and —NRC$_1$-C$_6$alkylene-;
L$^{B2}$ is either absent, or is selected from the group consisting of

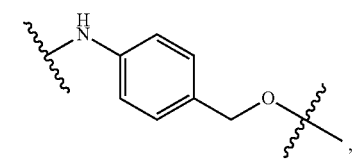

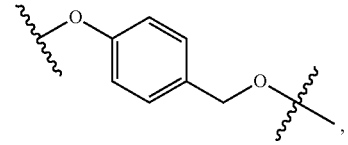

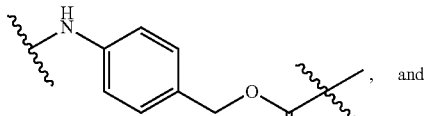

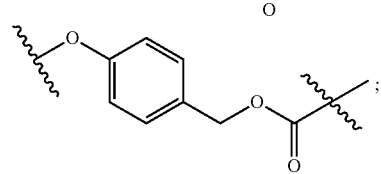

$L^{B3}$ is $AA_{0-12}$, wherein AA is independently for each occurrence a natural amino acid or a non-natural amino acid;
and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl)$_2$, —$C_1$-$C_{10}$ alkyl-$N(C_1$-$C_8$ alkyl)$_2$, —$C_1$-$C_3$ alkylthio, —$NO_2$ or —$C_1$-$C_{10}$ heterocyclyl, for each ring system in which R appears.

In some embodiments of Formula (II), L is -$L^B$-$L^A$, wherein $L^A$ is selected from the group consisting of

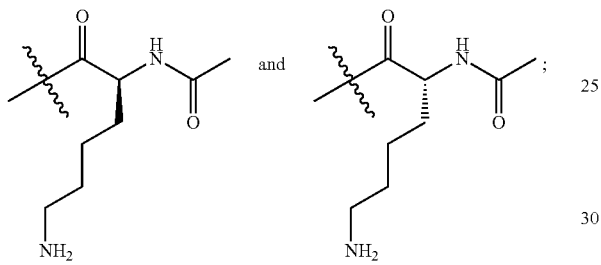

$L^B$ is -$L^{B1}$-$L^{B2}$-$L^{B3}$ wherein
$L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_1$-$C_6$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;
$L^{B2}$ is either absent, or is selected from the group consisting of

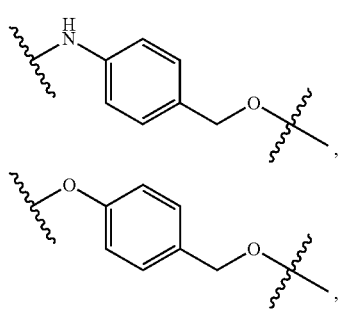

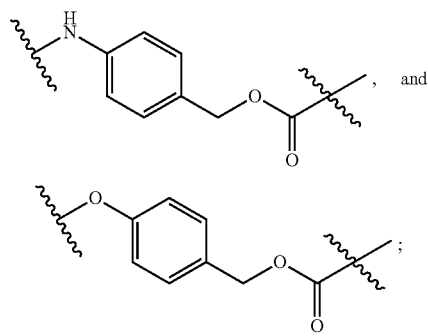

$L^{B3}$ is $AA_{0-12}$, wherein AA is independently for each occurrence a natural amino acid or a non-natural amino acid;
and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl)$_2$, —$C_1$-$C_{10}$ alkyl-$N(C_1$-$C_8$ alkyl)$_2$, —$C_1$-$C_3$ alkylthio, —$NO_2$ or —$C_1$-$C_{10}$ heterocyclyl, for each ring system in which R appears.

In some embodiments of Formula (II), L is -$L^B$-$L^A$, wherein $L^A$ is selected from the group consisting of

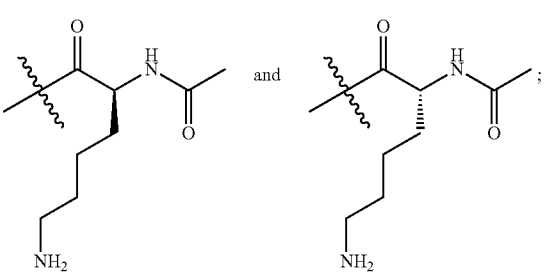 [SMILES: *C(=O)[C@H](CCCCN)NC(C)=O ; *C(=O)[C@@H](CCCCN)NC(C)=O]

$L^B$ is -$L^{B2}$-$L^{B3}$ wherein
$L^{B2}$ is

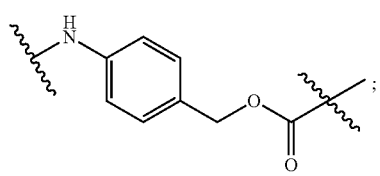 [SMILES: *Nc1ccc(COC(*)=O)cc1]

$L^{B3}$ $AA_{0-12}$, wherein AA is independently for each occurrence a natural amino acid or a non-natural amino acid.

In some embodiments of Formula (II), L is -$L^B$-$L^A$, wherein $L^A$ is selected from the group consisting of

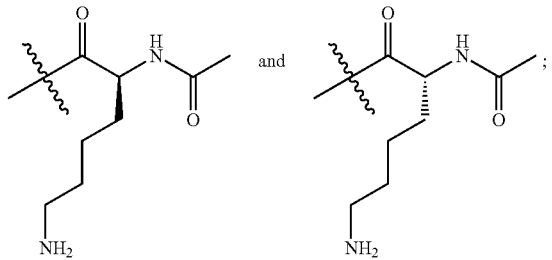 [SMILES: *C(=O)[C@H](CCCCN)NC(C)=O ; *C(=O)[C@@H](CCCCN)NC(C)=O]

$L^B$ is -$L^{B2}$-$L^{B3}$ wherein
$L^{B2}$ is

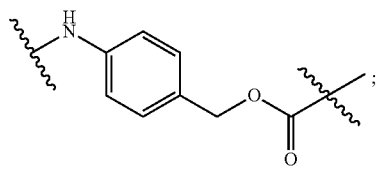 [SMILES: *Nc1ccc(COC(*)=O)cc1]

$L^{B3}$ is $AA_{0-12}$, wherein AA is independently for each occurrence a natural amino acid or a non-natural amino acid.

In some embodiments of Formula (II), L is

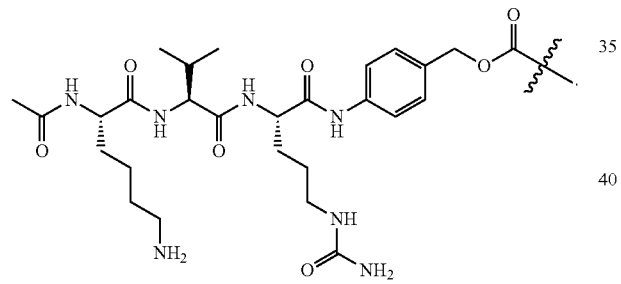

In some embodiments of Formula (II), L is -$L^B$-$L^A$, wherein
$L^A$ is —NHR;
$L^B$ is -$L^{B1}$-$L^{B2}$-$L^{B3}$ wherein
$L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is either absent, or is selected from the group consisting of

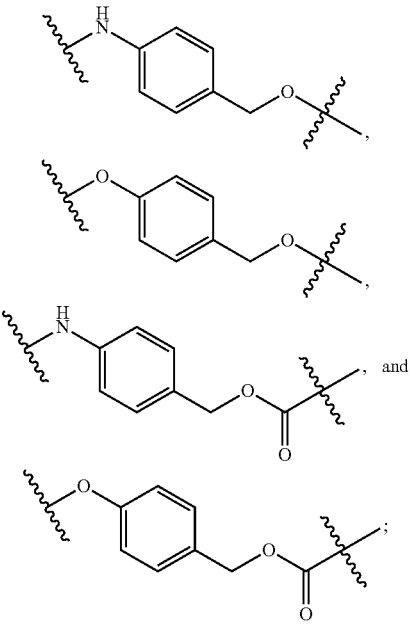

$L^{B3}$ is $AA_{0-12}$, wherein AA is independently for each occurrence a natural amino acid or a non-natural amino acid;
and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH($C_1$-$C_8$ alkyl), —N($C_1$-$C_8$ alkyl)$_2$, —NO$_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —NH$_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —NO$_2$ or —$C_1$-$C_{10}$ heterocyclyl, for each ring system in which R appears.

In some embodiments of Formula (II), L is -$L^B$-$L^A$, wherein
$L^A$ is —NH$_2$;
$L^B$ is -$L^{B1}$-$L^{B2}$-$L^{B3}$ wherein
$L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is either absent, or is selected from the group consisting of

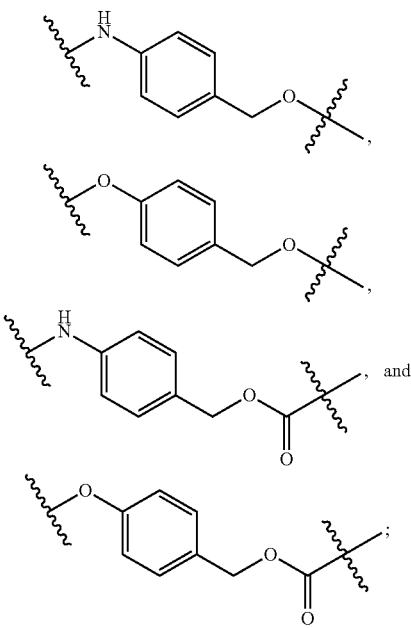

$L^{B3}$ is $AA_{0-12}$, wherein AA is independently for each occurrence a natural amino acid or a non-natural amino acid;
and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl$)_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl$)_2$, —$C_1$-$C_{10}$ alkyl-$N(C_1$-$C_8$ alkyl$)_2$, —$C_1$-$C_3$ alkylthio, —$NO_2$ or —$C_1$-$C_{10}$ heterocyclyl, for each ring system in which R appears.

In some embodiments of Formula (II), L is -$L^B$-$L^A$, wherein $L^A$ is —$NH_2$;
$L^B$ is -$L^{B1}$-
$L^{B1}$ is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;
and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl$)_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl$)_2$, —$C_1$-$C_{10}$ alkyl-$N(C_1$-$C_8$ alkyl$)_2$, —$C_1$-$C_3$ alkylthio, —$NO_2$ or —$C_1$-$C_{10}$ heterocyclyl, for each ring system in which R appears.

In some embodiments of Formula (II), L is -$L^B$-$L^A$, wherein $L^A$ is —$NH_2$; $L^B$ is -$L^{B1}$- wherein $L^B1$ is —$C_1$-$C_6$alkyl(OCH$_2$CH$_2$)$_{1-8}$—.

In some embodiments of Formula (II), L is —(CH$_2$)$_3$—(OCH$_2$CH$_2$)$_6$—NH$_2$.

In some embodiments of Formula (II), L is -$L^B$-$L^A$, wherein
$L^A$ is

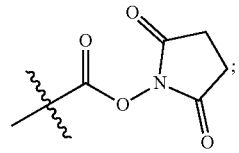 [SMILES: *C(=O)ON1C(=O)CCC1=O]

$L^B$ is selected from the group consisting of -$L^{B1}$-$L^{B2}$-$L^{B3}$ and -$L^{B2}$-$L^{B3}$-$L^{B1}$ wherein
$L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is either absent, or is selected from the group consisting of

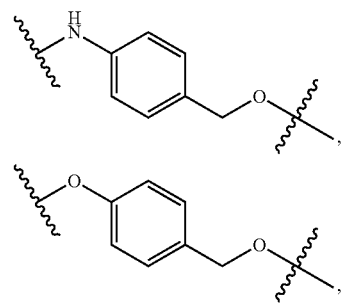

-continued

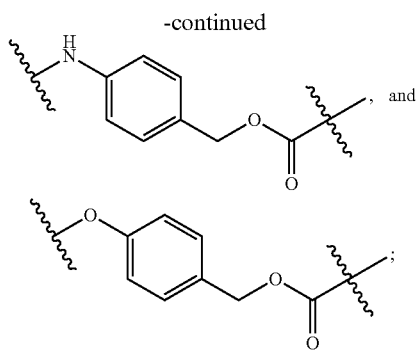

$L^{B3}$ is $AA_{0-12}$, wherein AA is independently for each occurrence a natural amino acid or a non-natural amino acid;
and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl)$_2$, —$C_1$-$C_{10}$ alkyl-$N(C_1$-$C_8$ alkyl)$_2$, —$C_1$-$C_3$ alkylthio, —$NO_2$ or —$C_1$-$C_{10}$ heterocyclyl, for each ring system in which R appears.

In some embodiments of Formula (II), L is -$L^B$-$L^A$, wherein
$L^A$ is

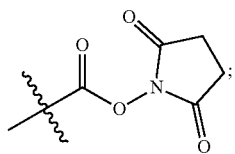 [SMILES: *C(=O)ON1C(=O)CCC1=O]

$L^B$ is -$L^{B1}$ wherein
$L^{B1}$ is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl (OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;
and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl)$_2$, —$C_1$-$C_{10}$ alkyl-$N(C_1$-$C_8$ alkyl)$_2$, —$C_1$-$C_3$ alkylthio, —$NO_2$ or —$C_1$-$C_{10}$ heterocyclyl, for each ring system in which R appears.

In some embodiments of Formula (II), L is -$L^B$-$L^A$, wherein
$L^A$ is

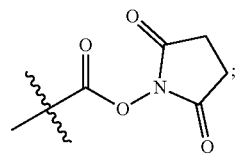 [SMILES: *C(=O)ON1C(=O)CCC1=O]

$L^B$ is -$L^{B1}$- wherein $L^{B1}$ is —C(O)$C_1$-$C_6$alkyl-.

In some embodiments of Formula (II), L is

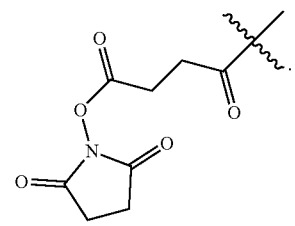 [SMILES: *C(=O)CCC(=O)ON1C(=O)CCC1=O]

In some embodiments of Formula (II), L is -($L^C$)$_1$-$L^B$-$L^A$, wherein
$L^A$ is selected from the group consisting of -halo; —NHR; —CO—H; —CO$_2$H; —S—S-aryl optionally substituted with —$NO_2$; —S—S-heteroaryl optionally substituted with —$NO_2$; alkyl-SO$_2$-heteroaryl; arylSO$_2$-heteroaryl-;

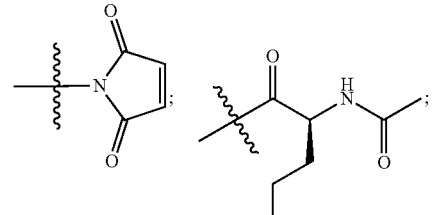

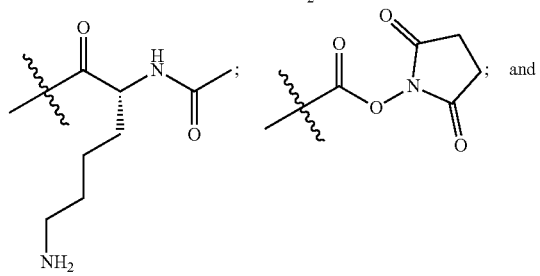

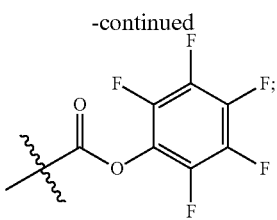

$L^B$ is selected from the group consisting of -$L^{B1}$-$L^{B2}$-$L^{B3}$ and -$L^{B2}$-$L^{B3}$-$L^{B1}$ wherein $L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is either absent, or is selected from the group consisting of

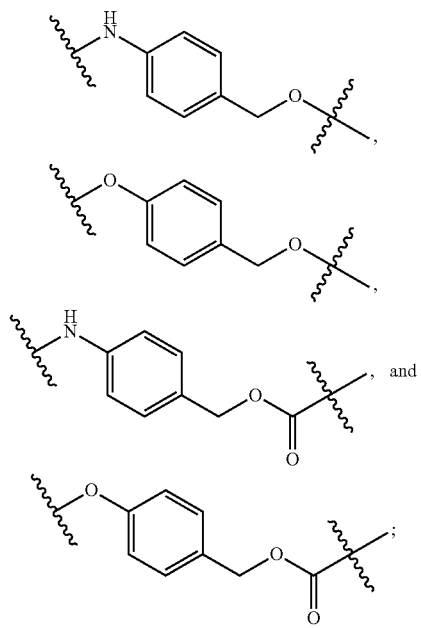

$L^{B3}$ is AA$_{0-12}$, wherein AA is independently for each occurrence a natural amino acid or a non-natural amino acid;

$L^C$ is selected from the group consisting of —CO— and —$C_1$-$C_6$alkylene; and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH($C_1$-$C_8$ alkyl), —N($C_1$-$C_8$ alkyl)$_2$, —NO$_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_0$ alkoxy, -halo, —$C_1$-$C_{10}$ alkylthio, -trifluoromethyl, —NH$_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —NO$_2$ or —$C_1$-$C_{10}$ heterocyclyl, for each ring system in which R appears.

In some embodiments of Formula (II), L is -($L^C$)$_1$-$L^B$-$L^A$, wherein $L^A$ is —NHR;

$L^B$ is -$L^{B1}$-$L^{B2}$-$L^{B3}$ wherein $L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_0$-$C_6$alkylene-NR—, and —NR$C_1$-$C_6$alkylene-;

$L^{B2}$ is either absent, or is selected from the group consisting of

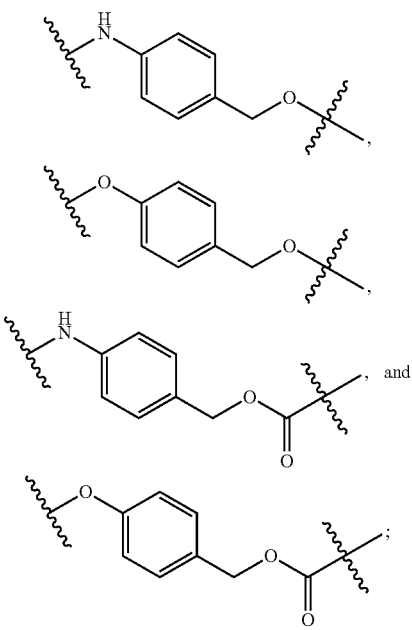

$L^{B3}$ is AA$_{0-12}$, wherein AA is independently for each occurrence a natural amino acid or a non-natural amino acid;

$L^C$ is selected from the group consisting of —CO— and —$C_1$-$C_6$alkylene; and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is -(L$^C$)$_1$-L$^B$-L$^A$, wherein

L$^A$ is —NH$_2$;

L$^B$ is -L$^{B1}$-L$^{B2}$-L$^{B3}$ wherein

L$^{B1}$ is either absent or is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$—NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_{1-6}$alkyl-, —N=CR-phenyl-O—C$_1$-C$_6$alkyl-, —N=CR-phenyl-O—C$_1$-C$_6$alkyl-C(O)—, —C(O)—C$_1$-C$_6$alkyl(OCH$_2$CH$_2$)$_{1-8}$NRC(O)—, —C(O)C$_1$-C$_6$alkyl-phenyl(NR—C(O)C$_1$-C$_6$alkyl)$_{14}$-, —C(O)C$_1$-C$_6$alkyl(OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1-20}$, —C$_1$-C$_6$alkylene-NR—, and —NRC$_1$-C$_6$alkylene-;

L$^{B2}$ is either absent, or is selected from the group consisting of

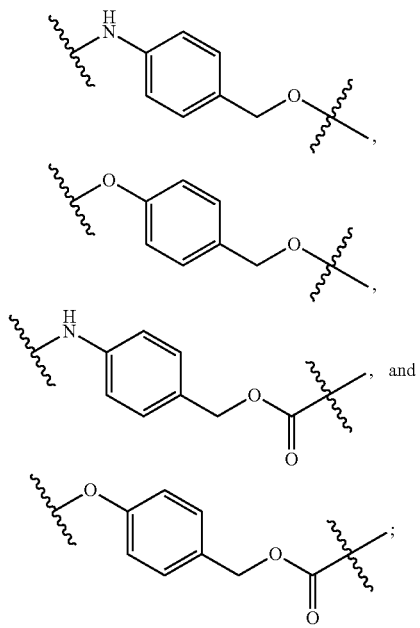

,

,

, and

;

L$^{B3}$ is AA$_{0-12}$, wherein AA is independently for each occurrence a natural amino acid or a non-natural amino acid;

L$^C$ is selected from the group consisting of —CO— and —C$_1$-C$_6$alkylene; and each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is -(L$^C$)$_1$-L$^B$-L$^A$, wherein

L$^A$ is —NH$_2$;

L$^B$ is -L$^{B1}$- wherein

L$^{B1}$ is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$—NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkyl NRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_{1-6}$alkyl-, —N=CR-phenyl-O—C$_1$-C$_6$alkyl-, —N=CR-phenyl-O—C$_1$-C$_6$alkyl-C(O)—, —C(O)—C$_1$-C$_6$alkyl(OCH$_2$CH$_2$)$_{1-8}$NRC(O)—, —C(O)C$_1$-C$_6$alkyl-phenyl(NR—C(O)C$_1$-C$_6$alkyl)$_{14}$-, —C(O)C$_1$-C$_6$alkyl(OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1-20}$, —C$_1$-C$_6$alkylene-NR—, and —NRC$_1$-C$_6$alkylene-;

L$^C$ is selected from the group consisting of —CO— and —C$_1$-C$_6$alkylene; and each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is -(L$^C$)$_1$-L$^B$-L$^A$, wherein

L$^A$ is —NH$_2$;

L$^B$ is -L$^{B1}$- wherein

L$^{B1}$ is two components selected from the group consisting of selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$—NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_{1-6}$alkyl-, —N=CR-phenyl-O—C$_1$-C$_6$alkyl-, —N=CR-phenyl-O—C$_1$-C$_6$alkyl-C(O)—, —C(O)—C$_1$-C$_6$alkyl(OCH$_2$CH$_2$)$_{1-8}$NRC(O)—, —C(O)C$_1$-C$_6$alkyl-phenyl(NR—C(O)C$_1$-C$_6$alkyl)$_{14}$-, —C(O)C$_1$-C$_6$alkyl(OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1\text{-}20}$, —C$_1$-C$_6$alkylene-NR—, and —NRC$_1$-C$_6$alkylene-;

L$^C$ is selected from the group consisting of —CO— and —C$_1$-C$_6$alkylene; and each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is -(L$^C$)$_1$-L$^B$-L$^A$, wherein

L$^A$ is —NH$_2$;

L$^B$ is -L$^{B1}$- wherein L$^{B1}$ is —C(O)NR— and —C$_1$-C$_6$alkyl(OCH$_2$CH$_2$)$_{1\text{-}8}$—;

L$^C$ is —C$_1$-C$_6$alkylene; and each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is —(CH$_2$)—CONH—(CH$_2$)$_2$—(OCH$_2$CH$_2$)$_2$—NH$_2$.

In some embodiments of Formula (II), L is —(CH$_2$)—CONH—(CH$_2$)$_2$—(OCH$_2$CH$_2$)$_7$—NH$_2$.

In some embodiments of Formula (II), L is -(L$^C$)$_1$-L$^B$-L$^A$, wherein L$^A$ is —NH$_2$; L$^B$ is -L$^{B1}$, L$^{B1}$- is —C(O)C$_1$-C$_6$alkyl; and L$^C$ is —CO—.

In some embodiments of Formula (II), L is —CO—(CH$_2$)$_2$—CO—NH$_2$.

In some embodiments of Formula (II), L is -(L$^C$)$_1$-L$^B$-L$^A$, wherein L$^A$ is —NH$_2$; L$^B$ is -L$^{B1}$- wherein L$^{B1}$ is —C(O)NRC$_1$-C$_6$alkyl- and —NRC$_1$-C$_6$alkylene-; L$^C$ is —C$_1$-C$_6$alkylene; and each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is —(CH$_2$)—CONH—(CH$_2$)$_3$—NH—(CH$_2$)$_4$—NH—(CH$_2$)$_3$—NH$_2$.

In some embodiments of Formula (II), L is L is -(L$^C$)$_1$-L$^B$-L$^A$, wherein L$^A$ is selected from the group consisting of

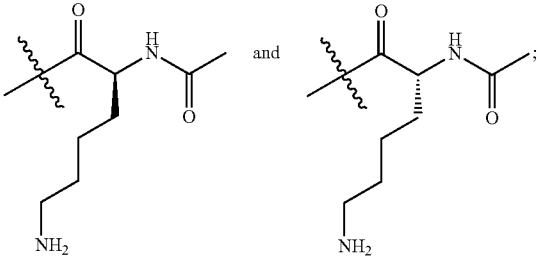 [SMILES: *C(=O)[C@H](CCCCN)NC(C)=O ; *C(=O)[C@@H](CCCCN)NC(C)=O]

L$^B$ is -L$^{B1}$-L$^{B3}$ wherein

L$^{B1}$ is either absent or is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1\text{-}8}$—, —C$_1$-C$_6$alkyl(OCH$_2$CH$_2$)$_{1\text{-}8}$—NR—, —C(O)C$_1$-C$_6$alkylNRC(O)—, —C(O)C$_1$-C$_6$alkyl(OCH$_2$CH$_2$)$_{1\text{-}8}$—, —C$_1$-C$_6$alkyl(OCH$_2$CH$_2$)$_{1\text{-}8}$—C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1\text{-}8}$NRC(O)CH$_2$—, —C(O)C$_1$-C$_6$alkyl-NRC(O)C$_{1\text{-}6}$alkyl-, —N=CR-phenyl-O—C$_1$-C$_6$alkyl-, —N=CR— phenyl-O—C$_1$-C$_6$alkyl-C(O)—, —C(O)—C$_1$-C$_6$alkyl(OCH$_2$CH$_2$)$_{1\text{-}8}$NRC(O)—, —C(O)C$_1$-C$_6$alkyl-phenyl(NR—C(O)C$_1$-C$_6$alkyl)$_{1\text{-}4}$-, —C(O)C$_1$-C$_6$alkyl(OCH$_2$CH$_2$)$_{1\text{-}8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1\text{-}20}$, —C$_1$-C$_6$alkylene-NR—, and —NRC$_1$-C$_6$alkylene-;

L$^{B3}$ is AA$_{0\text{-}12}$, wherein AA is independently for each occurrence a natural amino acid or a non-natural amino acid;

L$^C$ is —C$_1$-C$_6$alkylene; and each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is L is -(L$^C$)$_1$-L$^B$-L$^A$, wherein L$^A$ is selected from the group consisting of

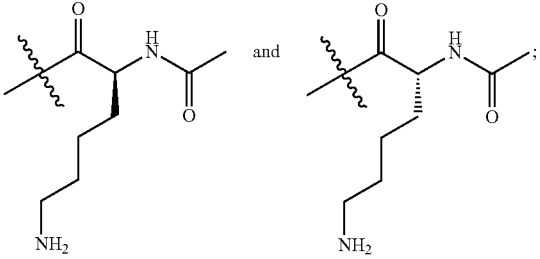 [SMILES: *C(=O)[C@H](CCCCN)NC(C)=O ; *C(=O)[C@@H](CCCCN)NC(C)=O]

L$^B$ is -L$^{B1}$-L$^{B3}$ wherein

L$^{B1}$ is two components selected from the group consisting of —C(O)NR—, —C(O)C$_1$-C$_6$alkyl-, —C(O)NRC$_1$-

C₆alkyl-, —C₁-C₆alkyl(OCH₂CH₂)₁₋₈—, —C₁-C₆alkyl(OCH₂CH₂)₁₋₈—NR—, —C(O)C₁-C₆alkylNRC(O)—, —C(O)C₁-C₆alkyl(OCH₂CH₂)₁₋₈—, —C₁-C₆alkyl(OCH₂CH₂)₁₋₈—C(O)—, —C₁-C₆alkyl-S—S—C₁-C₆alkyl NRC(O)CH₂—, —C₁-C₆alkyl(OCH₂CH₂)₁₋₈NRC(O)CH₂—, —C(O)C₁-C₆alkyl-NRC(O)C₁₋₆alkyl-, —N=CR-phenyl-O—C₁-C₆alkyl-, —N=CR— phenyl-O—C₁-C₆alkyl-C(O)—, —C(O)—C₁-C₆alkyl(OCH₂CH₂)₁₋₈NRC(O)—, —C(O)C₁-C₆alkyl-phenyl(NR—C(O)C₁-C₆alkyl)₁₋₄-, —C(O)C₁-C₆alkyl(OCH₂CH₂)₁₋₈—NRC(O)C₁-C₆alkyl-, —C₁-C₆alkyl-, —S—, —C(O)—CH(NR—C(O)C₁-C₆alkyl)-C₁-C₆alkyl-, (—CH₂—CH₂—O—)₁₋₂₀, —C₁-C₆alkylene-NR—, and —NRC₁-C₆alkylene-;

L^{B2} is either absent, or is selected from the group consisting of

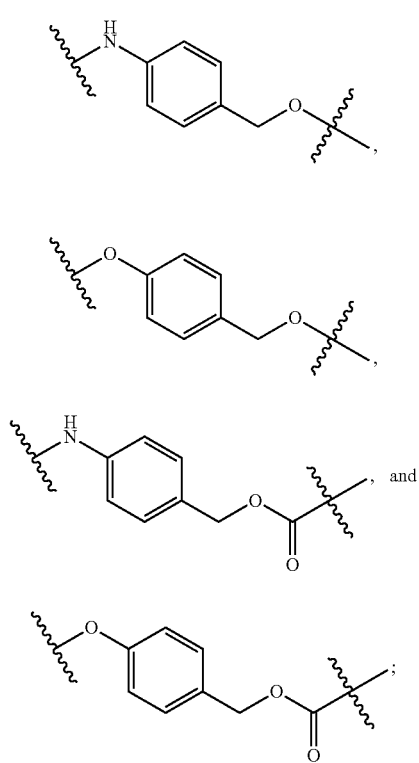

L^{B3} is AA₀₋₁₂, wherein AA is independently for each occurrence a natural amino acid or a non-natural amino acid;
L^{C} is —C₁-C₆alkylene; and
each R is independently selected from the group consisting of H, —C₁-C₂₀ alkyl, —C₂-C₆ alkenyl, —C₂-C₆ alkynyl, halo, hydroxyl, alkoxy, —NH₂, —NH(C₁-C₈ alkyl), —N(C₁-C₈ alkyl)₂, —NO₂, —C₆-C₁₄ aryl and —C₆-C₁₄ heteroaryl, wherein two or more R optionally join to form a ring or rings, and wherein said —C₆-C₁₄ aryl and —C₆-C₁₄ heteroaryl are optionally substituted with 1 to 5 substituents independently selected from —C₁-C₁₀ alkyl, —C₁-C₀ alkoxy, -halo, —C₁-C₁₀ alkyl-thio, -trifluoromethyl, —NH₂, —NH(C₁-C₈ alkyl), —N(C₁-C₈ alkyl)₂, —C₁-C₁₀ alkyl-N(C₁-C₈ alkyl)₂, —C₁-C₃ alkylthio, —NO₂ or —C₁-C₀ heterocyclyl, for each ring system in which R appears.

In some embodiments of Formula (II), L is L is -(L^{C})₁-L^{B}-L^{A}, wherein
L^{A} is selected from the group consisting of

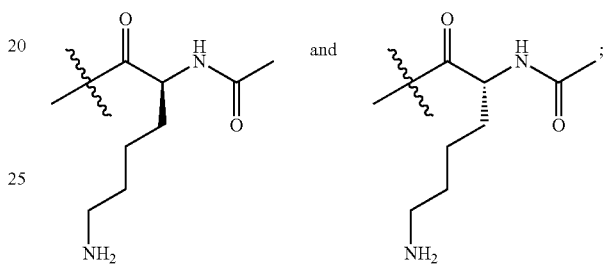

L^{B} is -L^{B1}-L^{B3} wherein
L^{B1} is —C(O)NR— and —C₁-C₆alkyl(OCH₂CH₂)₁₋₈—NR;
L^{B3} AA₂, wherein AA is independently for each occurrence a natural amino acid or a non-natural amino acid; and
L^{C} is —C₁-C₆alkylene.

In some embodiments of Formula (II), L is

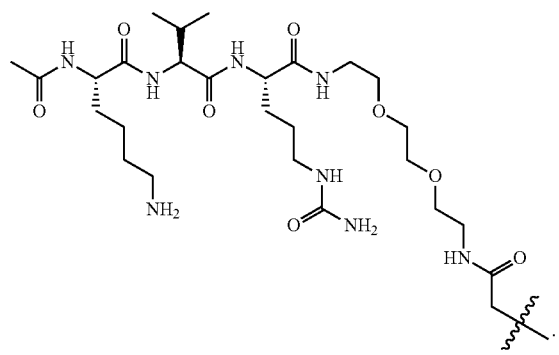 [SMILES: *CC(=O)NCCOCCOCCNC(=O)[C@H](CCCNC(N)=O)NC(=O)[C@@H](NC(=O)[C@H](CCCCN)NC(C)=O)C(C)C]

In some embodiments of Formula (II), L is

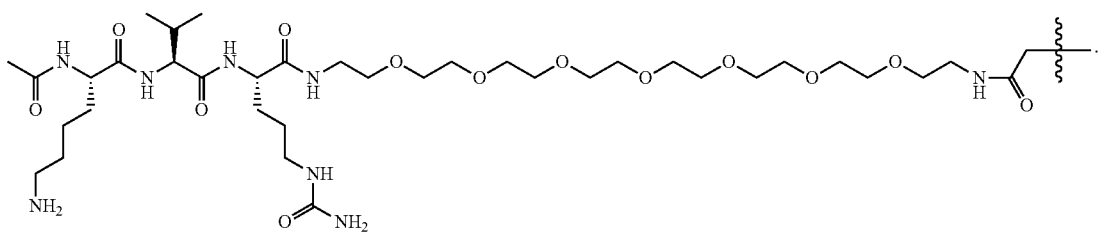 [SMILES: *CC(=O)NCCOCCOCCOCCOCCOCCOCCOCCNC(=O)[C@H](CCCNC(N)=O)NC(=O)[C@@H](NC(=O)[C@H](CCCCN)NC(C)=O)C(C)C]

In some embodiments of Formula (II), L is L is -(L)$_1$-L$^B$-L$^A$, wherein
L$^A$ is selected from the group consisting of

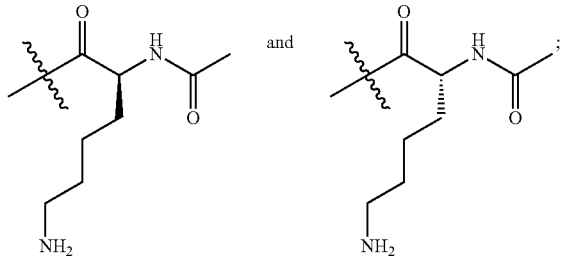 [SMILES: *C(=O)[C@H](CCCCN)NC(C)=O ; *C(=O)[C@@H](CCCCN)NC(C)=O]

and;

L$^B$ is -L$^{B1}$-L$^{B3}$ wherein
L$^{B1}$ is —C(O)NRC$_1$-C$_6$alkyl- and —NRC$_1$-C$_6$alkylene-;
L$^{B3}$ AA$_2$, wherein AA is independently for each occurrence a natural amino acid or a non-natural amino acid; and
L$^C$ is —C$_1$-C$_6$alkylene.

In some embodiments of Formula (II), L is

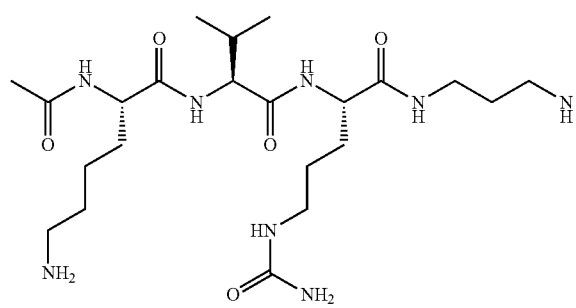

In some embodiments of Formula (II), L is L is -(L$^C$)$_1$-L$^B$-L$^A$, wherein
L$^A$ is selected from the group consisting of

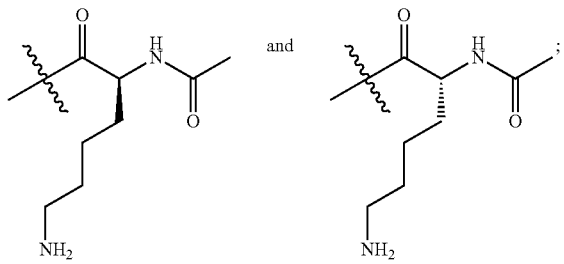 [SMILES: *C(=O)[C@H](CCCCN)NC(C)=O ; *C(=O)[C@@H](CCCCN)NC(C)=O]

L$^B$ is -L$^{B1}$-L$^{B2}$-L$^{B3}$ wherein
L$^{B1}$ is either absent or is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkyl NRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_{1-6}$alkyl-, —N=CR-phenyl-O—C$_1$-C$_6$alkyl-, —N=CR— phenyl-O—C$_1$-C$_6$alkyl-C(O)—, —C(O)—C$_1$-C$_6$alkyl (OCH$_2$CH$_2$)$_{1-8}$NRC(O)—, —C(O)C$_1$-C$_6$alkyl-phenyl (NR—C(O)C$_1$-C$_6$alkyl)$_{1-4}$-, —C(O)C$_1$-C$_6$alkyl (OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1-20}$, —C$_1$-C$_6$alkylene-NR—, and —NRC$_1$-C$_6$alkylene-;
L$^{B2}$ is

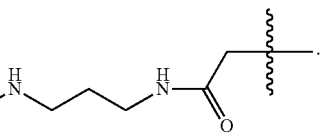

and;

L$^{B3}$ is AA$_{0-12}$, wherein AA is independently for each occurrence a natural amino acid or a non-natural amino acid;
L$^C$ is —C$_1$-C$_6$alkylene; and
each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is L is -(L$^C$)-L$^B$-L$^A$, wherein
L$^A$ is selected from the group consisting of

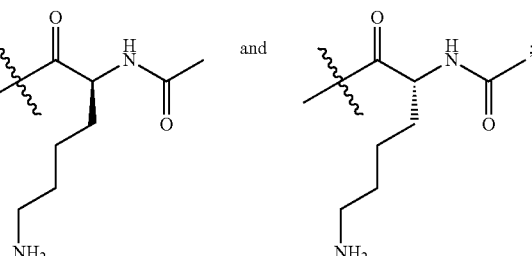

$L^B$ is $-L^{B1}-L^{B2}-L^{B3}$ wherein $L^{B1}$ is two components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is

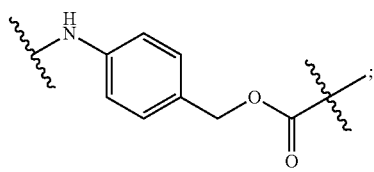 [SMILES: *Nc1ccc(COC(*)=O)cc1]

$L^{B3}$ AA$_{0-12}$, wherein AA is independently for each occurrence a natural amino acid or a non-natural amino acid;

$L^C$ is —$C_1$-$C_6$alkylene; and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH($C_1$-$C_8$ alkyl), —N($C_1$-$C_8$ alkyl)$_2$, —NO$_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —NH$_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —NO$_2$ or —$C_1$-$C_{10}$ heterocyclyl, for each ring system in which R appears.

In some embodiments of Formula (II), L is -(L$^C$)$_1$-L$^B$-L$^A$, wherein $L^A$ is selected from the group consisting of

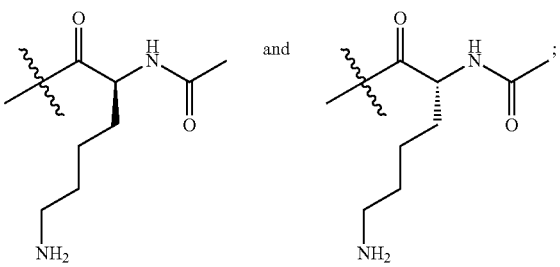 [SMILES: *C(=O)[C@H](CCCCN)NC(C)=O ; *C(=O)[C@@H](CCCCN)NC(C)=O]

$L^B$ is $-L^{B1}-L^{B2}-L^{B3}$ wherein $L^{B1}$ is —C(O)NR— and —$C_1$-$C_6$alkyl(OCH$_2$CH$_2$)$_{1-8}$—NR;

$L^{B2}$ is

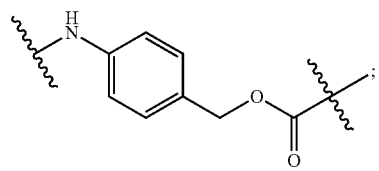 [SMILES: *Nc1ccc(COC(*)=O)cc1]

$L^{B3}$ AA$_2$, wherein AA is independently for each occurrence a natural amino acid or a non-natural amino acid; and $L^C$ is —$C_1$-$C_6$alkylene.

In some embodiments of Formula (II), L is

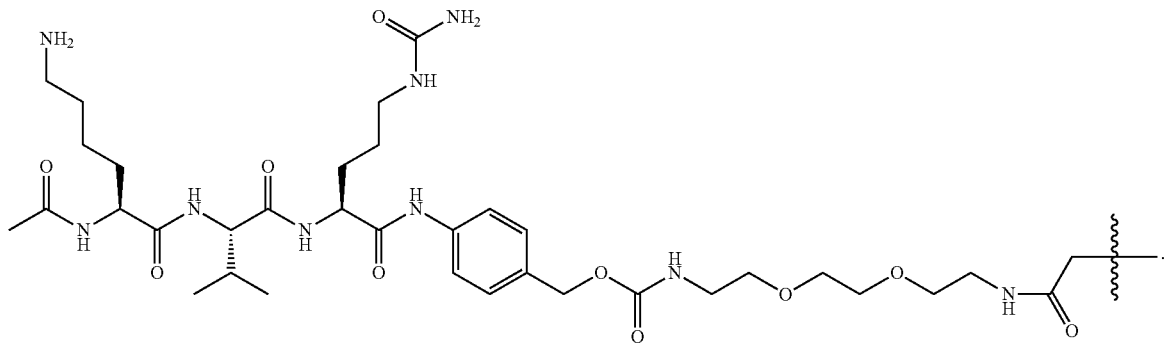 [SMILES: *CC(=O)NCCOCCOCCNC(=O)OCc1ccc(NC(=O)[C@H](CCCNC(N)=O)NC(=O)[C@@H](NC(=O)[C@H](CCCCN)NC(C)=O)C(C)C)cc1]

In some embodiments of Formula (II), L is -(L$^C$)$_1$-L$^B$-L$^A$, wherein $L^A$ is selected from the group consisting of

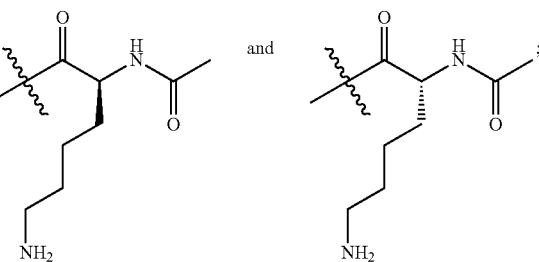

$L^B$ is -$L^{B1}$-$L^{B2}$-$L^{B3}$ wherein
  $L^{B1}$ is —C(O)NR$C_1$-$C_6$alkyl- and —NR$C_1$-$C_6$alkylene-;
  $L^{B2}$ is

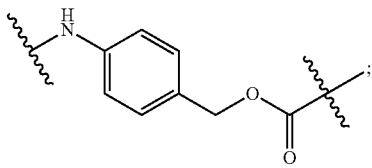 [SMILES: *Nc1ccc(COC(*)=O)cc1]

$L^{B3}$ $AA_2$, wherein AA is independently for each occurrence a natural amino acid or a non-natural amino acid;
$L^C$ is —$C_1$-$C_6$alkylene.
In some embodiments of Formula (II), L is

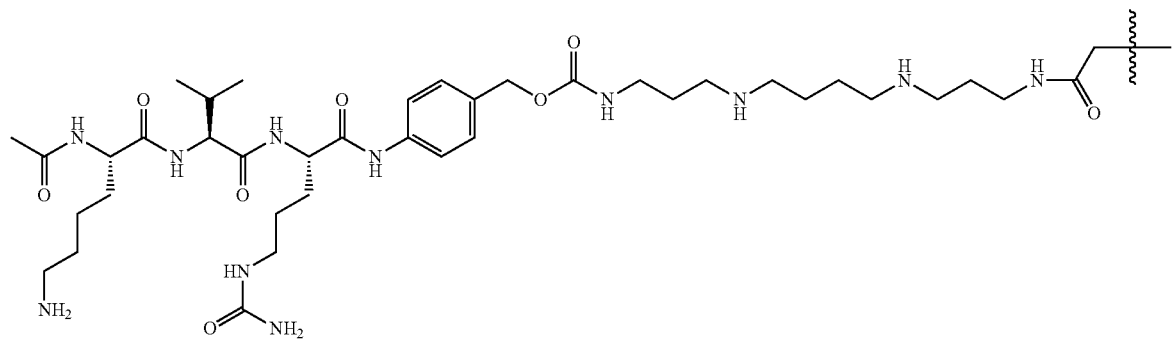 [SMILES: *CC(=O)NCCCNCCCCNCCCNC(=O)OCc1ccc(NC(=O)[C@H](CCCNC(N)=O)NC(=O)[C@@H](NC(=O)[C@H](CCCCN)NC(C)=O)C(C)C)cc1]

In some embodiments of Formula (II), L is -$(L^C)_2$-$L^B$-$L^A$, wherein
  $L^A$ is selected from the group consisting of -halo; —NHR; —CO—H; —$CO_2$H; —S—S-aryl optionally substituted with —$NO_2$; —S—S-heteroaryl optionally substituted with —$NO_2$; alkyl-$SO_2$-heteroaryl; aryl$SO_2$-heteroaryl-;

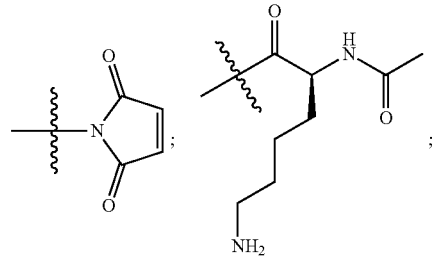

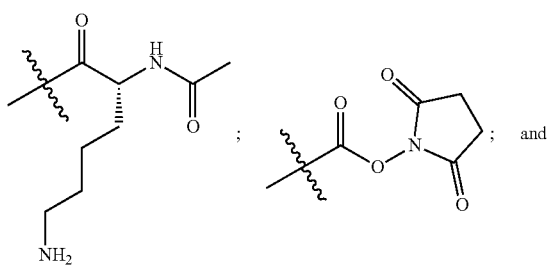

-continued

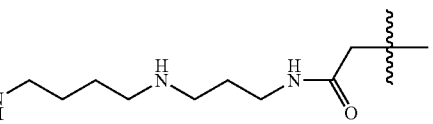

$L^B$ is -$L^{B1}$-$L^{B2}$-$L^{B3}$ wherein
  $L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;
  $L^{B2}$ is either absent, or is selected from the group consisting of

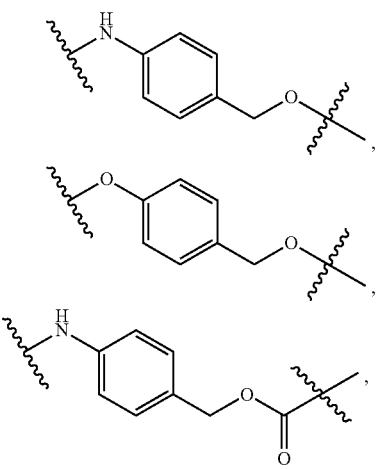

-continued

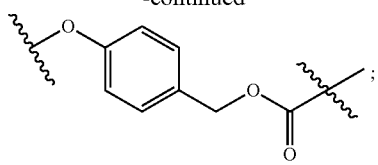

$L^{B3}$ is $AA_{0-12}$, wherein AA is independently for each occurrence a natural amino acid or a non-natural amino acid;

$L^C$ is either absent or is selected, independently for each occurrence, from the group consisting of —CO—, —$C_1$-$C_6$alkylene-, —NR$C_3$-$C_8$-heterocyclylNR—, —NR$C_3$-$C_8$-carbocyclylNR—, —NR$C_1$-$C_6$alkylNR—, —NR$C_1$-$C_6$alkylene-, —S—, —NR—, —NRNR—, —O(CR$_2$)$_{1-4}$S—S(CR$_2$)$_{1-4}$N(R)—, —NR$C_1$-$C_6$-alkylenephenyleneNR—, —NR$C_1$-$C_6$alkylenephenyleneSO$_2$NR—, —O$C_1$-$C_6$alkylS-S$C_1$-$C_6$alkylC(COOR)NR—, —NRC(COOR)$C_1$-$C_6$alkylS-S$C_1$-$C_6$alkylO—,

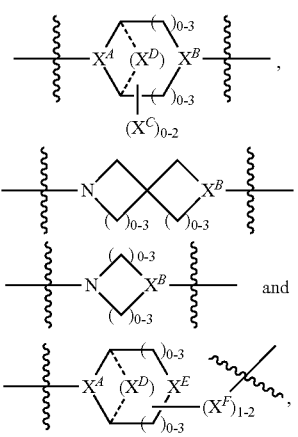

wherein
$X^A$ is selected from the group consisting of CR and N;
$X^B$ is selected from the group consisting of CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) and N;
each $X^C$ is R;
each $X^D$ is either absent or —(CH$_2$)$_{1-5}$—;
$X^E$ is selected from the group consisting of O, S, C(R)$_2$, C(R)(C(R)$_2$)$_{1-3}$—NR$_2$ and NR;
each $X^F$ is selected from the group consisting of (C(R)$_2$)$_{1-3}$—NR and C(R)$_2$—(C(R)$_2$)$_{1-3}$—O; and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH($C_1$-$C_8$ alkyl), —N($C_1$-$C_8$ alkyl)$_2$, —NO$_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —NH$_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —NO$_2$ or —$C_1$-$C_{10}$ heterocyclyl, for each ring system in which R appears.

In some embodiments of Formula (II), L is -(L$^C$)$_2$-L$^B$-L$^A$, wherein
$L^A$ is selected from the group consisting of -halo; —NHR; —CO—H; —CO$_2$H; —S—S-aryl optionally substituted with —NO$_2$; —S—S-heteroaryl optionally substituted with —NO$_2$; alkyl-SO$_2$-heteroaryl; arylSO$_2$-heteroaryl-;

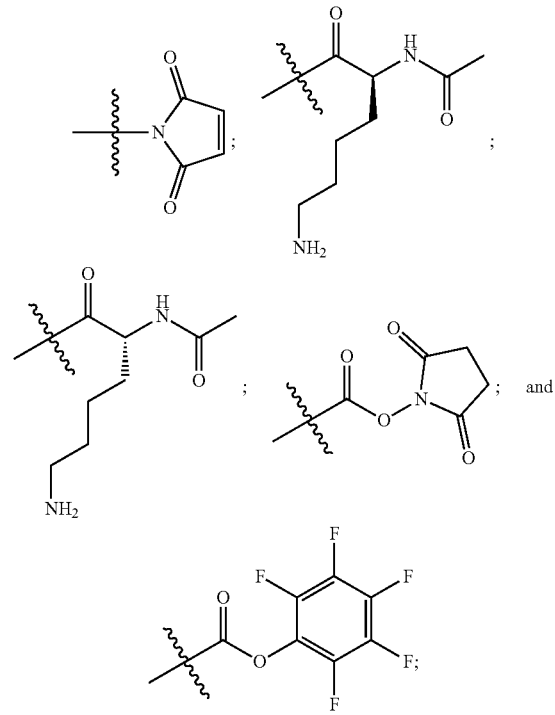

$L^B$ is -$L^{B1}$-$L^{B2}$-$L^{B3}$ wherein
$L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_1$-$C_6$alkyl-, —N═CR-phenyl-O—$C_1$-$C_6$alkyl-, —N═CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$ alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;
$L^{B2}$ is either absent, or is selected from the group consisting of

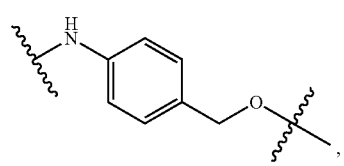

-continued

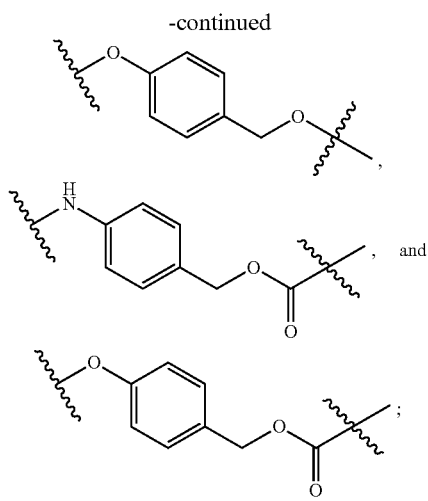

L$^{B3}$ is AA$_{0-12}$, wherein AA is independently for each occurrence a natural amino acid or a non-natural amino acid;

L$^C$ is —CO—, and —NRC$_1$-C$_6$-alkylenephenyleneNR; and each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is L is -(L$^C$)$_2$-L$^B$-L$^A$, wherein L$^A$ is selected from the group consisting of

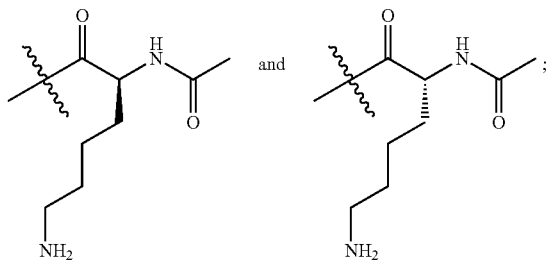 [SMILES: *C(=O)[C@H](CCCCN)NC(C)=O ; *C(=O)[C@@H](CCCCN)NC(C)=O]

L$^B$ is -L$^{B1}$-L$^{B3}$ wherein

L$^{B1}$ is either absent or is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$—NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_1$-C$_6$alkyl-, —N=CR-phenyl-O—C$_1$-C$_6$alkyl-, —N=CR— phenyl-O—C$_1$-C$_6$alkyl-C(O)—, —C(O)—C$_1$-C$_6$alkyl(OCH$_2$CH$_2$)$_{1-8}$NRC(O)—, —C(O)C$_1$-C$_6$alkyl-phenyl(NR—C(O)C$_1$-C$_6$alkyl)$_{1-4}$-, —C(O)C$_1$-C$_6$alkyl(OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1-20}$, —C$_1$-C$_6$alkylene-NR—, and —NRC$_1$-C$_6$alkylene-;

L$^{B3}$ is AA$_{0-12}$, wherein AA is independently for each occurrence a natural amino acid or a non-natural amino acid;

L$^C$ is —CO—, and —NRC$_1$-C$_6$-alkylenephenyleneNR; and each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears.

In some embodiments of Formula (II), L is L is -(L$^C$)$_2$-L$^B$-L$^A$, wherein L$^A$ is selected from the group consisting of

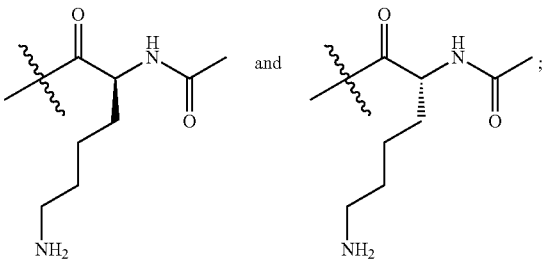 [SMILES: *C(=O)[C@H](CCCCN)NC(C)=O ; *C(=O)[C@@H](CCCCN)NC(C)=O]

L$^B$ is -L$^{B1}$-L$^{B2}$-L$^{B3}$ wherein

L$^{B1}$ is either absent or is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$—NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkylNRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_1$-C$_6$alkyl-, —N=CR-phenyl-O—C$_1$-C$_6$alkyl-, —N=CR— phenyl-O—C$_1$-C$_6$alkyl-C(O)—, —C(O)—C$_1$-C$_6$alkyl(OCH$_2$CH$_2$)$_{1-8}$NRC(O)—, —C(O)C$_1$-C$_6$alkyl-phenyl(NR—C(O)C$_1$-C$_6$alkyl)$_{1-4}$-, —C(O)C$_1$-C$_6$alkyl(OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1-20}$, —C$_1$-C$_6$alkylene-NR—, and —NRC$_1$-C$_6$alkylene-;

L$^{B2}$ is

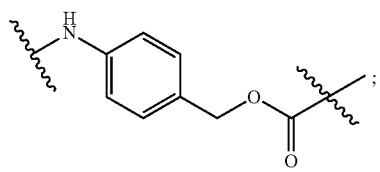 [SMILES: *Nc1ccc(COC(*)=O)cc1]

$L^{B3}$ $AA_{0-12}$, wherein AA is independently for each occurrence a natural amino acid or a non-natural amino acid;

$L^C$ is —CO—, and —NR$C_1$-$C_6$-alkylenephenyleneNR; and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears.

In some embodiments of Formula (II), L is L is -($L^C$)$_2$-$L^B$-$L^A$, wherein $L^A$ is selected from the group consisting of

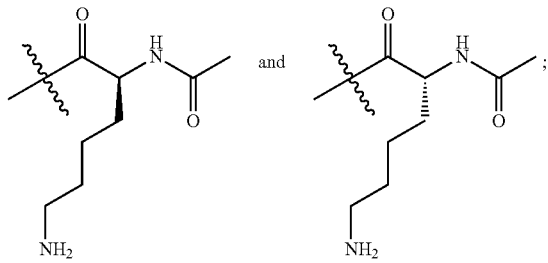 [SMILES: *C(=O)[C@H](CCCCN)NC(C)=O ; *C(=O)[C@@H](CCCCN)NC(C)=O]

and $L^B$ is -$L^{B2}$-$L^{B3}$ wherein $L^{B2}$ is

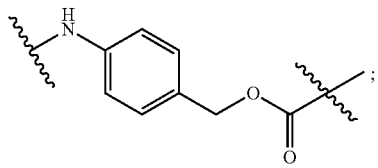 [SMILES: *Nc1ccc(COC(*)=O)cc1]

$L^{B3}$ $AA_{0-12}$, wherein AA is independently for each occurrence a natural amino acid or a non-natural amino acid;

$L^C$ is —CO—, and —NR$C_1$-$C_6$-alkylenephenyleneNR; and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears.

In some embodiments of Formula (II), L is -($L^C$)$_2$-$L^B$-$L^A$, wherein $L^A$ is selected from the group consisting of

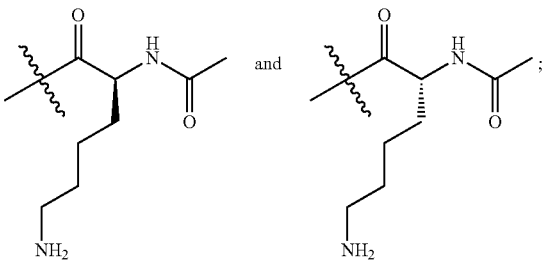

and $L^B$ is -$L^{B2}$-$L^{B3}$ wherein $L^{B2}$ is

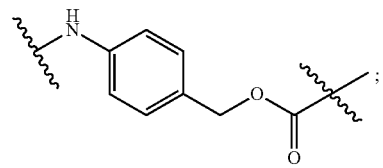 [SMILES: *Nc1ccc(COC(*)=O)cc1]

$L^{B3}$ $AA_2$, wherein AA is independently for each occurrence a natural amino acid or a non-natural amino acid; and $L^C$ is —CO—, and —NH$C_1$-$C_6$-alkylenephenyleneNH.

In some embodiments of Formula (II), L is

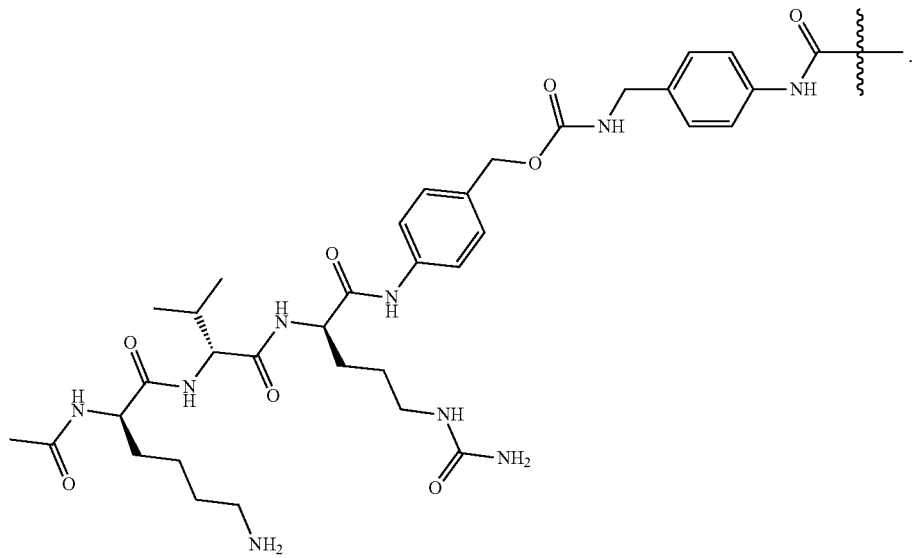 [SMILES: *C(=O)Nc1ccc(CNC(=O)OCc2ccc(NC(=O)[C@@H](CCCNC(N)=O)NC(=O)[C@H](NC(=O)[C@@H](CCCCN)NC(C)=O)C(C)C)cc2)cc1]

In some embodiments of Formula (II), L is -$L^B$-$L^A$, wherein $L^A$ is selected from the group consisting of -halo; —NHR; —CO—H; —$CO_2$H; —S—S-aryl optionally substituted with —$NO_2$; —S—S-heteroaryl optionally substituted with —$NO_2$; alkyl-$SO_2$-heteroaryl; aryl$SO_2$-heteroaryl-;

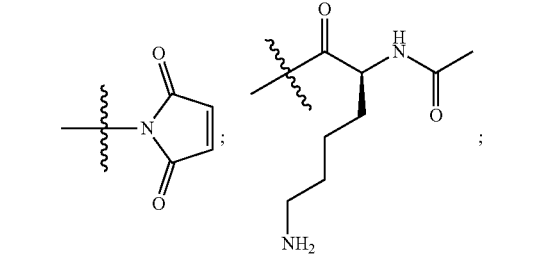

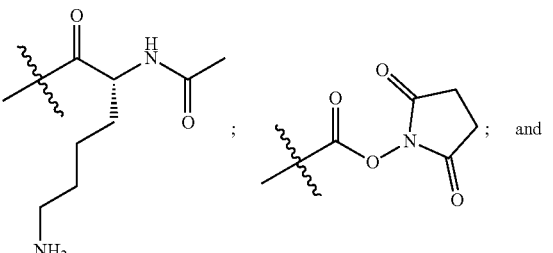

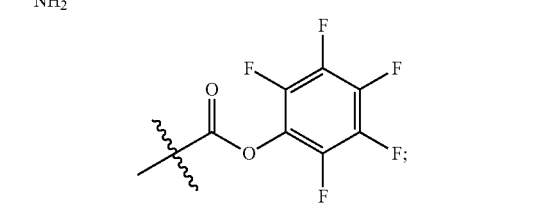

$L^B$ is -$L^{B2}$-$L^{B3}$-$L^{B1}$ wherein $L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR—phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is either absent, or is selected from the group consisting of

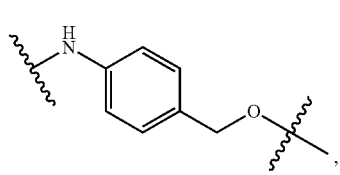

-continued

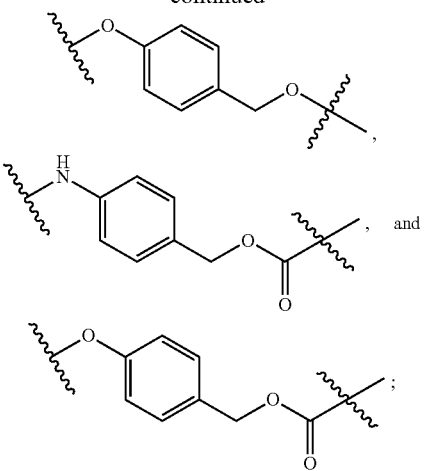

$L^{B3}$ is AA$_{0-12}$, wherein AA is independently for each occurrence a natural amino acid or a non-natural amino acid;

each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH($C_1$-$C_8$ alkyl), —N($C_1$-$C_8$ alkyl)$_2$, —NO$_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —NH$_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —NO$_2$ or —$C_1$-$C_{10}$ heterocyclyl, for each ring system in which R appears.

In some embodiments of Formula (II), L is -$L^B$-$L^A$, wherein $L^A$ is

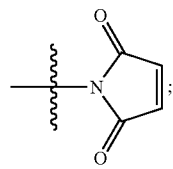 [SMILES: *N1C(=O)C=CC1=O]

$L^B$ is -$L^{B2}$-$L^{B3}$-$L^{B1}$ wherein $L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$, —$C_1$-$C_6$alkyl(OCH$_2$CH$_2$)$_{1-8}$—NR—, —C(O)$C_1$-$C_6$alkylNRC(O)—, —C(O)$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is either absent, or is selected from the group consisting of

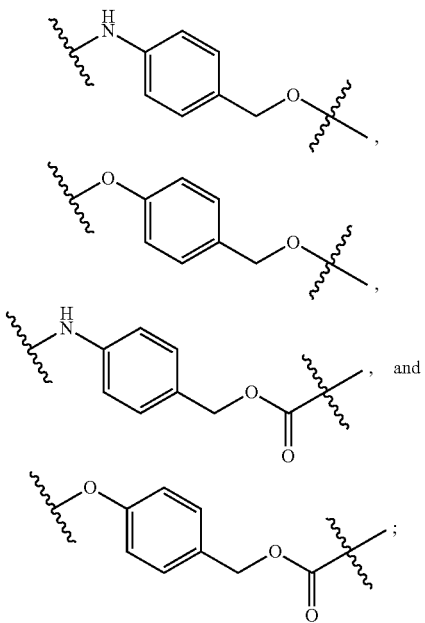

, and

;

$L^{B3}$ is $AA_{0-12}$, wherein AA is independently for each occurrence a natural amino acid or a non-natural amino acid;

and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl)$_2$, —$C_1$-$C_{10}$ alkyl-$N(C_1$-$C_8$ alkyl)$_2$, —$C_1$-$C_3$ alkylthio, —$NO_2$ or —$C_1$-$C_{10}$ heterocyclyl, for each ring system in which R appears.

In some embodiments of Formula (II), L is -$L^B$-$L^A$, wherein $L^A$ is

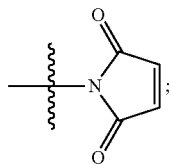 [SMILES: *N1C(=O)C=CC1=O]

;

$L^B$ is -$L^{B2}$-$L^{B3}$-$L^{B1}$ wherein $L^{B1}$ is either absent or is one or more components selected from the group consisting of —C(O)NR—, —C(O)$C_1$-$C_6$alkyl-, —C(O)NR$C_1$-$C_6$alkyl-, —$C_1$-$C_6$alkyl (OCH$_2$CH$_2$)$_{1-8}$—, —$C_1$-$C_6$alkyl(OCH$_2$CH$_2$)$_{1-8}$—NR—, —C(O)$C_1$-$C_6$alkylNRC(O)—, —$C_1$-$C_6$alkyl(OCH$_2$CH$_2$)$_{1-8}$—, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl(OCH$_2$CH$_2$)$_{1-8}$NRC(O) CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl (OCH$_2$CH$_2$)$_{1-8}$NRC(O)—, —C(O)$C_1$-$C_6$alkyl-phenyl (NR—C(O)$C_1$-$C_6$alkyl)$_{1-4}$-, —C(O)$C_1$-$C_6$alkyl (OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is

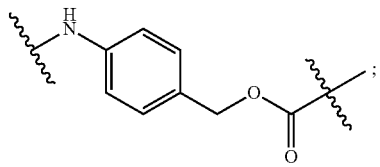 [SMILES: *Nc1ccc(COC(*)=O)cc1]

;

$L^{B3}$ $AA_{0-12}$, wherein AA is independently for each occurrence a natural amino acid or a non-natural amino acid; and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl)$_2$, —$C_1$-$C_{10}$ alkyl-$N(C_1$-$C_8$ alkyl)$_2$, —$C_1$-$C_3$ alkylthio, —$NO_2$ or —$C_1$-$C_{10}$ heterocyclyl, for each ring system in which R appears.

In some embodiments of Formula (II), L is -$L^B$-$L^A$, wherein $L^A$ is

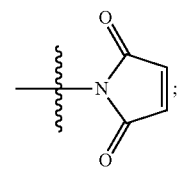 [SMILES: *N1C(=O)C=CC1=O]

;

$L^B$ is -$L^{B2}$-$L^{B3}$-$L^{B1}$ wherein $L^{B1}$ is one component selected from the group consisting of —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-8}$, —$C_1$-$C_6$alkyl (OCH$_2$CH$_2$)$_{1-8}$—NR—, —C(O)$C_1$-$C_6$alkylNRC (O)—, —C(O)$C_1$-$C_6$alkyl(OCH$_2$CH$_2$)$_{1-8}$, —$C_1$-$C_6$alkyl(OCH$_2$CH$_2$)$_{1-8}$—C(O)—, —$C_1$-$C_6$alkyl-S—S—$C_1$-$C_6$alkyl NRC(O)CH$_2$—, —$C_1$-$C_6$alkyl (OCH$_2$CH$_2$)$_{1-8}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR— phenyl-O—$C_1$-$C_6$alkyl-C(O)—, —C(O)—$C_1$-$C_6$alkyl(OCH$_2$CH$_2$)$_{1-8}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-8}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl-, (—CH$_2$—CH$_2$—O—)$_{1-20}$, —$C_1$-$C_6$alkylene-NR—, and —NR$C_1$-$C_6$alkylene-;

$L^{B2}$ is

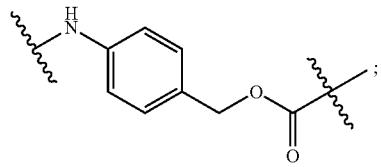 [SMILES: *Nc1ccc(COC(*)=O)cc1]

$L^{B3}$ AA$_2$, wherein AA is independently for each occurrence a natural amino acid or a non-natural amino acid; and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH($C_1$-$C_8$ alkyl), —N($C_1$-$C_8$ alkyl)$_2$, —NO$_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —NH$_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —NO$_2$ or —$C_1$-$C_{10}$ heterocyclyl, for each ring system in which R appears.

In some embodiments of Formula (II), L is -$L^B$-$L^A$, wherein $L^A$ is

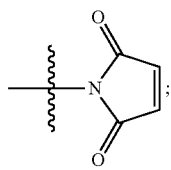 [SMILES: *N1C(=O)C=CC1=O]

$L^B$ is -$L^{B2}$-$L^{B3}$-$L^{B1}$ wherein $L^{B1}$ is —C(O)$C_1$-$C_6$alkyl-;
$L^{B2}$ is

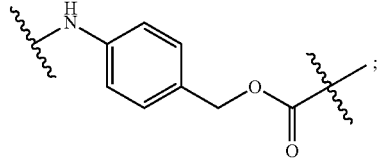 [SMILES: *Nc1ccc(COC(*)=O)cc1]

and $L^{B3}$ AA$_{0-12}$, wherein AA is independently for each occurrence a natural amino acid or a non-natural amino acid.

In some embodiments of Formula (II), L is

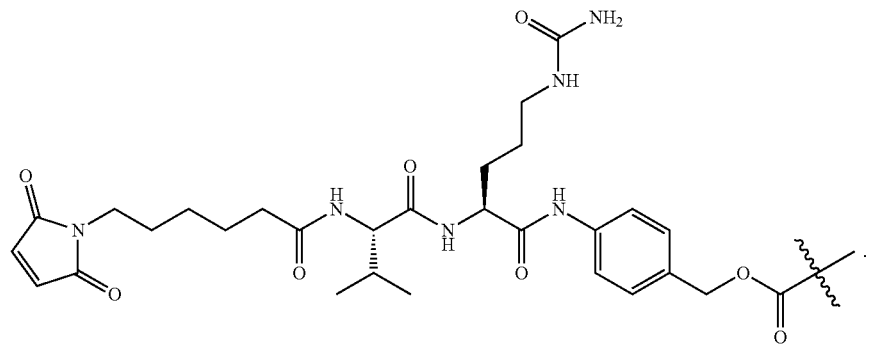 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

In some embodiments of Formula (II), L is $L^B$-$L^A$.
In some embodiments of Formula (II), L is -($L^C$)-$L^B$-$L^A$.
In some embodiments of Formula (II), L is -($L^C$)$_2$-$L^B$-$L^A$.
In some embodiments of Formula (II), $L^A$ is selected from the group consisting of —NH$_2$;

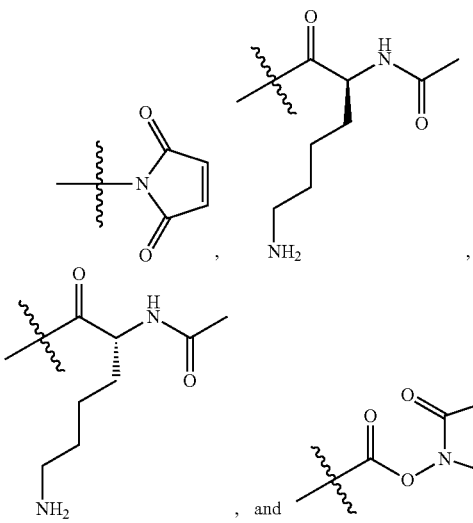

In some embodiments of Formula (II), $L^B$ is -$L^{B1}$-$L^{B2}$-$L^{B3}$.
In some embodiments of Formula (II), $L^B$ is -$L^{B2}$-$L^{B3}$-$L^{B1}$.
In some embodiments of Formula (II), $L^{B1}$ is absent.

In some embodiments of Formula (II), $L^{B1}$ is one component or two components, each selected, independently for each occurrence, from the group consisting of —C(O)NR—; —C(O)C$_1$-C$_6$alkyl-; —C$_1$-C$_6$alkyl(OCH$_2$CH$_2$)$_{1-8}$—; —C$_1$-C$_6$alkyl(OCH$_2$CH$_2$)$_{1-8}$—; —C$_1$-C$_6$alkyl(OCH$_2$CH$_2$)$_{1-8}$—NR; —C(O)NRC$_1$-C$_6$alkyl-; —C$_1$-C$_6$alkyl(OCH$_2$CH$_2$)$_{1-8}$—NR; and —NRC$_1$-C$_6$alkylene-.

In some embodiments of Formula (II), $L^{B2}$ is absent.

In some embodiments of Formula (II), $L^{B2}$ is

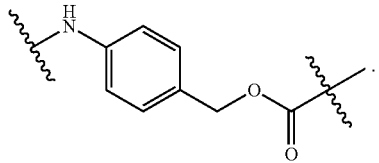 [SMILES: *Nc1ccc(COC(*)=O)cc1]

In some embodiments of Formula (II), $L^{B3}$ is absent.

In some embodiments of Formula (II), $L^{B3}$ is AA$_{0-12}$, $L^{B3}$ is AA$_{0-12}$, wherein AA is independently for each occurrence a natural amino acid or a non-natural amino acid.

In some embodiments of Formula (II), $L^{B3}$ is AA$_2$, $L^{B3}$ is AA$_{0-12}$, wherein AA is independently for each occurrence a natural amino acid or a non-natural amino acid.

In some embodiments of Formula (II), $L^C$ is absent.

In some embodiments of Formula (II), $L^C$ is selected, independently for each occurrence, from the group consisting of —C$_1$-C$_6$alkylene, —CO—, and —NRC$_1$-C$_6$-alkylenephenyleneNR.

In some embodiments of Formula (II), R is H.

In certain embodiments, the present invention relates to any of the aforementioned compounds of Formula (II) or Formula (IIA), or a pharmaceutically acceptable salt thereof, and attendant definitions, wherein the compound is selected from the group consisting of:

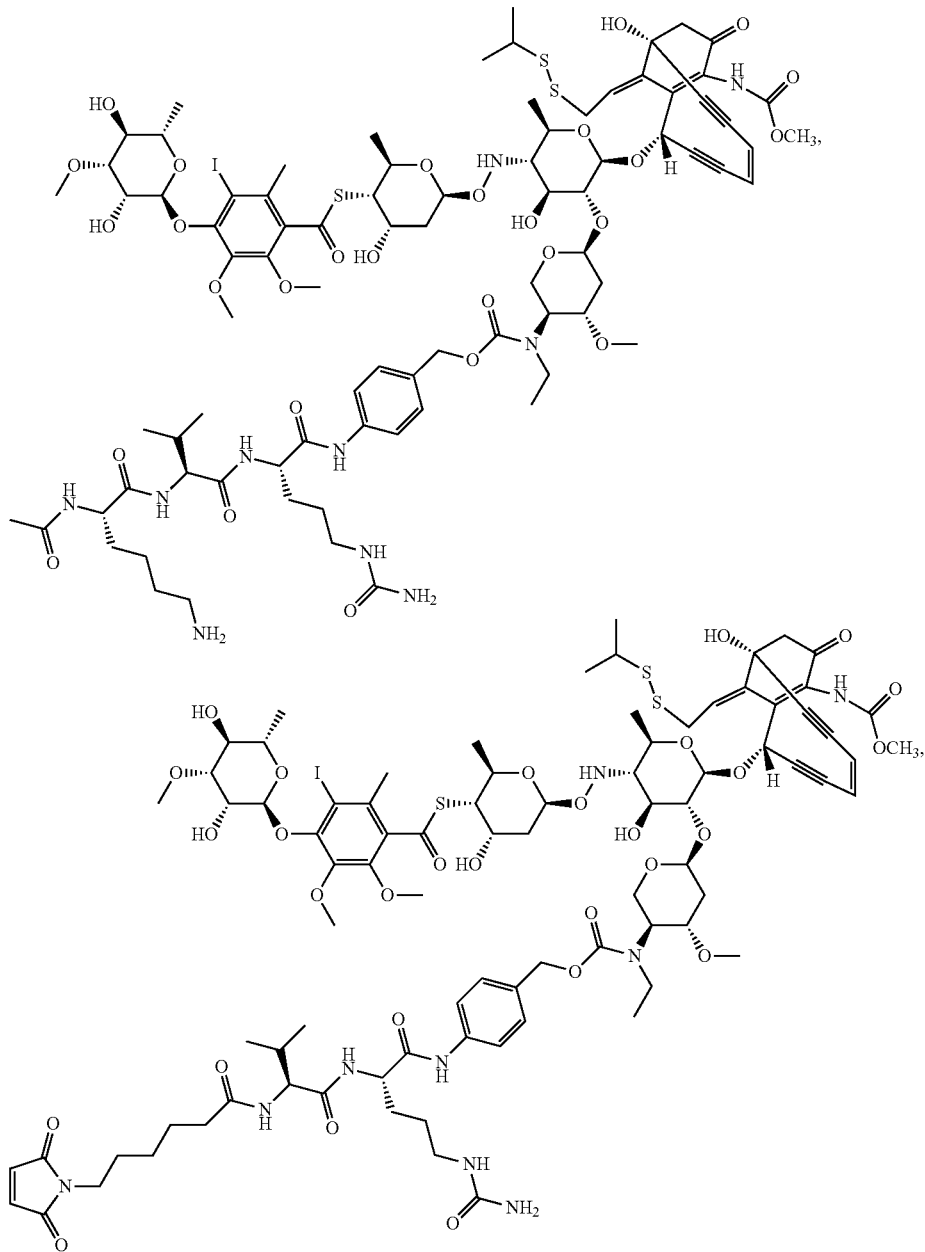

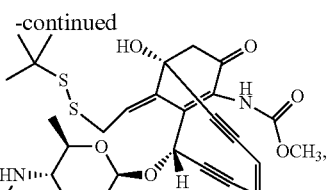
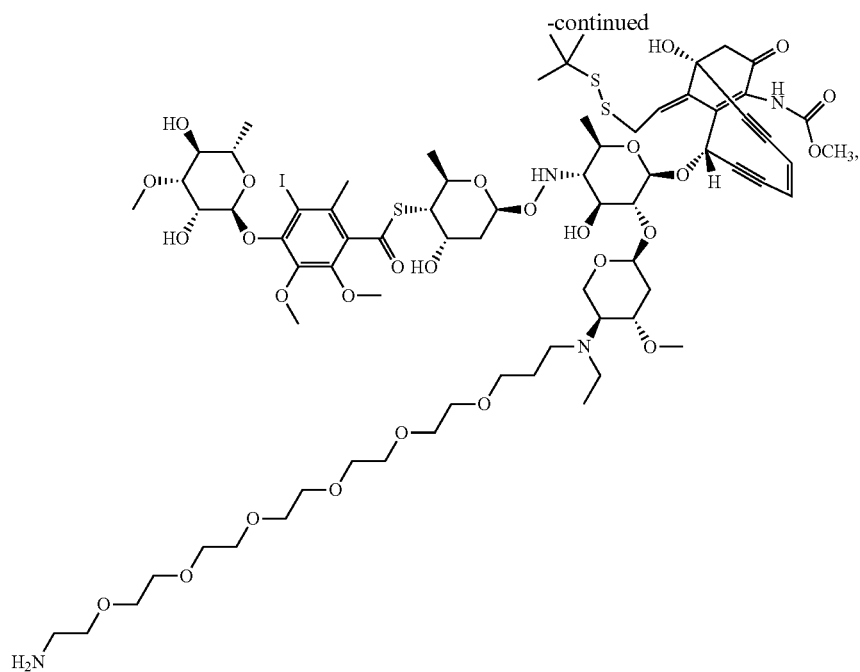
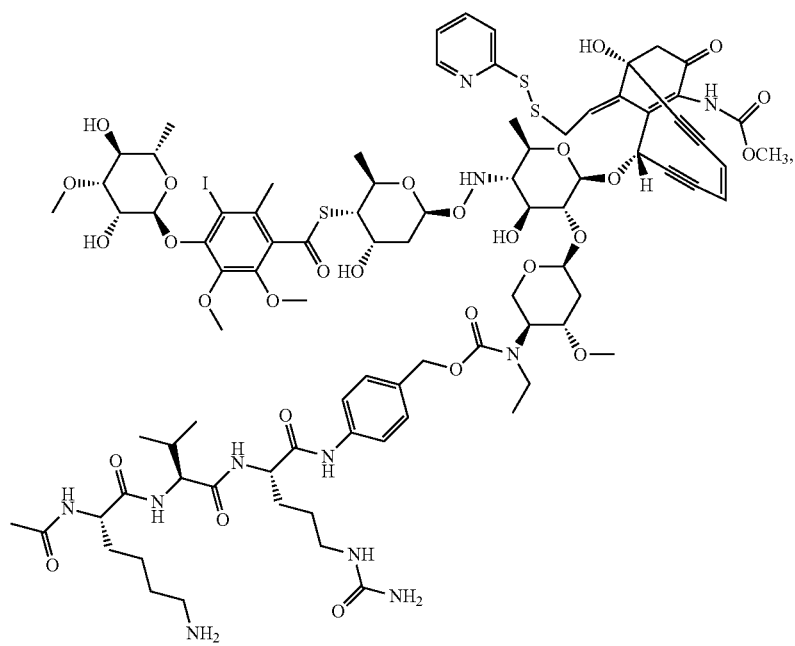

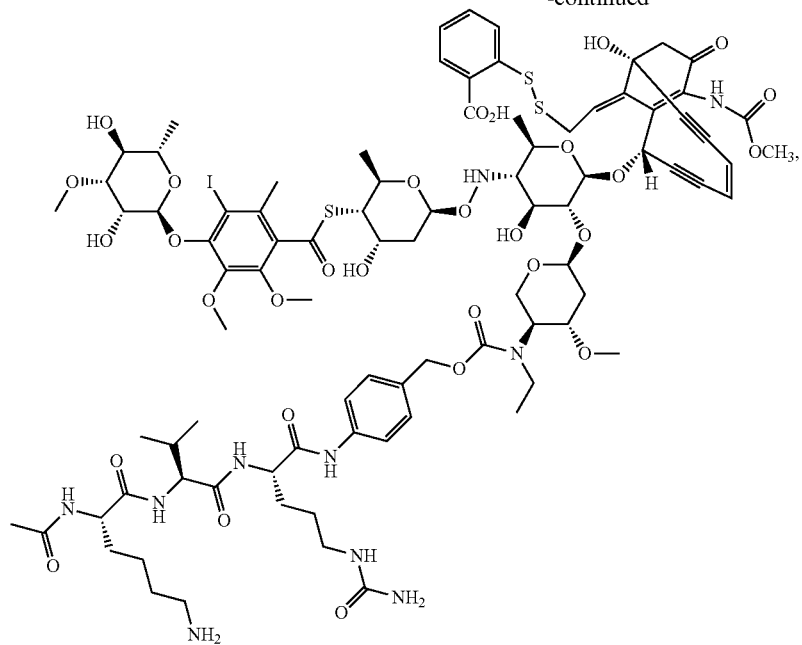
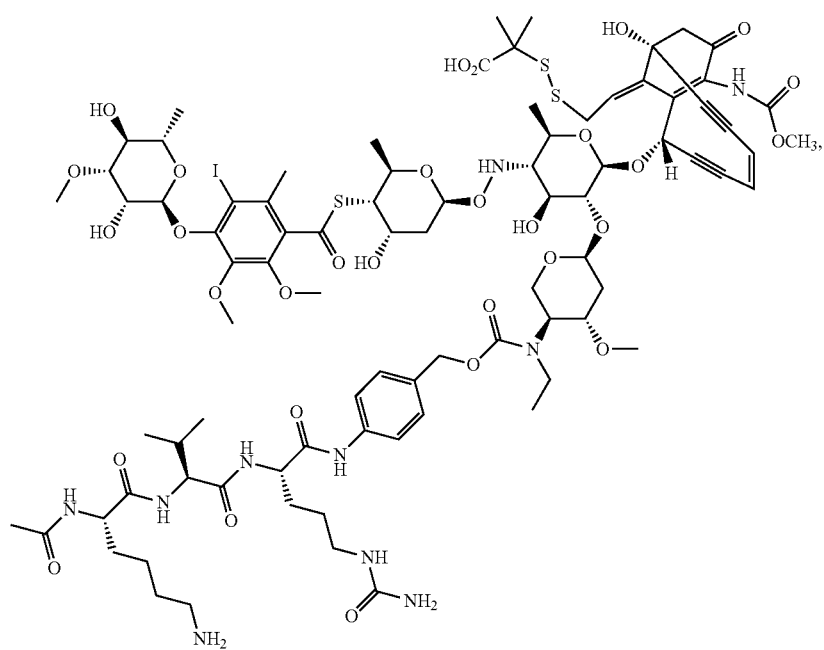

-continued
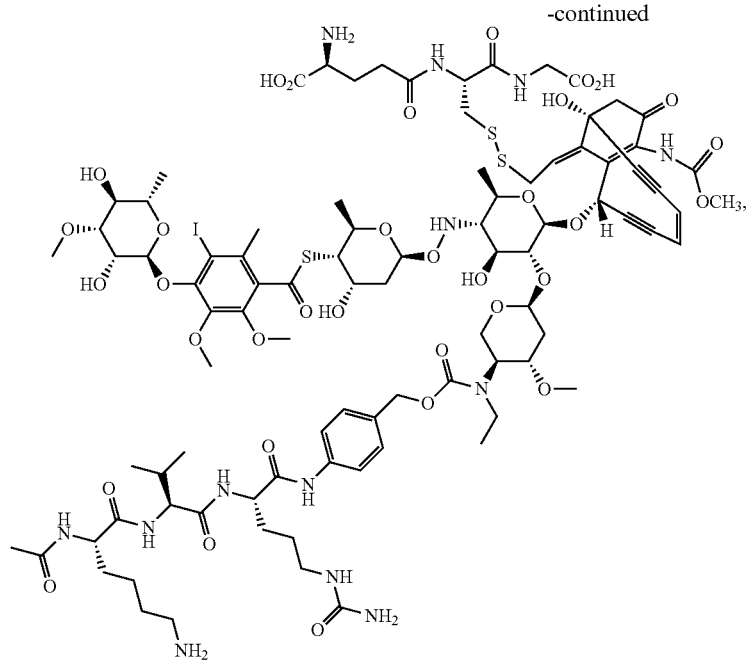
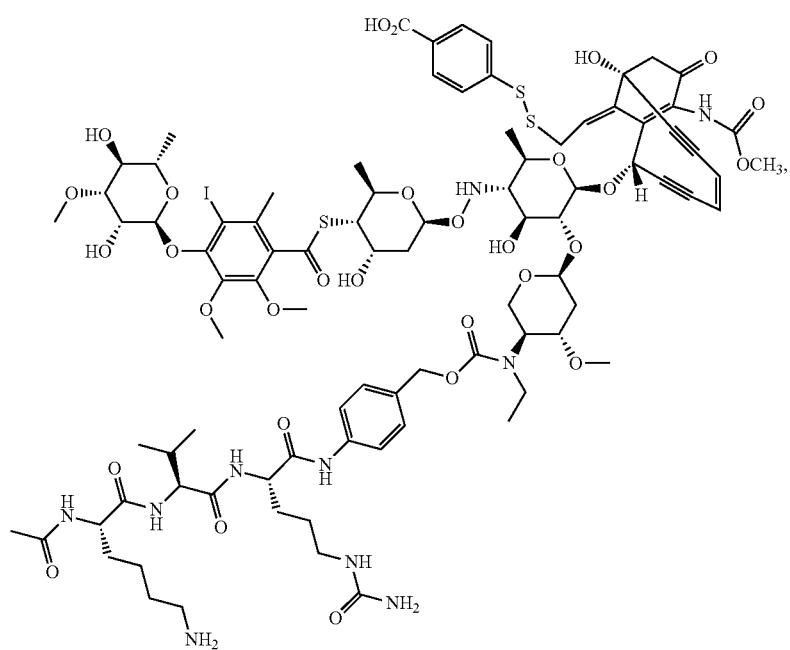

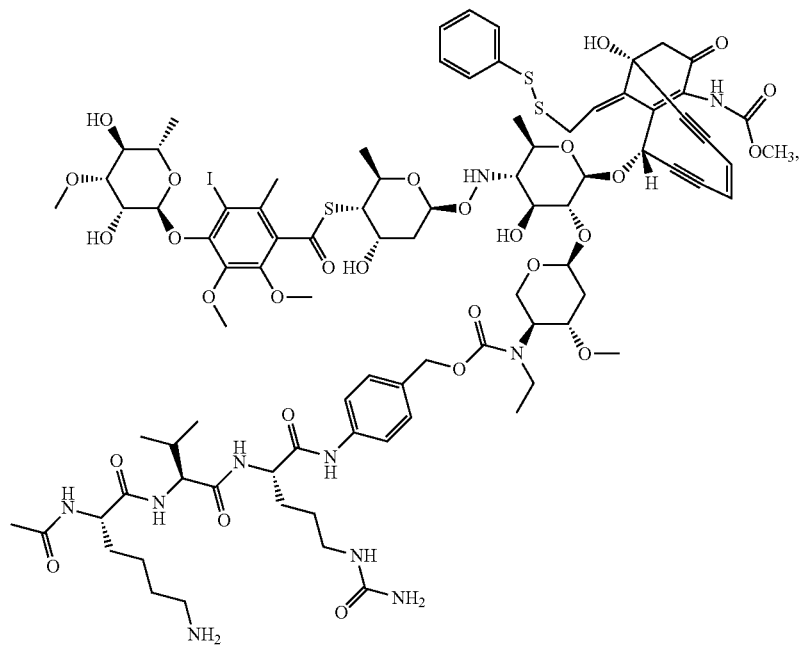
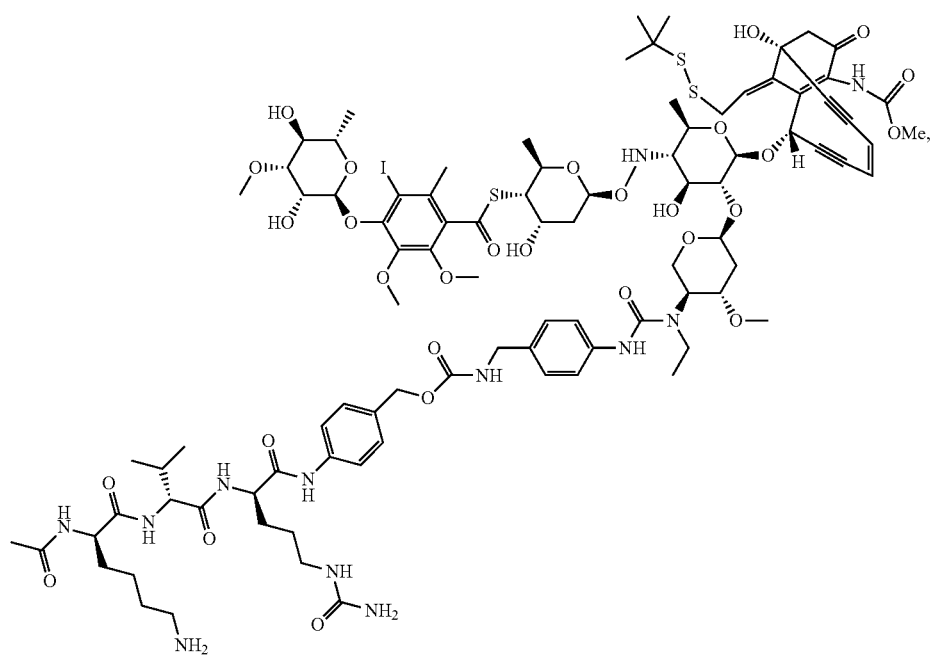

-continued
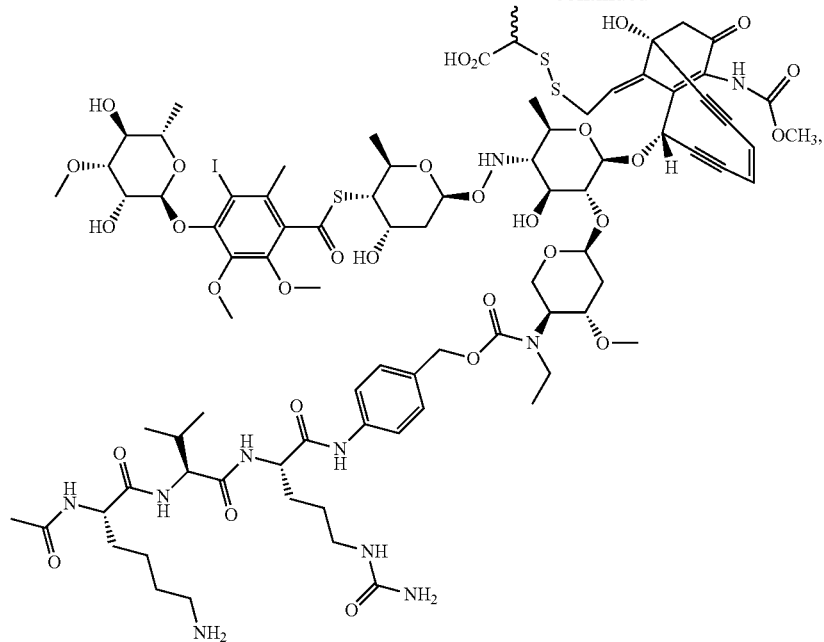
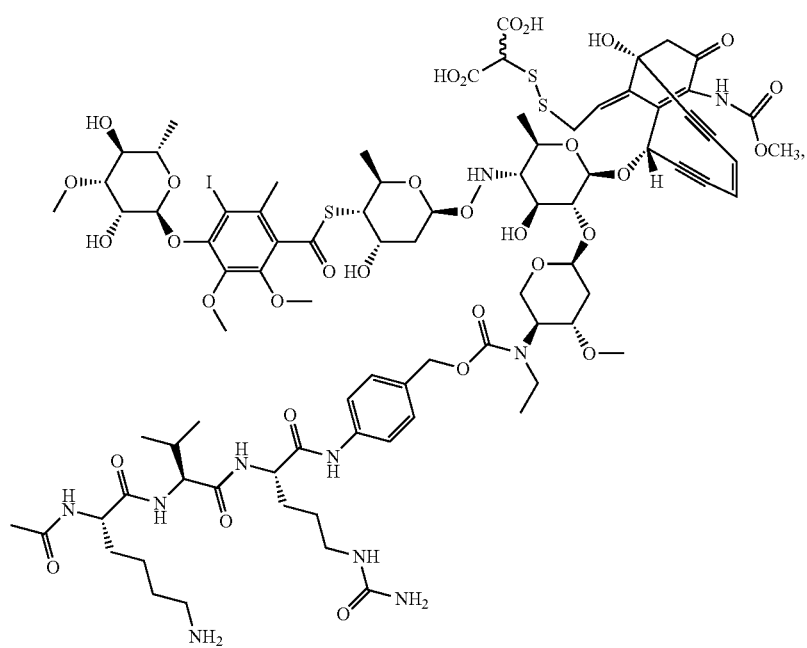

-continued
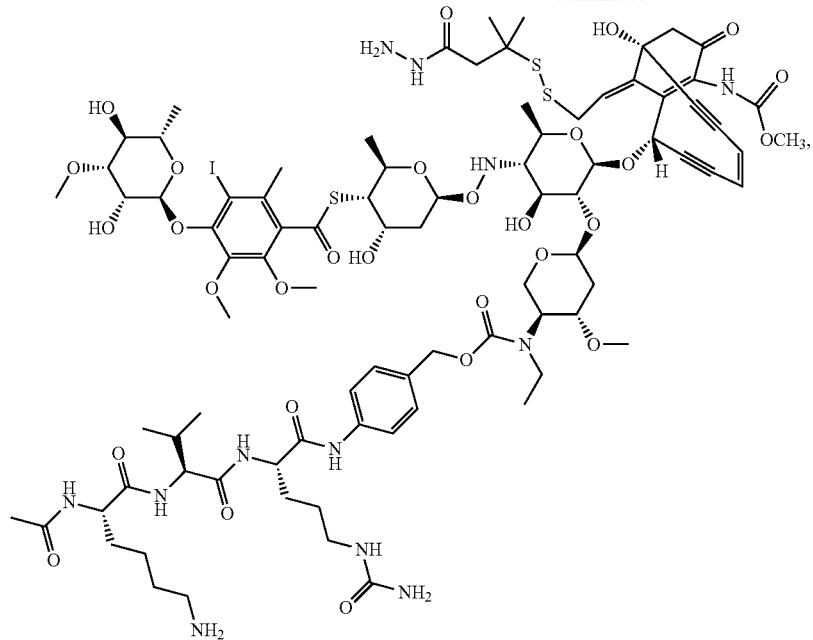
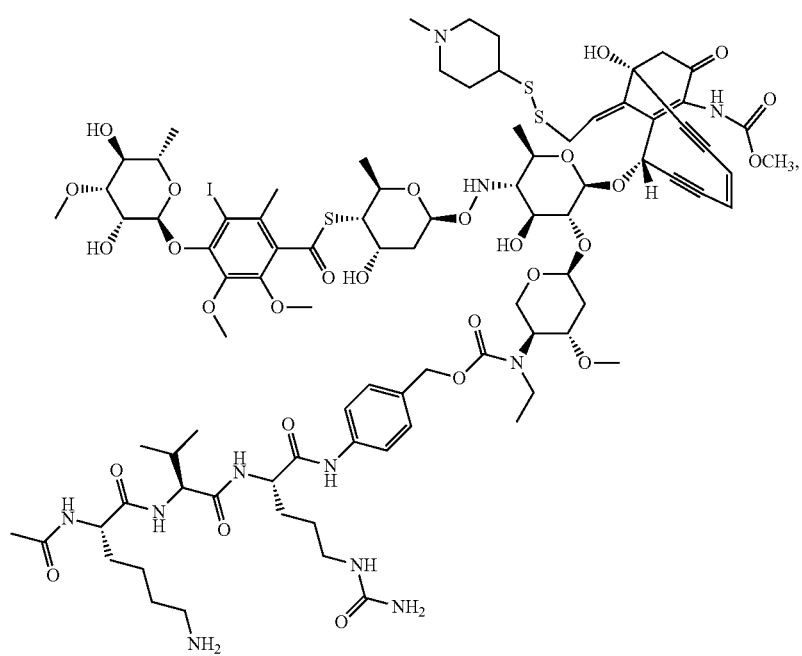

-continued
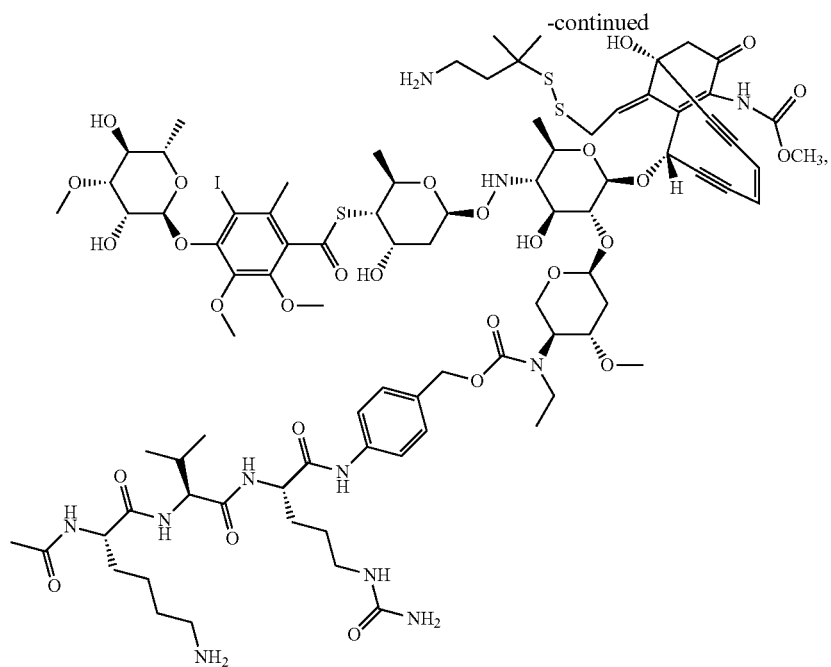
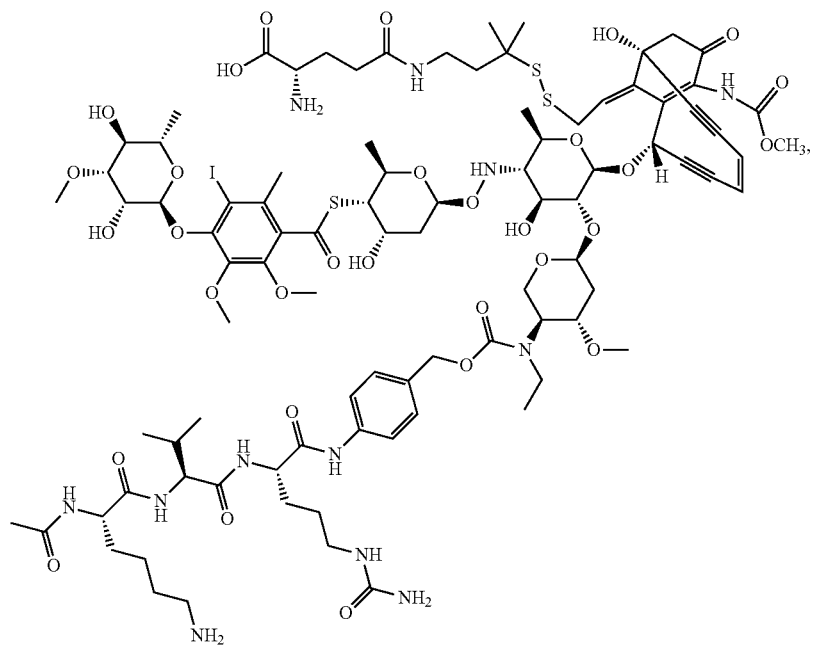

-continued
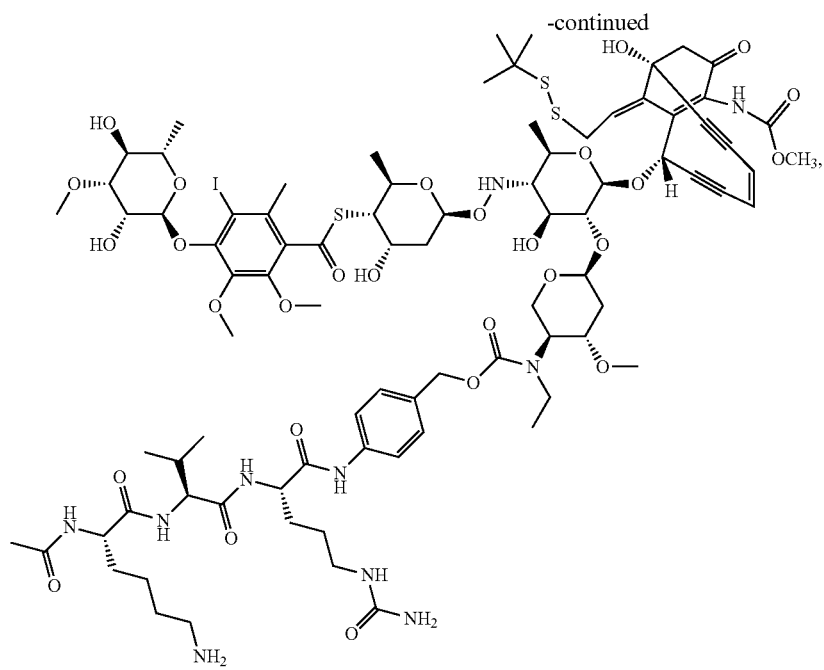
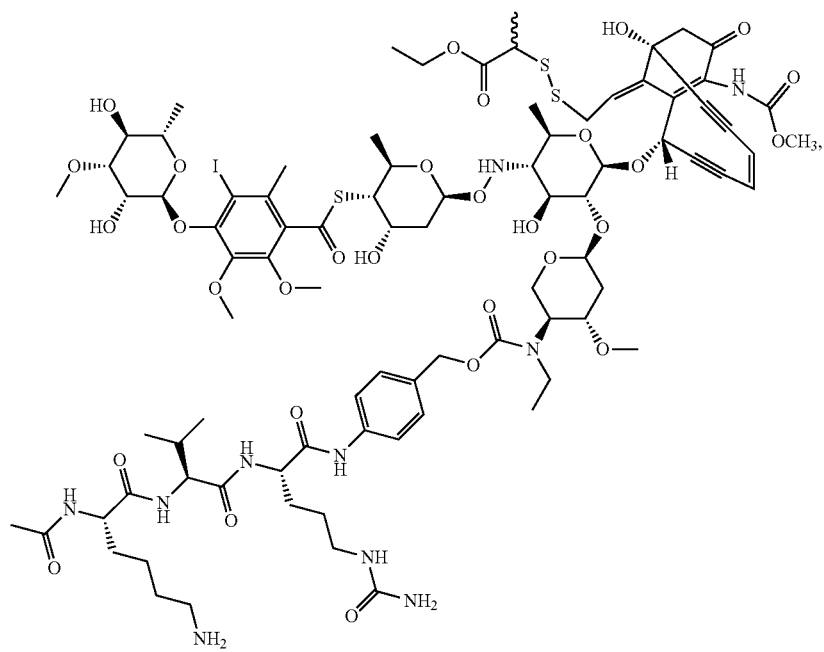

-continued
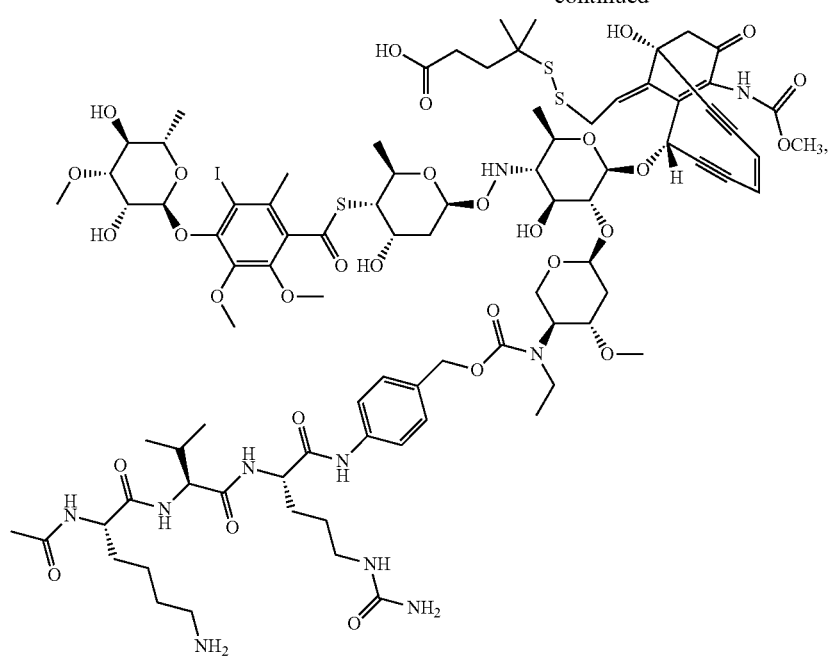
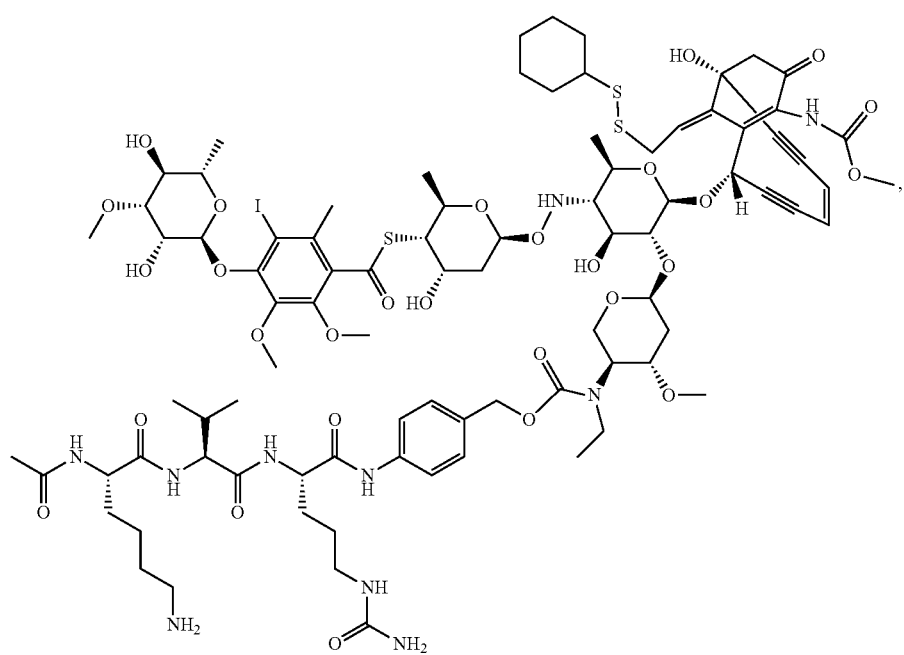

-continued
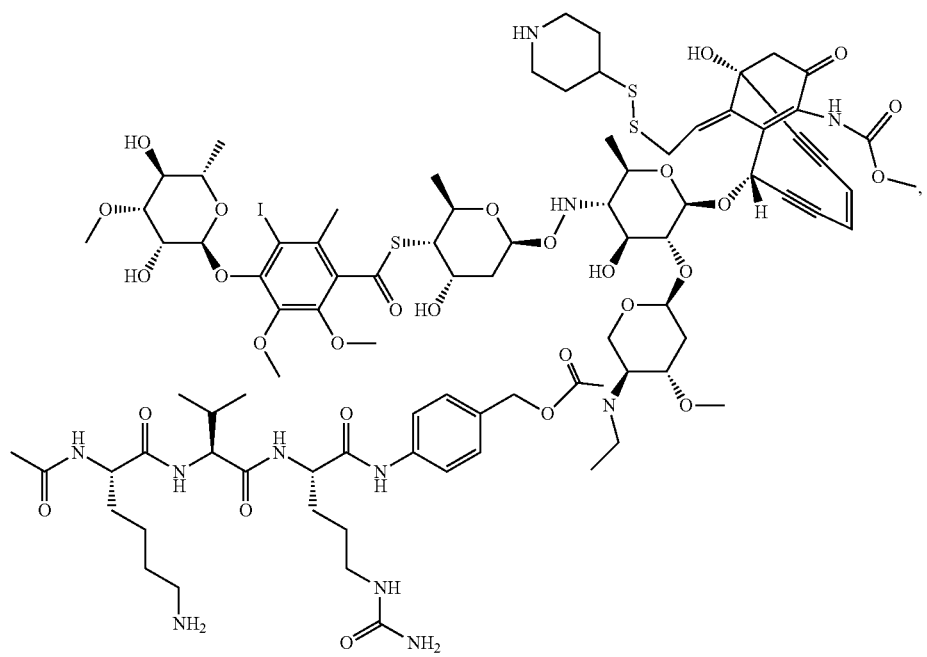
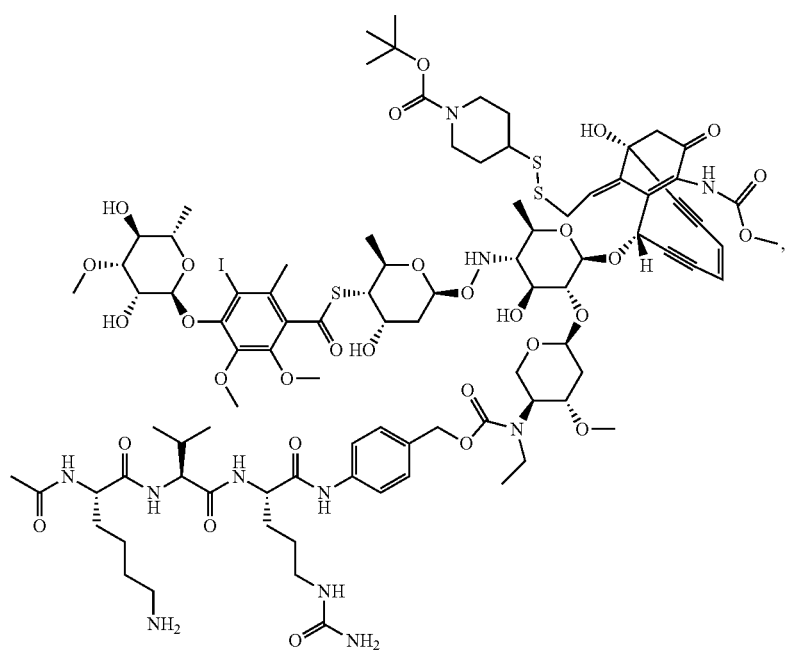

-continued
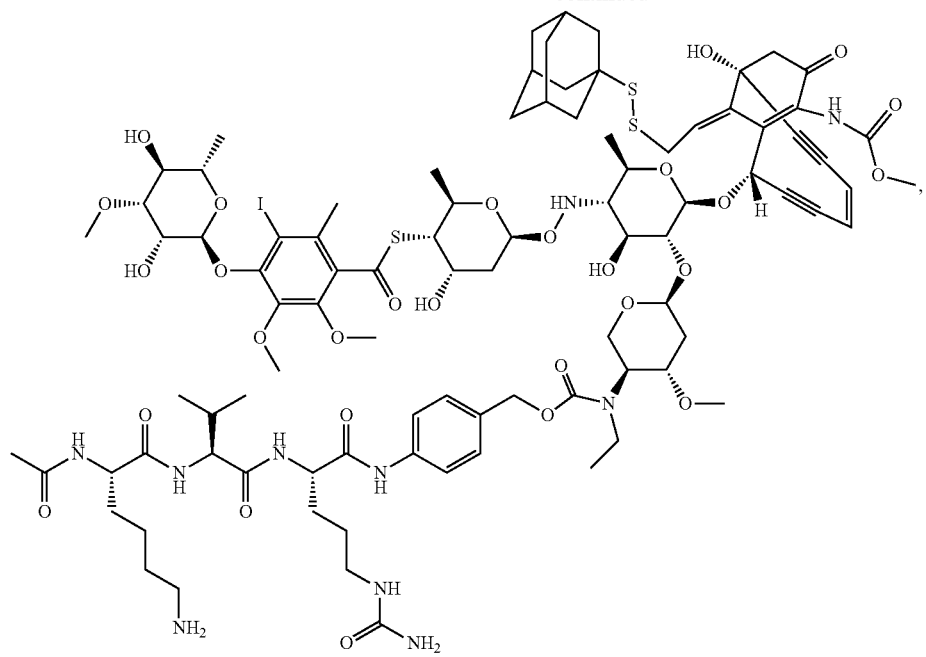
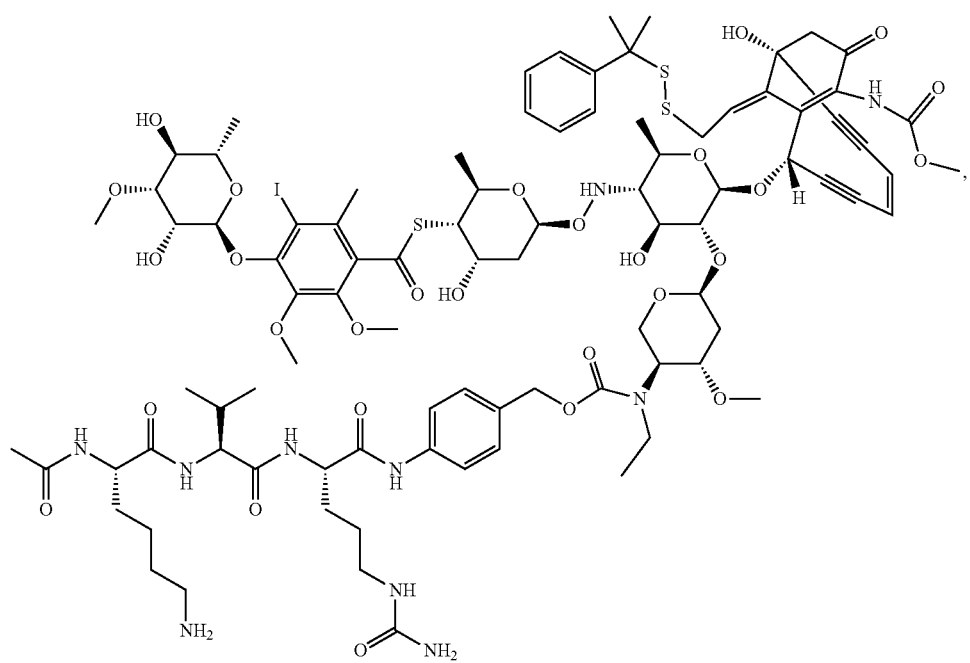

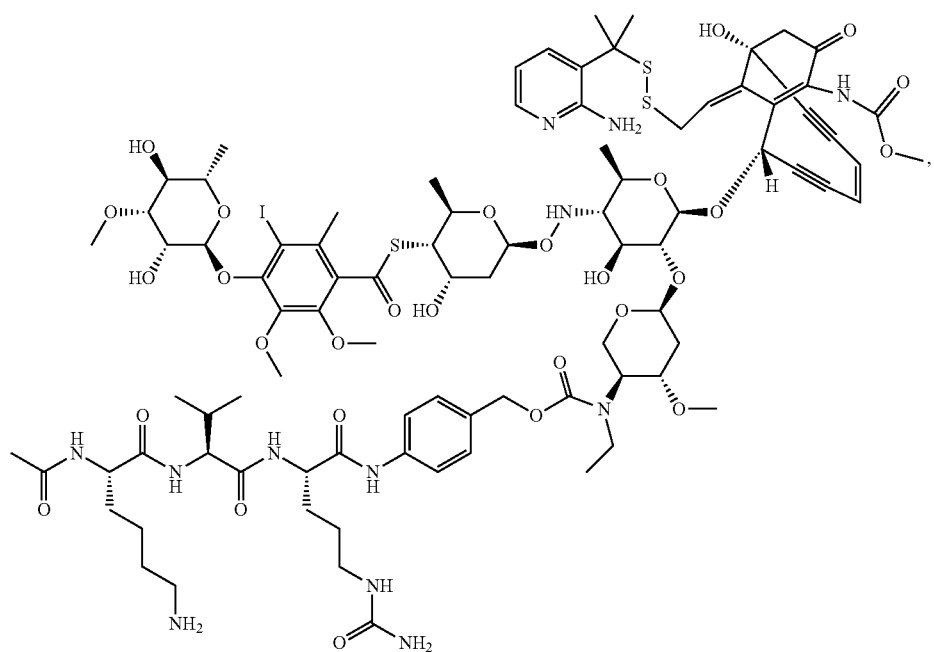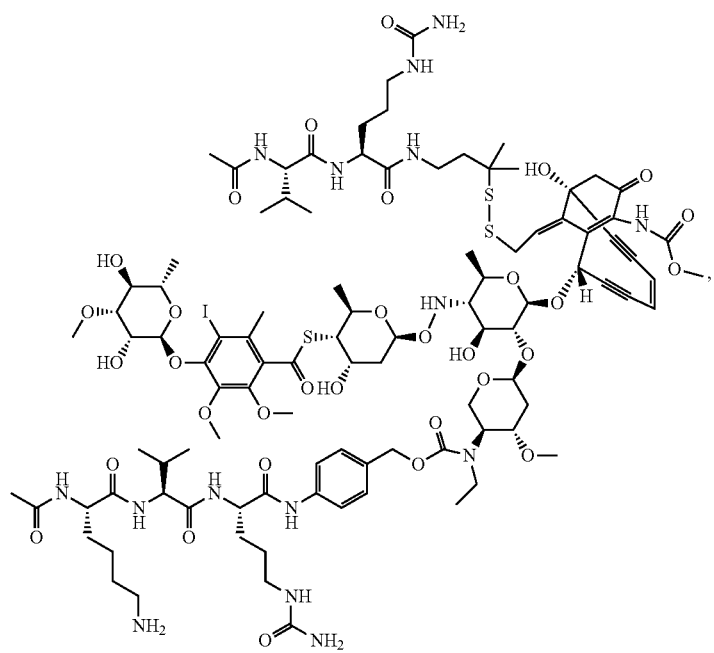

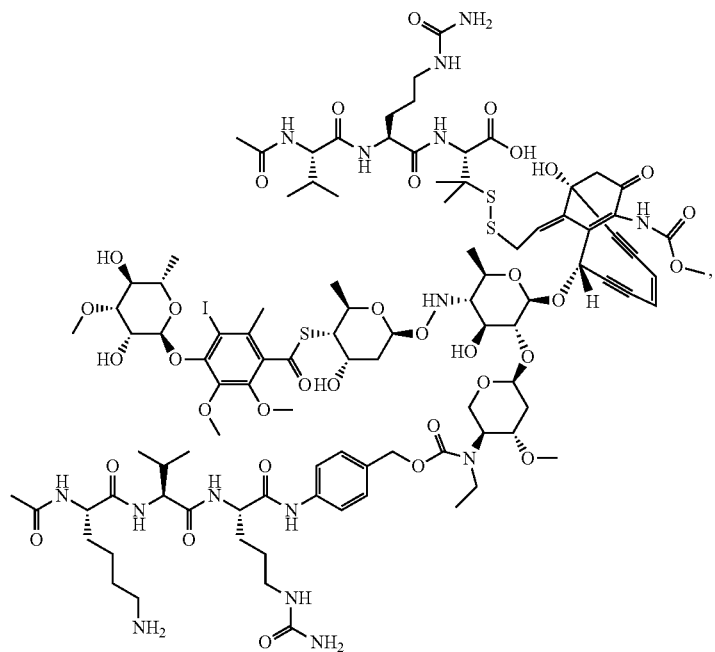
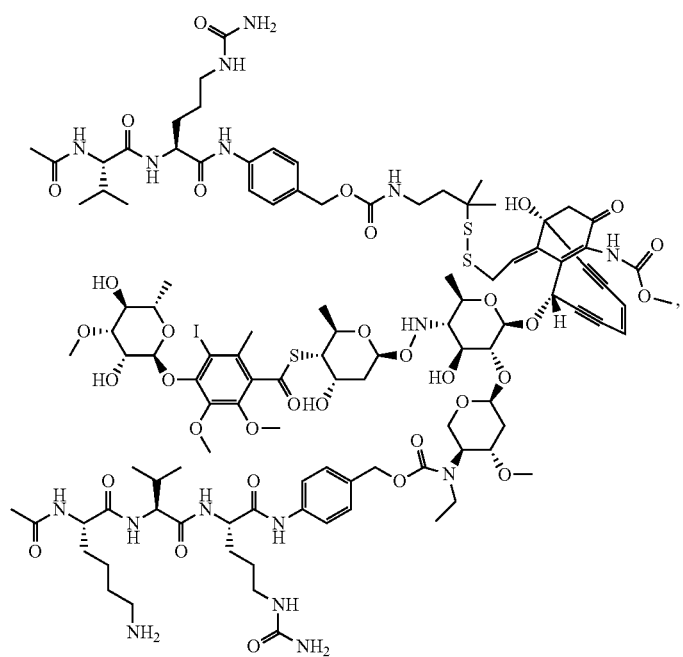

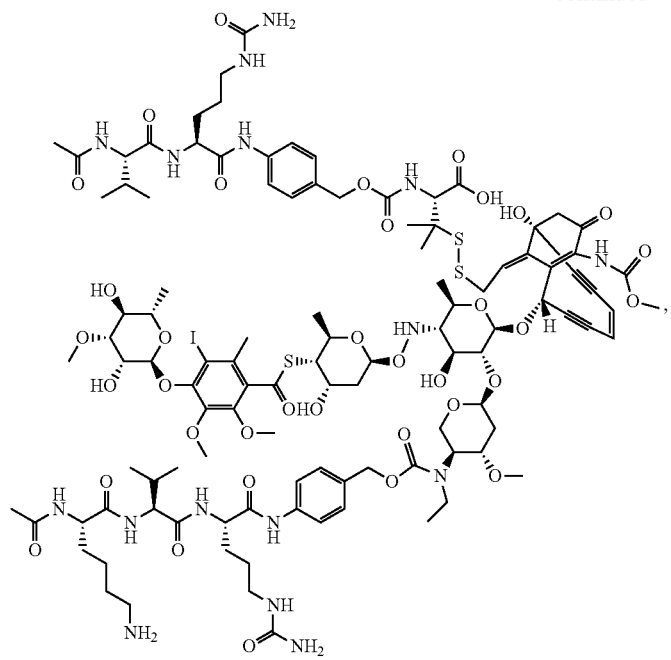
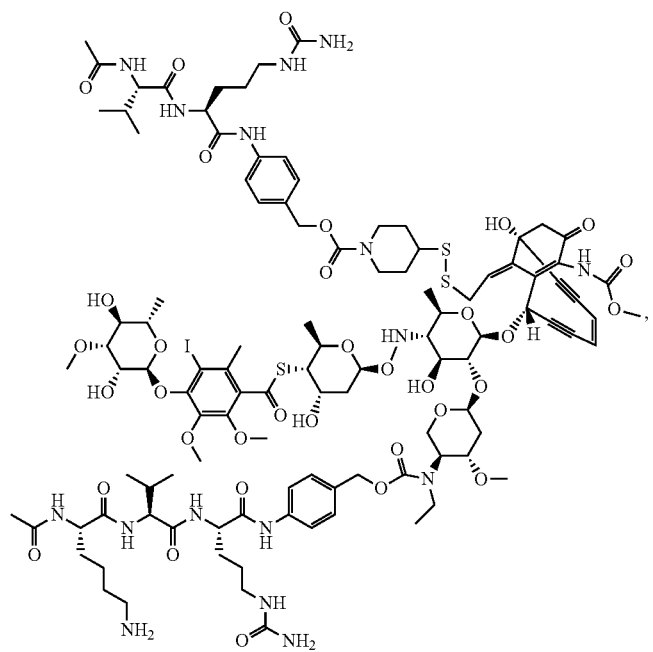

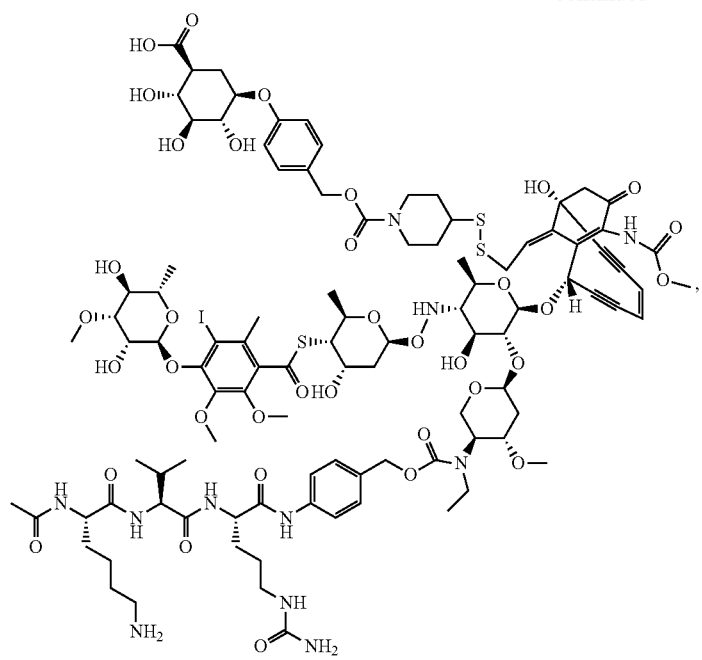
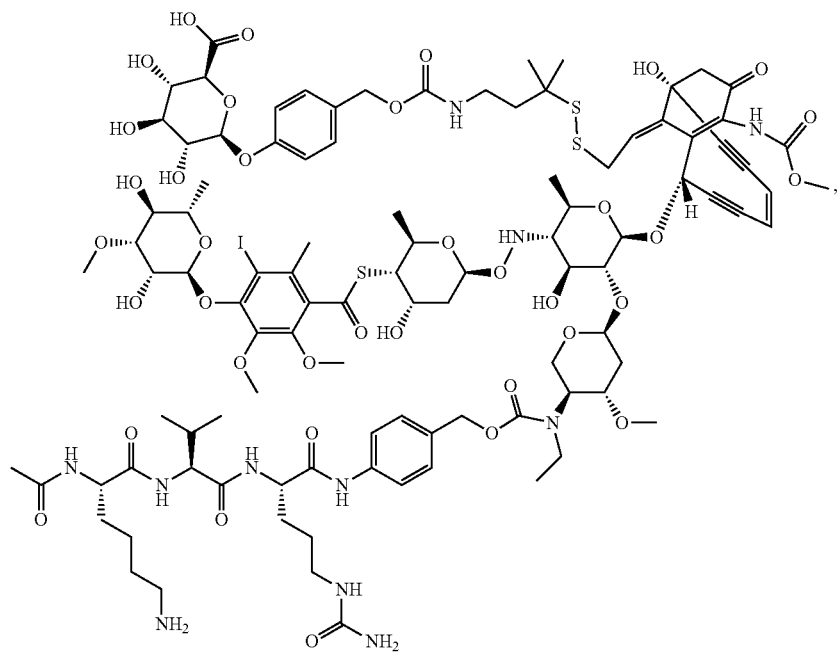

-continued
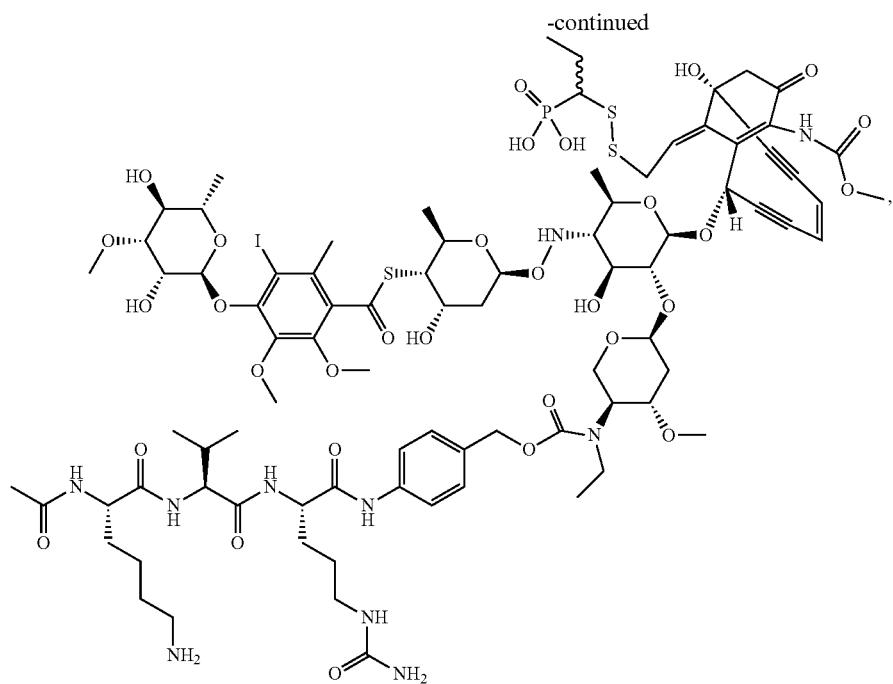
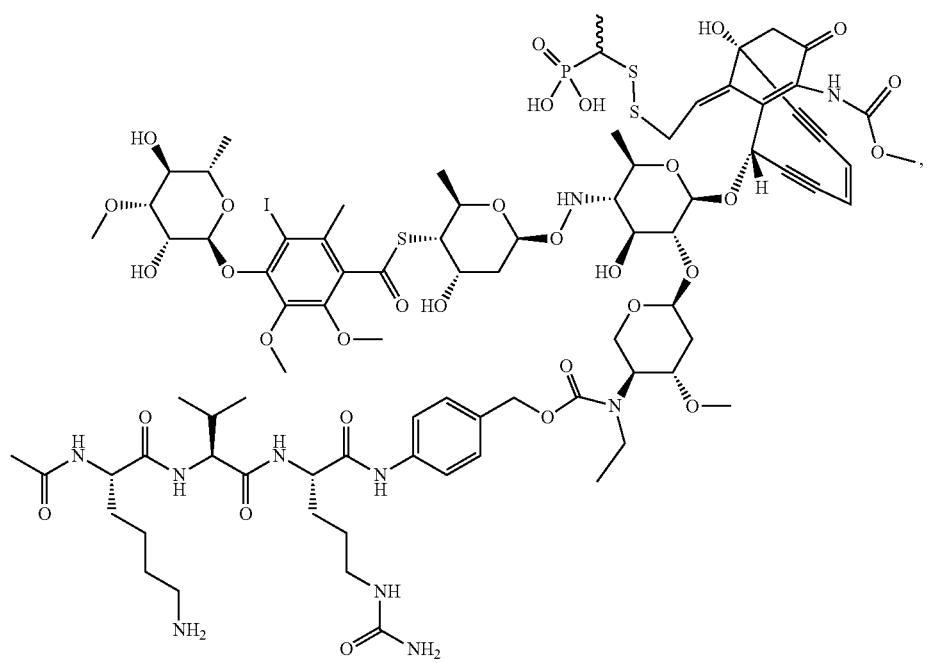

-continued
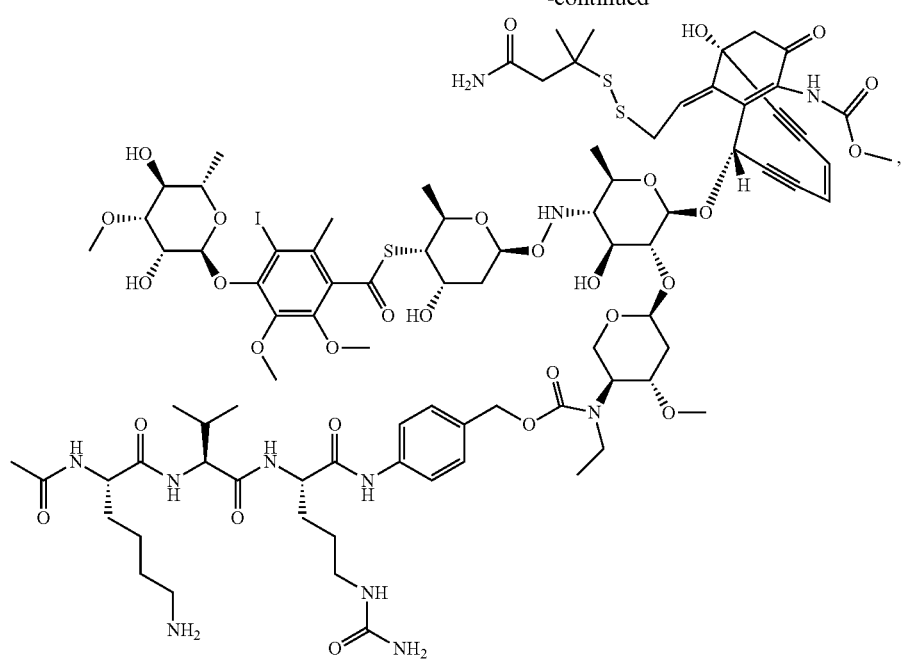
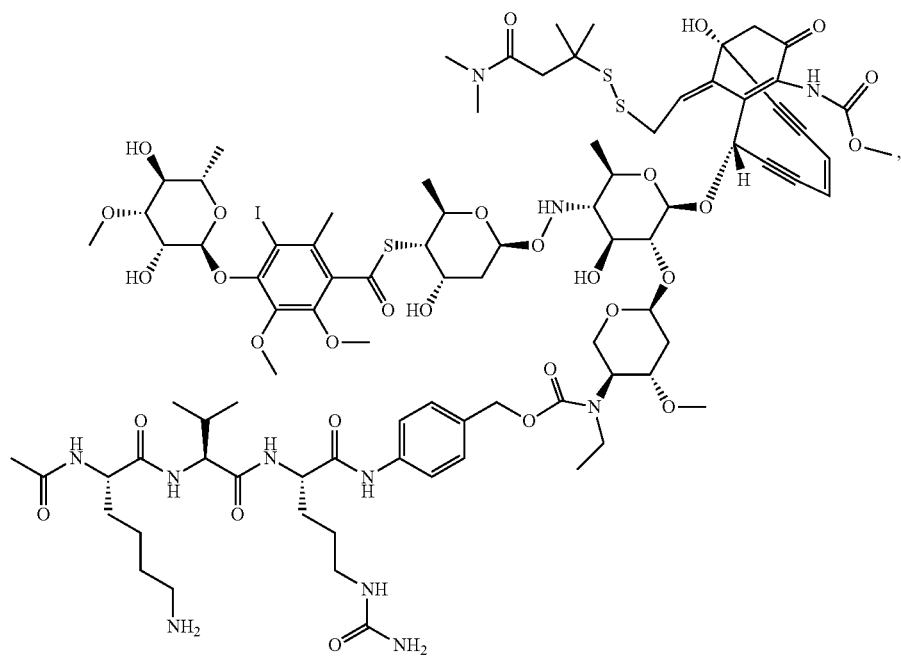

-continued
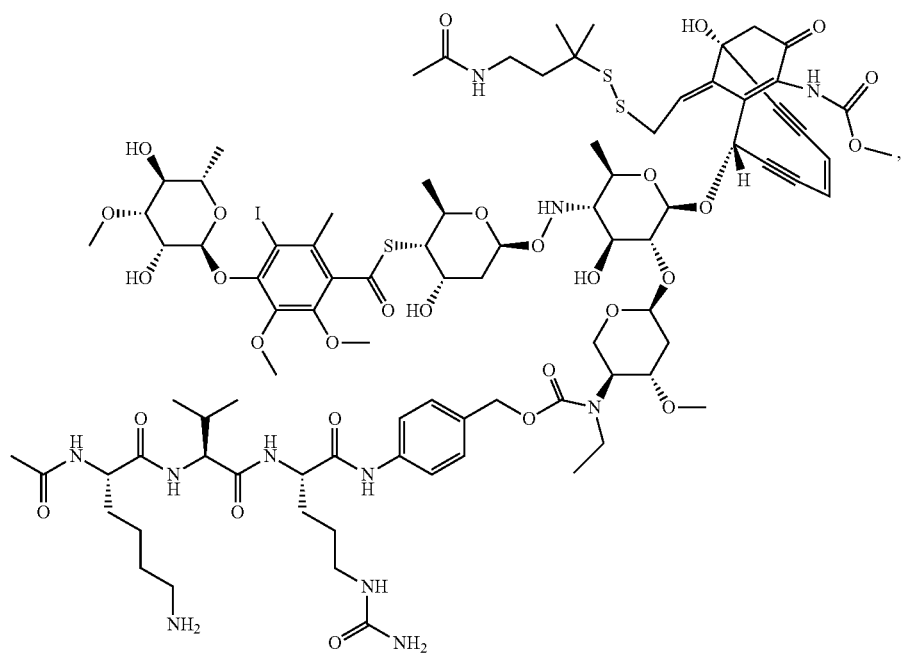
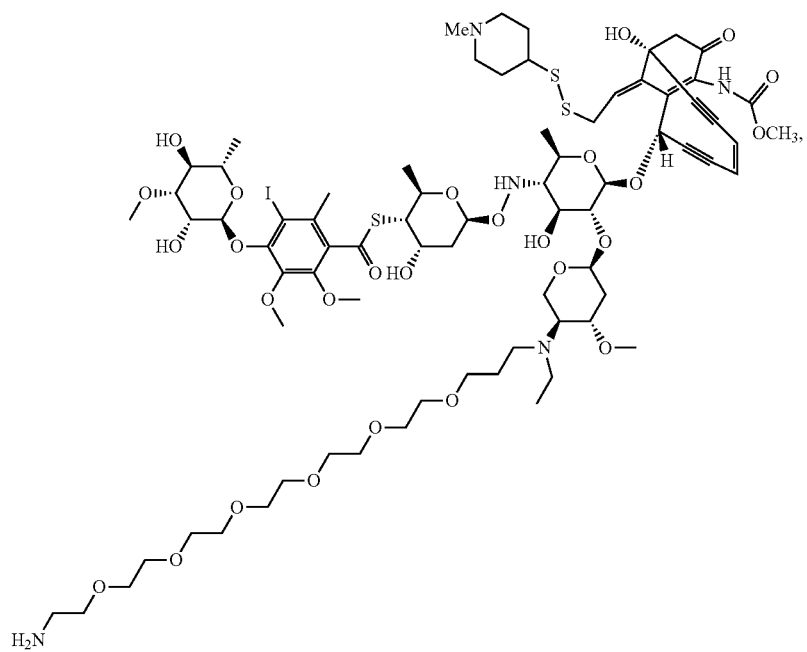

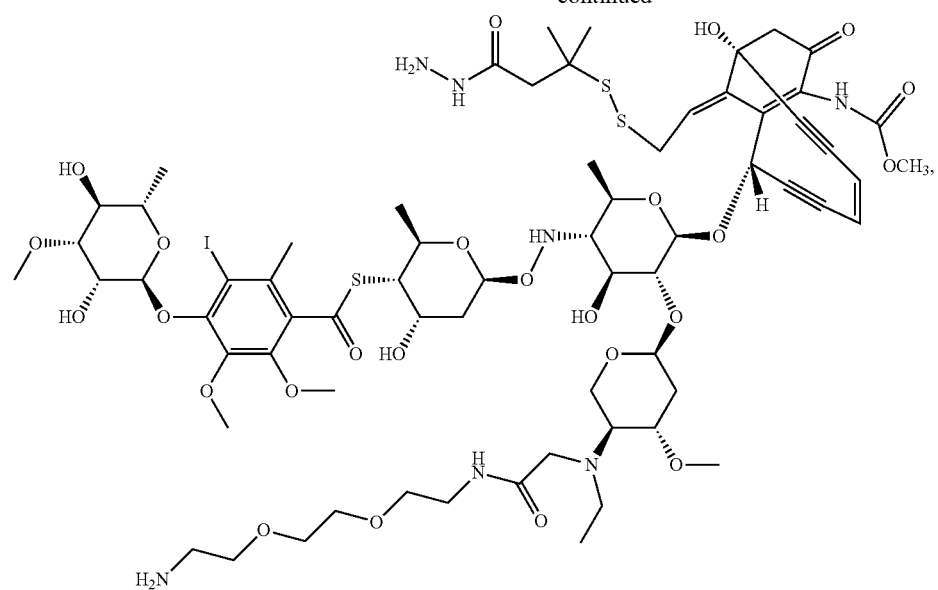
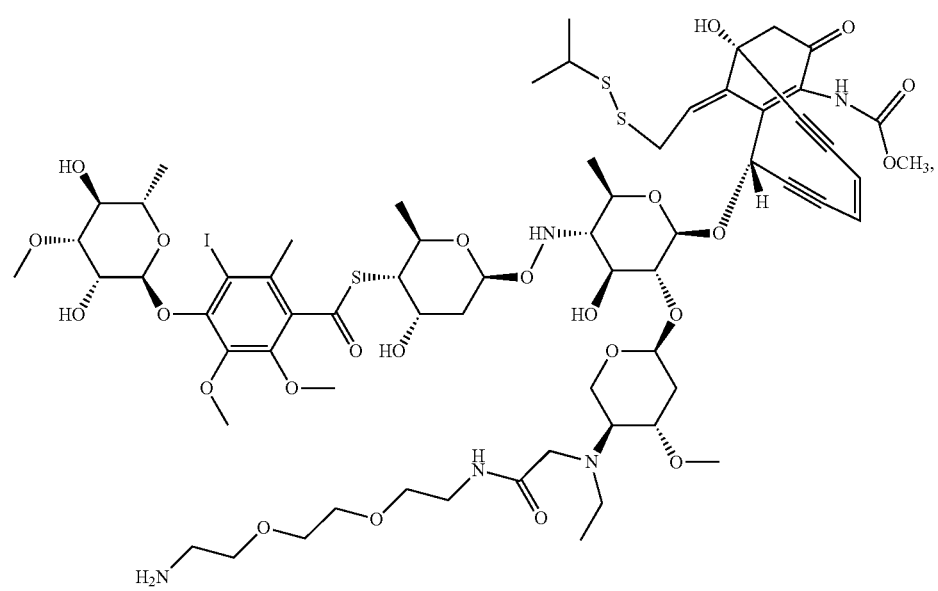

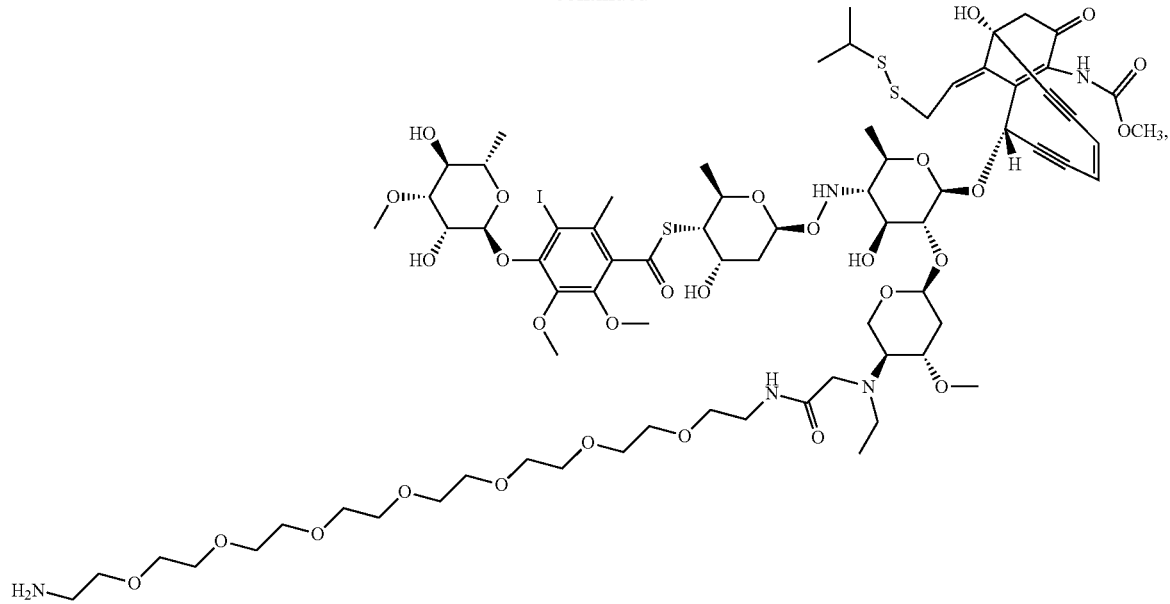
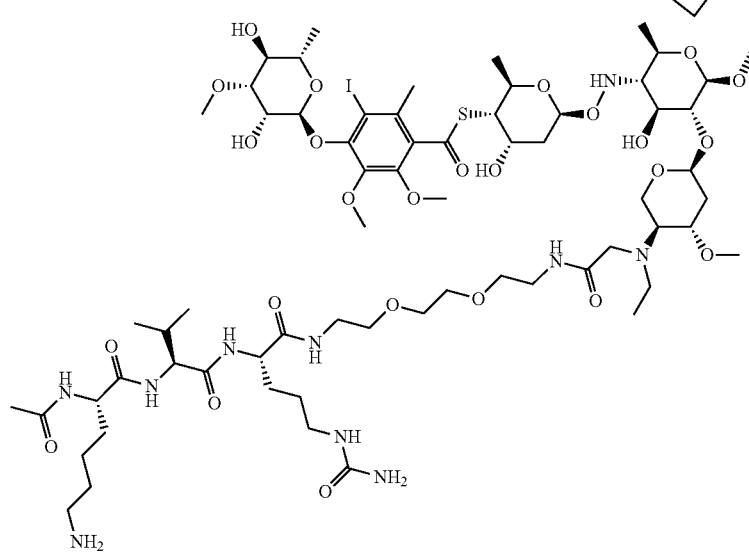

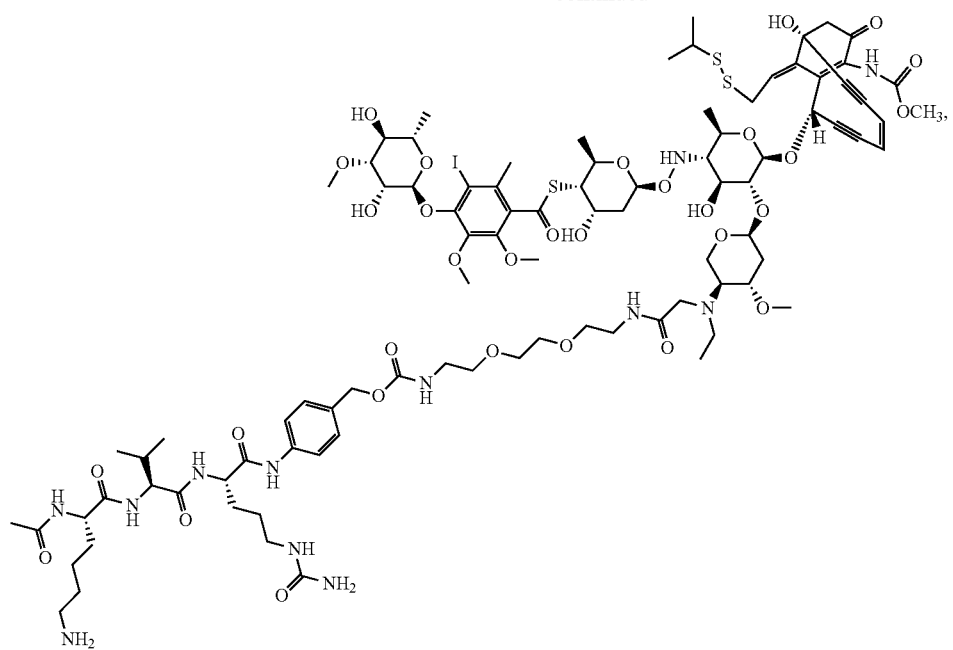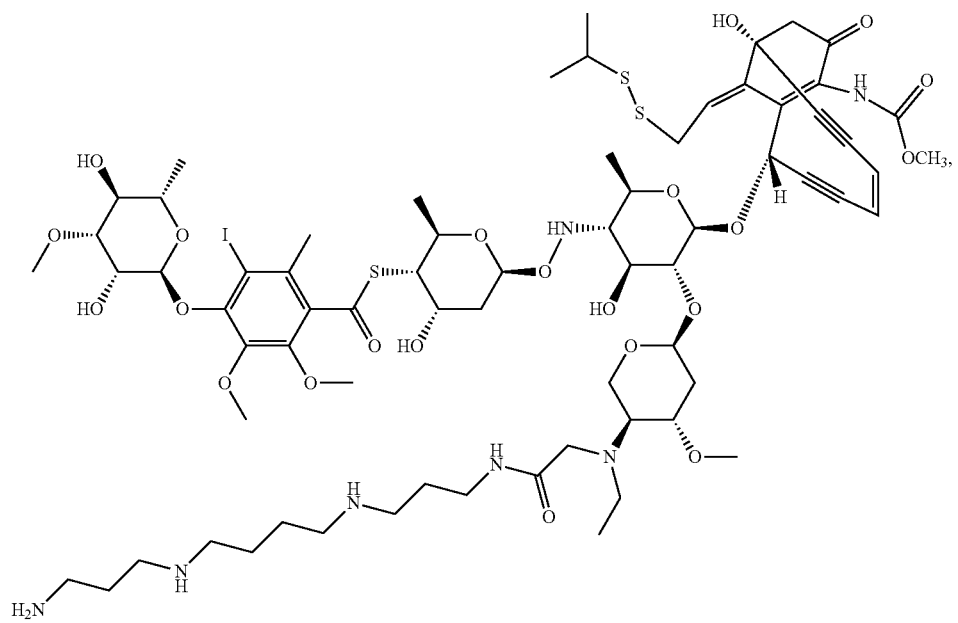

-continued
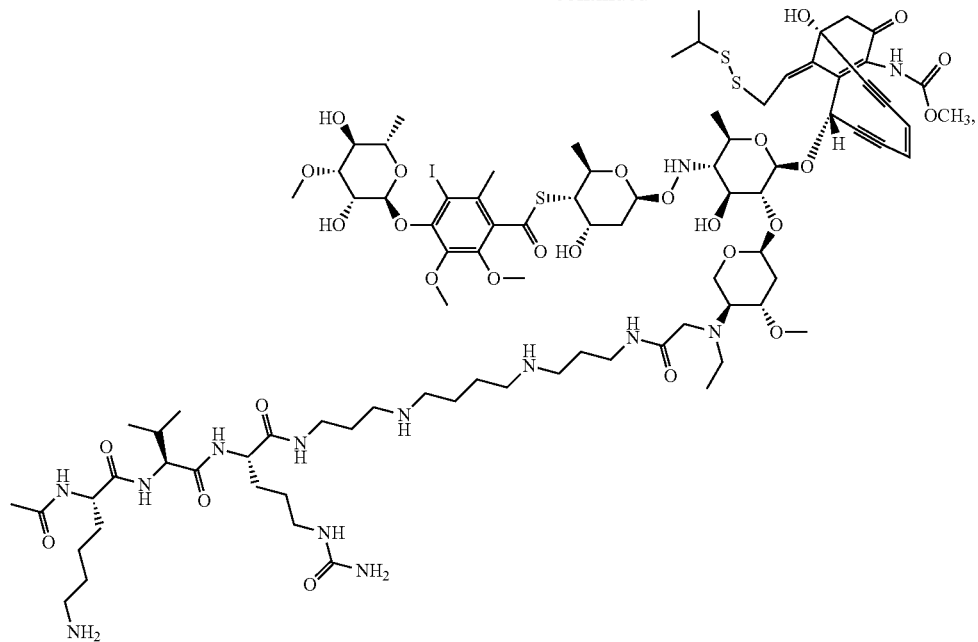
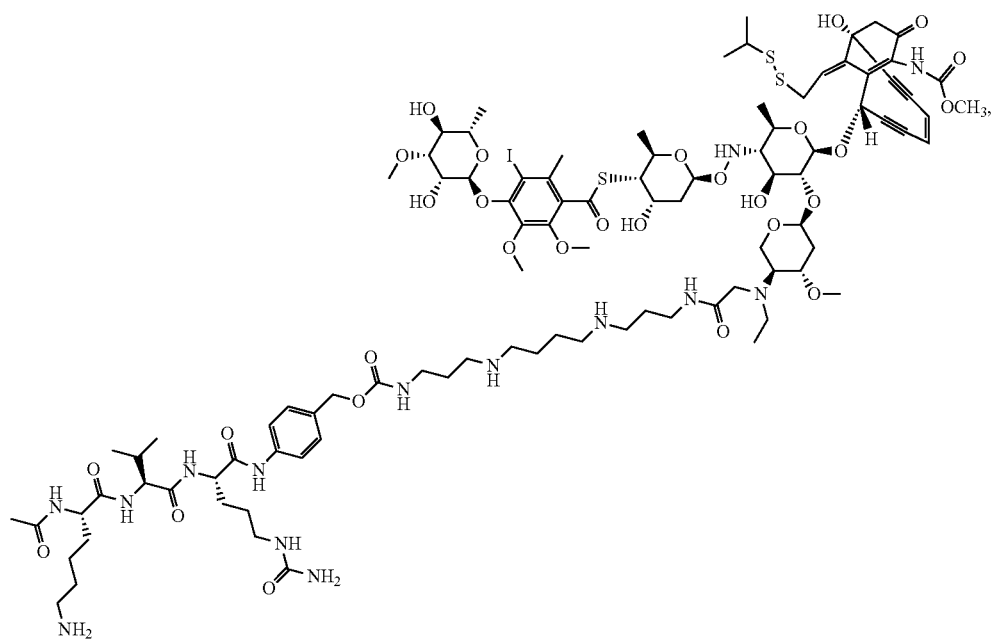

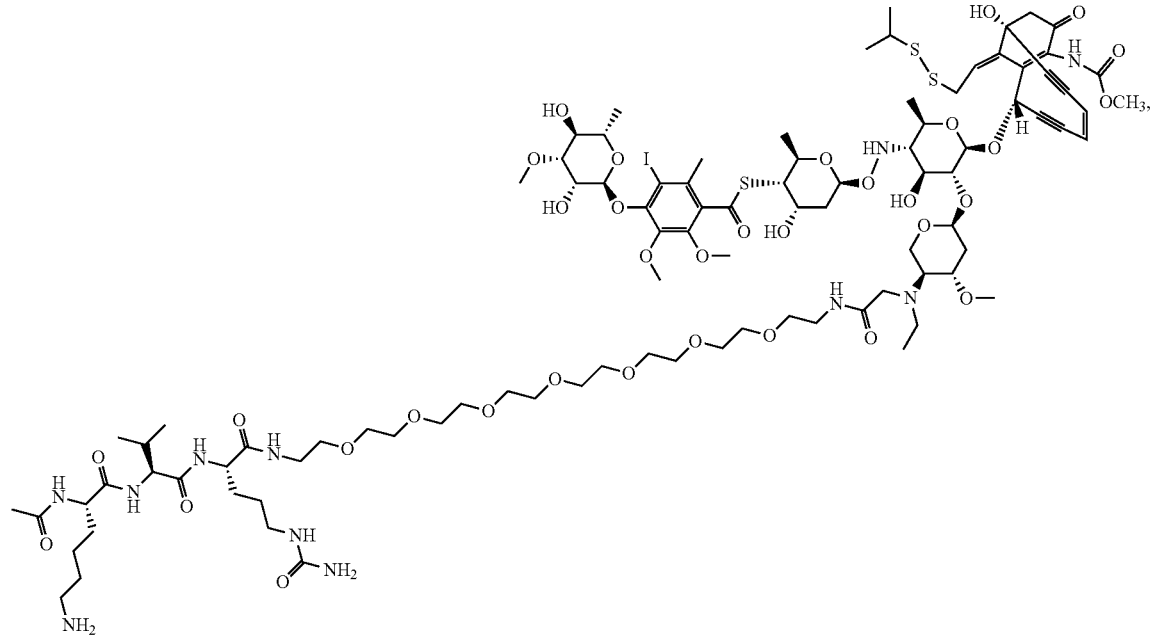
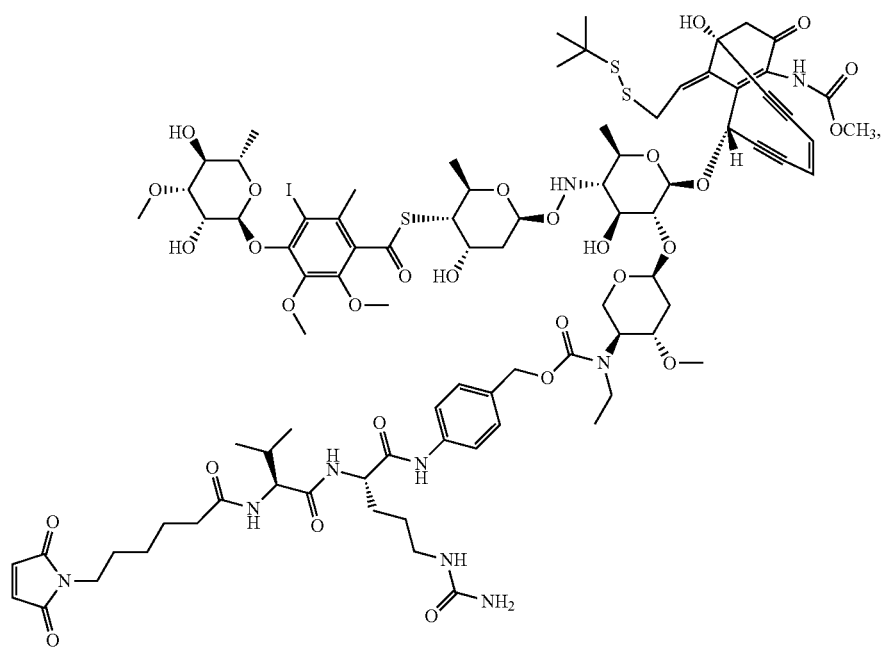

-continued
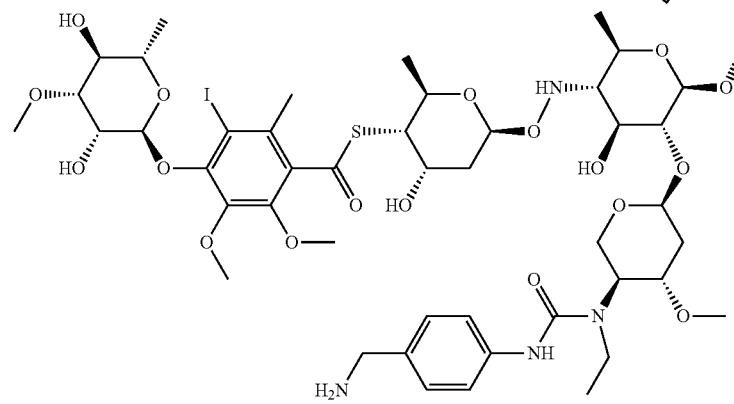
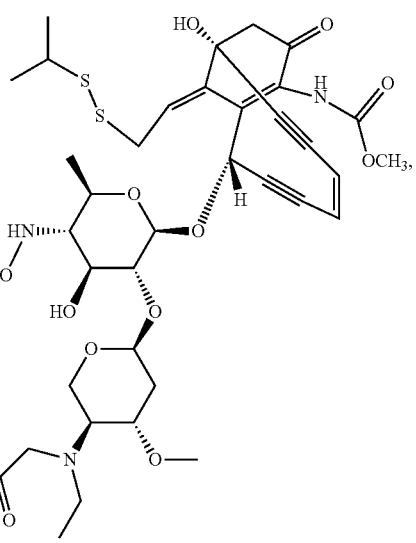
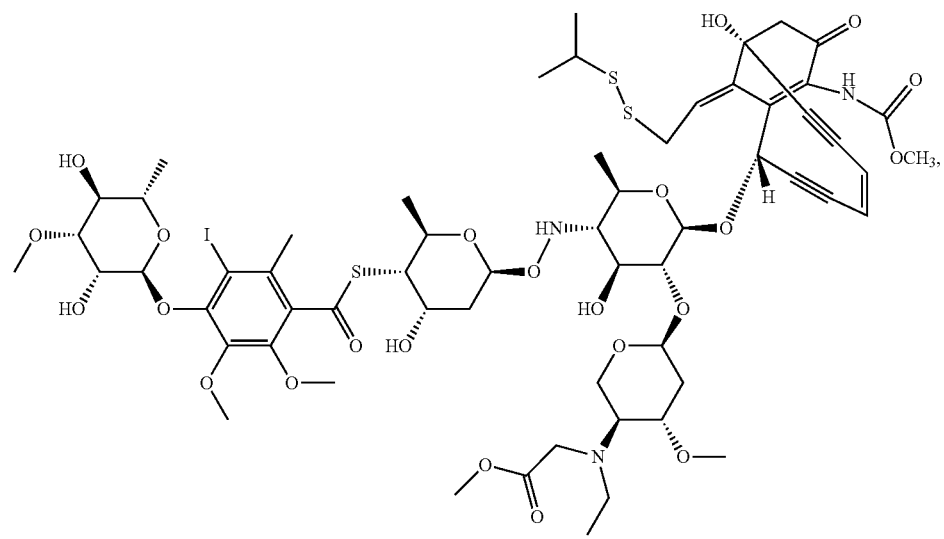

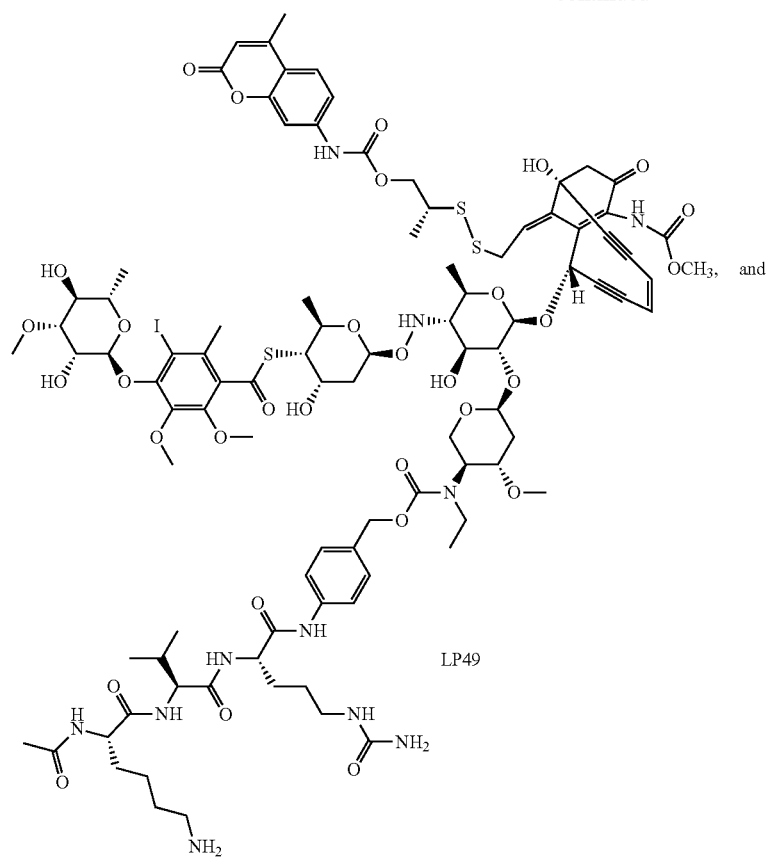
LP49, and
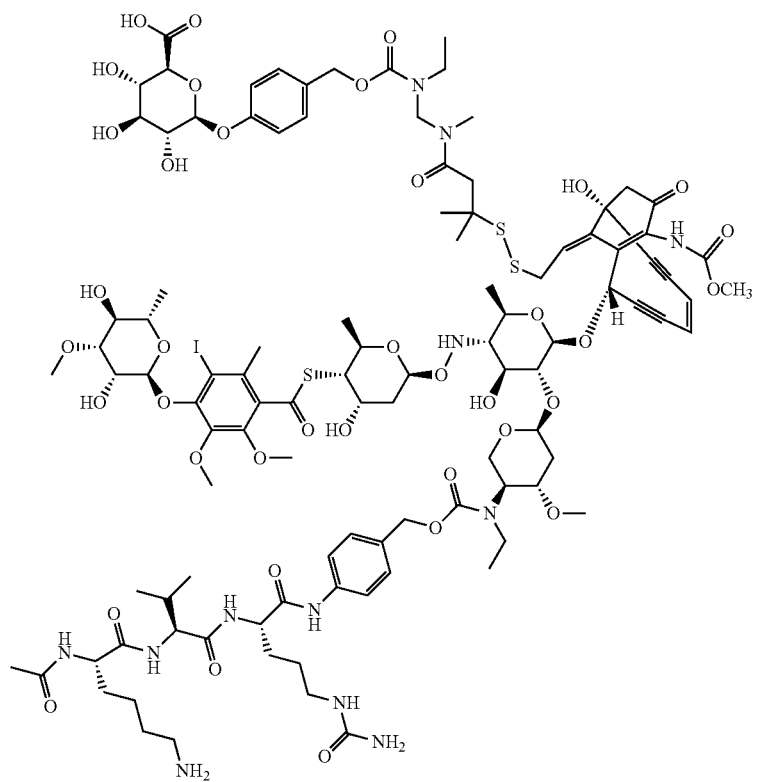

One of ordinary skill would recognise that some payload linker compounds, such as the compounds of Formula (II), or a pharmaceutically acceptable salt thereof, or the compounds of Formula (IIA), or a pharmaceutically acceptable salt thereof, are themselves useful as payload compounds.

Compounds of Formula (III) and Derivatives Thereof

The present invention also relates to a compound of Formula (III),

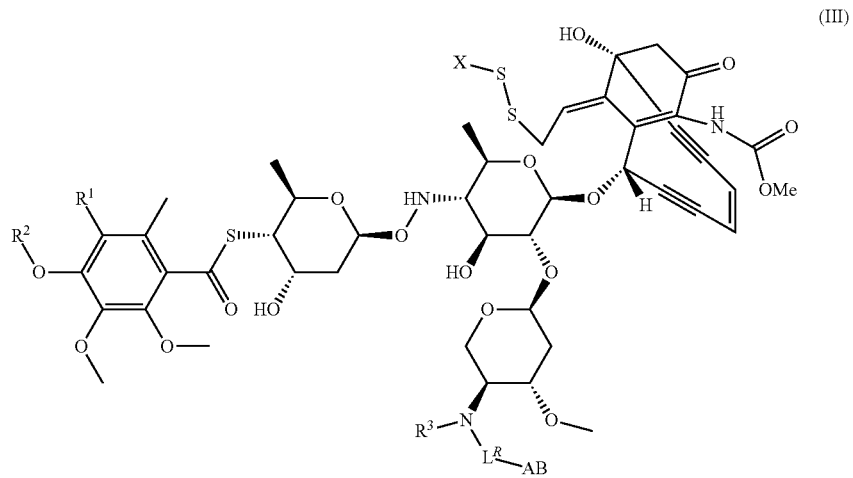

or a pharmaceutically acceptable salt thereof, wherein:
$R^1$ is selected from the group consisting of Br and I;
$R^2$ is selected from the group consisting of H and

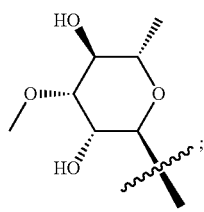

$R^3$ is selected from the group consisting of —$CH_3$, —$CH_2CH_3$, and —$CH(CH_3)_2$;
X is selected from the group consisting of:
  (i) —$CH_3$ optionally substituted by one $R^{10}$;
  (ii) —$C_2$-$C_8$alkyl optionally substituted by one $R^{10}$;
  (iii) —($C_0$-$C_6$alkyl)-$C_3$-$C_{10}$ carbocyclyl, which said $C_3$-$C_{10}$ carbocyclyl is optionally substituted by one $R^{10}$;
  (iv) —($C_0$-$C_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S;
  (v) —($C_0$-$C_6$alkyl)-phenyl, which said phenyl is optionally substituted by one $R^{10}$; and
  (vi) —($C_0$-$C_6$alkyl)-5 to 10 membered heteroaryl, which said 5 to 10 membered heteroaryl is optionally substituted by one $R^{10}$, and which said 5 to 10 membered heteroaryl comprises one, two or three heteroatoms independently selected from the group consisting of N, O and S;
and which X is optionally further substituted by 1, 2, 3, 4, 5, 6, 7, or 8 G;

$R^{10}$ is —$R^{10a}$-$R^{10b}$, wherein
  $R^{10a}$ is either absent or —$(CH_2)_n$—, which $R^{10a}$ is optionally substituted by 1, 2, 3, 4, 5, 6, 7, or 8 G;
  $R^{10b}$ is selected from the group consisting of:
    (i) —OH;
    (ii) —CN;
    (iii) —$PO_3H$;
    (iv) —$CO_2H$;
    (v) —$CO_2C_1$-$C_4$alkyl, which said $C_1$-$C_4$alkyl is optionally substituted by 1, 2, 3, 4, 5, or 6 E;
    (vi) —CO—$R^{11}$;
    (vii) —NH—$R^{11}$;
    (viii) —N($C_1$-$C_4$alkyl)-$R^{11}$, which said $C_1$-$C_4$alkyl is optionally substituted by 1, 2, 3, 4, 5, or 6 E;
    (ix) —CONH—$R^{11}$;
    (x) —CON($C_1$-$C_4$alkyl)-$R^{11}$, which said $C_1$-$C_4$alkyl is optionally substituted by 1, 2, 3, 4, 5, or 6 E;
    (xi) —CONHNH—$R^1$;
    (xii) —CONHN($C_1$-$C_4$alkyl)-$R^{11}$, which said $C_1$-$C_4$alkyl is optionally substituted by 1, 2, 3, 4, 5, or 6 E;
    (xiii) —CON($C_1$-$C_4$alkyl)NH—$R^{11}$, which said $C_1$-$C_4$alkyl is optionally substituted by 1, 2, 3, 4, 5, or 6 E;
    (xiv) —CON($C_1$-$C_4$alkyl)N($C_1$-$C_4$alkyl)-$R^{11}$, wherein each said $C_1$-$C_4$alkyl is independently optionally substituted by 1, 2, 3, 4, 5, or 6 E;
    (xv) —CON($R^{11}$)$NH_2$;
    (xvi) —CON($R^{11}$)NH($C_1$-$C_4$alkyl), which said $C_1$-$C_4$alkyl is optionally substituted by 1, 2, 3, 4, 5, or 6 E;
    (xvii) —CON($R^1$)N($C_1$-$C_4$alkyl)$_2$, wherein each said $C_1$-$C_4$alkyl is independently optionally substituted by 1, 2, 3, 4, 5, or 6 E;
    (xviii) —CONHN=C($C_1$-$C_4$alkyl)-$C_6H_4$—$OC_1$-$C_4$alkyl, wherein each said $C_1$-$C_4$alkyl is independently optionally substituted by 1, 2, 3, 4, 5, or 6 E;
    (xix) —CON($C_1$-$C_4$alkyl)N=C($C_1$-$C_4$alkyl)-$C_6H_4$—$OC_1$-$C_4$alkyl, wherein each said $C_1$-$C_4$alkyl is independently optionally substituted by 1, 2, 3, 4, 5, or 6 E;
    (xx) —N($R^{11}$)CO($C_1$-$C_4$alkyl), which said $C_1$-$C_4$alkyl is optionally substituted by 1, 2, 3, 4, 5, or 6 E;
    (xxi) —CH($CO_2H$)NH—$R^1$;
    (xxii) —CH($CO_2C_1$-$C_4$alkyl)NH—$R^{11}$, which said $C_1$-$C_4$alkyl is optionally substituted by 1, 2, 3, 4, 5, or 6 E;

(xxiii) —CH(NH$_2$)CO—R$^{11}$;
(xxiv) —CH(NH(C$_1$-C$_4$alkyl))CO—R$^{11}$, which said C$_1$-C$_4$alkyl is optionally substituted by 1, 2, 3, 4, 5, or 6 E;
(xxv) —CH(N(C$_1$-C$_4$alkyl)$_2$)CO—R$^{11}$, wherein each said C$_1$-C$_4$alkyl is independently optionally substituted by 1, 2, 3, 4, 5, or 6 E;
(xxvi) —CH(CO—R$^{11}$)NH—R$^1$; and
(xxvii) —CH(CO—R$^{11}$)N(C$_1$-C$_4$alkyl)-R$^{11}$, which said C$_1$-C$_4$alkyl is optionally substituted by 1, 2, 3, 4, 5, or 6 E;

R$^{11}$ is selected from the group consisting of —R$^{11a}$-R$^{11b}$-R$^{11c}$ and —R$^{11d}$-R$^{11e}$-R$^{11f}$, wherein
  R$^{11a}$ is either absent, or is selected from the group consisting of,

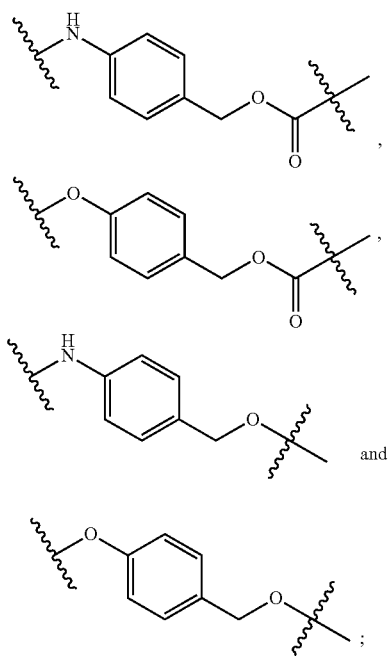

R$^{11b}$ is either absent, or is selected from the group consisting of

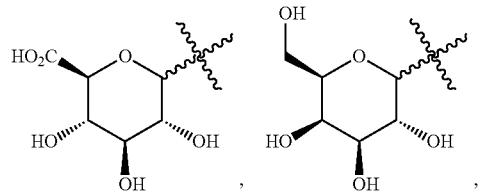

and AA$_r$, wherein AA is independently for each occurrence a natural amino acid or a non-natural amino acid;
R$^{11c}$ is either absent or is selected from the group consisting of —H, —C$_1$-C$_4$alkyl and —COC$_1$-C$_4$alkyl;
R$^{11d}$ is either absent or —(CH$_2$)$_t$—, which R$^{11d}$ when present is optionally substituted by 1, 2, 3, 4, 5, 6, 7, or 8 G;
R$^{11e}$ is either absent or selected from the group consisting of —O— and —NH—;
R$^{11f}$ is selected from the group consisting of C$_6$-C$_{12}$ aryl and 5 to 10 membered heteroaryl, which said 5 to 10 membered heteroaryl comprises one, two or three heteroatoms independently selected from the group consisting of N, O and S, and which R$^{11f}$ is optionally substituted by 1, 2, 3, 4, 5, 6, 7, or 8 G;
n is 1, 2, 3, 4, 5, or 6;
r is 1, 2, 3, 4, 5, 6, 7, 8, 9, 10, 11, 12, 13, 14, 15, 16, 17, 18, 19, or 20;
t is 1, 2, 3, 4, 5, or 6;
G is selected, independently for each occurrence, from the group consisting of —F, —Cl, —CN, —OH, —NH$_2$, —NH—C$_1$-C$_4$alkyl, —N(C$_1$-C$_4$alkyl)$_2$, —NO$_2$, —CO$_2$H, —C$_1$-C$_4$alkyl, —C$_1$-C$_4$alkylOH, —C$_1$-C$_4$alkylNH$_2$, —C$_1$-C$_4$haloalkyl, —C$_1$-C$_4$alkoxy, =O, —CO$_2$C$_1$-C$_4$alkyl, —OC(O)C$_1$-C$_4$alkyl, —NHC(O)C$_1$-C$_4$alkyl, —C(O)NHC$_1$-C$_4$alkyl, and —C(O)N(C$_1$-C$_4$alkyl)$_2$;
E is selected, independently for each occurrence, from the group consisting of —F, —Cl, —CN, —OH, —NH$_2$, —NHCH$_3$, —N(CH$_3$)$_2$, —NO$_2$, —CO$_2$H, —OCH$_3$, —OCF$_3$, and —CF$_3$;
L$^R$ is a [LINKER RADICAL]; and
AB is an antibody.

The present invention also relates to a compound of Formula (IIIA),

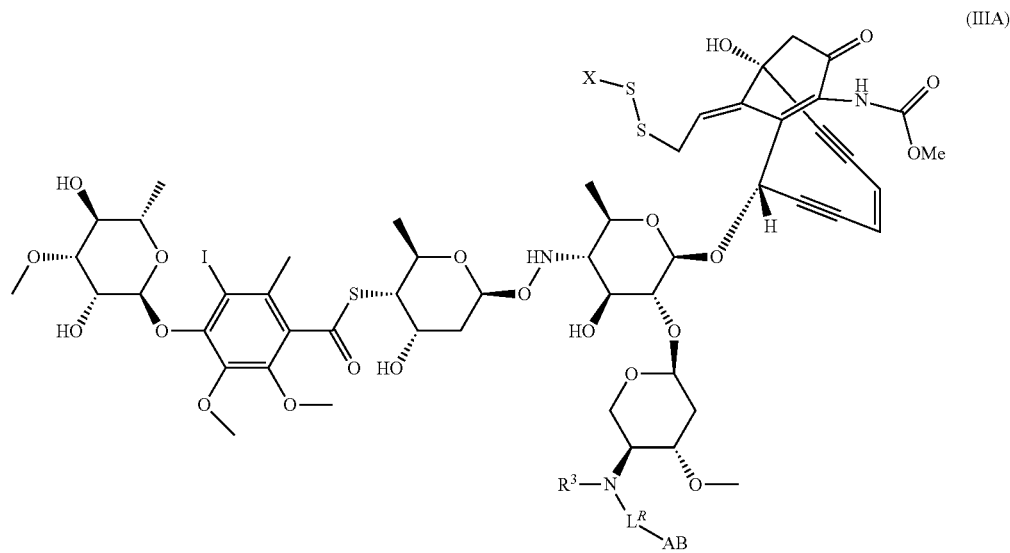

or a pharmaceutically acceptable salt thereof, wherein:
$R^3$ is selected from the group consisting of —CH$_3$, —CH$_2$CH$_3$, and —CH(CH$_3$)$_2$;
X is
X is selected from the group consisting of:
(i) —CH$_3$ optionally substituted by one $R^{10}$;
(ii) —C$_2$-C$_8$alkyl optionally substituted by one $R^{10}$;
(iii) —(C$_0$-C$_6$alkyl)-C$_3$-C$_{10}$ carbocyclyl, which said C$_3$-C$_{10}$ carbocyclyl is optionally substituted by one $R^{10}$;
(iv) —(C$_0$-C$_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S;
(v) —(C$_0$-C$_6$alkyl)-phenyl, which said phenyl is optionally substituted by one $R^{10}$; and
(vi) —(C$_0$-C$_6$alkyl)-5 to 10 membered heteroaryl, which said 5 to 10 membered heteroaryl is optionally substituted by one $R^{10}$, and which said 5 to 10 membered heteroaryl comprises one, two or three heteroatoms independently selected from the group consisting of N, O and S;
and which X is optionally further substituted by 1, 2, 3, 4, 5, 6, 7, or 8 G;
$R^{10}$ is —$R^{10a}$-$R^{10b}$, wherein
$R^{10a}$ is either absent or —(CH$_2$)$_n$—, which $R^{10a}$ is optionally substituted by 1, 2, 3, 4, 5, 6, 7, or 8 G;
$R^{10b}$ is selected from the group consisting of:
(i) —OH;
(ii) —CN;
(iii) —PO$_3$H;
(iv) —CO$_2$H;
(v) —CO$_2$C$_1$-C$_4$alkyl, which said C$_1$-C$_4$alkyl is optionally substituted by 1, 2, 3, 4, 5, or 6 E;
(vi) —CO—$R^{11}$;
(vii) —NH—$R^{11}$;
(viii) —N(C$_1$-C$_4$alkyl)-$R^{11}$, which said C$_1$-C$_4$alkyl is optionally substituted by 1, 2, 3, 4, 5, or 6 E;
(ix) —CONH—$R^{11}$;
(x) —CON(C$_1$-C$_4$alkyl)-$R^{11}$, which said C$_1$-C$_4$alkyl is optionally substituted by 1, 2, 3, 4, 5, or 6 E;
(xi) —CONHNH—$R^{11}$;
(xii) —CONHN(C$_1$-C$_4$alkyl)-$R^{11}$, which said C$_1$-C$_4$alkyl is optionally substituted by 1, 2, 3, 4, 5, or 6 E;
(xiii) —CON(C$_1$-C$_4$alkyl)NH—$R^{11}$, which said C$_1$-C$_4$alkyl is optionally substituted by 1, 2, 3, 4, 5, or 6 E;
(xiv) —CON(C$_1$-C$_4$alkyl)N(C$_1$-C$_4$alkyl)-$R^{11}$, wherein each said C$_1$-C$_4$alkyl is independently optionally substituted by 1, 2, 3, 4, 5, or 6 E;
(xv) —CON($R^{11}$)NH$_2$;
(xvi) —CON($R^{11}$)NH(C$_1$-C$_4$alkyl), which said C$_1$-C$_4$alkyl is optionally substituted by 1, 2, 3, 4, 5, or 6 E;
(xvii) —CON($R^{11}$)N(C$_1$-C$_4$alkyl)$_2$, wherein each said C$_1$-C$_4$alkyl is independently optionally substituted by 1, 2, 3, 4, 5, or 6 E;
(xviii) —CONHN=C(C$_1$-C$_4$alkyl)-C$_6$H$_4$—OC$_1$-C$_4$alkyl, wherein each said C$_1$-C$_4$alkyl is independently optionally substituted by 1, 2, 3, 4, 5, or 6 E;
(xix) —CON(C$_1$-C$_4$alkyl)N=C(C$_1$-C$_4$alkyl)-C$_6$H$_4$—OC$_1$-C$_4$alkyl, wherein each said C$_1$-C$_4$alkyl is independently optionally substituted by 1, 2, 3, 4, 5, or 6 E;

(xx) —N($R^{11}$)CO(C$_1$-C$_4$alkyl), which said C$_1$-C$_4$alkyl is optionally substituted by 1, 2, 3, 4, 5, or 6 E;
(xxi) —CH(CO$_2$H)NH—$R^{11}$;
(xxii) —CH(CO$_2$C$_1$-C$_4$alkyl)NH—$R^{11}$, which said C$_1$-C$_4$alkyl is optionally substituted by 1, 2, 3, 4, 5, or 6 E;
(xxiii) —CH(NH$_2$)CO—$R^{11}$;
(xxiv) —CH(NH(C$_1$-C$_4$alkyl))CO—$R^{11}$, which said C$_1$-C$_4$alkyl is optionally substituted by 1, 2, 3, 4, 5, or 6 E;
(xxv) —CH(N(C$_1$-C$_4$alkyl)$_2$)CO—$R^{11}$, wherein each said C$_1$-C$_4$alkyl is independently optionally substituted by 1, 2, 3, 4, 5, or 6 E;
(xxvi) —CH(CO—$R^{11}$)NH—$R^{11}$; and
(xxvii) —CH(CO—$R^{11}$)N(C$_1$-C$_4$alkyl)-$R^{11}$, which said C$_1$-C$_4$alkyl is optionally substituted by 1, 2, 3, 4, 5, or 6 E;
$R^{11}$ is selected from the group consisting of —$R^{11a}$-$R^{11b}$-$R^{11c}$ and —$R^{11d}$-$R^{11e}$-$R^{11f}$, wherein
$R^{11a}$ is either absent, or is selected from the group consisting of,

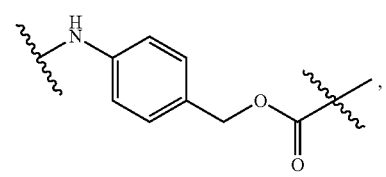

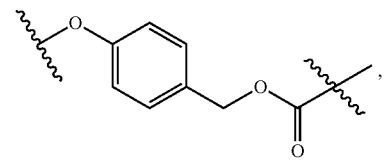

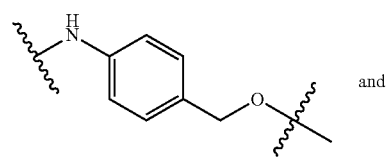

and

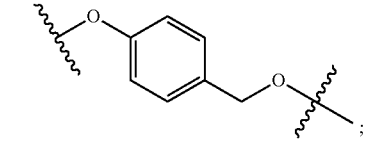

;

$R^{11b}$ is either absent, or is selected from the group consisting of

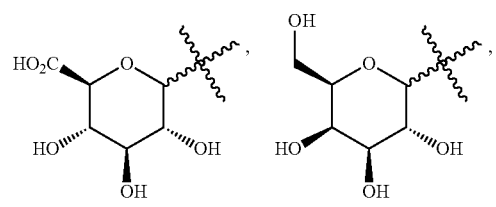

and AA$_r$, wherein AA is independently for each occurrence a natural amino acid or a non-natural amino acid;

R$^{11c}$ is either absent or is selected from the group consisting of —H, —C$_1$-C$_4$alkyl and —COC$_1$-C$_4$alkyl;

R$^{11d}$ is either absent or —(CH$_2$)$_t$—, which R$^{11d}$ when present is optionally substituted by 1, 2, 3, 4, 5, 6, 7, or 8 G;

R$^{11e}$ is either absent or selected from the group consisting of —O— and —NH—;

R$^{11f}$ is selected from the group consisting of C$_6$-C$_{12}$ aryl and 5 to 10 membered heteroaryl, which said 5 to 10 membered heteroaryl comprises one, two or three heteroatoms independently selected from the group consisting of N, O and S, and which R$^{11f}$ is optionally substituted by 1, 2, 3, 4, 5, 6, 7, or 8 G;

n is 1, 2, 3, 4, 5, or 6;

r is 1, 2, 3, 4, 5, 6, 7, 8, 9, 10, 11, 12, 13, 14, 15, 16, 17, 18, 19, or 20;

t is 1, 2, 3, 4, 5, or 6;

G is selected, independently for each occurrence, from the group consisting of —F, —Cl, —CN, —OH, —NH$_2$, —NH—C$_1$-C$_4$alkyl, —N(C$_1$-C$_4$alkyl)$_2$, —NO$_2$, —CO$_2$H, —C$_1$-C$_4$alkyl, —C$_1$-C$_4$alkylOH, —C$_1$-C$_4$alkylNH$_2$, —C$_1$-C$_4$haloalkyl, —C$_1$-C$_4$alkoxy, =O, —CO$_2$C$_1$-C$_4$alkyl, —OC(O)C$_1$-C$_4$alkyl, —NHC(O)C$_1$-C$_4$alkyl, —C(O)NHC$_1$-C$_4$alkyl, and —C(O)N(C$_1$-C$_4$alkyl)$_2$;

E is selected, independently for each occurrence, from the group consisting of —F, —Cl, —CN, —OH, —NH$_2$, —NHCH$_3$, —N(CH$_3$)$_2$, —NO$_2$, —CO$_2$H, —OCH$_3$, —OCF$_3$, and —CF$_3$;

L$^R$ is a [LINKER RADICAL]; and

AB is an antibody.

The present invention also relates to a compound of Formula (IV), or a pharmaceutically acceptable salt thereof, wherein:

R$^1$ is selected from the group consisting of Br and I;

R$^2$ is selected from the group consisting of H and

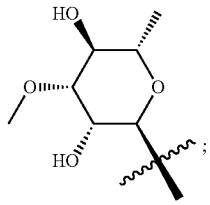

R$^3$ is selected from the group consisting of —CH$_3$, —CH$_2$CH$_3$, and —CH(CH$_3$)$_2$;

X is selected from the group consisting of:
(i) —CH$_3$ optionally substituted by one R$^{10}$;
(ii) —C$_2$-C$_8$alkyl optionally substituted by one R$^{10}$;
(iii) —(C$_0$-C$_6$alkyl)-C$_3$-C$_{10}$ carbocyclyl, which said C$_3$-C$_{10}$ carbocyclyl is optionally substituted by one R$^{10}$;
(iv) —(C$_0$-C$_6$alkyl)-3 to 10 membered heterocyclyl, which said 3 to 10 membered heterocyclyl is optionally substituted by one R$^{10}$, and which said 3 to 10 membered heterocyclyl comprises one, two or three heteroatoms independently selected from the group consisting of N, O and S;
(v) —(C$_0$-C$_6$alkyl)-phenyl, which said phenyl is optionally substituted by one R$^{10}$; and
(vi) —(C$_0$-C$_6$alkyl)-5 to 10 membered heteroaryl, which said 5 to 10 membered heteroaryl is optionally substituted by one R$^{10}$, and which said 5 to 10 membered heteroaryl comprises one, two or three heteroatoms independently selected from the group consisting of N, O and S;

and which X is optionally further substituted by 1, 2, 3, 4, 5, 6, 7, or 8 G;

R$^{10}$ is —R$^{10a}$-R$^{10b}$, wherein
R$^{10a}$ is either absent or —(CH$_2$)$_n$—, which R$^{10a}$ is optionally substituted by 1, 2, 3, 4, 5, 6, 7, or 8 G;

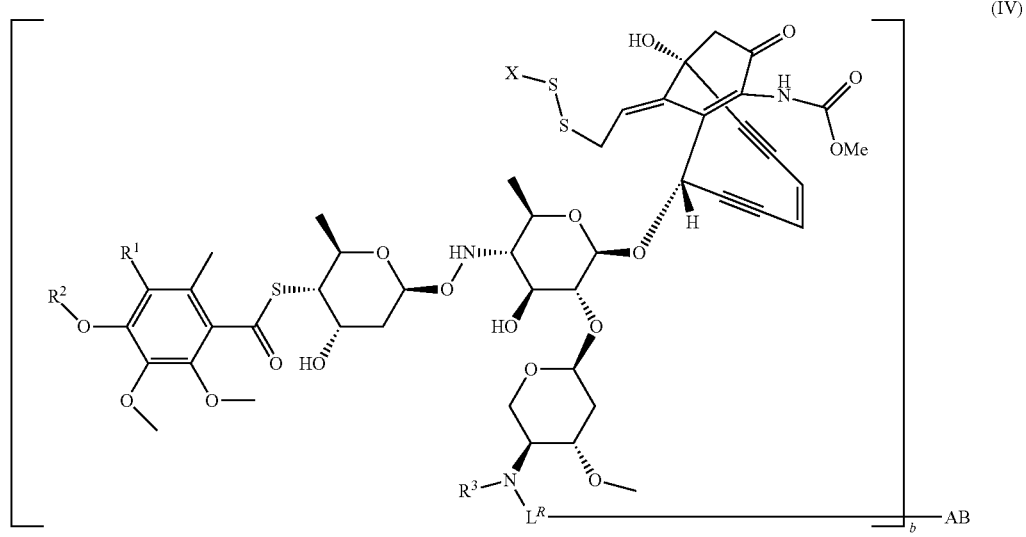

(IV)

$R^{10b}$ is selected from the group consisting of:
(i) —OH;
(ii) —CN;
(iii) —PO$_3$H;
(iv) —CO$_2$H;
(v) —CO$_2$C$_1$-C$_4$alkyl, which said C$_1$-C$_4$alkyl is optionally substituted by 1, 2, 3, 4, 5, or 6 E;
(vi) —CO—R$^{11}$;
(vii) —NH—R$^{11}$;
(viii) —N(C$_1$-C$_4$alkyl)-R$^{11}$, which said C$_1$-C$_4$alkyl is optionally substituted by 1, 2, 3, 4, 5, or 6 E;
(ix) —CONH—R$^{11}$;
(x) —CON(C$_1$-C$_4$alkyl)-R$^{11}$, which said C$_1$-C$_4$alkyl is optionally substituted by 1, 2, 3, 4, 5, or 6 E;
(xi) —CONHNH—R$^1$;
(xii) —CONHN(C$_1$-C$_4$alkyl)-R$^{11}$, which said C$_1$-C$_4$alkyl is optionally substituted by 1, 2, 3, 4, 5, or 6 E;
(xiii) —CON(C$_1$-C$_4$alkyl)NH—R$^{11}$, which said C$_1$-C$_4$alkyl is optionally substituted by 1, 2, 3, 4, 5, or 6 E;
(xiv) —CON(C$_1$-C$_4$alkyl)N(C$_1$-C$_4$alkyl)-R$^{11}$, wherein each said C$_1$-C$_4$alkyl is independently optionally substituted by 1, 2, 3, 4, 5, or 6 E;
(xv) —CON(R$^{11}$)NH$_2$;
(xvi) —CON(R$^{11}$)NH(C$_1$-C$_4$alkyl), which said C$_1$-C$_4$alkyl is optionally substituted by 1, 2, 3, 4, 5, or 6 E;
(xvii) —CON(R$^1$)N(C$_1$-C$_4$alkyl)$_2$, wherein each said C$_1$-C$_4$alkyl is independently optionally substituted by 1, 2, 3, 4, 5, or 6 E;
(xviii) —CONHN=C(C$_1$-C$_4$alkyl)-C$_6$H$_4$—OC$_1$-C$_4$alkyl, wherein each said C$_1$-C$_4$alkyl is independently optionally substituted by 1, 2, 3, 4, 5, or 6 E;
(xix) —CON(C$_1$-C$_4$alkyl)N=C(C$_1$-C$_4$alkyl)-C$_6$H$_4$—OC$_1$-C$_4$alkyl, wherein each said C$_1$-C$_4$alkyl is independently optionally substituted by 1, 2, 3, 4, 5, or 6 E;
(xx) —N(R$^{11}$)CO(C$_1$-C$_4$alkyl), which said C$_1$-C$_4$alkyl is optionally substituted by 1, 2, 3, 4, 5, or 6 E;
(xxi) —CH(CO$_2$H)NH—R$^1$;
(xxii) —CH(CO$_2$C$_1$-C$_4$alkyl)NH—R$^{11}$, which said C$_1$-C$_4$alkyl is optionally substituted by 1, 2, 3, 4, 5, or 6 E;
(xxiii) —CH(NH$_2$)CO—R$^{11}$;
(xxiv) —CH(NH(C$_1$-C$_4$alkyl))CO—R$^{11}$, which said C$_1$-C$_4$alkyl is optionally substituted by 1, 2, 3, 4, 5, or 6 E;
(xxv) —CH(N(C$_1$-C$_4$alkyl)$_2$)CO—R$^{11}$, wherein each said C$_1$-C$_4$alkyl is independently optionally substituted by 1, 2, 3, 4, 5, or 6 E;
(xxvi) —CH(CO—R$^{11}$)NH—R$^1$; and
(xxvii) —CH(CO—R$^{11}$)N(C$_1$-C$_4$alkyl)-R$^{11}$, which said C$_1$-C$_4$alkyl is optionally substituted by 1, 2, 3, 4, 5, or 6 E;

$R^{11}$ is selected from the group consisting of —R$^{11a}$-R$^{11b}$-R$^{11c}$ and —R$^{11d}$-R$^{11e}$-R$^{11f}$, wherein $R^{11a}$ is either absent, or is selected from the group consisting of,

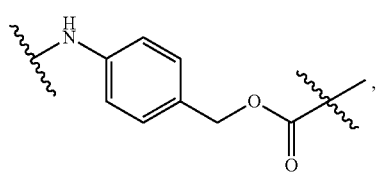

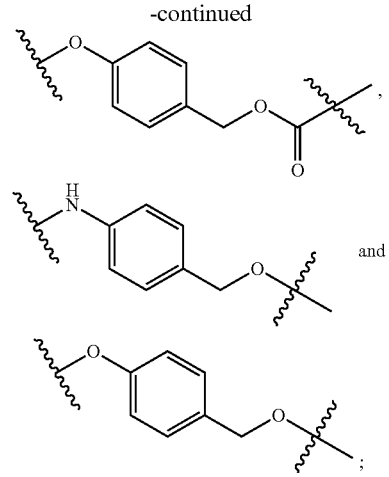

$R^{11b}$ is either absent, or is selected from the group consisting of

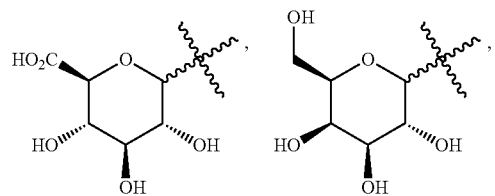

and AA$_r$, wherein AA is independently for each occurrence a natural amino acid or a non-natural amino acid;

$R^{11c}$ is either absent or is selected from the group consisting of —H, —C$_1$-C$_4$alkyl and —COC$_1$-C$_4$alkyl;

$R^{11d}$ is either absent or —(CH$_2$)$_t$—, which R$^{11d}$ when present is optionally substituted by 1, 2, 3, 4, 5, 6, 7, or 8 G;

$R^{11e}$ is either absent or selected from the group consisting of —O— and —NH—;

$R^{11f}$ is selected from the group consisting of C$_6$-C$_{12}$ aryl and 5 to 10 membered heteroaryl, which said 5 to 10 membered heteroaryl comprises one, two or three heteroatoms independently selected from the group consisting of N, O and S, and which R$^{11f}$ is optionally substituted by 1, 2, 3, 4, 5, 6, 7, or 8 G;

n is 1, 2, 3, 4, 5, or 6;
r is 1, 2, 3, 4, 5, 6, 7, 8, 9, 10, 11, 12, 13, 14, 15, 16, 17, 18, 19, or 20;
t is 1, 2, 3, 4, 5, or 6;
G is selected, independently for each occurrence, from the group consisting of —F, —Cl, —CN, —OH, —NH$_2$, —NH—C$_1$-C$_4$alkyl, —N(C$_1$-C$_4$alkyl)$_2$, —NO$_2$, —CO$_2$H, —C$_1$-C$_4$alkyl, —C$_1$-C$_4$alkylOH, —C$_1$-C$_4$alkylNH$_2$, —C$_1$-C$_4$haloalkyl, —C$_1$-C$_4$alkoxy, =O, —CO$_2$C$_1$-C$_4$alkyl, —OC(O)C$_1$-C$_4$alkyl, —NHC(O)C$_1$-C$_4$alkyl, —C(O)NHC$_1$-C$_4$alkyl, and —C(O)N(C$_1$-C$_4$alkyl)$_2$;

E is selected, independently for each occurrence, from the group consisting of —F, —Cl, —CN, —OH, —NH$_2$, —NHCH$_3$, —N(CH$_3$)$_2$, —NO$_2$, —CO$_2$H, —OCH$_3$, —OCF$_3$, and —CF$_3$;

$L^R$ is a [LINKER RADICAL];
AB is an antibody; and
b is 1-20.

The present invention also relates to a compound of Formula (IVA),

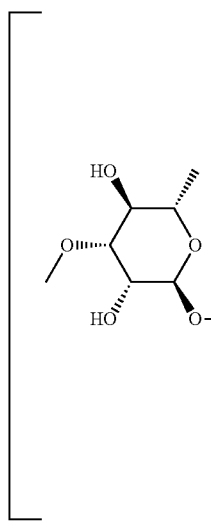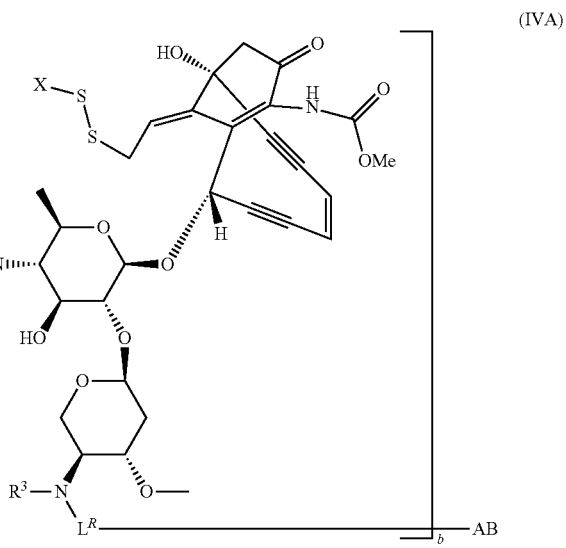

(IVA)

or a pharmaceutically acceptable salt thereof, wherein:
$R^3$ is selected from the group consisting of —$CH_3$, —$CH_2CH_3$, and —$CH(CH_3)_2$;
X is selected from the group consisting of:
(i) —$CH_3$ optionally substituted by one $R^{10}$;
(ii) —$C_2$-$C_8$alkyl optionally substituted by one $R^{10}$;
(iii) —($C_0$-$C_6$alkyl)-$C_3$-$C_{00}$ carbocyclyl, which said $C_3$-$C_{10}$ carbocyclyl is optionally substituted by one $R^{10}$;
(iv) —($C_0$-$C_6$alkyl)-3 to 10 membered heterocyclyl, which said 3 to 10 membered heterocyclyl is optionally substituted by one $R^{10}$, and which said 3 to 10 membered heterocyclyl comprises one, two or three heteroatoms independently selected from the group consisting of N, O and S;
(v) —($C_0$-$C_6$alkyl)-phenyl, which said phenyl is optionally substituted by one $R^{10}$; and
(vi) —($C_0$-$C_6$alkyl)-5 to 10 membered heteroaryl, which said 5 to 10 membered heteroaryl is optionally substituted by one $R^{10}$, and which said 5 to 10 membered heteroaryl comprises one, two or three heteroatoms independently selected from the group consisting of N, O and S;
and which X is optionally further substituted by 1, 2, 3, 4, 5, 6, 7, or 8 G;
$R^{10}$ is —$R^{10a}$-$R^{10b}$, wherein
$R^{10a}$ is either absent or —$(CH_2)_n$—, which $R^{10a}$ is optionally substituted by 1, 2, 3, 4, 5, 6, 7, or 8 G;
$R^{10b}$ is selected from the group consisting of:
(i) —OH;
(ii) —CN;
(iii) —$PO_3H$;
(iv) —$CO_2H$;
(v) —$CO_2C_1$-$C_4$alkyl, which said $C_1$-$C_4$alkyl is optionally substituted by 1, 2, 3, 4, 5, or 6 E;
(vi) —CO—$R^{11}$;
(vii) —NH—$R^{11}$;
(viii) —N($C_1$-$C_4$alkyl)-$R^{11}$, which said $C_1$-$C_4$alkyl is optionally substituted by 1, 2, 3, 4, 5, or 6 E;
(ix) —CONH—$R^{11}$;

(x) —CON($C_1$-$C_4$alkyl)-$R^{11}$, which said $C_1$-$C_4$alkyl is optionally substituted by 1, 2, 3, 4, 5, or 6 E;
(xi) —CONHNH—$R^{11}$;
(xii) —CONHN($C_1$-$C_4$alkyl)-$R^{11}$, which said $C_1$-$C_4$alkyl is optionally substituted by 1, 2, 3, 4, 5, or 6 E;
(xiii) —CON($C_1$-$C_4$alkyl)NH—$R^{11}$, which said $C_1$-$C_4$alkyl is optionally substituted by 1, 2, 3, 4, 5, or 6 E;
(xiv) —CON($C_1$-$C_4$alkyl)N($C_1$-$C_4$alkyl)-$R^{11}$, wherein each said $C_1$-$C_4$alkyl is independently optionally substituted by 1, 2, 3, 4, 5, or 6 E;
(xv) —CON($R^{11}$)$NH_2$;
(xvi) —CON($R^{11}$)NH($C_1$-$C_4$alkyl), which said $C_1$-$C_4$alkyl is optionally substituted by 1, 2, 3, 4, 5, or 6 E;
(xvii) —CON($R^{11}$)N($C_1$-$C_4$alkyl)$_2$, wherein each said $C_1$-$C_4$alkyl is independently optionally substituted by 1, 2, 3, 4, 5, or 6 E;
(xviii) —CONHN=C($C_1$-$C_4$alkyl)-$C_6H_4$—$OC_1$-$C_4$alkyl, wherein each said $C_1$-$C_4$alkyl is independently optionally substituted by 1, 2, 3, 4, 5, or 6 E;
(xix) —CON($C_1$-$C_4$alkyl)N=C($C_1$-$C_4$alkyl)-$C_6H_4$—$OC_1$-$C_4$alkyl, wherein each said $C_1$-$C_4$alkyl is independently optionally substituted by 1, 2, 3, 4, 5, or 6 E;
(xx) —N($R^{11}$)CO($C_1$-$C_4$alkyl), which said $C_1$-$C_4$alkyl is optionally substituted by 1, 2, 3, 4, 5, or 6 E;
(xxi) —CH($CO_2H$)NH—$R^1$;
(xxii) —CH($CO_2C_1$-$C_4$alkyl)NH—$R^{11}$, which said $C_1$-$C_4$alkyl is optionally substituted by 1, 2, 3, 4, 5, or 6 E;
(xxiii) —CH($NH_2$)CO—$R^{11}$;
(xxiv) —CH(NH($C_1$-$C_4$alkyl))CO—$R^{11}$, which said $C_1$-$C_4$alkyl is optionally substituted by 1, 2, 3, 4, 5, or 6 E;
(xxv) —CH(N($C_1$-$C_4$alkyl)$_2$)CO—$R^{11}$, wherein each said $C_1$-$C_4$alkyl is independently optionally substituted by 1, 2, 3, 4, 5, or 6 E;

(xxvi) —CH(CO—R$^{11}$)NH—R$^{11}$; and
(xxvii) —CH(CO—R$^{11}$)N(C$_1$-C$_4$alkyl)-R$^{11}$, which said C$_1$-C$_4$alkyl is optionally substituted by 1, 2, 3, 4, 5, or 6 E;
R$^{11}$ is selected from the group consisting of —R$^{11a}$-R$^{11b}$-R$^{11c}$ and —R$^{11d}$-R$^{11e}$-R$^{11f}$ wherein
R$^{11a}$ is either absent, or is selected from the group consisting of,

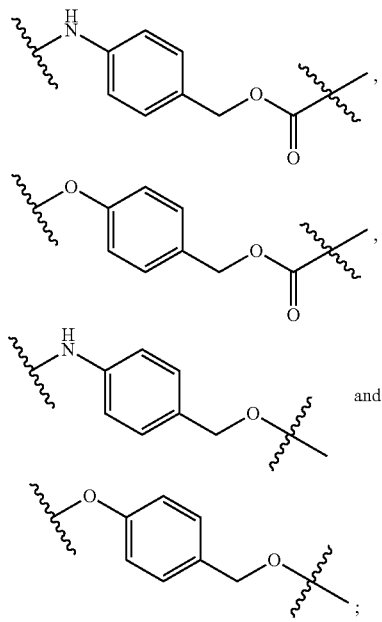

R$^{11b}$ is either absent, or is selected from the group consisting of

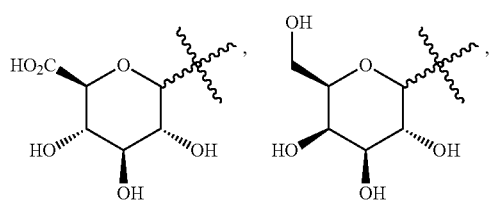

and AA$_r$, wherein AA is independently for each occurrence a natural amino acid or a non-natural amino acid;
R$^{11c}$ is either absent or is selected from the group consisting of —H, —C$_1$-C$_4$alkyl and —COC$_1$-C$_4$alkyl;
R$^{11d}$ is either absent or —(CH$_2$)$_t$—, which R$^{11d}$ when present is optionally substituted by 1, 2, 3, 4, 5, 6, 7, or 8 G;
R$^{11e}$ is either absent or selected from the group consisting of —O— and —NH—;
R$^{11f}$ is selected from the group consisting of C$_6$-C$_{12}$ aryl and 5 to 10 membered heteroaryl, which said 5 to 10 membered heteroaryl comprises one, two or three heteroatoms independently selected from the group consisting of N, O and S, and which R$^{11f}$ is optionally substituted by 1, 2, 3, 4, 5, 6, 7, or 8 G;
n is 1, 2, 3, 4, 5, or 6;
r is 1, 2, 3, 4, 5, 6, 7, 8, 9, 10, 11, 12, 13, 14, 15, 16, 17, 18, 19, or 20;
t is 1, 2, 3, 4, 5, or 6;
G is selected, independently for each occurrence, from the group consisting of —F, —Cl, —CN, —OH, —NH$_2$, —NH—C$_1$-C$_4$alkyl, —N(C$_1$-C$_4$alkyl)$_2$, —NO$_2$, —CO$_2$H, —C$_1$-C$_4$alkyl, —C$_1$-C$_4$alkylOH, —C$_1$-C$_4$alkylNH$_2$, —C$_1$-C$_4$haloalkyl, —C$_1$-C$_4$alkoxy, =O, —CO$_2$C$_1$-C$_4$alkyl, —OC(O)C$_1$-C$_4$alkyl, —NHC(O)C$_1$-C$_4$alkyl, —C(O)NHC$_1$-C$_4$alkyl, and —C(O)N(C$_1$-C$_4$alkyl)$_2$;
E is selected, independently for each occurrence, from the group consisting of —F, —Cl, —CN, —OH, —NH$_2$, —NHCH$_3$, —N(CH$_3$)$_2$, —NO$_2$, —CO$_2$H, —OCH$_3$, —OCF$_3$, and —CF$_3$;
L$^R$ is a [LINKER RADICAL];
AB is an antibody; and
b is 1-20.

The antibody drug conjugates (ADCs) of Formula (III), Formula (IIIA), Formula (IV) and Formula (IVA), or pharmaceutically acceptable salts thereof, comprise an antibody (AB) bound to a radical of the linker payload of Formula (II), or a pharmaceutically acceptable salt thereof, or to a radical of the linker payload of Formula (IIA), or a pharmaceutically acceptable salt thereof. The radical of the linker payload of Formula (II) or Formula (IIA), of their pharmaceutically acceptable salts, is formed when the linker payload is bound, through a suitable point of substitution on the linker unit to an antibody. The linker radical (L$^R$, sometimes referred to as "[LINKER RADICAL]" herein) is used merely to indicate that the linker substituent is now acting as a bifunctional substituent bound to both the payload and also the antibody. One of ordinary skill would understand that the radical of the linker payload of Formula (II) or Formula (IIA), or their pharmaceutically acceptable salts, is formed when the linker of the linker payload is bound to an antibody through a suitable point of substitution on the linker unit. Without wishing to be bound by theory, the antibody may be bound to the linker payload by displacement of the linker substituent L$^A$. This may occur when, for example, the linker comprises L$^A$ which is halo. Alternatively the antibody may be bound to the linker payload by addition to the linker substituent L$^A$. This may occur when, for example, the linker comprises L$^A$ which is

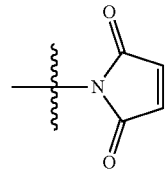 [SMILES: *N1C(=O)C=CC1=O]

and the antibody adds across the double bond to form

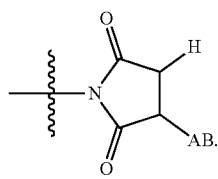

Alternatively the antibody may be bound to the linker payload by displacement of a suitable leaving group from substituent L$^A$. This may occur when, for example, the linker comprises $L^A$ which is —NHR, to form —NH-AB; or the linker comprises $L^A$ which is —CO—H, —CO$_2$H,

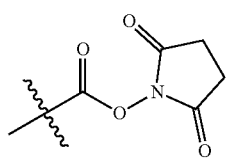 or 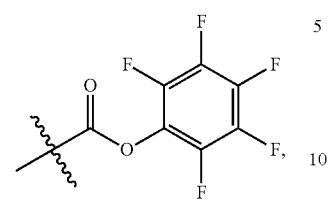

to form

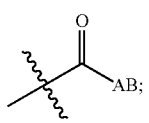

or the linker comprises $L^A$ which is —S—S-aryl optionally substituted with —NO$_2$ or —S—S-heteroaryl optionally substituted with —NO$_2$ to form —S-AB; or the linker comprises $L^A$ which is alkyl-SO$_2$-heteroaryl; arylSO$_2$-heteroaryl- to form heteroaryl-AB; or the linker comprises $L^A$ which is

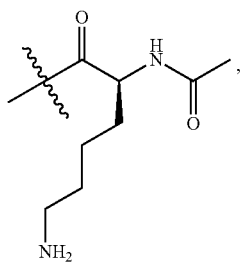 [SMILES: *C(=O)[C@H](CCCCN)NC(C)=O]

to form

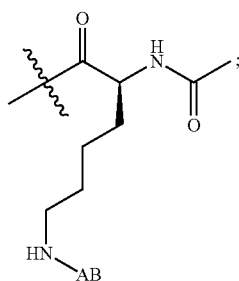

or the linker comprises $L^A$ which is

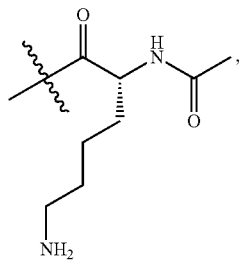 [SMILES: *C(=O)[C@@H](CCCCN)NC(C)=O]

to form

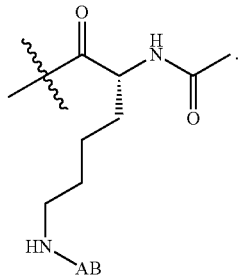

In some embodiments of this invention -$L^R$-AB is -$(L^C)_{1-3}$-$L^B$-$L^{AR}$-AB wherein:

$L^{AR}$-AB is selected from the group consisting of —AB; —NH-AB; —CO-AB; —S-AB; -heteroaryl-AB;

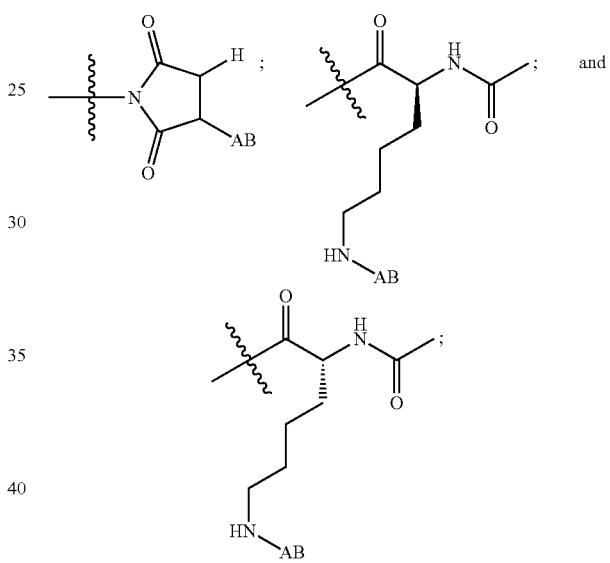

$L^B$ is selected from the group consisting of -$L^{B1}$-$L^{B2}$-$L^{B3}$ and -$L^{B2}$-$L^{B3}$-$L^{B1}$ wherein $L^{B1}$ is either absent or is one or more components selected from the group consisting of —C(O)NR—, —C(O)C$_1$-C$_6$alkyl-, —C(O)NRC$_1$-C$_6$alkyl-, —C$_1$-C$_6$alkyl(OCH$_2$CH$_2$)$_{1-8}$—, —C$_1$-C$_6$alkyl(OCH$_2$CH$_2$)$_{1-8}$—NR—, —C(O)C$_1$-C$_6$alkylNRC(O)—, —C(O)C$_1$-C$_6$alkyl(OCH$_2$CH$_2$)$_{1-8}$—, —C$_1$-C$_6$alkyl(OCH$_2$CH$_2$)$_{1-8}$—C(O)—, —C$_1$-C$_6$alkyl-S—S—C$_1$-C$_6$alkyl NRC(O)CH$_2$—, —C$_1$-C$_6$alkyl(OCH$_2$CH$_2$)$_{1-8}$NRC(O)CH$_2$—, —C(O)C$_1$-C$_6$alkyl-NRC(O)C$_{1-6}$alkyl-, —N=CR-phenyl-O—C$_1$-C$_6$alkyl-, —N=CR— phenyl-O—C$_1$-C$_6$alkyl-C(O)—, —C(O)—C$_1$-C$_6$alkyl(OCH$_2$CH$_2$)$_{1-8}$NRC(O)—, —C(O)C$_1$-C$_6$alkyl-phenyl(NR—C(O)C$_1$-C$_6$alkyl)$_{1-4}$-, —C(O)C$_1$-C$_6$alkyl(OCH$_2$CH$_2$)$_{1-8}$—NRC(O)C$_1$-C$_6$alkyl-, —C$_1$-C$_6$alkyl-, —S—, —C(O)—CH(NR—C(O)C$_1$-C$_6$alkyl)-C$_1$-C$_6$alkyl-, (—CH$_2$—CH$_2$—O—)$_{1-20}$, —C$_1$-C$_6$alkylene-NR—, and —NRC$_1$-C$_6$alkylene-;

$L^{B2}$ is either absent, or is selected from the group consisting of

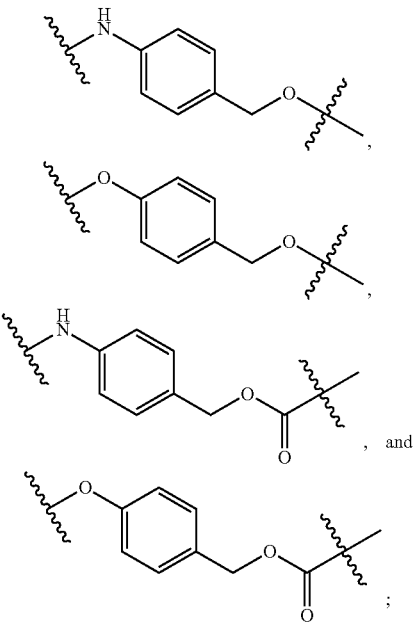 [SMILES: *Nc1ccc(CO*)cc1 ; *OCc1ccc(O*)cc1 ; *Nc1ccc(COC(*)=O)cc1 ; *Oc1ccc(COC(*)=O)cc1]

$L^{B3}$ is $AA_{0-12}$, wherein AA is independently for each occurrence a natural amino acid or a non-natural amino acid;
$L^C$ is either absent or is selected, independently for each occurrence, from the group consisting of —CO—, —$C_1$-$C_6$alkylene-, —$NRC_3$-$C_8$-heterocyclylNR—, —$NRC_3$-$C_8$-carbocyclylNR—, —$NRC_1$-$C_6$alkylNR—, —$NRC_1$-$C_6$alkylene-, —S—, —NR—, —NRNR—, —$O(CR_2)_{1-4}S$—$S(CR_2)_{1-4}N(R)$—, —$NRC_1$-$C_6$-alkylenephenyleneNR—, —$NRC_1$-$C_6$alkylenephenyleneSO$_2$NR—, —$OC_1C_6$alkylS-S$C_1$-$C_6$alkylC(COOR)NR—, —NRC(COOR)$C_1$-$C_6$alkylS-S$C_1$-$C_6$alkylO—,

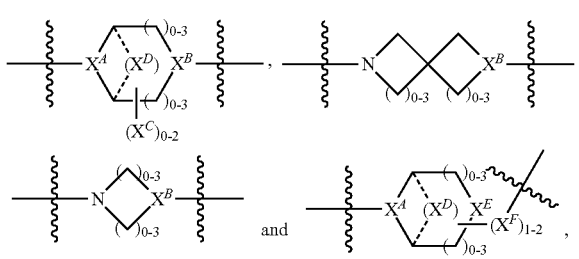

$X^A$ is selected from the group consisting of CR and N;
$X^B$ is selected from the group consisting of CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) and N;
each $X^C$ is R;
each $X^D$ is either absent or —(CH$_2$)$_{1-5}$—;
$X^E$ is selected from the group consisting of O, S, C(R)$_2$, C(R)(C(R)$_2$)$_{1-3}$—NR$_2$ and NR;
each $X^F$ is selected from the group consisting of (C(R)$_2$)$_{1-3}$—NR and C(R)$_2$—(C(R)$_2$)$_{1-3}$—O; and
each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH($C_1$-$C_8$ alkyl), —N($C_1$-$C_8$ alkyl)$_2$, —NO$_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —NH$_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —NO$_2$ or —$C_1$-$C_{10}$ heterocyclyl, for each ring system in which R appears.

In some embodiments of this invention $L^{AR}$-AB is selected from the group consisting of —NH-AB;

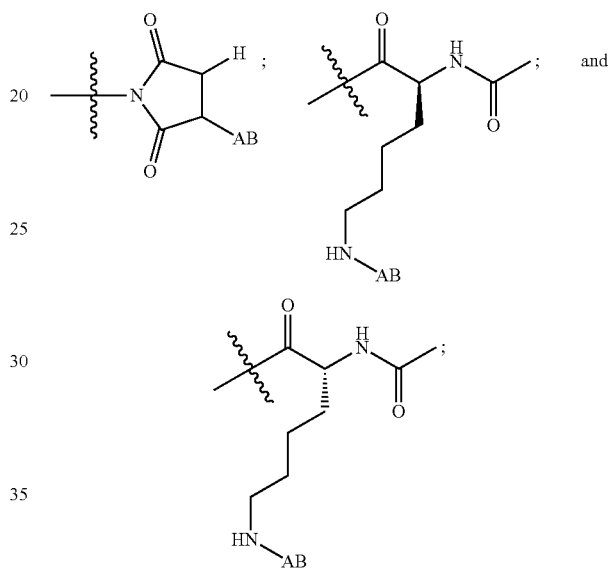

In some embodiments of this invention -$L^R$-AB is

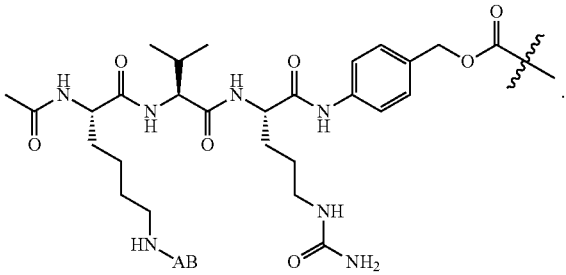

In some embodiments of this invention -$L^R$-AB is —(CH$_2$)$_3$—(OCH$_2$CH$_2$)$_6$—NH-AB.

In some embodiments of this invention -$L^R$-AB is —(CH$_2$)—CONH—(CH$_2$)$_2$—(OCH$_2$CH$_2$)$_2$—NH-AB.

In some embodiments of this invention -$L^R$-AB is —(CH$_2$)—CONH—(CH$_2$)$_2$—(OCH$_2$CH$_2$)$_7$—NH-AB.

In some embodiments of this invention -$L^R$-AB is —CO—(CH$_2$)$_2$—CO—NH-AB.

In some embodiments of this invention -$L^R$-AB is —(CH$_2$)—CONH—(CH$_2$)$_3$—NH—(CH$_2$)$_4$—NH—(CH$_2$)$_3$—NH-AB.

In some embodiments of this invention -L$^R$-AB is
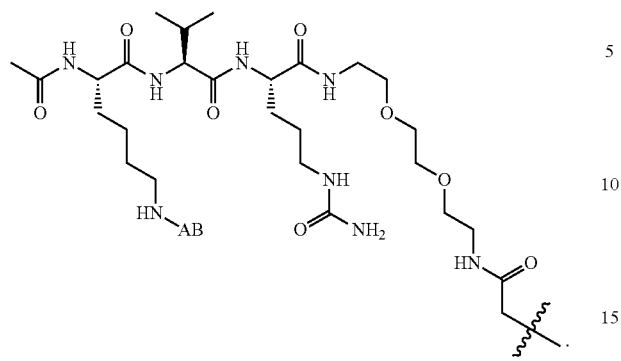
In some embodiments of this invention -L$^R$-AB is
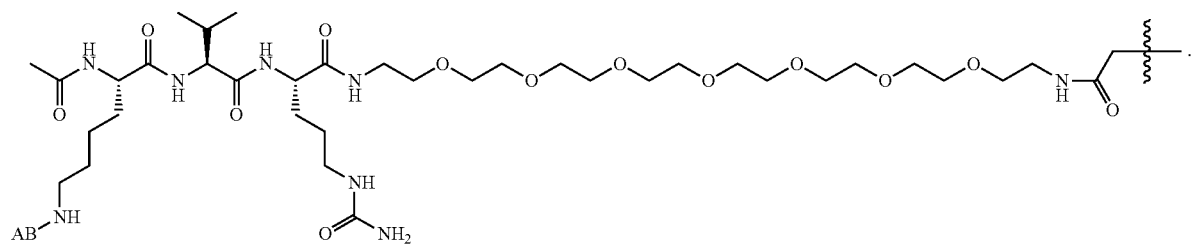
In some embodiments of this invention -L$^R$-AB is
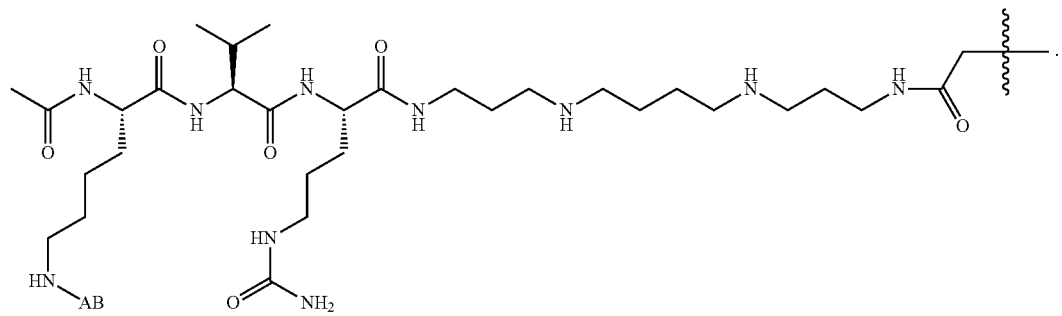
In some embodiments of this invention -L$^R$-AB is
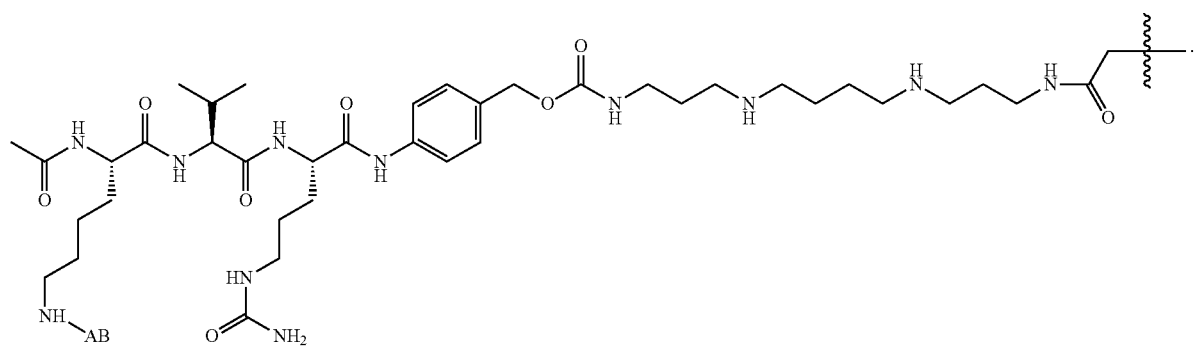

In some embodiments of this invention -L$^R$-AB is

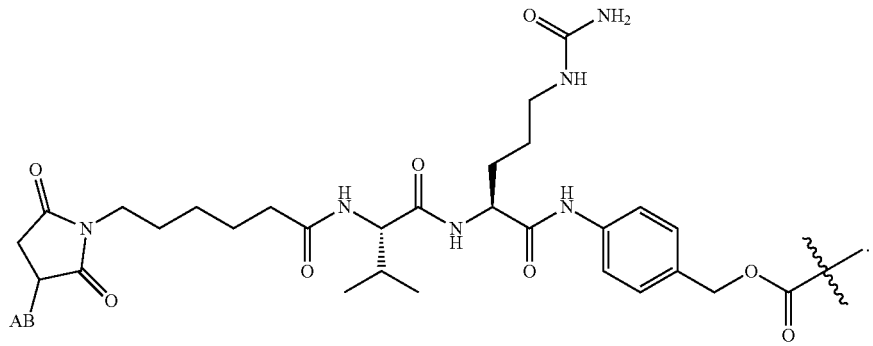

Each of the aspects and embodiments described herein with respect to Formula (I) are, either alone or, where applicable, in combination, also applicable to compounds of Formula (III), Formula (IIIA), Formula (IV) and Formula (IVA), to the extent they are not incompatible with the structure.

Each of the aspects and embodiments described herein with respect to Formula (II) and Formula (IIA), either alone or in combination with each of the aspects of embodiments described herein with respect to Formula (I) and Formula (IA), are also applicable to compounds Formula (III), Formula (IIA), Formula (IV) and Formula (IVA), to the extent they are not incompatible with the structure.

In certain embodiments, the present invention relates to any of the aforementioned compounds and attendant definitions, wherein AB is an antibody. In some embodiments, the antibody in the ADC as described herein is a monoclonal antibody, a polyclonal antibody, a human antibody, a humanized antibody, a chimeric antibody, a bispecific antibody, a minibody, a diabody, or an antibody fragment.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

The Antibody Unit (AB)

As noted above, the term "antibody" (or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. In addition, while certain aspects of the invention described herein refer to antibody drug conjugates, it is further envisioned that the antibody portion of the conjugate might be replaced with anything that specifically binds or reactively associates or complexes with a receptor, antigen or other receptive moiety associated with a given target-cell population. For example, instead of containing an antibody, a conjugate of the invention could contain a targeting molecule that binds to, complexes with, or reacts with a receptor, antigen or other receptive moiety of a cell population sought to be therapeutically or otherwise biologically modified. Example of such molecules include smaller molecular weight proteins, polypeptide or peptides, lectins, glycoproteins, non-peptides, vitamins, nutrient-transport molecules (such as, but not limited to, transferrin), or any other cell binding molecule or substances. In certain aspects, the antibody or other such targeting molecule acts to deliver a drug to the particular target cell population with which the antibody or other targeting molecule interacts.

Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These hetero atoms can be present on the antibody in the antibody's natural state, for example a naturally-occurring antibody, or can be introduced into the antibody via chemical modification or may be introduced into the antibody via genetic engineering such as a biochemical modification.

In one embodiment, an antibody unit has a sulfhydryl group and the antibody unit bonds via the sulfhydryl group's sulfur atom.

In another embodiment, the antibody has lysine residues that can react with activated esters (such esters include, but are not limited to, N-hydroxysuccinimde, pentafluorophenyl, and p-nitrophenyl esters) and thus form an amide bond consisting of the nitrogen atom of the antibody unit and a carbonyl.

In yet another aspect, the antibody unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the antibody unit can have one or more carbohydrate groups that can be chemically modified to have one or more sulfhydryl groups.

In yet another embodiment, the antibody unit can have one or more carbohydrate groups that can be oxidized to provide an aldehyde group (see, e.g., Laguzza, et al., 1989, J. Med. Chem. 32(3):548-55). The corresponding aldehyde can form a bond with a reactive site such as, for example, hydrazine and hydroxylamine. Other protocols for the modification of proteins for the attachment or association of drugs are described in Coligan et al., Current Protocols in Protein Science, vol. 2, John Wiley & Sons (2002) (incorporated herein by reference).

When the conjugates comprise non-immunoreactive protein, polypeptide, or peptide units instead of an antibody, useful non-immunoreactive protein, polypeptide, or peptide units include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-α and TGF-β, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art (e.g., Teng et al., 1983, Proc. Natl. Acad. Sci. USA. 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (for location of the CDR sequences, see, e.g., Kabat et al., 1991, Sequences of Proteins of Immunological Interest, Fifth Edition, National Institute of Health, Bethesda, Md.; Kabat E et al., 1980, J. Immunology 125(3):961-969).

Other useful antibodies include fragments of antibodies such as, but not limited to, F(ab')₂ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903). Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, The rise of monoclonal antibodies as therapeutics, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, any known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing.

In another embodiment, the antibody is selected from the group consisting of, but not limited to, a murine antibody for the treatment of ovarian cancer such as oregovomab (OVAREX®); a murine IgG$_{2a}$ antibody for the treatment of colorectal cancer such as edrecolomab (PANOREX®); an anti-EGFR IgG chimeric antibody for the treatment of epidermal growth factor positive cancers, such as head and neck cancer, for instance cetuximab (ERBITUX®); a humanized antibody for the treatment of sarcoma, such as a Humanized Monoclonal Antibody to the Vitronectin Receptor ($\alpha_v\beta_3$) like Vitaxin®; a humanized IgG$_1$ antibody for the treatment of chronic lymphocytic leukemia (CLL) such as alemtuzumab (CAMPATH I/H®); SMART ID10 which is a humanized anti-HLA-DR antibody for the treatment of non-Hodgkin's lymphoma; 1311 Lym-1 (ONCOLYM®) which is a radiolabeled murine anti-HLA-Dr10 antibody for the treatment of non-Hodgkin's lymphoma; a humanized anti-CD2 mAb for the treatment of Hodgkin's Disease or non-Hodgkin's lymphoma such as ALLOMUNE® labetuzumab (CEACIDE®) which is a humanized anti-CEA antibody for the treatment of colorectal cancer; bevacizumab (AVASTIN®) which is a humanized anti-VEGF-A mAb for the treatment of brain, colon, kidney, or lung cancer; Ibritumomab tiuxetan (ZEVALIN®) which is an anti-CD20 monoclonal antibody to the treatment of non-Hodgkin's lymphoma; ofatumumab (ARZERRA®) which is a human anti-CD20 monoclonal antibody for the treatment of chronic lymphocytic leukemia; panitumumab (VECTIBIX®) which is a human anti-EGFR monoclonal antibody for the treatment of colon cancer; rituximab (RITUXAN®) which is an anti-CD20 chimeric monoclonal antibody for the treatment of chronic lymphocytic leukemia and non-Hodgkin's lymphoma; tositumomab (BEXXAR®) which is an anti-CD20 monoclonal antibody for the treatment of non-Hodgkin's lymphoma; trastuzumab (HERCEPTIN®) which is an anti-HER2 receptor monoclonal antibody for the treatment of breast and stomach cancer; ipilimumab (YERVOY®) which is an anti-CTLA4 human monoclonal antibody for the treatment of melanoma; an anti-CD33 humanised monoclonal antibody, such as that used in MYLOTARG® (Wyeth/Pfizer, NY) which is anti-CD33 humanized monoclonal antibody conjugated to calicheamicin for the treatment of acute myelogenous leukemia; and an anti-CD 22 humanised monoclonal antibody, such as that used in inotuzumab ozogamicin (Wyeth/Pfizer, NY) which is an anti-CD22 humanized monoclonal antibody conjugated to calicheamicin for the treatment of acute lymphocytic leukemia and non-Hodgkin's lymphoma.

In another specific embodiment, the antibody is an anti-IL13 antibody, including anti-IL13 antibodies used in the treatment of cancer, for instance including, but not limited to, anti-IL-13Rα2 antibodies.

In another specific embodiment, the antibody is an anti-Notch antibody, including anti-Notch antibodies used in the treatment of cancer.

In certain embodiments, the antibody AB is bound to the linker via a sulfur bond or via a sulfur-sulfur bond.

In certain embodiments, the antibody AB is an anti-HER2 receptor monoclonal antibody, wherein HER is taken to mean human epidermal growth factor receptor.

In certain embodiments, the antibody AB is an anti-CD33 receptor monoclonal antibody, which CD33 receptor is also known as siglec-3.

In certain embodiments, the present invention relates to any of the aforementioned compounds of Formula (III) or Formula (IIIA), or a pharmaceutically acceptable salt thereof, and attendant definitions, wherein the compound is selected from the group consisting of:

211
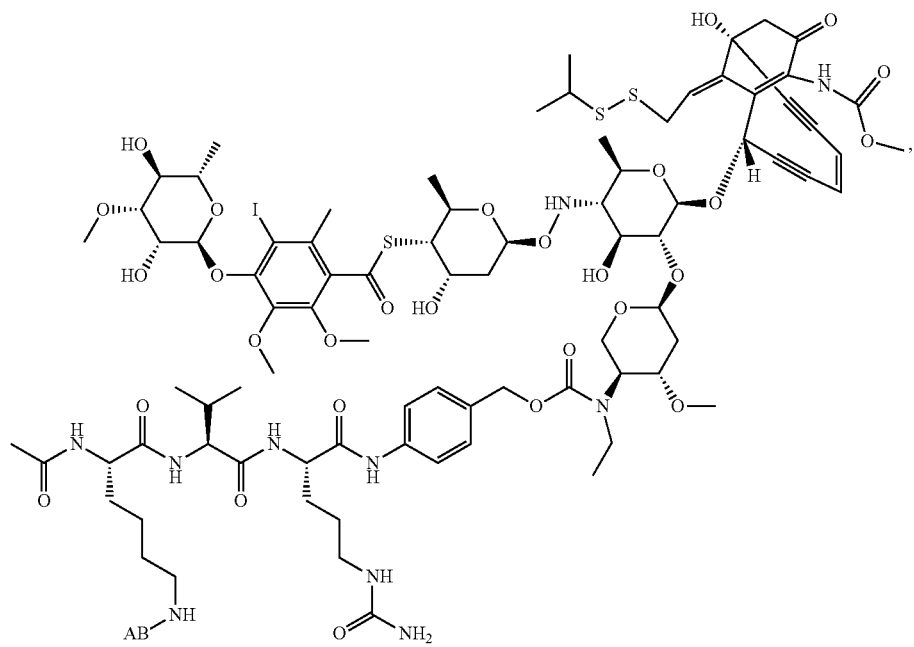
212
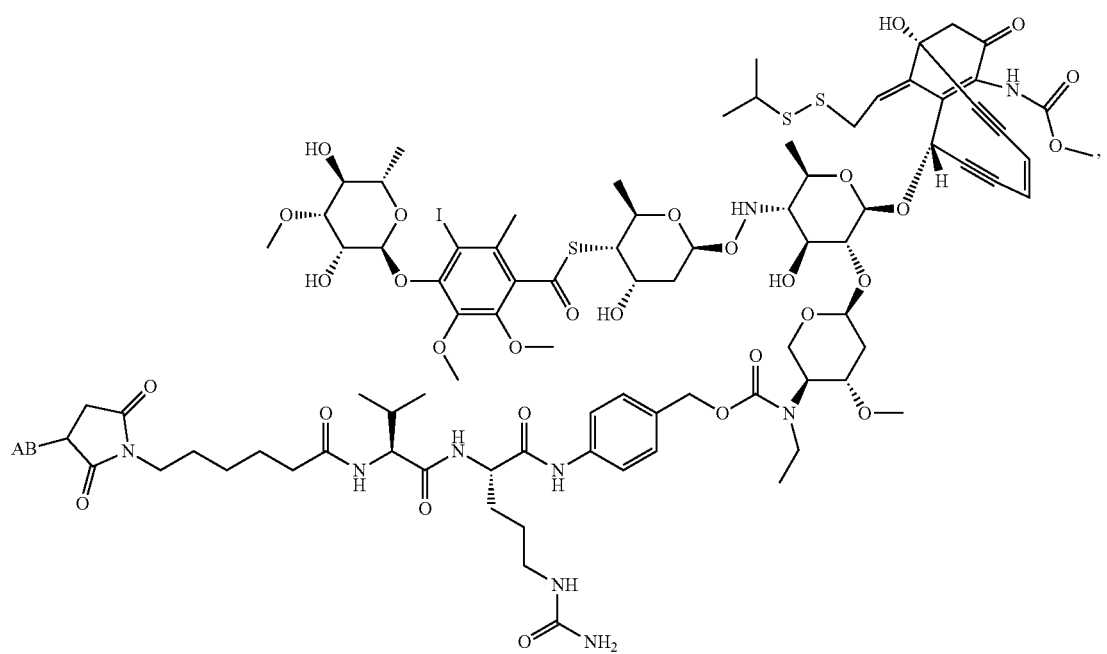

213 214
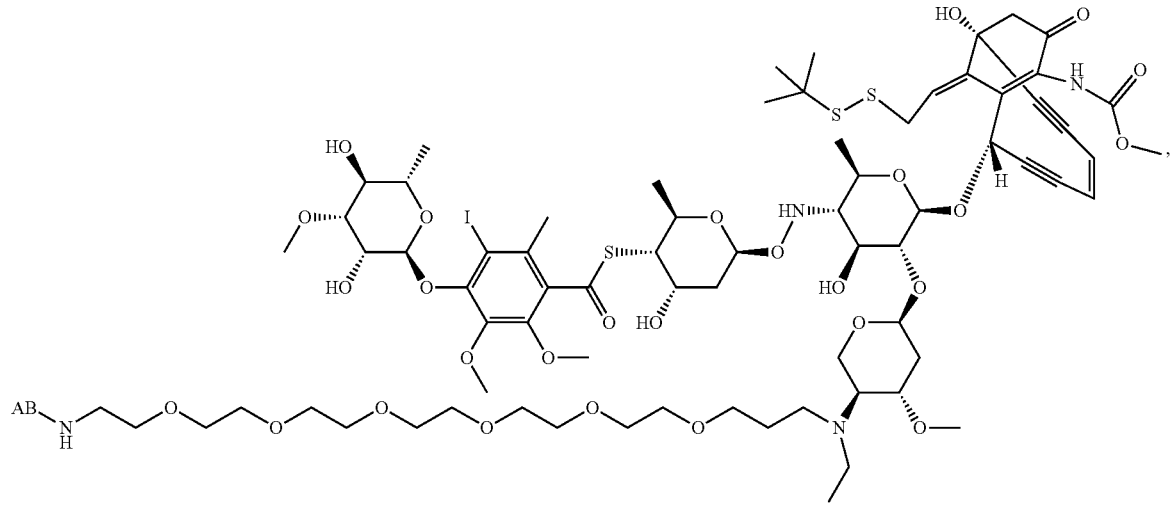
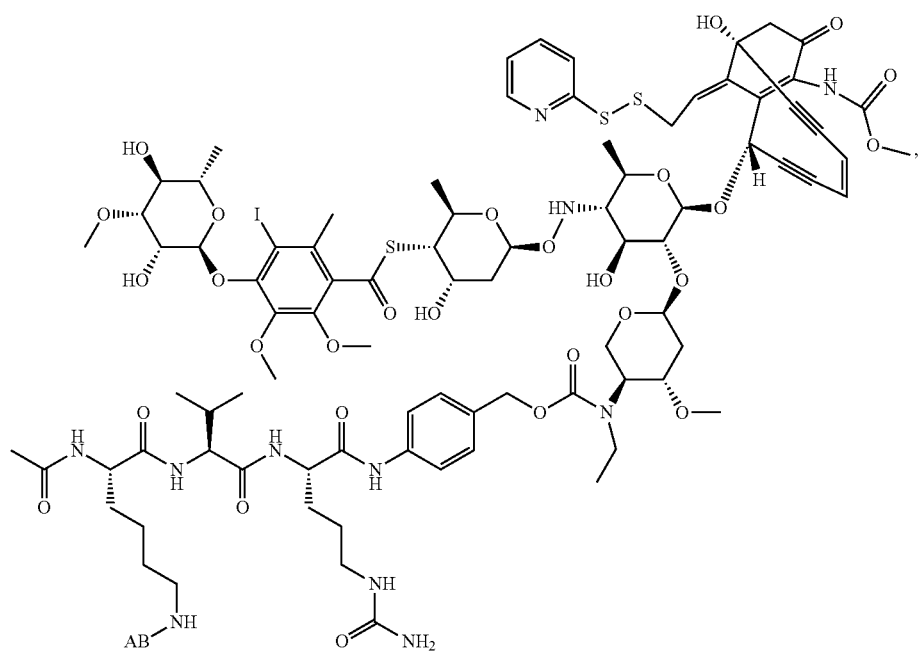

-continued
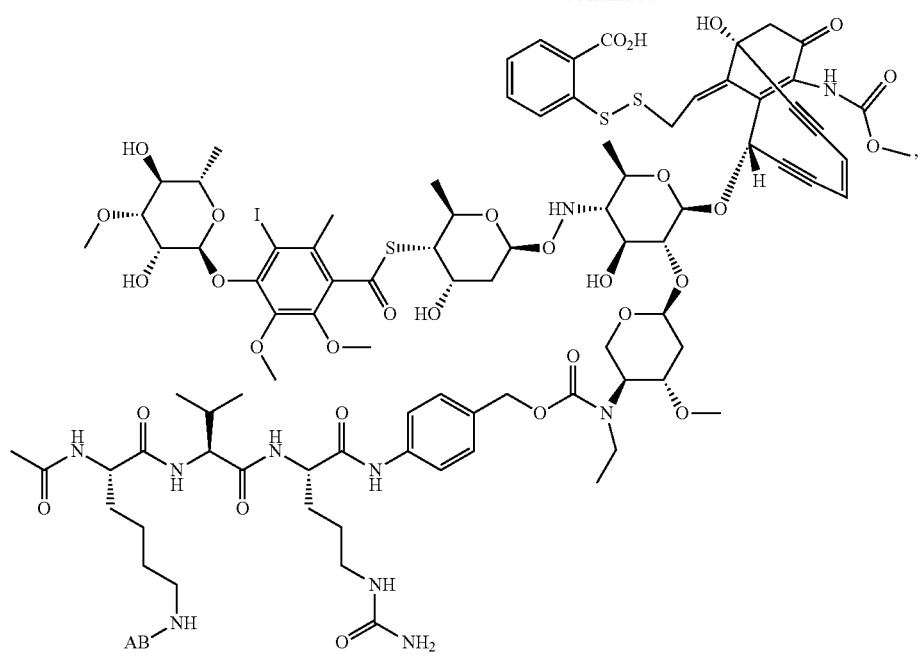
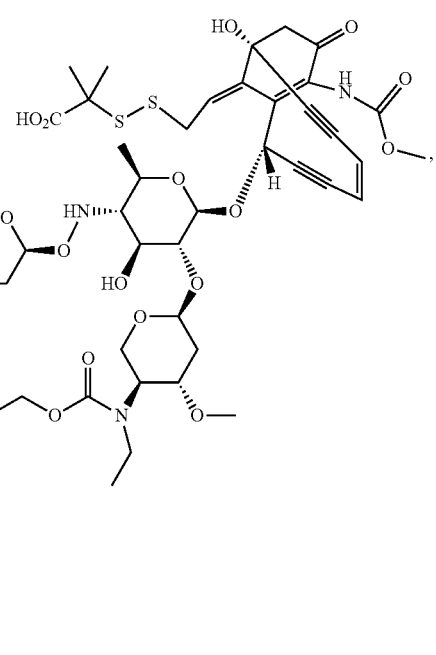

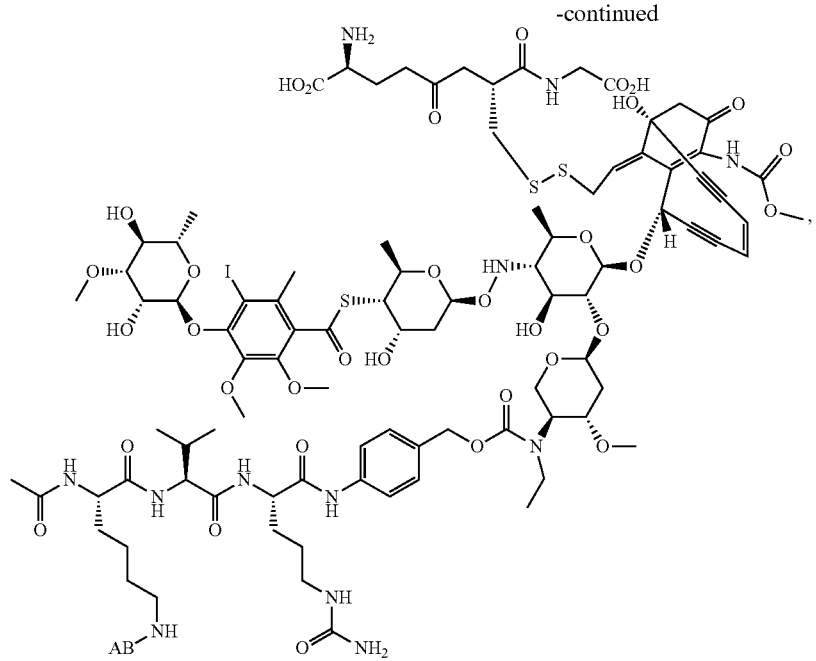
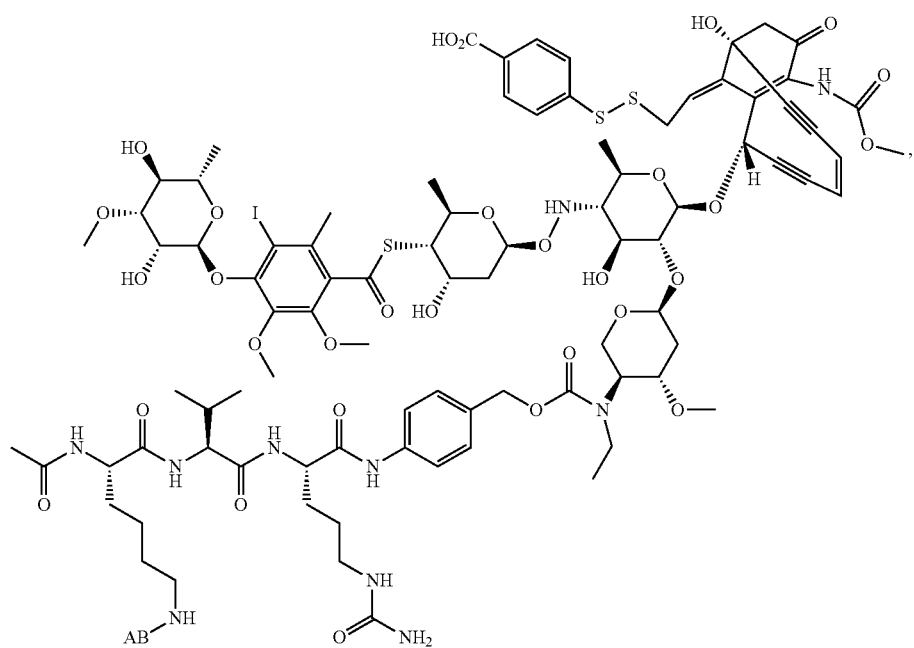

-continued
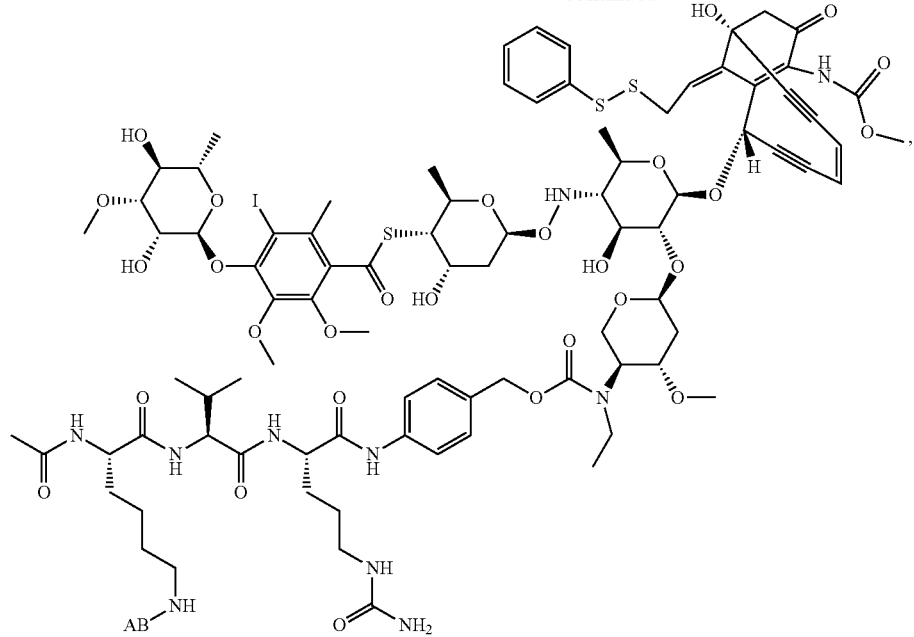
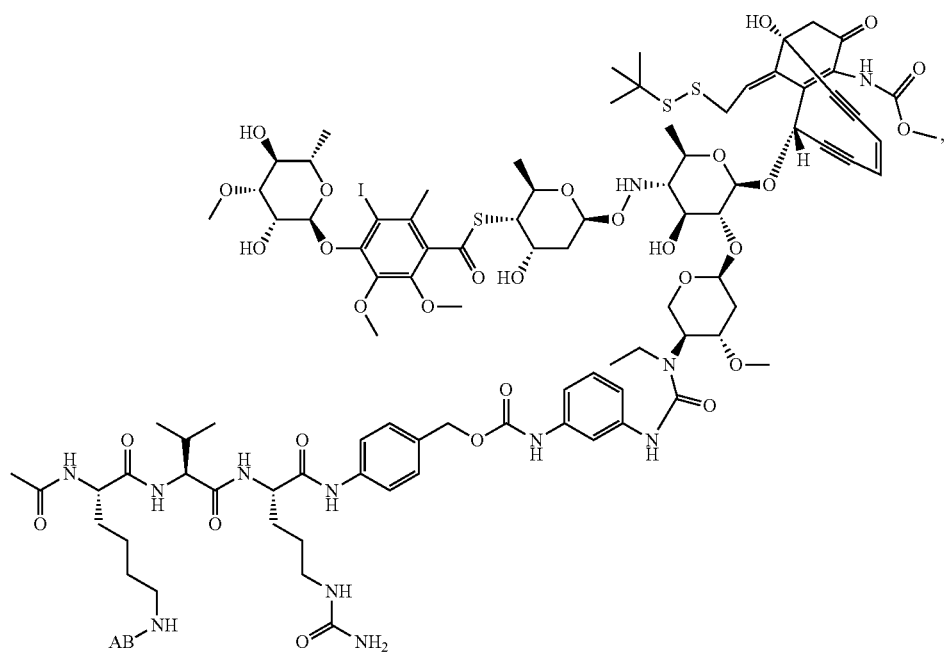

-continued
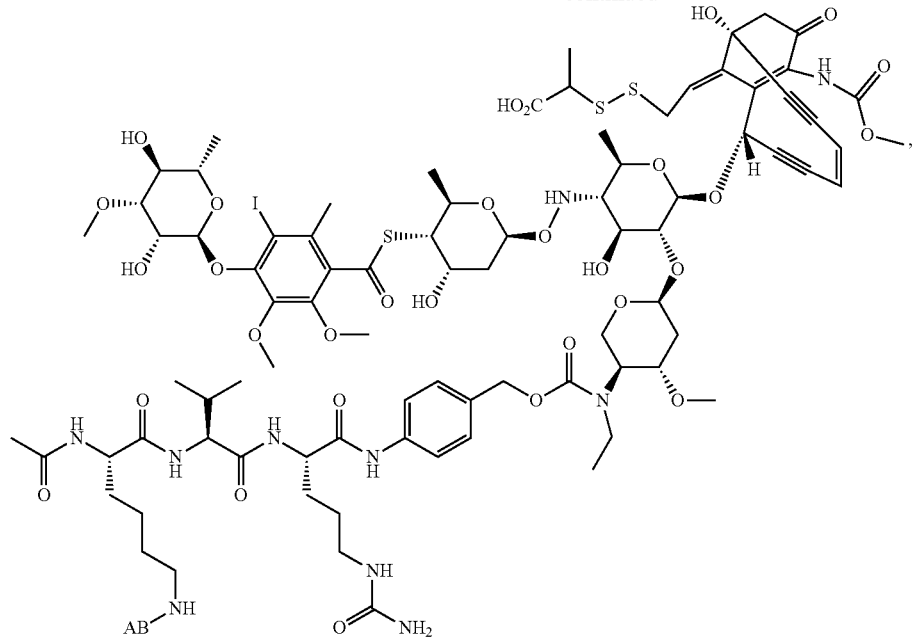
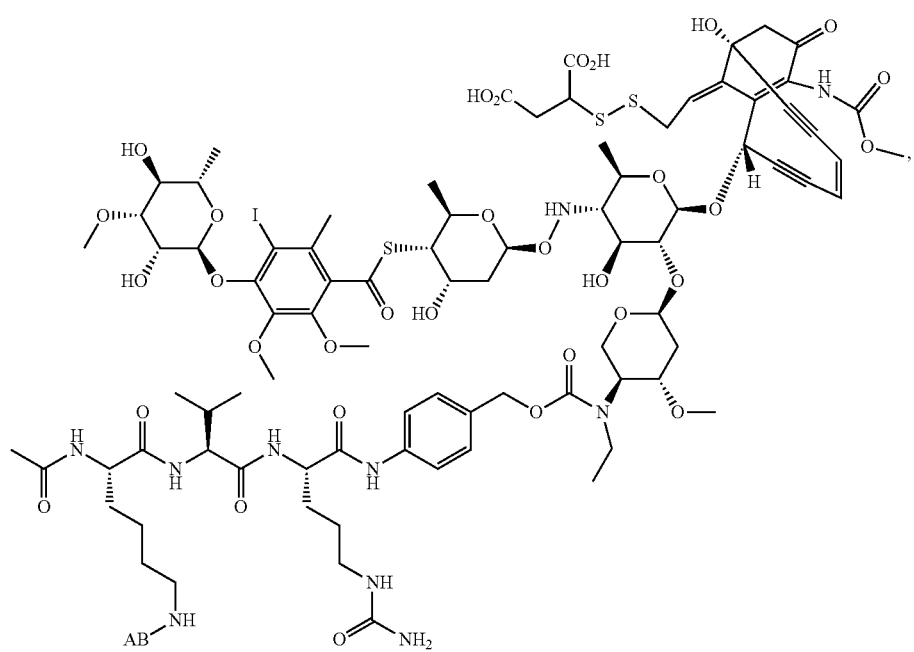

-continued
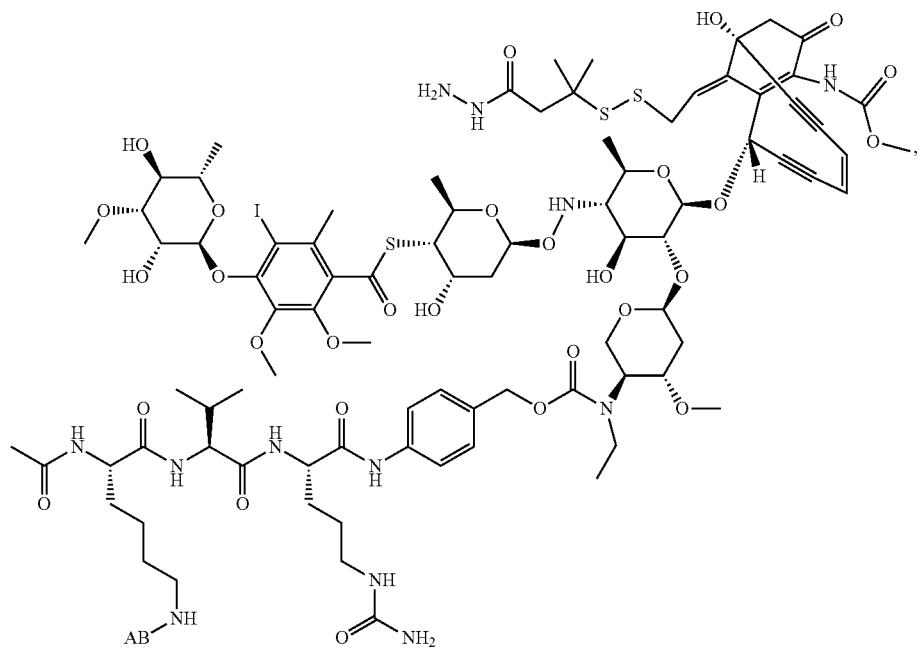
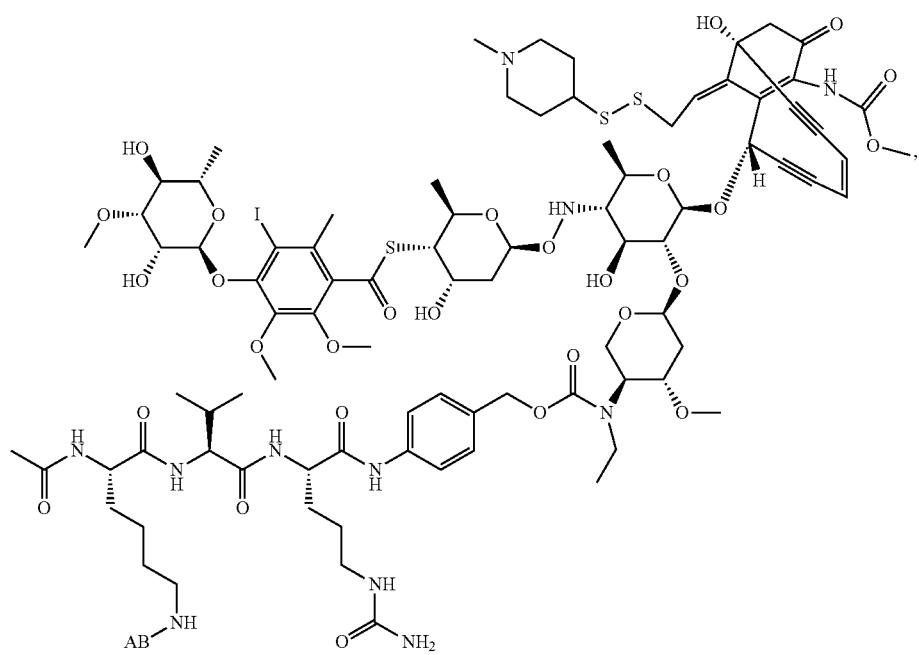

-continued
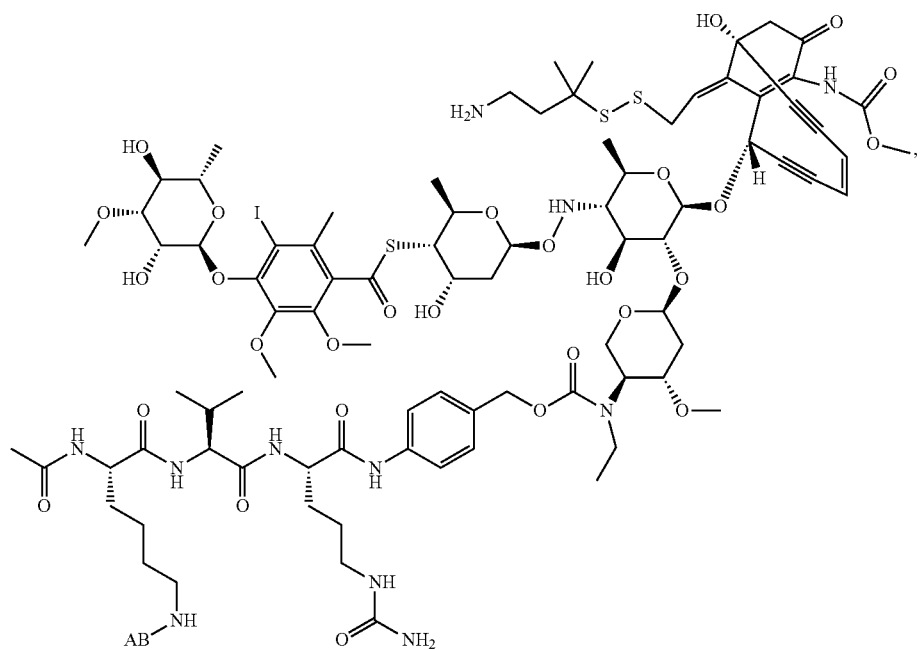
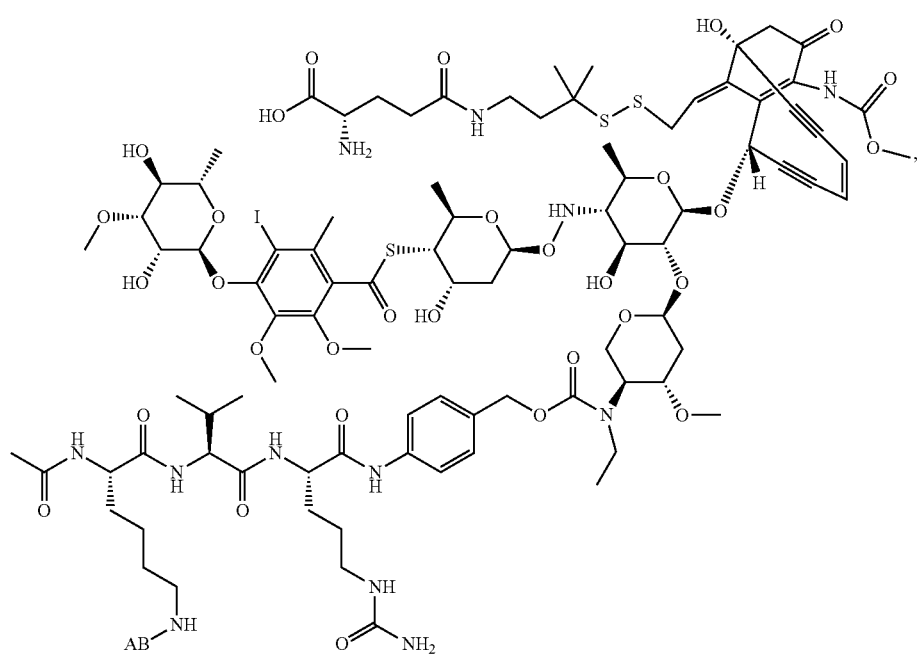

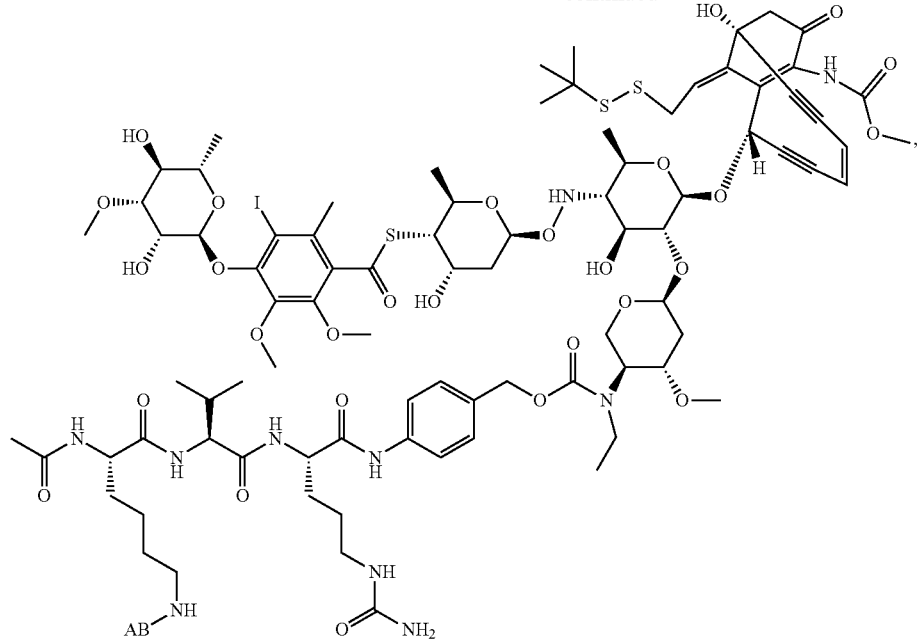
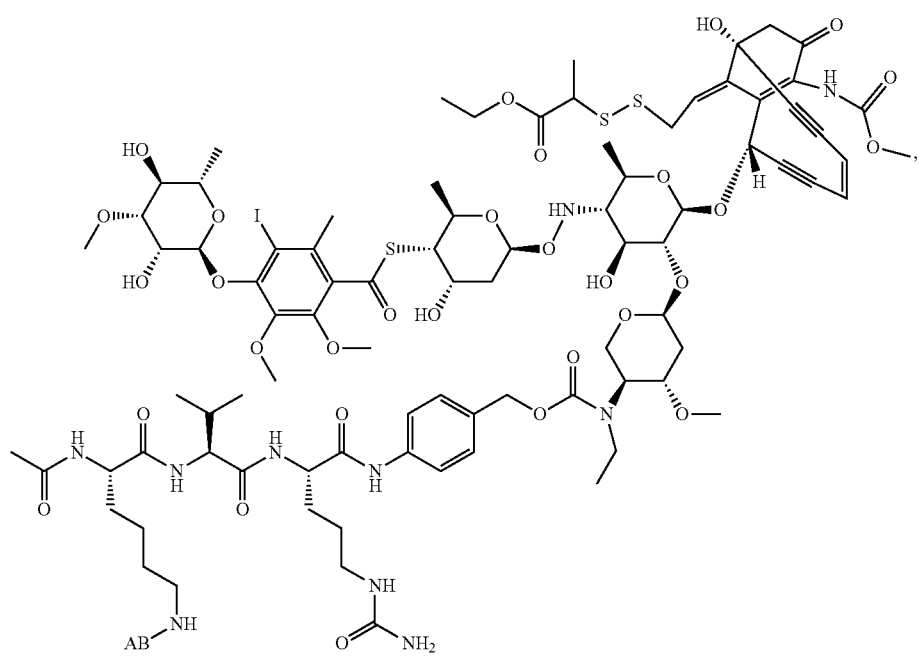

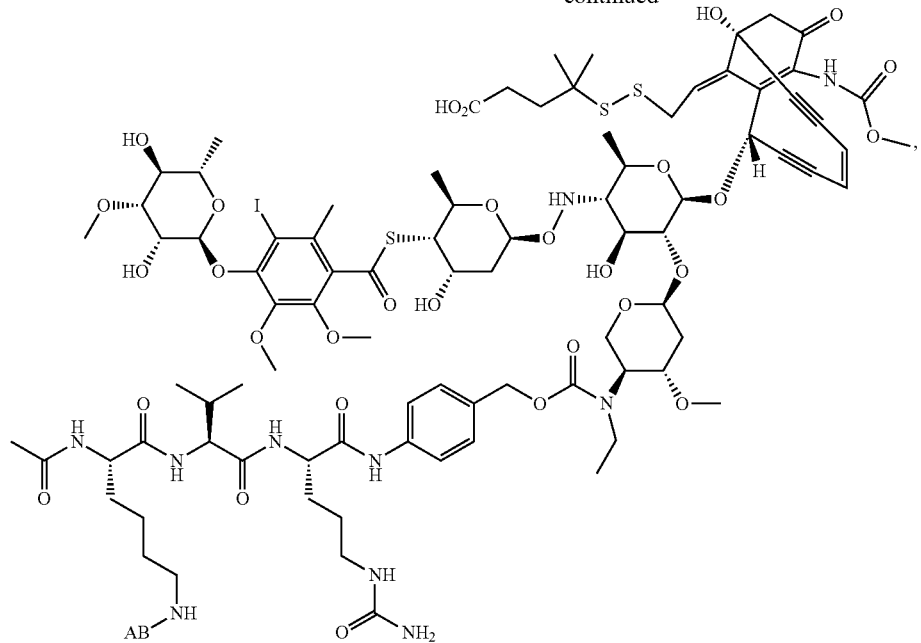
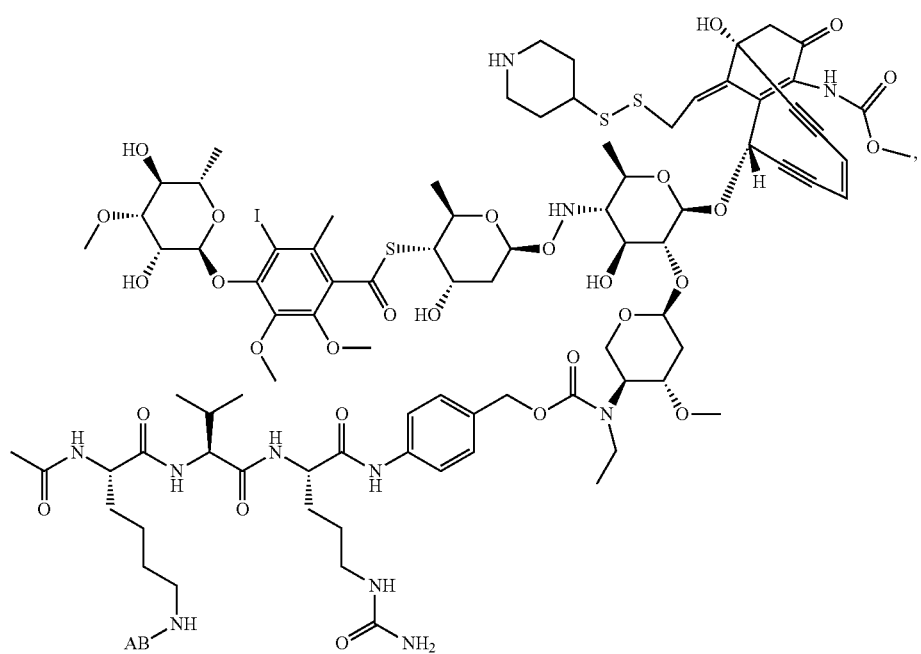

-continued
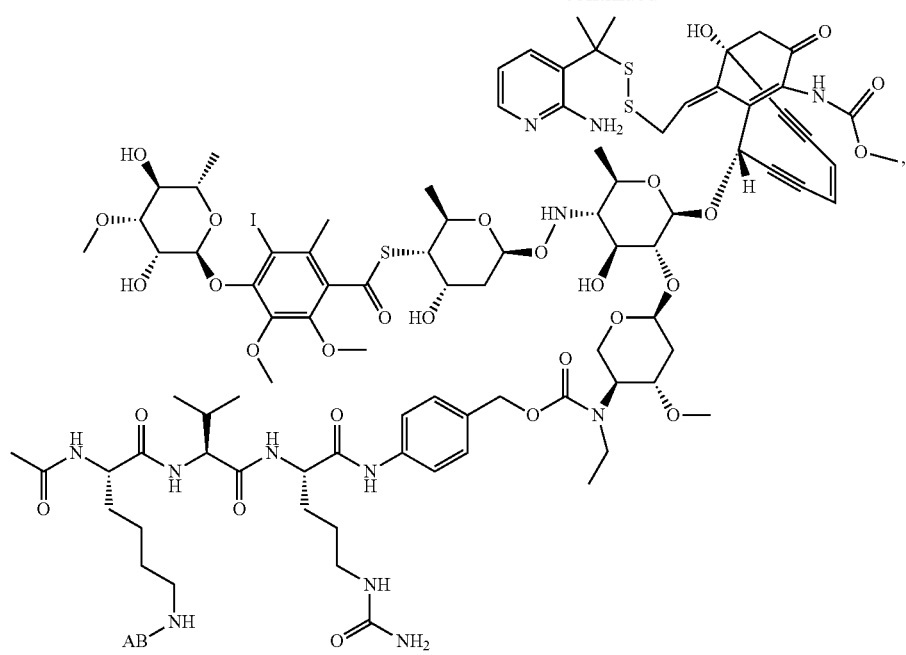
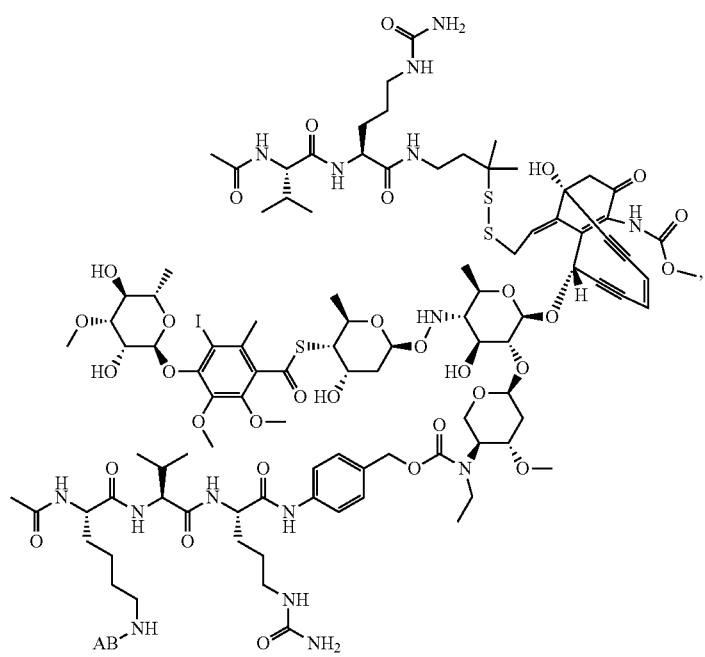

-continued
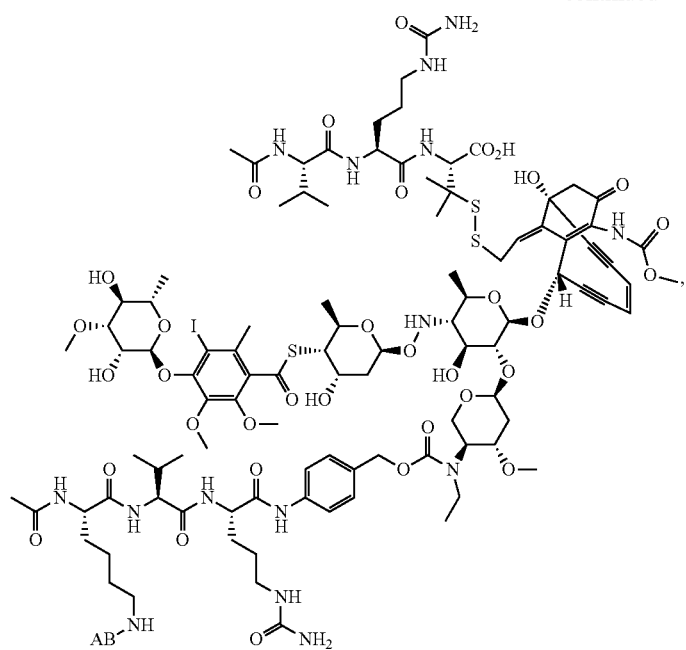
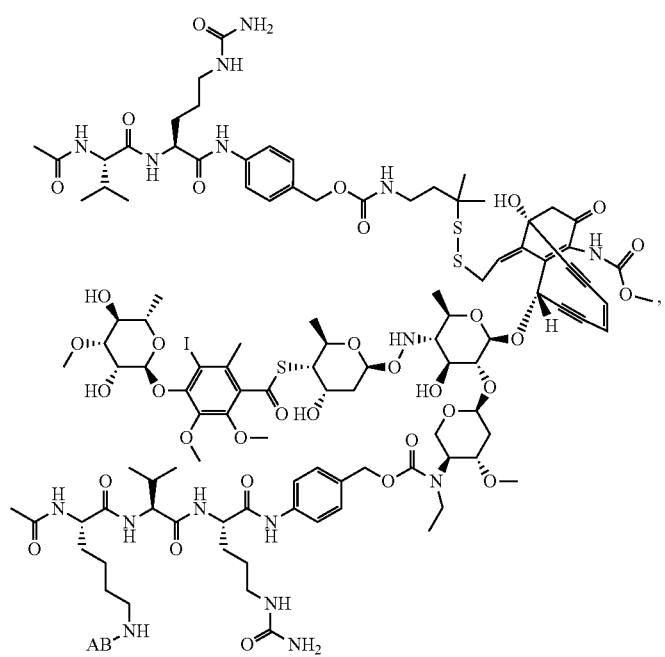

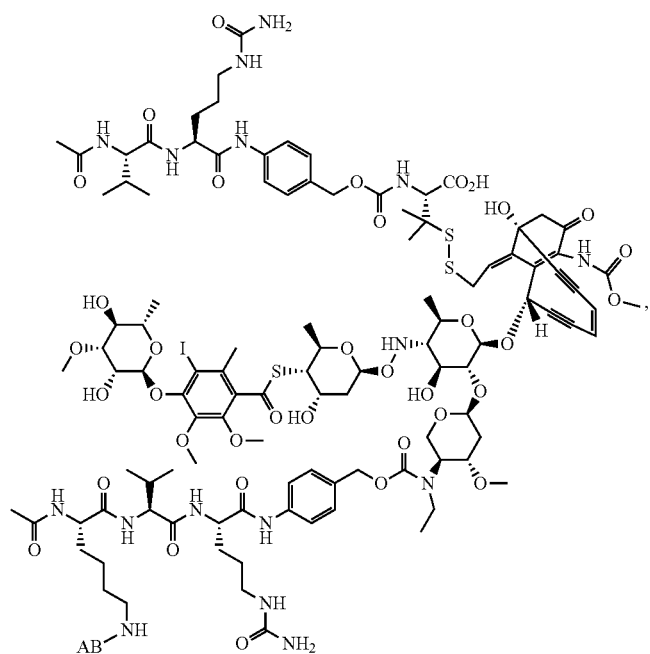
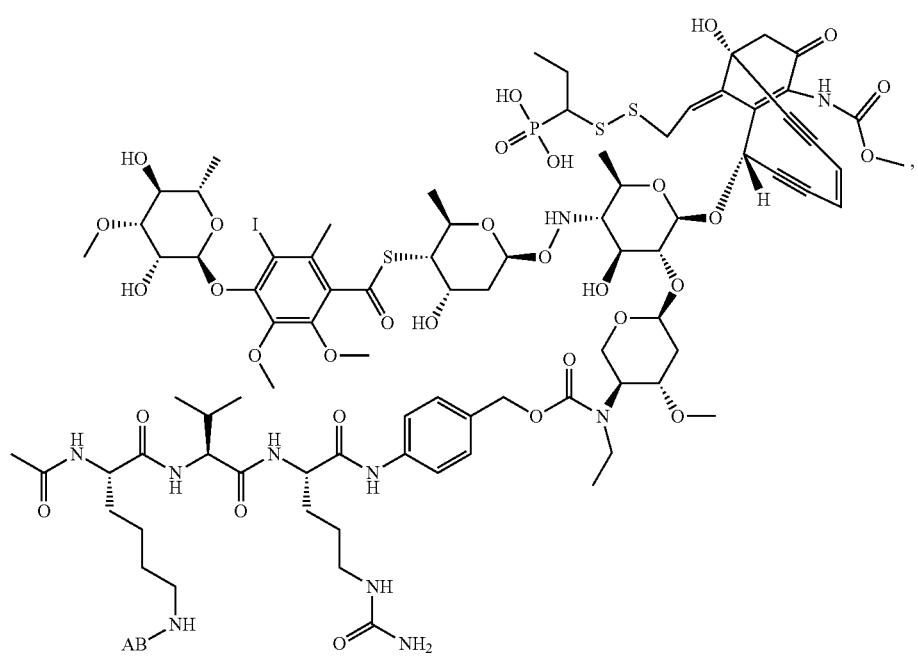

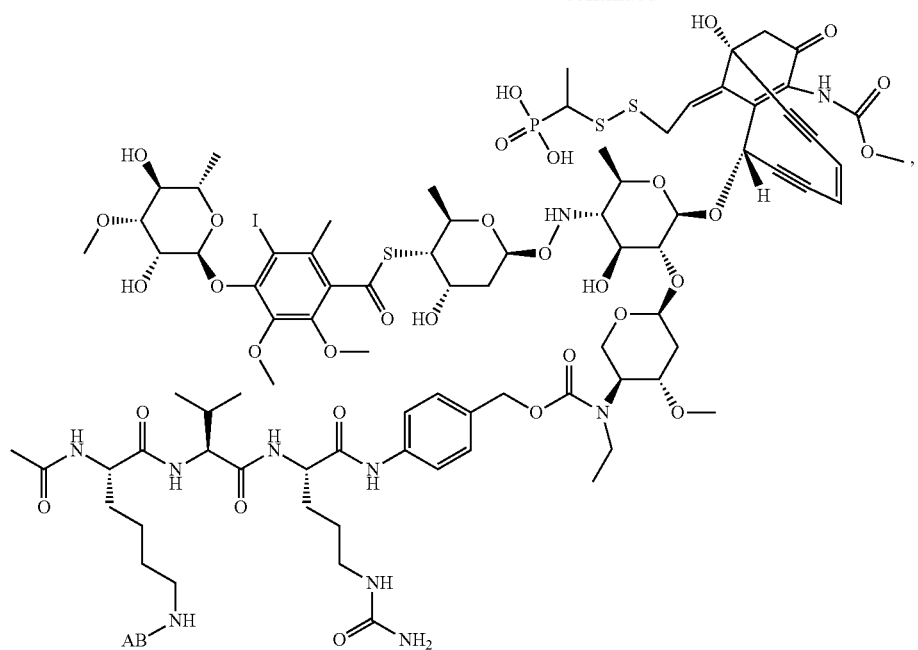
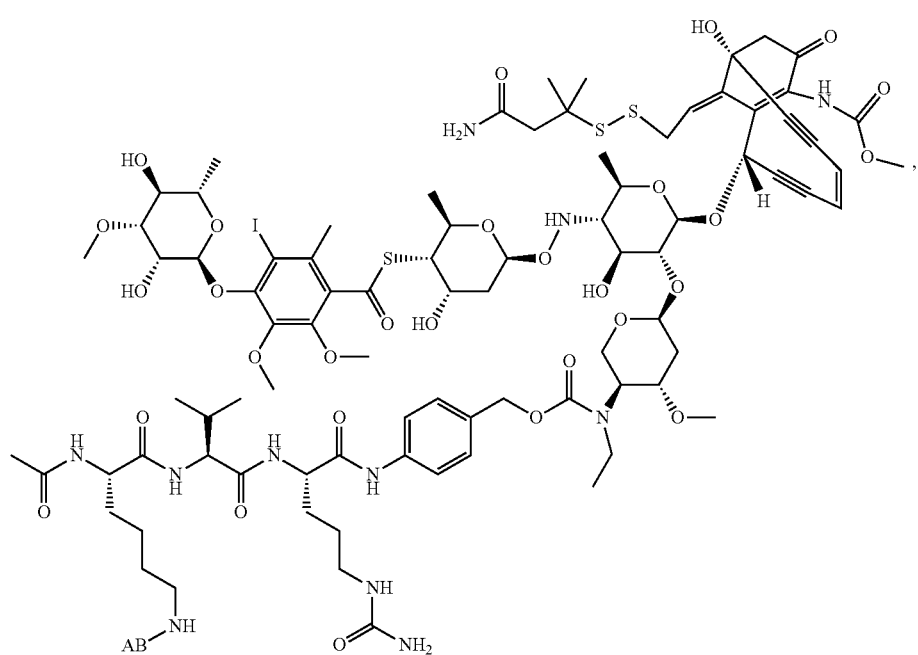

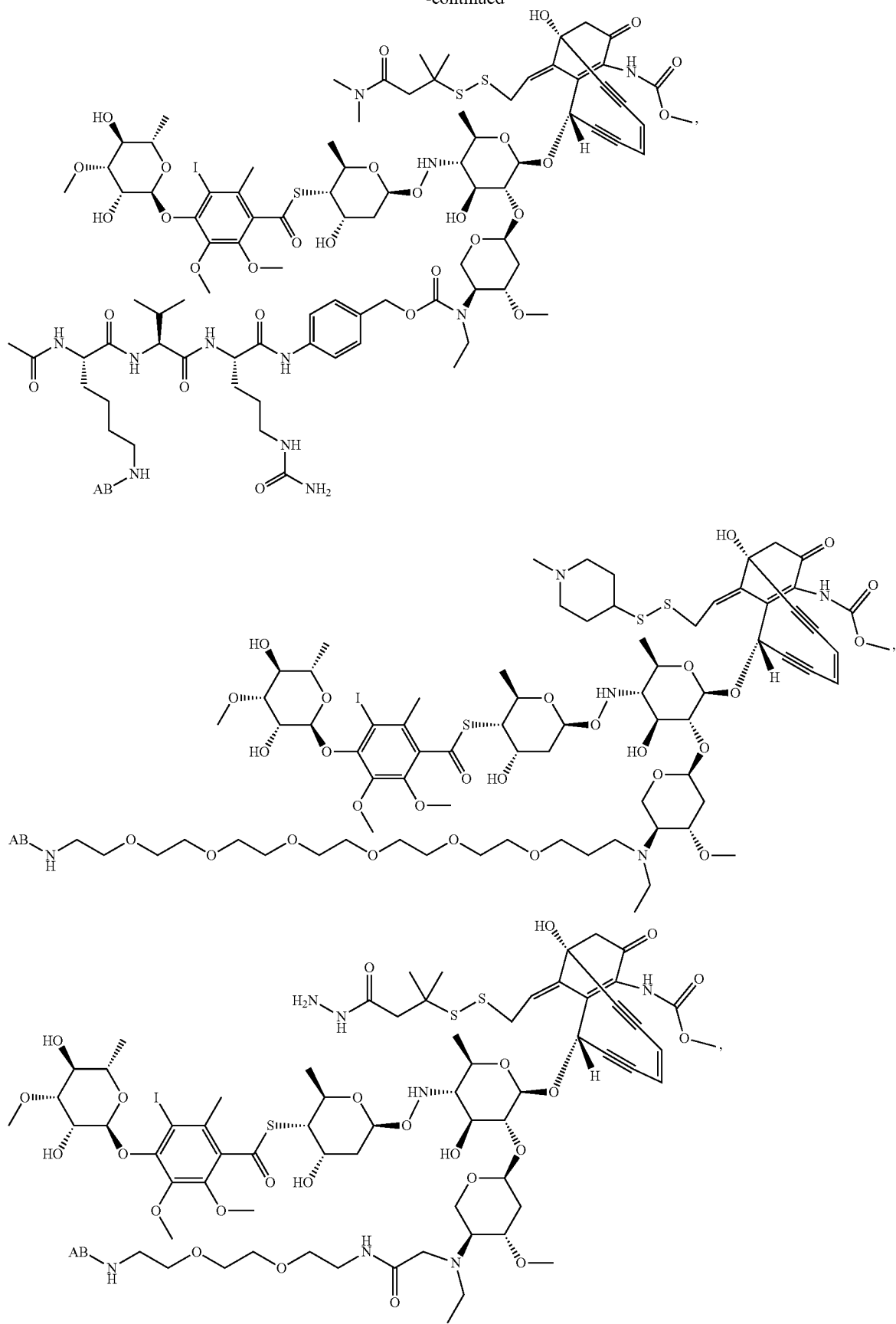

-continued
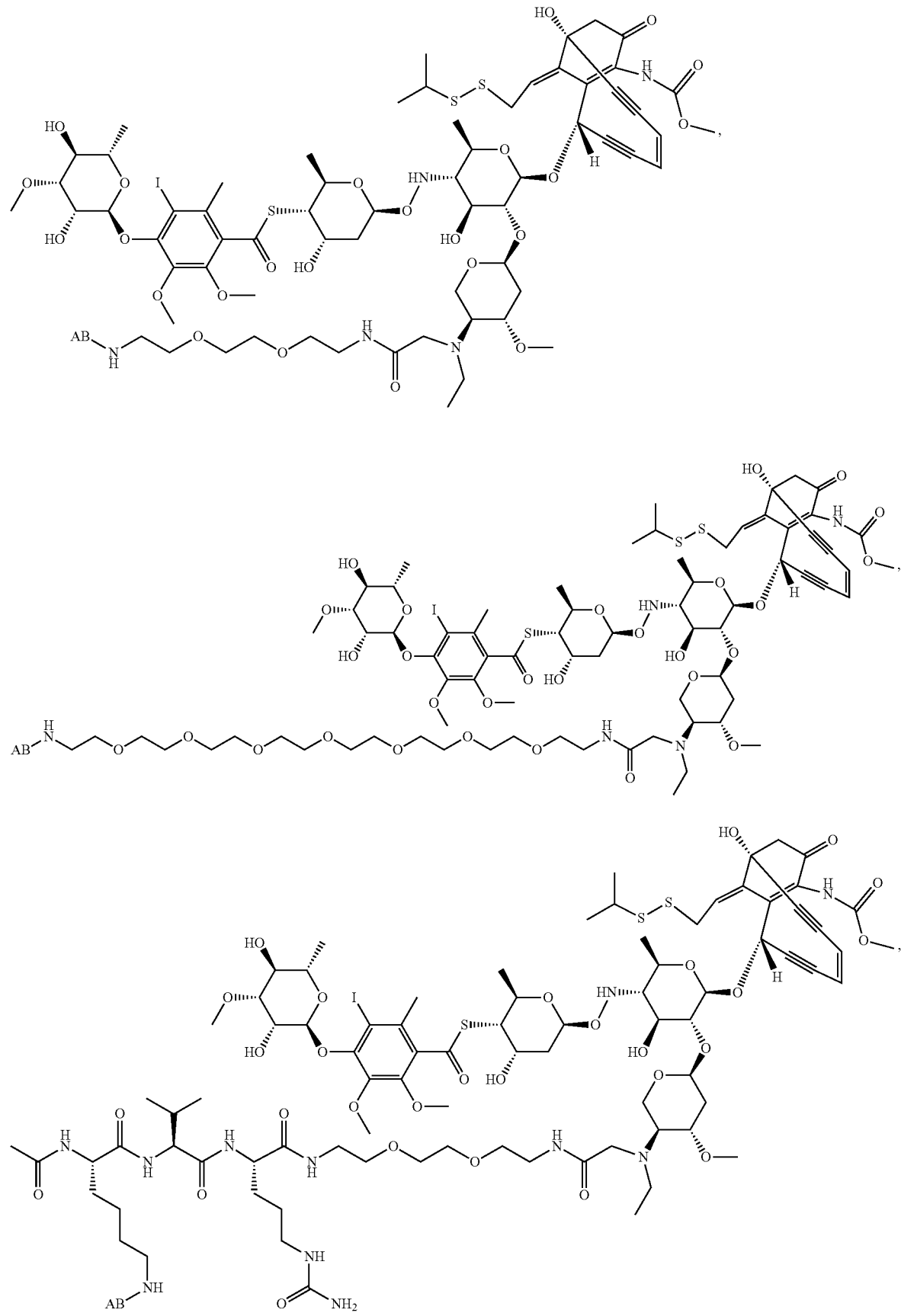

-continued
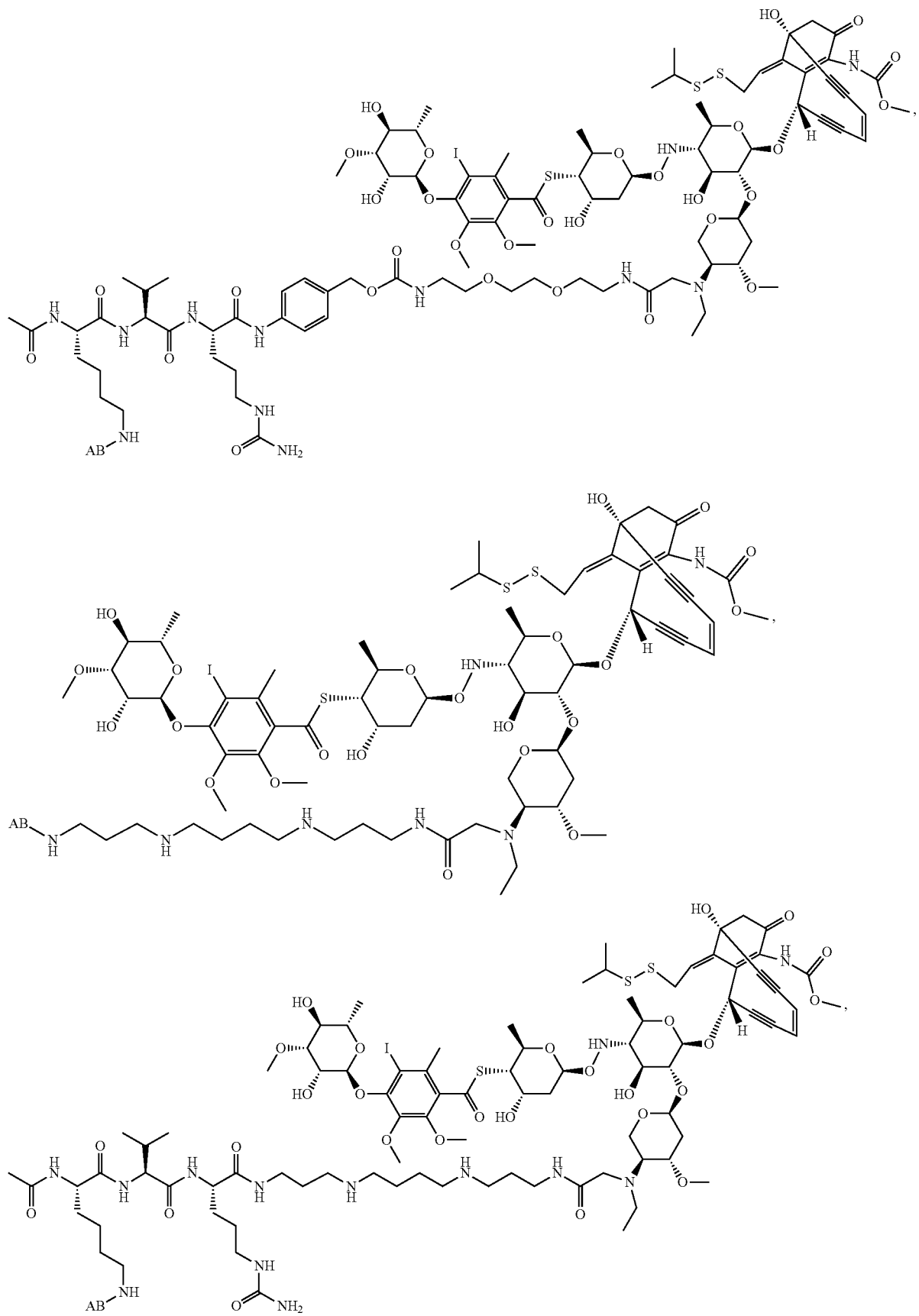

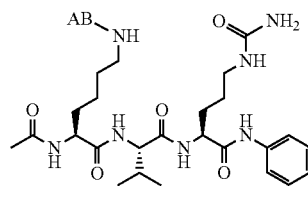
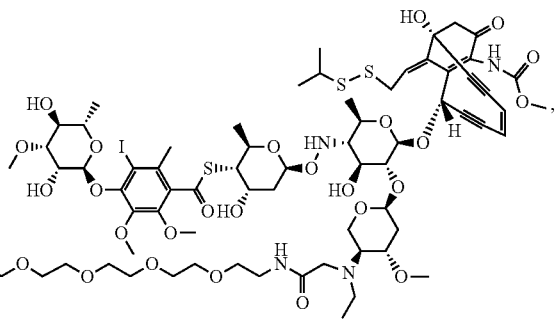
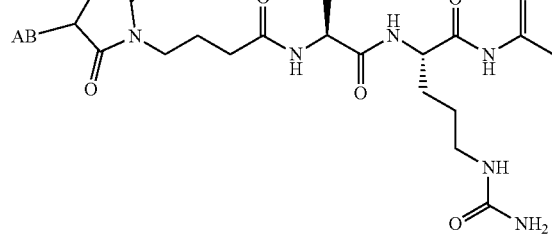
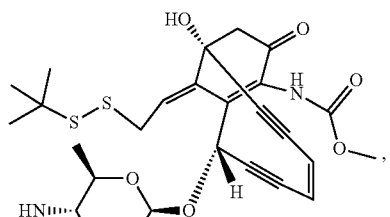
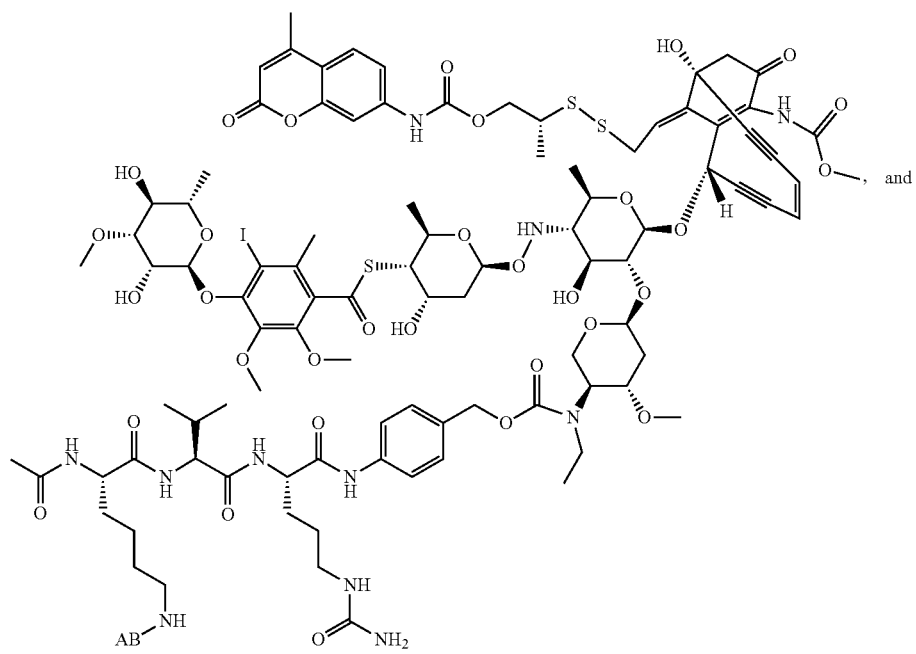

-continued

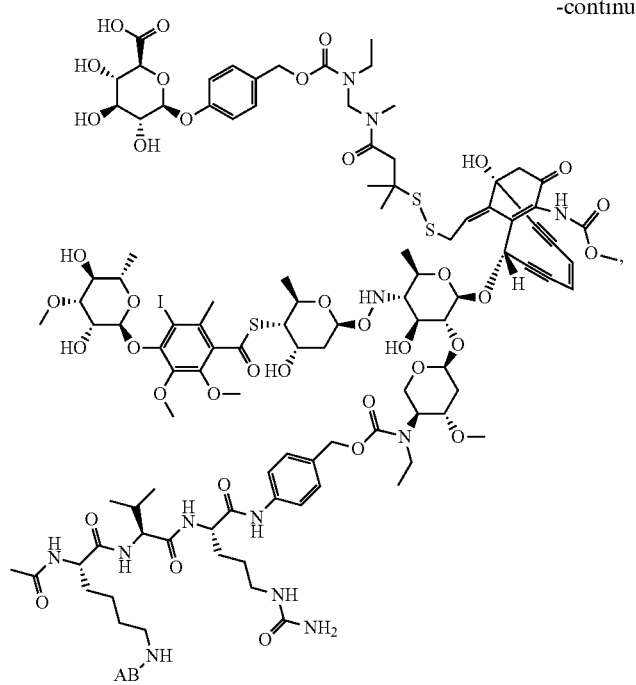

Another aspect of the invention relates to an antibody drug conjugate comprising any of the aforementioned compounds.

Another aspect of the invention relates to an antibody drug conjugate comprising an antibody and any one of the aforementioned compounds.

In certain embodiments, the present invention relates to any of the aforementioned antibody drug conjugates and attendant definitions, wherein the compound is covalently bound to the antibody.

In certain embodiments, the present invention relates to any of the aforementioned antibody drug conjugates and attendant definitions, wherein the antibody drug conjugate is loaded with from about 1 to about 20 payload linker compounds of the invention. In another embodiment, the present invention relates to any of the aforementioned antibody drug conjugates and attendant definitions, wherein the antibody drug conjugate is loaded with about 2, 3, 4, 5, 6, 7, 8, 9, or 10 payload linker compounds of the invention. In certain embodiments, the present invention relates to any of the aforementioned antibody drug conjugates and attendant definitions, wherein the antibody drug conjugate is loaded with about 3 or 4 payload linker compounds of the invention.

Probe Compounds of the Invention

Further embodiments of the invention include compounds of Formula (I), Formula (IA), Formula (II), Formula (IIA), Formula (III), Formula (IIIA), Formula (IV) and Formula (IVA), or pharmaceutically acceptable salts thereof, wherein substituent X is chosen such that it has fluorescent properties. Such compounds have additional use as chemical probe compounds. In one embodiment substituent X comprises an aromatic group which has fluorescent properties, for example a coumarin group. In one embodiment substituent X is

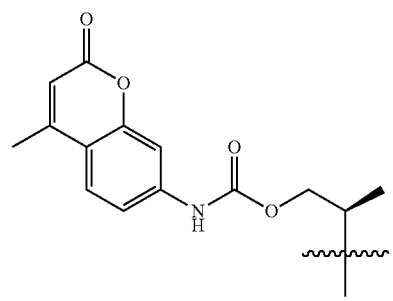 [SMILES: *[C@H](C)COC(=O)Nc1ccc2c(C)cc(=O)oc2c1]

Each of the aspects and embodiments described herein with respect to Formula (I) and Formula (IA) is also applicable to compounds of the invention where substituent X is chosen such that it has fluorescent properties.

Each of the aspects and embodiments described herein with respect to Formula (II) and Formula (IIA), either alone or in combination with each of the aspects of embodiments described herein with respect to Formula (I) and Formula (IA), is also applicable to compounds of the invention to the extent that they are compatible, where substituent X is chosen such that it has fluorescent properties.

Each of the aspects and embodiments described herein with respect to Formula (III) and Formula (IIIA), either alone or in combination with each of the aspects of embodiments described herein with respect to Formula (I), Formula (IA), Formula (II) or Formula (IIA), is also applicable to compounds of the invention to the extent that they are compatible, where substituent X is chosen such that it has fluorescent properties.

Each of the aspects and embodiments described herein with respect to Formula (IV) and Formula (IVA), either alone or in combination with each of the aspects of embodiments described herein with respect to Formula (I), Formula (IA), Formula (II) or Formula (IIA), is also applicable to compounds of the invention to the extent that they are compatible, where substituent X is chosen such that it has fluorescent properties.

Examples of such compounds include, but are not limited to, payload compounds such as
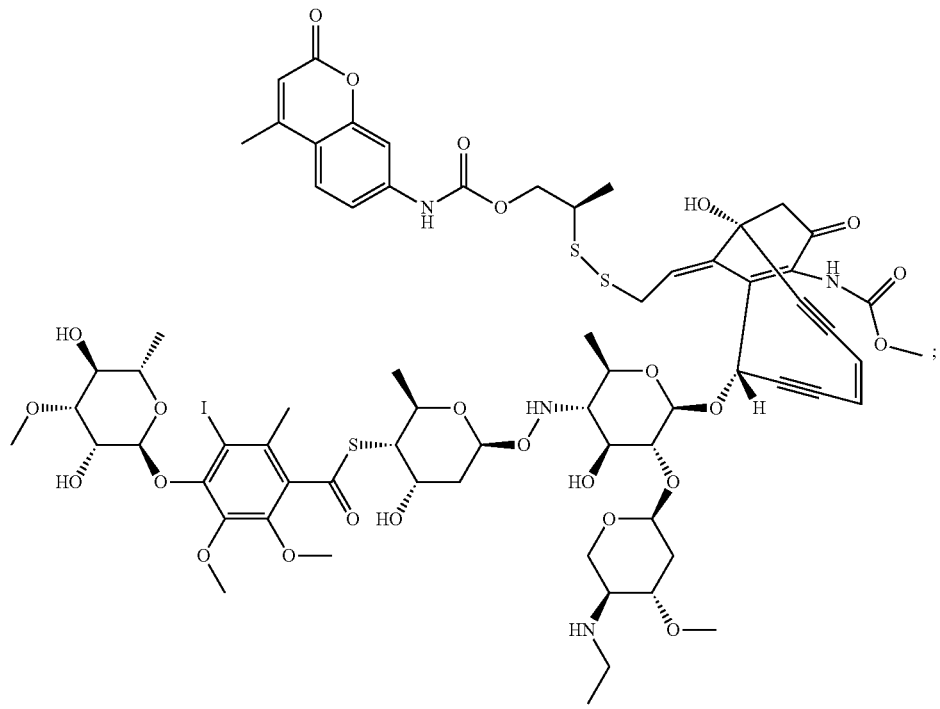
linker payload compounds such as
and antibody drug conjugate compounds such as
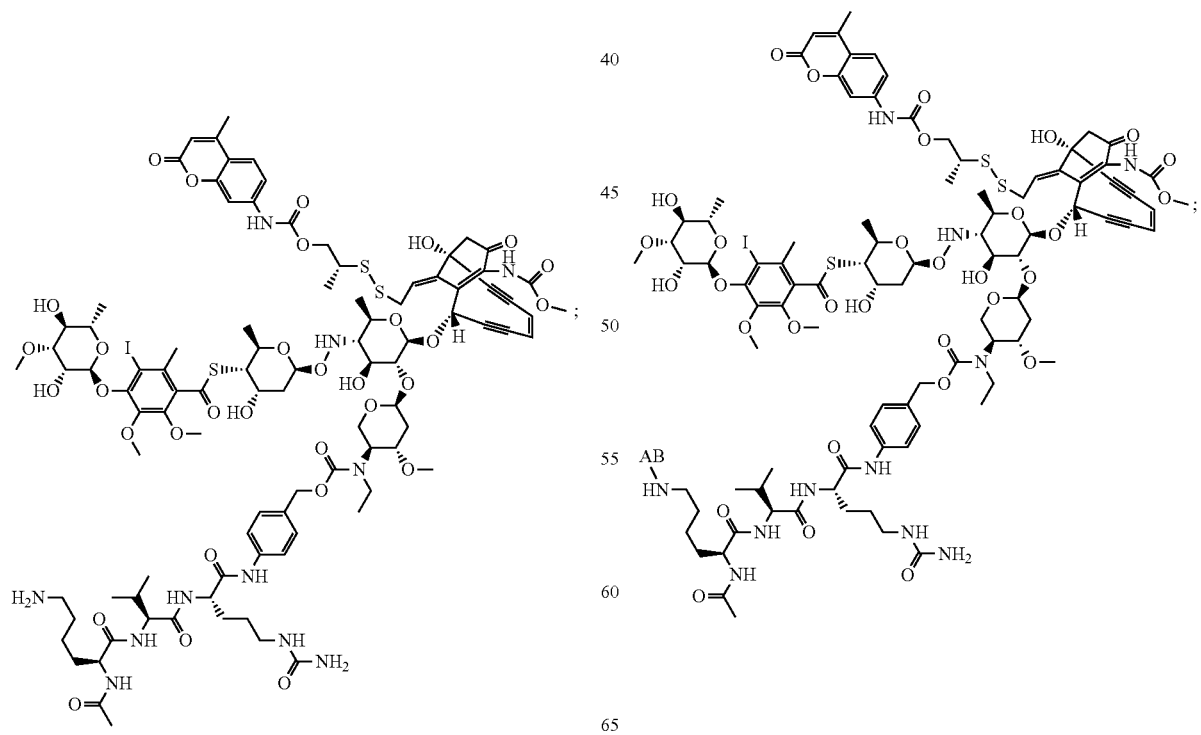
and pharmaceutically acceptable salts thereof.

In one embodiment, this invention relates to
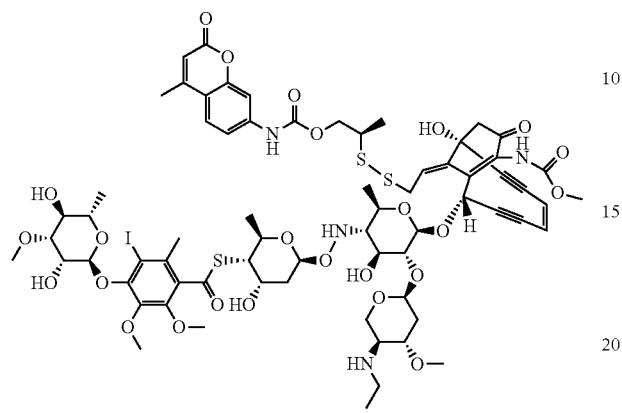
and pharmaceutically acceptable salts thereof.
In one embodiment, this invention relates to
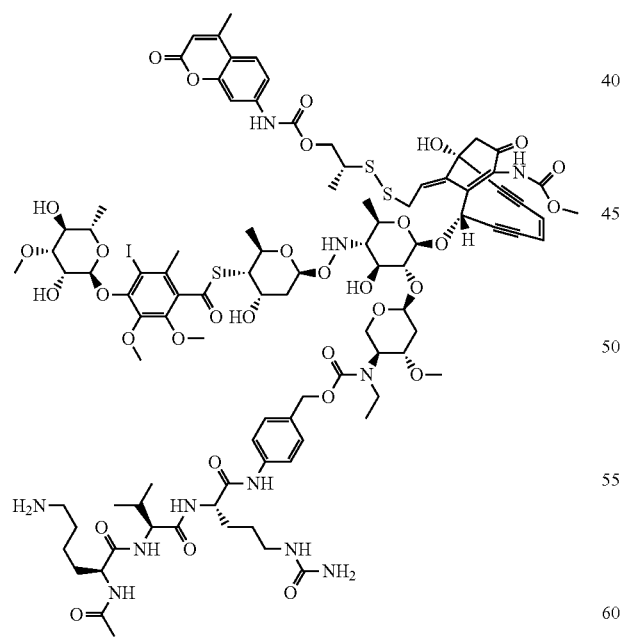
and pharmaceutically acceptable salts thereof.

In one embodiment, this invention relates to

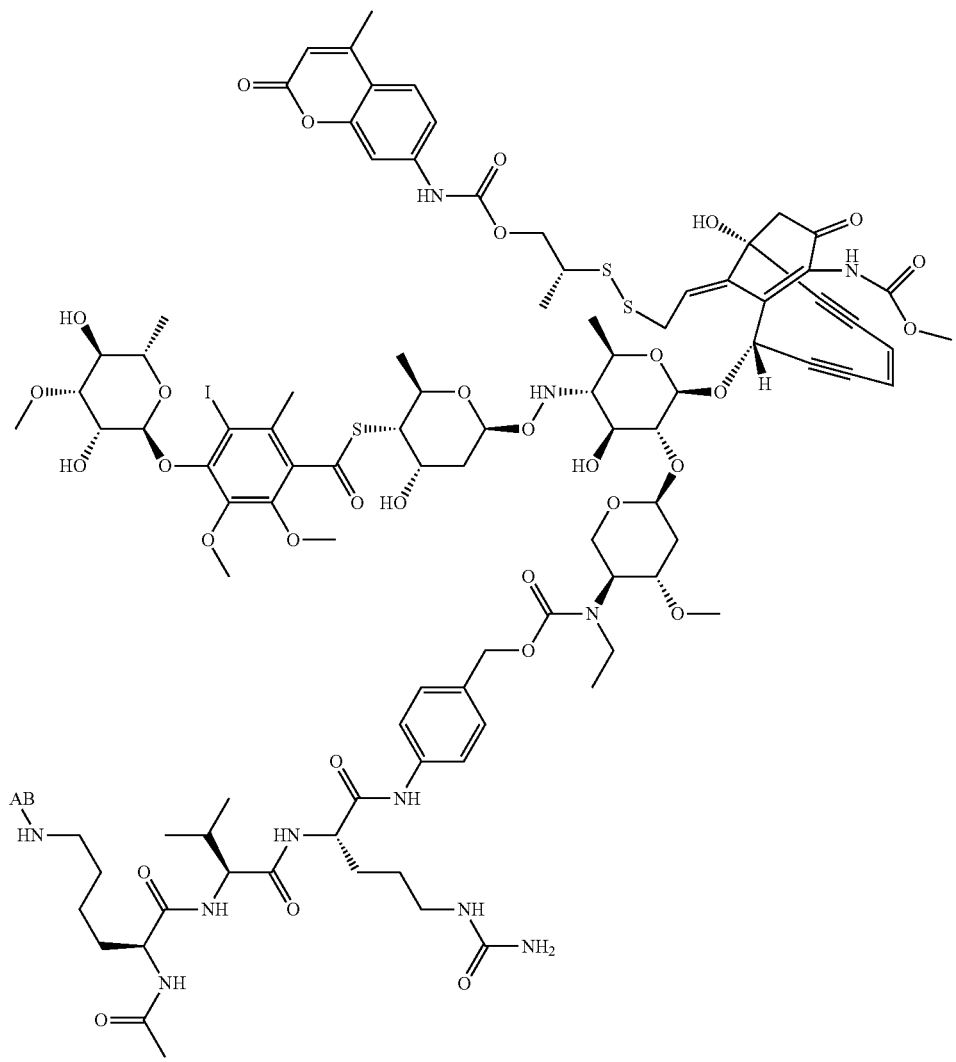

and pharmaceutically acceptable salts thereof.

Released Species of the Invention

Further embodiments of the invention also include the chemical species released from the antibody drug conjugate, inside or in the vicinity of the cancer cell or tumor cell.

Without wishing to be bound by theory, it is believed that when the compounds of the invention comprises a cleavable linker, the chemical species is released from the antibody drug conjugate by enzymatic and/or hydrolytic cleavage by one or more cancer cell or tumor cell-associated proteases, glycosideases, or by purely chemical means. The cleavage may occur at one or more suitable points of cleavage on the compound of the invention to release the chemical species. Without wishing to be bound by theory, for the present invention it is envisaged that cleavage may occur at one or more suitable points either in the antibody itself; in the linker and/or in substituent X. As such, it is envisaged that where the compound of the invention contains an antibody bound through a cleavable moiety, and elsewhere the compound contains one or more further cleavable moieties, such as in substituent X, then cleavage may occur at one or more cleavable moieties prior to release of the active compound. A single antibody drug conjugate may therefore potentially be cleaved in multiple positions in vivo such that the released species may differ.

Without wishing to be bound by theory, it is believed that when compounds of the invention comprise a non-cleavable linker, the chemical species is released from the antibody drug conjugate by enzymatic and/or hydrolytic cleavage by one or more cancer cell or tumor cell-associated proteases or glycosidases acting on one or more suitable points of cleavage on the antibody itself to release the chemical species. Further, it is envisaged that where the compound of the invention contains an antibody bound through a non-cleavable linker, and elsewhere the compound contains one or more further cleavable moieties, such as at subsitutent X, then cleavage may occur at one or more cleavable moieties prior to release of the active compound. A single antibody drug conjugate may therefore potentially be cleaved in multiple positions in vivo such that the released species may differ.

Without wishing to be bound by theory, for compounds of the present invention, suitable points of cleavage may include, but are not limited to, the calicheamicin amino sugar —N(R³)-LR, to release —N(R³)H; the terminal amino group of a polyethylene glycol substituent in the linker substituent; the terminal amino group of a polyethylene glycol in substituent in X; the amino group of a polyamine chain in the linker substituent; and the amino group of a polyamino chain in substituent X.

Compounds of the Invention

Compounds of the invention include compounds of any of the formulae described herein, or a pharmaceutically acceptable salt thereof. Unless indicated otherwise, compounds of the invention include payload compounds, payload linker compounds and anti-body drug conjugate compounds, including compounds of Formula (I), Formula (IA), Formula (II), Formula (IIA), Formula (III), Formula (IIIA), Formula (IV) and Formula (IVA). Compounds of the invention also include probe compounds described herein. Compounds of the invention also include the released species described herein.

Unless indicated otherwise, all references herein to the inventive compounds, or salt thereof, includes references to solvates, hydrates and complexes thereof; and to solvates, hydrates and complexes of salts thereof; including reference to polymorphs, stereoisomers, and isotopically labeled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate and pamoate [i.e., 1,1'-methylene-bis-(2-hydroxy-3-naphthoate)] salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Those compounds of the invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Finally, certain inventive compounds may themselves act as prodrugs of other of the inventive compounds.

In one embodiment, the invention relates to a prodrug of a compound of Formula (I), or a pharmaceutically acceptable salt thereof.

In one embodiment, the invention relates to a prodrug of a compound of Formula (IA), or a pharmaceutically acceptable salt thereof.

In one embodiment, the invention relates to a prodrug of a compound of Formula (II), or a pharmaceutically acceptable salt thereof.

In one embodiment, the invention relates to a prodrug of a compound of Formula (IIA), or a pharmaceutically acceptable salt thereof.

In one embodiment, the invention relates to a prodrug of a compound of Formula (III), or a pharmaceutically acceptable salt thereof.

In one embodiment, the invention relates to a prodrug of a compound of Formula (IIA), or a pharmaceutically acceptable salt thereof.

In one embodiment, the invention relates to a prodrug of a compound of Formula (IV), or a pharmaceutically acceptable salt thereof.

In one embodiment, the invention relates to a prodrug of a compound of Formula (IVA), or a pharmaceutically acceptable salt thereof.

Also included within the scope of the invention are metabolites of compounds of the formulae described herein, i.e., compounds formed in vivo upon administration of the drug.

The compounds of the formulae provided herein may have asymmetric carbon atoms. The carbon-carbon bonds of the compounds of the invention may be depicted herein using a solid line ( ——— or ⌇⌇⌇ ), a solid wedge ( ◥ ), or a dotted wedge ( ⦙⦙⦙ ). The use of a solid line ( ——— or, ⌇⌇⌇ ) to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of the formulae herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

"Enantiomerically pure" as used herein, describes a compound that is present as a single enentiomer and which is described in terms of enantiomeric excess (e.e.). Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, "diastereomerically pure" as used herein, describes a compound that is present as a diastereomer and which is described in terms of diastereomeric excess (d.e.). Preferably, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

The present invention also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, fluorine and chlorine, such as, but not limited to, $^2H$, $^3H$, $^{13}C$, $^{14}C$ $^{15}N$, $^{18}O$, $^{17}O$, $^{31}P$, $^{32}P$, $^{35}S$, $^{18}F$, $^{36}Cl$, $^{127}I$, $^{79}Br$ and $^{81}Br$. Certain isotopically-labeled compounds of the invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Therapeutics Uses of Compounds and Antibody Drug Conjugates Thereof

Another aspect of the invention relates to a method of using the compounds of the invention, or a pharmaceutically acceptable salt thereof, for treating pathological conditions such as cancer.

Another aspect of the invention relates to a method for killing or inhibiting the proliferation of tumor cells or cancer cells comprising treating tumor cells or cancer cells in a patient with an amount of a compound of the invention, or a pharmaceutically acceptable salt thereof, said amount being effective to kill or inhibit the proliferation of the tumor cells or cancer cells.

Another aspect of the invention relates to a method of using the compounds of the invention, or a pharmaceutically acceptable salt thereof, for treating abnormal cell growth.

Another aspect of the invention relates to a method of using the compounds of the invention, or a pharmaceutically acceptable salt thereof, for treating cancer.

Another aspect of the invention relates to compounds of the invention, or a pharmaceutically acceptable salt thereof, for use as a medicament.

Another aspect of the invention relates to compounds of the invention, or a pharmaceutically acceptable salt thereof, for use to treat pathological conditions such as cancer.

Another aspect of the invention relates to compounds of the invention, or a pharmaceutically acceptable salt thereof, for use to treat abnormal cell growth.

Another aspect of the invention relates to compounds of the invention, or a pharmaceutically acceptable salt thereof, for use to treat cancer.

Another aspect of the invention relates to use of compounds of the invention, or a pharmaceutically acceptable salt thereof, or a pharmaceutically acceptable salt thereof, the manufacture of a medicament for the treatment of pathological conditions such as cancer.

Another aspect of the invention relates to use of compounds of the invention, or a pharmaceutically acceptable salt thereof, or a pharmaceutically acceptable salt thereof, the manufacture of a medicament for the treatment of abnormal cell growth.

Another aspect of the invention relates to use of compounds of the invention, or a pharmaceutically acceptable salt thereof, or a pharmaceutically acceptable salt thereof, the manufacture of a medicament for the treatment of cancer.

Another aspect of the invention relates to a pharmaceutical composition for treating pathological conditions such as cancer, comprising a compound of the invention, or a pharmaceutically acceptable salt thereof.

Another aspect of the invention relates to a pharmaceutical composition for treating abnormal cell growth, comprising a compound of the invention, or a pharmaceutically acceptable salt thereof.

Another aspect of the invention relates to a pharmaceutical composition for treating cancer, comprising a compound of the invention, or a pharmaceutically acceptable salt thereof.

The compounds of the invention are useful for inhibiting the multiplication of a tumor cell or cancer cell, causing apoptosis in a tumor or cancer cell, or for treating cancer in a patient. The compounds of the invention can be used accordingly in a variety of settings for the treatment of animal cancers. Said conjugates can be used to deliver a compound of the invention to a tumor cell or cancer cell. Without being bound by theory, in one embodiment, the antibody of the conjugate binds to or associates with a cancer-cell or a tumor-cell-associated antigen, and the conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. In certain embodiments, once inside the cell, one or more specific peptide sequences are cleaved, for example enzymatically or hydrolytically cleaved by one or more tumor cell or cancer cell-associated proteases, resulting in release of a compound of the invention from the conjugate. The conjugate can be cleaved by an intracellular protease to release a compound of the invention. The released compound of the invention is then free to migrate within the cell and induce cytotoxic or cytostatic activities. Without wishing to be bound by theory, the released compound of the invention may also migrate to another cell, including a cell which does not express a suitable antigen, and induce cytotoxic or cytostatis activities. In an alternative embodiment, the compound of the invention is cleaved from conjugate outside the tumor cell or cancer cell, and the compound of the invention subsequently penetrates the cell.

In certain embodiments, the conjugates provide conjugation-specific tumor or cancer drug targeting, thus reducing general toxicity of the compounds of the invention.

In another embodiment, the antibody unit binds to the tumor cell or cancer cell.

In another embodiment, the antibody unit binds to a tumor cell or cancer cell antigen which is on the surface of the tumor cell or cancer cell.

In another embodiment, the antibody unit binds to a tumor cell or cancer cell antigen which is an extracellular matrix protein associated with the tumor cell or cancer cell.

The specificity of the antibody unit for a particular tumor cell or cancer cell can be important for determining those tumors or cancers that are most effectively treated.

The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

As used herein, "subject" refers to a human or animal subject. In certain preferred embodiments, the subject is a human.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

As used herein "cancer" refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

In certain embodiments of the methods provided herein, the abnormal cell growth is cancer, wherein the cancer is selected from the group consisting of bladder cancer, breast cancer, cervix cancer, colon cancer, prostate cancer, lung cancer (including NSCLC and SCLC), esophageal cancer, head and neck cancer, squamous cell carcinoma, colorectal cancer, kidney cancer, renal cell carcinoma (RCC), liver cancer, pancreatic cancer, gastric cancer, thyroid cancer, acute myelogenous leukemia (AML), myelodysplastic syndrome (MDS), melanoma, neurofibromatosis and hepatocellular carcinoma, endometrium cancer, lung cancer, esophagus cancer, ovary cancer, pancreas cancer, skin cancer, stomach cancer, and testes cancer; and blood born cancers including but not limited to leukemias and lymphomas.

Dosage Forms and Routes of Administration

Another aspect of the invention relates to pharmaceutical compositions including an effective amount of a compound of the invention or a pharmaceutically acceptable salt thereof, including a pay-load of the present invention, a pay-load linker compound of the present invention, and/or an antibody drug conjugate thereof and a pharmaceutically acceptable carrier or vehicle. In certain embodiments, the compositions are suitable for veterinary or human administration.

The present pharmaceutical compositions can be in any form that allows for the composition to be administered to a patient. For example, the composition can be in the form of a solid or liquid. Administration can be systemic or local. Typical routes of administration include, without limitation, oral, parenteral, ocular, intra-tumor intraduodenal routes, topical, and rectal administration. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a compound of the invention to be bioavailable upon administration of the composition to a patient. Compositions can take the form of one or more dosage units, where for example, a tablet can be a single dosage unit, and a container of a compound of the invention in liquid form can hold a plurality of dosage units. Alternatively, various delivery systems are known, e.g., encapsulation in liposomes, microparticles, microcapsules, capsules, etc., and can be used to administer a compound of the invention. In certain embodiments, more than one compound of the invention is administered to a patient.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound of the invention, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate. The choice of carrier and/or excipient will to a large extent depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Examples, without limitation, of excipients include calcium carbonate, calcium phosphate, various sugars and types of starch, cellulose derivatives, gelatin, vegetable oils and polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Solid formulations for oral administration may be formulated to be immediate and/or modified release. Modified release formulations include delayed-, sustained-, pulsed-, controlled-, targeted and programmed release. Suitable modified release formulations are described in U.S. Pat. No.

6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Liquid formulations include suspensions, solutions, emulsions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. In a composition for administration by injection, one or more of a surfactant, preservative, wetting agent, dispersing agent, suspending agent, buffer, stabilizer and isotonic agent can also be included.

In certain embodiments the pharmaceutically acceptable carrier can be liquid, such as water and oils, including those of petroleum, animal, vegetable or synthetic origin. The carriers can be saline, and the like. In addition, auxiliary, stabilizing and other agents can be used. In one embodiment, when administered to a patient, the compound or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents. Other examples of suitable pharmaceutical carriers are described in "Remington's Pharmaceutical Sciences" by E. W. Martin.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

In an embodiment, the compound of the invention is formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients can be mixed prior to administration.

In certain embodiments, it can be desirable to administer one or more compounds of the invention locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as silastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

In yet another embodiment, the compound of the invention can be delivered in a controlled release system, such as but not limited to, a pump or various polymeric materials can be used. In yet another embodiment, a controlled-release system can be placed in proximity of the target of the compound of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The composition can also include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The amount of a compound of the invention that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. Generally, the dosage of a compound of the invention administered to a patient is typically about 0.001 mg/kg to about 20 mg/kg of the patient's body weight. In one aspect, the dosage administered to a patient is between about 0.001 mg/kg to about 10 mg/kg of the patient's body weight. In another aspect, the dosage administered to a patient is between about 0.01 mg/kg and about 10 mg/kg of the patient's body weight. In yet another aspect, the dosage administered to a patient is between about 0.01 mg/kg and about 5 mg/kg of the patient's body weight. In yet another aspect the dosage administered is between about 0.01 mg/kg to about 3 mg/kg of the patient's body weight. In yet another aspect, the dosage administered is between about 0.1 mg/kg to about 3 mg/kg of the patient's body weight.

For intravenous administration, the composition can comprise from about 0.001 to about 100 mg of a compound of the invention per kg of the patient's body weight. In one aspect, the composition can include from about 0.01 to about 100 mg of a compound of the invention thereof per kg of the patient's body weight. In another aspect, the amount administered will be in the range from about 0.01 to about 25 mg/kg of body weight of a compound of the invention.

The compositions comprise an effective amount of a compound of the invention such that a suitable dosage will be obtained. Typically, this amount is at least about 0.001% of a compound of the invention by weight of the composition. In an exemplary embodiment, pharmaceutical compositions are prepared so that a parenteral dosage unit contains from about 0.001% to about 2% by weight of the amount of a compound of the invention.

Whether in solid or liquid form, the present compositions can include a second active pharmaceutical ingredient, including for example a pharmacological agent used in the treatment of cancer.

In one aspect this invention also relates to a pharmaceutical composition comprising an effective amount of a compound of the invention, or a pharmaceutically acceptable salt thereof, a pharmaceutically acceptable diluent, carrier or excipient and further comprising a therapeutically effective amount of another pharmaceutically active ingredient. In one embodiment the additional pharmaceutically active ingredient is an anti cancer agent. In one embodiment the additional pharmaceutically active ingredient is a chemotherapeutic agent. In one embodiment the additional pharmaceutically active ingredient is an immune oncology agent.

Kit of Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

Cancers, including, but not limited to, a tumor, metastasis, or other disease or disorder characterized by uncontrolled cell growth, can be treated or inhibited by administration of a compound of the invention.

In one embodiment this invention relates to a combination of a compound of the invention, or a pharmaceutically acceptable salt thereof, and another pharmaceutically active ingredient. In one embodiment the additional pharmaceutically active ingredient is an anti cancer agent.

As used herein, the term "combination therapy" refers to the administration of a compound of the invention together with an at least one additional pharmaceutical or medicinal agent (e.g., an anti-cancer agent), either sequentially or simultaneously.

As noted above, the compounds of the invention may be used in combination with one or more additional anti-cancer agents. When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

In other embodiments, methods for treating cancer are provided, including administering to a patient in need thereof an effective amount of a compound of the invention and an anti cancer agent. In one embodiment the anti cancer agent is a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. A compound of the invention can be administered to a patient that has also undergone surgery as treatment for the cancer.

In one embodiment of the present invention the anti-cancer agent used in conjunction with a compound of the invention and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCI3 inhibitors, COX-2 (cyclooxygenase II) inhibitors, integrins (alpha-v/beta-3), MMP-2 (matrix-metalloprotienase 2) inhibitors, and MMP-9 (matrix-metalloprotienase 9) inhibitors.

Preferred anti-angiogenesis agents include sunitinib (Sutent™), bevacizumab (Avastin™), axitinib (AG 13736), SU 14813 (Pfizer), and AG 13958 (Pfizer).

Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex™) and UCN 01 (Kyowa Hakko).

Other examples of anti-angiogenesis agents which can be used in conjunction with a compound of the invention and pharmaceutical compositions described herein include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™).

Other anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™).

Other anti-angiogenesis agents include ABT 510 (Abbott), apratastat (TMI 005), AZD 8955 (AstraZeneca), incyclinide (Metastat™), and PCK 3145 (Procyon).

Other anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa™), cetuximab (Erbitux™), erlotinib (Tarceva™), trastuzumab (Herceptin™), sunitinib (Sutent™), imatinib (Gleevec™), and PD325901 (Pfizer).

Additional examples of signal transduction inhibitors which may be used in conjunction with a compound of the invention and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38).

Other examples of signal transduction inhibitor include PF-2341066 (Pfizer), PF-299804 (Pfizer), canertinib (CI 1033), pertuzumab (Omnitarg™), Lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), lapatinib (Tycerb™), pelitinib (EKB 569), and pertuzumab (Omnitarg™).

Other examples of signal transduction inhibitors include ARRY 142886 (Array Biopharm), everolimus (Certican™), zotarolimus (Endeavor™), temsirolimus (Torisel™), AP 23573 (ARIAD), and VX 680 (Vertex).

Additionally, other signal transduction inhibitors include XL 647 (Exelixis), sorafenib (Nexavar™), LE-AON (Georgetown University), and GI-4000 (Globelmmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), palbociclib (PD 0332991, Pfizer), crizotinib (Pfizer), and AG 024322 (Pfizer).

This invention contemplates the use of compounds of the invention together with classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, episteride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with compounds of the invention include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, 10-hydroxycamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

The invention also contemplates the use of the compounds of the invention together with dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutami c acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with a compound of the invention, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paciltaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™-radiation therapy)), bexarotene (Targretin™), Tesmilifene (DPPE-enhances efficacy of cytotoxics)), Theratope™ (Biomira), Tretinoin (Vesanoid™), tirapazamine (Trizaone™), motexafin gadolinium (XCytrin™) Cotara™ (mAb), and NBI-3001 (Protox Therapeutics), polyglutamate-paclitaxel (Xyotax™) and combinations thereof.

Further examples of classical antineoplastic agents used in combination therapy with a compound of the invention, optionally with one or more other agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

The invention also contemplates the use of the compounds of the invention together with an immunomodulatory agent, for example an immunosuppressant or an immune enhance. Examples of such agents include, but are not limited to a PD-L1 antagonist or inhibit, such s an anti-PD-1 antibody. Examples of such anti-PD-L1 antibodies may include, e.g., avelumab (formerly MSB0010718C, Merck/Pfizer) or the antibodies described in WO 2013/079174A1 and US 2014/0241917, which is incorporated by reference (Merck), or MED14736 (AstraZeneca) [described in WO2011/066389 and US2013/034559], or lambrolizumab. Examples of such agents may also include a CTLA-4 antibody, antibodies directed against tumor-necrosis factor (TNF) receptors 4-1BB and Ox40 (e.g., an anti-OX-40 antibody or anti-4-1 BB antibody), an anti-cancer antigen vaccine, a P-cadherin LP-Dual-Affinity Re-Targeting protein, or another antibody drug conjugate. In one embodiment, the immunomodulatory agent is an anti-CTLA4 antibody, e.g., tremelimumab (formerly CP-675, 206, a full human IgG2 Mab); ipilimumab (MDX-0120; Medarex; Bristol-Myers Squibb. In another aspect, the second active agent is p53 cancer vaccine, p53 epitope vaccine, and other cancer vaccines (e.g., to activate dendritic cells).

In some embodiments, the patient also receives an additional treatment, such as radiation therapy. In a specific embodiment, the compound of the invention is administered concurrently with the chemotherapeutic agent or with radiation therapy. In another specific embodiment, the chemotherapeutic agent or radiation therapy is administered prior or subsequent to administration of a compound of the invention.

A chemotherapeutic agent can be administered over a series of sessions. Any one or a combination of the chemotherapeutic agents, such a standard of care chemotherapeutic agent(s), can be administered.

Additionally, methods of treatment of cancer with a compound of the invention are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The compounds of the invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stein cells are harvested and purged of all cancer cells, the animal's remaining bone-marrow cell population is then eradicated via the administration of a high dose of a compound of the invention with or without accompanying high dose radiation therapy, and the stem cell graft is infused back into the animal. Supportive care is then provided while bone marrow function is restored and the patient recovers.

Synthesis of Compounds of the Invention and Antibody Drug Conjugates Thereof

The compounds and conjugates of the invention can be made using the synthetic procedures outlined below in the Exemplification.

As described in more detail below, the compounds and conjugates of the invention can be prepared using a section of a linker unit having a reactive site for binding to the compound.

Conventional conjugating methods for ADCs include chemical modification through either the lysine side chain amines, or through the cysteine sulfhydryl groups activated by reducing the interchain disulfide bonds. Mylotarg, brentuximab vedotin and KADCYLA® (ado-trastuzumab emtansine) are examples of ADCs using these conventional methods.

Enzymatic approaches using a transglutaminase and/or sortase for making ADCs have also been explored. Transglutaminases belong to a family of enzymes that catalyze acyl addition to a primary amine. Conjugation using a transglutaminase provides the advantages of high selectivity, simplified reaction procedures, and mild reaction conditions. See, e.g., Strop et al., Chemistry & Biology, 20:161-167 (2013); and Farias et al., Bioconj. Chem. 25(2):240-250 (2014). US2013-0230543 and US2013-0122020 describe transglutaminase-mediated site-specific conjugation of antibodies and small molecules.

Conjugation with Transglutaminase

In certain embodiments, a compound of the invention may be covalently crosslinked to an Fc-containing or Fab-containing polypeptide engineered with an acyl donor glutamine-containing tag (e.g., Gln-containing peptide tags or Q-tags) or an endogenous glutamine made reactive (i.e., the ability to form a covalent bond as an acyl donor in the presence of an amine and a transglutaminase) by polypeptide engineering (e.g., via amino acid deletion, insertion, substitution, mutation, or any combination thereof on the polypeptide), in the presence of transglutaminase, provided that the compound of the invention comprises an amine donor agent (e.g., small molecule comprising or attached to a reactive amine), thereby forming a stable and homogenous population of an engineered Fc-containing polypeptide conjugate with the amine donor agent being site-specifically conjugated to the Fc-containing or Fab-containing polypeptide through the acyl donor glutamine-containing tag or the exposed/accessible/reactive endogenous glutamine. As example, compounds of the invention may be conjugated as described in International Patent Application Serial No. PCT/IB2011/054899, whose entire contents are incorporated herein by reference. In certain embodiments, to facilitate conjugation of the compound of the invention to an Fc-containing or Fab-containing polypeptide engineered with an acyl donor glutamine-containing tag or an endogenous glutamine made reactive by polypeptide engineering, or by other methods known to those skilled in the art such as deglycosation, in the presence of transglutaminase, Z is $NH_2$.

Conjugation to the Human Light Chain Kappa Domain Constant Region

In certain embodiments, a compound of the invention may be covalently attached to the side chain of $K^{188}$ of the human light chain kappa domain constant region (CLK) (full light chain numbering according to Kabat). For example, compounds of the invention may be conjugated as described in U.S. patent application Ser. No. 13/180,204, or WO2012/007896 whose entire contents are incorporated herein by reference. In certain embodiments, to facilitate conjugation to K188 CLK (CLK-K80), Z is

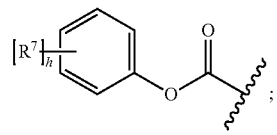

$R^7$ is independently selected for each occurrence from the group consisting of F, Cl, I, Br, $NO_2$, CN and $CF_3$; and h is 1, 2, 3, 4 or 5. In certain embodiments, to facilitate conjugation to $K^{188}$ CLK (CLK-K80), Z is

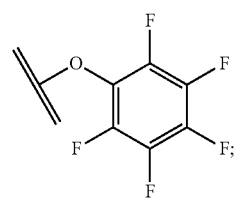

Conjugation with Linkers Comprising Succinimides, Including Rind-Opened Versions In an altenative embodiment, a compound of the invention may be conjugated via a succinimide-based linker or a ring-opened succinimide-based linker.

The invention is further described in the following examples, which are not intended to limit the scope of the invention.

EXEMPLIFICATION

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wisconsin). Products were generally dried under vacuum before being carried on to further reactions or submitted for biological testing. Mass spectrometry data is reported from either liquid chromatography-mass spectrometry (LCMS or LC-MS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction Protocol (length of reaction and temperature) may vary. In general, reactions were followed by thin layer chromatography (TLC) or mass spectrometry and/or LCMS, and subjected to work-up when appropriate. Purifications may vary between experiments: in general, solvents and the solvent ratios used for eluants/gradients were chosen to provide appropriate $R_f$s or retention times.

Compound names were generated with ACD Labs software.

Analytical LC-MS, HPLC and GC Conditions Used for Analyses:
Analytical LC-MS Conditions:
Method 1: Phenomenex Luna C18 (2), 150×3.0 mm, 5 μm column; Mobile phase A: 0.1% formic acid in water (v/v); Mobile phase B: 0.1% formic acid in acetonitrile (v/v); Gradient: 20% to 100% B over 5 minutes, then 100% B for 0.5 minutes, then gradient: 100% to 20% B over 0.5 minutes; Flow rate: 1.5 mL/minute. Temperature: not controlled; Detection: DAD 210, 254 nm; MS (+) range 200-2000 daltons; Injection volume: 10 μL; Instrument: Agilent 1100 HPLC.
Method 2: Phenomenex Luna C18 (2), 150×3.0 mm, 5 μm column; Mobile phase A: 0.1% formic acid in water (v/v); Mobile phase B: 0.1% formic acid in acetonitrile (v/v); Gradient: 20% to 100% B over 5 minutes, then gradient: 100% to 20% B over 0.5 minutes; Flow rate: 1.5 mL/minute. Temperature: not controlled; Detection: DAD 210, 254 nm; MS (+) range 200-2000 daltons; Injection volume: 10 μL; Instrument: Agilent 1100 HPLC
Method 3: Phenomenex Luna C18 (2), 150×3.0 mm, 5 μm column; Mobile phase A: 0.1% formic acid in water (v/v); Mobile phase B: 0.1% formic acid in acetonitrile (v/v); Gradient: 20% to 95% B over 8 minutes, then 100% B over 2 minutes; Flow rate: 1 mL/minute. Temperature: not controlled; Detection: DAD 210, 254 nm; MS (+) range 200-2000 daltons; Injection volume: 10 μL; Instrument: Agilent 1100 HPLC Method 4: Waters Acquity UPLC HSS T3, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 2.5 minutes, 95% B over 0.35 minute; Flow rate: 1.25 mL/minute. Temperature: 60° C.; Detection: 200-450 nm; MS (+) range 100-2000 daltons; Injection volume: 5 μL; Instrument: Waters Acquity.
Method 5: Waters Acquity UPLC BEH, 2.1 mm×50 mm, C18, 1.7 μm; Mobile phase A:: 0.1% formic acid in water (v/v); Mobile phase B: 0.1% formic acid in acetonitrile (v/v); Gradient: 5% B over 0.1 minute, 5% to 95% B over 0.7 minutes, 95% B over 0.1 minutes; Flow rate: 1.25 mL/minute. Temperature: 60° C.; Detection: 200-450 nm; MS (+) range 100-1200 daltons; Injection volume: 5 μL; Instrument: Waters Acquity.
Method 6: Phenomenex Luna C18 (2), 150×3.0 mm, 5 μm column; Mobile phase A: 0.1% formic acid in water (v/v); Mobile phase B: 0.1% formic acid in acetonitrile (v/v); Gradient: 20% to 100% B over 3 minutes, then 100% B for 0.25 minutes; Flow rate: 2.0 mL/minute. Temperature: not controlled; Detection: DAD 210, 254 nm; MS (+) range 200-3000 daltons; Injection volume: 5 μL; Instrument: Agilent 1260 HPLC.
Method 7: Phenomenex Luna C18 (2), 150×3.0 mm, 5 μm column; Mobile phase A: 0.1% formic acid in water (v/v); Mobile phase B: 0.1% formic acid in acetonitrile (v/v); Gradient: 20% to 100% B over 8 minutes, then 100% B for 2 minutes; Flow rate: 2.0 mL/minute. Temperature: not controlled; Detection: DAD 210, 254 nm; MS (+) range 200-3000 daltons; Injection volume: 5 μL; Instrument: Agilent 1260 HPLC.
Method 8: Waters UPLC BEH C18, 2.1×150 mm, 1.7 μm column; Mobile phase A: 0.1% formic acid in water (v/v); Mobile phase B: 0.1% formic acid in acetonitrile (v/v); Gradient: 5% to 95% B over 11.5 minutes; Flow rate: 0.25 mL/minute. Temperature: 40C; Detection: Waters SYNAPT G2 mass spectrometer coupled with ACQUITY UPLC; Injection volume: 2 uL
Method 9: Chromolith RP-18e, 25×2 mm column; Mobile phase A: 0.038% trifluoroacetic acid in water (v/v); Mobile phase B: 0.016% trifluroacetic acid in acetonitrile (v/v); Gradient: 5% to 95% B over 0.7 minutes followed by isocratic elution using 95% B for 0.4 minutes; Flow rate: 1.5 mL/minute. Temperature: 50 C; Detection: DAD 220 nm; MS (+) range 0-1000; Injection volume: 3 μL; Instrument: Shimadzu $L^C$-2010.
Method 10: Phenomenex Luna C18 (2), 150×4.6 mm, 5 μm column; Mobile phase A: 10 mM phosphate buffer, pH7; Mobile phase B: 0.02% acetic acid in acetonitrile (v/v); Gradient: 20% to 95% B over 10 minutes; Flow rate: 1.0 mL/minute. Temperature: not controlled; Detection: DAD 210, 254 nm; MS (+) range 200-3000 daltons; Injection volume: 5 μL; Instrument: Agilent 1260 HPLC.
Method 11: Phenomenex Luna C18 (2), 150×3.0 mm, 5 μm column; Mobile phase A: 0.1% formic acid in water (v/v); Mobile phase B: 0.1% formic acid in acetonitrile (v/v); Gradient: 20% to 100% B over 5 minutes, then gradient: 100% to 20% B over 0.5 minutes; Flow rate: 1.5 mL/minute. Temperature: not controlled; Detection: DAD 210, 254 nm; MS (+) range 200-3000 daltons; Injection volume: 5 μL; Instrument: Agilent 1260 HPLC
Method 12: Waters Acquity UPLC HSS T3, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 1.0 minutes, 95% B over 0.35 minute; Flow rate: 1.25 mL/minute. Temperature: 60° C.; Detection: 200-450 nm; MS (+) range 100-2000 daltons; Injection volume: 5 µL; Instrument: Waters Acquity.

Method 13: Column: Chromolith Flash RP-18e 25-2 mm; Mobile Phase A: 0.04 trifluoroacetic acid in water (v/v); Mobile Phase B: 0.02% trifluoroacetic acid in acetonitrile (v/v); Gradient: 5% to 95% B over 0.7 minutes, 95% B over 0.4 minutes; Flow rate: 1.5 mL/min; Temperature: 50° C.; Detection: ESI, UV 220 nm; MS(+) range: 0-1000 daltons: Injection volume: 0.5-2 µL; Instrument: SHIMADZU 2010.

Method 14: Column: Xbridge Shield RP 18 5 µm, 2.1×50 mm; Mobile Phase A: 0.1% formic acid in water (v/v); Mobile Phase B: 0.1% formic acid in acetonitrile; Gradient: 0% to 95% solvent B over 3 minutes, 95% B over 1 minute; Flow rate: 1 mL/min; Ion Source: ESI; Ion Mode: Positive; Nebulization Gas: nitrogen; Drying Gas: nitrogen; Flow: 5 L/min; Nebulizer Pressure: 30 psig; Gas Temperature: 325° C. Capillary Voltage: 3.5 KV; Fragmentor Voltage: 50 V; Instrument: Agilent G1969A.

Method 18: Phenomenex Luna C18 (2), 150×3.0 mm, 5 µm column; Mobile phase A: 0.1% formic acid in water (v/v); Mobile phase B: 0.1% formic acid in acetonitrile (v/v); 10% B over 0.5 minutes, then gradient: 10% to 100% B over 4 minutes, then 100% B over 0.25 minutes; Flow rate: 1.5 mL/minute. Temperature: not controlled; Detection: DAD 210, 254 nm; MS (+) range 200-3000 daltons; Injection volume: 5 µL; Instrument: Agilent 1260 HPLC Analytical High Performance Liquid Chromatography (HPLC) Conditions:

Method 15: Column: YMC-pack ODS-A 150×4.6 mm, 5 µm; Mobile Phase A: 0.1% trifluoroacetic acid in water; Mobile Phase B: 0.1% trifluoroacetic acid in acetonitrile; Gradient 0% to 95% solvent B over 10 minutes, 95% over 5 minutes; Flow rate: 1.0 mL/minutes; Temperature: 30° C.; Instrument: Agilent 1100 HPLC-BG Method 16: Column: Atlantis HILIC Silica 150×4.6 mm, 5 µm; Mobile Phase A: 0.1% trifluoroacetic acid in water; Mobile Phase B: 0.1% trifluoroacetic acid in acetonitrile; Gradient 100% to 70% solvent B over 10 minutes, 70% over 5 minutes; Flow rate: 1.0 mL/minutes; Temperature: 30° C.; Instrument: Agilent 1100 HPLC-BG Analytical Gas Chromatography (GC) Conditions:

Method 17: Column: HP-5 30 m×0.32 mm×0.25 um FILM; Carrier gas: nitrogen; Total Flow: 153.3/min; Split: 1:100; Injector: 250° C.; Detector (FID): 300° C.; Column temperature: 40° C. (2 min) to 250° C. (2 min), rate=15° C./min; Injection volume: 2-3 µL; Instrument: Shimadzu GC-2010 GC-C Preparative HPLC Conditions Used for Purifications:

Method A: Phenomenex Luna C18, 100×30 mm, 5 µm column; Mobile phase A: 0.02% acetic acid and 2.5% acetonitrile in water (v/v); Mobile phase B: 0.02% acetic acid in acetonitrile (v/v); Gradient: 20% to 90% B over 20 minutes; Flow rate: 20 mL/minute. Temperature: not controlled; Detection: DAD 210, 254 nm; Injection volume: up to 5 mL. Instrument: Gilson 215.

Method B: Phenomenex Luna C18, 100×30 mm, 5 µm column; Mobile phase A: 0.02% acetic acid and 2.5% acetonitrile in water (v/v); Mobile phase B: 0.02% acetic acid in acetonitrile (v/v); Gradient: 20% to 95% B over 20 minutes; Flow rate: 20 mL/minute. Temperature: not controlled; Detection: DAD 210, 254 nm; Injection volume: up to 5 mL. Instrument: Gilson 215.

Method C: Phenomenex Luna C18, 100×30 mm, 5 µm column; Mobile phase A: 0.02% acetic acid and 2.5% acetonitrile in water (v/v); Mobile phase B: 0.02% acetic acid in acetonitrile (v/v); Gradient: 10% to 90% B over 20 minutes; Flow rate: 20 mL/minute. Temperature: not controlled; Detection: DAD 210, 254 nm; Injection volume: up to 5 mL. Instrument: Gilson 215.

Method D: Phenomenex Luna C18, 100×30 mm, 5 µm column; Mobile phase A: 0.02% acetic acid and 2.5% acetonitrile in water (v/v); Mobile phase B: 0.02% acetic acid in acetonitrile (v/v); Gradient: 20% to 100% B over 20 minutes; Flow rate: 20 mL/minute. Temperature: not controlled; Detection: DAD 210, 254 nm; Injection volume: up to 5 mL. Instrument: Gilson 215.

Method E: Phenomenex Luna C18, 100×30 mm, 5 µm column; Mobile phase A: 0.02% acetic acid and 2.5% acetonitrile in water (v/v); Mobile phase B: 0.02% acetic acid in acetonitrile (v/v); Gradient: 10% to 80% B over 20 minutes; Flow rate: 20 mL/minute. Temperature: not controlled; Detection: DAD 210, 254 nm; Injection volume: up to 5 mL. Instrument: Gilson 215.

Method F: Phenomenex Luna C18, 100×30 mm, 5 µm column; Mobile phase A: 0.02% acetic acid and 2.5% acetonitrile in water (v/v); Mobile phase B: 0.02% acetic acid in acetonitrile (v/v); Gradient: 20% to 80% B over 20 minutes; Flow rate: 20 mL/minute. Temperature: not controlled; Detection: DAD 210, 254 nm; Injection volume: up to 5 mL. Instrument: Gilson 215.

Method G: Phenomenex Luna C18, 100×30 mm, 5 µm column; Mobile phase A: 0.02% acetic acid and 2.5% acetonitrile in water (v/v); Mobile phase B: 0.02% acetic acid in acetonitrile (v/v); Gradient: 10% to 95% B over 20 minutes; Flow rate: 20 mL/minute. Temperature: not controlled; Detection: DAD 210, 254 nm; Injection volume: up to 5 mL. Instrument: Gilson 215.

Method H: Phenomenex Luna C18, 100×30 mm, 5 µm column; Mobile phase A: 0.02% acetic acid in water (v/v); Mobile phase B: 0.02% acetic acid in acetonitrile (v/v); Gradient: 15% to 95% B over 20 minutes; Flow rate: 20 mL/minute. Temperature: not controlled; Detection: DAD 210, 254 nm; Injection volume: up to 5 mL. Instrument: Gilson 215.

Method I: Phenomenex Luna C18, 150×30 mm, 5 µm column; Mobile phase A: 0.02% acetic acid in water (v/v); Mobile phase B: 0.02% acetic acid in acetonitrile (v/v); Gradient: 5% to 100% B over 20 minutes; Flow rate: 20 mL/minute. Temperature: not controlled; Detection: DAD 210, 254 nm; Injection volume: up to 5 mL. Instrument: Gilson 215.

Method J: Phenomenex Luna C18, 100×30 mm, 5 µm column; Mobile phase A: 0.02% trifluoroacetic acid in water (v/v); Mobile phase B: 0.02% acetic acid in acetonitrile (v/v); Gradient: 5% to 60% B over 12 minutes; Flow rate: 20 mL/minute. Temperature: not controlled; Detection: DAD 210, 254 nm; Injection volume: up to 5 mL. Instrument: Gilson 215.

Method K: Phenomenex Luna C18, 100×30 mm, 5 µm column; Mobile phase A: 0.02% trifluoroacetic acid in water (v/v); Mobile phase B: 0.02% acetic acid in acetonitrile (v/v); Gradient: 25% to 100% B over 12 minutes; Flow rate: 20 mL/minute. Temperature: not controlled; Detection: DAD 210, 254 nm; Injection volume: up to 5 mL. Instrument: Gilson 215.

Method L: Phenomenex Luna C18, 100×30 mm, 5 µm column; Mobile phase A: 0.02% trifluoroacetic acid in water (v/v); Mobile phase B: 0.02% acetic acid in acetonitrile (v/v); Gradient: 20% to 100% B over 12 minutes; Flow rate: 20 mL/minute. Temperature: not controlled; Detection: DAD 210, 254 nm; Injection volume: up to 5 mL. Instrument: Gilson 215.

Method M: Phenomenex Luna C18, 100×30 mm, 5 μm column; Mobile phase A: 0.02% acetic acid in water (v/v); Mobile phase B: 0.02% acetic acid in acetonitrile (v/v); Gradient: 30% to 100% B over 20 minutes; Flow rate: 20 mL/minute. Temperature: not controlled; Detection: DAD 210, 254 nm; Injection volume: up to 5 mL. Instrument: Gilson 215.
Method N: Waters Xbridge Prep OBD C18, 100×19 mm, 5 μm column; Mobile phase A: 0.1% trifluoroacetic acid in water (v/v); Mobile phase B: 0.1% trifluroacetic acid in acetonitrile (v/v); Gradient: 23% to 43% B over 10 minutes; Flow rate: 25 mL/minute. Temperature: not controlled.
Method O: Durashell C18, 150×25 mm, 5 μm column; Mobile phase A: 0.05% aqueous ammonium hydroxide in water (v/v); Mobile phase B: acetonitrile; Gradient: 5% to 35% B over 10 minutes, 35% B over 2 minutes; Flow rate: 25 mL/minute. Temperature: not controlled.
Method P: Durashell C18, 150×25 mm, 5 μm column; Mobile phase A: 0.05% aqueous ammonium hydroxide in water (v/v); Mobile phase B: acetonitrile; Gradient: 51% to 71% B over 10 minutes, 71% B over 2 minutes; Flow rate: 30 mL/minute. Temperature: not controlled.

Preparation of Linkers, Thiols, and Key Intermediates:

Preparation of $N^2$-acetyl-$N^6$-[(9H-fluoren-9-yl-methoxy)carbonyl]-L-lysyl-L-valyl-$N^5$-carbamoyl-L-ornithine (L1)

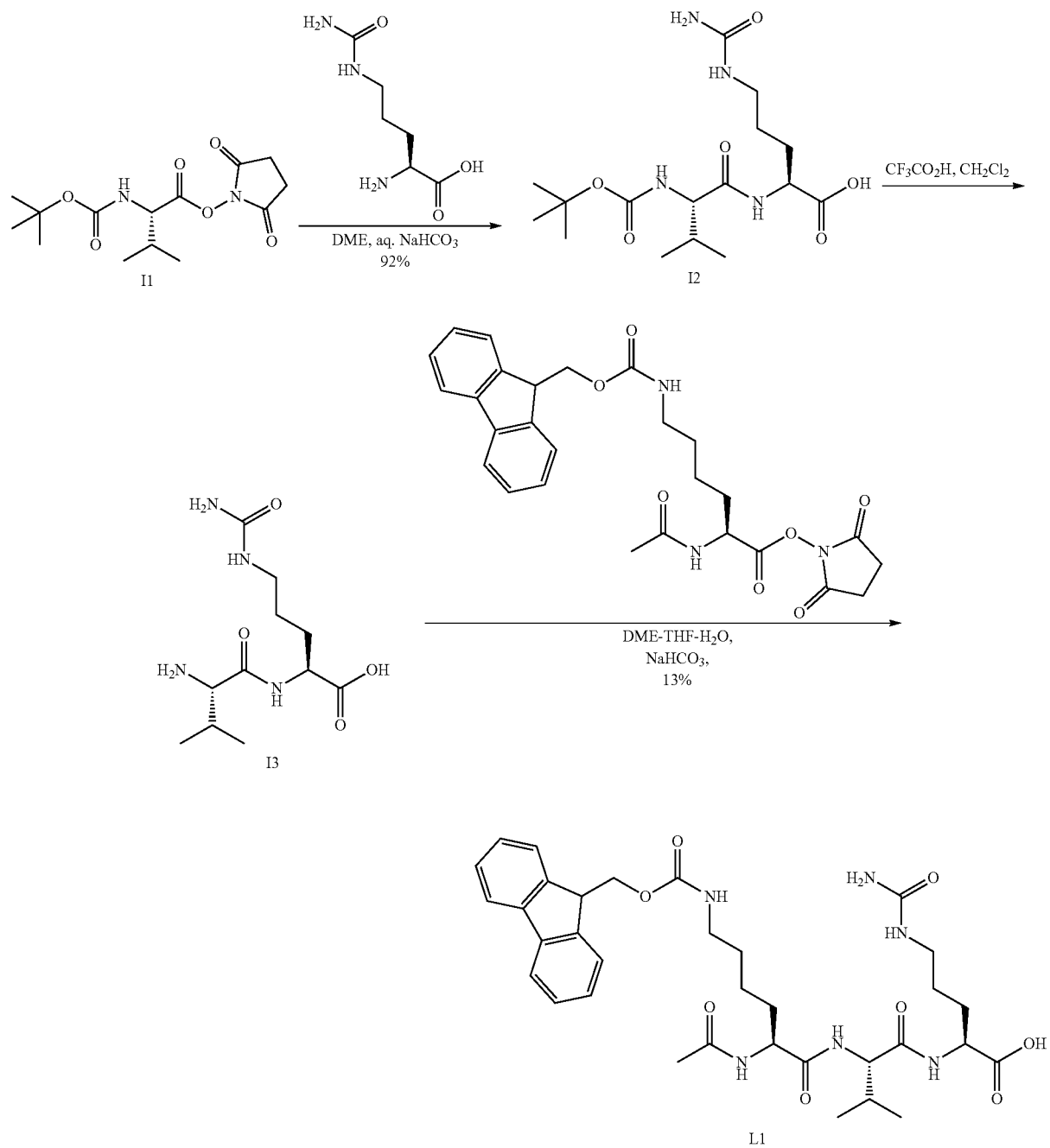

Step 1: Synthesis of N-(tert-butoxycarbonyl)-L-valyl-N$^5$-carbamoyl-L-ornithine A solution of 2,5-dioxopyrrolidin-1-yl N-(tert-butoxycarbonyl)-L-valinate (1.0 g, 3.18 mmol) in dimethoxyethane (8 mL) was added to a solution of N$^5$-carbamoyl-L-ornithine in tetrahydrofuran (2 ml). Aqueous sodium bicarbonate (282 mg, 3.34 mmol) in water (8 mL) was then added, and the resulting suspension was stirred for four days at room temperature. Aqueous citric acid (15% solution, 100 mL) was then added and the mixture was extracted with a mixture of ethyl acetate and 2-propanol (10:1, 2×100 ml). The combined extracts were washed with water (2×100 ml), dried over anhydrous sodium sulfate, and concentrated to obtain viscous colorless oil. This oil was then triturated with diethyl ether to provide 1.1 g (92%) of the desired product as a white solid, which was used directly in the next step without further purification. LC-MS m/z 373.5 [M−H+]; retention time=1.89 minutes (Method 1)

Step 2: Synthesis of L-valyl-N$^5$-carbamoyl-L-ornithine

To a stirred suspension of N-(tert-butoxycarbonyl)-L-valyl-N$^5$-carbamoyl-L-ornithine (1 g, 2.67 mmol) in dry dichloromethane (10 mL) at 5° C. was added trifluoroacetic acid (6 mL). The mixture was allowed to warm to room temperature and was then stirred for 3 h. The mixture was then concentrated, and the resulting residue was washed with tert-butyl methyl ether and filtered to give 1.15 g of the desired crude product as a white solid, which was used directly without further purification.

Step 3: Synthesis of N$^2$-acetyl-N$^6$-[(9H-fluoren-9-ylmethoxy)carbonyl]-L-lysyl-L-valyl-N-carbamoyl-L-ornithine (L1)

To a stirred solution of L-valyl-N$^5$-carbamoyl-L-ornithine (200 mg, 0.515 mmol) and 2,5-dioxopyrrolidin-1-yl N$^2$-acetyl-N$^6$-[(9H-fluoren-9-ylmethoxy)carbonyl]-L-lysinate (261 mg, 0.515 mmol) in a mixture of dimethoxyethane-water-tetrahydrofuran (1:1:2, 40 mL) was added sodium bicarbonate (108 mg, 1.29 mmol) and the mixture was stirred at room temperature for ~20 h. The mixture was then acidified to pH 2 by addition of aqueous hydrochloric acid (pH paper) and extracted with a mixture of ethyl acetate-2-propanol (10:1, 3×50 mL). Pooled extracts were dried over anhydrous sodium sulfate, filtered, concentrated, and the resulting residue was purified by reverse phase chromatography (Method N). Product containing fractions were lyophilized to provide 44 mg (13%) of the desired product (L1) as a white solid. LC-MS m/z 667.1 [M−H+]; retention time=0.752 minutes (Method 9).

Preparation of N$^2$-acetyl-N$^6$-[(9H-fluoren-9-yl methoxy)carbonyl]-L-lysyl-L-valyl-N$^5$-carbamoyl-N-[4-({[(pentafluorophenoxy)carbonyl]oxy}methyl)phenyl]-L-ornithinamide (L2)

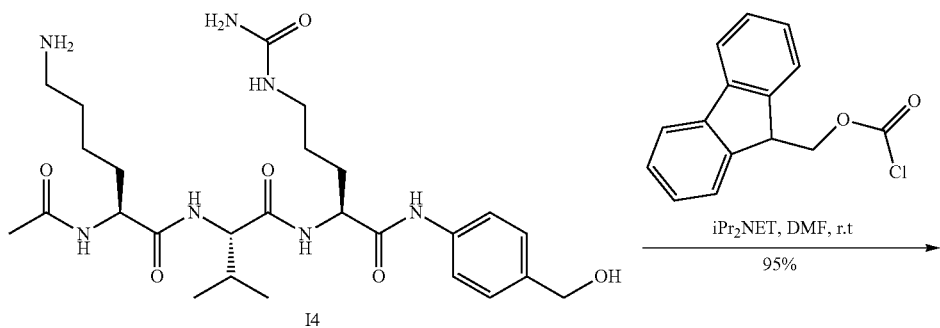

I4

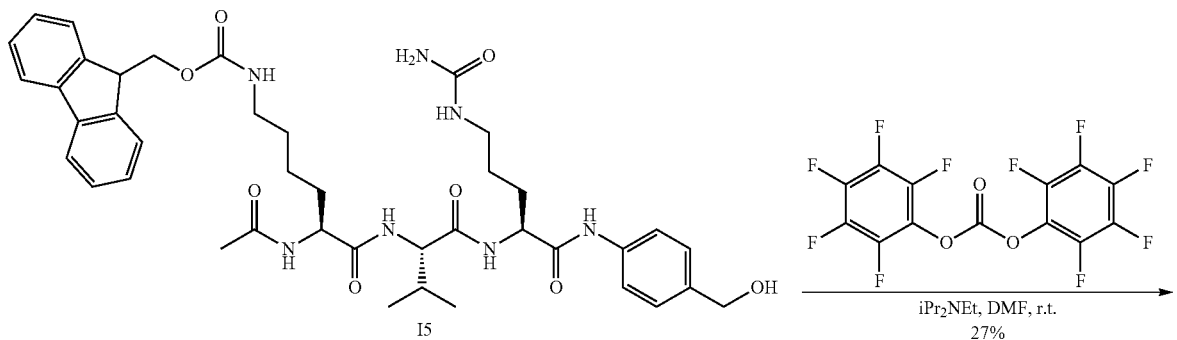

I5

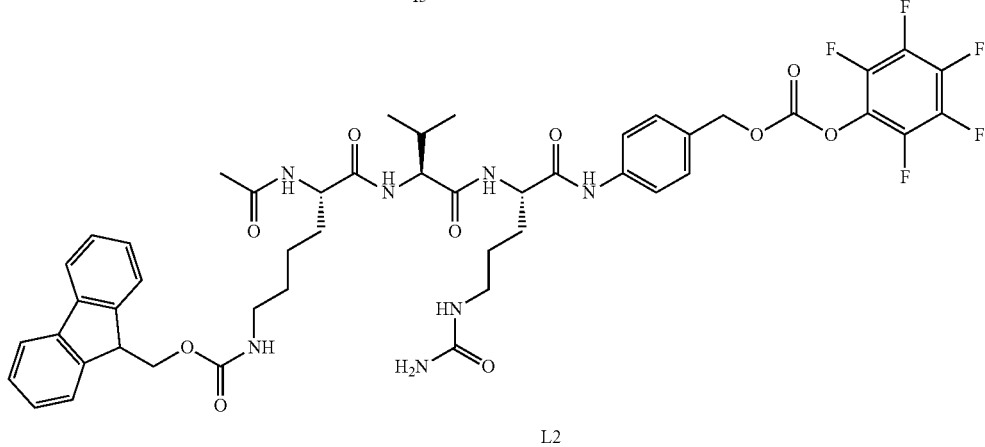

L2

Step 1: Synthesis of $N^2$-acetyl-$N^6$-[(9H-fluoren-9-ylmethoxy)carbonyl]-L-lysyl-L-valyl-$N^5$-carbamoyl-N-[4-(hydroxymethyl)phenyl]-L-ornithinamide To a solution of $N^2$-acetyl-L-lysyl-L-valyl-$N^5$-carbamoyl-N-[4-(hydroxymethyl)phenyl]-L-ornithinamide (see International patent application PCT/IB2013/059553, published as WO 2014/068443 on 8 May 2014, the contents of which are incorporated herein by reference in their entirety) (370.0 mg, 0.557 mmol) in N,N-dimethylformamide (8 mL) was added 9-fluorenylmethylchloroformate (173 mg, 0.669 mmol) and N,N-diisopropylethylamine (216 mg, 1.67 mmol, 0.291 mL) at room temperature. The reaction mixture was allowed to stir at room temperature for 2 h. Diethyl ether (10 mL) was introduced to the reaction mixture and white solid was collected by filtration to afford 410 mg (95%) of the desired product as a white solid. LC-MS m/z 772.5 [M−H+]; retention time=1.42 minutes (Method 4).

Step 2: Synthesis of $N^2$-acetyl-$N^6$-[(9H-fluoren-9-ylmethoxy)carbonyl]-L-lysyl-L-valy-$N^5$-carbamoyl-N-[4-({[(pentafluorophenoxy)carbonyl]oxy}methyl)phenyl]-L-ornithinamide To a solution of $N^2$-acetyl-$N^6$-[(9H-fluoren-9-ylmethoxy)carbonyl]-L-lysyl-L-valyl-$N^5$-carbamoyl-N-[4-(hydroxymethyl)phenyl]-L-ornithinamide (349 mg, 0.491 mmol) in N,N-dimethylformamide (10 mL) was added bis(pentafluorophenyl)carbonate (387 mg, 0.982 mmol) and followed by N,N-diisopropylethylamine (0.342 mL, 0.96 mmol) at room temperature. The reaction mixture was allowed to stir at room temperature for 2 h. The crude reaction mixture was purified by reverse phase HPLC (Method H). Product containing fractions were immediately lyophilized to afford 132 mg (27%) of the desired product (L2) as a white solid. LC-MS m/z 982.6 [M−H+]; retention time=2.10 minutes (Method 4).

Preparation of 9H-fluoren-9-ylmethyl (21-oxo-3,6,9,12,15,18-hexaoxahenicos-1-yl)carbamate (L3)

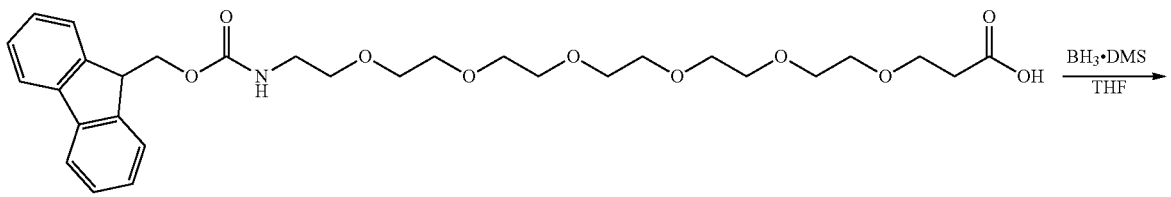

I6

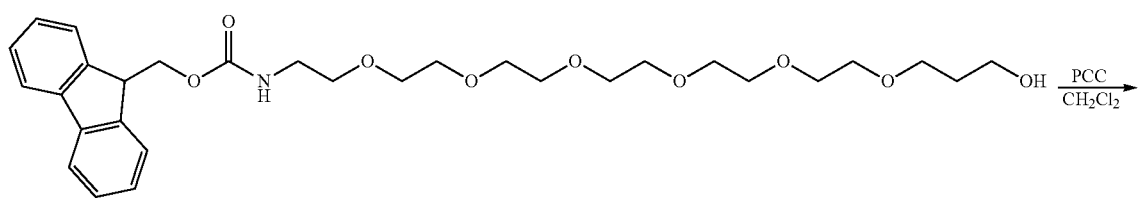

I7

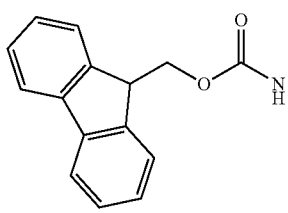

L3

Step 1: Synthesis of 9H-fluoren-9-ylmethyl (21-hydroxy-3,6,9,12,15,18-hexaoxahenicos-1-yl)carbamate A 2.0 M solution of boranedimethylsulfide complex in tetrahydrofuran (188 uL, 0.375 mmol) was added to a solution of 1-(9H-fluoren-9-yl)-3-oxo-2,7,10,13,16,19,22-heptaoxa-4-azapentacosan-25-oic acid (108 mg, 0.188 mmol) in tetrahydrofuran at 0° C. After three hours, methanol (2 mL) was added to the reaction mixture, followed by saturated aqueous ammonium chloride solution (1 mL) to quench excess reagent. After one hour, the reaction mixture was diluted with ethyl acetated (75 mL) and washed with water (25 mL) and brine (25 mL). The organic layer was dried over anhydrous sodium sulfate, filtered and concentrated to afford 110 mg of the desired product. LC-MS m/z 562.3 [M+H+]; retention time=1.02 minutes (Method 5).

Step 2: Synthesis of 9H-fluoren-9-ylmethyl (21-oxo-3,6,9,12,15,18-hexaoxahenicos-1-yl)carbamate A mixture of pyridinium chlorochromate (87 mg, 0.39 mmol) and silica gel (82 mg) was added to a solution of 9H-fluoren-9-ylmethyl (21-hydroxy-3,6,9,12,15,18-hexaoxahenicos-1-yl)carbamate (110 mg, 0.16 mmol) in dichloromethane. After 6 hours, the reaction mixture was filtered and washed with 1N aqueous hydrochloric acid solution. The organic layer was dried over anhydrous sodium sulfate, filtered and concentrated. The residue was purified by silica gel chromatography (0 to 10% methanol in dichloromethane). Product containing fractions were concentrated to afford 61 mg of the desired product (L3). LC-MS m/z 560.3 [M+H+]; retention time=1.12 minutes (Method 5).

Preparation of 9H-fluoren-9-ylmethyl [2-(2-{2[(iodoacetyl)amino]ethoxy}ethoxy)ethyl]-carbamate (L4)

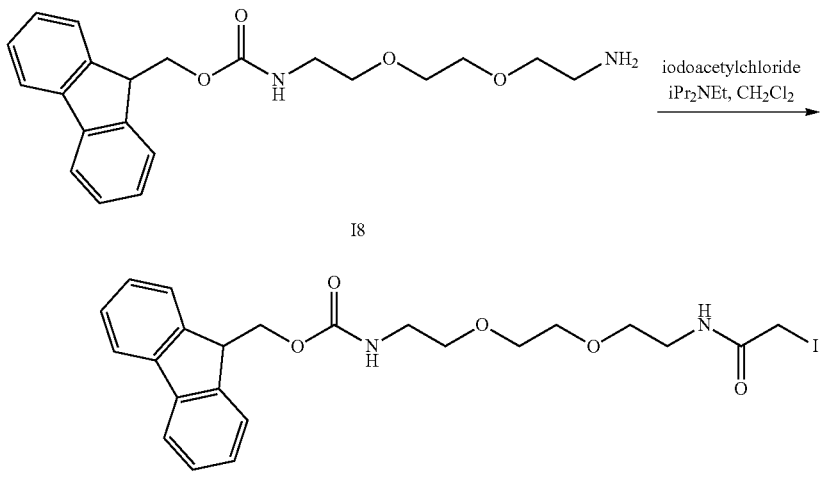

L4

Iodoacetyl chloride (744 mg, 3.64 mmol) was added to a solution of 9H-fluoren-9-ylmethyl {2-[2-(2-aminoethoxy)ethoxy]ethyl}carbamate (674 mg, 1.82 mmol) and trimethylamine (1840 mg, 18.2 mmol, 2.48 mL) in tetrahydrofuran (20 mL) and dichloromethane (8 mL) in an ice water bath. The contents were stirred for 2 hours, then evaporated under reduced pressure, redissolved in ethyl acetate (40 mL) and extracted with hydrochloric acid (0.5M, 2×20 mL), saturated aqueous sodium bicarbonate (2×20 mL) and dried over anhydrous magnesium sulfate. The crude reaction mixture was purified by normal-phase silica-gel chromatography, elution conducted with 10%-100% ethyl acetate in heptane over 20 column volumes. Product containing fractions were evaporated under reduced pressure to obtain 370 mg (38%) of the desired product (L4). LC-MS m/z 539.0 [M+H+]; retention time=0.88 minutes (Method 5).

Preparation of 9H-fluoren-9-ylmethyl (3-aminopropyl)(4-{[(9H-fluoren-9-ylmethoxy)carbonyl](3-{[(9H-fluoren-9-ylmethoxy)carbonyl]amino}propyl)amino}butyl)carbamate (L5)
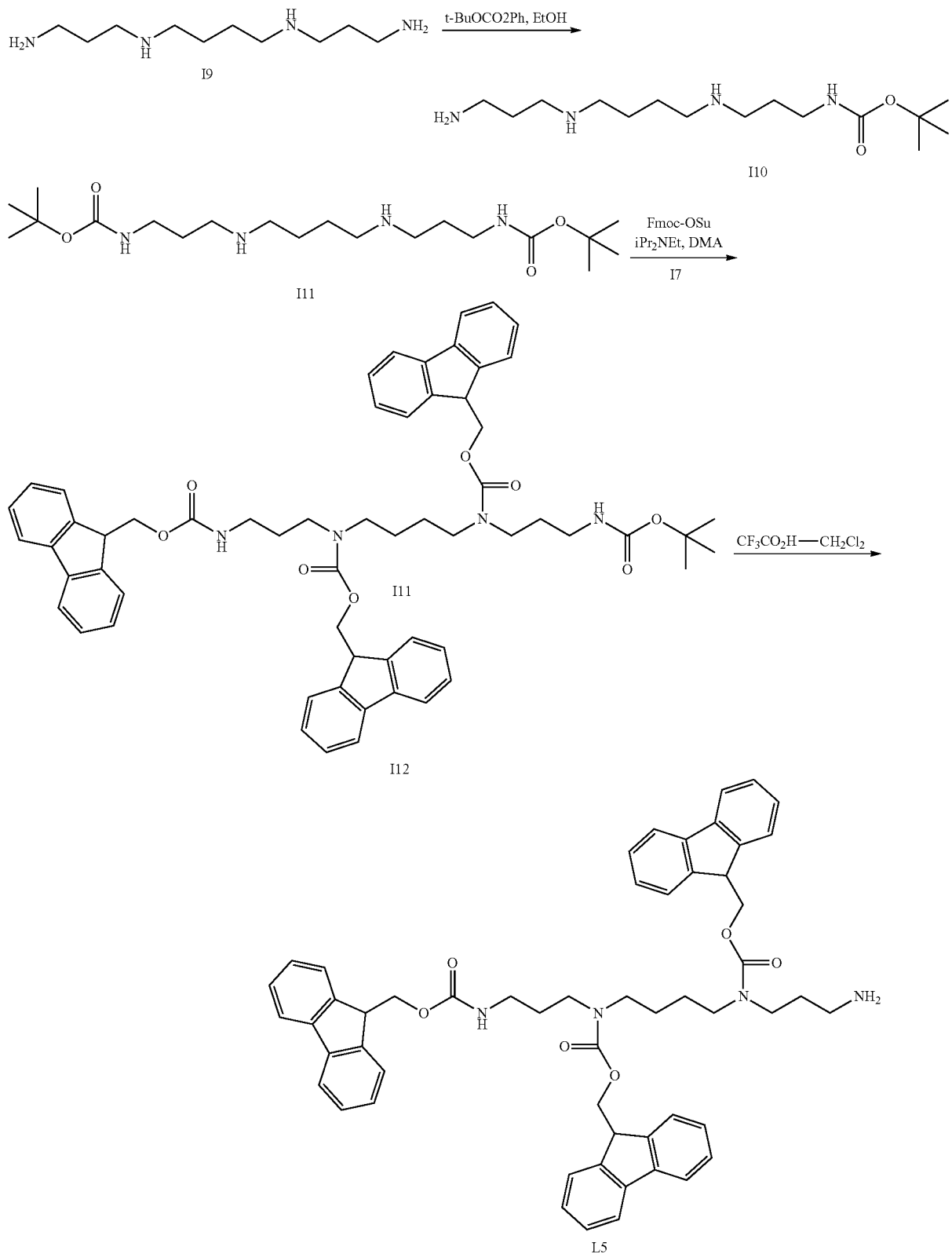

Step 1: Synthesis of tert-butyl [3-({4-[(3-aminopropyl)amino]butyl}amino)propyl]carbamate Neat tert-butyl phenyl carbonate (284 mg, 271 uL, 1.46 mmol) was added to a solution of N,N'-bis(3-aminopropyl)butane-1,4-diamine (296.0 mg, 1.46 mmol) in ethanol (2.0 mL) and the contents heated to reflux with stirring for 18 hours. The reaction mixture was concentrated to a pale yellow-colorless oil under vacuum and purified by reverse phase HPLC (Method J). Product containing fractions were lyophilized to obtain 221 mg (23%) of the desired product. LC-MS m/z 303.3 [M+H+]; retention time=0.26 minutes (Method 5). 73 mg (8%) Of tert-butyl (2,2-dimethyl-4-oxo-3-oxa-5,9,14-triazaheptadecan-17-yl)carbamate was also obtained; LC-MS m/z 403.4 [M+H$^+$]; retention time=0.47 minutes (Method 5).

Step 2: Synthesis of 9H-fluoren-9-ylmethyl {9,14-bis[(9H-fluoren-9-ylmethoxy)carbonyl]-2,2-dimethyl-4-oxo-3-oxa-5,9,14-triazaheptadecan-17-yl}carbamate 9-Fluorenylmethoxycarbonyl chloride (66.0 mg, 0.255 mmol) was added to a stirring solution of tert-butyl [3-({4-[(3-aminopropyl)amino]butyl}amino)propyl]carbamate (47 mg, 0.073 mmol) and N,N-diisopropylethylamine (56.5 mg, 0.438 mmol, 76.1 uL) in N,N-dimethylacetamide (500.0 uL). After 3 hours, the reaction mixture was purified by reverse phase HPLC (Method K). Product containing fractions were lyophilized to obtain 66 mg (93%) the desired product. LC-MS m/z 991.6 [M+Na$^+$]; retention time=1.33 minutes (Method 5).

Step 3: Synthesis of 9H-fluoren-9-ylmethyl (3-aminopropyl) (4-{[(9H-fluoren-9-ylmethoxy)carbonyl](3-{[(9H-fluoren-9-ylmethoxy)carbonyl]amino}propyl)amino}butyl)carbamate 9H-Fluoren-9-ylmethyl {9,14-bis[(9H-fluoren-9-ylmethoxy)carbonyl]-2,2-dimethyl-4-oxo-3-oxa-5,9,14-triazaheptadecan-17-yl}carbamate (65 mg, 0.067 mmol) was dissolved in a stirring solution of dichloromethane (2.5 mL) containing trifluoroacetic acid (0.5 mL). After 1 hour, the reaction mixture was purified by reverse phase HPLC (Method K). Product containing fractions were lyophilized to obtain 64 mg (97%) of the desired product (L5). LC-MS m/z 869.5 [M+H+]; retention time=0.99 minutes (Method 5).

Preparation of N$^2$-acetyl-N$^6$-[(9H-fluoren-9-ylmethoxy)carbonyl]-L-lysyl-L-valyl-N-(3-{(4-{(3-aminopropyl)[(9H-fluoren-9-ylmethoxy)carbonyl]amino}butyl)[(9H-fluoren-9-ylmethoxy)carbonyl]amino}propyl)-N$^5$-carbamoyl-L-ornithinamide (L6)

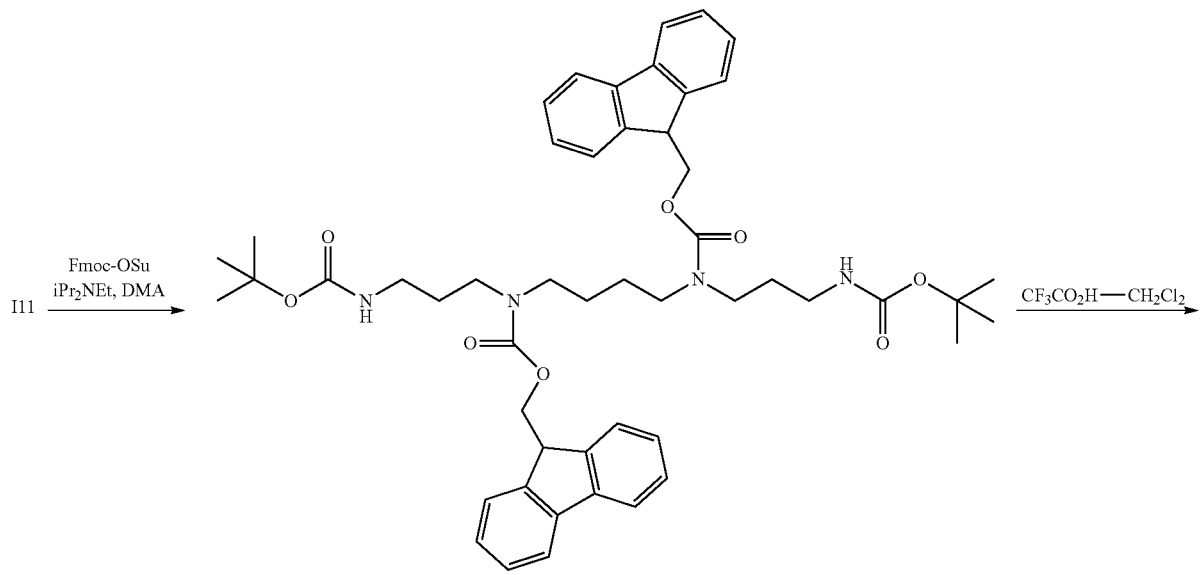

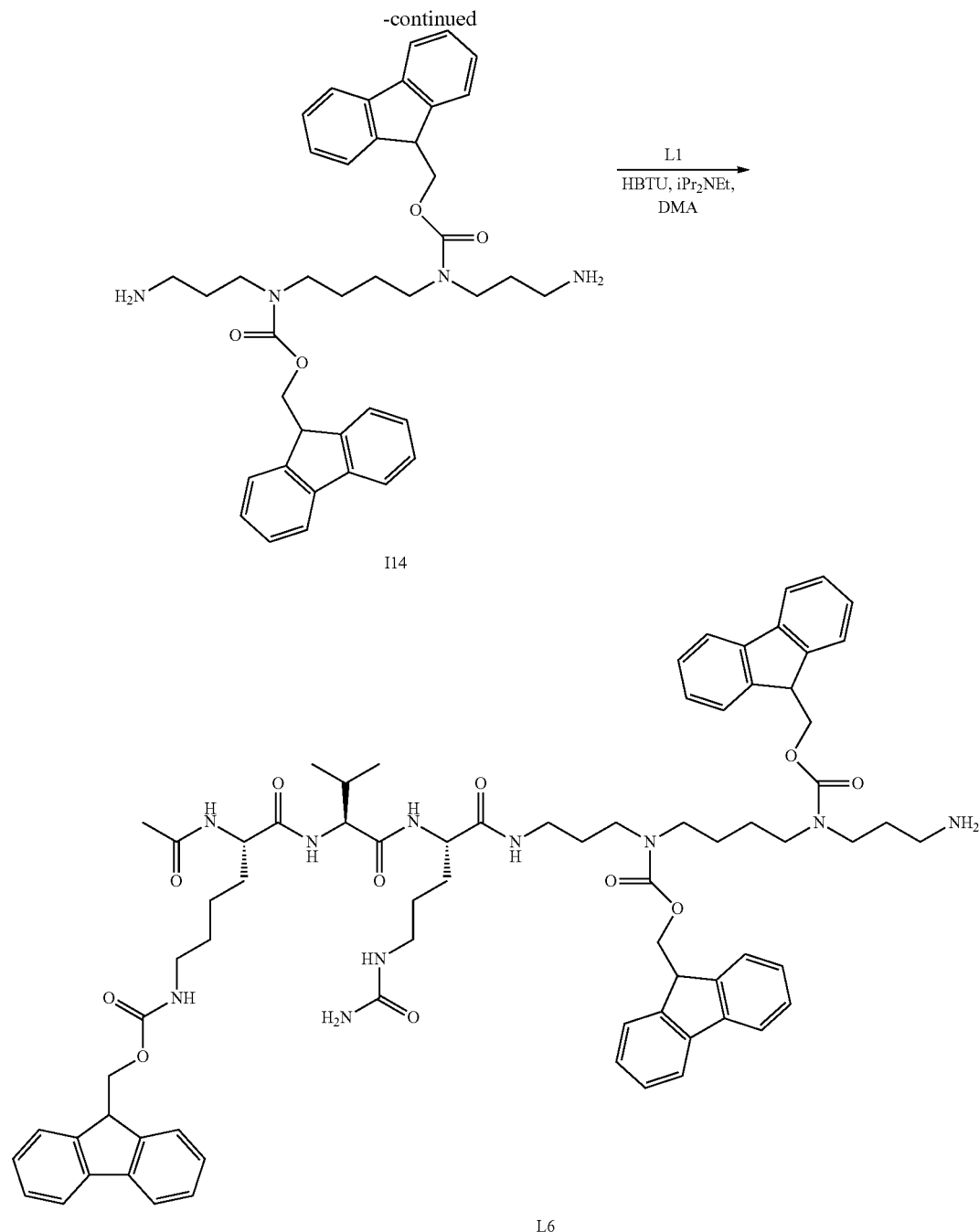

Step 1: Synthesis of bis(9H-fluoren-9-ylmethyl) butane-1,4-diylbis({3-[(tert-butoxycarbonyl)amino]propyl}carbamate)

9-Fluorenylmethoxycarbonyl chloride (62.0 mg, 0.24 mmol) was added to a stirring solution of tert-butyl (2,2-dimethyl-4-oxo-3-oxa-5,9,14-triazaheptadecan-17-yl)carbamate (72 mg, 0.11 mmol) and N,N-diisopropylethylamine (148 mg, 1.14 mmol, 199 uL) in N,N-dimethylacetamide (1000 uL). After 3 hours, the reaction mixture was purified by reverse phase HPLC (Method K). Product containing fractions were evaporated under reduced pressure to obtain the desired product (96 mg, 99%). LC-MS m/z 869.5 [M+Na$^+$]; retention time=1.23 minutes (Method 5).

Step 2: Synthesis of bis(9H-fluoren-9-ylmethyl) butane-1,4-diylbis[(3-aminopropyl)carbamate]

9 bis(9H-fluoren-9-ylmethyl) butane-1,4-diylbis({3-[(tert-butoxycarbonyl)amino]propyl}carbamate) (90 mg, 0.11 mmol) was dissolved in a stirring solution of dichloromethane (4 mL) and trifluoroacetic acid (1 mL). After 1 hour, the reaction mixture was purified by reverse phase HPLC (Method K). Product containing fractions were evaporated under reduced pressure to obtain the desired product (79 mg, 86%). LC-MS m/z 647.5 [M+H+]; retention time=0.69 minutes (Method 5).

Step 3: Synthesis of $N^2$-acetyl-$N^6$-[(9H-fluoren-9-ylmethoxy)carbonyl]-L-lysyl-L-valyl-N-(3-{(4-{(3-aminopropyl)[(9H-fluoren-9-ylmethoxy)carbonyl]amino}butyl)[(9H-fluoren-9-ylmethoxy)carbonyl]amino}propyl)-$N^5$-carbamoyl-L-ornithinamide A solution of bis(9H-fluoren-9-ylmethyl) butane-1,4-diyl-bis[(3-aminopropyl)carbamate] (37.8 mg, 0.0432 mmol) was added a pre-activated solution of $N^2$-acetyl-$N^6$-[(9H-fluoren-9-ylmethoxy)carbonyl]-L-lysyl-L-valyl-$N^5$-carbamoyl-L-ornithine (7.2 mg, 0.011 mmol), N,N,N',N'-tetramethyl-O-(1H-benzotriazol-1-yl)uronium hexafluorophosphate (4.10 mg, 0.0108 mmol) and N,N-diisopropylethylamine (5.58 mg, 0.0432 mmol, 7.51 uL) in N,N-dimethylacetamide (1.0 mL). After 1 hour, the reaction mixture was purified by reverse phase HPLC (Method L). Product containing fractions were lyophilized to obtain 9.1 mg (60%) of the desired product (L6). LC-MS m/z 1295.8 [M+H+]; retention time=0.94 minutes (Method 5).

Preparation of $N^2$-acetyl-$N^6$-[(9H-fluoren-9-yl methoxy)carbonyl]-L-lysyl-L-valyl-N-[({4-[(3-{(4-{(3-aminopropyl)[(9H-fluoren-9-ylmethoxy)carbonyl]amino}butyl)[(9H-fluoren-9-ylmethoxy)carbonyl]amino}propyl)amino]benzyl}oxy)carbonyl]-$N^5$-carbamoyl-L-ornithinamide (L7)

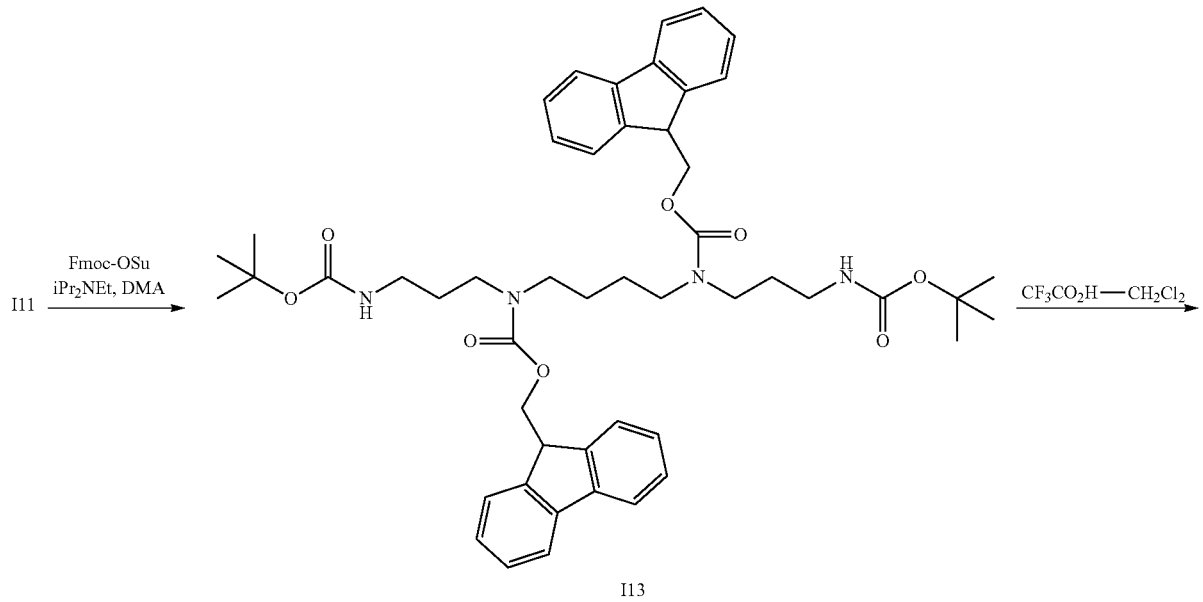

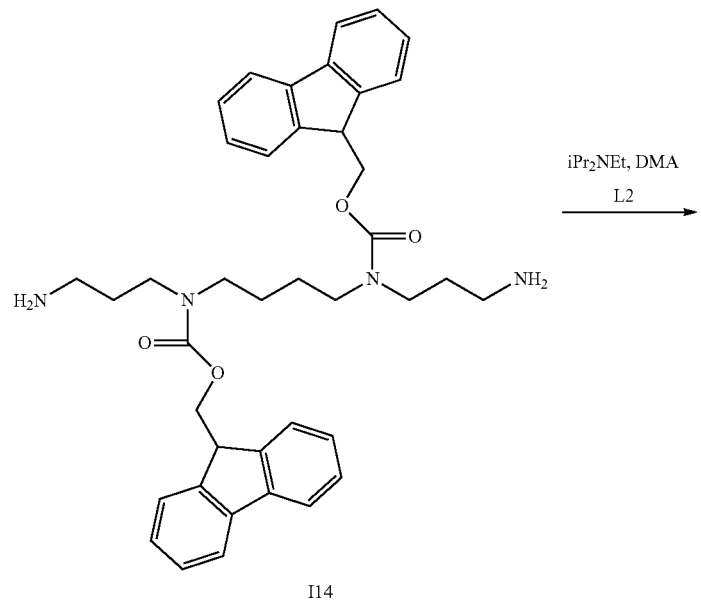

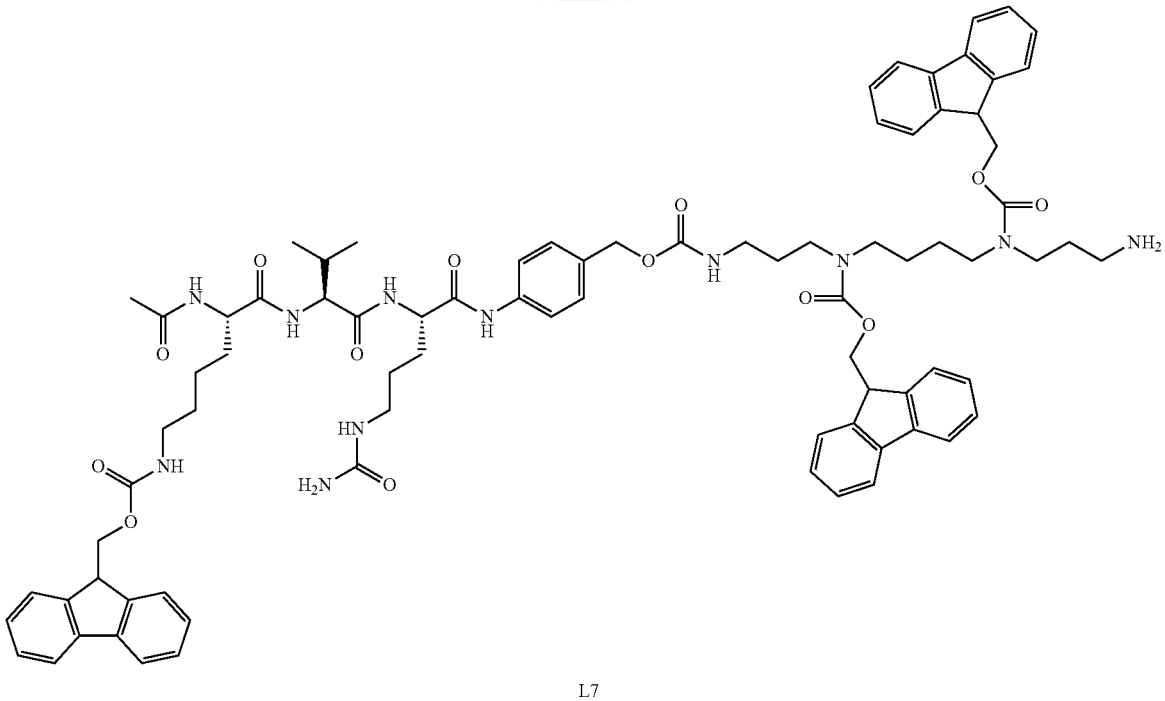 [SMILES: CC(=O)N[C@@H](CCCCNC(=O)OCC1c2ccccc2-c2ccccc21)C(=O)N[C@H](C(=O)N[C@@H](CCCNC(N)=O)C(=O)Nc1ccc(COC(=O)NCCCN(CCCCN(CCCN)C(=O)OCC2c3ccccc3-c3ccccc32)C(=O)OCC2c3ccccc3-c3ccccc32)cc1)C(C)C]

L7

Step 1: Synthesis of bis(9H-fluoren-9-ylmethyl) butane-1,4-diylbis({3-[(tert-butoxycarbonyl)amino]propyl}carbamate)

9-Fluorenylmethoxycarbonyl chloride (62.0 mg, 0.24 mmol) was added to a stirring solution of tert-butyl (2,2-dimethyl-4-oxo-3-oxa-5,9,14-triazaheptadecan-17-yl)carbamate (72 mg, 0.11 mmol) and N,N-diisopropylethylamine (148 mg, 1.14 mmol, 199 uL) in N,N-dimethylacetamide (1000 uL). After 3 hours, the reaction mixture was purified by reverse phase HPLC (Method K). Product containing fractions were evaporated under reduced pressure to obtain the desired product (96 mg, 99%). LC-MS m/z 869.5 [M+Na$^+$]; retention time=1.23 minutes (Method 5).

Step 2: Synthesis of bis(9H-fluoren-9-ylmethyl) butane-1,4-diylbis[(3-aminopropyl)carbamate]

9 bis(9H-fluoren-9-ylmethyl) butane-1,4-diylbis({3-[(tert-butoxycarbonyl)amino]propyl}carbamate) (90 mg, 0.11 mmol) was dissolved in a stirring solution of dichloromethane (4 mL) and trifluoroacetic acid (1 mL). After 1 hour, the reaction mixture was purified by reverse phase HPLC (Method K). Product containing fractions were evaporated under reduced pressure to obtain the desired product (79 mg, 86%). LC-MS m/z 647.5 [M+H$^+$]; retention time=0.69 minutes (Method 5).

Step 3: Synthesis of N$^2$-acetyl-N$^6$-[(9H-fluoren-9-ylmethoxy)carbonyl]-L-lysyl-L-valyl-N-[({4-[(3-{(4-{(3-aminopropyl)[(9H-fluoren-9-ylmethoxy)carbonyl]amino}butyl)[(9H-fluoren-9-ylmethoxy)carbonyl]amino}propyl)amino]benzyl}oxy)carbonyl]-N$^5$-carbamoyl-L-ornithinamide N$^2$-Acetyl-N$^6$-[(9H-fluoren-9-ylmethoxy)carbonyl]-L-lysyl-L-valyl-N$^5$-carbamoyl-N-[4-({[(pentafluorophenoxy)carbonyl]oxy}methyl)phenyl]-L-ornithinamide (L2, 7.5 mg, 0.0076 mmol) was added to a solution of bis(9H-fluoren-9-ylmethyl) butane-1,4-diylbis[(3-aminopropyl)carbamate] (26.7 mg, 0.0306 mmol) and N,N-diisopropylethylamine (3.95 mg, 0.0306 mmol, 5.31 uL) in N,N-dimethylacetamide (1.0 mL). After 1 hour, the reaction mixture was purified by reverse phase HPLC (Method L). Product containing fractions were lyophilized to obtain 9.0 mg (76%) of the desired product (L7). LC-MS m/z 1444.9[M+H$^+$]; retention time=0.95 minutes (Method 5)

Preparation of 2-[4-(trifluoromethyl)phenyl]propane-2-thiol (T1)

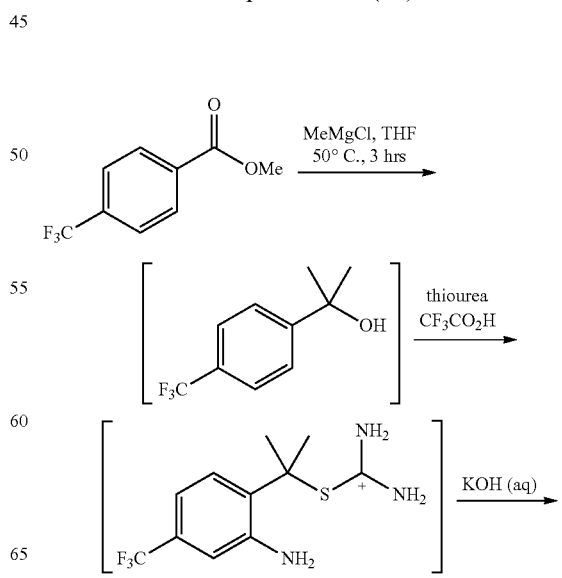

-continued

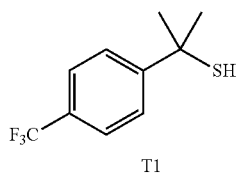

T1

A solution of methylmagnesium chloride (4.0 mL, 12.0 mmol, 3.0 M) in tetrahydrofuran was added to a solution of methyl-4-(trifluoromethyl)benzoate (612 mg, 3.00 mmol) in tetrahydrofuran (3.0 mL) and heated to 50° C. After 3 hours the reaction was quenched with 1M HCl and adjusted to pH 5, then extracted with diethyl ether (3×20 mL), dried over anhydrous sodium sulfate and concentrated in vacuo. The crude oil was then treated with a solution of thiourea (685 mg, 9.00 mmol) in trifluoroacetic acid (5 mL). After 3 hours the volatiles were stripped and the crude residue was treated with aqueous potassium hydroxide (10 mL, 3.0M). After 1 hour the solution was adjusted to pH 5, extracted with diethyl ether (2×15 mL), dried over anhydrous sodium sulfate. The resultant product (T1) was used without further purification. LC-MS m/z 221.1 [M+H$^+$]; retention time=1.16 minutes (Method 12).

The following were prepared by the procedure described above for the preparation of T1, through reaction of the appropriate ester:

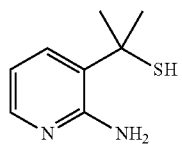

T2: 2-(2-Aminopyridin-3-yl)propane-2-thiol. LC-MS m/z 169.2 [M+H$^+$]; retention time=0.44 minutes (Method 12).

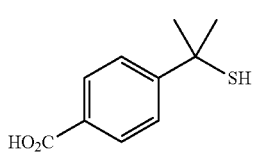

T3: 4-(2-Sulfanylpropan-2-yl)benzoic acid. LC-MS m/z 197.2 [M+H$^+$]; retention time=0.80 minutes (Method 12).

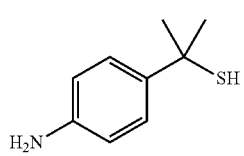

T4: 2-(4-Aminophenyl)propane-2-thiol.

Preparation of 2-(2-aminophenyl)propane-2-thiol (T5)

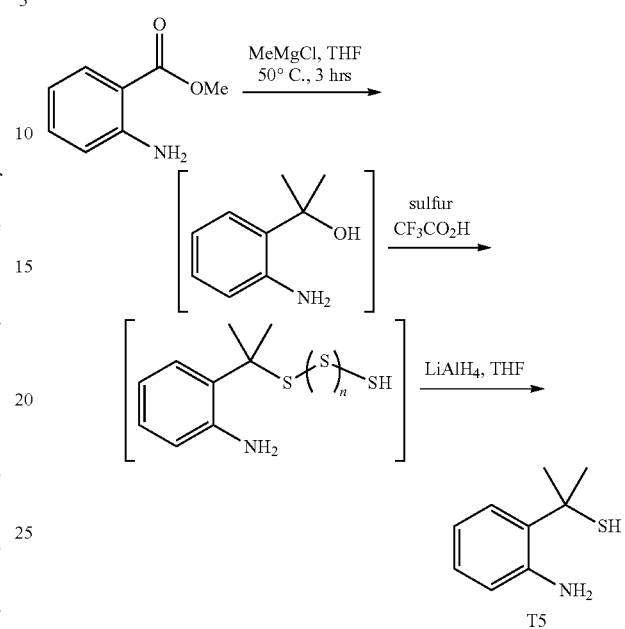

A solution of methylmagnesium chloride (4.0 mL, 12.0 mmol, 3.0 M) in tetrahydrofuran was added to a solution of methyl-2-aminobenzoate (453 mg, 3.0 mmol) in tetrahydrofuran (3.0 mL) and heated to 50 C. After 3 hours the reaction was quenched with 1M HCl and adjusted to pH 5, then extracted with diethyl ether (3×20 mL), dried over anhydrous sodium sulfate and concentrated in vacuo. The crude oil was then treated with a solution of sulfur (770 mg, 24.0 mmol) in trifluoroacetic acid (2.0 mL) with stirring. After 3 hours the volatiles were stripped and the crude residue was treated with lithium aluminum hydride (569 mg, 15.0 mmol, 15.0 mL, 1.0 M) in tetrahydrofuran. After stirring for 12 hours the solution was treated with citric acid at pH 5 and extracted with diethyl ether (3×50 mL), dried over anhydrous sodium sulfate. The resultant product (T5) was used directly without further purification. LC-MS m/z 168.2 [M+H$^+$]; retention time=0.72 minutes (Method 12).

Preparation of N-acetyl-L-valyl-N$_5$-carbamoyl-N-[4-({[(4-nitrophenoxy)carbonyl]oxy}methyl)phenyl]-L-ornithinamide

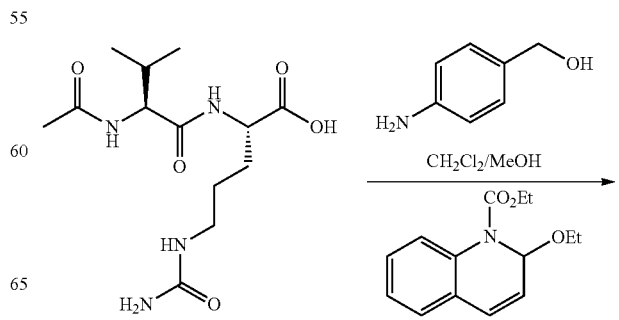

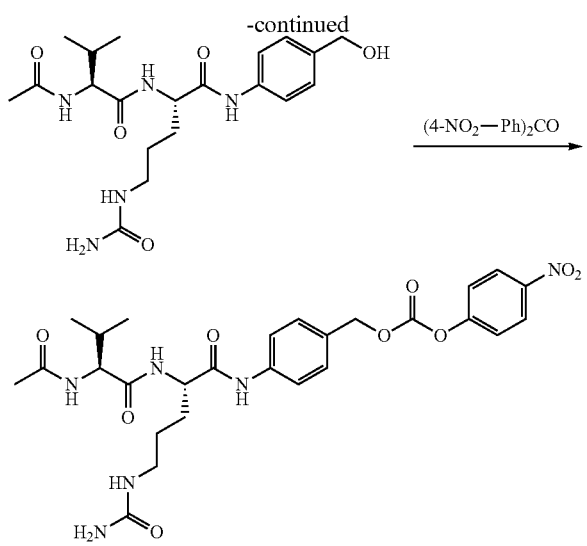

Step 1: Synthesis of N-acetyl-L-valyl-N⁵-carbamoyl-N-[4-(hydroxymethyl)phenyl]-L-ornithinamide To a solution of N-acetyl-L-valyl-N⁵-carbamoyl-L-ornithine (300.0 mg, 0.948 mmol), 4-aminobenzyl alcohol (0.140 g, 1.14 mmol) in dichloromethane (10.0 mL) and methanol (5 mL) was added 2-ethoxy-1-ethoxycarbonyl-1,2-dihydroquinoline (0.296 g, 1.14 mmol). After stirring for 24 hours, an additional portion of 2-ethoxy-1-ethoxycarbonyl-1,2-dihydroquinoline (0.148 g, 0.57 mmol). After 18 hours silica-gel was added to the mixture and the solvent was removed in vacuo; the crude mixture was purified by normal-phase chromatography dichloromethane/methanol to afford 75 mg (19%) of the product. LC-MS m/z 422.5 [M+H⁺]; retention time=0.51 minutes (Method 12).

Step 2: Synthesis of N-acetyl-L-valyl-N⁵-carbamoyl-N-[4-({[(4-nitrophenoxy)carbonyl]oxy}methyl)phenyl]-L-ornithinamide A solution of bis(4-nitrophenyl) carbonate (108 mg, 0.356 mmol), trimethylamine (54.0 mg, 0.53 mmol, 74 uL) in N,N-dimethylacetamide (3.0 mL) was added to N-acetyl-L-valyl-N⁵-carbamoyl-N-[4-(hydroxymethyl)phenyl]-L-ornithinamide (75.0 mg, 0.18 mmol). After 24 hours, silica gel was added and the mixture was concentrated in vacuo. The crude mixture was purified by normal-phase chromatography dichloromethane/methanol to afford 63 mg (63%) the product. LC-MS m/z 587.4 [M+H⁺]; retention time=0.78 minutes (Method 12).

Preparation of N-acetyl-L-valyl-N⁵-carbamoyl-N-[4-({[(3-methyl-3-sulfanylbutyl)carbamoyl]oxy}methyl)phenyl]-L-ornithinamide (T6)

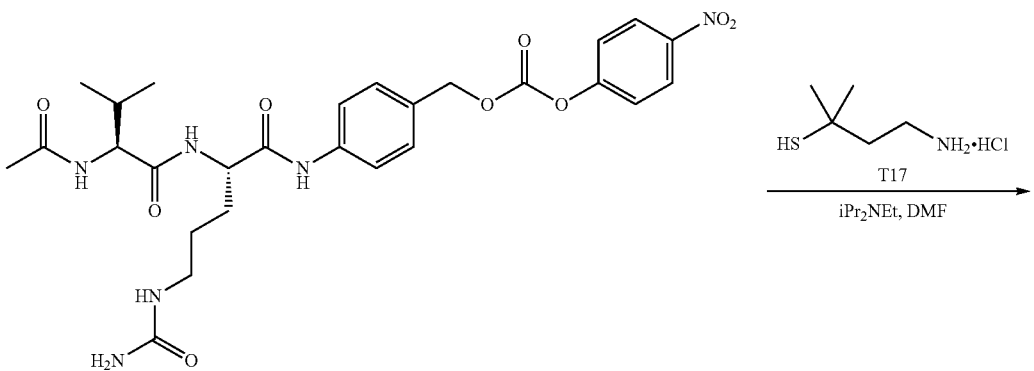

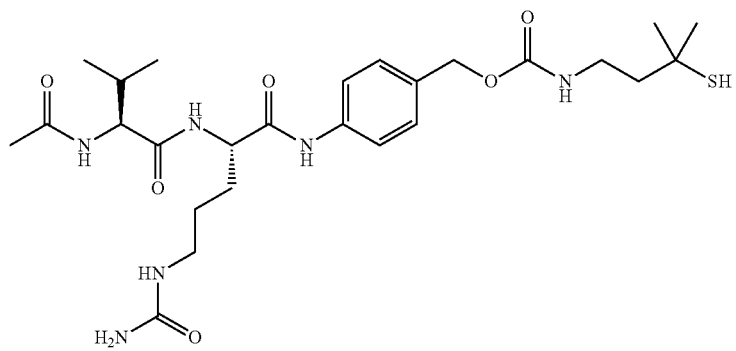

T6

Solid 4-amino-2-methylbutane-2-thiol hydrochloride (5.97 mg, 0.0384 mmol) was added to a suspension of N-acetyl-L-valyl-$N^5$-carbamoyl-$N^5$-[4-({[(4-nitrophenoxy)carbonyl]oxy}methyl)phenyl]-L-ornithinamide (15 mg, 0.026 mmol), N,N-diisopropylethylamine (9.91 mg, 0.0767 mmol, 13.3 uL) in acetonitrile (2.0 mL). After 24 hours, the reaction mixture was purified directly by reverse phase HPLC (Method L). Product containing fractions were lyophilized to provide 9.7 mg (67%) of the desired product (T6) LC-MS m/z 567.5 [M+H$^+$]; retention time=0.73 minutes (Method 12).

The following were prepared by the procedure described above for the preparation of T6, through reaction of the appropriate amino-thiol with N-acetyl-L-valyl-$N^5$-carbamoyl-N-[4-({[(4-nitrophenoxy)carbonyl]oxy}methyl) phenyl]-L-ornithinamide:

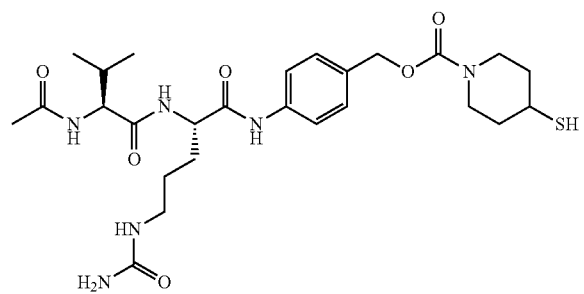 [SMILES: CC(=O)N[C@H](C(=O)N[C@@H](CCCNC(N)=O)C(=O)Nc1ccc(COC(=O)N2CCC(S)CC2)cc1)C(C)C]

T7: N-Acetyl-L-valyl-$N^5$-carbamoyl-N-[4-({[(4-sulfanylpiperidin-1-yl)carbonyl]oxy}methyl)phenyl]-L-ornithinamide. LC-MS m/z 565.7 [M+H$^+$]; retention time=0.65 minutes (Method 12).

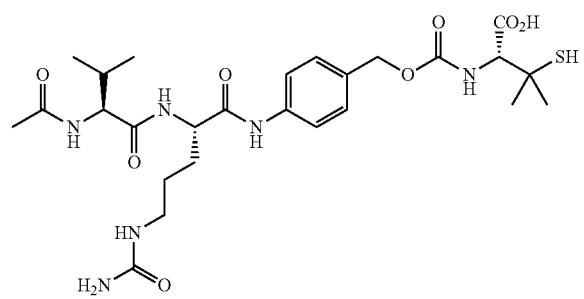 [SMILES: CC(=O)N[C@H](C(=O)N[C@@H](CCCNC(N)=O)C(=O)Nc1ccc(COC(=O)N[C@H](C(=O)O)C(C)(C)S)cc1)C(C)C]

T8: N-acetyl-L-valyl-$N^5$-carbamoyl-N-{4-[({[(1R)-1-carboxy-2-methyl-2-sulfanylpropyl]carbamoyl}oxy)methyl]phenyl}-L-ornithinamide. LC-MS m/z 597.7 [M+H$^+$]; retention time=0.66 minutes (Method 12).

Preparation of N-acetyl-L-valyl-$N^5$-carbamoyl-N-(3-methyl-3-sulfanylbutyl)-L-ornithinamide (T9)

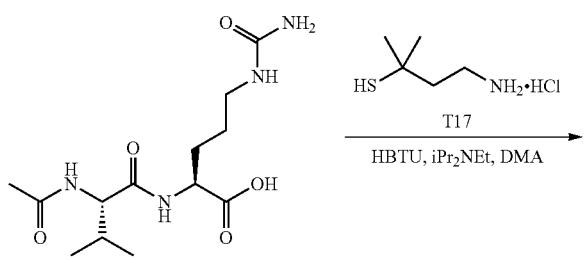

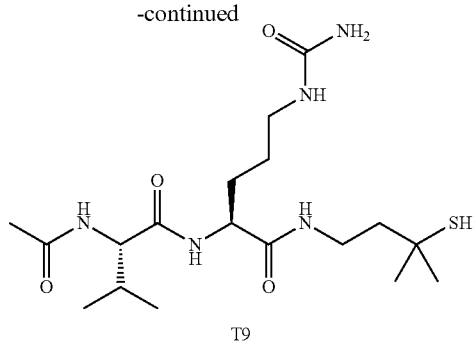

A solution of 4-amino-2-methylbutane-2-thiol hydrochloride (11.9 mg, 0.0765 mmol) was added to a pre-activated solution of N-acetyl-L-valyl-$N^5$-carbamoyl-L-ornithine (22 mg, 0.070 mmol), N,N,N',N'-tetramethyl-O-(1H-benzotriazol-1-yl)uronium hexafluorophosphate (26.4 mg, 0.0695 mmol), N,N-diisopropylethylamine (36.0 mg, 0.278 mmol, 48.4 uL) in N,N-dimethylacetamide (400 uL). After 30 minutes the reaction mixture was purified directly by reverse phase HPLC (Method L). Product containing fractions were lyophilized to provide 10.6 mg (37%) of the desired product (P9). LC-MS m/z 418.5 [M+H$^+$]; retention time=0.60 minutes (Method 12).

The following was prepared by the procedure described above for the preparation of T9, through reaction of the appropriate amino-thiol with N-acetyl-L-valyl-$N^5$-carbamoyl-L-ornithine:

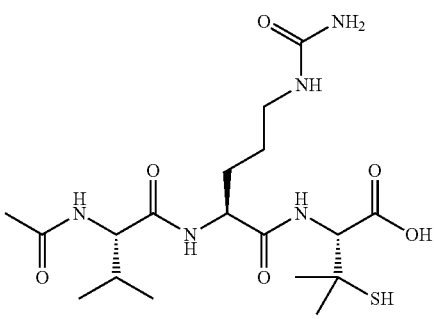 [SMILES: CC(=O)N[C@H](C(=O)N[C@@H](CCCNC(N)=O)C(=O)N[C@H](C(=O)O)C(C)(C)S)C(C)C]

T10: N-acetyl-L-valyl-$N^5$-carbamoyl-L-ornithyl-3-sulfanyl-L-valine. LC-MS m/z 448.5 [M+H$^+$]; retention time=0.56 minutes (Method 12).

Preparation of methyl 4-({[(4-nitrophenoxy)carbonyl]oxy}methyl)phenyl 2,3,4-tri-O-acetyl-D-glucopyranosiduronate

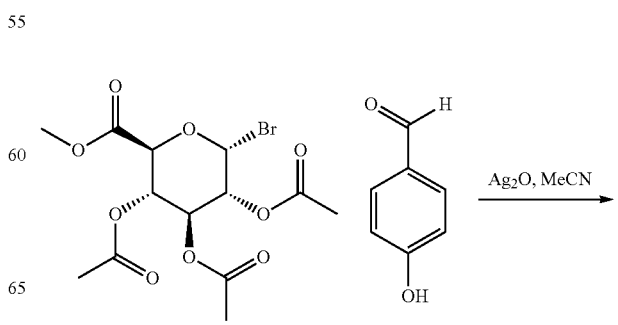

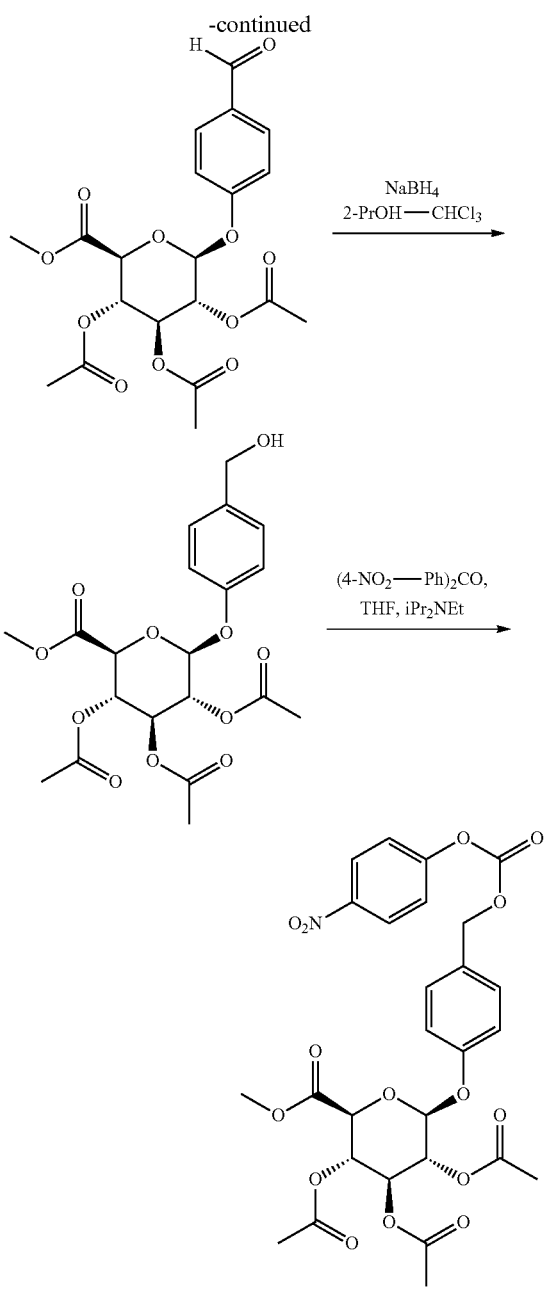

Step 1: Synthesis of 4-formylphenyl methyl 2,3,4-tri-O-acetyl-beta-D-glucopyranosiduronate To a solution of methyl 2,3,4-tri-O-acetyl-D-glucopyranosyluronate bromide (1.06 g, 2.5 mmol) in acetonitrile (40 mL) in a foil wrapped flask were added 4-hydroxybenzaldehyde (940 mg, 7.69 mmol) followed by silver oxide (2.82 g, 12.2 mmol). After stirring in the dark for four hours, the solution was filtered through celite, concentrated in vacuo. The residue was dissolved in ethyl acetate (140 ml) and dichloromethane (70 mL) and partioned with saturated sodium bicarbonate (5×100 ml), then brine (100 mL) and dried over magnesium sulfate. The volatiles were stripped to afford 1.01 g (92%) of the product. LC-MS m/z 456.3 [M+H$_2$O']; retention time=0.76 minutes (Method 12).

Step 2: Synthesis of 4-(hydroxymethyl)phenyl methyl 2,3,4-tri-O-acetyl-beta-D-glucopyranosiduronate To a solution of 4-formylphenyl methyl 2,3,4-tri-O-acetyl-beta-D-glucopyranosiduronate (1.0 g, 2.3 mmol) in chloroform (20 mL) and isopropanol (5 mL) at OC was added silica-gel (500 mg) and sodium borohydride (94.9 mg, 2.51 mmol). After 30 minutes the solution was poured into ice water, the organic layer was collected, then filtered through celite and subsequently washed with brine (20 mL), dried over magnesium sulfate and concentrated in vacuo. The residue was triturated with diethyl ether to yield 885 mg (97%) of the product. LC-MS m/z 458.3 [M+H$_2$O']; retention time=0.74 minutes (Method 12).

Step 3: Synthesis of methyl 4-({[(4-nitrophenoxy)carbonyl]oxy}methyl)phenyl 2,3,4-tri-O-acetyl-D-glucopyranosiduronate To a solution of 4-(hydroxymethyl)phenyl methyl 2,3,4-tri-O-acetyl-beta-D-glucopyranosiduronate (885.0 mg, 2.01 mmol) in tetrahydrofuran (15 mL) and N,N-diisopropylethylamine (398 mg, 3.01 mmol, 530 uL) was added bis(4-nitrophenyl) carbonate (1260 mg, 4.02 mmol). After 48 h, the reaction was concentrated in vacuo, redissolved in ethyl acetate (50 mL), washed with a solution of with 10% sodium bisulfate (4×30 mL), brine (30 mL) and then dried over magnesium sulfate and concentrated in vacuo. The residue was purified by silica gel chromatography ethyl acetate/heptane eluent to afford 1186 mg (98%) of the desired product. LC-MS m/z 623.4 [M+H$_2$O']; retention time=0.94 minutes (Method 12).

Preparation of 4-({[(3-methyl-3-sulfanylbutyl)carbamoyl]oxy}methyl)phenyl beta-D-glucopyranosiduronic Acid (T11)

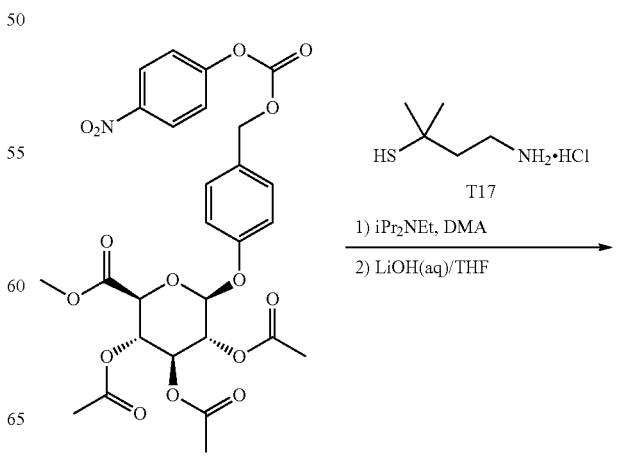

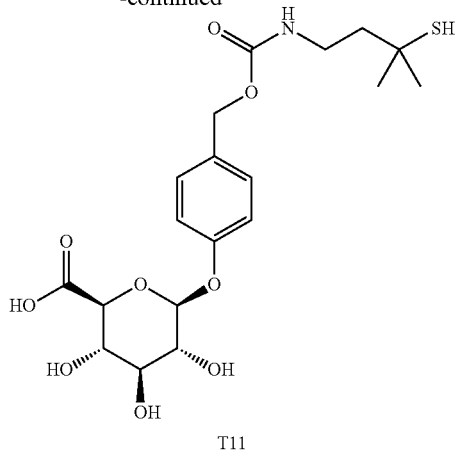

T11

To a solution of methyl 4-({[(4-nitrophenoxy)carbonyl] oxy}methyl)phenyl 2,3,4-tri-O-acetyl-D-glucopyranosiduronate (188 mg, 0.310 mmol) and N,N-diisopropylethylamine (81.9 mg, 0.621 mmol, 109 uL) in tetrahydrofuran (2.0 mL) and N,N-dimethylacetamide (1.0 mL) was added 4-amino-2-methylbutane-2-thiol hydrochloride (58.0 mg, 0.373 mmol). After heating to 60 C for 18 hours, the contents were extracted with 5% citric acid (2×25 mL) and diethyl ether and concentrated in vacuo. The residue was dissolved in tetrahydrofuran (5 mL) cooled to OC and lithium hydroxide (59.5 mg, 2.48 mmol, 2.48 mL, 1.0 M) was added. After 1 hour at OC the reaction was complete and acetic acid (150 uL, 8equiv) was added, the contents were concentrated and purified by reverse phase HPLC to afford 40.4 mg (29%) of the desired product (T11). LC-MS m/z 444.4 [M−H—]; retention time=0.65 minutes (Method 12).

The following was prepared by the procedure described above for the preparation of T11, through reaction of the appropriate amino-thiol with methyl 4-({[(4-nitrophenoxy) carbonyl]oxy}methyl) phenyl 2,3,4-tri-O-acetyl-D-glucopyranosiduronate:

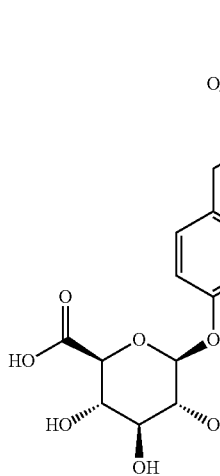

T12: 4-({[(4-sulfanylpiperidin-1-yl)carbonyl] oxy}methyl)phenyl beta-D-glucopyranosiduronic acid. LC-MS m/z 442.4 [M−H]; retention time=0.64 minutes (Method 12).

Preparation of (1-sulfanylpropyl)phosphonic Acid (T13)

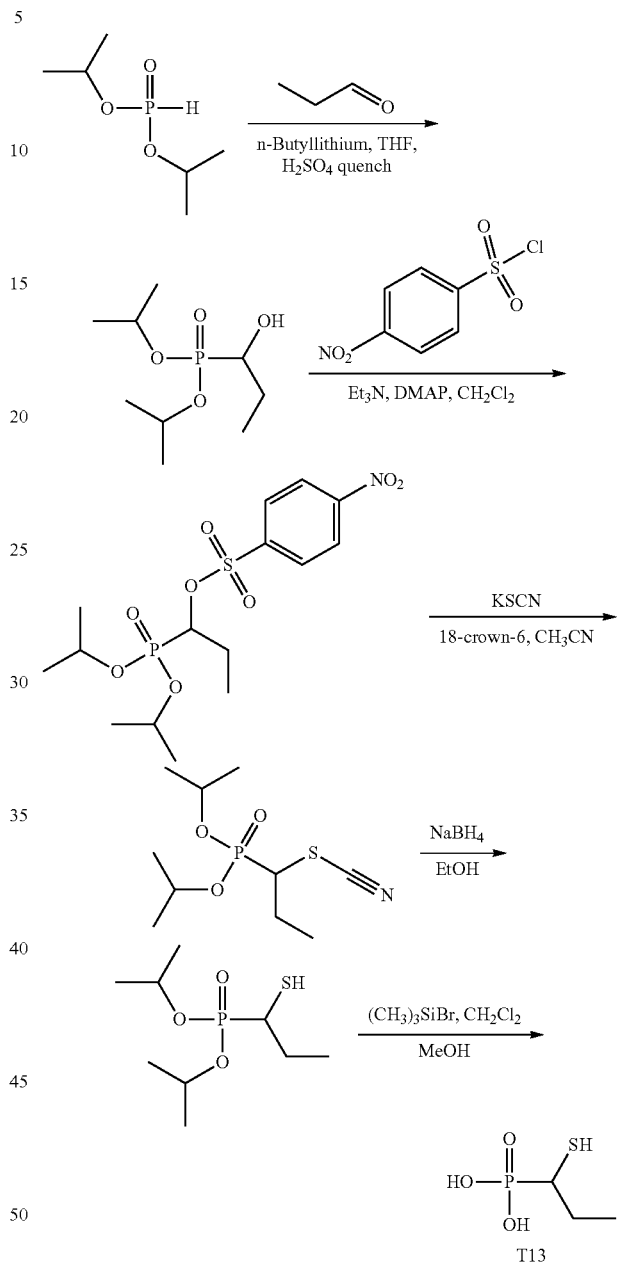

Step 1: Synthesis of dipropan-2-yl (1-hydroxypropyl)phosphonate n-Butyllithium solution in hexanes (2.5 M, 2.89 mL, 7.22 mmol) was added drop wise over 5 minutes to a stirred solution of dipropan-2-yl phosphonate (6.0 g, 36.11 mmol) in dry tetrahydrofuran (60 mL) at −72° C. under a nitrogen atmosphere. After 30 minutes, a solution of propanal (2.88 mL, 39.7 mmol) in tetrahydrofuran (10 mL) was added to the reaction mixture over 10 minutes. After one hour, concentrated sulfuric acid (779 mg, 7.94 mmol) was added drop-wise to the reaction mixture, and the mixture was allowed to warm to ambient temperature over 10 minutes.

The reaction mixture was concentrated, and the residue was poured into water (100 mL). The mixture was extracted with ethyl acetate (3×100 mL). The combined extracts were washed with brine, dried over anhydrous sodium sulfate and concentrated to give 7 g of product, which was used in the next step without further purification.

Step 2: Synthesis of dipropan-2-yl (1-hydroxypropyl)phosphonate

N,N-dimethylpyridin-4-amine (46.3 mg, 0.379 mmol) was added to a stirred solution of dipropan-2-yl (1-hydroxypropyl)phosphonate (850 mg, 3.79 mmol) in dry dichloromethane (17 mL) and triethylamine (1.32 mL, 9.48 mmol). The resulting mixture was cooled to 0° C. and 4-nitrophenylsulfonyl chloride (1.01 g, 4.55 mmol) was added. The reaction mixture was allowed to warm to ambient temperature. After 18 hours, the mixture was diluted with dichloromethane (50 mL) and washed with brine. The organic layer was dried over anhydrous sodium sulfate and concentrated. The residue (1.7 g) was purified by column chromatography on silica gel (ethyl acetate/petroleum ether 1:4 to 1:2) to afford 830 mg of the desired product. LC-MS m/z 432.0 [M+Na$^+$]; retention time=0.854 minutes (Method 13).

Step 3: Synthesis of dipropan-2-yl (1-thiocyanatopropyl)phosphonate

A mixture of dipropan-2-yl (1-hydroxypropyl)phosphonate (7.7 g, 18.81 mmol), potassium thiocyanate (7.31 g, 75.2 mmol) and 18-crown-6 (1.99 g, 7.52 mmol) in acetonitrile (200 mL) was heated to reflux for 26 hours. The reaction mixture was allowed to cool to ambient temperature and was filtered. The residue was washed with acetonitrile and then dissolved in ethyl acetate (200 mL). The solution was washed with water (3×100 mL) and brine. The organic layer was dried over anhydrous sodium sulfate and was concentrated in vacuo to give 4.57 g of the crude product, which was used in the next step without further purification.

Step 4: Synthesis of dipropan-2-yl (1-sulfanylpropyl)phosphonate

Sodium borohydride (2.71 g, 71.6 mmol) was added to a stirred solution of dipropan-2-yl (1-thiocyanatopropyl)phosphonate (3.6 g, 14.33 mmol) in ethanol (95%, 80 mL) at 5° C. The reaction mixture was allowed to warm to ambient temperature. After 72 hours, the mixture was diluted with water (100 mL), cooled to 5° C., and excess base was quenched with aqueous hydrochloric acid solution (4M, 40 mL). The reaction mixture was extracted with ethyl acetate (3×100 mL). The combined organic extracts were washed with brine, dried over anhydrous sodium sulfate and concentrated in vacuo. The residue was purified by column chromatography on silica gel (ethyl acetate/petroleum ether 1:4 to 1:2) to afford 3.0 g of the desired product.

Step 5: Synthesis of (1-sulfanylpropyl)phosphonic Acid

Bromo(trimethyl)silane (11.5 mL, 87.4 mmol) was added to a stirred solution of dipropan-2-yl (1-sulfanylpropyl) phosphonate (300 mg, 12.5 mmol) in anhydrous dichloromethane (45 mL) at 0° C. The reaction mixture was allowed to warm to ambient temperature. After 20 hours, the reaction mixture was concentrated in vacuo. The residue was dissolved in dichloromethane/methanol (45 mL/15 mL) and stirred for 2 hours. The reaction mixture was concentrated in vacuo to afford 1.94 g of the desired product (T13). LC-MS m/z 157.0 [M+H$^+$](Method 14); HPLC retention time=4.30 minutes (Method 15).

The following was prepared using the procedure described above for the preparation of T13, through reaction of the appropriate aldehyde with dipropan-2-yl phosphonate:

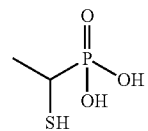

(1-sulfanylethyl)phosphonic acid (T14)
LC-MS m/z 143.0 [M+$^H$] (Method 14); HPLC retention time=4.64 minutes (Method 16).

Preparation of N,N,3-trimethyl-3-sulfanylbutanamide (T15)

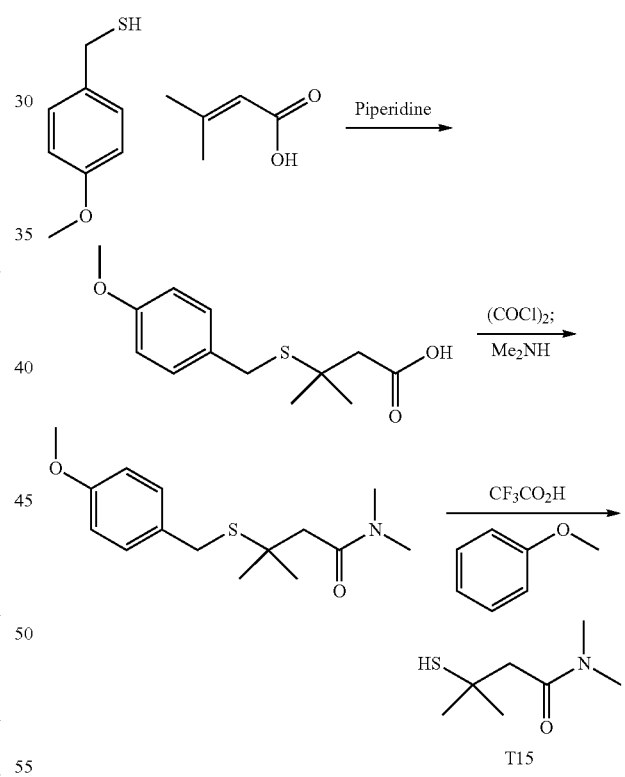

Step 1: Synthesis of 3-[(4-methoxybenzyl)sulfanyl]-3-methylbutanoic Acid

3-Methylbut-2-enoic acid (179 g, 1.78 mol) was added to piperidine (276 g, 3.24 mol), followed by (4-methoxyphenyl)methanethiol (250 g, 1.62 mol) while maintaining the temperature at 35° C. The reaction mixture was heated to 80° C. After 20 hours, t-butyl methyl ether (1.0 L) was added to the mixture, and the reaction mixture was filtered. The residue was partitioned between a biphasic mixture of ethyl acetate (1.5 L) and aqueous hydrochloric acid (1.0 L, 3 M). The organic phase was washed with brine, dried over anhydrous sodium sulfate and concentrated in vacuo to afford 338 g of the product, which was used directly in the next step without purification. LC-MS m/z 275.9 [M+Na⁺]; retention time=0.783 minutes (Method 13).

Step 2: Synthesis of 3-[(4-methoxybenzyl)sulfanyl]-N,N,3-trimethylbutanamide

A few drops of N,N-dimethylformamide were added to a solution of 3-[(4-methoxybenzyl)sulfanyl]-3-methylbutanoic acid (3.5 g, 13.76 mmol) in dichloromethane (40 mL). The solution was cooled to 5° C. and oxalyl chloride (2620 mg, 20.6 mmol) was added to the reaction mixture. After 3 hours, the reaction mixture was concentrated to dryness to give the crude acid chloride (4.3 g). A solution of N,N-dimethylamine in tetrahydrofuran (2M, 20 mL, 40 mmol) was added to a solution of the acid chloride (2.3 g, 8.431 mmol) in tetrahydrofuran (10 mL) at 5° C. After 3 hours, ethyl acetate (60 mL) was added to the reaction mixture, the organic layer was separated and concentrated. The resulting residue was purified by silica gel column chromatography (dichloromethane/methanol 20/1) to give 1.55 g of the desired product as a white solid. LC-MS m/z 303.9 [M+Na⁺]; retention time=0.777 minutes (Method 13).

Step 3: Synthesis of N,N,3-trimethyl-3-sulfanylbutanamide

Trifluoroacetic acid (7.5 mL) was added to a solution of 3-[(4-methoxybenzyl)sulfanyl]-N,N,3-trimethylbutanamide (1.5 g, 5.33 mmol) in methoxybenzene (3 mL). The reaction was stirred at 50° C. under a nitrogen atmosphere. After 20 hours, the reaction was concentrated, and the residue was purified by silica gel column chromatography (petroleum ether/ethyl acetate 1:0 to 1:1) to afford 310 mg of the desired product (T15). LC-MS m/z 162.1 [M+H] (Method 14); GC retention time=10.2 minutes (Method 17).

The following was prepared using the procedure described above for the preparation of T15, through reaction of ammonium hydroxide with 3-[(4-methoxybenzyl)sulfanyl]-3-methylbutanoic acid:

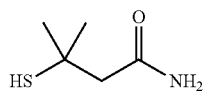

3-methyl-3-sulfanylbutanamide (T16) LC-MS m/z 134.1 [M+H⁺] (Method 14); GC retention time=9.66 minutes (Method 17).

Preparation of 4-amino-2-methylbutane-2-thiol (T17)

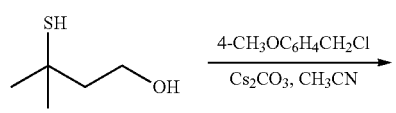

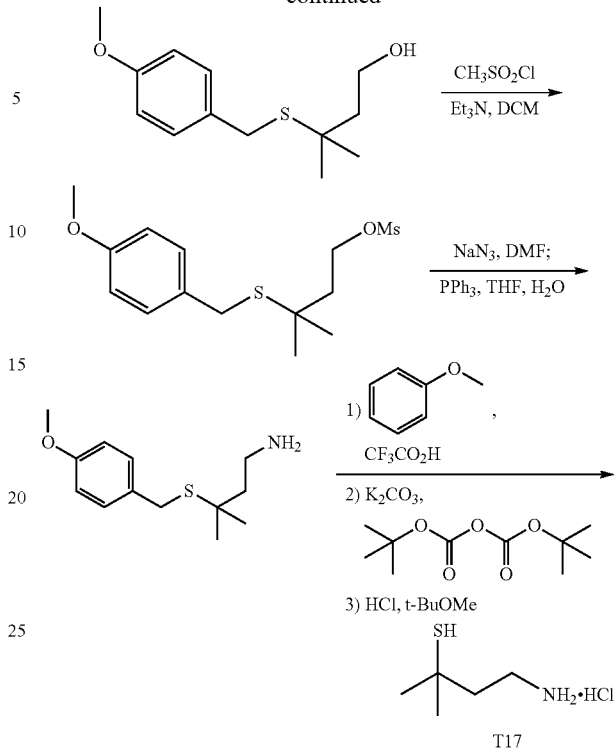

Step 1: Synthesis of 3-[(4-methoxybenzyl)sulfanyl]-3-methylbutan-1-ol 1-(Chloromethyl)-4-methoxybenzene (71.8 g, 0.458 mol) was added to a stirred mixture of 3-methyl-3-sulfanylbutan-1-ol (54 g, 0.449 mol) and cesium carbonate (146 g, 0.449 mol) in acetonitrile (500 mL) at 10° C. After 2 hours, the mixture was filtered and the filter cake was washed with dichloromethane (200 mL). The residue was dissolved in ethyl acetate (600 mL), and the solution was washed with aqueous potassium hydroxide (2M, 2×250 mL), brine (250 mL), dried over anhydrous sodium sulfate and concentrated in vacuo to give 103 g of the desired crude product, which was used directly in the next step without purification.

Step 2: Synthesis of 3-[(4-methoxybenzyl)sulfanyl]-3-methylbutyl methanesulfonate Methanesulfonyl chloride (54 g, 0.47 mol) was added drop-wise to a solution of 3-[(4-methoxybenzyl)sulfanyl]-3-methylbutan-1-ol (103 g, 0.478 mol) and triethylamine (65 g, 0.64 mol) in dry dichloromethane (700 mL) at 10° C. under an atmosphere of nitrogen. After an hour, the reaction mixture was washed with water (250 mL), aqueous saturated sodium bicarbonate and brine. The organic phase was dried over anhydrous sodium sulfate and concentrated in vacuo to afford 135 g of the desired product, which was used directly in the next step without further purification.

Step 3: Synthesis of 3-[(4-methoxybenzyl)sulfanyl]-3-methylbutan-1-amine

Sodium azide (28.1 g, 0.432 mol) was added portion-wise to a stirred solution of 3-[(4-methoxybenzyl)sulfanyl]-3-methylbutyl methanesulfonate (135 g, 423 mmol) in N,N- dimethylformamide (600 mL). The reaction mixture was heated to 50° C. After 18 hours, the mixture was poured into water (300 mL) and extracted with ethyl acetate/hexane (1:13×500 mL). The combined extracts were washed with water (3×500 mL), brine (200 mL), dried over anhydrous sodium sulfate, and concentrated in vacuo to give the crude azide as a yellow oil. Triphenylphosphine (221 g, 0.844 mol) was added to a solution of this crude azide in water/tetrahydrofuran (200 mL/1400 mL). The reaction mixture was heated to 30° C. After 20 hours, the mixture was concentrated, and the residue was purified by column chromatography on silica gel (ethyl acetate/petroleum ether 2:1, then methanol/dichloromethane 1:8) to give 84 g of the desired product as a yellow oil. LC-MS m/z 239.9 [M+Na$^+$]; retention time=0.669 minutes (Method 13).

Step 4: Synthesis of
4-amino-2-methylbutane-2-thiol

Trifluoroacetic acid (400 mL) was added to a solution of 3-[(4-methoxybenzyl)sulfanyl]-3-methylbutan-1-amine (84 g, 304 mmol) in methoxybenzene (160 mL). The reaction mixture was heated to 50° C. After 20 hours, the mixture was concentrated in vacuo. The residue was dissolved in water (600 mL) and extracted with petroleum ether (300 mL). The aqueous layer was diluted with methanol (400 mL). Potassium carbonate (84.1 g, 609 mmol) was added followed by di-tert-butyl dicarbonate (73.1 g, 335 mmol) at 10° C. After 1 hour, the reaction mixture was filtered, and the filtrate was extracted with ethyl acetate (3×300 mL). The combined organic extracts were washed with brine, dried over anhydrous sodium sulfate and concentrated in vacuo. The residue was purified by column chromatography on silica gel (ethyl acetate/petroleum ether 1:20 to 1:10) to give 59 g of the crude Boc-protected amine. A solution of hydrochloric acid in ethyl acetate (4 M, 500 mL) was added to a solution of this Boc-protected amine (59 g, 268 mmol) in anhydrous tert-butyl methyl ether (300 mL) at 10° C. The reaction mixture was allowed to warm to ambient temperature. After 3 hours, the mixture was filtered and the filter cake was washed with ethyl acetate/tert-butyl methyl ether (1:1, 200 mL) to afford 32.4 g of the desired product (T17) as a white solid (as the hydrochloride salt). LC-MS m/z 120.1 [M+H$^+$] (Method 14); HPLC retention time=5.22 minutes (Method 15).

Preparation of
N-(3-methyl-3-sulfanylbutyl)acetamide (T18)

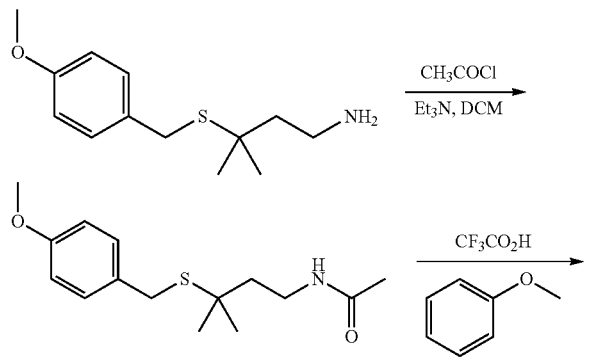

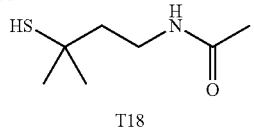

T18

Step 1: Synthesis of N-{3-[(4-methoxybenzyl)sulfanyl]-3-methylbutyl}acetamide

Acetyl chloride (0.317 mL, 4.46 mmol) was added to a solution of 3-[(4-methoxybenzyl)sulfanyl]-3-methylbutan-1-amine (970 mg, 4.05 mmol) and triethylamine (0.843 mL, 6.08 mmol) in dichloromethane (20 mL) at 0° C. The reaction mixture was allowed to warm to ambient temperature. After 1 hour, the solution was washed with saturated aqueous citric acid solution (20 mL) and brine (20 mL). The organic layer was dried over anhydrous sodium sulfate and concentrated to afford 1.1 g of the crude product, which was used in the next step without further purification.

Step 2: Synthesis of
N-(3-methyl-3-sulfanylbutyl)acetamide

N-{3-[(4-methoxybenzyl)sulfanyl]-3-methylbutyl}acetamide (1 g, 4 mmol) was dissolved in methoxybenzene (3 mL), and trifluoroacetic acid (7.5 ml) was added to the solution. The reaction mixture was heated to 50° C. After 20 hours, the reaction mixture was concentrated, and the residue was purified by silica gel chromatography (dichloromethane/methanol 1:0 to 15:1) to afford 550 mg of the desired product (T18). LC-MS m/z 162.1 [M+H$^+$] (Method 14); GC retention time=11.3 minutes (Method 17).

Preparation of
N-methyl-N-(3-methyl-3-sulfanylbutyl)acetamide
(T19)

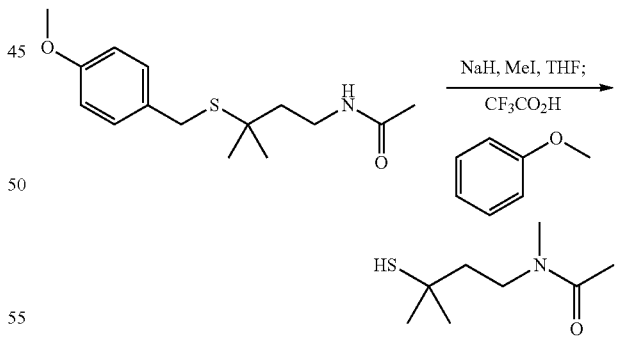

T19

Step 1: Synthesis of
N-methyl-N-(3-methyl-3-sulfanylbutyl)acetamide

A solution of N-{3-[(4-methoxybenzyl)sulfanyl]-3-methylbutyl}acetamide (500 mg, 1.78 mmol) in anhydrous tetrahydrofuran (8.88 mL) was added drop wise to a stirred suspension of sodium hydride (85.3 mg of a 60% dispersion in mineral oil) at 0° C. under a nitrogen atmosphere. After 40 minutes, iodomethane (265 mg, 1.87 mmol) was added to the reaction mixture. After 16 hours, another portion of sodium hydride (85.3 mg of a 60% dispersion in mineral oil) was added. After 24 hours, excess hydride reagent was quenched with water (20 mL) and the mixture was extracted with ethyl acetate (3×20 mL). The combined organic extracts were washed with brine, dried over anhydrous sodium sulfate and concentrated. The residue was purified by flash column chromatography on silica gel (dichloromethane/methanol 9:1) to afford the crude methylated product. This material was dissolved in methoxybenzene (3 mL), and trifluoroacetic acid (7.5 ml) was added to the reaction mixture and the reaction mixture was heated to 50° C. After 20 hours, the reaction mixture was concentrated, and the residue was purified by silica gel chromatography (dichloromethane/methanol 1:0 to 15:1) to afford 410 mg of the desired product (T19). LC-MS m/z 176.2 [M+H$^+$] (Method 14); GC retention time=11.6 minutes (Method 17).

Preparation of
3-methyl-3-(methyldisulfanyl)butanoic acid

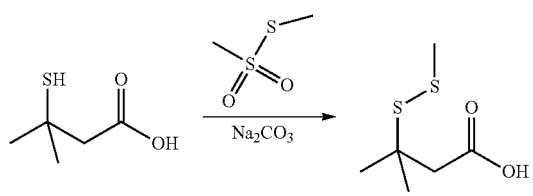

Step 1: Synthesis of
3-methyl-3-(methyldisulfanyl)butanoic acid

Sodium carbonate (1480 mg, 13.9 mmol) was added to a solution of 3-methyl-3-sulfanylbutanoic acid (1700 mg, 12.67 mmol) in water (15 mL). The reaction mixture was cooled to 5° C., and a solution of S-methyl methanesulfonothioate (1760 mg, 13.9 mmol) in ethanol (8 mL) was added under a nitrogen atmosphere. The reaction mixture was allowed to warm to ambient temperature. After 18 hours, saturated aqueous sodium bicarbonate solution (8 mL) and water (15 mL) were added to reaction mixture. The mixture was concentrated in vacuo to remove ethanol. The residual aqueous solution was acidified to pH 2 with aqueous hydrochloric acid (1 M) and was extracted with ethyl acetate (2×30 mL). The combined organic layers were dried over anhydrous sodium sulfate, filtered and concentrated. The residue was purified by silica gel chromatography (dichloromethane/methanol 1:0 to 10:1) to afford 1700 mg of the desired product. $^1$H NMR (400 MHz, CHLOROFORM-d) δ=2.73 (s, 2H), 2.47 (s, 3H), 1.50 (s, 6H).

Preparation of 4-{[(ethyl{[methyl(3-methyl-sulfanylbutanoyl)amino]methyl}carbamoyl)oxy]methyl}phenyl methyl 2,3,4-tri-O-acetyl-beta-D-glucopyranosiduronate (T20)

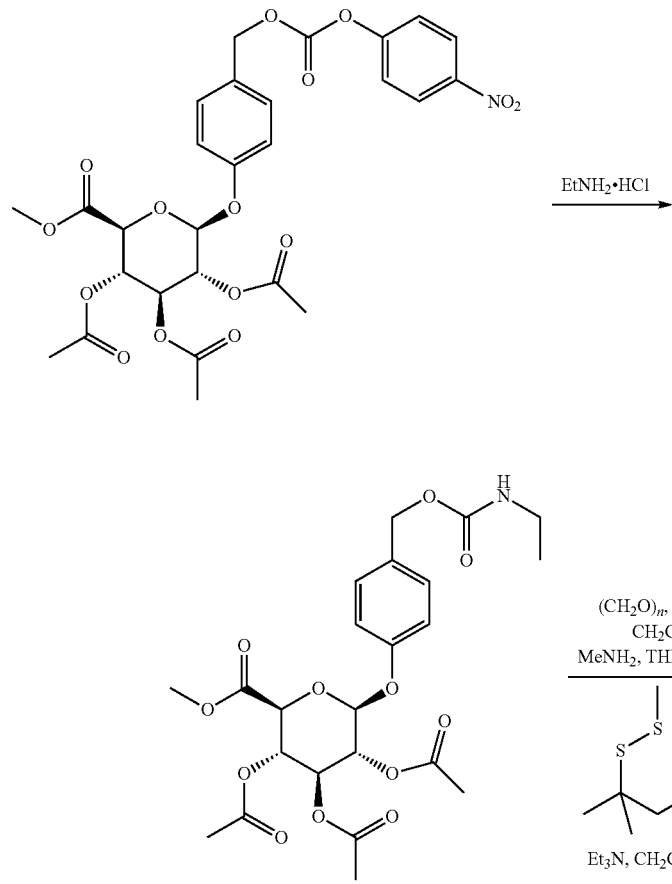

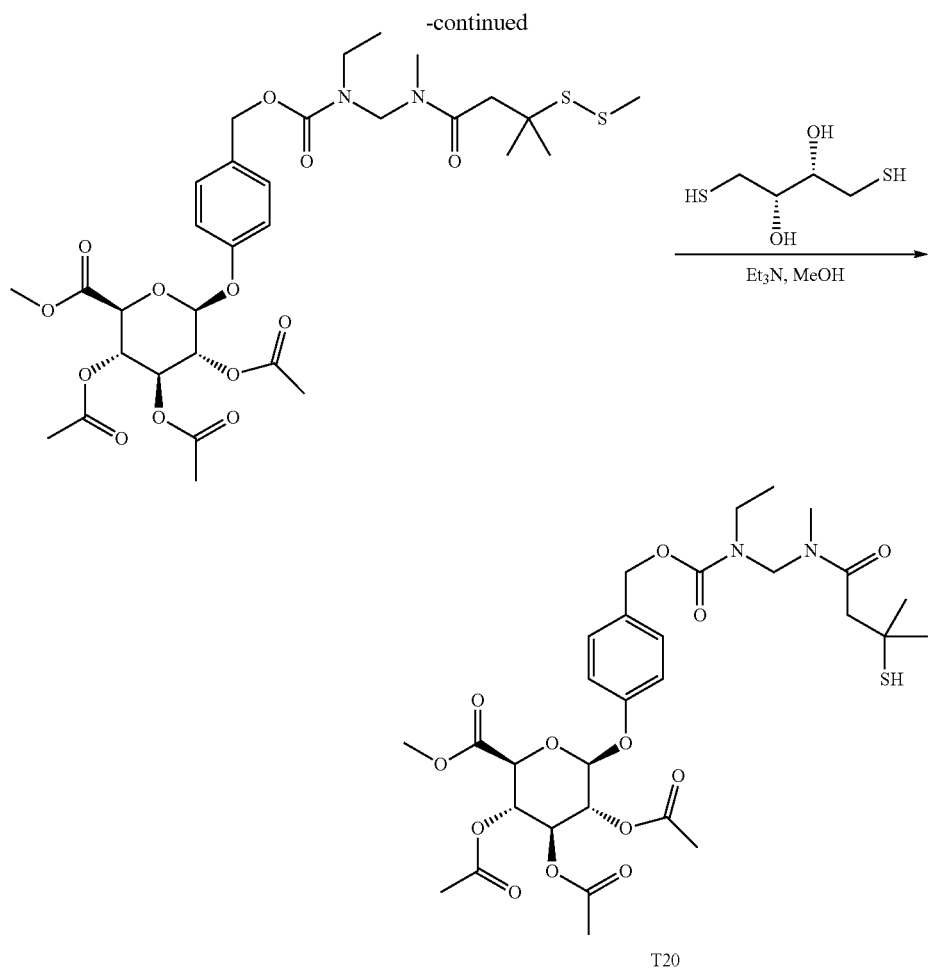

T20

Step 1: Synthesis of 4-{[(ethylcarbamoyl)oxy]methyl}phenyl methyl 2,3,4-tri-O-acetyl-beta-D-glucopyranosiduronate Ethylamine hydrochloride salt (1640 mg, 20.1 mmol) was added to neat methyl 4-({[(4-nitrophenoxy)carbonyl]oxy}methyl)phenyl 2,3,4-tri-O-acetyl-D-glucopyranosiduronate (6090 mg, 10.06 mmol) at 0-10° C. After three hours, the reaction mixture was poured into water (450 mL), and the aqueous layer was extracted with ethyl acetate (2×200 mL). The combined organic layers were washed with aqueous hydrochloric acid (1M) and brine, and dried over anhydrous sodium sulfate. The solution was concentrated, and the residue was purified by silica gel chromatography (petroleum ether/ethyl acetate 1:0 to 0:1) to afford 3.5 g of the desired product. LC-MS m/z 534.1 [M+Na$^+$]; retention time=0.781 minutes (Method 13).

Step 2: Synthesis of 4-(9-ethyl-4,4,7-trimethyl-6,10-dioxo-11-oxa-2,3-dithia-7,9-diazadodecan-12-yl)phenyl methyl 2,3,4-tri-O-acetyl-beta-D-glucopyranosiduronate Paraformaledehyde (1932 mg) was added to a solution of 4-{[(ethylcarbamoyl)oxy]methyl}phenyl methyl 2,3,4-tri-O-acetyl-beta-D-glucopyranosiduronate (1288 mg, 2.18 mmol) in dichloromethane (25 mL) at 0° C. followed by a solution of chlorotrimethylsilane (821 mg, 7.55 mmol) in dichloromethane (7.5 mL). The reaction mixture was allowed to warm to ambient temperature. After an hour, the reaction mixture was filtered. The filtrate was added dropwise to a solution of methylamine (3.90 mL, 2 M in tetrahydrofuran) in tetrahydrofuran (25 mL) at −30° C. After one hour, the reaction mixture was warmed to 0° C. and triethylamine (1.41 mL, 10.1 mmol) was added. In a separate reaction vessel, a solution of oxalyl chloride (843.7 mg, 6.51 mmol) in dichloromethane (6.5 mL) was added to a solution of 3-methyl-3-(methyldisulfanyl)butanoic acid (960 mg, 5.32 mmol) and a trace amount of dimethyl formamide (6 drops) in dichlormethane (20 mL) at 0° C. The solution was allowed to warm to ambient temperature and after one hour was concentrated. The crude acid chloride was dissolved in dichloromethane (10 mL) and was added to the reaction mixture. After 16 hours, the reaction mixture was allowed to warm ambient temperature and was purified by reverse phase HPLC (Method 0). Product containing fractions were lyophilized to obtain 347 mg of the desired product. LC-MS m/z 739.2 [M+Na$^+$]; retention time=0.896 minutes (Method 13).

Step 3: Synthesis of 4-{[(ethyl{[methyl(3-methylsulfanyl butanoyl)amino]methyl}carbamoyl)oxy]methyl}phenyl methyl 2,3,4-tri-O-acetyl-beta-D-glucopyranosiduronate (T20)

(2S,3S)-1,4-Disulfanylbutane-2,3-diol (68.8 mg, 0.447 mmol) and triethylamine (0.62 mL, 4.47 mmol) were added to a solution of 4-(9-ethyl-4,4,7-trimethyl-6,10-dioxo-11-oxa-2,3-dithia-7,9-diazadodecan-12-yl)phenyl methyl 2,3,4-tri-O-acetyl-beta-D-glucopyranosiduronate (160 mg, 0.223 mmol) in methanol (16 mL). After four hours, the reaction mixture was concentrated, and the residue was purified by reverse phase HPLC (Method P). Product containing fractions were lyophilized to obtain 40 mg of the desired product (T20). LC-MS m/z 692.8 [M+Na$^+$]; retention time=0.751 minutes (Method 13).

Preparation of Calicheamicin Payloads

Preparation of S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1 (12),5-di ene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P1)

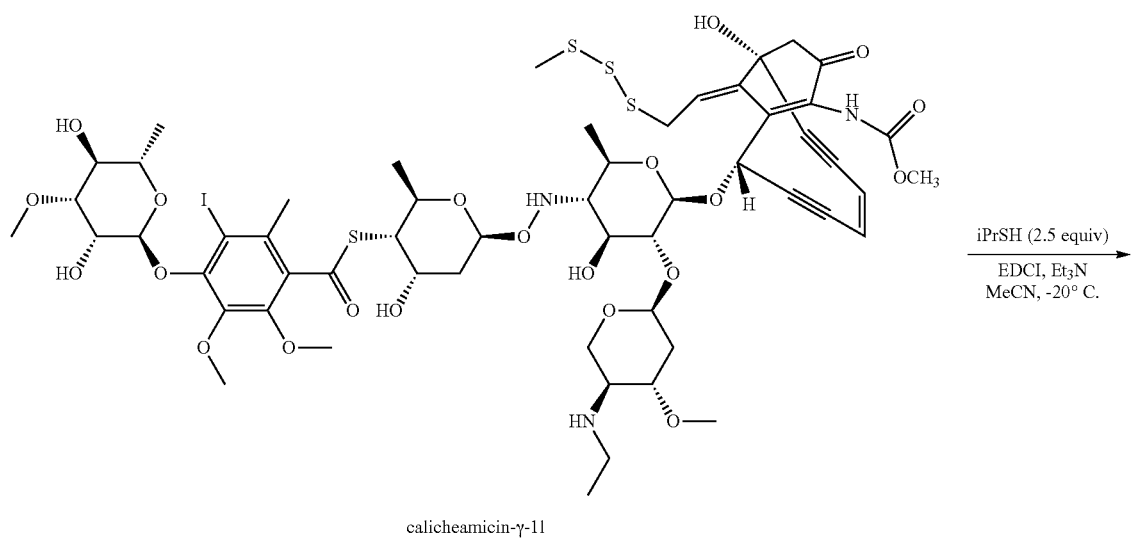

calicheamicin-γ-11

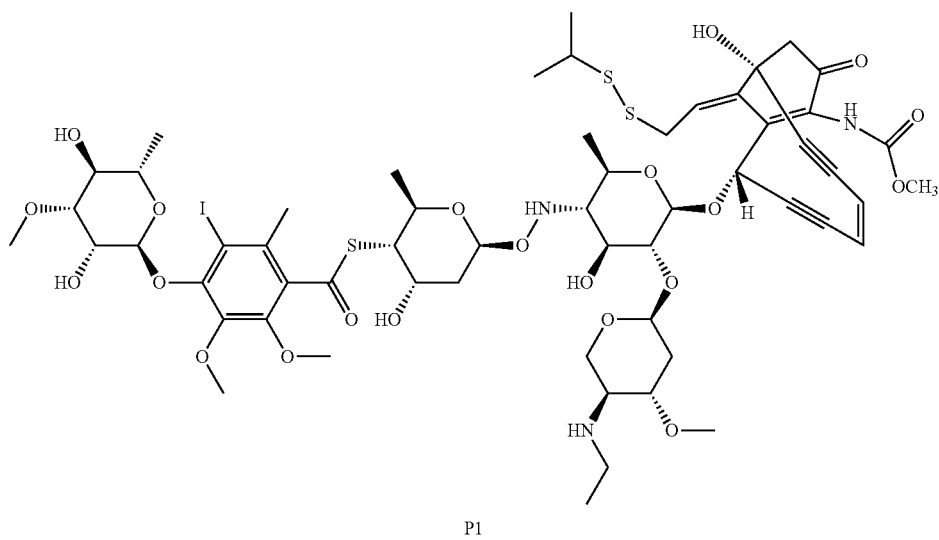

P1

Propane-2-thiol (14.6, 0.186 mmol) was added to a solution of S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,5Z, 9R, 13E)-9-hydroxy-12-[(methoxycarbonyl)amino]-13-[2-(methyltrisulfanyl)ethylidene]-11-oxobicyclo[7.3.1]trideca-1 (12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate [calicheamicin-$\gamma^1_I$] (102 mg, 0.0745 mmol), N-(3-dimethylaminopropyl)-N'-ethylcarbodiimide hydrochloride (15 mg, 0.0745 mmol) and triethylamine (52 uL, 0.373 mmol) in acetonitrile (3 mL) at −20° C. After 24 hours, the reaction mixture was purified by reverse phase HPLC (Method C). Product containing fractions were lyophilized to obtain 60 mg of the desired product (P1). LC-MS m/z 1364.5 [M+H$^+$]; retention time=3.99 minutes (Method 1).

The following were prepared by the procedure described above for the preparation of P1, through reaction of the appropriate thiol with S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,5Z,9R,13E)-9-hydroxy-12-[(methoxycarbonyl)amino]-13-[2-(methyltrisulfanyl) ethylidene]-11-oxobicyclo[7.3.1]trideca-1(12), 5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate [calicheamicin-$\gamma^1_I$]:

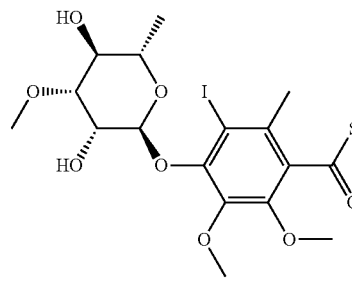
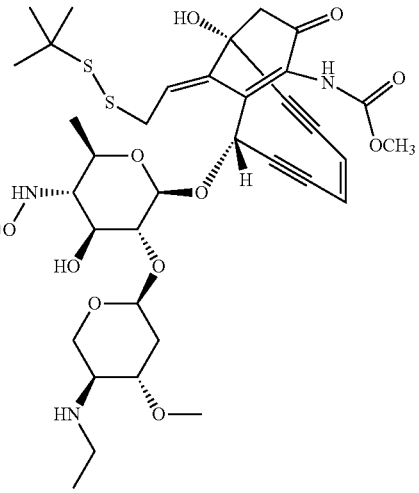

P2: S-[(2R,3S,4S,6S)-6-({[(2R,3S,4S,5R,6R)-6-{[(2S,5Z,9R,13E)-13-[2-(Tert-butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1378.2 [M+H$^+$]; retention time=3.07 minutes (Method 3).

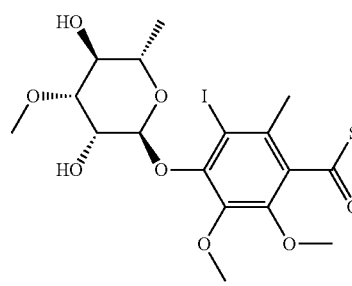
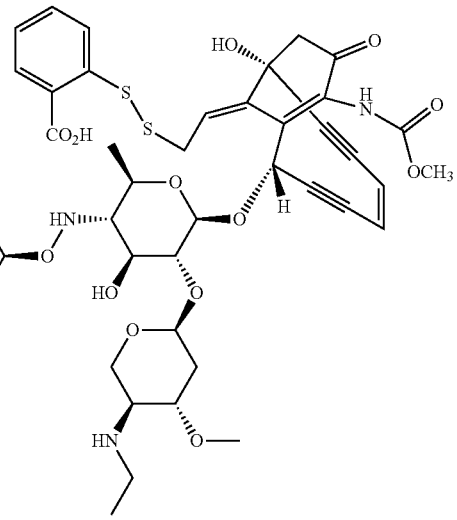

P3: 2-{[(2E)-2-{(1R,8S)-8-{[(2R,3R,4S,5S,6R)-5-[({(2S,4S,5S,6R)-5-[(4-{[(2S,3R,4R,5S,6S)-3,5-Dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}benzoic acid. LC-MS m/z 1442.3 [M+H⁺]; retention time=3.78 minutes (Method 1).

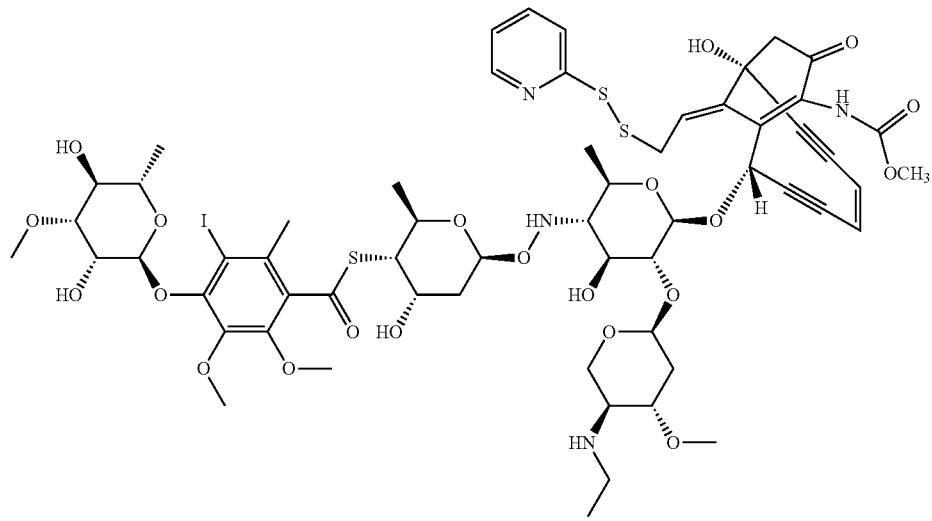 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSc3ccccn3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P4: S-[(2R,3S,4S,6S)-6-({[(2R,3S,4S,5R,6R)-5-{[(2S,4S,5S)-5-(Ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]-trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1441.6 [M+H⁺]; retention time=3.75 minutes (Method 1).

Preparation of 4-{[(2E)-2-{(1R,4Z,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methyl benzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}-4-methylpentanoic acid (P5)

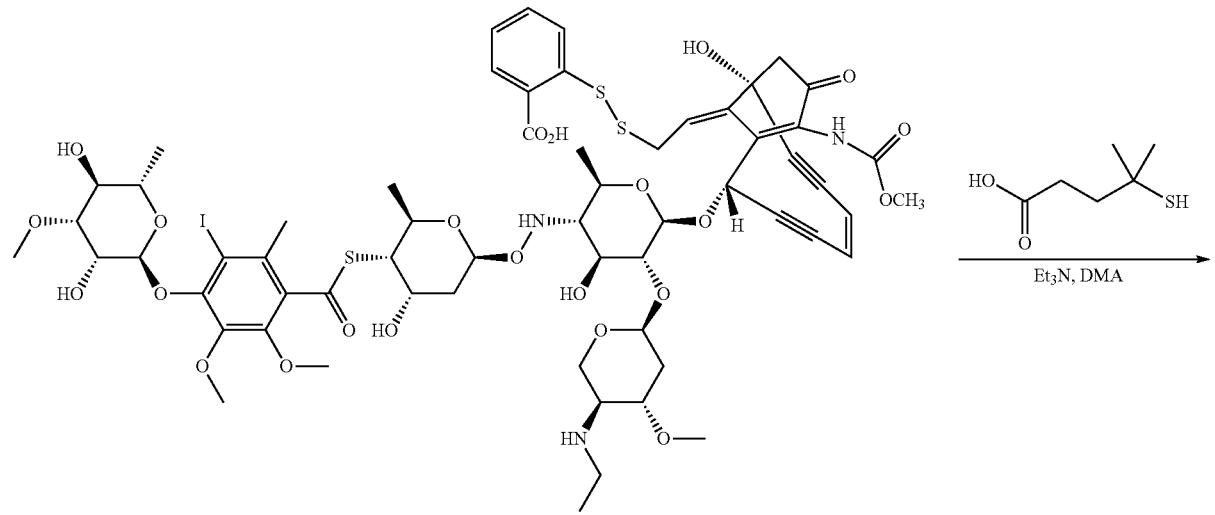

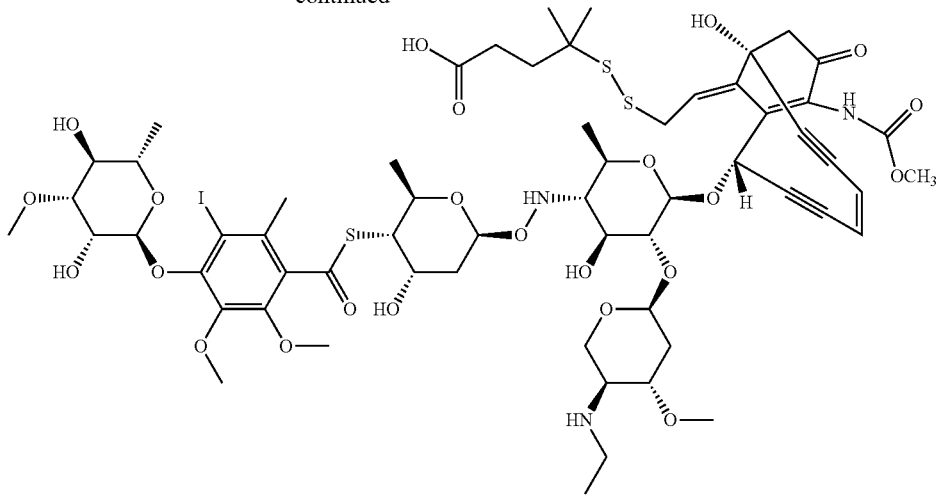

P5

4-methyl-4-sulfanylpentanoic acid (6.4 mg, 0.043 mmol) was added to a solution of 2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydr oxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}benzoic acid (6.5 mg, 0.0043 mmol) and triethylamine (3.0 µL, 2.2 mg, 0.022 mmol) in N,N-dimethylacetamide (300 uL). After 24 hours, the reaction mixture was purified by reverse phase HPLC (Method A). Product containing fractions were lyophilized to provide 6.0 mg of the desired product (P5). LC-MS m/z 1436.6 [M+H$^+$]; retention time=3.92 minutes (Method 1).

Preparation of 2-{[(2E)-2-{(1R,8S)-8-{[(2R,3R,4S,5S,6R)-5-[({(2S,4S,5S,6R)-5-[(4-{[(2S,3R,4R,5S,6S)-3,5-di hydroxy-4-methoxy-6-methyltetrahydro-2H-pyran-2-yl]oxy}-3-iodo-5,6-dimethoxy-2-methyl benzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}butanedioic acid (P6)

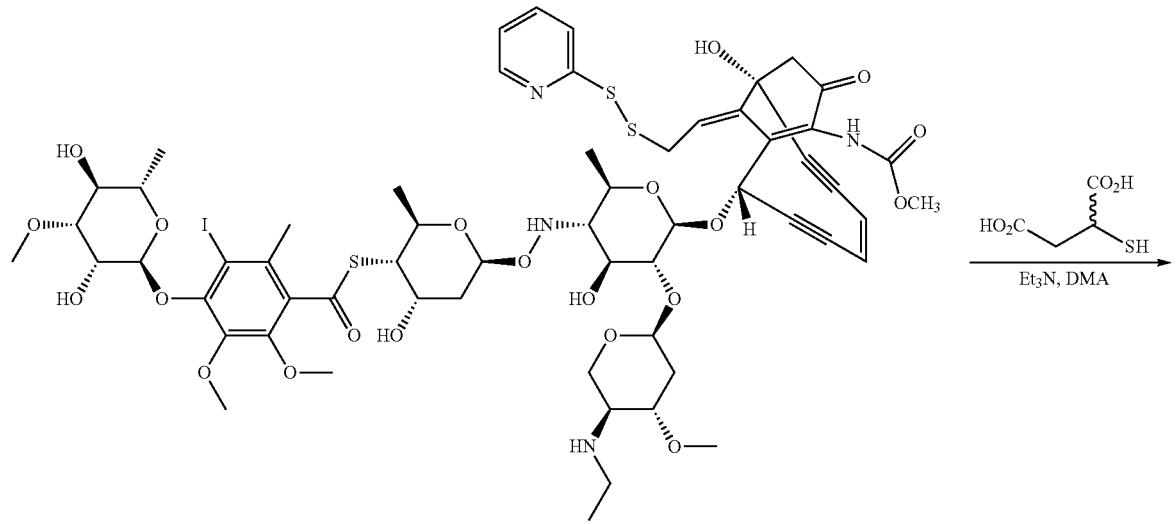

P4

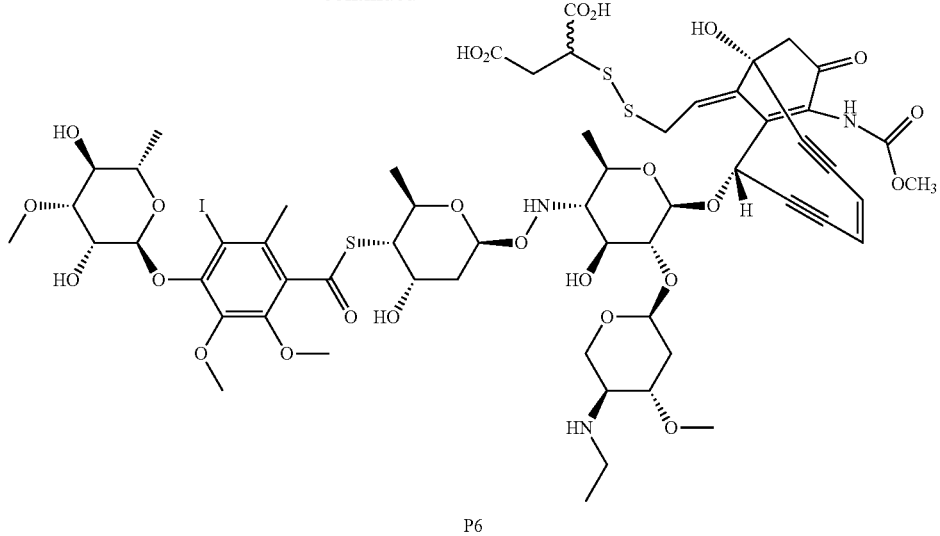

P6

2-Sulfanylbutanedioic acid (1.0 mg, 0.0063 mmol) was added to a solution of S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (6.1 mg, 0.0042 mmol) and triethylamine (1.2 µL, 0.85 mg, 0.0084 mmol) in N,N-dimethylacetamide (209 uL). After 4 hours, the reaction mixture was purified by reverse phase HPLC (Method A). Product containing fractions were lyophilized to provide 4.3 mg of the desired product (P6). LC-MS m/z 1438.5 [M+H⁺]; retention time=3.71 minutes (Method 1).

The following were prepared by an identical procedure to that described above for the preparation of P5 or P6, through reaction of the appropriate thiol and 2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}benzoic acid (P3) and/or S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]-trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P4):

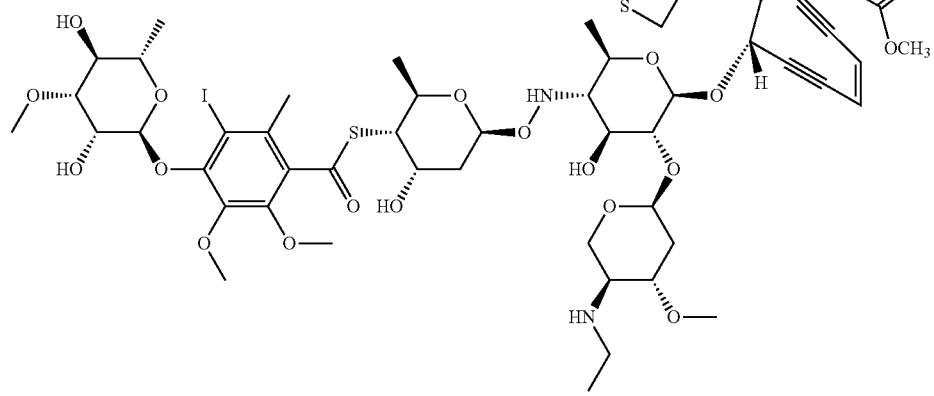

P7: S-[(2R,3S,4S,6S)-6-({[(2R,3S,4S,5R,6R)-5-{[(2S,4S,5S)-5-(Ethylamino)-4-methoxytetrahydro-2H-pyran-2-yl]oxy}-6-{[(2S,5Z,9R,13E)-13-{2-[(4-hydrazinyl-2-methyl-4-oxobutan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1436.5 [M+H$^+$]; retention time=2.26 minutes (Method 6).

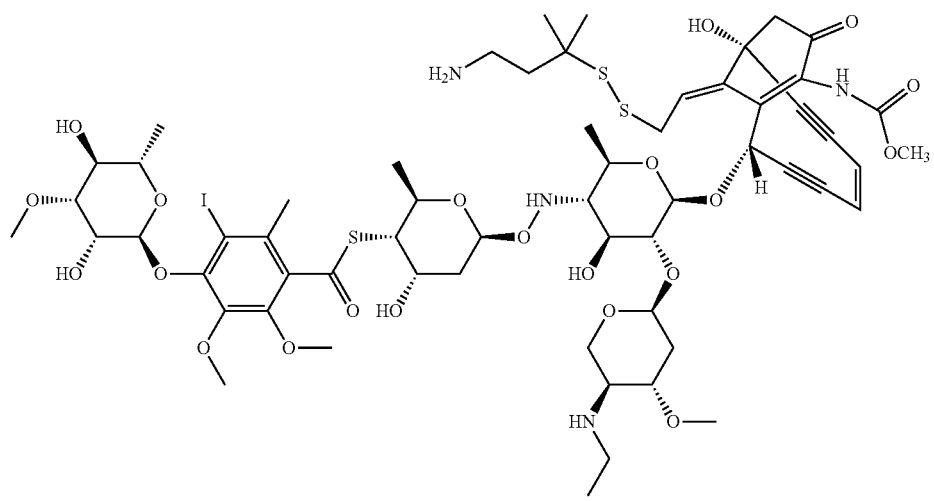 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)CCN)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P8: S-[(2R,3S,4S,6S)-6-({[(2R,3S,4S,5R,6R)-6-{[(2S,9R,13E)-13-{2-[(4-Amino-2-methylbutan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1407.4 [M+H$^+$]; retention time=1.94 minutes (Method 6).

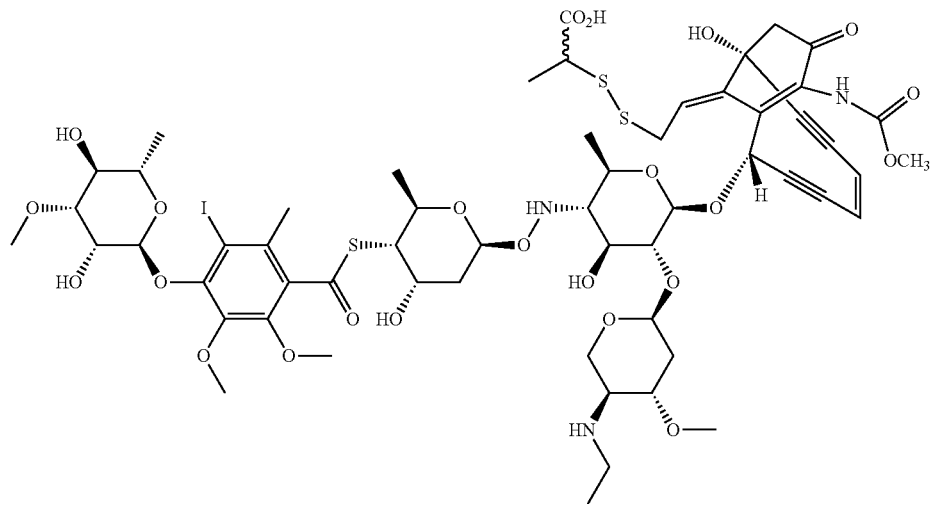 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)C(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P9: 2-{[(2E)-2-{(1R,8S)-8-{[(2R,3R,4S,5S,6R)-5-[({(2S,4S,5S,6R)-5-[(4-{[(2S,3R,4R,5S,6S)-3,5-Dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}propanoic acid. LC-MS m/z 1394.5 [M+H$^+$]; retention time=3.55 minutes (Method 2).

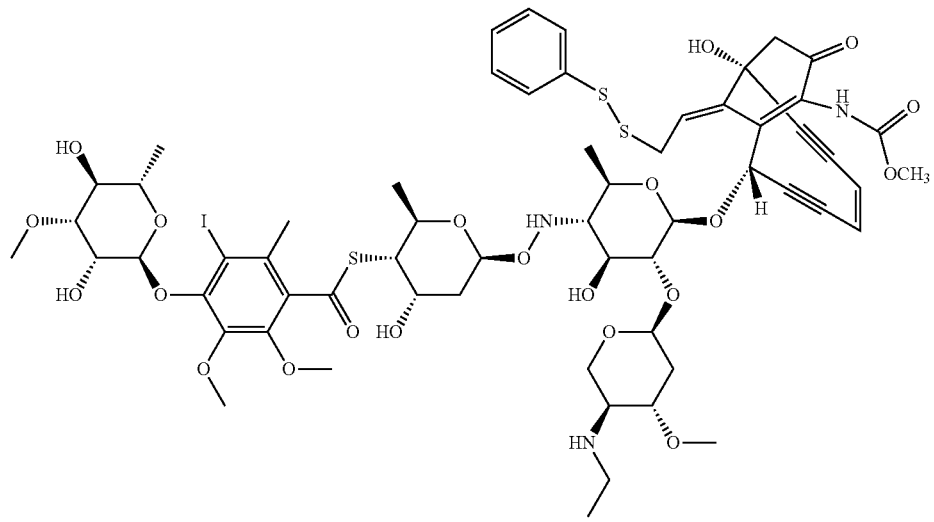 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSc3ccccc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P10: S-[(2R,3S,4S,6S)-6-({[(2R,3S,4S,5R,6R)-5-{[(2S,4S,5S)-5-(Ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(phenyldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1398.5 [M+H$^+$]; retention time=4.94 minutes (Method 2).

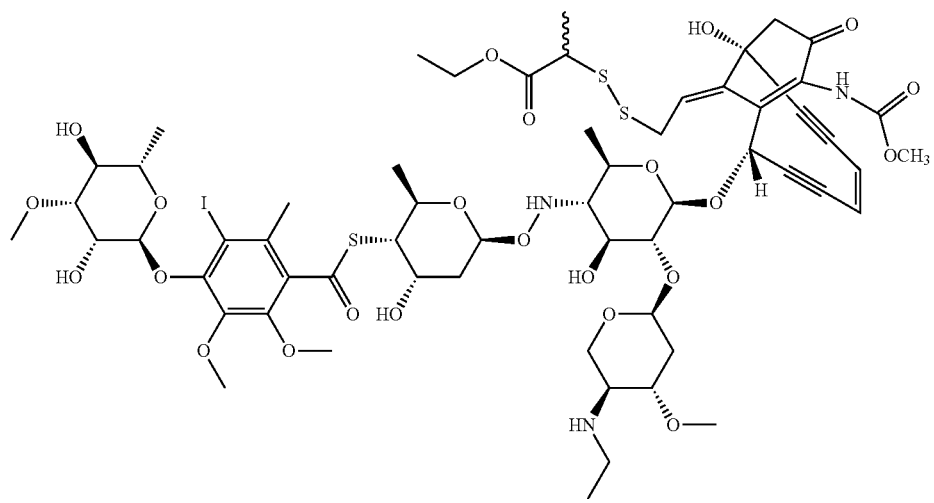 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)C(=O)OCC)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P11: Ethyl 2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}propanoate. LC-MS m/z 1422.6 [M+H$^+$]; retention time=3.92 minutes (Method 3).

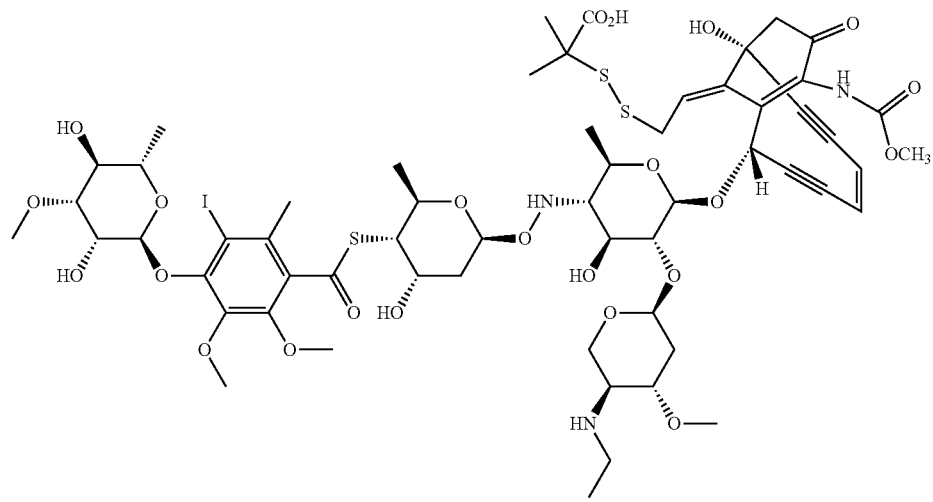 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)C(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P12: 2-{[(2E)-2-{(1R,8S)-8-{[(2R,3R,4S,5S,6R)-5-[({(2S,4S,5S,6R)-5-[(4-{[(2S,3R,4R,5S,6S)-3,5-Dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diyn-13-ylidene}ethyl]disulfanyl}-2-methylpropanoic acid. LC-MS m/z 1408.6 [M+H$^+$]; retention time=4.79 minutes (Method 3).

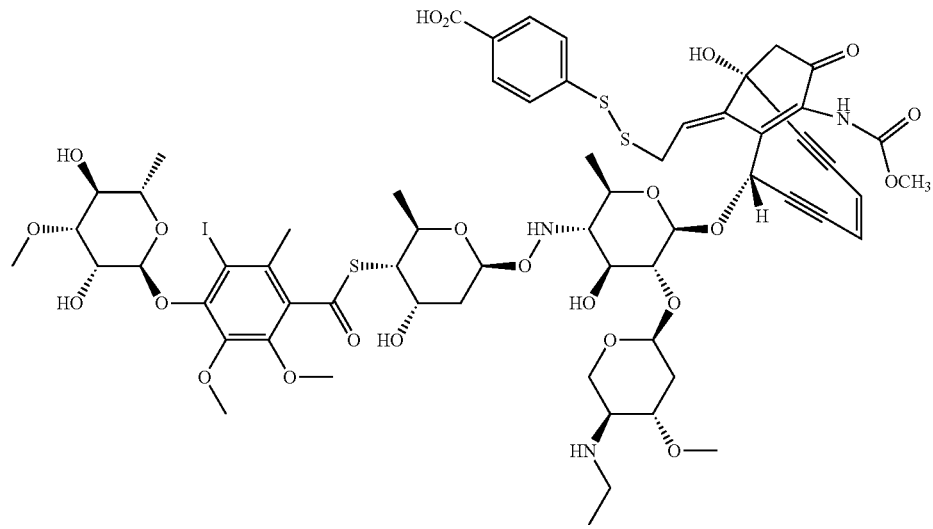 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSc3ccc(C(=O)O)cc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P13: 4-{[(2E)-2-{(1R,8S)-8-{[(2R,3R,4S,5S,6R)-5-[({(2S,4S,5S,6R)-5-[(4-{[(2S,3R,4R,5S,6S)-3,5-Dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}benzoic acid. LC-MS m/z 1442.5 [M+H$^+$]; retention time=3.74 minutes (Method 2).

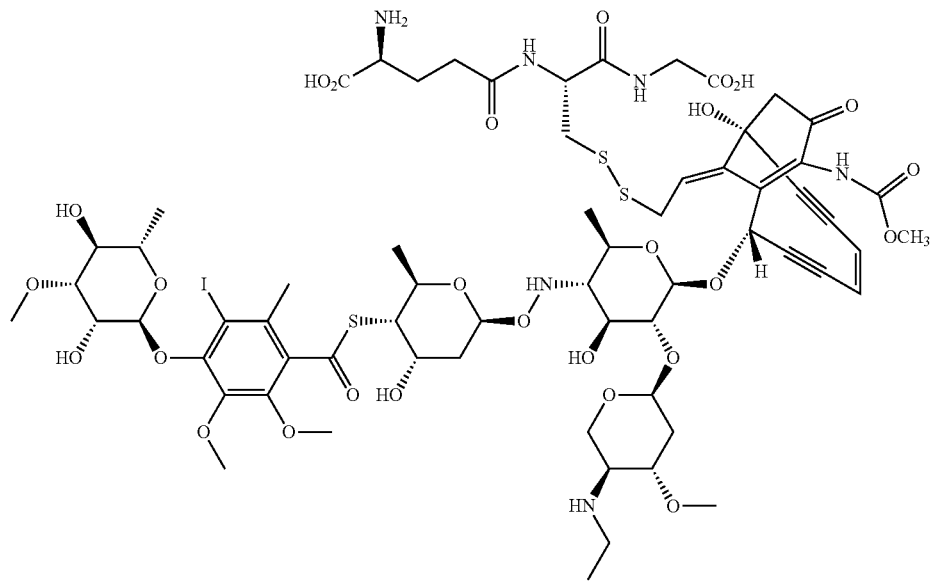 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC[C@H](NC(=O)CC[C@H](N)C(=O)O)C(=O)NCC(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P14: (2S)-2-Amino-5-{[(2R)-1-[(carboxymethyl)amino]-3-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}-1-oxopropan-2-yl]amino}-5-oxopentanoic acid. LC-MS m/z 1595.6 [M+H$^+$]; retention time=2.87 minutes (Method 2).

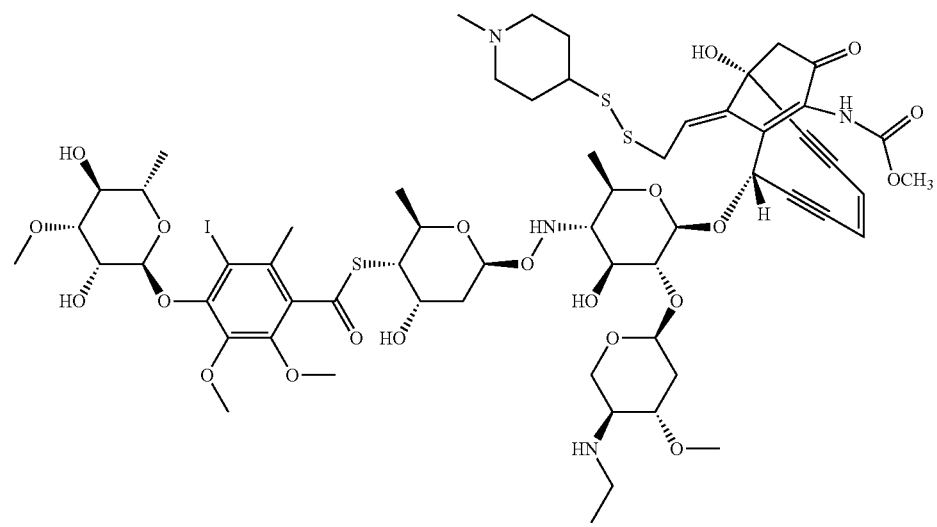 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC3CCN(C)CC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P15: S-[(2R,3S,4S,6S)-6-({[(2R,3S,4S,5R,6R)-5-{[(2S,4S,5S)-5-(Ethylamino)-4-methoxytetrahydro-2H-pyran-2-yl]oxy}-4-hydroxy-6-{[(2S,5Z,9R,13 E)-9-hydroxy-12-[(methoxycarbonyl)amino]-13-{2-[(1-methylpiperidin-4-yl)disulfanyl]ethylidene}-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1419.3 [M+H⁺]; retention time=2.70 minutes (Method 3).

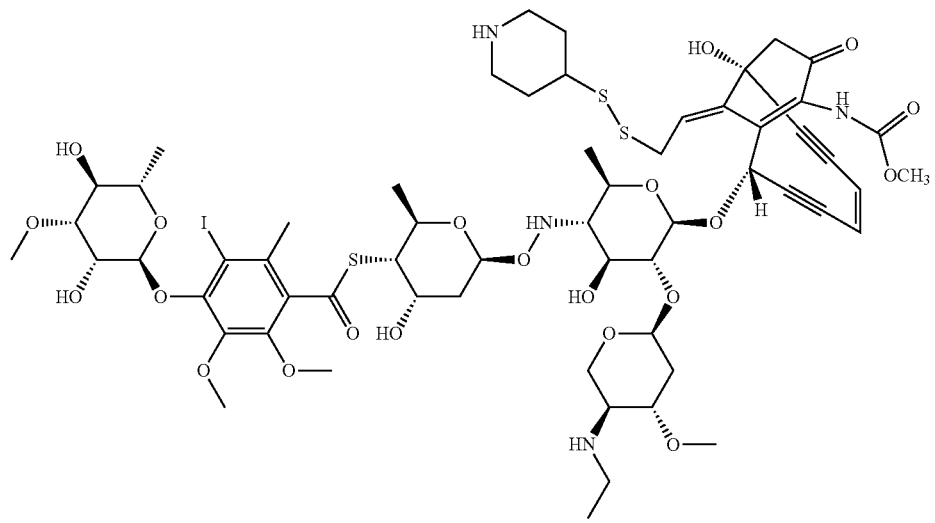 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC3CCNCC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P16: S-[(2R,3S,4S,6S)-6-({[(2R,3S,4S,5R,6R)-5-{[(2S,4S,5S) 5-(ethylamino)-4-methoxytetrahydro-2H-pyran-2-yl]oxy}-4-hydroxy-6-{[(2S,9R,13E)-9 hydroxy-12-[(methoxycarbonyl)amino]-11-oxo-13-[2-(piperidin-4-yl disulfanyl)ethylidene]bicyclo[7.3.1]trideca-1 (12),5-diene-3,7-diyn-2-yl]oxy}-2-methyltetrahydro-2H-pyran-3-yl] amino}oxy)-4-hydroxy-2-methyltetrahydro-2H-pyran-3-yl] 4-{[(2S,3R,4R,5S,6S)-3,5-dihydroxy-4-methoxy-6-methyl-tetrahydro-2H-pyran-2-yl]oxy}-3-iodo-5,6-dimethoxy-2-methylbenzenecarbothioate. LC-MS m/z 1405.4 [M+H⁺]; retention time=1.91 minutes (Method 6).

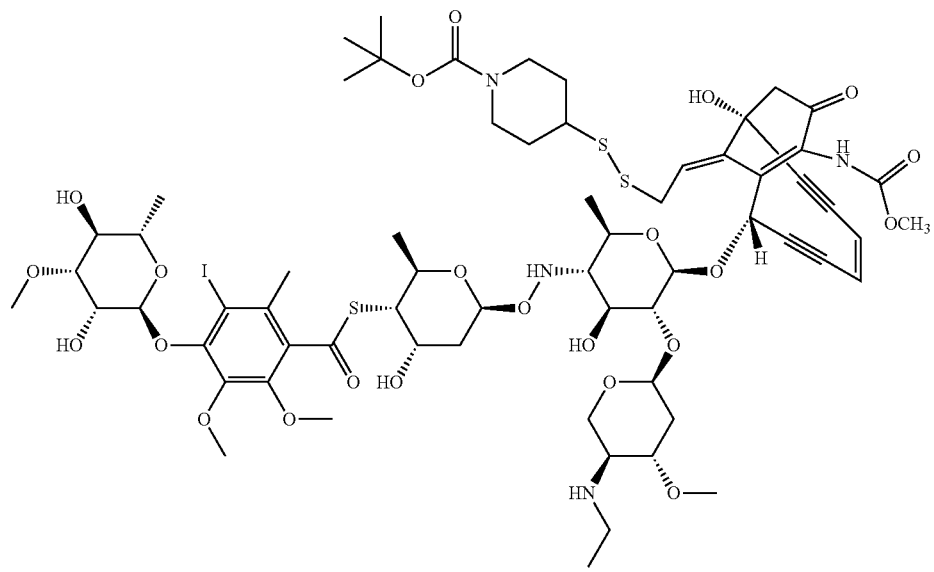 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC3CCN(C(=O)OC(C)(C)C)CC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P17: tert-butyl 4-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11 oxobicyclo[7.3.1]trideca-4,9-diene-2,6-diyn-13-ylidene}ethyl]disulfanyl}piperidine-1-carboxylate. LC-MS m/z 1505.5 [M+H⁺]; retention time=2.48 minutes (Method 6).

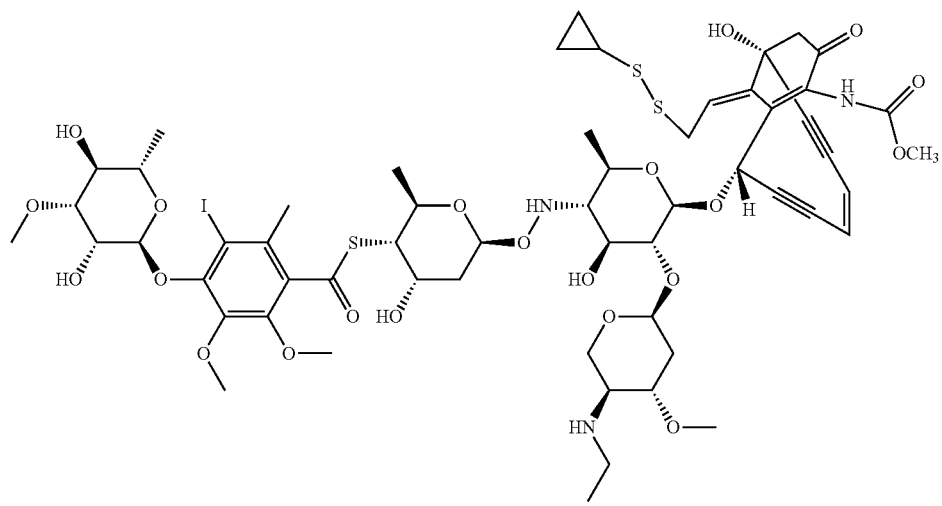

P18: S-[(2R,3S,4S,6S)-6-({[(2R,3S,4S,5R,6R)-6-{[(2S,9R,13E)-13-[2-(cyclopropyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1362.3 [M+H⁺]; retention time=5.81 minutes (Method 7).

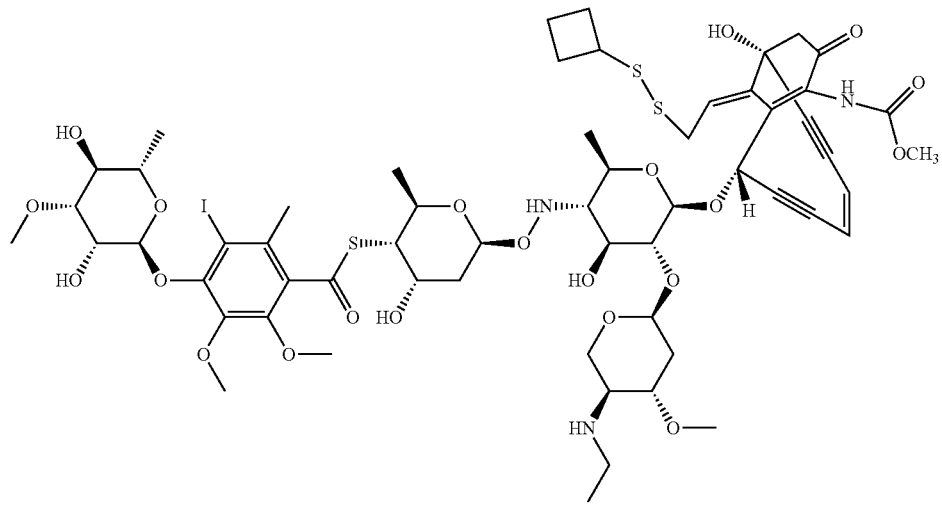

P19: S-[(2R,3S,4S,6S)-6-({[(2R,3S,4S,5R,6R)-6-{[(2S,9R,13E)-13-[2-(cyclobutyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1376.3 [M+H⁺]; retention time=6.04 minutes (Method 7).

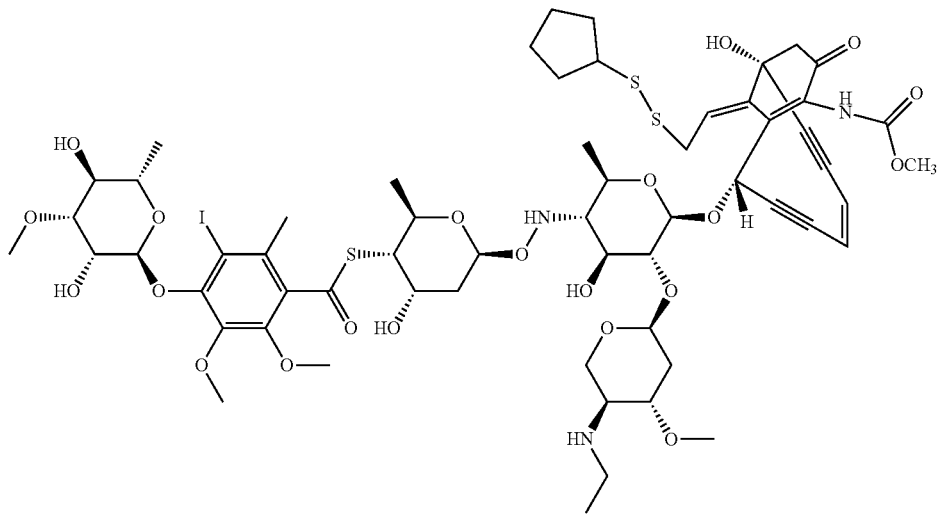

P20: S-[(2R,3S,4S,6S)-6-({[(2R,3S,4S,5R,6R)-6-{[(2S,9R,13E)-13-[2-(cyclopentyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1390.4 [M+H⁺]; retention time=6.08 minutes (Method 7).

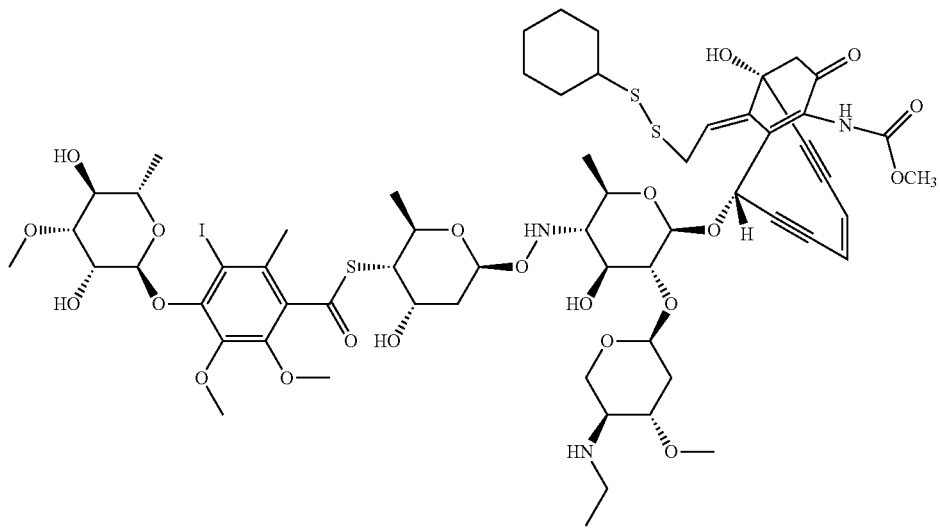

P21: S-[(2R,3S,4S,6S)-6-({[(2R,3S,4S,5R,6R)-6-{[(2S,9R,13E)-13-[2-(cyclohexyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1404.4 [M+H⁺]; retention time=6.34 minutes (Method 7).

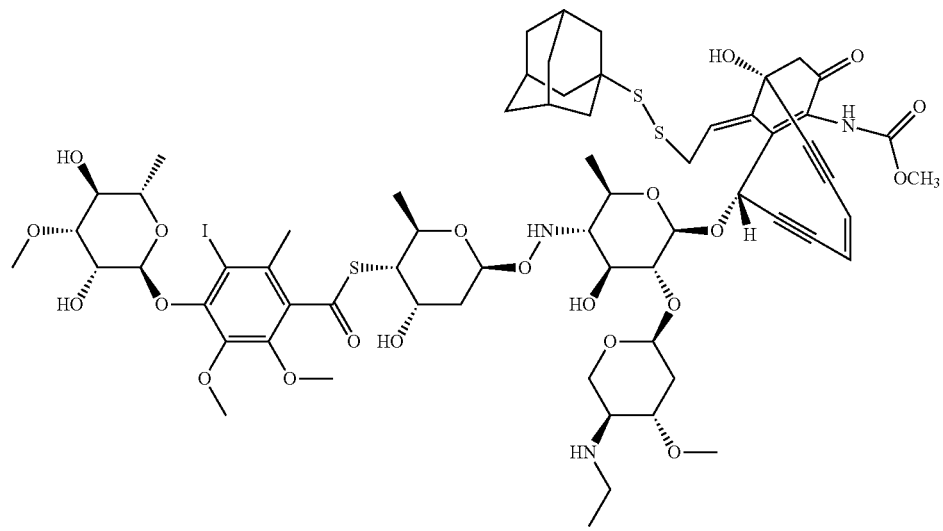 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC34CC5CC(CC(C5)C3)C4)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P22: S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(tricyclo[3.3.1.1~3,7~]dec-1 yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1456.5 [M+H⁺]; retention time=6.71 minutes (Method 7).

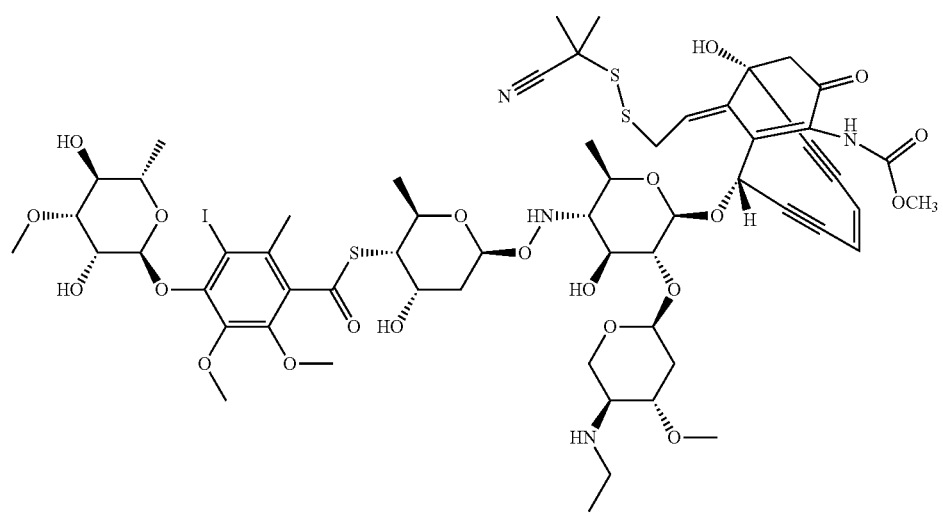 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)C#N)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P23: S-[(2R,3S,4S,6S)-6-({[(2R,3S,4S,5R,6R)-6-{[(2S,9R,13E)-13-{2-[(2-cyanopropan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1389.4 [M+H$^+$]; retention time=5.79 minutes (Method 7).

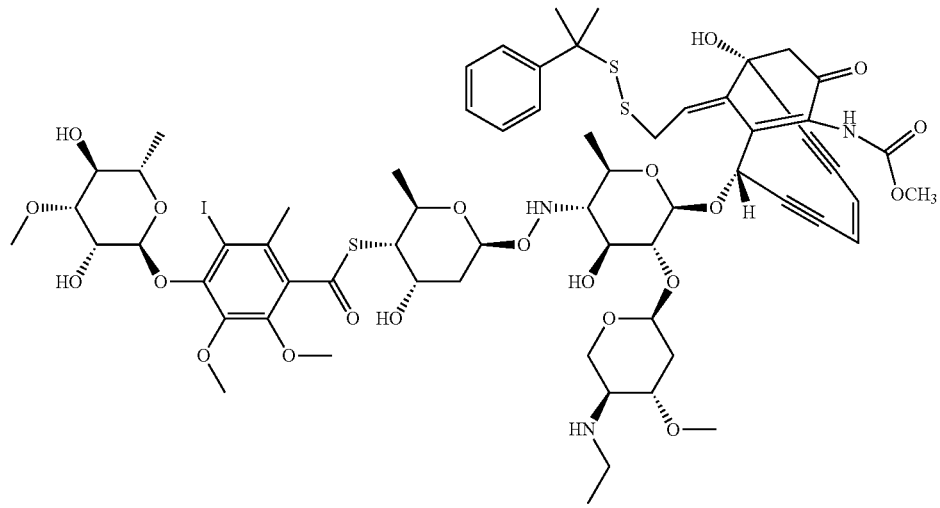 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)c3ccccc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P24: S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-{2-[(2-phenylpropan-2-yl)disulfanyl]ethylidene}bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1440.4 [M+H$^+$]; retention time=1.92 minutes (Method 6).

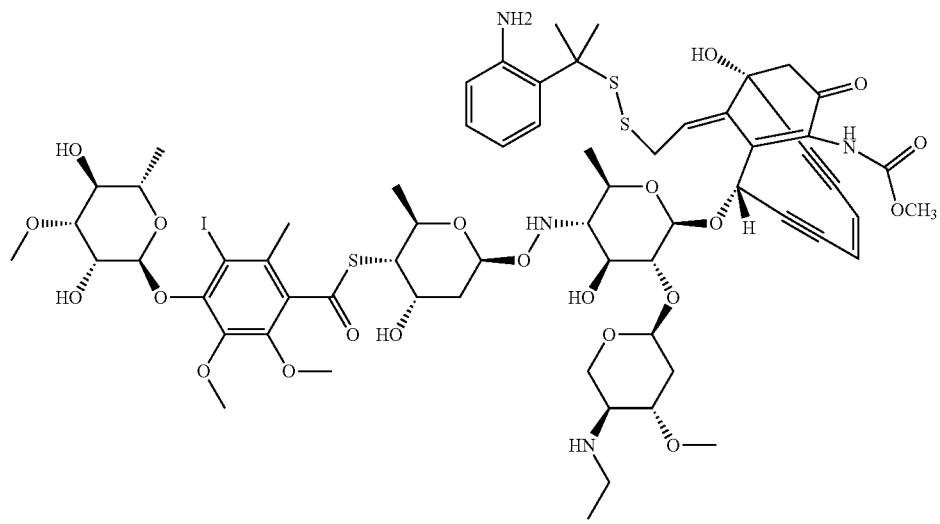 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)c3ccccc3N)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P25: S-[(2R,3S,4S,6S)-6-({[(2R,3S,4S,5R,6R)-6-{[(2S,9R,13E)-13-(2-{[2-(2-aminophenyl)propan-2-yl]disulfanyl}ethylidene)-9-hydroxy-12-[(methoxycarbonyl)amino]-11-oxobicyclo[7.3.1]trideca-1 (12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1455.5 [M+H⁺]; retention time=2.43 minutes (Method 6).

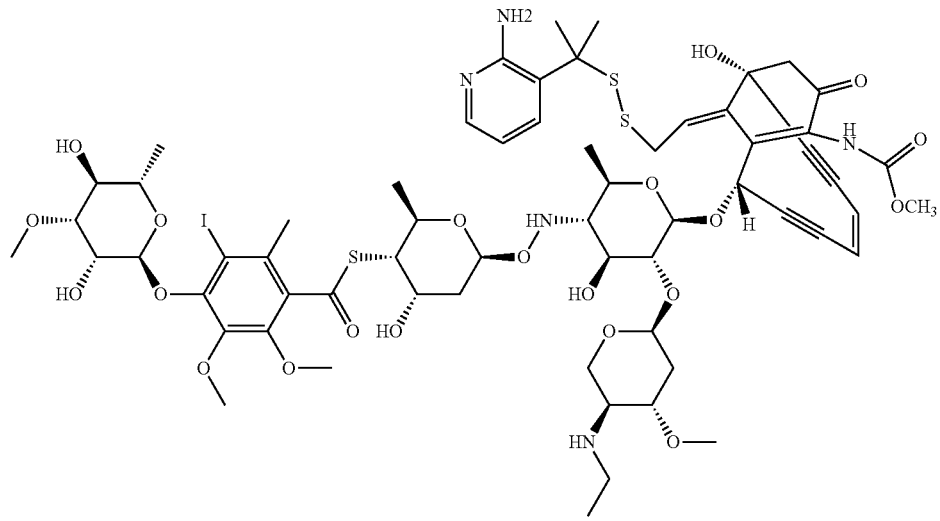 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)c3cccnc3N)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P26: S-[(2R,3S,4S,6S)-6-({[(2R,3S,4S,5R,6R)-6-{[(2S,9R,13E)-13-(2-{[2-(2-aminopyridin-3-yl)propan-2-yl]disulfanyl}ethylidene)-9-hydroxy-12-[(methoxycarbonyl)amino]-11-oxobicyclo[7.3.1]trideca-1 (12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1456.4 [M+H⁺]; retention time=1.96 minutes (Method 6).

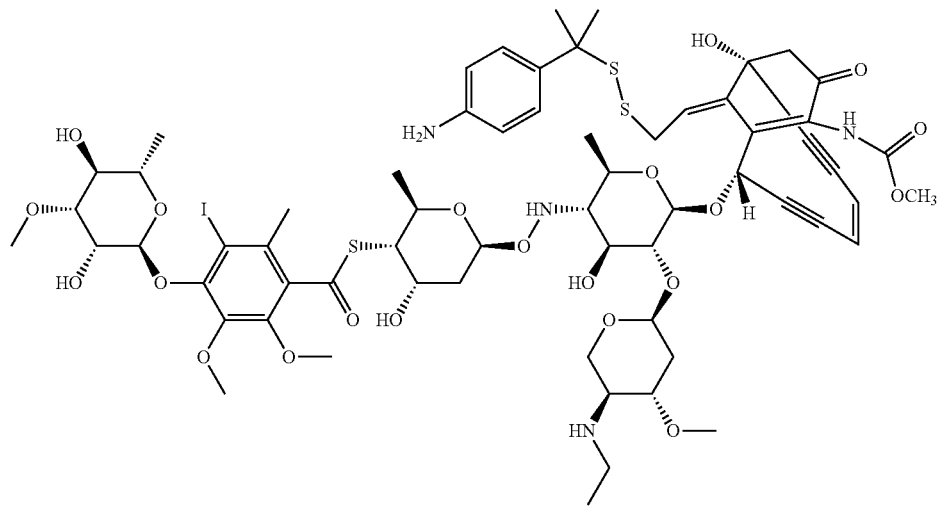 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)c3ccc(N)cc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P27: S-[(2R,3S,4S,6S)-6-({[(2R,3S,4S,5R,6R)-6-{[(2S,9R,13E)-13-(2-{[2-(4-aminophenyl)propan-2-yl]disulfanyl}ethylidene)-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1455.5 [M+H$^+$]; retention time=2.17 minutes (Method 6).

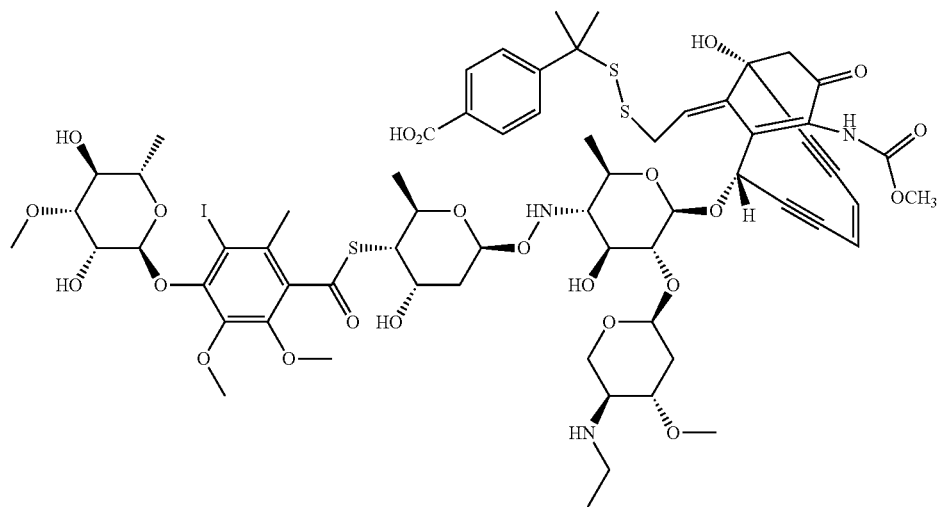 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)c3ccc(C(=O)O)cc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P28: S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-({2-[4-(trifluoromethyl)phenyl]propan-2-yl}disulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1508.4 [M+H$^+$]; retention time=2.60 minutes (Method 6).

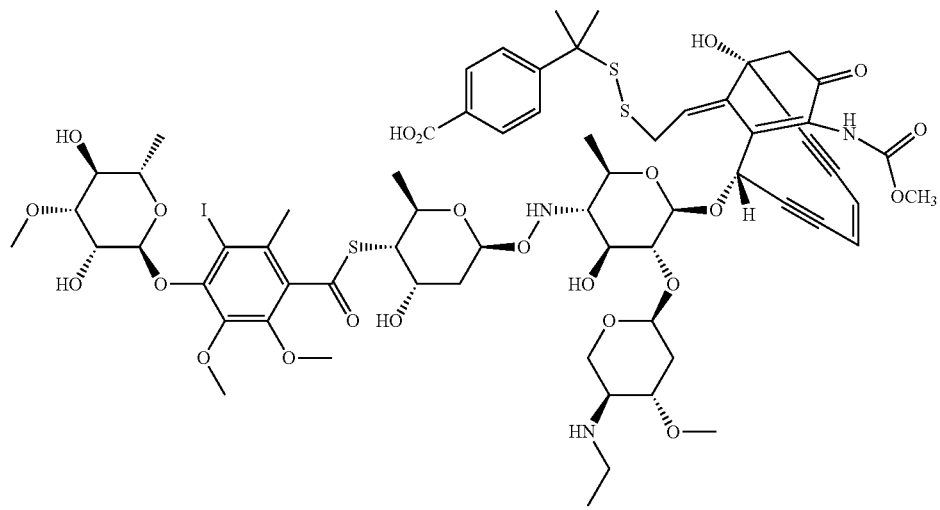 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)c3ccc(C(=O)O)cc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P29: 4-(2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}propan-2-yl)benzoic acid. LC-MS m/z 1484.4 [M+H$^+$]; retention time=2.33 minutes (Method 6).

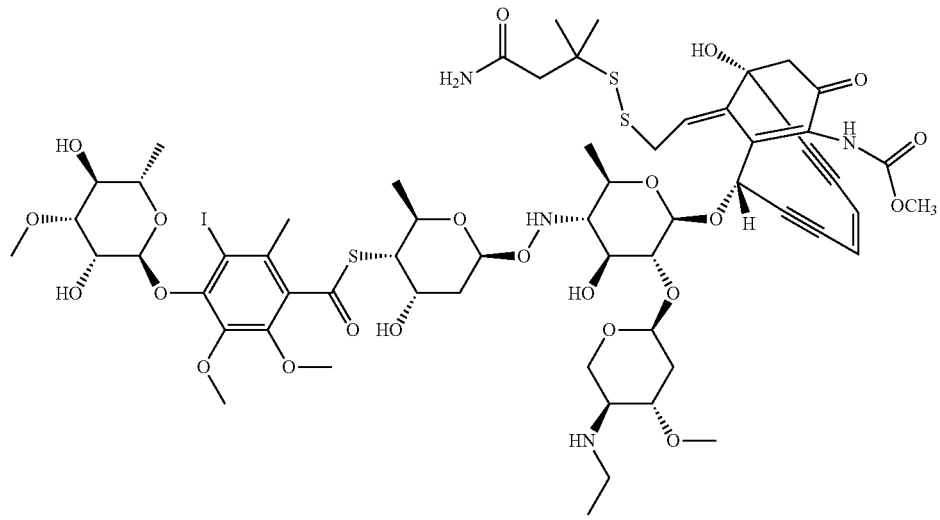 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)CC(N)=O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P30: S-[(2R,3S,4S,6S)-6-({[(2R,3S,4S,5R,6R)-6-{[(2S,9R,13E)-13-{2-[(4-amino-2-methyl-4-oxobutan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1421.4 [M+H$^+$]; retention time=2.11 minutes (Method 6).

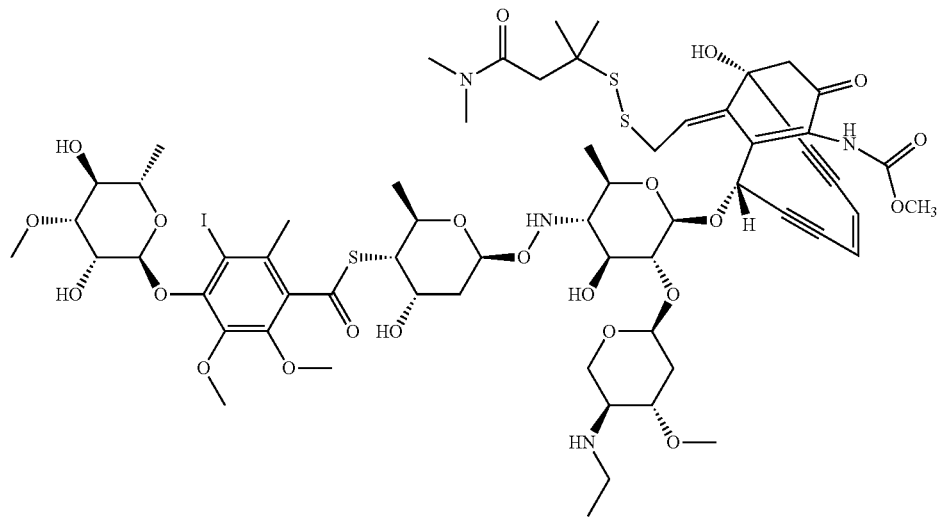 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)CC(=O)N(C)C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P31: S-[(2R,3S,4S,6S)-6-({[(2R,3S,4S,5R,6R)-6-{[(2S,9R,13E)-13-(2-{[4-(dimethylamino)-2-methyl-4-oxobutan-2-yl]disulfanyl}ethylidene)-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1449.4 [M+H⁺]; retention time=2.18 minutes (Method 6).

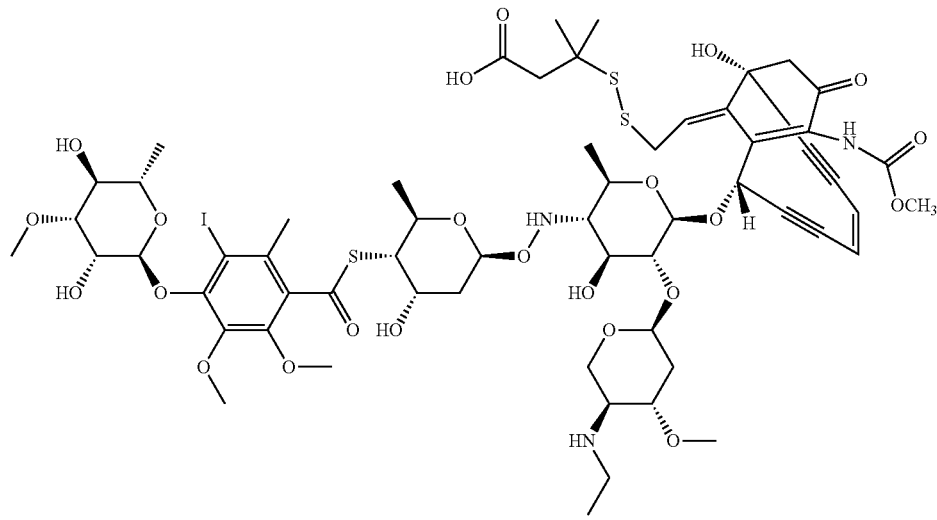 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)CC(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P32: 3-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}-3-methylbutanoic acid. LC-MS m/z 1422.4 [M+H⁺]; retention time=2.17 minutes (Method 6).

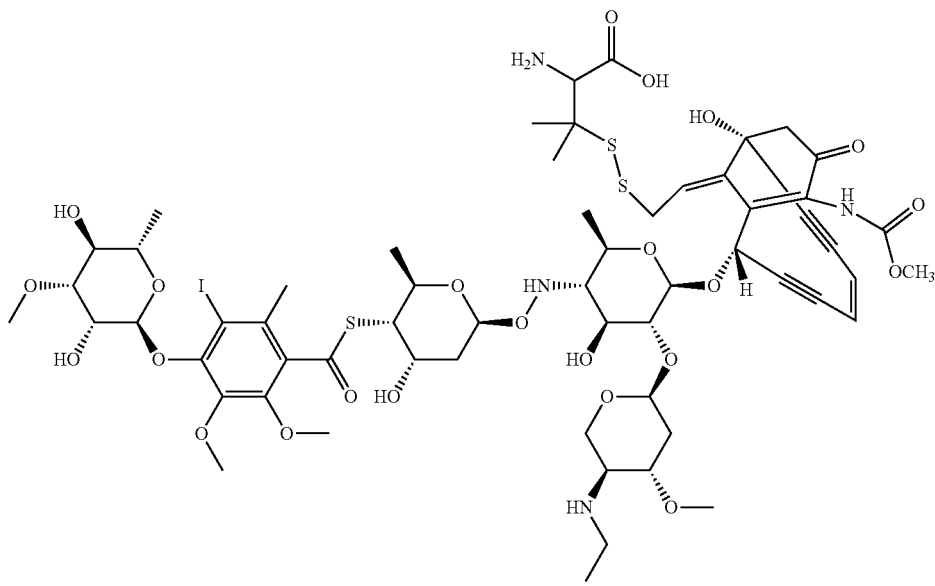 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)C(N)C(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P33: (2R)-2-amino-3-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}-3-methylbutanoic acid. LC-MS m/z 1437.4 [M+H⁺]; retention time=2.03 minutes (Method 6).

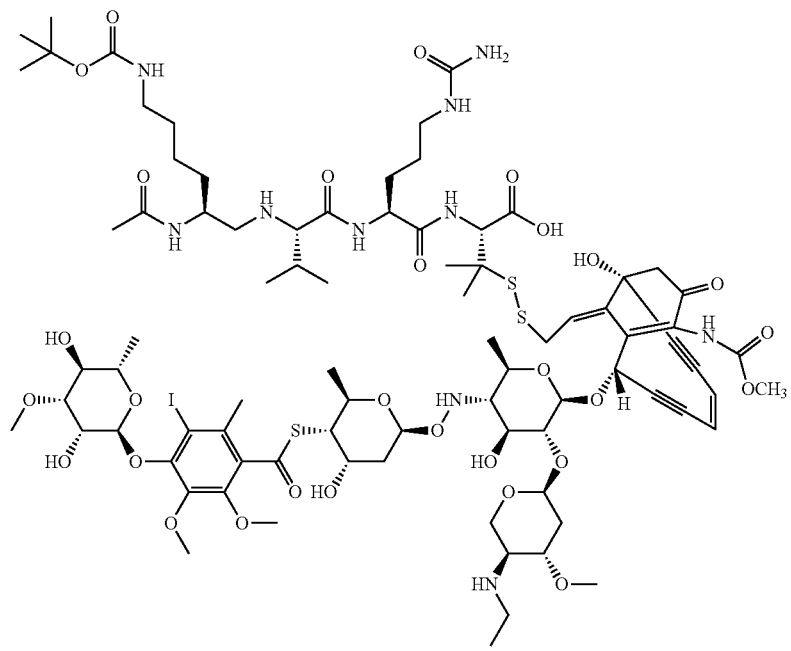 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)[C@H](NC(=O)[C@H](CCCNC(N)=O)NC(=O)[C@@H](NC[C@H](CCCCNC(=O)OC(C)(C)C)NC(C)=O)C(C)C)C(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P34: (10S,13S,16S,19R)-10-(acetylamino)-16-[3-(carbamoylamino)propyl]-19-(2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}propan-2-yl)-2,2-dimethyl-4,11,14,17-tetraoxo-13-(propan-2-yl)-3-oxa-5,12,15,18-tetraazaicosan-20-oic acid. LC-MS m/z 1964.0 [M+H⁺]; retention time=3.10 minutes (Method 11).

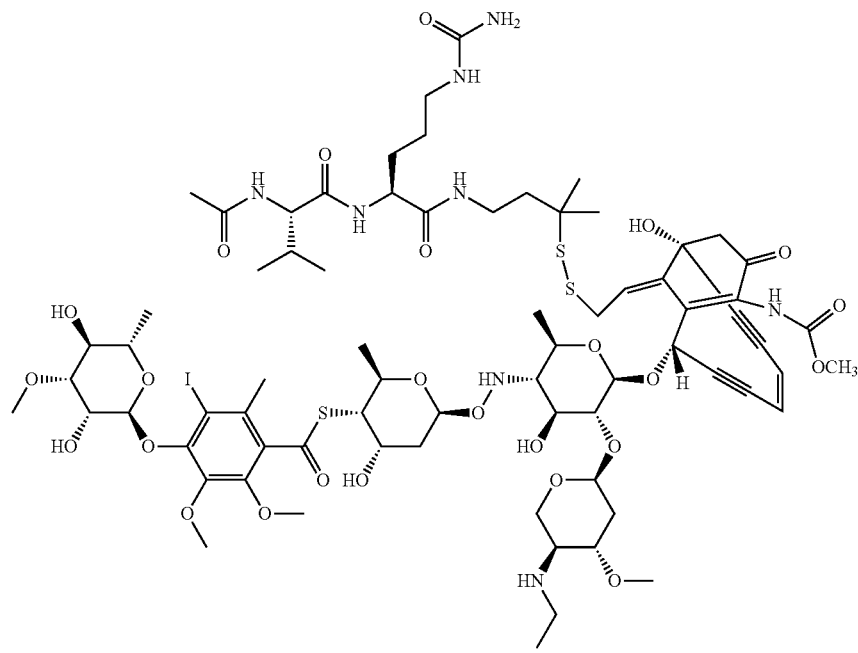 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)CCNC(=O)[C@H](CCCNC(N)=O)NC(=O)[C@@H](NC(C)=O)C(C)C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P35: S-[(2R,3S,4S,6S)-6-({[(2R,3S,4S,5R,6R)-6-{[(2S,9R,13E)-13-[(10S,13S)-10-[3-(carbamoylamino)propyl]-5,5-dimethyl-9,12,15-trioxo-13-(propan-2-yl)-3,4-dithia-8,11,14-triazahexadec-1-ylidene]-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1705.6 [M+H$^+$]; retention time=2.15 minutes (Method 6).

P36: S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-13-[2-({2-methyl-1-[(2-phenoxyethyl)amino]propan-2-yl}disulfanyl)ethylidene]-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1513.5 [M+H$^+$]; retention time=2.20 minutes (Method 11).

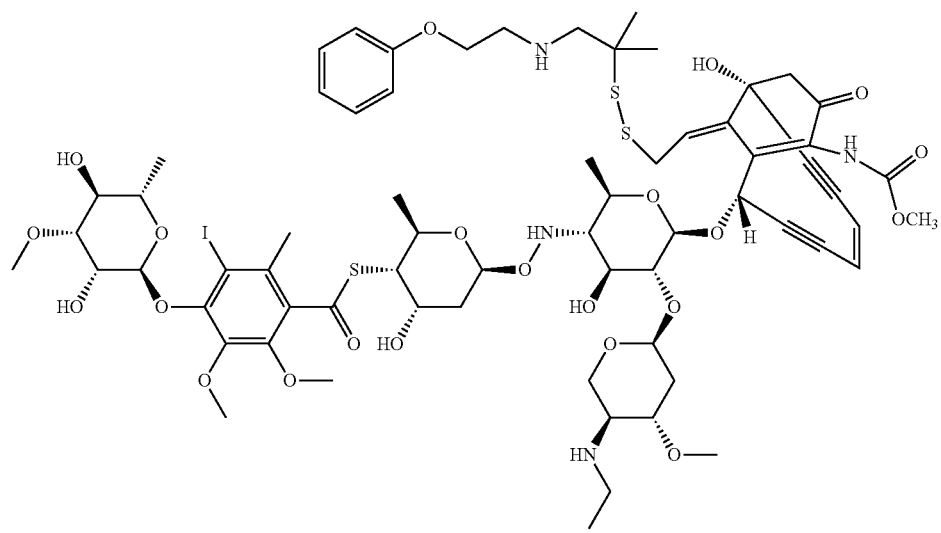 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)CNCCOc3ccccc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

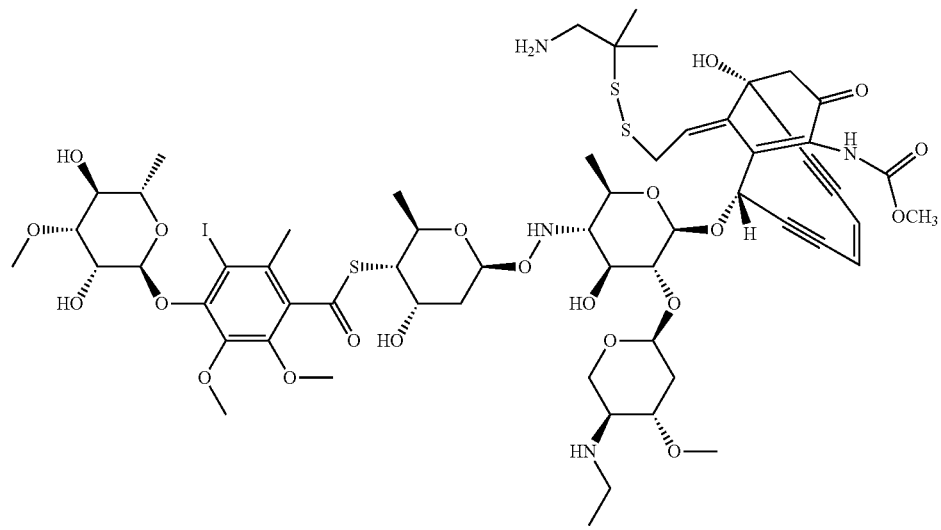 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)CN)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

P37: S-[(2R,3S,4S,6S)-6-({[(2R,3S,4S,5R,6R)-6-{[(2S,9R,13E)-13-{2-[(1-amino-2-methylpropan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1393.4 [M+H⁺]; retention time=2.07 minutes (Method 11).

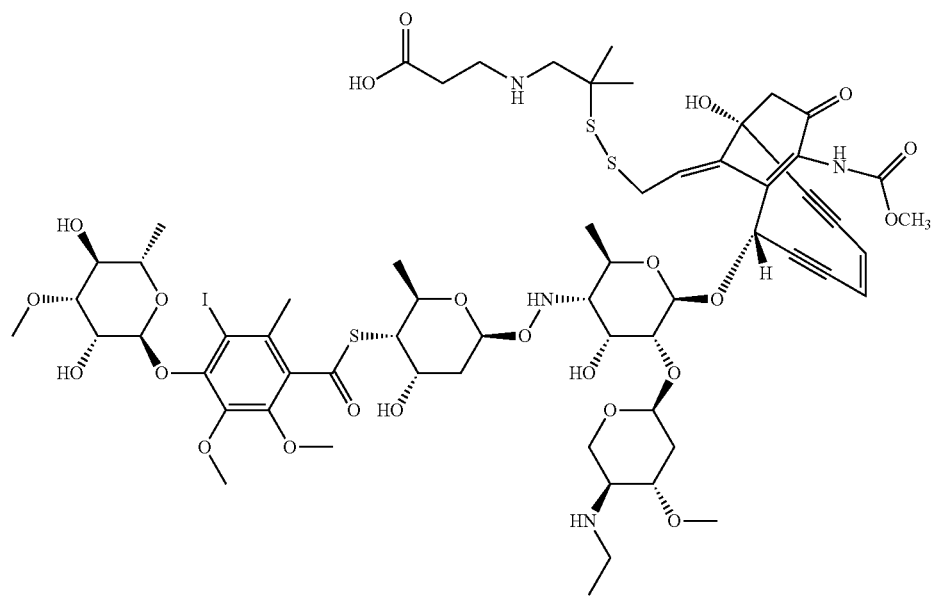 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)CNCCC(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@H]2O)C[C@@H]1OC]

P38: 3-[(2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}-2-methylpropyl)amino]propanoic acid. LC-MS m/z 1465.4 [M+H⁺]; retention time=2.15 minutes (Method 11).

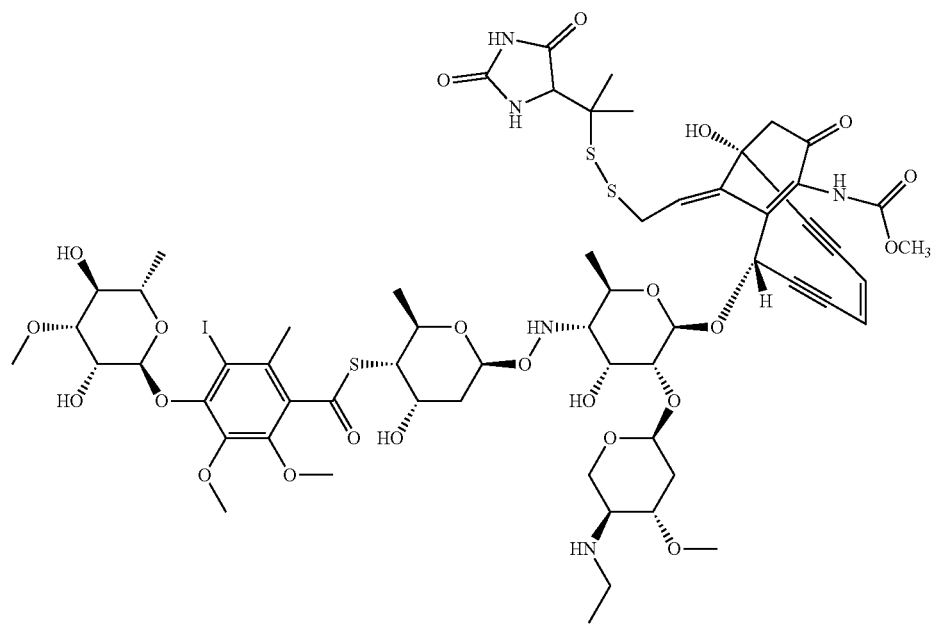 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSC(C)(C)C3NC(=O)NC3=O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@H]2O)C[C@@H]1OC]

P39: S-[(2R,3S,4S,6S)-6-({[(2R,3S,4S,5R,6R)-6-{[(2S, 9R,13E)-13-(2-{[2-(2,5-dioxoimidazolidin-4-yl)propan-2-yl]disulfanyl}ethylidene)-9-hydroxy-12-[(methoxycarbonyl)amino]-11-oxobicyclo[7.3.1]trideca-1(12), 5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1462.3 [M+H⁺]; retention time=2.35 minutes (Method 11).

P40: S-[(2R,3S,4S,6S)-6-({[(2R,3S,4S,5R,6R)-6-{[(2S, 9R,13E)-13-{2-[(3,5-dimethylpyridin-4-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1427.3 [M+H⁺]; retention time=2.11 minutes (Method 6).

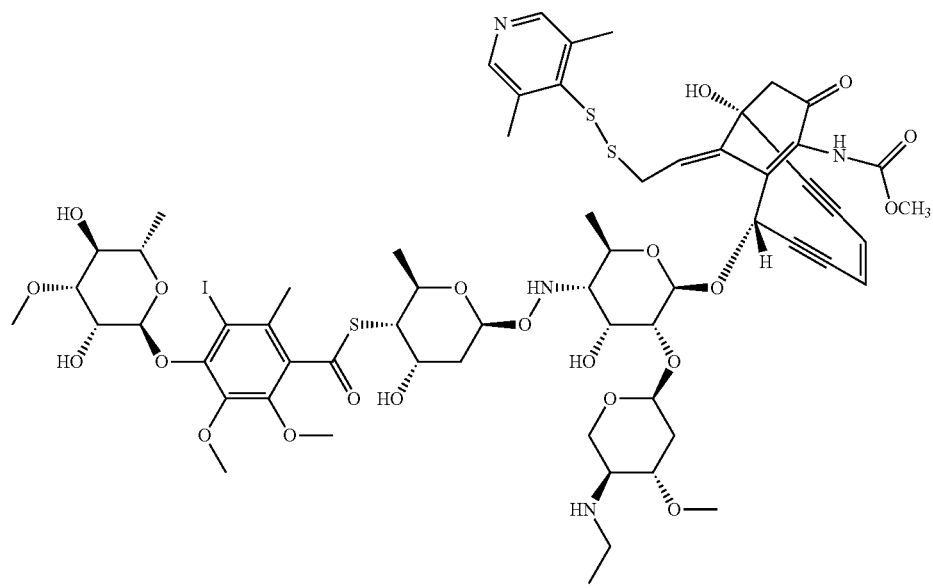 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSSc3c(C)cncc3C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@H]2O)C[C@@H]1OC]

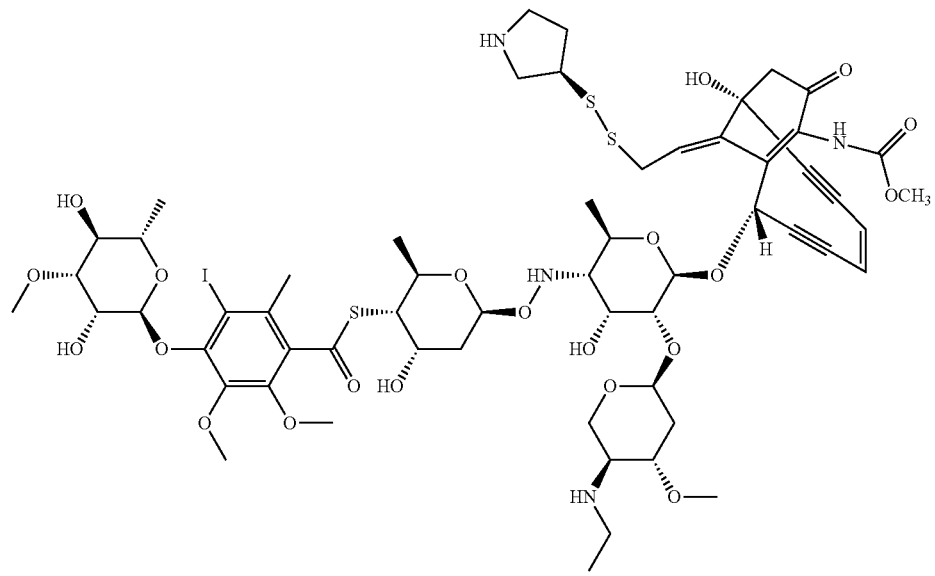 [SMILES: CCN[C@H]1CO[C@@H](O[C@H]2[C@H](O[C@H]3C#C/C=C\C#C[C@]4(O)CC(=O)C(NC(=O)OC)=C3/C4=C\CSS[C@@H]3CCNC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@H]2O)C[C@@H]1OC]

P41:S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-{2-[(3R)-pyrrolidin-3-yldisulfanyl]ethylidene}bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1391.4 [M+H⁺]; retention time=2.07 minutes (Method 6).

P42: (2R)-2-amino-5-[(3-{[(2E)-2-{(1R,4Z,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}-3-methylbutyl)amino]-5-oxopentanoic acid. LC-MS m/z 1536 [M+H⁺]; retention time=4.18 minutes (Method 3).

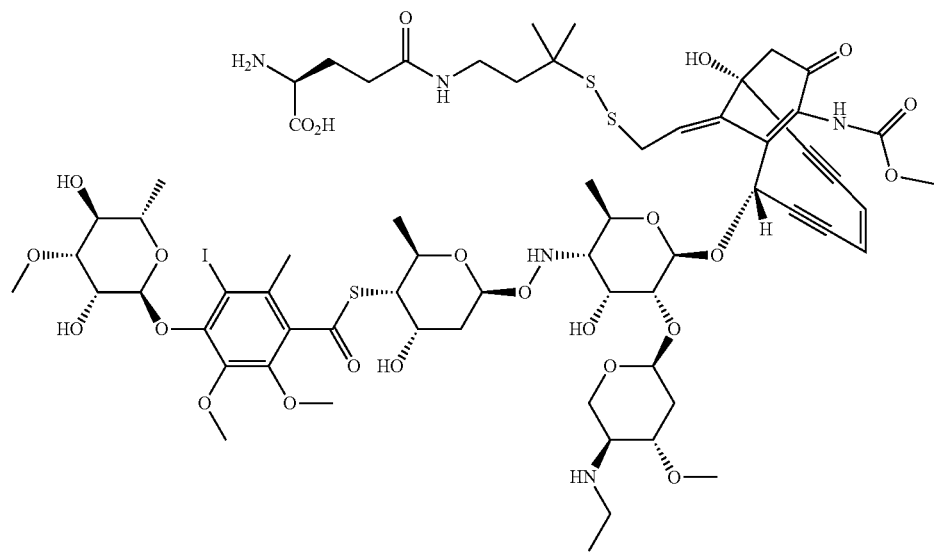

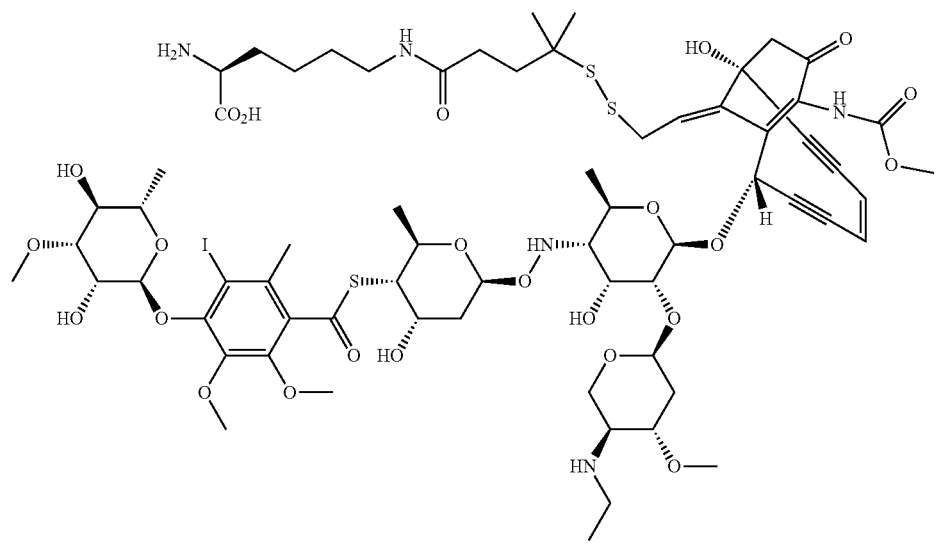

P43: (2S)-2-amino-6-[(4-{[(2E)-2-{(1R,4Z,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}-4-methylpentanoyl)amino]hexanoic acid. LC-MS m/z 1565 [M+H$^+$]; retention time=4.05 minutes (Method 3).

P44: S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(pyridin-4-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1399.1 [M+H$^+$]; retention time=4.44 minutes (Method 3).

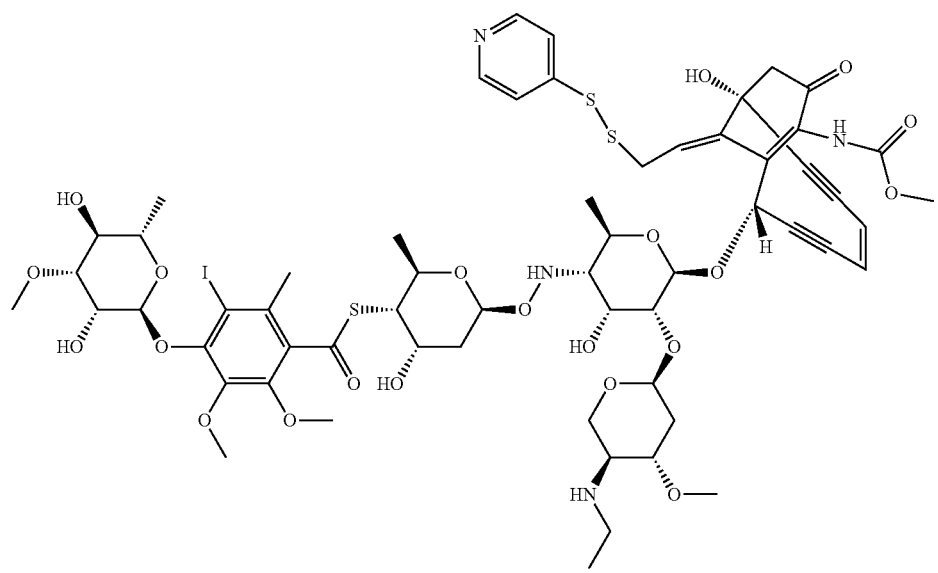

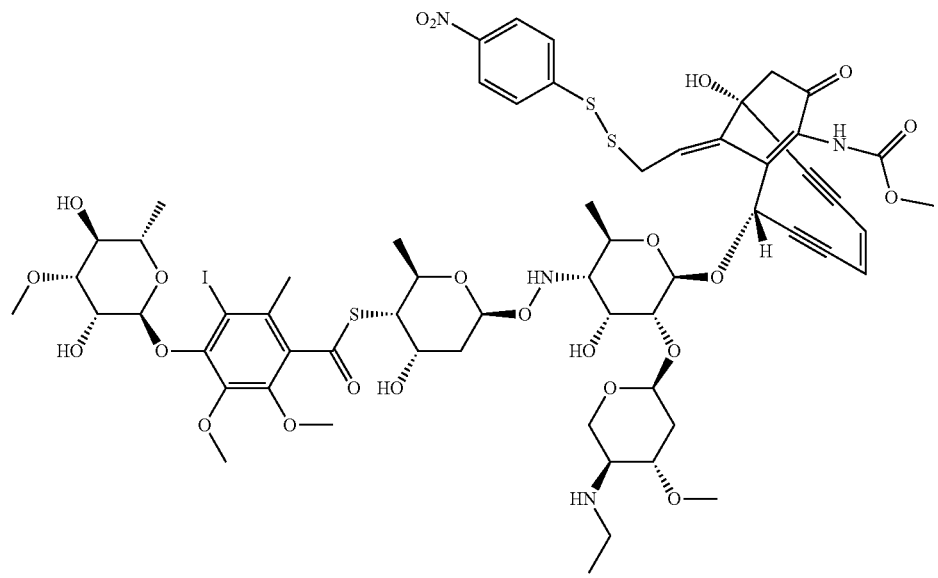

P45: S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-13-{2-[(4-nitrophenyl)disulfanyl]ethylidene}-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1443.5 [M+H⁺]; retention time=3.08 minutes (Method 3).

P46: 2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}pyridine-3-carboxylic acid. LC-MS m/z 1443.4 [M+H⁺]; retention time=4.52 minutes (Method 3).

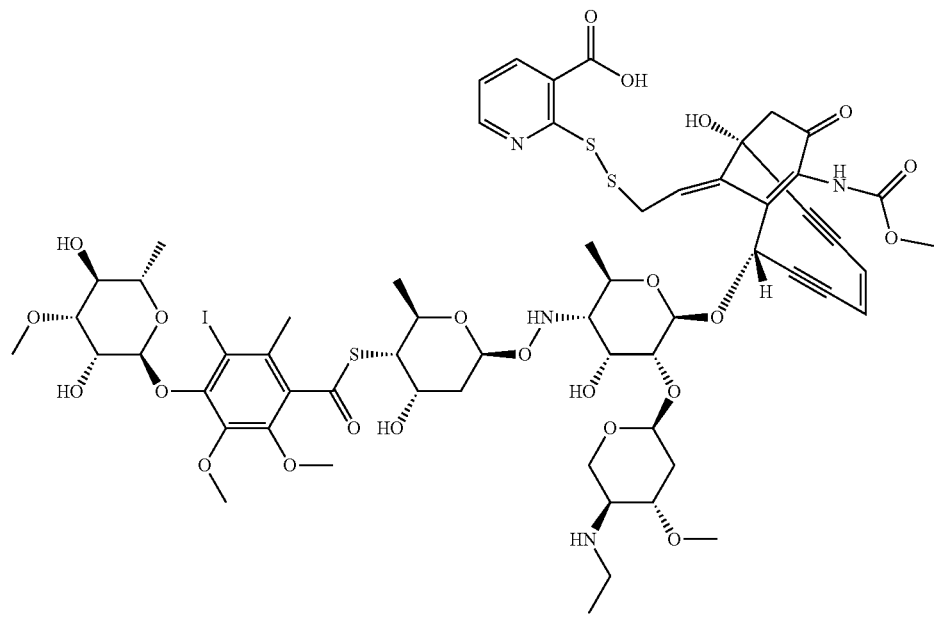

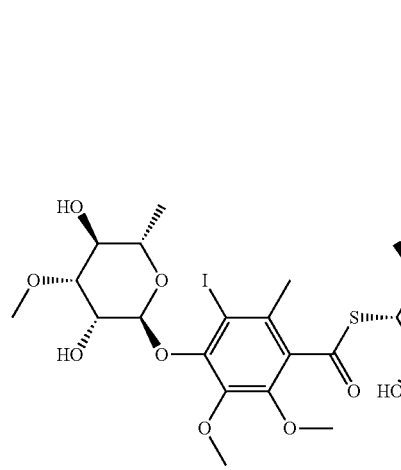
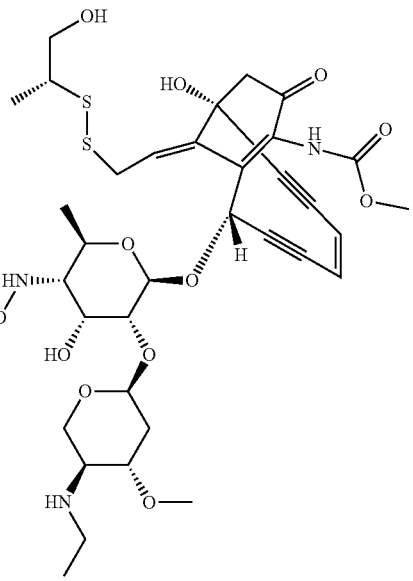

P47: S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-13-(2-{[(2R)-1-hydroxypropan-2-yl]disulfanyl}ethylidene)-12-[(methoxycarbonyl)amino]-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1380.5 [M+H⁺]; retention time=3.01 minutes (Method 1).

P48: S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-13-{2-[(4-{(2E)-2-[1-(4-methoxyphenyl)ethylidene]hydrazinyl}-2-methyl-4-oxobutan-2-yl)disulfanyl]ethylidene}-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate. LC-MS m/z 1568.4 [M+H⁺]; retention time=2.39 minutes (Method 6).

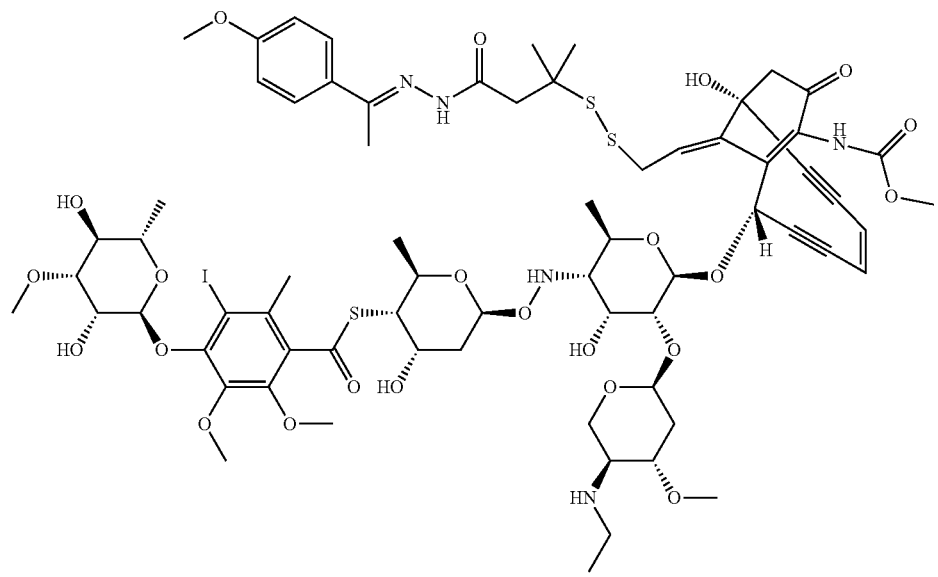

Preparation of S-[(2R,3S,4S,6S)-6-({[(2R,3S,4S,5R,6R)-6-{[(2S,9R,13E)-13-[2-(tert-butyldisulfanyl)ethylidene]-9-hydroxy-12-[(methoxycarbonyl)amino]-11-oxobicyclo[7.3.1]trideca-1 (12),5-diene-3,7-diyn-2-yl]oxy}-5-{[(2 S,4S,5S)-5-(ethyl{[4-({[(9H-fluoren-9-ylmethoxy)carbonyl]amino}methyl)phenyl]carbamoyl}amino)-4-methoxytetrahydro-2H-pyran-2-yl]oxy}-4-hydroxy-2-methyltetrahydro-2H-pyran-3-yl]amino}oxy)-4-hydroxy-2-m ethyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P49)

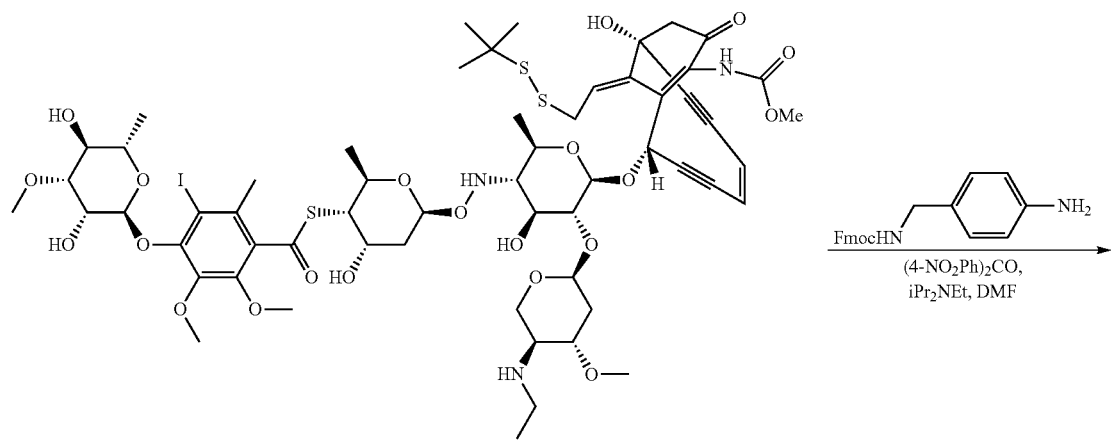

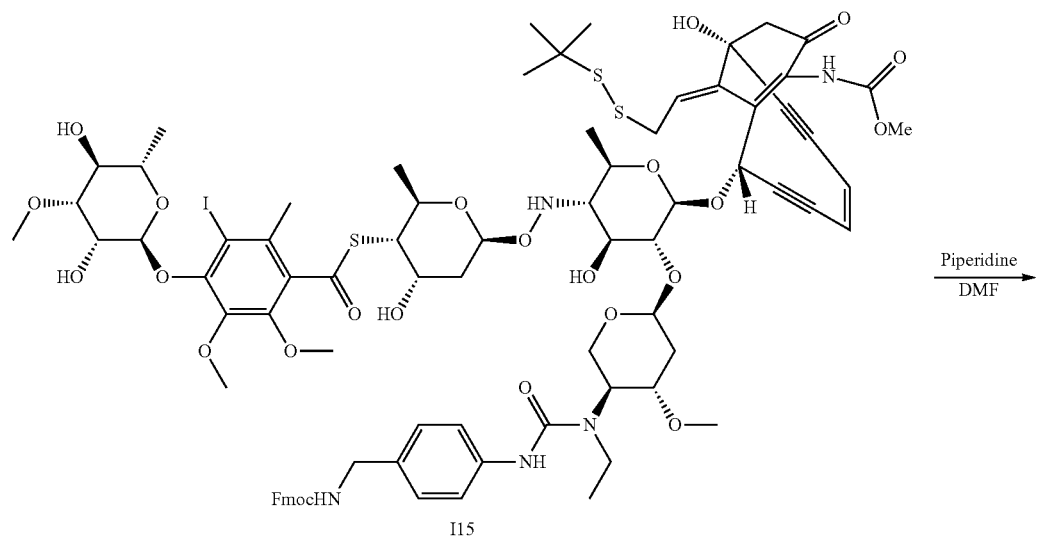

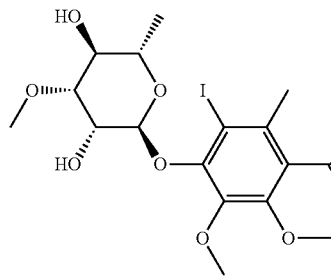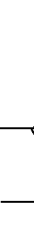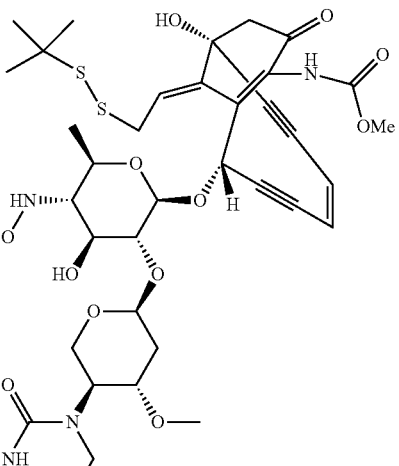

P49

Step 1: Synthesis of S-[(2R,3S,4S,6S)-6-({[(2R,3S,4S,5R,6R)-6-{[(2S,9R,13E)-13-[2-(tert- butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2 S,4S,5S)-5-(ethyl{[4-({[(9H-fluoren-9-ylmethoxy)carbonyl]amino}methyl)phenyl]carbamoyl}amino)-4-methoxytetrahydro-2H-pyran-2-yl]oxy}-4-hydroxy-2-methyltetrahydro-2H-pyran-3-yl]amino}oxy)-4-hydroxy-2-m ethyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate N,N-Diisopropylethylamine (22 μL, 16 mg, 0.12 mmol) was added to a solution of 9H-fluoren-9-ylmethyl (4-aminobenzyl)carbamate (26.2 mg, 0.0761 mmol) and bis(pentafluorophenyl)carbonate (29.5 mg, 0.0734 mmol) in N,N-dimethylacetamide (250 uL) at −30° C. After one hour, S-[(2R,3S,4S,6S)-6-({[(2R,3S,4S,5R,6R)-6-{[(2S,5Z,9R,13E)-13-[2-(tert- butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P2) (8.8 mg, 0.0061 mmol) was added to the reaction mixture, and the reaction mixture was allowed to warm to ambient temperature. After 4 hours, the reaction mixture was purified by reverse phase HPLC (Method M). Product containing fractions were lyophilized to provide 6.1 mg of the desired product. LC-MS m/z 1748.6 [M+H$^+$]; retention time=1.07 min minutes (Method 5).

Step 2: Synthesis of S-[(2R,3S,4S,6S)-6-({[(2R,3S,4S,5R,6R)-6-{[(2S,9R,13E)-13-[2-(tert- butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2 S,4S,5S)-5-(ethyl{[4-({[(9H-fluoren-9-ylmethoxy)carbonyl]amino}methyl)phenyl]carbamoyl}amino)-4-methoxytetrahydro-2H-pyran-2-yl]oxy}-4-hydroxy-2-methyltetrahydro-2H-pyran-3-yl]amino}oxy)-4-hydroxy-2-m ethyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P50)

Piperidine (3.4 μL, 3.0 mg, 0.035 mmol) was added to a solution of S-[(2R,3S,4S,6S)-6-({[(2R,3S,4S,5R,6R)-6-{[(2S,9R,13E)-13-[2-(tert-butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2 S,4S,5S)-5-(ethyl{[4-({[(9H-fluoren-9-ylmethoxy)carbonyl]amino}methyl)phenyl]carbamoyl}amino)-4-methoxytetrahydro-2H-pyran-2-yl]oxy}-4-hydroxy-2-methyltetrahydro-2H-pyran-3-yl]amino}oxy)-4-hydroxy-2-m ethyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (6.1 mg, 0.0035 mmol) in N,N-dimethylacetamide (400 uL) at 0° C. After 3.5 hours, the reaction mixture was purified by reverse phase HPLC (Method C). Product containing fractions were lyophilized to provide 3.1 mg of the desired product (P49). LC-MS m/z 1526.6 [M+H$^+$]; retention time=4.61 minutes (Method 3).

Preparation of {[(3S,4S,6S)-6-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-2-{[(2S,9R,13E)-9-hydroxy-12-[(methoxycarbonyl)amino]-11-oxo-13-[2-(propan-2-yldisulfanyl)ethylidene]bicyclo[7.3.1]trideca-1 (12),5-diene-3,7-diyn-2-yl]oxy}-6-methyltetrahydro-2H-pyran-3-yl]oxy}-4-methoxytetrahydro-2H-pyran-3-yl](ethyl)amino}acetic acid (P50)

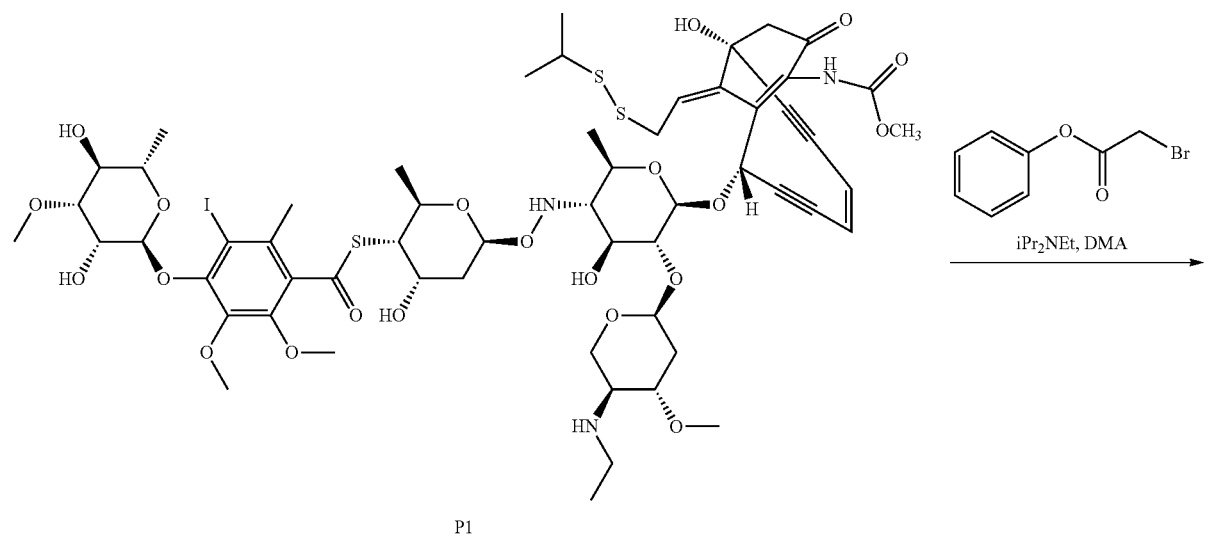

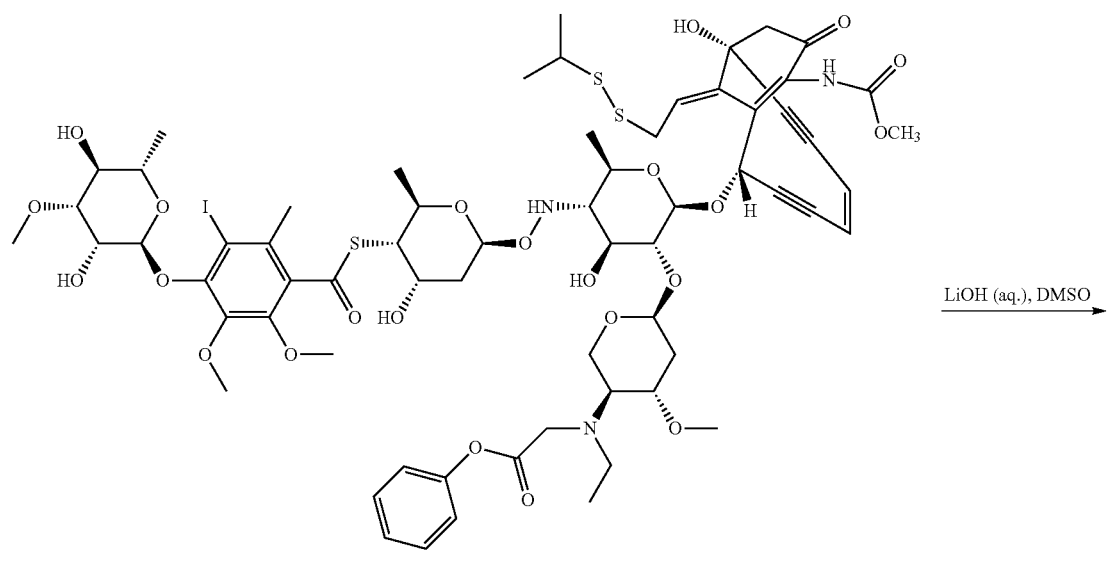

-continued

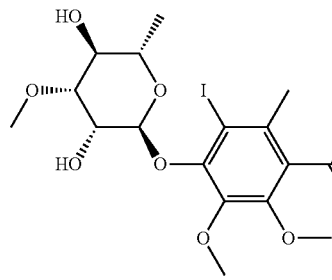 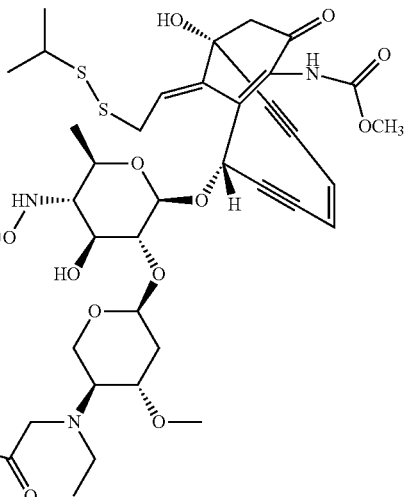

P50

Step 1: Synthesis of phenyl {[(3S,4S,6S)-6-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydr oxy-6-methyltetrahydro-2H-pyran-2-yl}oxy)amino]-4-hydroxy-2-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-6-methyltetrahydro-2H-pyran-3-yl]oxy}-4-methoxytetrahydro-2H-pyran-3-yl](ethyl)amino}acetate Phenyl bromoacetate (149 mg, 0.695 mmol) was added to a solution of S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,5Z,9R,13E)-9-hydroxy-12-[(methoxycarbonyl)amino]-11-oxo-13-[2-(propan-2-yl disulfanyl)ethylidene]bicyclo[7.3.1]trideca-1 (12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P1) (99.0 mg, 0.070 mmol), N,N-diisopropylethylamine (89.8 mg, 0.695 mmol, 124 uL) in N,N-dimethylacetamide (3000 uL) and stirred at 35° C. After 3 days the reaction mixture was purified by reverse phase HPLC (Method A). Product containing fractions were lyophilized to obtain the desired product (76.9 mg, 71%). LC-MS m/z 1498.4 [M+H$^+$]; retention time=4.71 minutes (Method 1).

Step 2: Synthesis of {[(3S,4S,6S)-6-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-m ethyltetrahydro-2H-pyran-2-yl}oxy)amino]-4-hydroxy-2-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-6-methyltetrahydro-2H-pyran-3-yl]oxy}-4-methoxytetrahydro-2H-pyran-3-yl](ethyl)amino}acetic Acid An aqueous solution of lithium hydroxide (1.51 mg, 62.9 umol, 62.9 uL, 1.0 M) was added to a solution of phenyl {[(3S,4S,6S)-6-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydr oxy-6-methyltetrahydro-2H-pyran-2-yl}oxy)amino]-4-hydroxy-2-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-6-methyltetrahydro-2H-pyran-3-yl]oxy}-4-methoxytetrahydro-2H-pyran-3-yl](ethyl)amino}acetate (24.5 mg, 15.7 umol) in dimethylsulfoxide (1000 uL) and water (300 uL) After 30 minutes the reaction mixture was quenched with acetic acid (4.72 mg, 78.6 umol, 4.50 uL), then purified by reverse phase HPLC (Method A). Product containing fractions were lyophilized to obtain 4.9 mg (22%) of the desired product (P50). LC-MS m/z 1422.30 [M+H$^+$]; retention time=2.69 minutes (Method 6).

Preparation of methyl {[(3S,4S,6S)-6-{[(2R,3R,4S, 5S,6R)-5-[({(2S,4S,5S,6R)-5-[(4-{[(2S,3R,4R,5S, 6S)-3,5-di hydroxy-4-methoxy-6-methyltetrahydro-2H-pyran-2-yl]oxy}-3-iodo-5,6-dimethoxy-2-methyl benzoyl)sulfanyl]-4-hydroxy-6-methyltetrahydro-2H-pyran-2-yl}oxy)amino]-4-hydroxy-2-{[(2S,9R, 13E)-9-hydroxy-12-[(methoxycarbonyl)amino]-11-oxo-13-[2-(propan-2-yldisulfanyl)ethylidene]bicycle [7.3.1]trideca-1(12),5-diene-3,7-diyn-2-yl]oxy}-6-methyltetrahydro-2H-pyran-3-yl]oxy}-4-methoxytet-rahydro-2H-pyran-3-yl](ethyl)amino}acetate (P51)

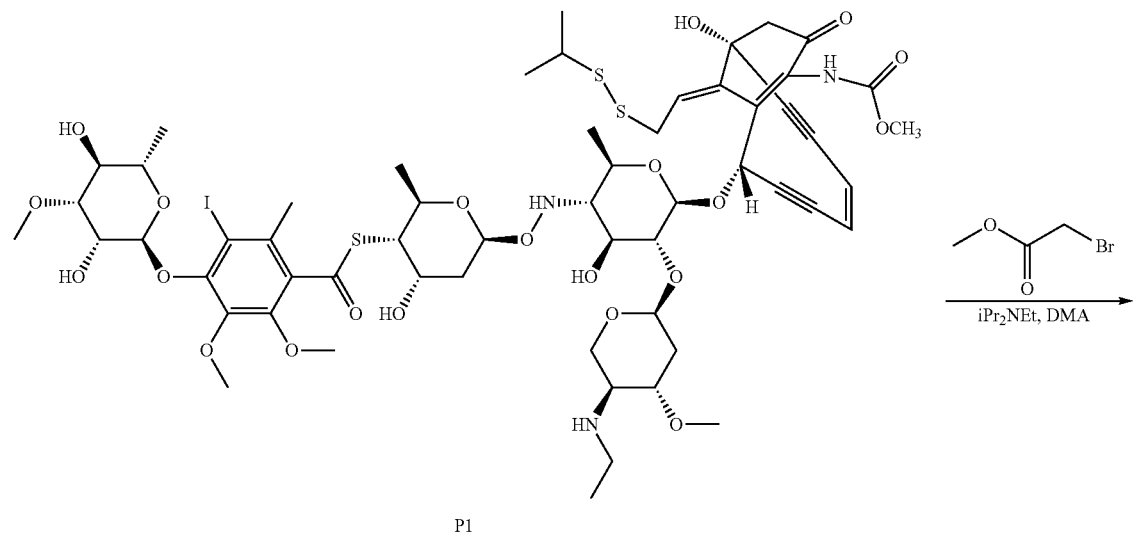

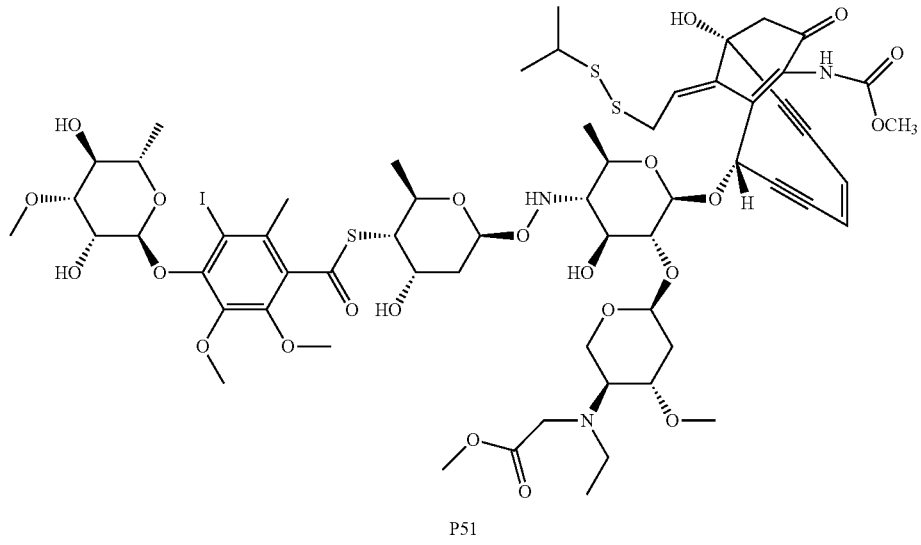

Methyl bromoacetate (41 mg, 0.267 mmol) was added to a solution of S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,5Z,9R,13E)-9-hydroxy-12-[(methoxycarbonyl)amino]-11-oxo-13-[2-(propan-2-yl disulfanyl)ethylidene]bicyclo[7.3.1]trideca-1 (12), 5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5, 6-dimethoxy-2-methylbenzenecarbothioate (P1) (19 mg, 0.013 mmol) and N,N-diisopropylethylamine (69 mg, 0.534 mmol, 95 uL) in N,N-dimethylacetamide (600 uL) and the mixture was stirred at 35° C. After 24 hours the reaction mixture was purified directly by reverse phase HPLC (Method A). Product containing fractions were lyophilized to obtain 76.9 mg (71%) of the desired product (P51). LC-MS m/z 1436.5 [M+H$^+$]; retention time=0.88 minutes (Method 12).

Preparation of S-[(2R,3S,4S,6S)-6-({[(2R,3S,4S,5R, 6R)-5-{[(2S,4S,5S)-5-(ethylamino)-4-methoxytetra- hydro-2H-pyran-2-yl]oxy}-4-hydroxy-6-{[(2S,9R, 13E)-9-hydroxy-12-[(methoxycarbonyl)amino]-13- (2-{[(2R)-1-{[(4-methyl-2-oxo-2H-chromen-7-yl) carbamoyl]oxy}propan-2-yl]disulfanyl}ethylidene)- 11-oxobicyclo[7.3.1]trideca-1(12),5-diene-3,7-diyn- 2-yl]oxy}-2-methyltetrahydro-2H-pyran-3-yl] amino}oxy)-4-hydroxy-2-methyltetrahydro-2H- pyran-3-yl] 4-{[(2S,3R,4R,5S,6S)-3,5-dihydroxy-4- methoxy-6-methyltetrahydro-2H-pyran-2-yl]oxy}-3- iodo-5,6-dimethoxy-2-methyl benzenecarbothioate (P52)

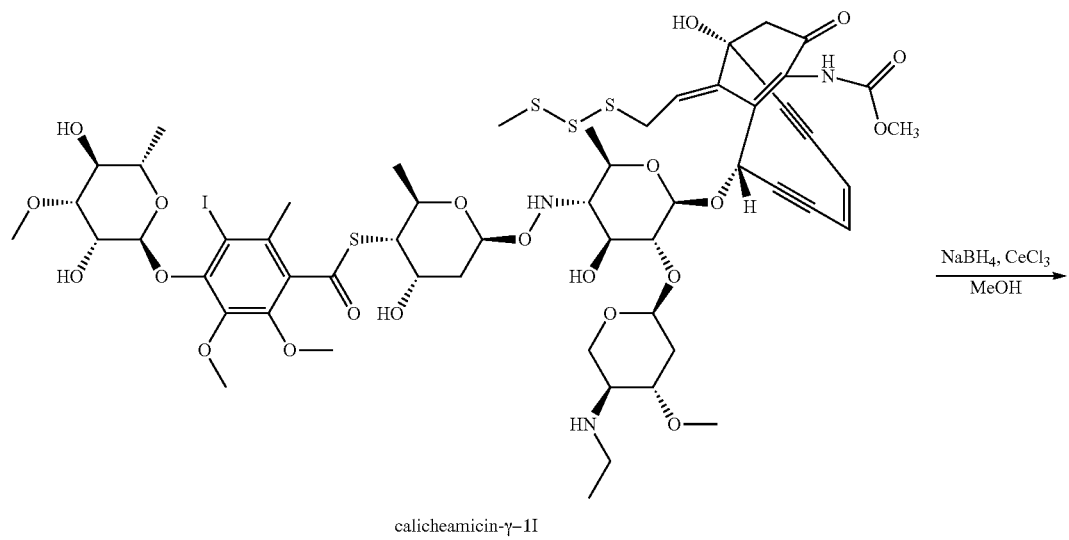

calicheamicin-γ–1I

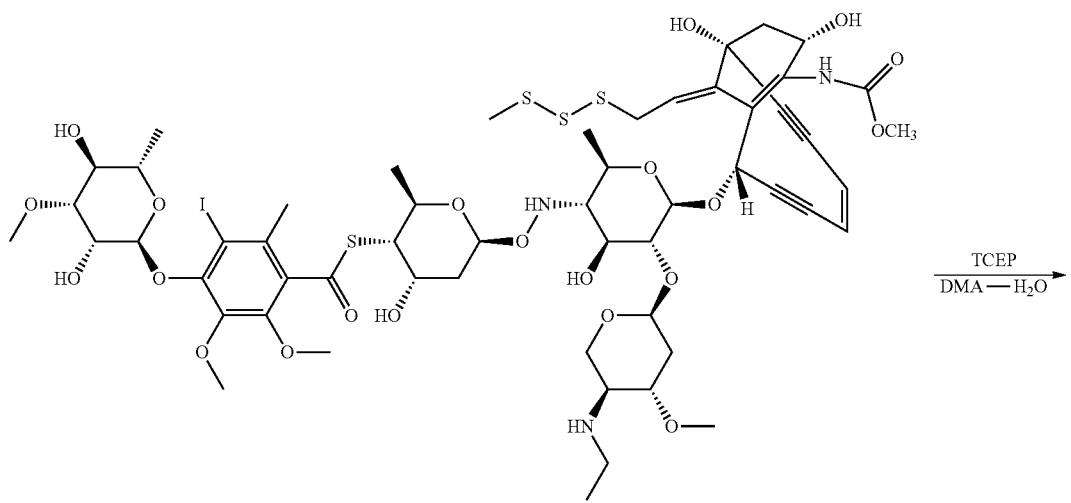

I17

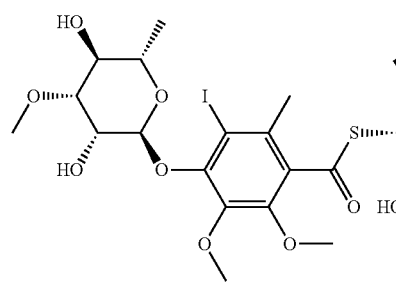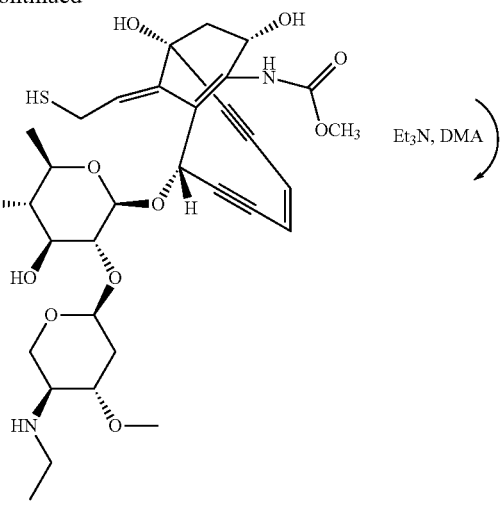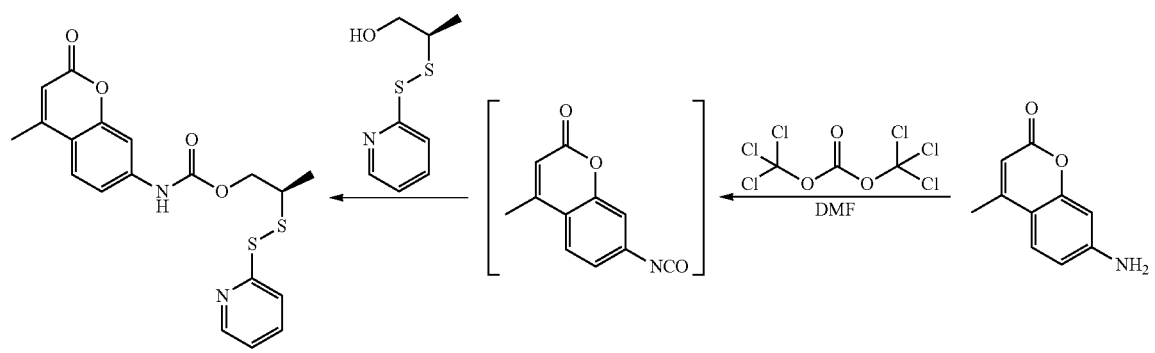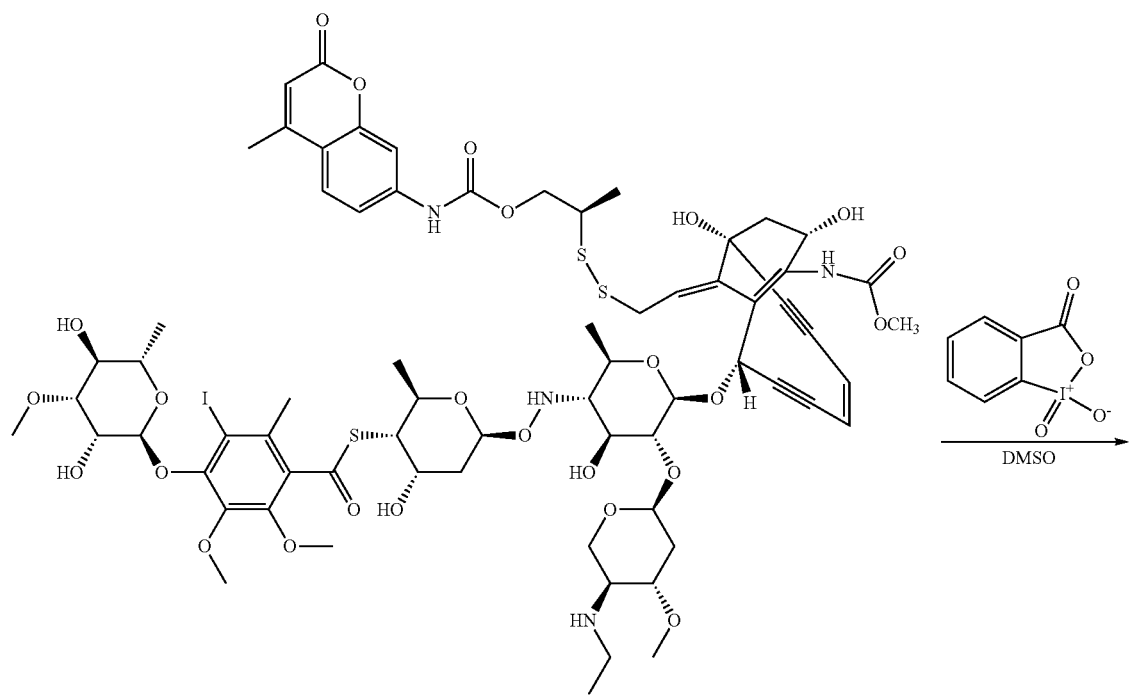

-continued

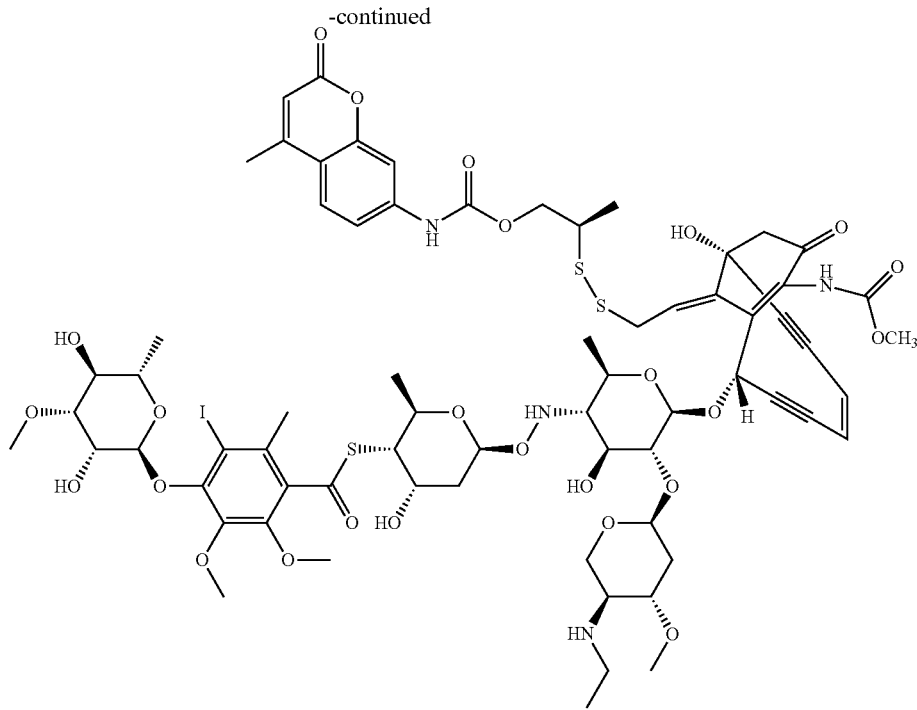

P52

Step 1: Synthesis of S-[(2R,3S,4S,6S)-6-({[(2R,3S,4S,5R,6R)-6-{[(2S,9R,11S, 13E)-9,11-dihydroxy-12-[(methoxycarbonyl)amino]-13-[2-(methyltrisulfanyl)ethylidene]bicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate A solution of sodium borohydride (2.76 mg, 0.0693 mmol) and cerium (III) chloride heptahydrate (51.6 mg, 0.139 mmol) in methanol (400.0 uL) was added to S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,5Z, 9R, 13E)-9-hydroxy-12-[(methoxycarbonyl)amino]-13-[2-(methyltrisulfanyl)ethylidene]-11-oxobicyclo[7.3.1]trideca-1 (12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate [calicheamicin-$\gamma^1_1$] (50.5 mg, 0.0370 mmol). After 2 h, the reaction mixture was purified by reverse phase HPLC (Method F). Product containing fractions were lyophilized to provide 18.8 mg of the desired product. LC-MS m/z 1370.3 [M+H$^+$]; retention time=5.5 minutes (Method 7).

Step 2: Synthesis of S-[(2R,3S,4S,6S)-6-({[(2R,3S,4S,5R,6R)-6-{[(2S,9R,11S, 13E)-9,11-dihydroxy-12-[(methoxycarbonyl)amino]-13-(2-sulfanylethylidene)bicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate A tris(2-carboxyethyl)phosphine solution in water (30 mg, 100 umol, 200 uL, 0.5 M) was added to a solution of S-[(2R,3S,4S,6S)-6-({[(2R,3S,4S,5R,6R)-6-{[(2S,9R,11S, 13E)-9,11-dihydroxy-12-[(methoxycarbonyl)amino]-13-[2-(methyltrisulfanyl)ethylidene]bicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (18.8 mg, 13.1 μmol) in N,N-dimethylacetamide (400 μL) and 7.4 pH phosphate buffer solution (200 μL). After 15 minutes, the reaction mixture was purified by reverse phase HPLC (Method F). Product containing fractions were lyophilized to provide 11.1 mg of the desired product. LC-MS m/z 1292.3 [M+H$^+$]; retention time=2.2 minutes (Method 8).

Step 3: Synthesis of (2R)-2-(pyridin-2-yldisulfanyl)propyl (4-methyl-2-oxo-2H-chromen-7-yl)carbamate N,N'-Diisopropylethylamine (114 mg, 150 uL, 0.863 mmol) was added to a solution of bis(trichloromethyl)

carbonate (128 mg, 0.432 mmol) and 7-amino-4-methylcoumarin (75.6 mg, 0.432 mmol) in N,N-dimethylformamide (2.0 mL) at ambient temperature. After 1 h, this mixture was added to a flask containing (R)-2-(pyridin-2-yldisulfanyl) propan-1-ol (43.6 mg, 0.217 mmol), and the reaction mixture was stirred for 2 h, then purified directly by reverse phase HPLC (Method M). Product containing fractions were lyophilized to provide 16.9 mg of (2R)-2-(pyridin-2-yldisulfanyl)propyl (4-methyl-2-oxo-2H-chromen-7-yl)carbamate Step 4: Synthesis of S-[(2R,3S,4S,6S)-6-({[(2R,3S,4S,5R,6R)-6-{[(2S,9R,11S, 13E)-9,11-dihydroxy-12-[(methoxycarbonyl)amino]-13-(2-{[(2R)-1-{[(4-methyl-2-oxo-2H-chromen-7-yl)carbamoyl]oxy}propan-2-yl]disulfanyl}ethylidene)bicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (2R)-2-(pyridin-2-yldisulfanyl)propyl (4-methyl-2-oxo-2H-chromen-7-yl)carbamate (1.98 mg, 0.00492 mmol) was dissolved in N,N-dimethylacetamide (100 uL) and N,N'-diisopropyl ethylamine (0.927 mg, 1.24 uL, 0.00703 mmol) and S-[(2R,3S,4S,6S)-6-({[(2R,3S,4S,5R,6R)-6-{[(2S,9R,11S, 13E)-9,11-dihydroxy-12-[(methoxycarbonyl)amino]-13-(2-sulfanylethylidene)bicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (1.9 mg, 0.0014 mmol). After 72 hours, the reaction mixture was purified by reverse phase HPLC (Method A). Product containing fractions were lyophilized to provide 1 mg of the desired product. LC-MS m/z 1583.4 [M+H$^+$]; retention time=2.4 minutes (Method 8).

Step 5: Synthesis of S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-13-(2-{[(2R)-1-{[(4-methyl-2-oxo-2H-chromen-7-yl)carbamoyl]oxy}propan-2-yl]disulfanyl}ethylidene)-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate 1-Hydroxy-1,2-benziodoxol-3(H)-one 1-oxide (1.36 mg, 2.43 umol) was added to a solution of S-[(2R,3S,4S,6S)-6-({[(2R,3S,4S,5R,6R)-6-{[(2S,9R,11S,13E)-9,11-dihydroxy-12-[(methoxycarbonyl)amino]-13-(2-{[(2R)-1-{[(4-methyl-2-oxo-2H-chromen-7-yl)carbamoyl]oxy}propan-2-yl]disulfanyl}ethylidene)bicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (non-preferred name) (1.0 mg, 0.6 μmol) in dimethylsulfoxide (200.0 μL). After 6 days, the reaction mixture was purified by reverse phase HPLC (Method A). Product containing fractions were lyophilized to provide 0.1 mg of the desired product (P52). LC-MS m/z 1581.4 [M+H$^+$]; retention time=5.8 minutes (Method 7).

Preparation of Calicheamicin Linker-Payoads

Example 1: Preparation of S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)-amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(propan-2-yldisulfanyl)ethyl idene]bicyclo-[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP1)

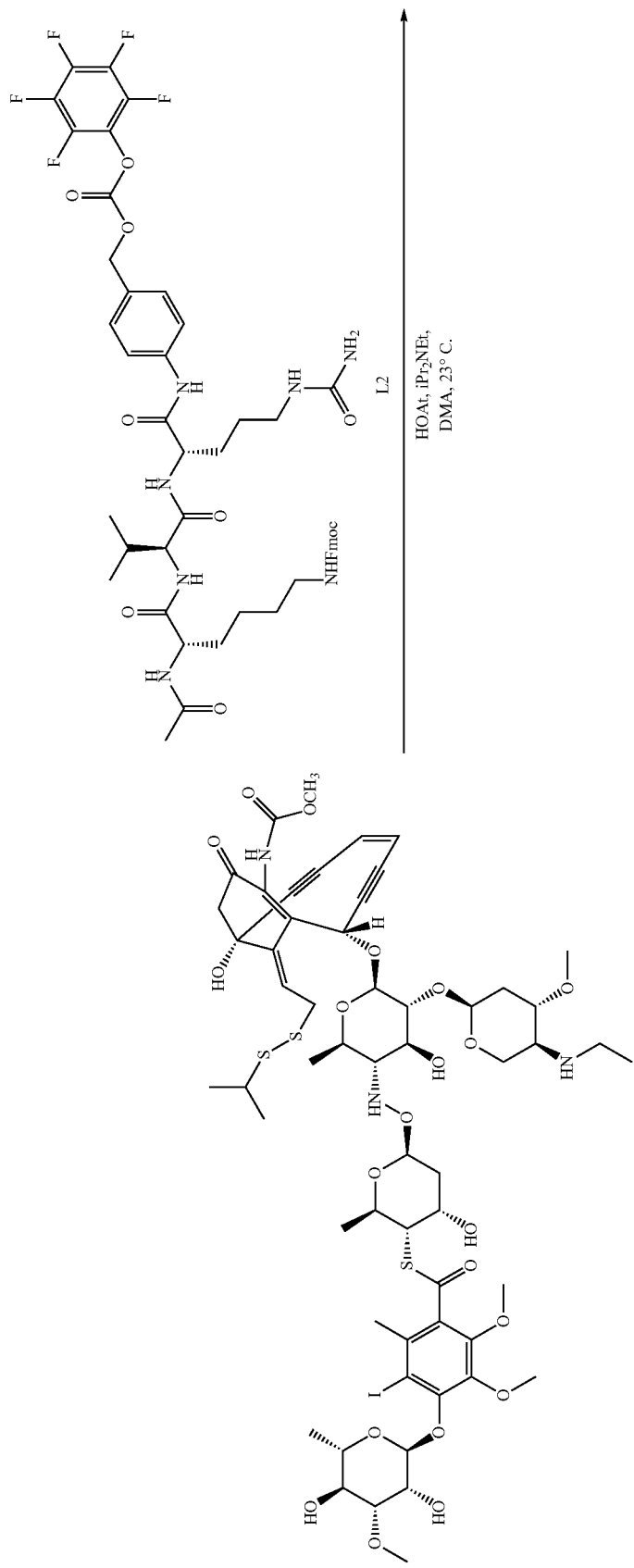

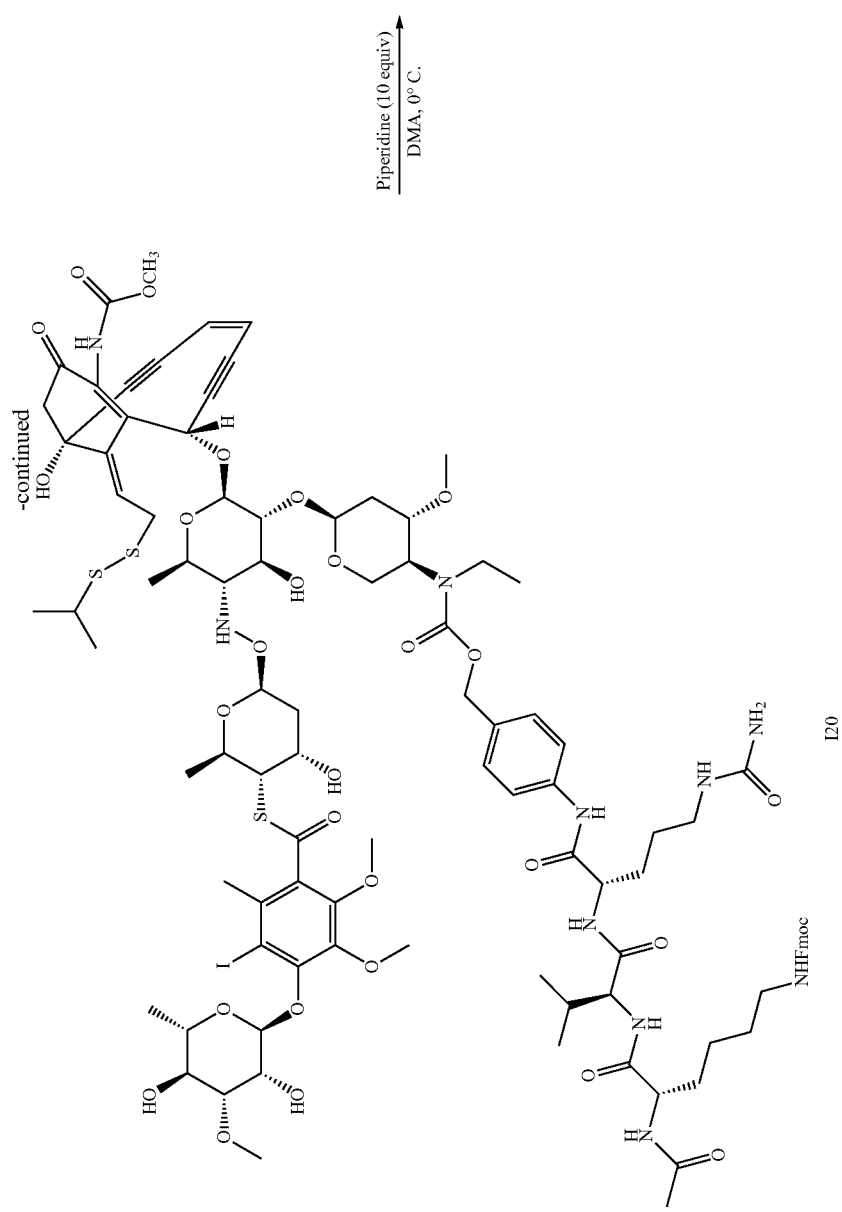

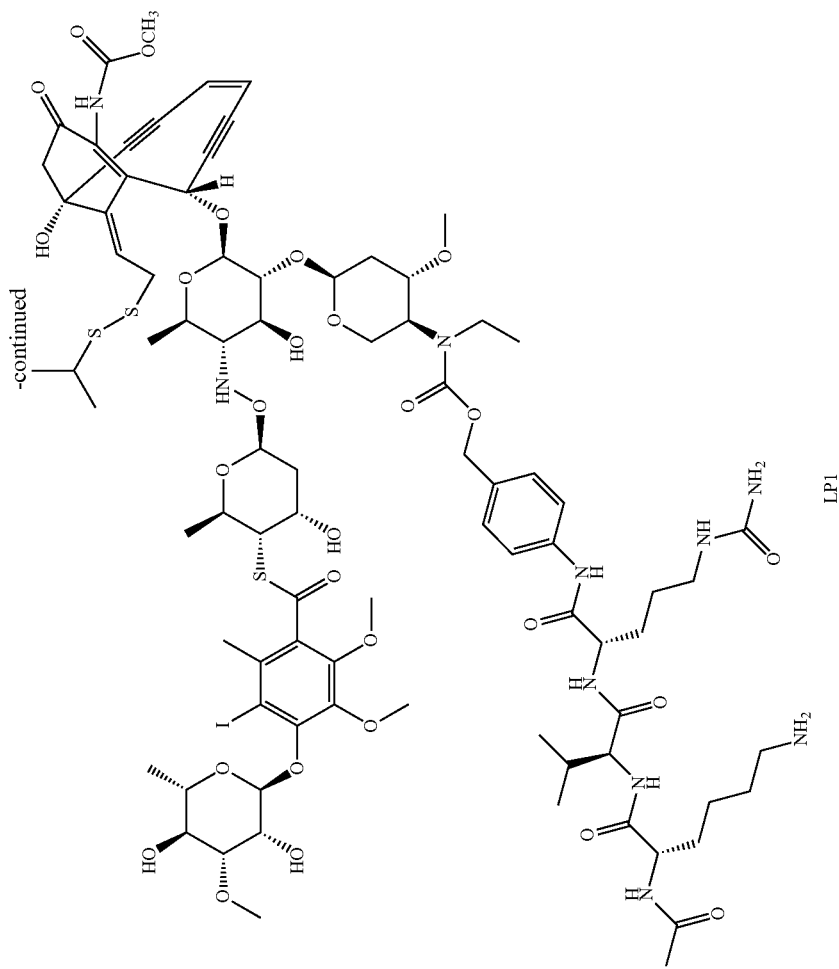

Step 1: Synthesis of S-[(2R,3S,4S,6S)-6-({[(2R,3S, 4S,5R,6R)-5-({(2S,4S,5S)-5-[{[(4-{[(9S,12S,15S)-9- (acetylamino)-15-[3-(carbamoylamino)propyl]-1- (9H-fluoren-9-yl)-3,10,13,16-tetraoxo-12-(propan-2- yl)-2-oxa-4,11,14-triazahexadecan-16-yl] amino}benzyl)oxy]carbonyl}(ethyl)amino]-4- methoxytetrahydro-2H-pyran-2-yl}oxy)-4-hydroxy- 6-{[(2S,9R, 13E)-9-hydroxy-12-[(methoxycarbonyl) amino]-11-oxo-13-[2-(propan-2-yldisulfanyl) ethylidene]bicyclo[7.3.1]trideca-1(12),5-diene-3,7- diyn-2-yl]oxy}-2-methyltetrahydro-2H-pyran-3-yl] amino}oxy)-4-hydroxy-2-methyltetrahydro-2H- pyran-3-yl] 4-{[(2S,3R,4R,5S,6S)-3,5-dihydroxy-4- methoxy-6-methyltetrahydro-2H-pyran-2-yl]oxy}-3- iodo-5,6-dimethoxy-2-methylbenzenecarbothioate N,N-Diisopropylethylamine (17.6 uL, 13.2 mg, 0.100 mmol) was added to a solution of S-[(2R,3S,4S6S)-6- ({[(2R,3S,4S,5R,6R)-5-({(2S,4S,5S)-5-[{[(4-{[(2S)-2- {[(2S)-2-{[(2S)-2-(acetylamino)-6-aminohexanoyl]amino}- 3-methylbutanoyl]amino}-5-(carbamoylamino)pentanoyl] amino}benzyl)oxy]carbonyl}(ethyl)amino]-4-methoxytet- rahydro-2H pyran-2-yl}oxy)-4-hydroxy-6- {[(2S,9R,13E)- 9-hydroxy-12-[(methoxycarbonyl)amino]-11-oxo-13-[2- (propan-2-yldisulfanyl)ethylidene]bicyclo[7.3.1]trideca-1 (12), 5-di ene-3,7-diyn-2-yl]oxy}-2-methyltetrahydro-2H- pyran-3-yl]amino}oxy)-4-hydroxy-2-methyltetrahydro-2H- pyran-3-yl] 4-{[(2S,3R,4R,5S,6S)-3,5-dihydroxy-4- methoxy-6-methyltetrahydro-2H-pyran-2-yl]oxy}-3-iodo-5, 6-dimethoxy-2-methylbenzenecarb- othioate (P1) (35.7 mg, 0.0251 mmol), $N^2$-acetyl-$N^6$-[(9H-fluoren-9- ylmethoxy)carbonyl]-L-lysyl-L-valyl-N-carbamoyl-N-[4- ({[(pentafluorophenoxy)carbonyl]oxy}methyl)phenyl]-L- ornithinamide (32.0 mg, 0.0326 mmol) and 3H-[1,2,3]tri- azolo[4,5-b]pyridin-3-ol (1.22 mg, 0.00877 mmol) in N,N- dimethylacetamide (251 μL). After 3 hours, another portion of 3H-[1,2,3]triazolo[4,5-b]pyridin-3-ol (1.22 mg, 0.00877 mmol) was added to the reaction mixture. After 24 hours, the reaction mixture was purified by reverse phase HPLC (Method B). Product containing fractions were lyophilized to obtain the desired product (37.8 mg). LC-MS m/z 2161.7 [M+H$^+$]; retention time=5.57 minutes (Method 1).

Step 2: Synthesis of S-[(2R,3S,4S,6S)-6-({[(2R,3S, 4S,5R,6R)-5-({(2S,4S,5S)-5-[{[(4-{[(2S)-2-{[(2S)- 2-{[(2S)-2-(acetylamino)-6-aminohexanoyl]amino}- 3-methylbutanoyl]amino}-5-(carbamoylamino) pentanoyl]amino}benzyl)oxy]carbonyl}(ethyl) amino]-4-methoxytetrahydro-2H-pyran-2-yl}oxy)-4- hydroxy-6-{[(2S,9R,13E)-9-hydroxy-12- [(methoxycarbonyl)amino]-11-oxo-13-[2-(propan-2- yldisulfanyl)ethylidene]bicyclo[7.3.1]trideca-1(12), 5-diene-3,7-diyn-2-yl]oxy}-2-methyltetrahydro-2H- pyran-3-yl]amino}oxy)-4-hydroxy-2- methyltetrahydro-2H-pyran-3-yl] 4-{[(2S,3R,4R,5S, 6S)-3,5-dihydroxy-4-methoxy-6-methyltetrahydro- 2H-pyran-2-yl]oxy}-3-iodo-5,6-dimethoxy-2- methylbenzenecarbothioate Piperidine (16.8 uL. 14.5 mg, 0.170 mmol) was added to a solution of S-[(2R,3S,4S,6S)-6-({[(2R,3S,4S,5R,6R)-5- ({(2S,4S,5S)-5-[{[(4-{[(9S,12S,15S)-9-(acetylamino)-15- [3-(carbamoylamino)propyl]-1-(9H-fluoren-9-yl)-3,10,13, 16-tetraoxo-12-(propan-2-yl)-2-oxa-4,11,14-triazahexade- can-16-yl]amino}benzyl)oxy]carbonyl}(ethyl)amino]-4- methoxytetrahydro-2H-pyran-2-yl}oxy)-4-hydroxy-6- {[(2S,9R, 13E)-9-hydroxy-12-[(methoxycarbonyl)amino]- 11-oxo-13-[2-(propan-2-yldisulfanyl)ethylidene]bicyclo [7.3.1]trideca-1(12),5-diene-3,7-diyn-2-yl]oxy}-2-methyl- tetrahydro-2H-pyran-3-yl]amino}oxy)-4-hydroxy-2- methyltetrahydro-2H-pyran-3-yl] 4-{[(2S,3R,4R,5S,6S)-3, 5-dihydroxy-4-methoxy-6-methyltetrahydro-2H-pyran-2- yl]oxy}-3-iodo-5,6-dimethoxy-2-methylbenzeneca- rbothioate (37.8, 0.0170 mmol) in N,N-dimethylacetamide (500 uL) at 0° C. After 2 hours, the reaction mixture was purified by reverse phase HPLC (Method C). Product con- taining fractions were lyophilized to provide 30.1 mg of the desired product (LP1). LC-MS m/z 1939.8 [M+H$^+$]; reten- tion time=3.99 minutes (Method 1).

Example 2: Preparation of S-[(2R,3S,4S,6S)-6- ({[(2R,3S,4S,5R,6R)-5-({(2S,4S,5S)-5-[{[(4-{[(2S)- 5-(carbamoylamino)-2-{[(2S)-2-{[6-(2,5-dioxo-2,5- dihydro-1H-pyrrol-1-yl)hexanoyl]amino}-3-meth- ylbutanoyl]amino}pentanoyl]amino}benz yl)oxy] carbonyl}(ethyl)amino]-4-methoxytetrahydro-2H- pyran-2-yl}oxy)-4-hydroxy-6-{[(2S,5Z,9R,13E)-9- hydroxy-12-[(methoxycarbonyl)amino]-11-oxo-13- [2-(propan-2-yldisulfanyl)ethylidene]bicyclo[7.3.1] tri deca-1 (12),5-diene-3,7-diyn-2-yl]oxy}-2- methyltetrahydro-2H-pyran-3-yl]amino}oxy)-4- hydroxy-2-methyltetrahydro-2H-pyran-3-yl]4-{[(2S, 3R,4R,5S,6S)-3,5-dihydroxy-4-methoxy-6- methyltetrahydro-2H-pyran-2-yl]oxy}-3-iodo-5,6- dimethoxy-2-methylbenzenecarbothioate (LP2)

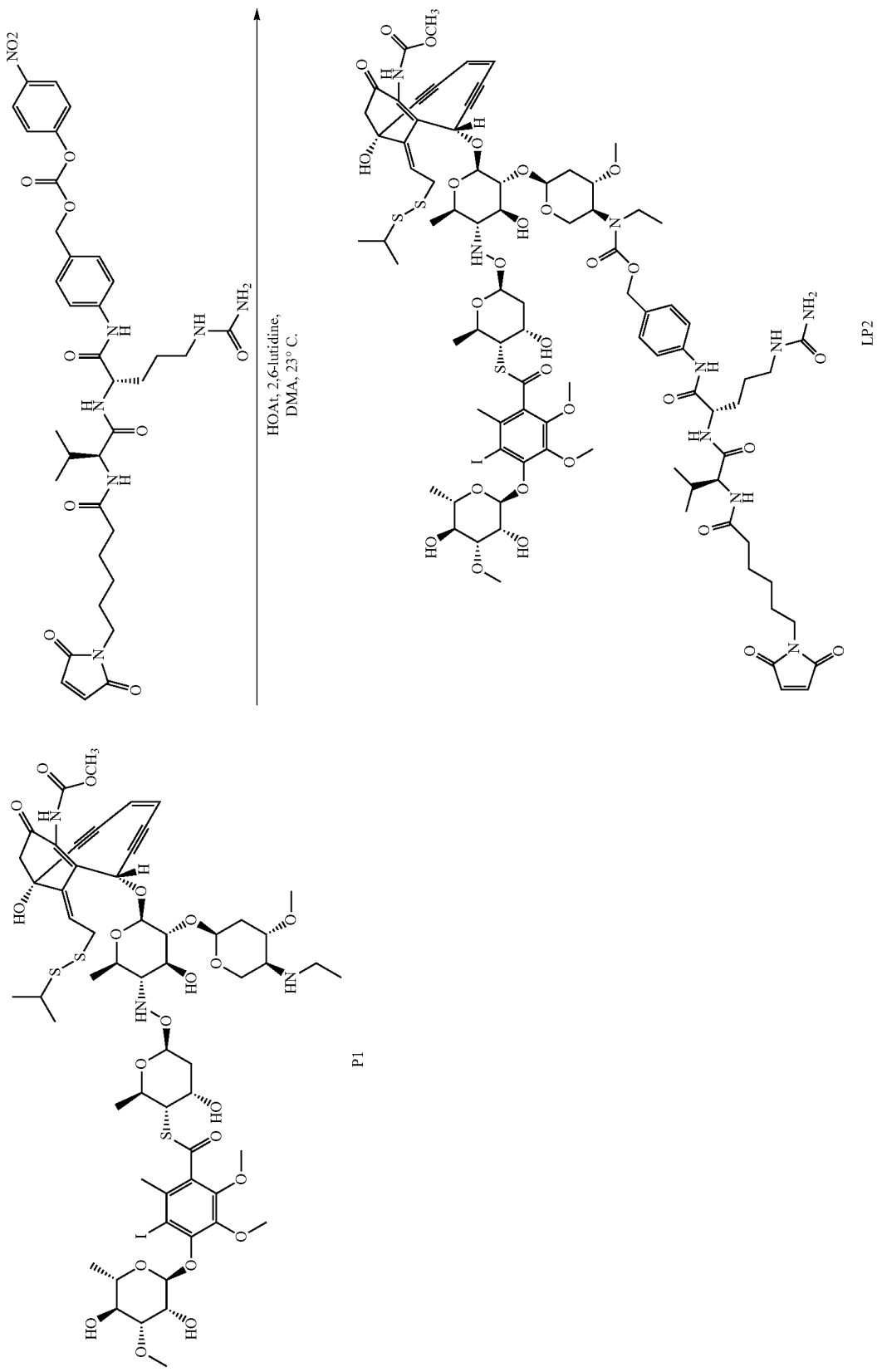

2,6-Lutidine (9 uL, 8.41 mg, 0.076 mmol) was added to a solution of S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P1)

(35.7 mg, 0.0251 mmol), N-[6-(2,5-dioxo-2,5-dihydro-1H-pyrrol-1-yl)hexanoyl]-L-valyl-N⁵-carbamoyl-N-[4-({[(4-nitrophenoxy)carbonyl]oxy}methyl)phenyl]-L-ornithinamide (14.2 mg, 0.0192 mmol) and 3H-[1,2,3]triazolo[4,5-b]pyridin-3-ol (2.67 mg, 0.0192 mmol) in N,N-dimethylacetamide (300 uL). After 24 hours, the reaction mixture was purified by reverse phase HPLC (Method I). Product containing fractions were lyophilized to obtain 7.6 mg of the desired product (LP2). LC-MS m/z 1964 [M+H⁺]; retention time=1.8 minutes (Method 5).

Example 3: Preparation of S-[(2R,3S,4S,6S)-6-({[(2R,3S,4S,5R,6R)-5-({(2S,4S,5S)-5-[(21-amino-4,7,10,13,16,19-hexaoxahenicos-1-yl)(ethyl)amino]-4-methoxytetrahydro-2H-pyran-2-yl}oxy)-6-{[(2S,9R,13E)-13-[2-(tert-butyldisulfanyl) ethylidene]-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP3)

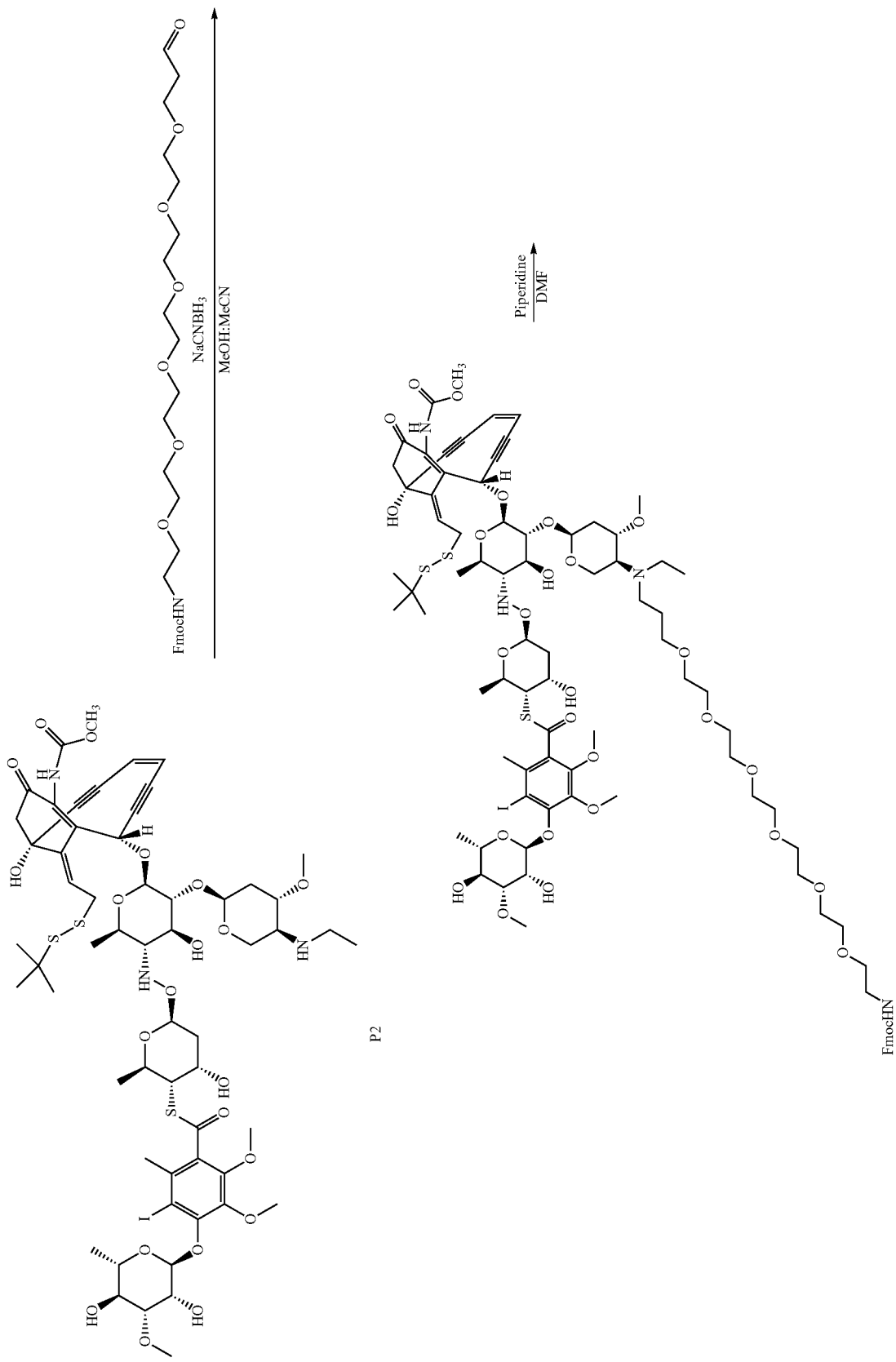

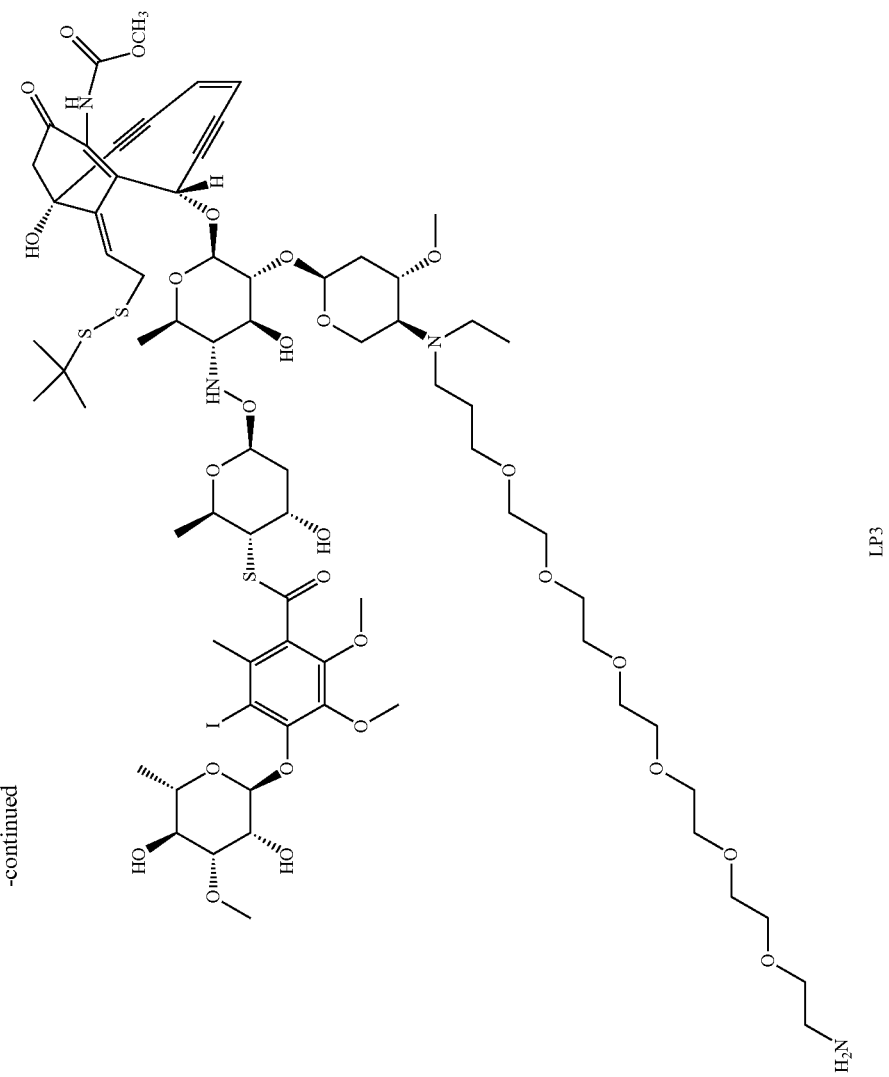

Step 1: Synthesis of S-[(2R,3S,4S,6S)-6-({[(2R,3S,4S,5R,6R)-6-{[(2S,9R,13E)-13-[2-(tert- butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2 S,4S,5S)-5-{ethyl[1-(9H-fluoren-9-yl)-3-oxo-2,7,10,13,16,19,22-heptaoxa-4-azapentacosan-25-yl]amino}-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate Acetic acid (0.9 uL, 1 mg, 0.02 mmol) was added to a solution of 9H-fluoren-9-ylmethyl (21-oxo-3,6,9,12,15,18-hexaoxahenicos-1-yl)carbamate (8.7 mg, 0.016 mmol) and S-[(2R,3S,4S,6S)-6-({[(2R,3S,4S,5R,6R)-6-{[(2S,5Z,9R,13E)-13-[2-(tert-butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P2) (5.5 mg, 0.0040 mmol) in a methonal:acetonitrile (1:2) mixture. After 2 hours, sodium cyanoborohydride (2.6 mg, 0.040 mmol) was added to the reaction mixture. After 20 hours, the reaction mixture was purified by reverse phase HPLC (Method B). Product containing fractions were lyophilized to provide 2.6 mg of the desired product. LC-MS m/z 1921.6 [M+H$^+$]; retention time=5.79 min minutes (Method 3).

Step 2: Synthesis of S-[(2R,3S,4S,6S)-6-({[(2R,3S,4S,5R,6R)-5-({(2S,4S,5S)-5-[(21-amino-4,7,10,13,16,19-hexaoxahenicos-1-yl)(ethyl)amino]-4-methoxytetrahydro-2H-pyran-2-yl}oxy)-6-{[(2S,9R,13E)-13-[2-(tert-butyldisulfanyl) ethylidene]-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate Piperidine (2.0 uL, 1.7 mg, 0.020 mmol) was added to a solution of the S-[(2R,3S,4S,6S)-6-({[(2R,3S,4S,5R,6R)-6-{[(2S,9R,13E)-13-[2-(tert-butyldisulfanyl)ethylidene]-9-hydroxy-12-[(methoxycarbonyl)amino]-11-oxobicyclo [7.3.1]trideca-1(12),5-diene-3,7-diyn-2-yl]oxy}-5-{[(2S,4S,5S)-5-{ethyl[1-(9H-fluoren-9-yl)-3-oxo-2,7,10,13,16,19,22-heptaoxa-4-azapentacosan-25-yl]amino}-4-methoxytetrahydro-2H-pyran-2-yl]oxy}-4-hydroxy-2-methyltetrahydro-2H-pyran-3-yl]amino}oxy)-4-hydr oxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (2.6 mg, 0.0014 mmol) in N,N-dimethylformamide at 0° C. After 3 hours, the reaction mixture was purified by reverse phase HPLC (Method F). Product containing fractions were lyophilized to provide 2.6 mg of the desired product (LP3). LC-MS m/z 1699.6 [M+H$^+$]; retention time=1.37 minutes (Method 4).

Example 4: Preparation of S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]trideca-1 (12),5-diene-3,7-diyn-2-yl]oxy}-2-methyltetrahydro-2H-pyran-3-yl]amino}oxy)-4-hydroxy-2-methyltetrahydro-2H-pyran-3-yl]4-{[(2S,3R,4R,5S,6S)-3,5-di hydroxy-4-methoxy-6-methyltetrahydro-2H-pyran-2-yl]oxy}-3-iodo-5,6-dimethoxy-2-methylbenzenecarbothioate (LP4)

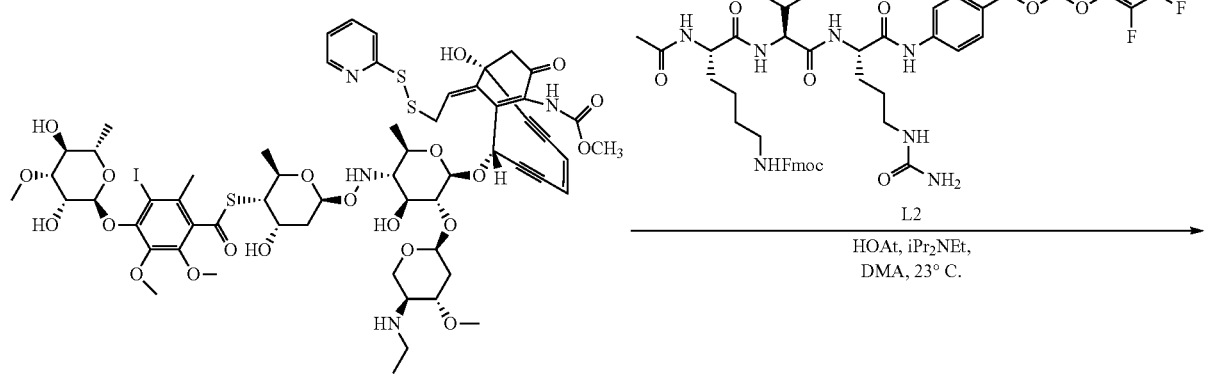

P4

L2

HOAt, iPr$_2$NEt, DMA, 23° C.

-continued
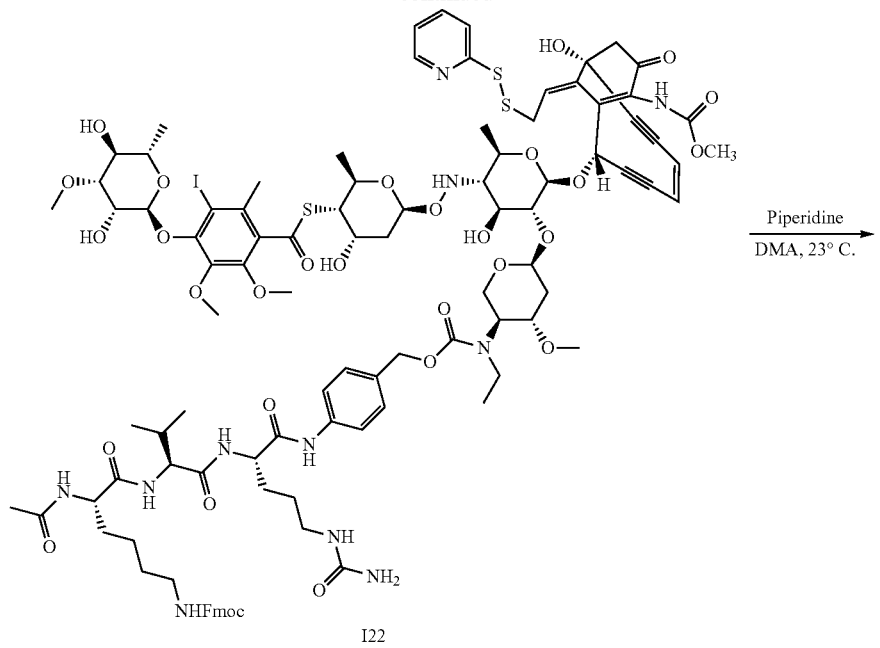
I22
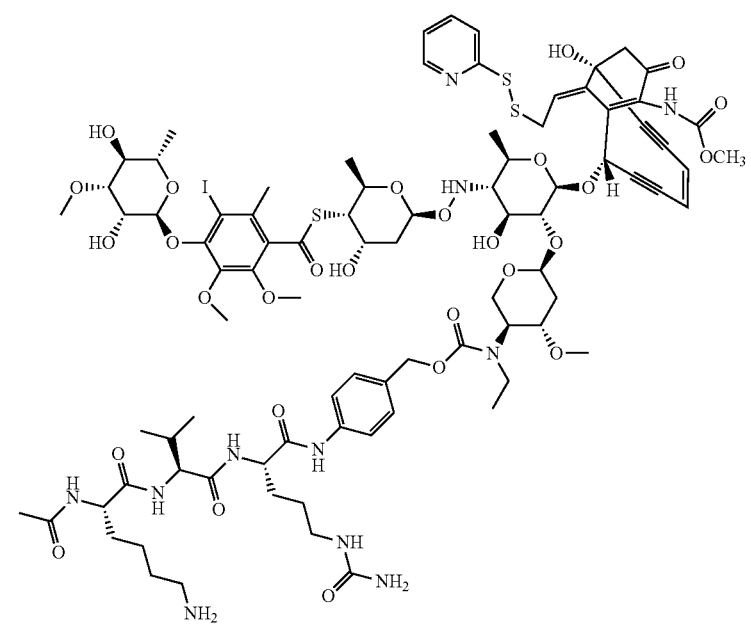
LP4

Step 1: Synthesis of S-[(2R,3S,4S,6S)-6-({[(2R,3S,4S,5R,6R)-5-({(2S,4S,5S)-5-[{[(4-{[(9S,12S,15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triazahexadecan-16-yl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate N,N-Diisopropylethylamine (13.1 uL, 9.83 mg, 0.0746 mmol) was added to a solution of S-[(2R,3,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (27.2 mg, 0.0186 mmol), $N^2$-acetyl-$N^6$-[(9H-fluoren-9-yl methoxy)carbonyl]-L-lysyl-L-valyl-$N^5$-carbamoyl-N-[4-({[(pentafluorophenoxy)carbonyl]oxy}methyl)phenyl]-L-ornithinamide (23.8 mg, 0.0242 mmol) and 3H-[1,2,3]triazolo[4,5-b]pyridin-3-ol (0.78 mg, 0.0056 mmol) in N,N-dimethylacetamide (186 uL). After 2 hours, another portion of 3H-[1,2,3]triazolo[4,5-b]pyridin-3-ol (0.8 mg, 0.006 mmol) was added to the reaction mixture. After 24 hours, the reaction mixture was purified by reverse phase HPLC (Method B). Product containing fractions were lyophilized to obtain the desired product (42.1 mg). LC-MS m/z 2196.8 [M+H$^+$]; retention time=5.30 minutes (Method 1).

Step 2: Synthesis of S-[(2R,3S,4S,6S)-6-({[(2R,3S,4S,5R,6R)-5-({(2S,4S,5S)-5-[{[(4-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate Piperidine (1.8 uL, 1.55 mg, 0.018 mmol) was added to a solution of S-[(2R,3S,4S,6S)-6-({[(2R,3S,4S,5R,6R)-5-({(2S,4S,5S)-5-[{[(4-{[(9S,12S,15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triazahexadecan-16-yl]amino}benzyl)oxy]carbonyl}(ethyl)amino]-4-methoxytetrahydro-2H-pyran-2-yl}oxy)-4-hydroxy-6-{[(2S,9R, 13E)-9-hydroxy-12-[(methoxycarbonyl)amino]-11-oxo-13-[2-(pyridin-2-yldisulfanyl) ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (8.2 mg, 0.0036 mmol) in N,N-dimethylacetamide (200 uL). After 1 hour, the reaction mixture was purified directly by reverse phase HPLC (Method C). Product containing fractions were lyophilized to provide 2.4 mg of the desired product (LP4). LC-MS m/z 1974 [M+H$^+$]; retention time=4.7 minutes (Method 3).

Example 5: Preparation of 2-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}benzoic acid (LP5)

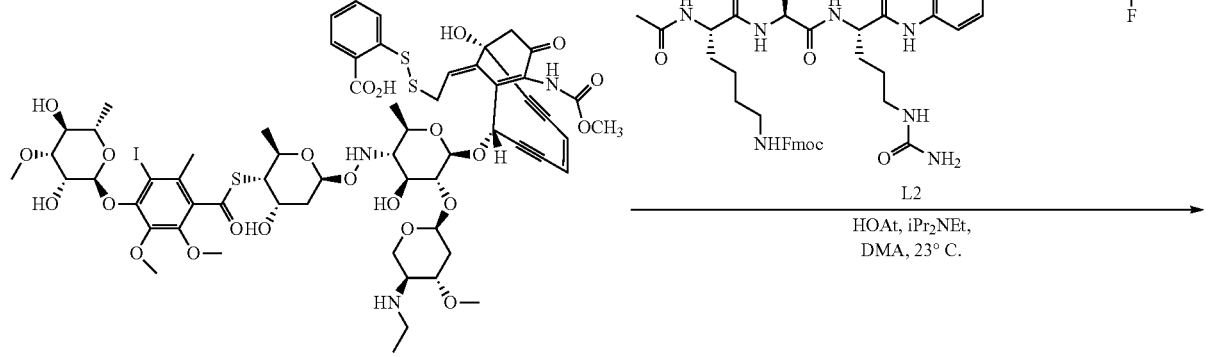

P3

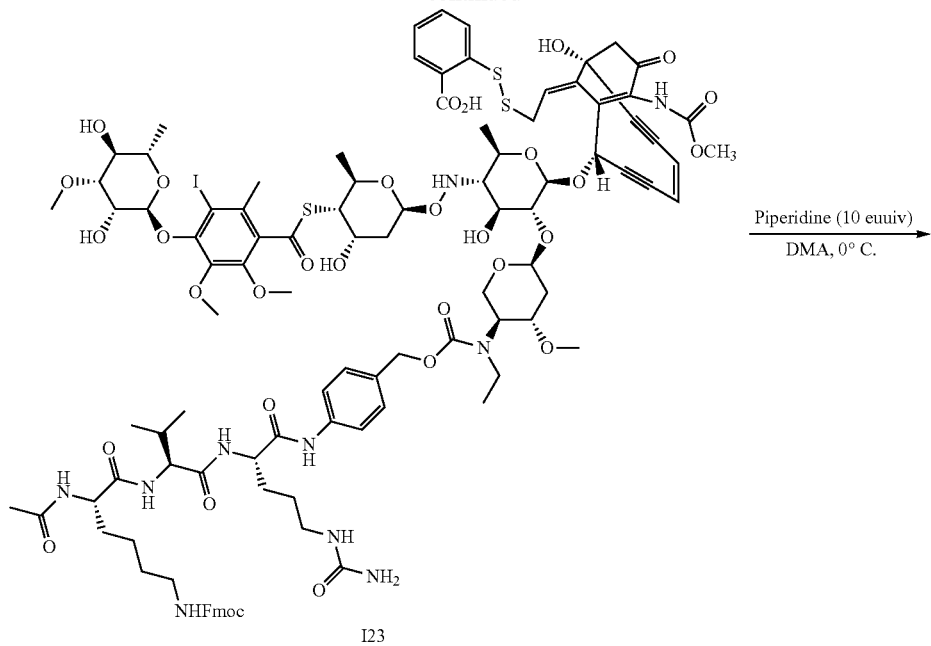
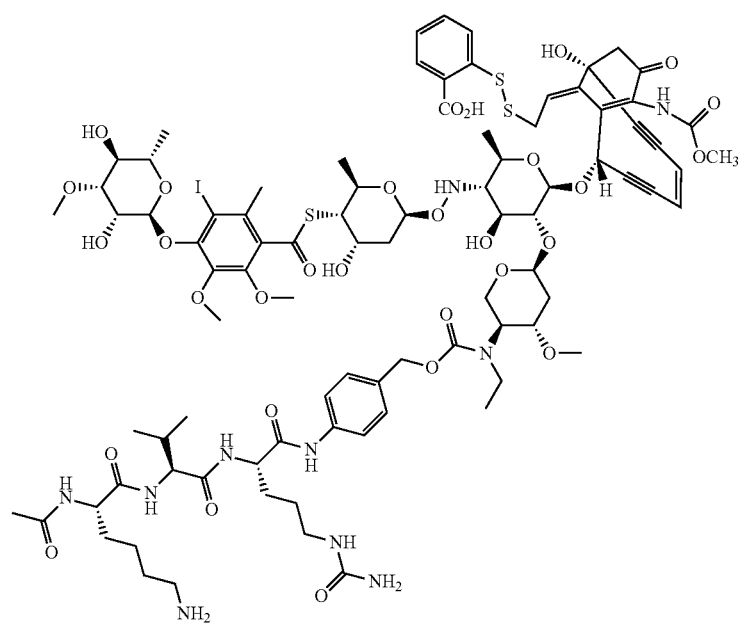

Step 1: Synthesis of 2-{[(2E)-2-{(1R,8S)-8-({(2R,3R,4S,5S,6R)-3-({(2S,4S,5S)-5-[{[(4-{[(9S,12S,15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triazahexadecan-16-yl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}benzoic acid N,N-Diisopropylethylamine (10.1 uL, 7.55 mg, 0.0572 mmol) was added to a solution of $N^2$-acetyl-$N^6$-[(9H-fluoren-9-ylmethoxy)carbonyl]-L-lysyl-L-valyl-$N^5$-carbamoyl-N-[4-({[(pentafluorophenoxy)carbonyl]oxy}methyl)phenyl]-L-ornithinamide (18.3 mg, 0.0186 mmol), 2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.1]trideca-4,9-diene-2,6-diyn-13-ylidene}ethyl]disulfanyl}benzoic acid (P3) (21.5 mg, 0.0143 mmol) and 3H-[1,2,3]triazolo[4,5-b]pyridin-3-ol (0.7 mg, 0.005 mmol) in N,N-dimethylacetamide (143 uL). After 3 hours, another portion of 3H-[1,2,3]triazolo[4,5-b]pyridin-3-ol (0.7 mg, 0.005 mmol) was added to the reaction mixture. After 24 hours, the reaction mixture was purified directly by reverse phase HPLC (Method B). Product containing fractions were lyophilized to obtain the desired product (25.8 mg). LC-MS m/z 2239.8 [M+H$^+$]; retention time=5.26 minutes (Method 1).

Step 2: Synthesis of 2-{[(2E)-2-{(1R,8S)-8-({(2R,3R,4S,5S,6R)-3-({(2S,4S,5S)-5-[{[(4-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}benzoic acid Piperidine (3.86 μL, 3.33 mg, 0.0391 mmol) was added to a solution of 2-{[(2E)-2-{(1R,8S)-8-({(2R,3R,4S,5S,6R)-3-({(2S,4S,5S)-5-[{[(4-{[(9R,12R, 15R)-9-(acetylamino)-15-[3-(carbamoylamino)propyl]-1-(9H-fluoren-9-yl)-3,10,13,16-tetraoxo-12-(propan-2-yl)-2-oxa-4,11,14-triazahexadecan-16-yl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}benzoic acid (9 mg, 0.004 mg) in N,N-dimethylacetamide at 0° C. After 2 hours, the reaction mixture was purified by reverse phase HPLC (Method C). Product containing fractions were lyophilized to provide 7.9 mg of the desired product (LP5). LC-MS m/z 2017.8 [M+H$^+$]; retention time=3.55 minutes (Method 1).

Example 6: Preparation of 2-{[(2E)-2-{(1R,8S)-8-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methyl benzoyl)sulfanyl]-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl}oxy)amino]-3-{[(2S,4S,5S)-5-(ethylamino)-4-methoxytetrahydro-2H-pyran-2-yl]oxy}-4-hydroxy-6-methyltetrahydro-2H-pyran-2-yl]oxy}-1-hydroxy-10-[(methoxycarbonyl)amino]-11-oxobicyclo[7.3.]trideca-4,9-diene-2,6-diyn-13-ylidene}ethyl]disulfanyl}-2-methylpropanoic acid (LP6)

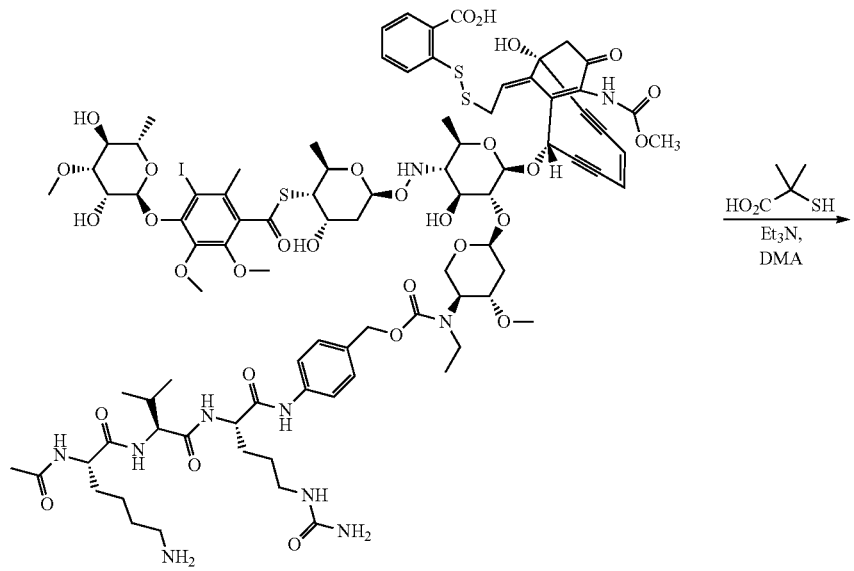

LP5

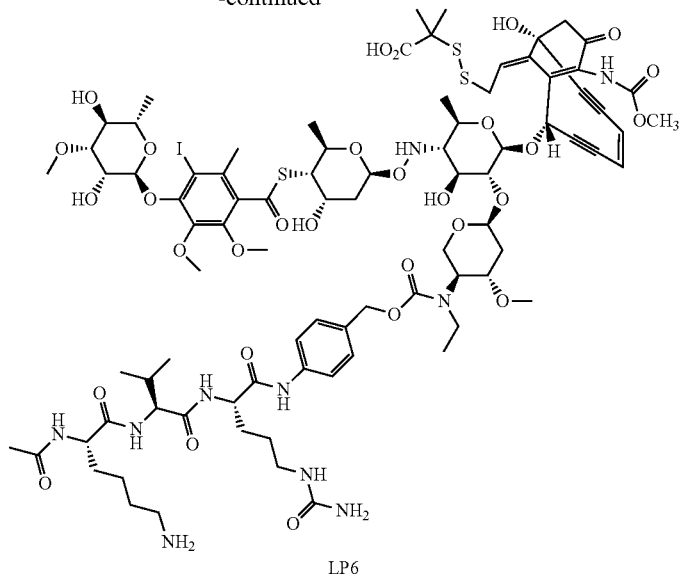

LP6

2-Methyl-2-sulfanylpropanoic acid (7.89 mg, 0.0591 mmol) was added to a solution of 2-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yloxy)amino]-4-hydroxy-6-methyltetrahydro-2H-pyran-2-yloxy)-1-hydroxy-10-[(methoxycarbonyl)amino]-11-oxobicyclo[7.3.1]trideca-4,9-diene-2,6-diyn-13-ylidene}ethyl]disulfanyl}benzoic acid (LP5) (12.3, 0.00592 mmol) and triethylamine (4.12 μL, 2.99 mm, 0.0296 mmol) in N,N-dimethylacetamide (592 uL). After 3 hours, the reaction mixture was purified directly by reverse phase HPLC (Method A). Product containing fractions were lyophilized to provide 10.3 mg of the desired produce (LP6). LC-MS m/z 1983.8 [M+H⁺]; retention time=5.15 min minutes (Method 3).

Example 7: Preparation of (2S)-5-({(2R)-3-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methyl benzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}-1-[(carboxymethyl)amino]-1-oxopropan-2-yl}amino)-2-amino-5-oxopentanoic acid (LP7)

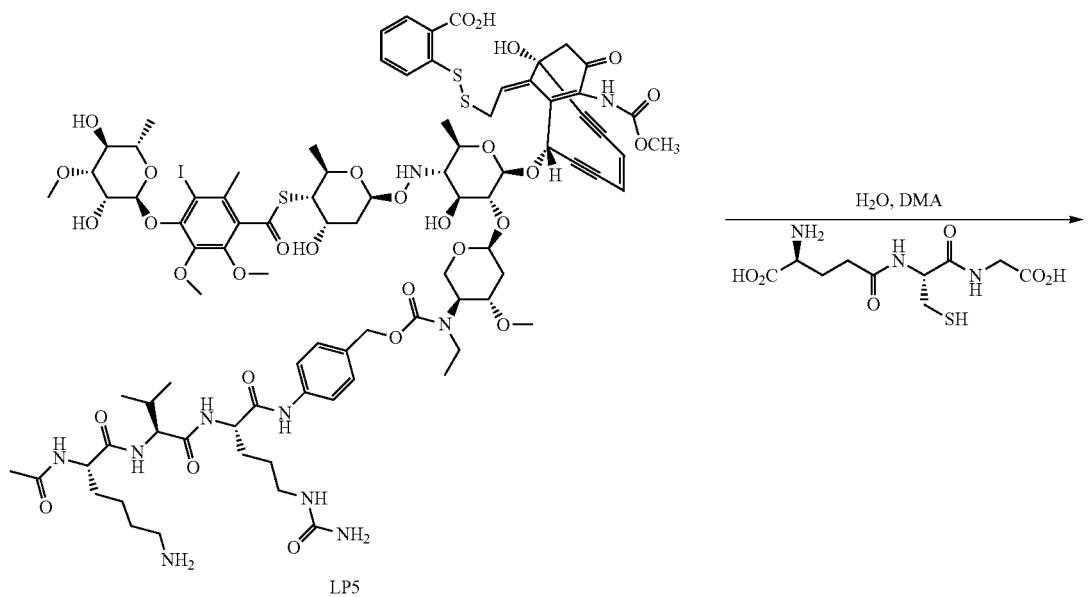

LP5

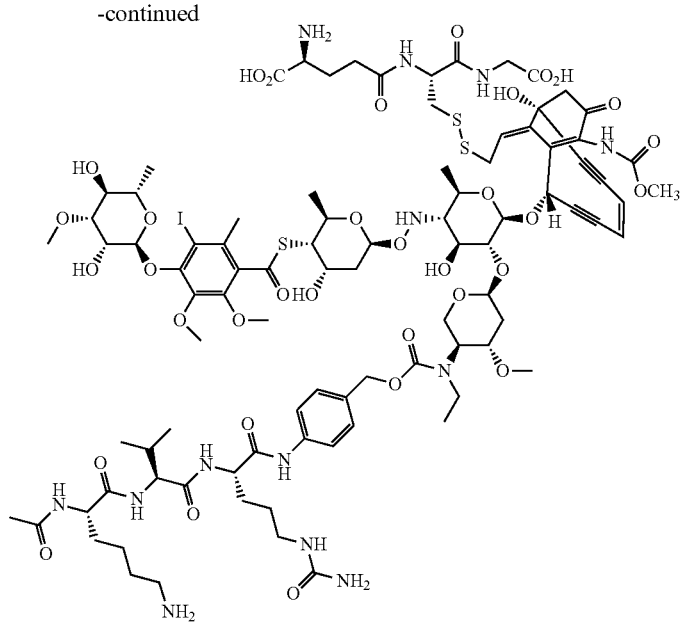

LP7

A solution of glutathione (6.0 mg, 0.019 mmol) in phosphate buffered aqueous saline solution (pH 7.4, 50 uL) was added to a solution of 2-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}benzoic acid (LP5) (4.0 mg, 0.002 mmol) in N,N-dimethylacetamide (400 uL) and water (200 uL) at 40° C. After 1 hour, the reaction mixture was purified directly by reverse phase HPLC (Method E). Product containing fractions were lyophilized to provide 3.1 mg of the desired product (LP7). LC-MS m/z 2171.0 [M+H+]; retention time=3.37 min minutes (Method 1).

417

Example 8: Preparation of 4-{[(2E)-2-{(1R,8S)-8-({(2R,3R,4S,5S,6R)-3-({(2S,4S,5S)-5-[{[(4-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10 O-[(methoxycarbonyl)amino]-11-oxobicyclo[7.3.1]trideca-4,9-diene-2,6-diyn-13-ylidene}ethyl]disulfanyl}benzoic acid

418

4-Sulfanylbenzoic acid (0.7 mg, 0.004 mmol) was added to a solution of S-[(2R,3S,4S,6S)-6-({[(2R,3S,4S,5R,6R)-5-({(2S,4S,5S)-5-[{[(4-{[(9S,12S, 15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triazahexadecan-16-yl]amino}benzyl)oxy]carbonyl}(ethyl)amino]-4-methoxytetrahydro-2H-pyran-2-yl}oxy)-4-hydroxy-6-{[(2S,9R, 13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (122)

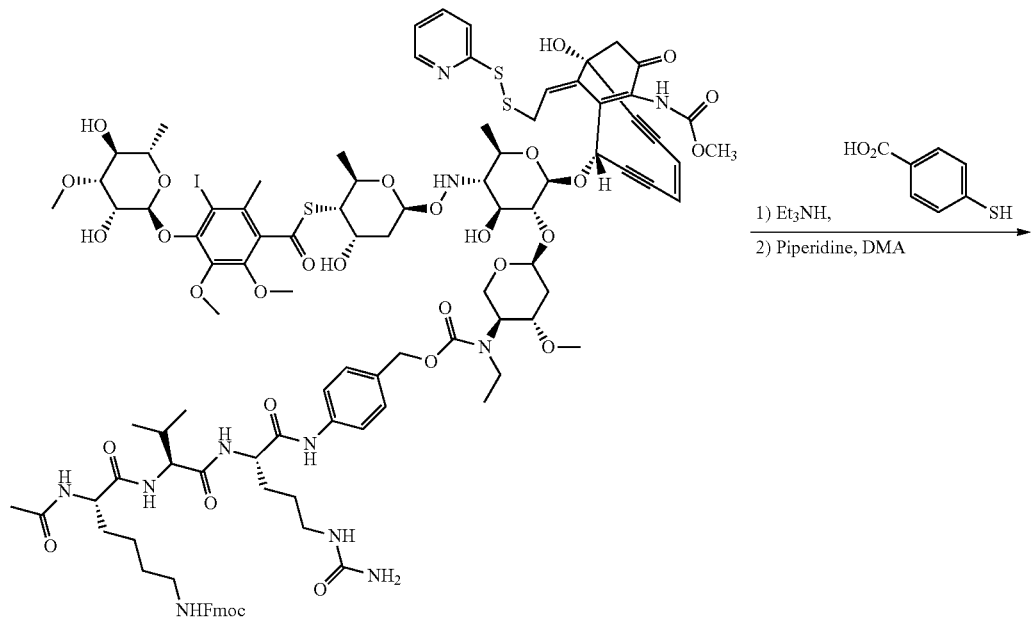

I22

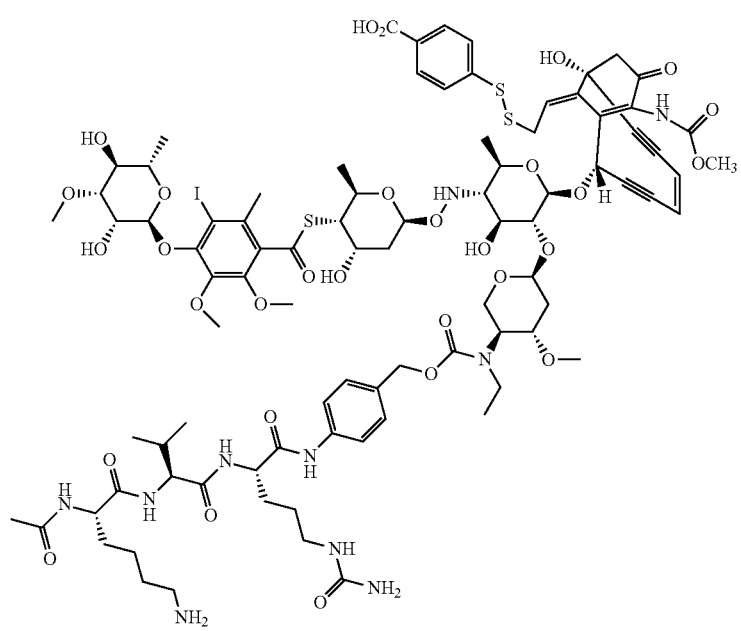

LP8

(8.1 mg, 0.0036 mmol) and triethylamine (2.5 μL, 1.8 mg, 0.018 mmol) in N,N-dimethylacetamide (179 uL). After 20 minutes, the reaction mixture was cooled to 0° C., and piperidine (3.5 uL, 3.1 mg, 0.036 mmol) was added to the reaction mixture. After 1.5 hours, the reaction mixture was purified directly by reverse phase HPLC (Method A). Product containing fractions were lyophilized to provide 4.1 mg of the desired product (LP8). LC-MS m/z 2017.8 [M+H$^+$]; retention time=3.86 minutes (Method 1).

Example 9: Preparation of S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-amino-hexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-1-oxo-13-[2-(phenyldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl]4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP9)

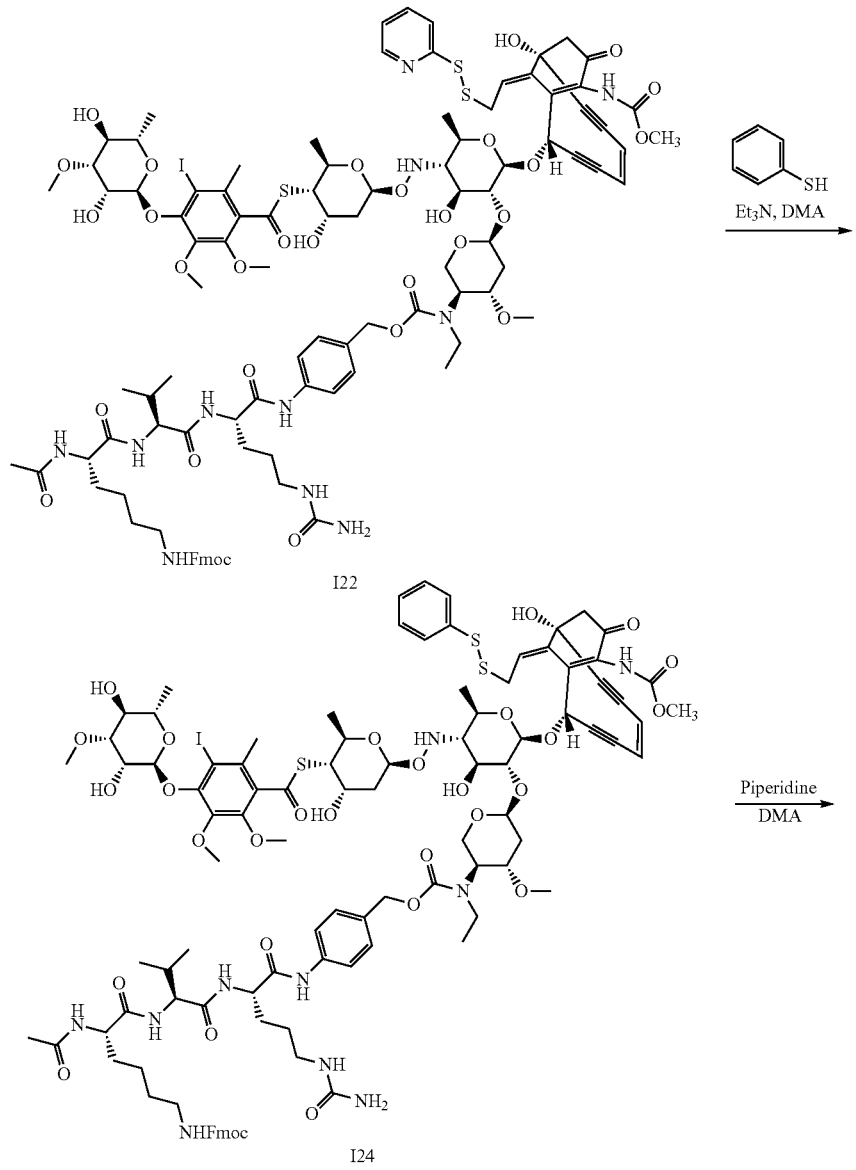

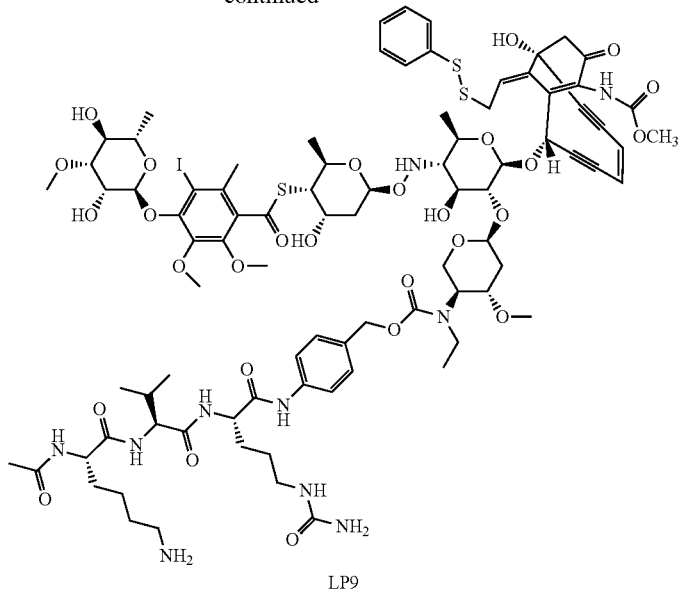

LP9

Step 1: Synthesis of S-[(2R,3S,4S,6S)-6-({[(2R,3S, 4S,5R,6R)-5-({(2S,4S,5S)-5-[{[(4-{[(9S,12S,15S)-9- (acetylamino)-15-[3-(carbamoylamino)propyl]-1- (9H-fluoren-9-yl)-3,10,13,16-tetraoxo-12-(propan-2- yl)-2-oxa-4,11,14-triazahexadecan-16-yl] amino}benzyl)oxy]carbonyl}(ethyl)amino]-4- methoxytetrahydro-2H-pyran-2-yl}oxy)-4-hydroxy- 6-{[(2S,9R,13E)-9-hydroxy-12-[(methoxycarbonyl) amino]-11-oxo-13-[2-(phenyldisulfanyl)ethylidene] bicyclo[7.3.1]trideca-1(12),5-diene-3,7-diyn-2-yl] oxy}-2-methyltetrahydro-2H-pyran-3-yl] amino}oxy)-4-hydroxy-2-methyltetrahydro-2H- pyran-3-yl] 4-{[(2S,3R,4R,5S,6S)-3,5-dihydroxy-4- methoxy-6-methyltetrahydro-2H-pyran-2-yl]oxy}-3- iodo-5,6-dimethoxy-2-methylbenzenecarbothioate A solution of benzenethiol (0.17 mg, 0.0015 mmol) in N,N-dimethylacetamide was added to a solution of S-[(2R, 3S,4S,6S)-6-({[(2R,3S,4S,5R,6R)-5-({(2S,4S,5S)-5-[{[(4- {[(9S,12S,15S)-9-(acetylamino)-15-[3-(carbamoylamino) propyl]-1-(9H-fluoren-9-yl)-3,10,13,16-tetraoxo-12-(pro- pan-2-yl)-2-oxa-4,11,14-triazahexadecan-16-yl]amino} benzyl)oxy]carbonyl}(ethyl)amino]-4-methoxytetrahydro- 2H-pyran-2-yl}oxy)-4-hydroxy-6-{[(2S,9R,13E)-9-hy- droxy-12-[(methoxycarbonyl)amino]-11-oxo-1342-(pyri- din-2-yldisulfanyl)ethylidene]bicyclo[7.3.1]trideca-1(12),5- diene-3,7-diyn-2-yl]oxy}-2-methyltetrahydro-2H-pyran-3- yl]amino}oxy)-4-hydroxy-2-methyltetrahydro-2H-pyran-3- yl] 4-{[(2S,3R,4R,5S,6S)-3,5-dihydroxy-4-methoxy-6- methyltetrahydro-2H-pyran-2-yl]oxy}-3-iodo-5,6- dimethoxy-2-methylbenzenecarbothioate (I22) (5 mg, 0.002 mmol) and triethylamine (0.62 µL, 0.45 mg, 0.004 mmol) in N,N-dimethylacetamide (100 uL). After 1 hour, the reaction mixture was purified by reverse phase HPLC (Method D). Product containing fractions were lyo- philized to provide 1.8 mg of the desired product. LC-MS m/z 2196.0 [M+H$^+$]; retention time=5.69 min minutes (Method 2).

Step 2: Synthesis of S-[(2R,3S,4S,6S)-6-({[(2R,3S, 4S,5R,6R)-5-({(2S,4S,5S)-5-[{[(4-{[(2S)-2-{[(2S)- 2-{[(2S)-2-(acetylamino)-6-aminohexanoyl]amino}- 3-methylbutanoyl]amino}-5-(carbamoylamino) pentanoyl]amino}benzyl)oxy]carbonyl}(ethyl) amino]-4-methoxytetrahydro-2H-pyran-2-yl}oxy)-4- hydroxy-6-{[(2S,9R,13E)-9-hydroxy-12- [(methoxycarbonyl)amino]-11-oxo-13-[2- (phenyldisulfanyl)ethylidene]bicyclo[7.3.1]trideca-1 (12),5-diene-3,7-diyn-2-yl]oxy}-2-methyltetrahydro- 2H-pyran-3-yl]amino}oxy)-4-hydroxy-2- methyltetrahydro-2H-pyran-3-yl] 4-{[(2S,3R,4R,5S, 6S)-3,5-dihydroxy-4-methoxy-6-methyltetrahydro- 2H-pyran-2-yl]oxy}-3-iodo-5,6-dimethoxy-2- methylbenzenecarbothioate Piperidine (0.8 µL, 0.7 mg, 0.008 mmol) was added to a solution of S-[(2R,3S,4S,6S)-6-({[(2R,3S,4S,5R,6R)-5- ({(2S,4S,5S)-5-[{[(4-{[(9S,12S,15S)-9-(acetylamino)-15- [3-(carbamoylamino)propyl]-1-(9H-fluoren-9-yl)-3,10,13, 16-tetraoxo-12-(propan-2-yl)-2-oxa-4,11,14-triazahexade- can-16-yl]amino}benzyl)oxy]carbonyl}(ethyl)amino]-4- methoxytetrahydro-2H-pyran-2-yl}oxy)-4-hydroxy-6- {[(2S,9R, 13E)-9-hydroxy-12-[(methoxycarbonyl)amino]- 11-oxo-13-[2-(phenyldisulfanyl)ethylidene]bicyclo[7.3.1] trideca-1(12),5-diene-3,7-diyn-2-yl]oxy}-2-methyltetra- hydro-2H-pyran-3-yl]amino}oxy)-4-hydroxy-2- methyltetrahydro-2H-pyran-3-yl] 4-{[(2S,3R,4R,5S,6S)-3, 5-dihydroxy-4-methoxy-6-methyltetrahydro-2H-pyran-2- yl]oxy}-3-iodo-5,6-dimethoxy-2-methylbenzenecar- bothioate (1.8 mg, 0.0008 mmol) in N,N-dimethylacetamide at 0° C. After 2 hours, the reaction mixture was purified directly by reverse phase HPLC (Method C). Product con- taining fractions were lyophilized to provide 1.2 mg of the desired product (LP9). LC-MS m/z 1973.9 [M+H$^+$]; reten- tion time=4.01 minutes (Method 2).

Example 10: Preparation of S-[(2R,3S,4S,6S)-6-({[(2R,3S,4S,5R,6R)-5-({(2S,4S,5S)-5-[({4-[({[(4-{[(2R)-2-{[(2R)-2-{[(2R)-2-{[(2R)-2-(acetylamino)-6-aminohexanoyl]amino}-3-methylbutanoyl]amino}-5-(carbamoylamino)pentanoyl]amino}benzyl)oxy]carbonyl}amino)methyl]phenyl}carbamoyl) (ethyl)amino]-4-methoxytetrahydro-2H-pyran-2-yl}oxy)-6-{[(2S,9R,13E)-13-[2-(tert-butyldisulfanyl)ethylidene]-9-hydroxy-12-[(methoxycarbonyl)amino]-11-oxobicyclo [7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP10)

N,N-Diisopropylethylamine (1.0 uL, 0.77 mg, 0.0059 mmol) and 2,6-lutidine (1.4 uL, 1.3 mg, 0.012 mmol) were added to a solution of $N^2$-acetyl-$N^6$-[(9H-fluoren-9-ylmethoxy)carbonyl]-L-lysyl-L-valyl-$N^5$-carbamoyl-N-[4-({[(4-nitrophenoxy)carbonyl]oxy}methyl)phenyl]-L-ornithinamide (7.3 mg, 0.0078 mmol), S-[(2R,3S,4S,6S)-6-({[(2R,3S,4S,5R,6R)-6-{[(2S,9R,13E)-13-[2-(tert-butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-{[(2 S,4S,5S)-5-(ethyl{[4-({[(9H-fluoren-9-ylmethoxy)carbonyl]amino}methyl)phenyl]carbamoyl}amino)-4-methoxytetrahydro-2H-pyran-2-yl]oxy}-4-hydroxy-2-methyltetrahydro-2H-pyran-3-yl]amino}oxy)-4-hydroxy-2-m ethyltetrahydro-2H-pyran-3-yl] 4-{[(2S,3R,4R,5S,6S)-3,5-dihydroxy-4-methoxy-6-methyltetrahydro-2H-pyran-2-yl]oxy-3-iodo-5,6-dimethoxy-2-methylbenzenecarbothioate (P49) (3.1 mg, 0.0020 mmol) and 3H-[1,2,3]triazolo[4,5-b]

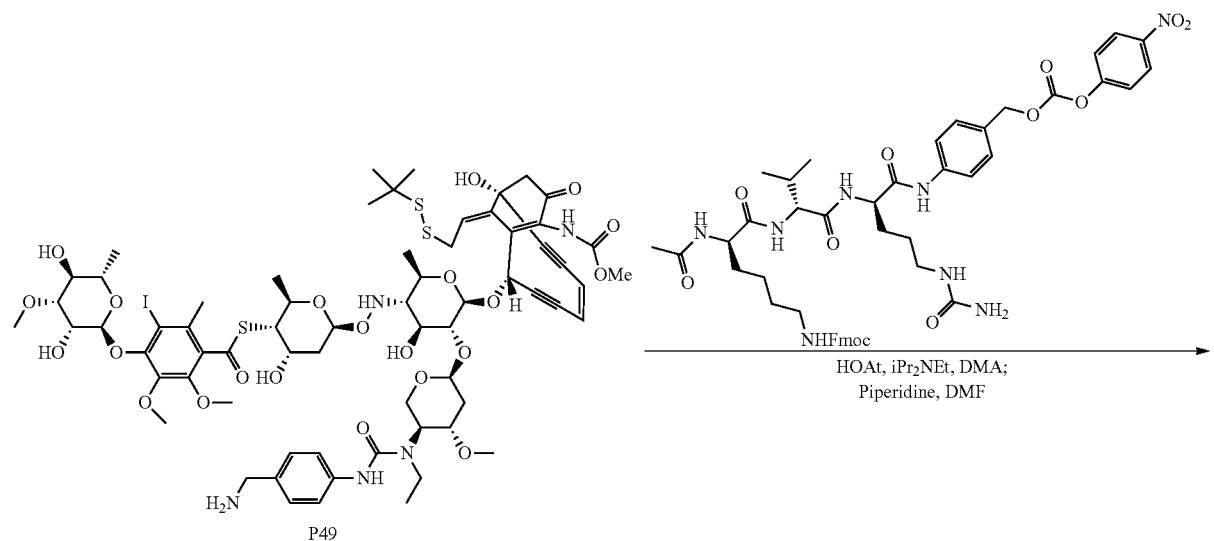

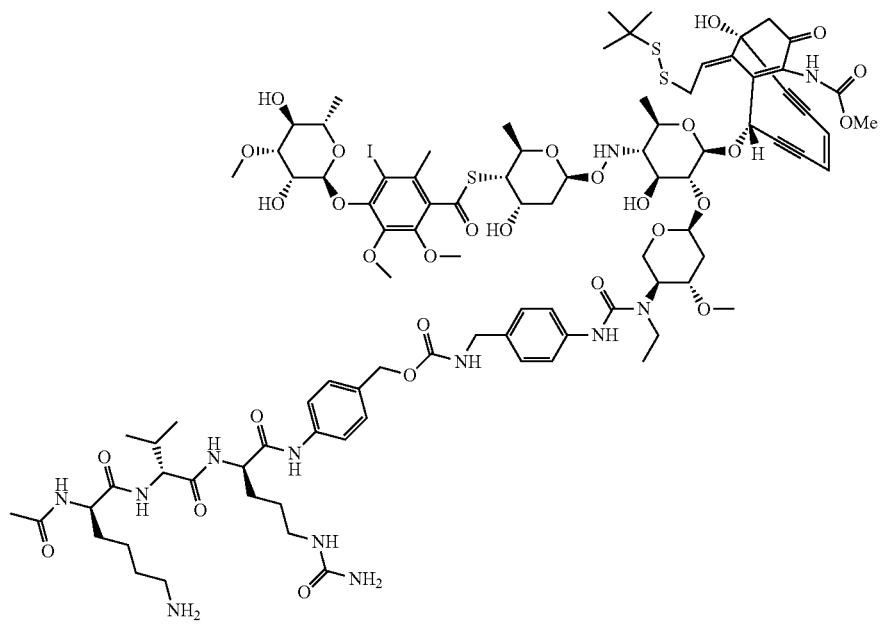

pyridin-3-ol (0.5 mg, 0.004 mmol) in N,N-dimethylacetamide (400 uL). After two hours, the reaction mixture was purified directly by reverse phase HPLC (Method D). Product containing fractions were lyophilized to afford the protected product. The solid residue was dissolved in N,N-dimethylformamide (500 uL). The reaction mixture was cooled to 0 C and piperidine (3.4 mL, 3.0 mg, 0.035 mmol) was added. After two hours, the reaction mixture was purified directly by reverse phase HPLC (Method C). Product containing fractions were lyophilized to provide 3.0 mg of the desired product (LP10). LC-MS m/z 2101.7 [M+H$^+$]; retention time=4.65 minutes (Method 3).

The following were prepared according to the procedure of Example 6 by reaction of the appropriate thiols with 2-{[(2E)-2-{(1R,8S)-8-({(2R,3R,4S,5S,6R)-3-({(2S,4S,5S)-5-[{[(4-{[(2S)- 2-{[(2S)-2-{[(2S)-2-(acetylamino)-6-aminohexanoyl]amino]-3-methylbutanoyl]amino]-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}benzoic acid (LP5), and/or alternatively by the procedures of Example 8 by reaction of the appropriate thiol with S-[(2R,3S,4S,6S)-6-({[(2R,3S,4S,5R,6R)-5-({(2S,4S,5S)-5-[{[(4-{[(9S,12S,15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triazahexadecan-16-yl]amino}benzyl)oxy]carbonyl}(ethyl)amino]-4-methoxytetrahydro-2H-pyran-2-yl}oxy)-4-hydroxy-6-{[(2S,9R, 13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (I22) followed by Fmoc deprotection:

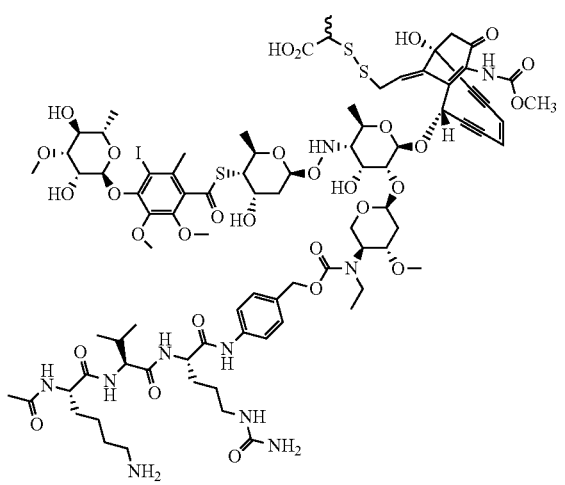 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)C(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@H]2O)C[C@@H]1OC]

Example 11: LP11: 2-{[(2E)-2-{(1R,8S)-8-({(2R,3R,4S,5S,6R)-3-({(2S,4S,5S)-5-[{[(4-{[(2S)-2-{[(2S)-2-{[(2S)-2-(Acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}propanoic acid LC-MS m/z 1969.7 [M+H$^+$]; retention time=4.81 min minutes (Method 3).

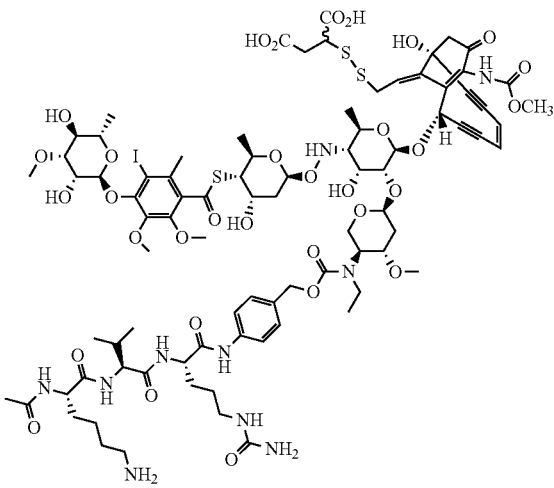 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(CC(=O)O)C(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@H]2O)C[C@@H]1OC]

Example 12: LP12: 2-{[(2E)-2-{(1R,8S)-8-({(2R,3R,4S,5S,6R)-3-({(2S,4S,5S)-5-[{[(4-{[(2S)-2-{[(2S)-2-{[(2S)-2-(Acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}butanedioic acid LC-MS m/z 2013.9 [M+H$^+$]; retention time=3.45 min minutes (Method 1).

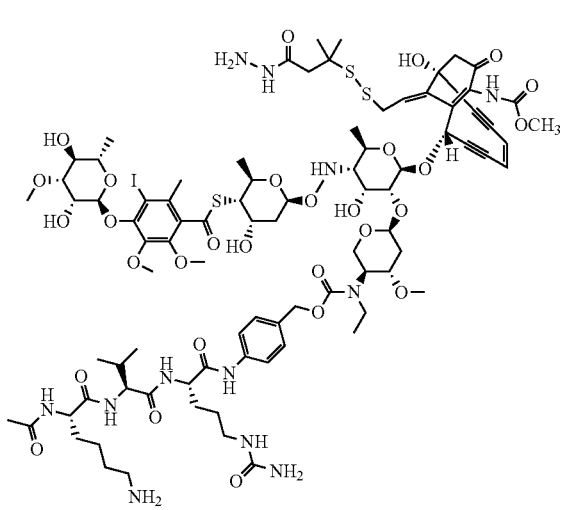 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)(C)CC(=O)NN)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@H]2O)C[C@@H]1OC]

Example 13: LP13: S-[(2R,3S,4S,6S)-6-({[(2R,3S,4S,5R,6R)-5-({(2S,4S,5S)-5-[{[(4-{[(2S)-2-{[(2S)-2-{[(2S)-2-(Acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R,13E)-13-{2-[(4-hydrazinyl-2-methyl-4-oxobutan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2011.9 [M+H$^+$]; retention time=3.57 min minutes (Method 2)

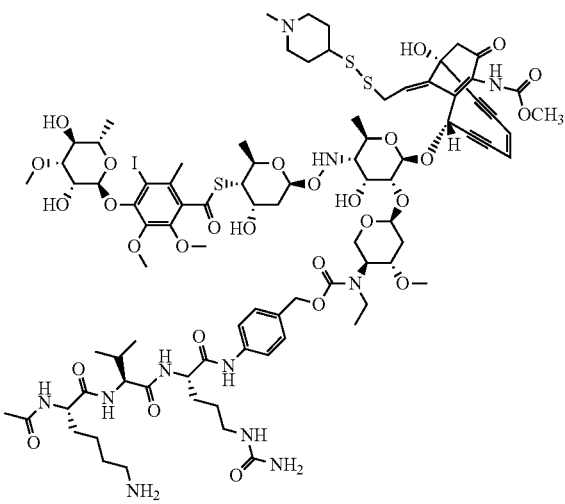 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC3CCN(C)CC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@H]2O)C[C@@H]1OC]

Example 14: LP14: S-[(2R,3S,4S,6S)-6-({[(2R,3S,4S,5R,6R)-5-({(2S,4S,5S)-5-[{[(4-{[(2S)-2-{[(2S)-2-{[(2S)-2-(Acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,5Z,9R,13E)-9-hydroxy-12-[(methoxycarbonyl)amino]-13-{2-[(1-methylpiperidin-4-yl)disulfanyl]ethylidene}-1-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1995 [M+H$^+$]; retention time=3.30 minutes (Method 3).

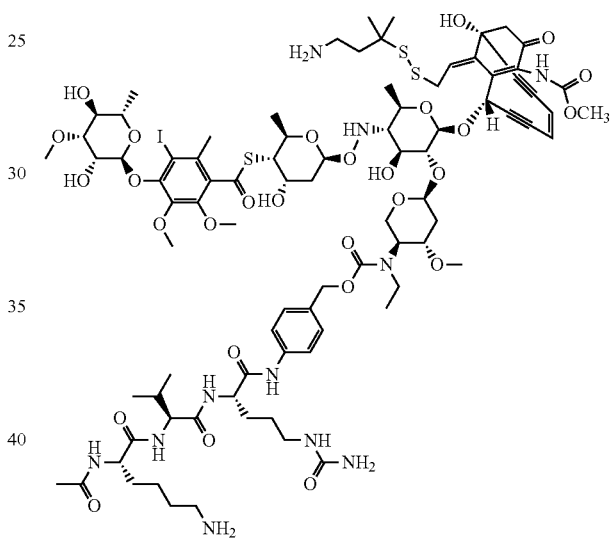

Example 15: LP15: S-[(2R,3S,4S,6S)-6-({[(2R,3S,4S,5R,6R)-5-({(2S,4S,5S)-5-[{[(4-{[(2S)-2-{[(2S)-2-{[(2S)-2-(Acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R, 13E)-13-{2-[(4-amino-2-methylbutan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1984 [M+H$^+$]; retention time=4.1 minutes (Method 3).

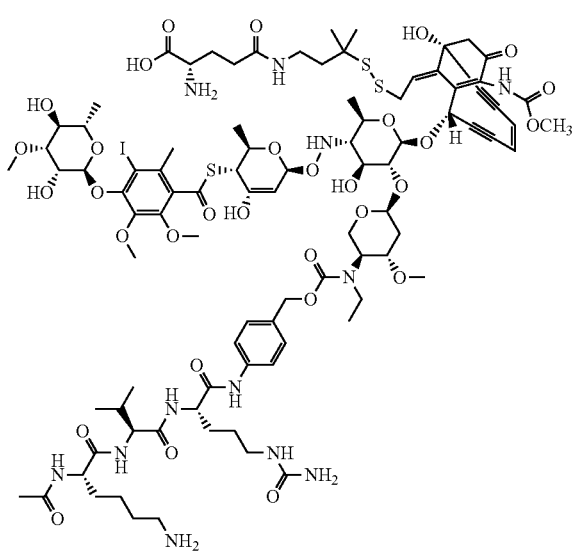

Example 16: LP16: S-[(2R,3S,4S,6S)-6-({[(2R,3S,4S,5R,6R)-5-({(2S,4S,5S)-5-[{[(4-{[(2S)-5-(Carbamoylamino)-2-{[(2S)-2-{[6-(2,5-dioxo-2,5-dihydro-1H-pyrrol-1-yl)hexanoyl]amino}-3-methylbutanoyl]amino}pentanoyl]amino}benzyl)oxy]carbonyl}(ethyl)amino]-4-methoxytetrahydro-2H-pyran-2-yl}oxy)-4-hydroxy-6-{[(2S,5Z,9R,13 E)-9-hydroxy-12-[(methoxycarbonyl)amino]-11-oxo-13-[2-(propan-2-yldisulfanyl)ethylidene]bicyclo[7.3.1]tri deca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2112 [M+H$^+$]; retention time=5.3 minutes (Method 8).

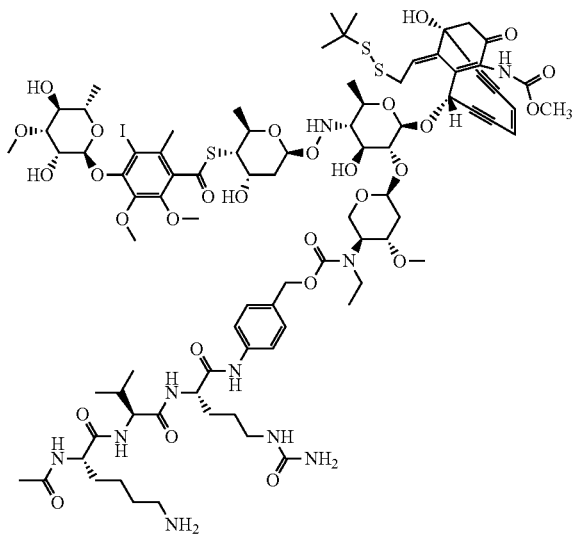 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)(C)C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 17: LP17: S-[(2R,3S,4S,6S)-6-({[(2R,3S,4S,5R,6R)-5-({(2S,4S,5S)-5-[{[(4-{[(2S)-2-{[(2S)-2-{[(2S)-2-(Acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,5Z,9R,13E)-13-[2-(tert-butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1953.5 [M+H$^+$]; retention time=3.14 minutes (Method 3).

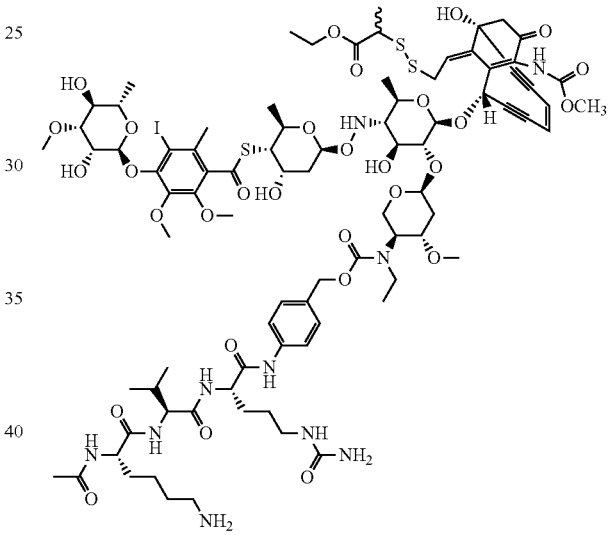

Example 18: LP18: Ethyl 2-{0 (2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}propanoate LC-MS m/z 1997.8 [M+H$^+$]; retention time=3.79 minutes (Method 1).

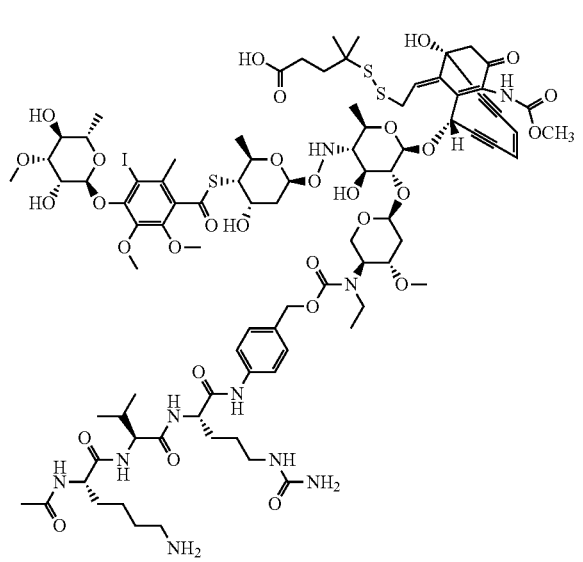 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)(C)CCC(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 19: LP19: 4-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}-4-methylpentanoic acid LC-MS m/z 2011.9 [M+H$^+$]; retention time=3.02 minutes (Method 2).

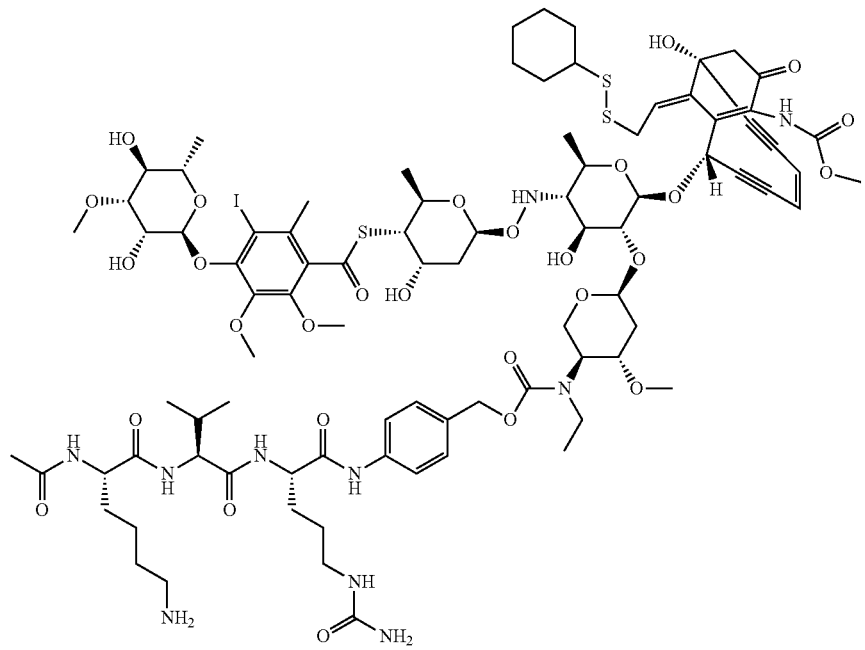 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC3CCCCC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 20: LP20: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R, 13E)-13-[2-(cyclohexyldisulfanyl)ethylidene]-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1979.7 [M+H$^+$]; retention time=2.43 minutes (Method 6).

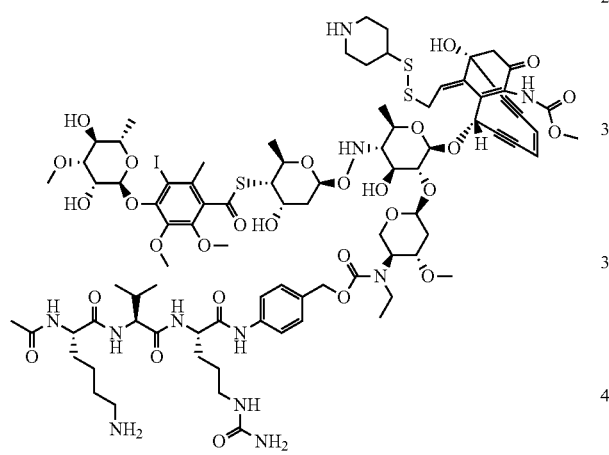

Example 21: LP21: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(piperidin-4-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1980.7 [M+H$^+$]; retention time=1.99 minutes (Method 6).

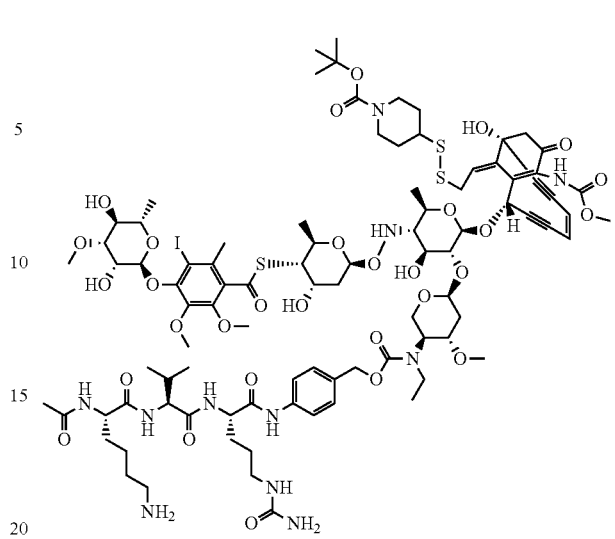

Example 22: LP22: Tert-butyl 4-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}piperidine-1-carboxylate LC-MS m/z 2080.7 [M+H$^+$]; retention time=2.42 minutes (Method 6).

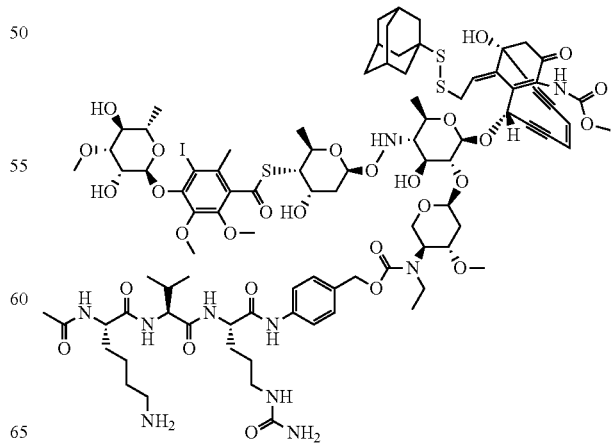

Example 23: LP23: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(tricyclo[3.3.1.1-3,7-]dec-1-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2031.8 [M+H$^+$]; retention time=2.55 minutes (Method 6).

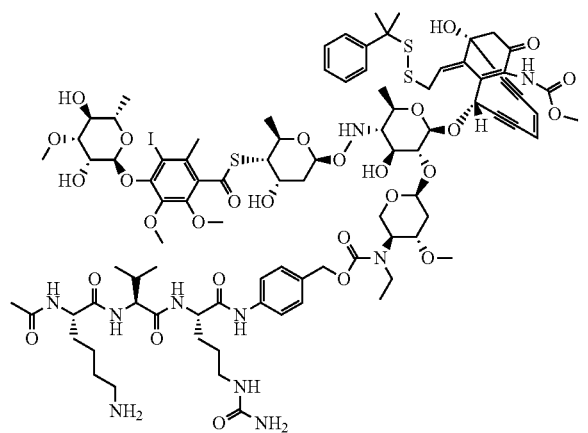 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)(C)c3ccccc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 24: LP24: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-{2-[(2-phenylpropan-2-yl)disulfanyl]ethylidene}bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2015.7 [M+H$^+$]; retention time=2.44 minutes (Method 6).

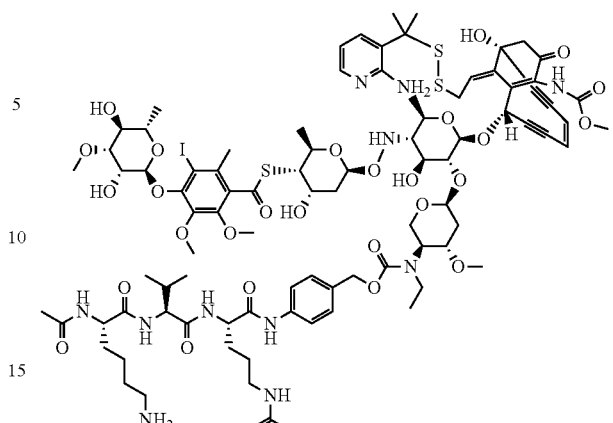

Example 25: LP25: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R, 13E)-13-(2-{[2-(2-aminopyridin-3-yl)propan-2-yl]disulfanyl}ethylidene)-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2031.7 [M+H$^+$]; retention time=2.04 minutes (Method 6).

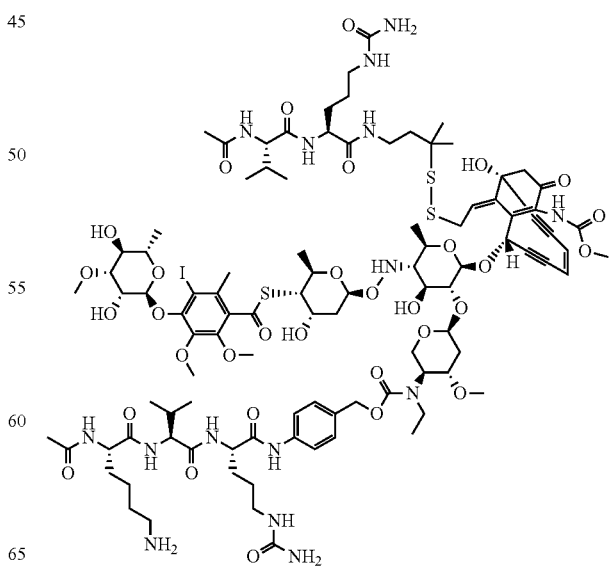

Example 26: LP26: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R,13E)-13-[(10S,13S)-10-[3-(carbamoylamino)propyl]-5,5-dimethyl-9,12,15-trioxo-13-(propan-2-yl)-3,4-dithia-8,11,14-triazahexadec-1-yl idene]-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2280.9 [M+H$^+$]; retention time=2.43 minutes (Method 11).

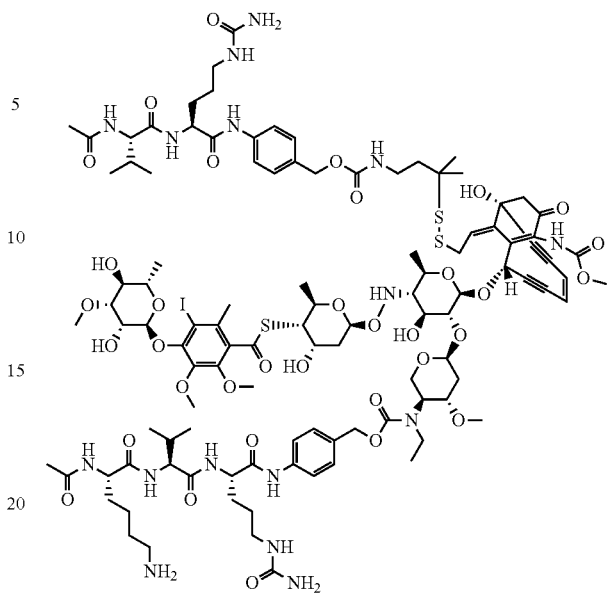

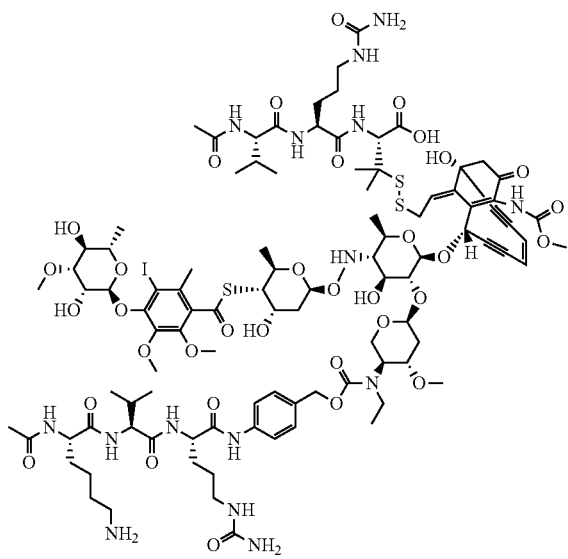 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)(C)[C@H](NC(=O)[C@H](CCCNC(N)=O)NC(=O)[C@@H](NC(C)=O)C(C)C)C(=O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 27: LP27: (2R)-3-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}-2-{[(2S)-2-{[(2S)-2-(acetylamino)-3-methylbutanoyl]amino}-5-(carbamoylamino)pentanoyl]amino}-3-methylbutanoic acid LC-MS m/z 2310.9 [M+H$^+$]; retention time=2.42 minutes (Method 11).

Example 28: LP28: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R,13E)-13-(2-{[4-({[(4-{[(2S)-2-{[(2S)-2-(acetylamino)-3-methylbutanoyl]amino}-5-(carbamoylamino)pentanoyl]amino}benzyl)oxy]carbonyl}amino)-2-methylbutan-2-yl]disulfanyl}ethylidene)-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2431 [M+H$^+$]; retention time=2.53 minutes (Method 11).

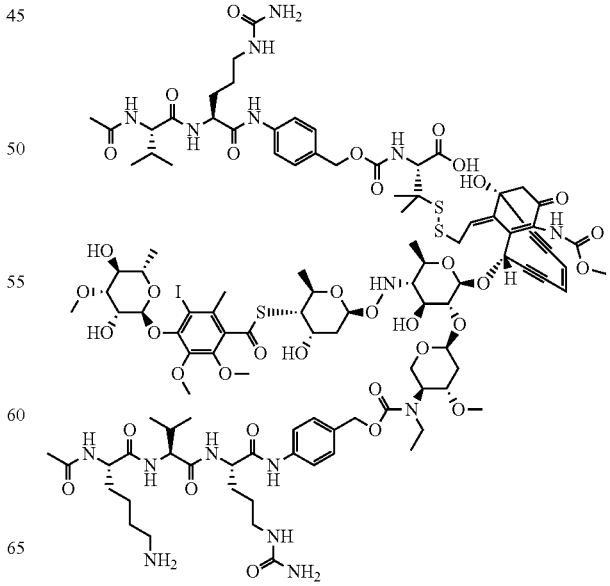

Example 29: LP29: (2R)-3-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}-2-({[(4-{[(2S)-2-{[(2S)-2-(acetylamino)-3-methylbutanoyl]amino}-5-(carbamoylamino)pentanoyl]amino}benzyl)oxy]carbonyl}amino)-3-methylbutanoic acid LC-MS m/z 2461 [M+H$^+$]; retention time=2.45 minutes (Method 11).

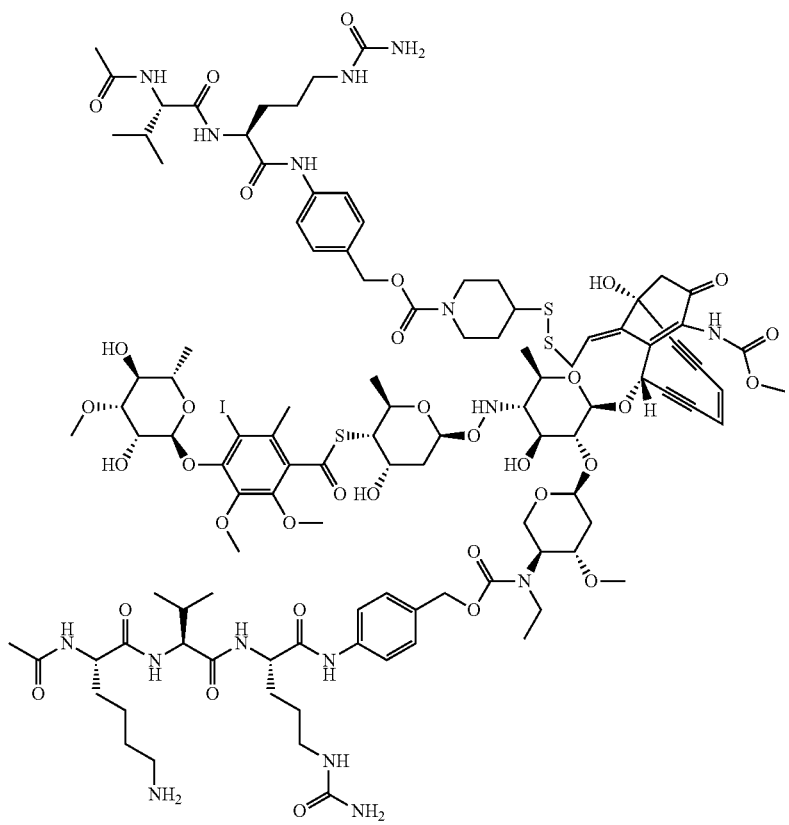 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC3CCN(C(=O)OCc4ccc(NC(=O)[C@H](CCCNC(N)=O)NC(=O)[C@@H](NC(C)=O)C(C)C)cc4)CC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 30: LP30: 4-{[(2S)-2-{[(2S)-2-(acetylamino)-3-methylbutanoyl]amino}-5-(carbamoylamino)pentanoyl]amino}benzyl 4-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexan]am]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}piperidine-1-carboxylate LC-MS m/z 2428 [M+H$^+$]; retention time=2.52 minutes (Method 11).

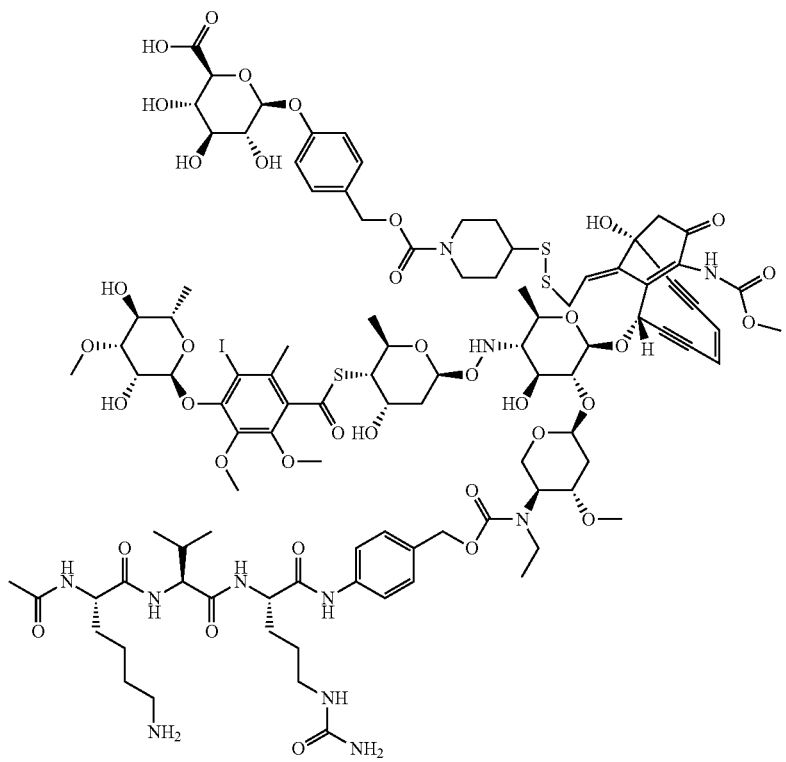 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC3CCN(C(=O)OCc4ccc(O[C@@H]5O[C@H](C(=O)O)[C@@H](O)[C@H](O)[C@H]5O)cc4)CC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 31: LP31: (2S,3S,4S,5R,6S)-6-[4-({[(4-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}piperidin-1-yl)carbonyl]oxy}methyl)phenoxy]-3,4,5-trihydroxytetrahydro-2H-pyran-2-carboxylic acid

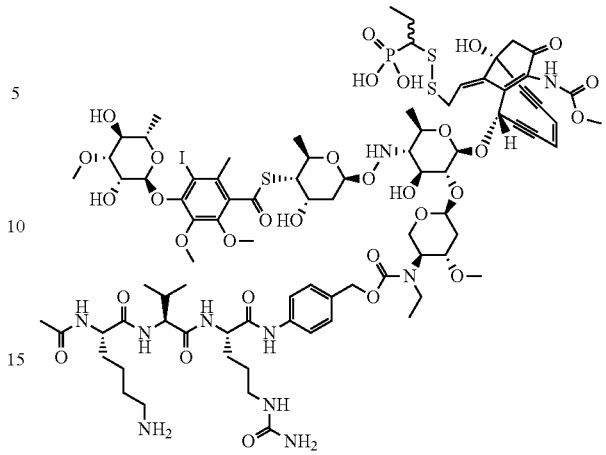

LC-MS m/z 2306.8 [M+H$^+$]; retention time=2.52 minutes (Method 11).

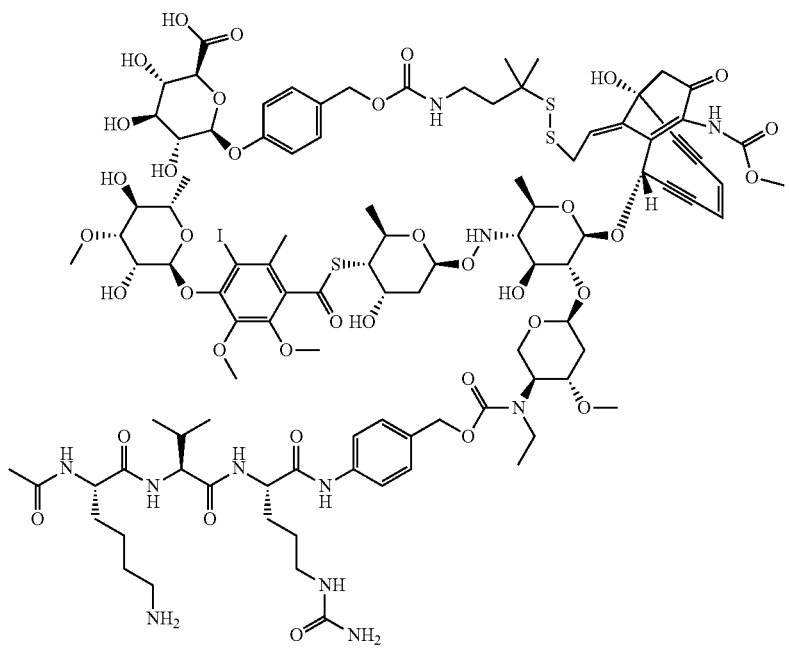 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)(C)CCNC(=O)OCc3ccc(O[C@@H]4O[C@H](C(=O)O)[C@@H](O)[C@H](O)[C@H]4O)cc3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 32: LP32: (2S,3S,4S,5R)-6-[4-({[(3-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}-3-methylbutyl)carbamoyl]oxy}methyl)phenoxy]-3,4,5-trihydroxytetrahydro-2H-pyran-2-carboxylic acid LC-MS m/z 2308.8 [M+H$^+$]; retention time=2.54 minutes (Method 11).

Example 33: LP33: (1-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}propyl)phosphonic acid LC-MS m/z 2019.6 [M+H$^+$]; retention time=2.20 minutes (Method 6).

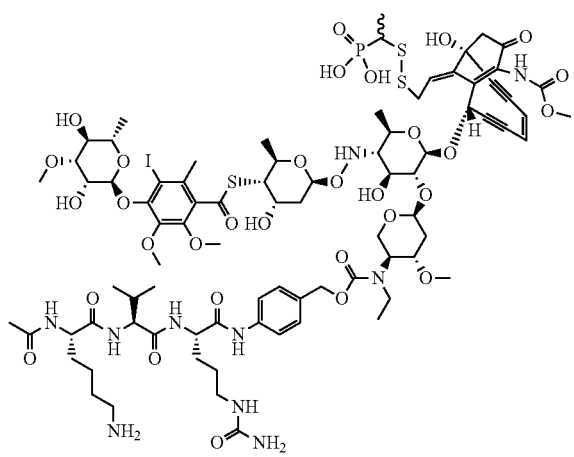 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)P(=O)(O)O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 34: LP34: (1-{[(2E)-2-{(1R,8S)-8-[({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]aminol-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}ethyl)phosphonic acid. LC-MS m/z 2005.7 [M+H$^+$]; retention time=2.2 minutes (Method 6)

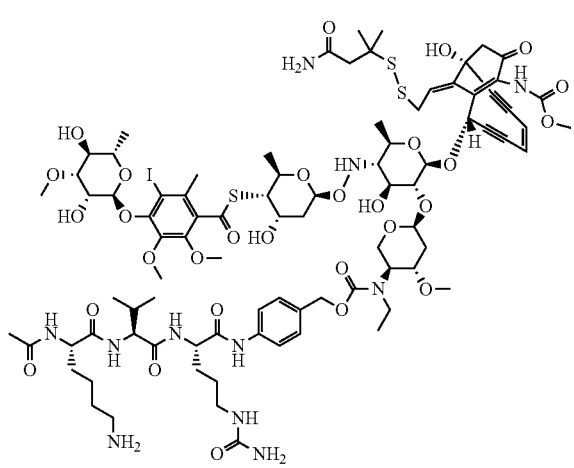 [SMILES: CCN(C(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)(C)CC(N)=O)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 35: LP35: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R, 13E)-13-{2-[(4-amino-2-methyl-4-oxobutan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1996.7 [M+H$^+$]; retention time=2.43 minutes (Method 11).

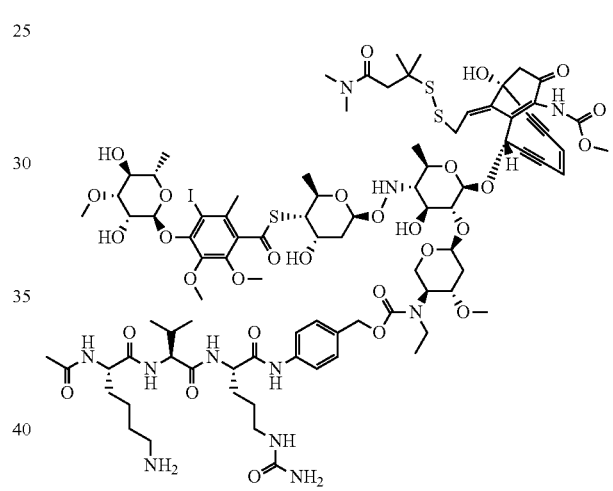

Example 36: LP36: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methyl butanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R,13E)-13-(2-{[4-(dimethylamino)-2-methyl-4-oxobutan-2-yl]disulfanyl}ethylidene)-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2024.8 [M+H$^+$]; retention time=2.49 minutes (Method 11).

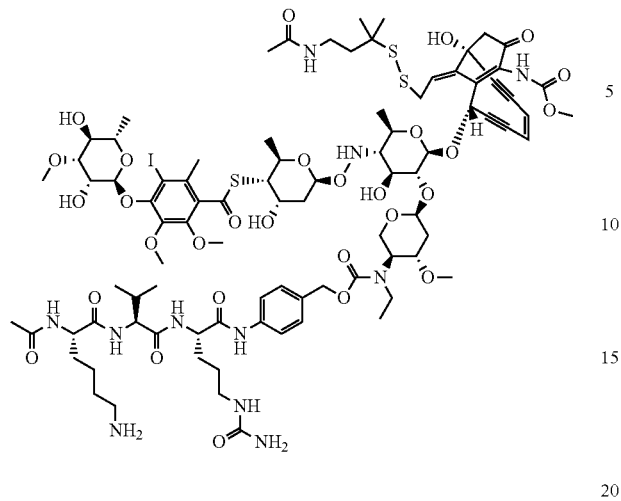

Example 37: LP37: S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-6-{[(2S,9R, 13E)-13-(2-{[4-(acetylamino)-2-methylbutan-2-yl]disulfanyl}ethylidene)-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 2024.7[M+H$^+$]; retention time=2.47 minutes (Method 11).

The following was prepared by the procedure of Example 3 by reaction of 9H-fluoren-9-ylmethyl (21-oxo-3,6,9,12,15,18-hexaoxahenicos-1-yl)carbamate with S-[(2R,3S,4S,6S)-6-({[(2R,3S,4S,5R,6R)-5-{[(2S,4S,5S)-5-(Ethylamino)-4-methoxytetrahydro-2H-pyran-2-yl]oxy}-4-hydroxy-6-{[(2S,5Z, 9R, 13E)-9-hydroxy-12-[(methoxycarbonyl)amino]-13-{2-[(1-methylpiperidin-4-yl)disulfanyl]ethylidene}-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P15) followed by Fmoc-deprotection:

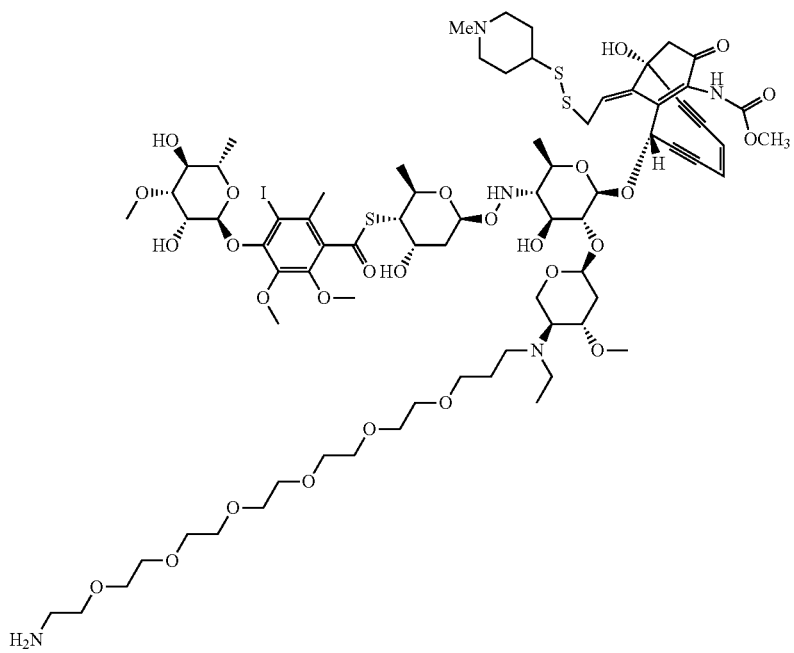 [SMILES: CCN(CCCOCCOCCOCCOCCOCCOCCN)[C@H]1CO[C@@H](O[C@H]2[C@H](O[C@H]3C#C/C=C\C#C[C@]4(O)CC(=O)C(NC(=O)OC)=C3/C4=C\CSSC3CCN(C)CC3)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 38: LP38: S-[(2R,3S,4S,6S)-6-({[(2R,3S,4S,5R,6R)-5-({(2S,4S,5S)-5-[(21-Amino-4,7,10,13,16,19-hexaoxahenicos-1-yl)(ethyl)amino]-4-methoxytetrahydro-2H-pyran-2-yl}oxy)-4-hydroxy-6-{[(2S,9R,13E)-9-hydroxy-12-[(methoxycarbonyl)amino]-13-{2-[(1-methylpiperidin-4-yl)disulfanyl]ethylidene}-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1740.6 [M+H⁺]; retention time=0.61 minutes (Method 5).

Example 39: Preparation of S-[(2R,3S,4S,6S)-6-({[(2R,3S,4S,5R,6R)-5-{[(2S,4S,5S)-5-{[2-({2-[2-(2-aminoethoxy)ethoxy]ethyl}amino)-2-oxoethyl](ethyl)amino}-4-methoxytetrahydro-2H-pyran-2-yl]oxy}-6-{[(2S,9R,13E)-13-{2-[(4-hydrazin yl-2-methyl-4-oxobutan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-di hydroxy-4-methoxy-6-methyltetrahydro-2H-pyran-2-yl]oxy}-3-iodo-5,6-dimethoxy-2-methylbenzenecarbothioate (LP39)

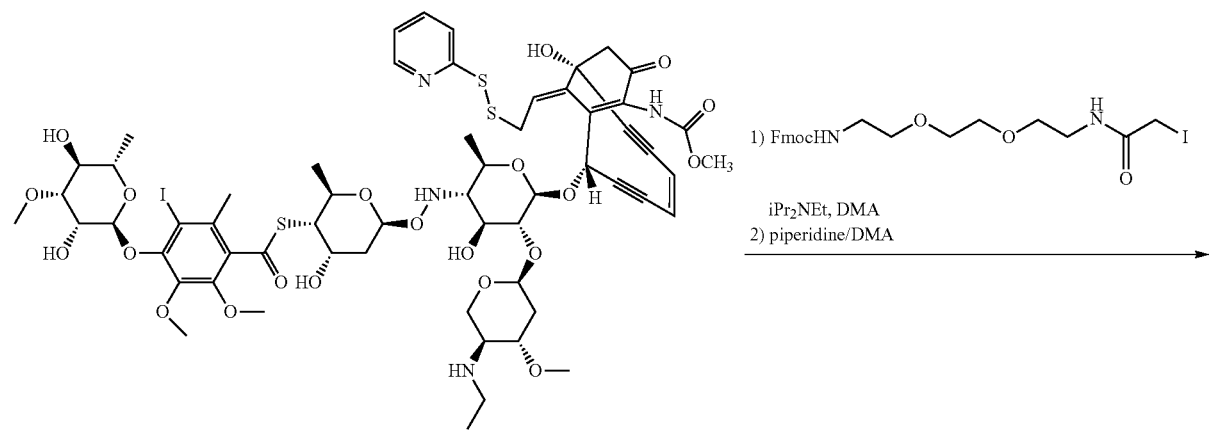

P4

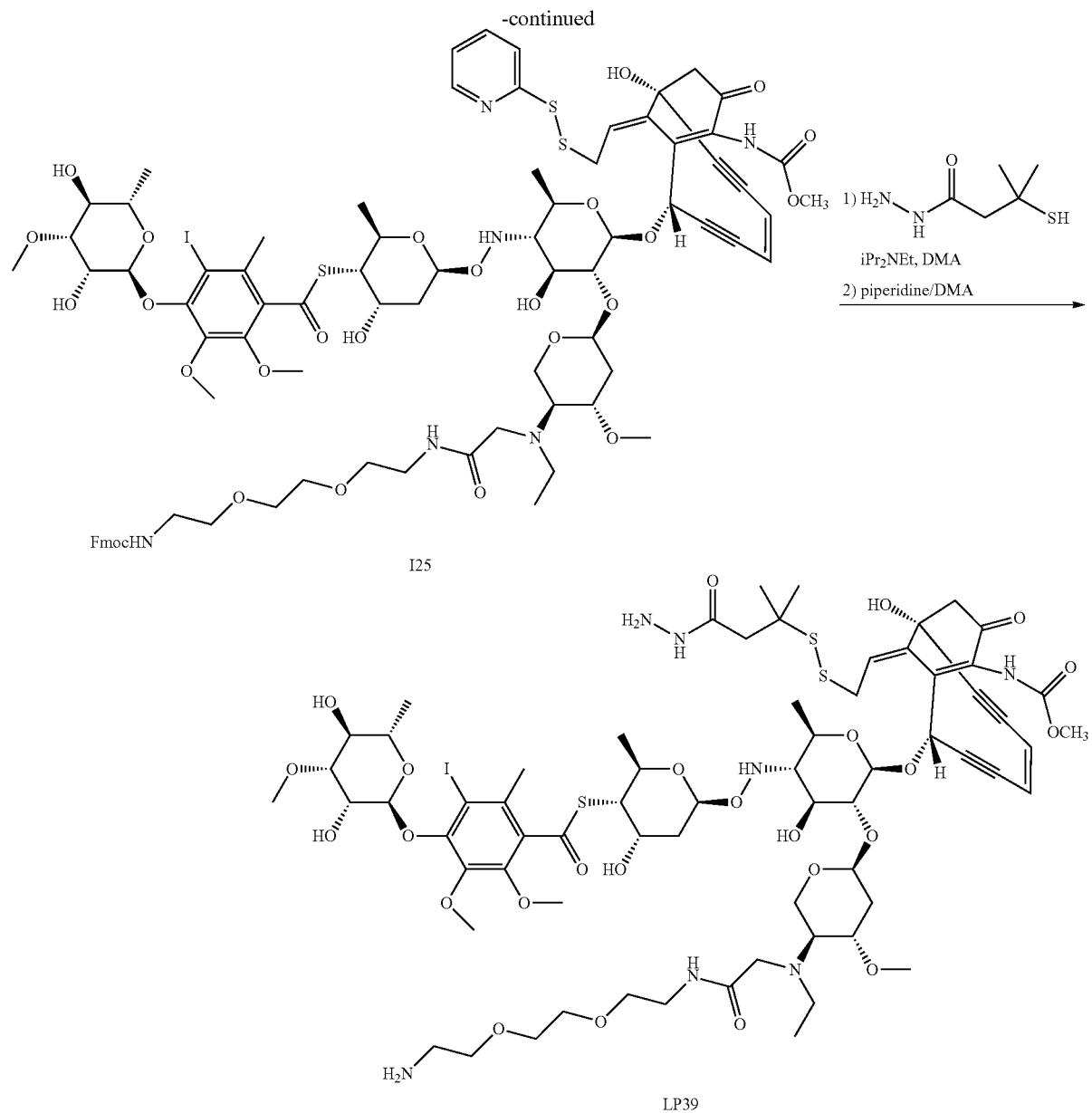

Step 1: Synthesis of S-[(2R,3S,4S,6S)-6-({[(2R,3S, 4S,5R,6R)-5-{[(2S,4S,5S)-5-{ethyl[1-(9H-fluoren-9-yl)-3,14-dioxo-2,7,10-trioxa-4,13-diazapentadecan-15-yl]amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate 9H-Fluoren-9-ylmethyl [2-(2-{2-[(iodoacetyl)amino]ethoxy}ethoxy)ethyl]carbamate (82.0 mg, 0.15 mmol) was added to a solution of S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(pyridin-2-yldi sulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P4) (20 mg, 0.014 mmol), N,N-diisopropylethylamine (8.86 mg, 0.0685 mmol, 12.0 uL) in N,N-dimethylacetamide (500 uL) and the contents were heated to 45° C. After 3 days the reaction mixture was purified directly by reverse phase HPLC (Method B). Product containing fractions were lyophilized to obtain the desired product (7.0 mg). LC-MS m/z 1809.668 [M+H$^+$]; retention time=1.32 minutes (Method 5).

Step 2: Synthesis of S-[(2R,3S,4S,6S)-6-({[(2R,3S,4S,5R,6R)-5-{[(2S,4S,5S)-5-{[2-({2-[2-(2-amino-ethoxy)ethoxy]ethyl}amino)-2-oxoethyl](ethyl)amino}-4-methoxytetrahydro-2H-pyran-2-yl]oxy}-6-{[(2S,9R,13E)-13-{2-[(4-hydrazin yl-2-methyl-4-oxobutan-2-yl)disulfanyl]ethylidene}-9-hydroxy-12-[(methoxycarbonyl)amino]-11-oxobicyclo[7.3.1]trideca-1(12),5-diene-3,7-diyn-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP39)

3-Methyl-3-sulfanylbutanehydrazide (1.34 mg, 0.00727 mmol) was added to a solution of S-[(2R,3S,4S,6S)-6-({[(2R,3S,4S,5R,6R)-5-{[(2S,4S,5S)-5-{ethyl[1-(9H-fluoren-9-yl)-3,14-dioxo-2,7,10-trioxa-4,13-diazapentadecan-15-yl]amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (6.8 mg, 0.0036 mmol) and triethylamine (1.10 mg, 0.0109 mmol, 1.49 uL) in N,N-dimethylacetamide (0.9 mL). After 3 hours, piperidine (6.19 mg, 0.0727 mmol, 7.18 uL) was added neat and stirred for an additional 1 hour. The reaction mixture was purified directly by reverse phase HPLC (Method B). Product containing fractions were lyophilized to obtain 2.8 mg of the desired product (LP39). LC-MS m/z 1624.7 [M+H$^+$]; retention time=3.38 minutes (Method 1).

Example 40: Preparation of S-[(2R,3S,4S,6S)-6-({[(2R,3S,4S,5R,6R)-5-{[(2S,4S,5S)-5-{[2-({2-[2-(2-aminoethoxy)ethoxy]ethyl}amino)-2-oxoethyl](ethyl)amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1 (12),5-diene-3,7-diyn-2-yl]oxy}-2-methyltetrahydro-2H-pyran-3-yl]amino}oxy)-4-hydroxy-2-methyltetrahydro-2H-pyran-3-yl]4-{[(2S,3R,4R,5S,6S)-3,5-di hydroxy-4-methoxy-6-methyltetrahydro-2H-pyran-2-yl]oxy}-3-iodo-5,6-dimethoxy-2-methylbenzenecarbothioate (LP40)

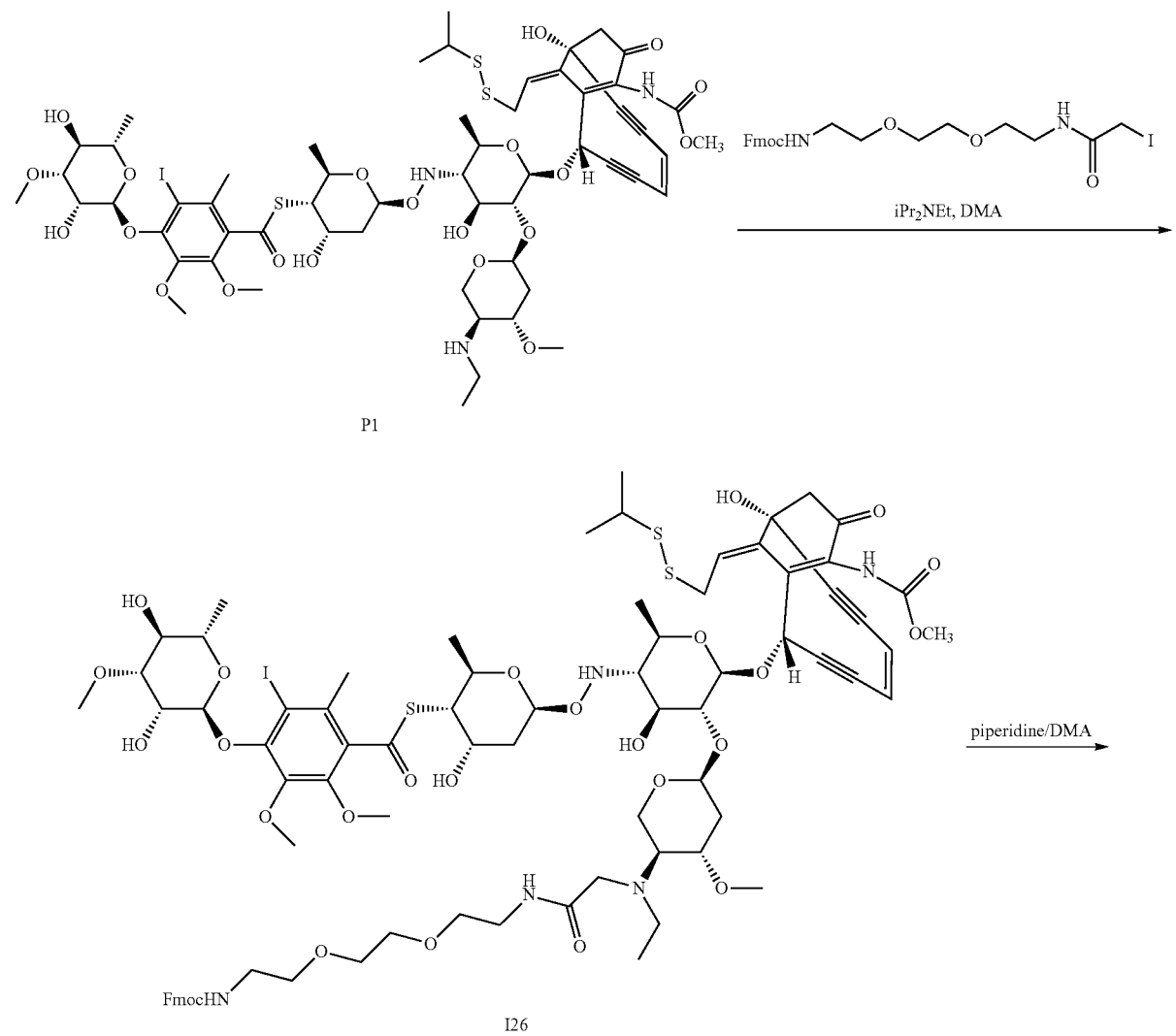

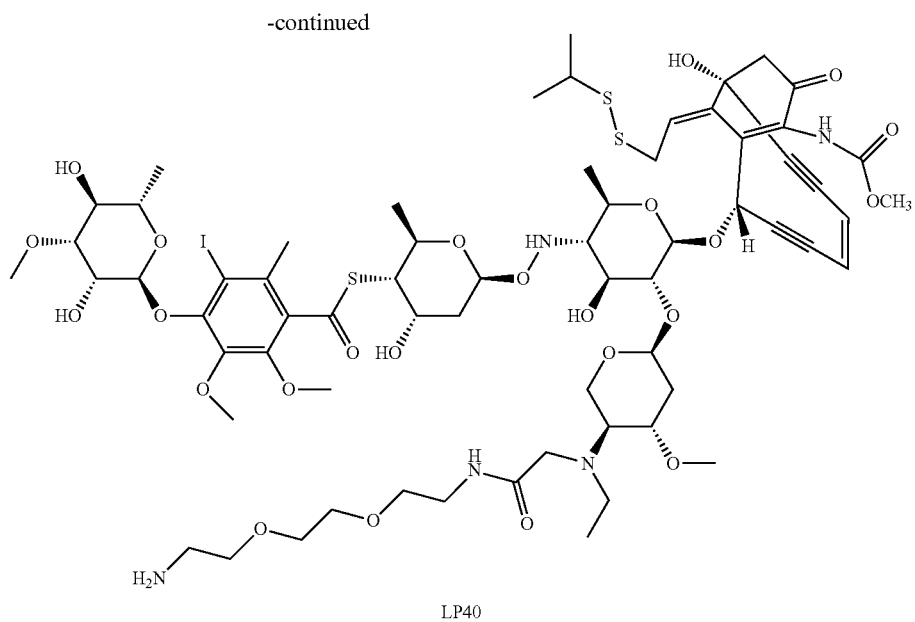

LP40

Step 1: Synthesis of S-[(2R,3S,4S,6S)-6-({[(2R,3S,4S,5R,6R)-5-{[(2S,4S,5S)-5-{ethyl[1-(9H-fluoren-9-yl)-3,14-dioxo-2,7,10-trioxa-4,13-diazapentadecan-15-yl]amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate 9H-Fluoren-9-ylmethyl [2-(2-{2-[(iodoacetyl)amino]ethoxy}ethoxy)ethyl]carbamate (83.2 mg, 0.154 mmol) was added to a solution of S-[(2R,3S,4S,6S)-6-({[(2R,3S,4S,5R,6R)-5-{[(2S,4S,5S)-5-(ethylamino)-4-methoxytetrahydro-2H-pyran-2-yl]oxy}-4-hydroxy-6-{[(2S,5Z,9R,13E)-9-hydroxy-12-[(methoxycarbonyl)amino]-11-oxo-13-[2-(propan-2-yl disulfanyl)ethylidene]bicyclo[7.3.1]trideca-1 (12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P1) (22.0 mg, 0.015 mmol), N,N-diisopropylethylamine (20.0 mg, 0.154 mmol, 26.9 uL) in N,N-dimethylacetamide (0.5 mL) and heated to 45° C. After 5 days the reaction mixture was purified directly by reverse phase HPLC (Method B). Product containing fractions were lyophilized to obtain the desired product (11.4 mg). LC-MS m/z 1624.7 [M+H⁺]; retention time=3.38 minutes (Method 1).

Step 2: S-[(2R,3S,4S,6S)-6-({[(2R,3S,4S,5R,6R)-5-{[(2S,4S,5S)-5-{Ethyl[1-(9H-fluoren-9-yl)-3,14-dioxo-2,7,10-trioxa-4,13-diazapentadecan-15-yl]amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1 (12),5-diene-3,7-diyn-2-yl]oxy}-2-methyltetrahydro-2H-pyran-3-yl]amino}oxy)-4-hydroxy-2-methyltetrahydro-2H-pyran-3-yl]

4-{[(2S,3R,4R,5S,6S)-3,5-Dihydroxy-4-methoxy-6-methyltetrahydro-2H-pyran-2-yl]oxy}-3-iodo-5,6-dimethoxy-2-methylbenzenecarbothioate (11.4 mg, 0.00621 mmol) was treated with a solution of N,N-dimethylacetamide (0.5 mL) and piperidine (10.6 mg, 0.124 mmol, 12.3 uL). After stirring for 4 hours the reaction mixture was purified directly by reverse phase HPLC (Method B). Product containing fractions were lyophilized to obtain 6.8 mg (40%) of the desired product (LP40). LC-MS m/z 1552.7 [M+H⁺]; retention time=3.69 minutes (Method 1).

Example 41: Preparation of S-[(2R,3S,4S,6S)-6-({[(2R,3S,4S,5R,6R)-5-({(2S,4S,5S)-5-[(26-amino-2-oxo-6,9,12,15,18,21,24-heptaoxa-3-azahexacos-1-yl)(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[(2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyl tetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methyl-benzenecarbothioate (LP41)

3-iodo-5,6-dimethoxy-2-methylbenzoyl)sulfanyl]-4-hydroxy-6-methyltetrahydro-2H-pyran-2-yl}oxy)amino]-4-hydroxy-2-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-6-methyltetrahydro-2H-pyran-3-yl]oxy}-4-methoxytetrahydro-2H-pyran-3-yl](ethyl)amino}acetic acid (P50) (3.1 mg, 2.1 umol), N,N,N',N'-tetramethyl-O-(1H-benzotriazol-1-yl)uronium hexafluorophosphate (0.872 mg, 2.30 umol) and N,N-diisopropylethylamine (1.35 mg, 10.5 umol, 1.82 uL) in N,N-dimethylacetamide (500 uL). After 15 minutes, piperidine (7.12 mg, 83.6 umol, 8.26 uL) was added neat and stirred for an additional 30 minutes. The

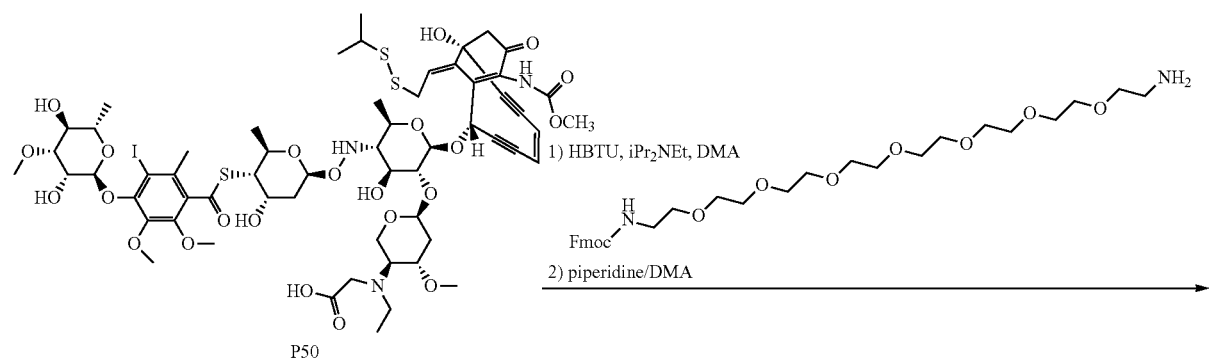

P50

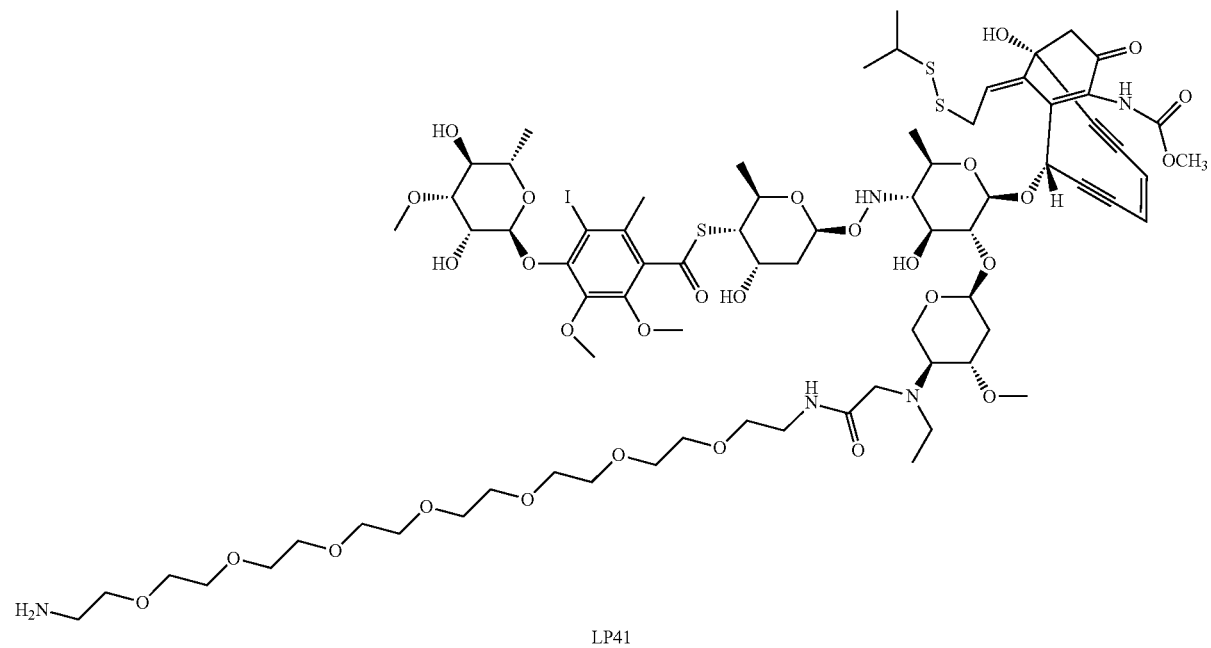

LP41

9H-Fluoren-9-ylmethyl (23-amino-3,6,9,12,15,18,21-heptaoxatricos-1-yl)carbamate (1.92 mg, 2.72 umol) was added to a solution of {[(3S,4S,6S)-6-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}- reaction mixture was purified directly by reverse phase HPLC (Method A). Product containing fractions were lyophilized to obtain 2.4 mg (61%) of the desired product (LP41). LC-MS m/z 1772.87 [M+H$^+$]; retention time=0.75 minutes (Method 5).

Example 42: Preparation of S-[(2R,3S,4S,6S)-6-({[(2R,3S,4S,5R,6R)-5-{[(2S,4S,5S)-5-{[(14S,17S,20S)-20-(4-aminobutyl)-14-[3-(carbamoylamino)propyl]-2,13,16,19,22-pentaoxo-17-(propan-2-yl)-6,9-dioxa-3,12,15,18,21-pentaazatricos-1-yl](ethyl)amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1 (12),5-diene-3,7-diyn-2-yl]oxy}-2-methyltetrahydro-2H-pyran-3-yl]amino}oxy)-4-hydroxy-2-methyltetrahydro-2H-pyran-3-yl]4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP42)

oxoethyl](ethyl)amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP40) (1.8 mg, 1.1 umol) was added to a pre-activated solution of $N^2$-acetyl-$N^6$-[(9H-fluoren-9-ylmethoxy)carbonyl]-L-lysyl-L-valyl-$N^5$-carbamoyl-L-ornithine (L1) (0.933 mg, 1.40 umol), N,N,N',N'-tetramethyl-O-(1H-benzotriazol-1-yl)uronium hexafluorophosphate (0.531 mg, 1.40 umol) and N,N-diisopropylethylamine (0.695 mg, 5.38 umol, 0.936 uL) in N,N-dimethylacetamide (200 uL). After 1 hour, piperidine

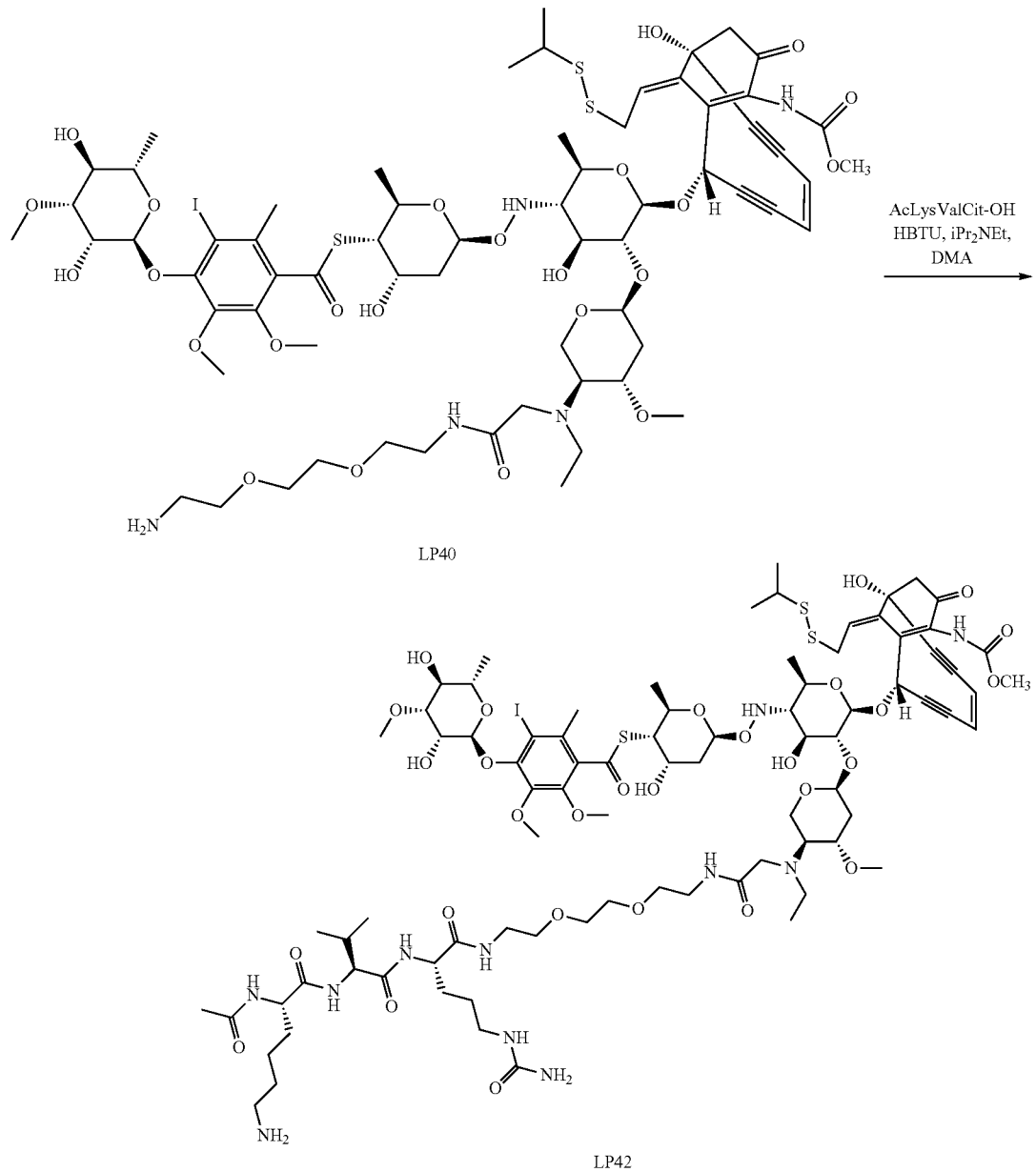

LP40

LP42

S-[(2R,3S,4S,6S)-6-({[(2R,3S,4S,5R,6R)-5-{[(2S,4S,5S)-5-{[2-({2-[2-(2-Aminoethoxy)ethoxy]ethyl}amino)-2-

(2.75 mg, 32.3 umol, 3.19 uL) was added neat to the reaction and allowed to stand for an additional 45 minutes. The reaction mixture was then purified directly by reverse phase HPLC (Method A). Product containing fractions were lyophilized to obtain 1.1 mg (49%) of the desired product (LP42). LC-MS m/z 1979.92 [M+H$^+$]; retention time=0.72 minutes (Method 5).

Example 43: Preparation of S-[(2R,3S,4S,6S)-6-({[(2R,3S,4S,5R,6R)-5-{[(2S,4S,5S)-5-{[1-(4-{[(2S)-2-{[(2S)-2-{[(2S)-2-(acetylamino)-6-aminohexanoyl]amino}-3-methylbutanoyl]amino}-5-(carbamoylamino)pentanoyl]amino}phenyl)-3,14-di oxo-2,7,10-trioxa-4,13-diazapentadecan-15-yl](ethyl)amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl]4-{[(2S,3R,4R,5S,6S)-3,5-dihydroxy-4-methoxy-6-m ethyltetrahydro-2H-pyran-2-yl]oxy}-3-iodo-5,6-dimethoxy-2-methylbenzenecarbothioate (LP43)

N$^2$-Acetyl-N$^6$-[(9H-fluoren-9-ylmethoxy)carbonyl]-L-lysyl-L-valyl-N$^5$-carbamoyl-N-[4-({[(pentafluorophenoxy)carbonyl]oxy}methyl)phenyl]-L-ornithinamide (L2) (1.37 mg, 1.40 umol) was added to a solution of S-[(2R,3S,4S,6S)-6-({[(2R,3S,4S,5R,6R)-5-{[(2S,4S,5S)-5-{[2-({2-[2-(2-aminoethoxy)ethoxy]ethyl}amino)-2-oxoethyl](ethyl)amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP40) (1.8 mg, 1.1 umol), N,N-diisopropylethylamine (0.695 mg, 5.38 umol, 0.936 uL) in N,N-dimethylacetamide (200 uL). After 1 hour, piperidine (2.75 mg, 32.3 umol, 3.19 uL) was added to the reaction neat and allowed to stand for 45 minutes. The reaction mixture was purified directly by reverse phase HPLC (Method A). Prod-

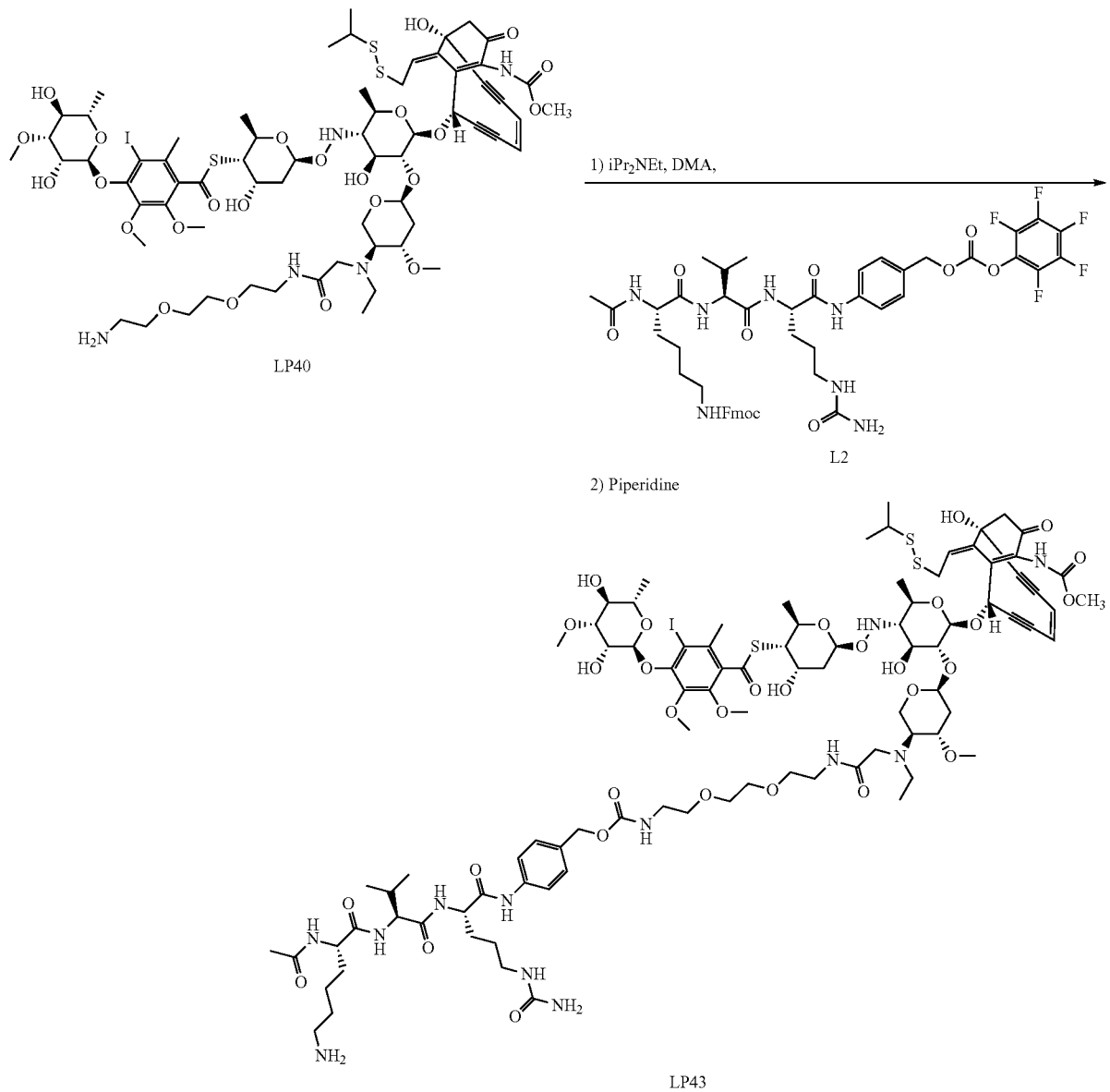

uct containing fractions were lyophilized to obtain 1.0 mg (41%) of the desired product (LP43). LC-MS m/z 1064.569 [M+2H$^{2+}$]; retention time=0.74 minutes (Method 5).

The following was prepared by the procedure of Example 41 through reaction of 9H-fluoren-9-ylmethyl (3-aminopropyl)(4-{[(9H-fluoren-9-ylmethoxy)carbonyl](3-{[(9H-fluoren-9-ylmethoxy)carbonyl]amino}propyl)amino}butyl)carbamate (L5) with {[(3S,4S,6S)-6-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-2-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-6-methyltetrahydro-2H-pyran-3-yl]oxy}-4-methoxytetrahydro-2H-pyran-3-yl](ethyl)amino}acetic acid (P50) followed by Fmoc deprotection:

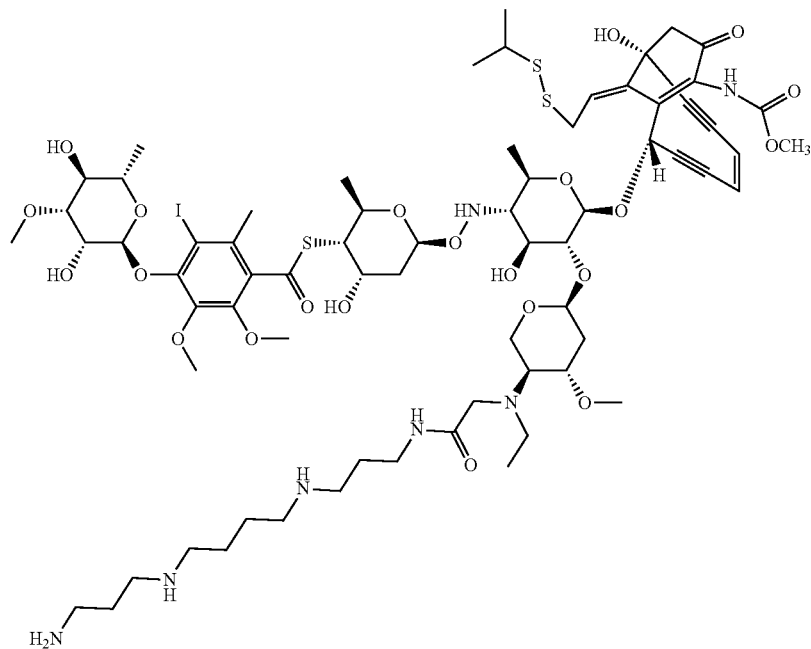 [SMILES: CCN(CC(=O)NCCCNCCCCNCCCN)[C@H]1CO[C@@H](O[C@H]2[C@H](O[C@H]3C#C/C=C\C#C[C@]4(O)CC(=O)C(NC(=O)OC)=C3/C4=C\CSSC(C)C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 44: LP44: S-[(2R,3S,4S,6S)-6-({[(2R,3S,4S,5R,6R)-5-({(2S,4S,5S)-5-[(2-{[3-({4-[(3-aminopropyl)amino]butyl}amino) propyl]amino}-2-oxoethyl) (ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1606.67 [M+H$^+$]; retention time=0.70 minutes (Method 5).

The following was prepared according to the procedure of Example 41 through reaction of N$^2$-acetyl-N$^6$-[(9H-fluoren-9-ylmethoxy)carbonyl]-L-lysyl-L-valyl-N-(3-{(4-{(3-aminopropyl)[(9H-fluoren-9-ylmethoxy)carbonyl]amino}butyl)[(9H-fluoren-9-ylmethoxy)carbonyl]amino}propyl)-N-carbamoyl-L-ornithinamide (L6) with {[(3S,4S,6S)-6-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-m ethyltetrahydro-2H-pyran-2-yl}oxy)amino]-4-hydroxy-2-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-6-methyltetrahydro-2H-pyran-3-yl]oxy}-4-methoxytetrahydro-2H-pyran-3-yl](ethyl)amino}acetic acid (P50), followed by Fmoc deprotection:

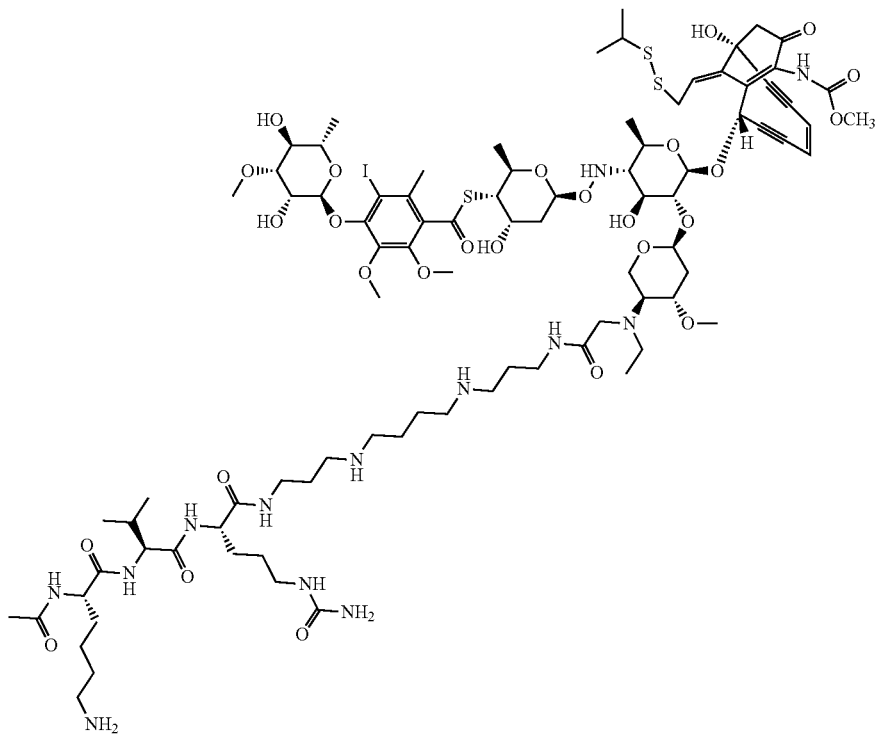 [SMILES: CCN(CC(=O)NCCCNCCCCNCCCNC(=O)[C@H](CCCNC(N)=O)NC(=O)[C@@H](NC(=O)[C@H](CCCCN)NC(C)=O)C(C)C)[C@H]1CO[C@@H](O[C@H]2[C@H](O[C@H]3C#C/C=C\C#C[C@]4(O)CC(=O)C(NC(=O)OC)=C3/C4=C\CSSC(C)C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 45: LP45: S-[(2R,3S,4S,6S)-6-({[(2R,3S,4S,5R,6R)-5-{[(2S,4S,5S)-5-{[(4S,7S,10S)- 4-(4-aminobutyl)-10-[3-(carbamoylamino)propyl]-2,5,8,11,26-pentaoxo-7-(propan-2-yl)-3,6,9,12,16,21,25-heptaazaheptacosan-27-yl](ethyl)amino}-4-methoxytetrahydro-2H-pyran-2-yl]oxy}-4-hydroxy-6-{[(2S,9R,13 E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1017.11 [M+2H$^2$+]; retention time=0.68 minutes (Method 5).

The following was prepared according to the procedure of Example 41 through reaction of N$^2$-acetyl-N$^6$-[(9H-fluoren-9-ylmethoxy)carbonyl]-L-lysyl-L-valyl-N-[({4-[(3-{(4-{(3-aminopropyl)[(9H-fluoren-9-ylmethoxy)carbonyl]amino}butyl)[(9H-fluoren-9-ylmethoxy)carbonyl]amino}propyl)amino]benzyl}oxy)carbonyl]-N$^5$-carbamoyl-L-ornithinamide (L7) with {[(3S,4S,6S)-6-{[(2R,3R,4S,5S,6R)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-m ethyltetrahydro-2H-pyran-2-yl}oxy)amino]-4-hydroxy-2-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-6-methyltetrahydro-2H-pyran-3-yl]oxy}-4-methoxytetrahydro-2H-pyran-3-yl](ethyl)amino}acetic acid (P50), followed by Fmoc deprotection:

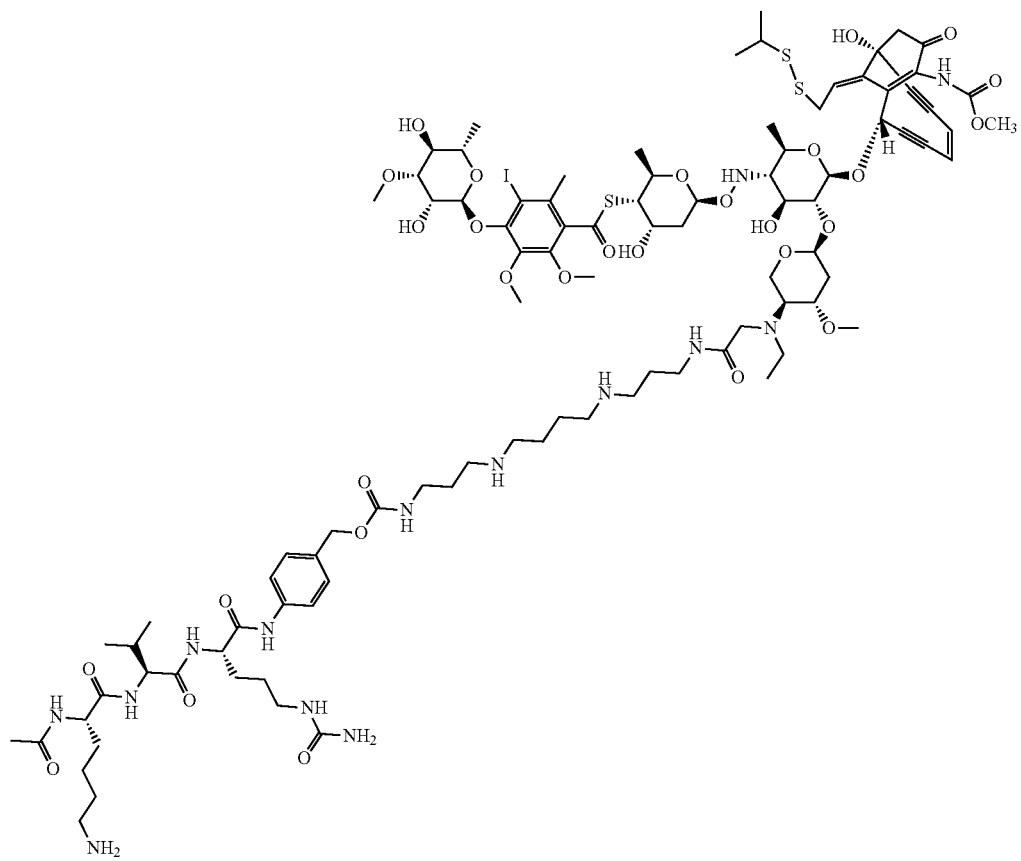 [SMILES: CCN(CC(=O)NCCCNCCCCNCCCNC(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

Example 46: LP46: S-[(2R,3S,4S,6S)-6-({[(2R,3S,4S,5R,6R)-5-{[(2S,4S,5S)-5-{[1-(4-{[(2S)-2-{[(2S)-2-{[(2S)-2-(acetylamino)-6-aminohexanoyl]amino}-3-methylbutanoyl]amino}-5-(carbamoylamino)pentanoyl]amino}phenyl)-3,18-di oxo-2-oxa-4,8,13,17-tetraazanonadecan-19-yl](ethyl)amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1091.79 [M+2H$^2$+]; retention time=0.72 minutes (Method 5).

The following was prepared according to the procedure of Example 41 through reaction of N$^2$-acetyl-N$^6$-[(9H-fluoren-9-ylmethoxy)carbonyl]-L-lysyl-L-valyl-N$^5$-carbamoyl-L-ornithine (L1) with —S-[(2R,3S,4S,6S)-6-({[(2R,3S,4S,5R,6R)-5-({(2S,4S,5S)-5-[(26-amino-2-oxo-6,9,12,15,18,21,24-heptaoxa-3-azahexacos-1-yl)(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyl tetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP41) followed by Fmoc-deprotection:

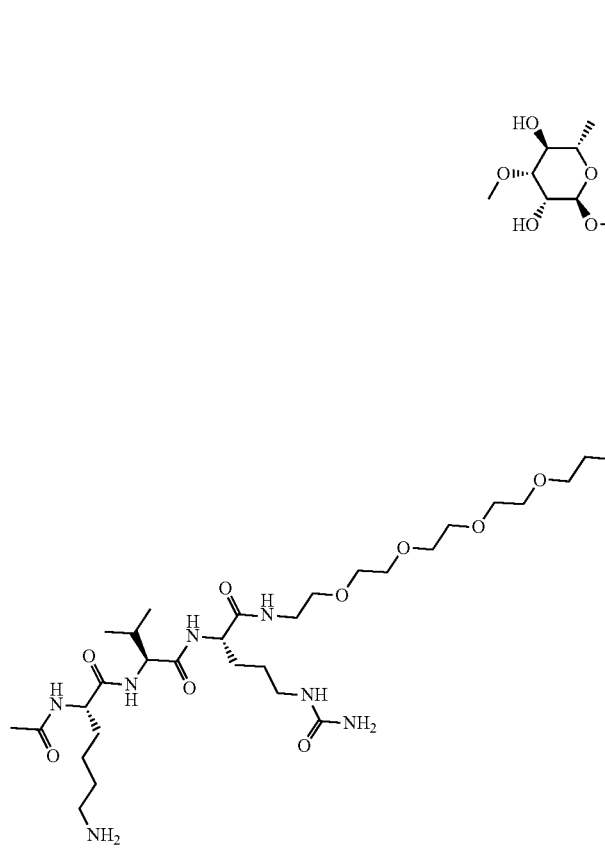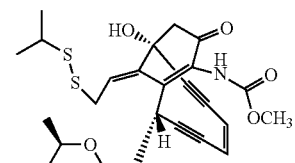

Example 47: LP47: S-[(2R,3S,4S,6S)-6-({[(2R,3S,4S,5R,6R)-5-{[(2S,4S,5S)-5-{[(29S,32S,35S)-35-(4-aminobutyl)-29-[3-(carbamoylamino) propyl]-2,28,31,34,37-pentaoxo-32-(propan-2-yl)-6,9,12,15,18,21,24-heptaoxa-3,27,30,33,36-pentaazaoctatriacont-1-yl](ethyl)amino}-4-methoxytetrahydro-2H-pyran-2-yl]oxy}-4-hydroxy-6-{[(2S,9R,13E)-9-hydroxy-12-[(methoxycarbonyl)amino]-11-oxo-13-[2-(propan-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate LC-MS m/z 1100.438 [M+2H$^2$+]; retention time=0.80 minutes (Method 5)

471

Example 48: Preparation of S-[(2R,3S,4S,6S)-6-({[(2R,3S,4S,5R,6R)-6-{[(2S,5Z,9R,13E)-13-[2-(tert-butyldisulfanyl)ethylidene]-9-hydroxy-12-[(methoxycarbonyl)amino]-11-oxobicyclo[7.3.1]trideca-1(12),5-diene-3,7-diyn-2-yl]oxy}-5-({(2S,4S,5S)-5-[{[(4-{[(2S)-5-(carbamoylamino)-2-{[(2S)-2-{[6-(2,5-dioxo-2,5-dihydro-1H-pyrrol-1-yl)hexanoyl]amino}-3-methylbutanoyl]amino}pentanoyl]amino}benzyl)oxy]carbonyl}(ethyl)amino]-4-methoxytetrahydro-2H-pyran-2-yl}oxy)-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (LP48)

472

9-hydroxy-12-[(methoxycarbonyl)amino]-11-oxobicyclo[7.3.1]trideca-1(12),5-diene-3,7-diyn-2-yl]oxy}-5-{[(2S,4S,5S)-5-(ethylamino)-4-methoxytetrahydro-2H-pyran-2-yl]oxy}-4-hydroxy-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (P2)

(14 mg, 0.010 mmol), N-[6-(2,5-dioxo-2,5-dihydro-1H-pyrrol-1-yl)hexanoyl]-L-valyl-N$^5$-carbamoyl-N-[4-({[(4-nitrophenoxy)carbonyl]oxy}methyl)phenyl]-L-ornithinamide (7.4 mg, 0.010 mmol) and 3H-[1,2,3]triazolo[4,5-b]pyridin-3-ol (1.407 mg, 0.0102 mmol) in N,N-dimethylacetamide (250 uL). After 18 hours, the reaction mixture was purified by reverse phase HPLC (Method I). Product containing

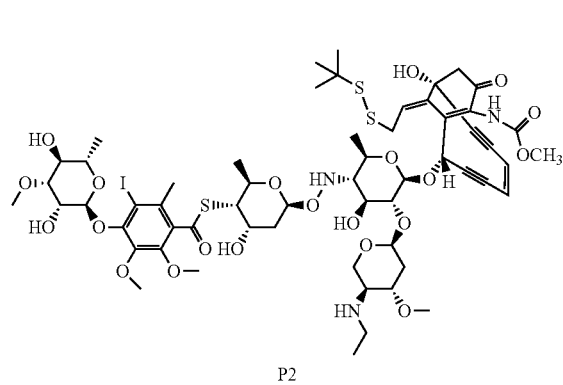

P2

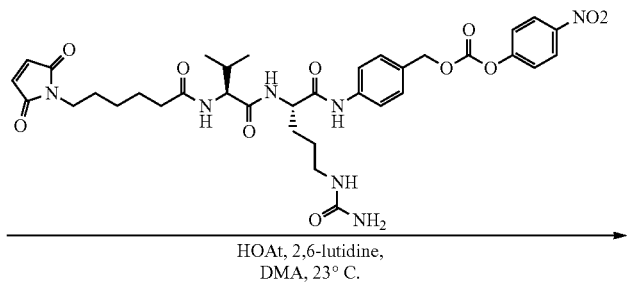

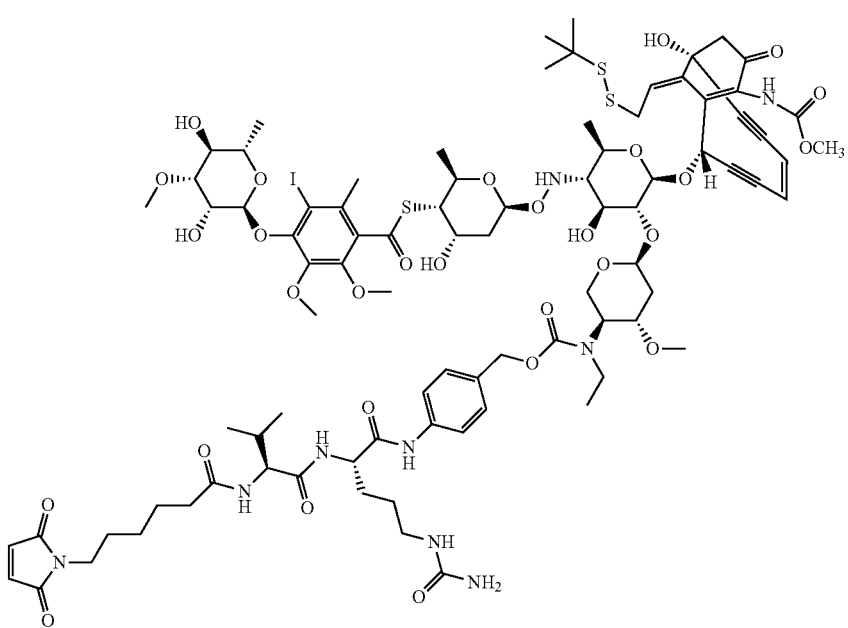

LP48

2,6-Lutidine (4.8 uL, 4.4 mg, 0.040 mmol) was added to a solution of S-[(2R,3S,4S,6S)-6-({[(2R,3S,4S,5R,6R)-6-{[(2S,5Z,9R,13E)-13-[2-(Tert-butyldisulfanyl)ethylidene]- fractions were lyophilized to obtain 4.5 mg of the desired product (LP48). LC-MS m/z 1998 [M+Na$^+$]; retention time=6.19 minutes (Method 10).

Example 49: Preparation of S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-amino-hexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-13-(2-{[(2R)-1-{[(4-methyl-2-oxo-2H-chromen-7-yl)carbamoyl]oxy}propan-2-yl]disulfanyl}ethylidene)-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methyl benzenecarbothioate (LP49)

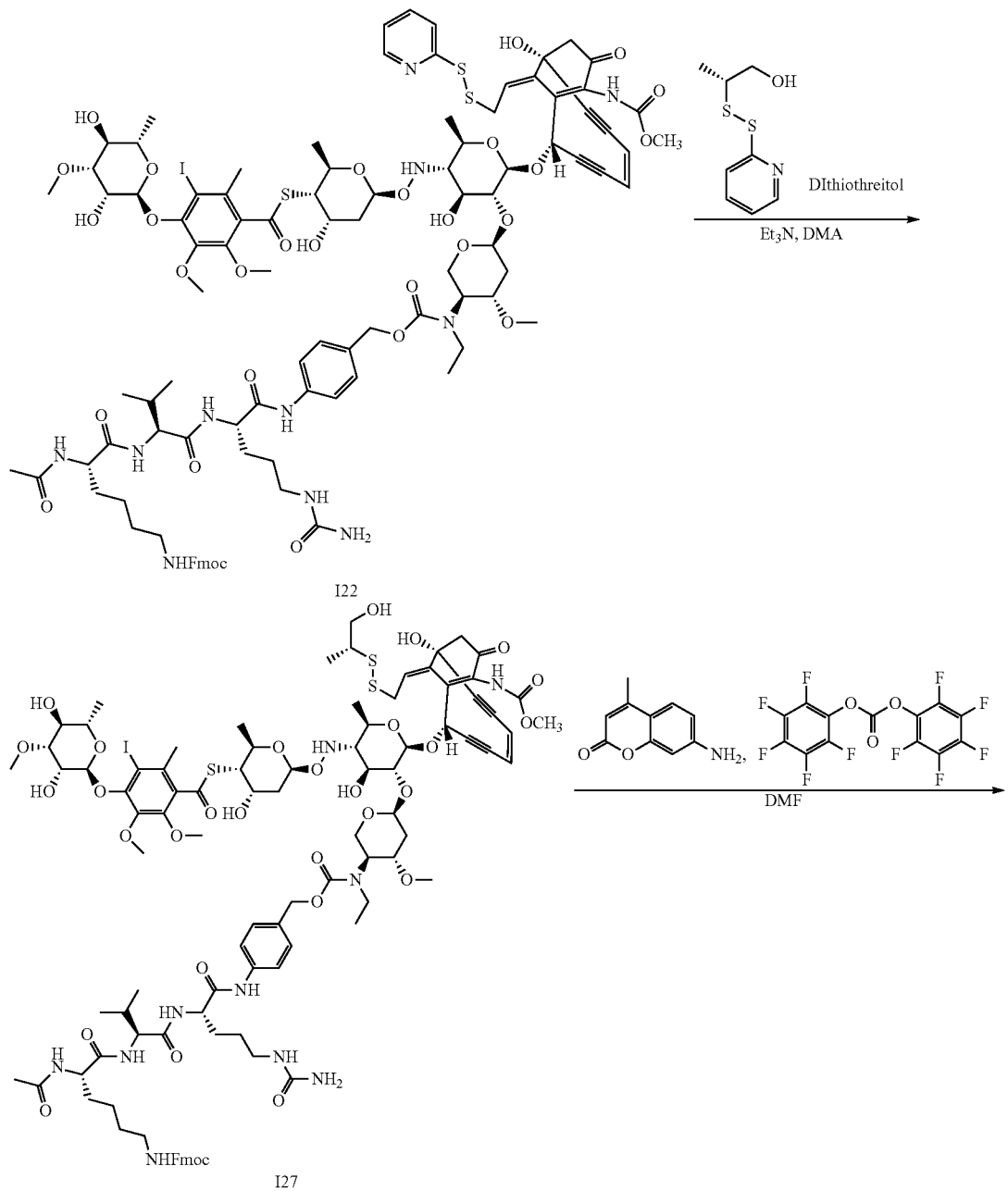

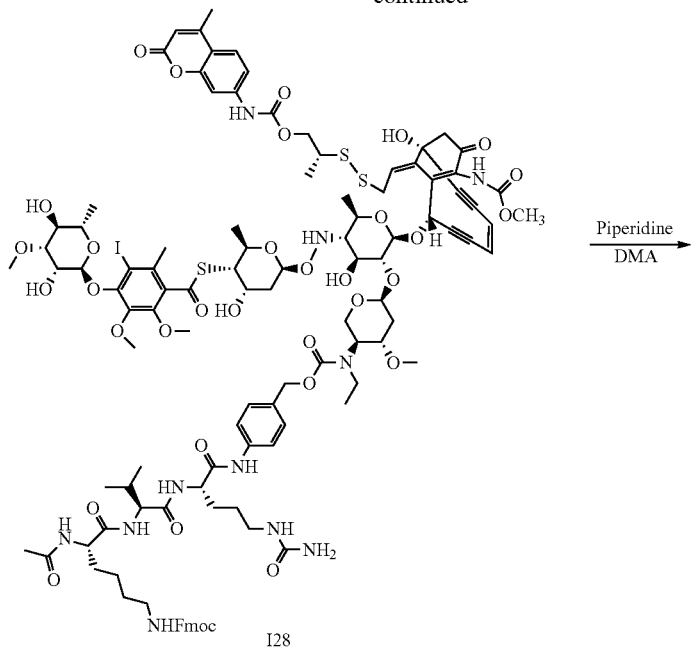
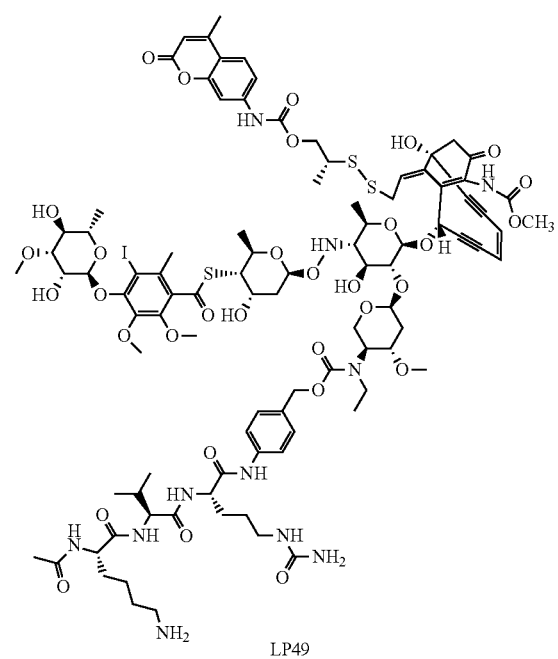

Step 1: Synthesis of S-[(2R,3S,4S,6S)-6-({[(2R,3S,4S,5R,6R)-5-({(2S,4S,5S)-5-[{[(4-{[(9S,12S,15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triaza hexadecan-16-yl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-13-(2-{[(2R)-1-hydroxypropan-2-yl]disulfanyl}ethylidene)-12-[(methoxy carbonyl)amino]-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (2R)-2-(2-pyridinyldithio)-1-propanol (4.5 mg, 0.022 mmol) was added to a solution of 1,4-dithiothreitol (2.5 mg, 0.106 mmol) in N,N-dimethylacetamide (380 uL). After 3 hours, S-[(2R,3S,4S,6S)-6-({[(2R,3S,4S,5R,6R)-5-({(2S,4S,5S)-5-[{[(4-{[(9S,12S,15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triazahexadecan-16-yl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-11-oxo-13-[2-(pyridin-2-yldisulfanyl)ethylidene]bicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (17.2 mg, 0.0072 mmol) was added to the reaction mixture. After 2 h, the reaction mixture was purified by reverse phase HPLC (Method B). Product containing fractions were lyophilized to provide 10 mg of the desired product. LC-MS m/z 2176.7 [M+H$^+$]; retention time=7.74 minutes (Method 7).

Step 2: Synthesis of S-[(2R,3S,4S,6S)-6-({[(2R,3S,4S,5R,6R)-5-({(2S,4S,5S)-5-[{[(4-{[(9S,12S,15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triaza hexadecan-16-yl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-13-(2-{[(2R)-1-{[(4-methyl-2-oxo-2H-chromen-7-yl)carbamoyl]oxy}propan-2-yl]disulfanyl}ethylidene)-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate N,N'-Diisopropylethylamine (114 mg, 150 uL, 0.863 mmol) was added to a solution of bis(trichloromethyl) carbonate (128 mg, 0.432 mmol) and 7-amino-4-methylcoumarin (75.6 mg, 0.432 mmol) in N,N-dimethylformamide (2.0 mL) at ambient temperature. After 1 h, a 1-mL aliquot of the reaction mixture was removed and added to S-[(2R,3S,4S,6S)-6-({[(2R,3S,4S,5R,6R)-5-({(2S,4S,5S)-5-[{[(4-{[(9S,12S,15S)-9-(acetylamino)-15-[3-(carbamoylamino) propyl]-1-(9H-fluoren-9-yl)-3,10,13,16-tetraoxo-12-(propan-2-yl)-2-oxa-4,11,14-triaza hexadecan-16-yl]amino}benzyl)oxy]carbonyl}(ethyl)amino]-4-methoxytetrahydro-2H-pyran-2-yl}oxy)-4-hydroxy-6-{[(2S,9R, 13E)-9-hydroxy-13-(2-{[(2R)-1-hydroxypropan-2-yl]disulfanyl}ethylidene)-12-[(methoxy carbonyl)amino]-11-oxobicyclo[7.3.1]trideca-1(12),5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (6.1 mg, 0.0027 mmol). N,N'-Diisopropyl ethylamine (10.8 mg, 14.4 uL, 0.0818 mmol) was added to the reaction mixture. After 1 h, the reaction mixture was purified by reverse phase HPLC (Method B). Product containing fractions were lyophilized to provide 2.3 mg of the desired product. LC-MS m/z 2378.7 [M+H$^+$]; retention time=3.31 minutes (Method 6).

Step 3: Synthesis of S-[(2R,3S,4S,6S)-6-({[(2R,3S,4S,5R,6R)-5-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino) pentanoyl]amino}benzyl)oxy]carbonyl}(ethyl) amino]-4-methoxytetrahydro-2H-pyran-2-yl}oxy)-4-hydroxy-6-{[(2S,9R,13E)-9-hydroxy-12-[(methoxycarbonyl)amino]-13-(2-{[(2R)-1-{[(4-methyl-2-oxo-2H-chromen-7-yl)carbamoyl]oxy}propan-2-yl]disulfanyl}ethylidene)-11-oxobicyclo[7.3.1]trideca-1(12), 5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate Piperidine (5 uL, 4 mg, 0.05 mmol) was added to a solution of S-[(2R,3S,4S,6S)-6-({[(2R,3S,4S,5R,6R)-5-({(2S,4S,5S)-5-[{[(4-{[(9S,12S,15S)-9-(acetylamino)-15-[3-(carbamoylamino)propyl]-1-(9H-fluoren-9-yl)-3,10,13,16-tetraoxo-12-(propan-2-yl)-2-oxa-4,11,14-triaza hexadecan-16-yl]amino}benzyl)oxy]carbonyl}(ethyl)amino]-4-methoxytetrahydro-2H-pyran-2-yl}oxy)-4-hydroxy-6-{[(2S,9R,13E)-9-hydroxy-12-[(methoxycarbonyl)amino]-13-(2-{[(2R)-1-{[(4-methyl-2-oxo-2H-chromen-7-yl)carbamoyl]oxy}propan-2-yl]disulfanyl}ethylidene)-11-oxobicyclo[7.3.1]trideca-1(12), 5-diene-3,7-diyn-2-yl]oxy}-2-methyltetrahydro-2H-pyran-3-yl]amino}oxy)-4-hydroxy-2-methyltetrahydro-2H-pyran-3-yl] 4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzenecarbothioate (2.4 mg, 0.010 mmol) in N,N-dimethylacetamide (300 uL). After 1 hour, the reaction mixture was purified by reverse phase HPLC (Method A). Product containing fractions were lyophilized to provide 2.4 mg of the desired product (LP49). LC-MS m/z 2156.8 [M+H$^+$]; retention time=5.8 minutes (Method 7).

Example 50: Preparation of (2S,3S,4S,5R,6S)-6-{4-[(13E)-13-{(1R,8S)-8-({(2R,3R,4S,5S,6R)-3-({(2S,4S,5S)-5-[{[(4-{[(2S)-2-{[(2S)-2-{[-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dim ethoxy-2-methyl benzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}-4-ethyl-6,9,9-trimethyl-3,7-dioxo-2-oxa-10,11-dithia-4,6-diazatridec-1-yl]phenoxy}-3,4,5-trihydroxytetrahydro-2H-pyran-2-carboxylic acid (LP50)

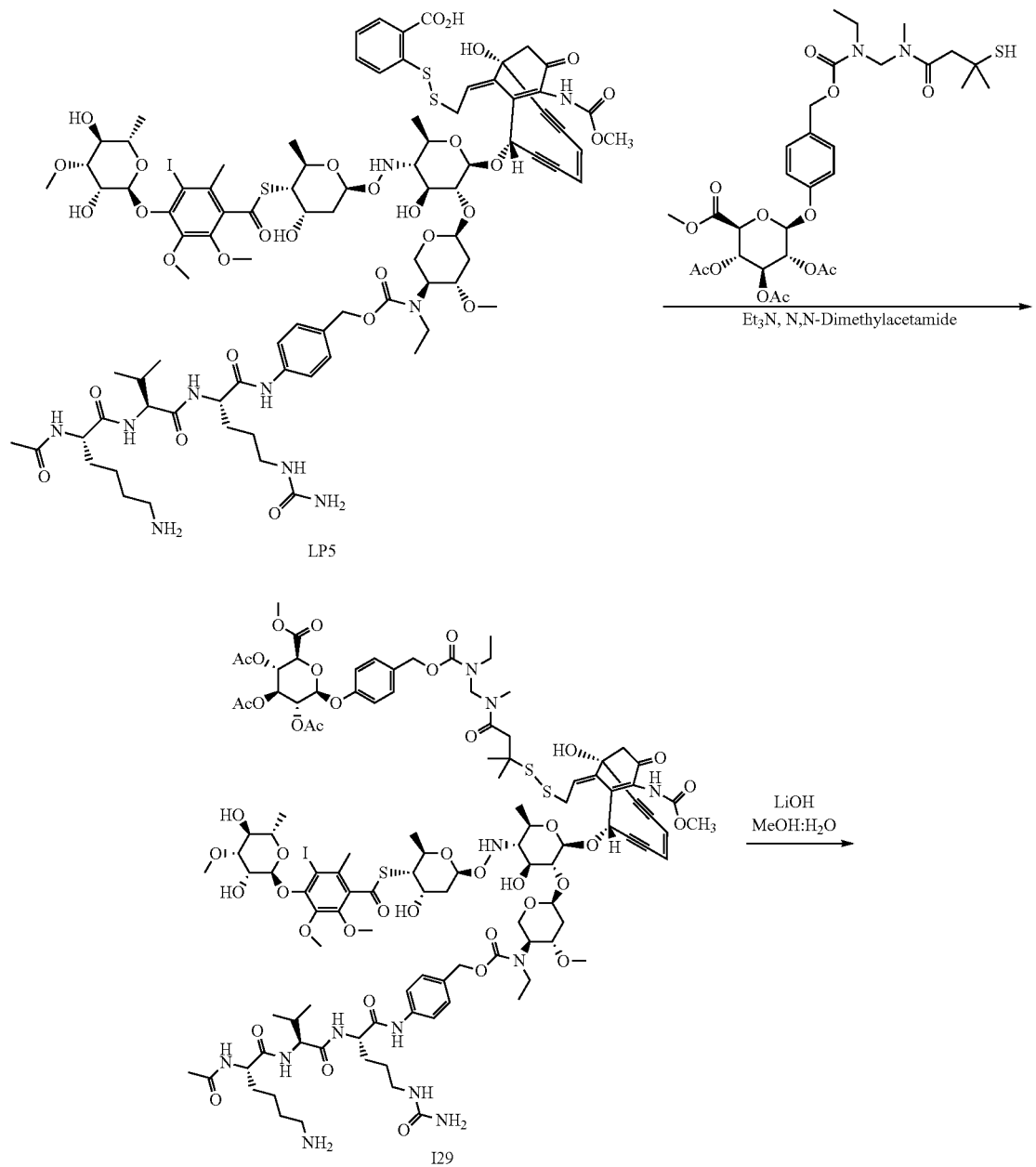

-continued

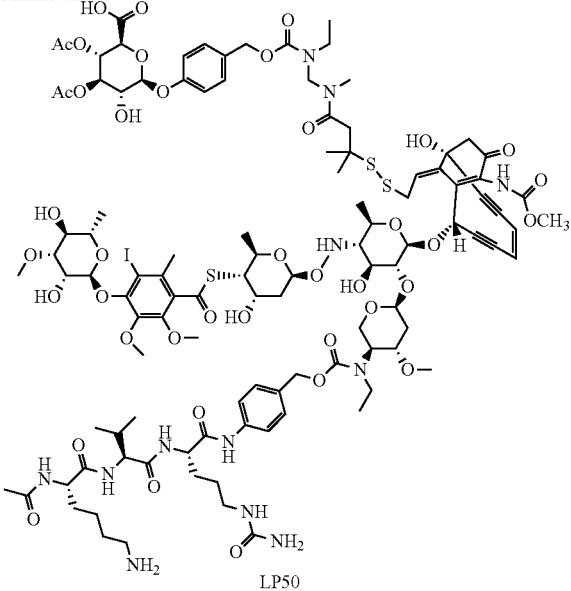

LP50

Step 1: Synthesis of methyl (2S,3S,4S,5R,6S)-6-{4-[(13E)-13-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}-4-ethyl-6,9,9-trimethyl-3,7-dioxo-2-oxa-10,11-dithia-4,6-diazatridec-1-yl]phenoxy}-3,4,5-tris(acetyloxy)tetrahydro-2H-pyran-2-carboxylate A solution of 4-{[(ethyl{[methyl(3-methyl-sulfanylbutanoyl)amino]methyl}carbamoyl)oxy]methyl}phenyl methyl 2,3,4-tri-O-acetyl-beta-D-glucopyranosiduronate (T20) (11.3 mg, 0.0168 mmol) and triethylamine (3.35 µL, 2.43 mg, 0.0240 mmol) in N,N-dimethylacetamide (120 µL) was added to 2-{[(2E)-2-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methylbenzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}benzoic acid (LP5) (5 mg, 0.002 mmol). After 5 hours, the reaction mixture was purified directly by reverse phase HPLC (Method A). Product containing fractions were lyophilized to provide 3 mg of the desired product. LC-MS m/z 2534.0 [M+H$^+$]; retention time=2.77 min minutes (Method 18).

Step 2: Synthesis of 2S,3S,4S,5R,6S)-6-{4-[(13E)-13-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dim ethoxy-2-methyl benzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}-4-ethyl-6,9,9-trimethyl-3,7-dioxo-2-oxa-10,11-dithia-4,6-diazatridec-1-yl]phenoxy}-3,4,5-trihydroxytetrahydro-2H-pyran-2-carboxylic acid (LP50)

A solution of lithium hydroxide (0.249 mg, 0.0104 mmol) in water (10 µL) was added to a solution of methyl (2S,3S,4S,5R,6S)-6-{4-[(13E)-13-{(1R,8S)-8-({(2R,3R,4S,5S,6R)-3-({(2S,4S,5S)-5-[{[(4-{[(2S)-2-{[(2S)-2-{[(2S)-2-(acetylamino)-6-aminohexanoyl]amino}-3-methylbutanoyl]amino}-5-(carbamoylamino)pentanoyl]amino}benzyl)oxy]carbonyl}(ethyl)amino]-4-methoxytetrahydro-2H-pyran-2-yl}oxy)-5-[({(2S,4S,5S,6R)-5-[(4-{[(2S,3R,4R,5S,6S)-3,5-dihydroxy-4-methoxy-6-methyltetrahydro-2H-pyran-2-yl]oxy}-3-iodo-5,6-dimethoxy-2-methyl benzoyl)sulfanyl]-4-hydroxy-6-methyltetrahydro-2H-pyran-2-yl}oxy)amino]-4-hydroxy-6-methyltetrahydro-2H-pyran-2-yl}oxy)-1-hydroxy-10-[(methoxycarbonyl)amino]-11-oxobicyclo[7.3.1]trideca-4,9-diene-2,6-diyn-13-ylidene}-4-ethyl-6,9,9-trimethyl-3,7-dioxo-2-oxa-10,11-dithia-4,6-diazatridec-1-yl]phenoxy}-3,4,5-tris(acetyloxy)tetrahydro-2H-pyran-2-carboxylate (3 mg, 0.001 mmol) in methanol (400 µL) and water (400 µL). After 40 minutes, the reaction mixture was purified directly by reverse phase HPLC (Method A). Product containing fractions were lyophilized to provide 2.2 mg of the desired produc (LP50). LC-MS m/z 2393.9 [M+H$^+$]; retention time=2.55 min minutes (Method 18).

General Procedures for Conjugation of Calicheamicin LPs

General procedure A:

The conjugation reaction was conducted in 25-50 mM tris(hydroymethyl)aminoethane (tris) buffer (pH 8) containing 150 mM sodium chloride (NaCl), and 12% dimethyl sulfoxide (DMSO) at approximately 5 mg/mL protein concentration. The antibody was buffer exchanged into water or dilute phosphate buffered saline (PBS) prior to use and was treated sequentially with the appropriate volumes of 1M Tris (pH 8), 5M NaCl, and DMSO in order to achieve the above concentrations. The appropriate linker payload (15-20 equivalents mol/mol) was added as a 30 mM stock solution in DMSO followed by transglutaminase powder (Ajinomoto Activa, 2-fold wt. eq. over the antibody wt.). The reaction was rotated at room temperature overnight. The loading was checked by LCMS or hydrophobic interaction chromatography (HIC). If the reaction was incomplete, an additional aliquot of transglutaminase and/or linker-payload was added and the rotation was continued for an additional 3-6 hours.

Reaction workup typically involved buffer exchange into PBS followed by purification by size exclusion chromatography (GE Superdex 200 10/300 GL). The resulting antibody drug conjugate (ADC) was characterized by analytical HIC, size exclusion chromatography (SEC), and LCMS per the methods described below.

General procedure B:

The conjugation reaction was conducted in 25-50 mM tris buffer (pH 7.5) containing 150 mM NaCl, and 5-7% DMSO at approximately 5 mg/mL protein concentration. The antibody was buffer exchanged into water or dilute PBS prior to use and was treated sequentially with the appropriate volumes of 1M Tris (pH 7.5), 5M NaCl, and DMSO in order to achieve the above concentrations. The appropriate linker payload (15-20 equivalents mol/mol) was added as a 30 mM stock solution in DMSO followed by transglutaminase powder (Ajinomoto Activa, 2-fold wt. eq. over the antibody wt.). The reaction was rotated at room temperature overnight. The loading was checked by LCMS or HIC. If the reaction was incomplete, an additional aliquot of transglutaminase and/or linker-payload was added and the rotation was continued for an additional 3-6 hours.

Reaction workup typically involved buffer exchange into PBS followed by purification by size exclusion chromatography (GE Superdex 200 10/300 GL). The resulting ADC was characterized by analytical HIC, SEC, and LCMS per the methods described below.

General procedure C:

Reduction/reoxidation of the engineered cysteine mutant was performed by the method outlined in WO2013093809. The resulting antibody (in PBS, pH 7.4) was treated with PBS and DMA in order provide a ~5 mg/mL stock solution of antibody in 20% DMA (vol/vol). The resulting solution was treated with 6 equivalents (mol/mol) of the appropriate maleimide linker-payload and after thorough mixing was allowed to stand at rt for 2h. In cases of incomplete reaction, the temperature was increased to 37° C. for ~1 h. The crude reaction was buffer exchanged into PBS and purified by SEC (GE Superdex200, PBS eluent) and the monomeric fractions were pooled for analysis.

General Analytical Methods for Conjugation Examples

LCMS: Column=Waters BEH300-C4, 2.1×100 mm (P/N=186004496); Instrument=Acquity UPLC with an SQD2 mass spec detector; Flow rate=0.7 mL/min; Temperature=80° C.; Buffer A=water+0.1% formic acid; Buffer B=acetonitrile+0.1% formic acid. The gradient runs from 3% B to 95% B over 2 minutes, holds at 95% B for 0.75 min, and then re-equilibrates at 3% B. The sample is reduced with DTT immediately prior to injection. The eluate is monitored by LCMS (400-2000 daltons) and the protein peak is deconvoluted using MaxEnt1. DAR is reported as a weight average loading as has been previously described.

Alternatively, non-reducing LCMS analysis was performed using an Aquity H-class UPLC connected to a Xevo G2-XS TOF mass spectrometer. The separation was performed using a BEH-C18 column (2.1 µm×50 mm, P/N 186002350) at 80° C. A gradient from 10% acetonitrile to 95% acetonitrile in water (+0.1% formic acid) was performed. MS data was collected from 1500-3000 m/z (positive mode). The entire protein peak was selected for deconvolution using MaxEnt software. Typical injection size is 0.1 µg.

SEC: Column: Superdex200 (5/150 GL); Mobile phase: Phosphate buffered saline containing 2% acetonitrile, pH 7.4; Flow rate=0.25 mL/min; Temperature=ambient; Instrument: Agilent 1100 HPLC.

HIC: Column: TSKGel Butyl NPR, 4.6 mm×3.5 cm (P/N=S0557-835); Buffer A=1.5 M ammonium sulfate containing 10 mM phosphate, pH 7; Buffer B=10 mM phosphate, pH 7+20% isopropyl alcohol; Flow rate=0.8 mL/min; Temperature=ambient; Gradient=0% B to 100% B over 12 minutes, hold at 100% B for 2 minutes, then re-equilibrate at 100% A; Instrument: Agilent 1100 HPLC.

Antibodies Used for Conjugation:

```
CD33-11A1-v1417-H16-K222R-hG1
Heavy chain: EVQLVESGGG LVQPGGSLRL SCAASGYIFT DYVTHWVRQA PGKGLEWIAY

INPYNDGTKY NERFKGRFTI SSDNAKNSLY LQMNSLRAED TAVYYCARDY RYEIYGMDYW

GQGTLVTVSS ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP KSCDRTHTCP

PCPAPELLGG PSVFLFPPKP KDTLMISRTP EVTCVVVDVS HEDPEVKFNW YVDGVEVHNA

KTKPRELLQG STYRVVSVLT VLHQDWLNGK EYKCKVSNKA LPAPIEKTIS KAKGQPREPQ

VYTLPPSREE MTKNQVSLTC LVKGFYPSDI AVEWESNGQP ENNYKTTPPV LDSDGSFFLY

SKLTVDKSRW QQGNVFSCSV MHEALHNHYT QKSLSLSPG
```

-continued

Ligh chain: DIQLTQSPSS LSASVGDRVT ITCRASSSVG YMHWYQQKPG KAPKLLIYDT
SQLASGVPSR FSGSGSGTDF TLTISSLQPE DFATYYCQLW NSNPLTFGGG TKVEIKRTVA
APSVFIFPPS DEQLKSGTAS VVCLLNNFYP REAKVQWKVD NALQSGNSQE SVTEQDSKDS
TYSLSSTLTL SKADYEKHKV YACEVTHQGL SSPVTKSFNR GEC CD33-11A1-v1417-kN92S-H16-D55A-K222R-hG1
Heavy chain: EVQLVESGGG LVQPGGSLRL SCAASGYIFT DYVTHWVRQA PGKGLEWIAY
INPYNAGTKY NERFKGRFTI SSDNAKNSLY LQMNSLRAED TAVYYCARDY RYEIYGMDYW
GQGTLVTVSS ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP KSCDRTHTCP
PCPAPELLGG PSVFLFPPKP KDTLMISRTP EVTCVVVDVS HEDPEVKFNW YVDGVEVHNA
KTKPRELLQG STYRVVSVLT VLHQDWLNGK EYKCKVSNKA LPAPIEKTIS KAKGQPREPQ
VYTLPPSREE MTKNQVSLTC LVKGFYPSDI AVEWESNGQP ENNYKTTPPV LDSDGSFFLY
SKLTVDKSRW QQGNVFSCSV MHEALHNHYT QKSLSLSPG Light chain: DIQLTQSPSS LSASVGDRVT ITCRASSSVG YMHWYQQKPG KAPKLLIYDT
SQLASGVPSR FSGSGSGTDF TLTISSLQPE DFATYYCQLW SSNPLTFGGG TKVEIKRTVA
APSVFIFPPS DEQLKSGTAS VVCLLNNFYP REAKVQWKVD NALQSGNSQE SVTEQDSKDS
TYSLSSTLTL SKADYEKHKV YACEVTHQGL SSPVTKSFNR GEC Neg-8-8-H16-K222R-hG1
Heavy chain: EVQLLESGGG LVQPGGSLRL SCAASGFTFS SYAMSWVRQA PGKGLEWVSA
ISGSGGSTYY ADSVKGRFTI SRDNSKNTLY LQMNSLRAED TAVYYCAKDL NSRGTIIHYW
GQGTLVTVSS ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP KSCDKTHTCP
PCPAPELLGG PSVFLFPPKP KDTLMISRTP EVTCVVVDVS HEDPEVKFNW YVDGVEVHNA
KTKPRELLQG STYRVVSVLT VLHQDWLNGK EYKCKVSNKA LPAPIEKTIS KAKGQPREPQ
VYTLPPSREE MTKNQVSLTC LVKGFYPSDI AVEWESNGQP ENNYKTTPPV LDSDGSFFLY
SKLTVDKSRW QQGNVFSCSV MHEALHNHYT QKSLSLSPG Light chain: DIVMTQSPSS LSASVGDRVT ITCRASQSIS SYLNWYQQKP GKAPKLLIYA
ASSLQSGVPS RFSGSGSGTD FTLTISSLQP EDFATYYCQQ SYSTPLTFGG GTKVEIKGTV
AAPSVFIFPP SDEQLKSGTA SVVCLLNNFY PREAKVQWKV DNALQSGNSQ ESVTEQDSKD
STYSLSSTLT LSKADYEKHK VYACEVTHQG LSSPVTKSFN RGEC CD33-11A1-v1417-LCQ05-H16-K222R-hG1
Heavy chain: EVQLVESGGG LVQPGGSLRL SCAASGYIFT DYVTHWVRQA PGKGLEWIAY
INPYNDGTKY NERFKGRFTI SSDNAKNSLY LQMNSLRAED TAVYYCARDY RYEIYGMDYW
GQGTLVTVSS ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP KSCDRTHTCP
PCPAPELLGG PSVFLFPPKP KDTLMISRTP EVTCVVVDVS HEDPEVKFNW YVDGVEVHNA
KTKPRELLQG STYRVVSVLT VLHQDWLNGK EYKCKVSNKA LPAPIEKTIS KAKGQPREPQ
VYTLPPSREE MTKNQVSLTC LVKGFYPSDI AVEWESNGQP ENNYKTTPPV LDSDGSFFLY
SKLTVDKSRW QQGNVFSCSV MHEALHNHYT QKSLSLSPG -continued Light chain: DIQLTQSPSS LSASVGDRVT ITCRASSSVG YMHWYQQKPG KAPKLLIYDT
SQLASGVPSR FSGSGSGTDF TLTISSLQPE DFATYYCQLW NSNPLTFGGG TKVEIKRTVA
APSVFIFPPS DEQLKSGTAS VVCLLNNFYP REAKVQWKVD NALQSGNSQE SVTEQDSKDS
TYSLSSTLTL SKADYEKHKV YACEVTHQGL SSPVTKSFNR GECGGLLQGP P Her2-PT-H16-K222R-hG1
Heavy chain: EVQLVESGGG LVQPGGSLRL SCAASGFNIK DTYIHWVRQA PGKGLEWVAR
IYPTNGYTRY ADSVKGRFTI SADTSKNTAY LQMNSLRAED TAVYYCSRWG GDGFYAMDYW
GQGTLVTVSS ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP KSCDRTHTCP
PCPAPELLGG PSVFLFPPKP KDTLMISRTP EVTCVVVDVS HEDPEVKFNW YVDGVEVHNA
KTKPRELLQG STYRVVSVLT VLHQDWLNGK EYKCKVSNKA LPAPIEKTIS KAKGQPREPQ
VYTLPPSREE MTKNQVSLTC LVKGFYPSDI AVEWESNGQP ENNYKTTPPV LDSDGSFFLY
SKLTVDKSRW QQGNVFSCSV MHEALHNHYT QKSLSLSPG Light chain: DIQMTQSPSS LSASVGDRVT ITCRASQDVN TAVAWYQQKP GKAPKLLIYS
ASFLYSGVPS RFSGSRSGTD FTLTISSLQP EDFATYYCQQ HYTTPPTFGQ GTKVEIKRTV
AAPSVFIFPP SDEQLKSGTA SVVCLLNNFY PREAKVQWKV DNALQSGNSQ ESVTEQDSKD
STYSLSSTLT LSKADYEKHK VYACEVTHQG LSSPVTKSFN RGEC CD33-11A1-v1417-H7C-hG1
Heavy chain: EVQLVESGGG LVQPGGSLRL SCAASGYIFT DYVTHWVRQA PGKGLEWIAY
INPYNDGTKY NERFKGRFTI SSDNAKNSLY LQMNSLRAED TAVYYCARDY RYEIYGMDYW
GQGTLVTVSS ASTKGPSVFP LAPSSKSTLL QGSGGTAALG CLVKDYFPEP VTVSWNSGAL
TSGVHTFPAV LQSSGLYSLS SVVTVPSSSL GTQTYICNVN HKPSNTKVDK KVEPKSCDKT
HTCPPCPAPE LLGGPSVFLF PPKPKDTLMI SRTPEVTCVV VDVSHEDPEV KFNWYVDGVE
VHNAKTKPRE EQYNSTYRVV SVLTVLHQDW LNGKEYKCKV SNKALPAPIE KTISKAKGQP
REPQVYTLPP SREEMTKNQV SLTCLVKGFY PSDIAVEWES NGQPENNYKT TPPVLDSDGS
FFLYSKLTVD KSRWQQGNVF SCSVMHEALH NHYTQKSLSL SPG Light chain: DIQLTQSPSS LSASVGDRVT ITCRASSSVG YMHWYQQKPG KAPKLLIYDT
SQLASGVPSR FSGSGSGTDF TLTISSLQPE DFATYYCQLW NSNPLTFGGG TKVEIKRTVA
APSVFIFPPS DEQLKSGTAS VVCLLNNFYP REAKVQWKVD NALQSGNSQE SVTEQDSKDS
TYSLSSTLTL SKADYEKHKV YACEVTHQGL SSPVTKSFNR GEC Her2-PT-H7C-K222R-hG1
Heavy chain: EVQLVESGGG LVQPGGSLRL SCAASGFNIK DTYIHWVRQA PGKGLEWVAR
IYPTNGYTRY ADSVKGRFTI SADTSKNTAY LQMNSLRAED TAVYYCSRWG GDGFYAMDYW
GQGTLVTVSS ASTKGPSVFP LAPSSKSTLL QGSGGTAALG CLVKDYFPEP VTVSWNSGAL
TSGVHTFPAV LQSSGLYSLS SVVTVPSSSL GTQTYICNVN HKPSNTKVDK KVEPKSCDRT
HTCPPCPAPE LLGGPSVFLF PPKPKDTLMI SRTPEVTCVV VDVSHEDPEV KFNWYVDGVE
VHNAKTKPRE EQYNSTYRVV SVLTVLHQDW LNGKEYKCKV SNKALPAPIE KTISKAKGQP
REPQVYTLPP SREEMTKNQV SLTCLVKGFY PSDIAVEWES NGQPENNYKT TPPVLDSDGS
FFLYSKLTVD KSRWQQGNVF SCSVMHEALH NHYTQKSLSL SPG -continued Light chain: DIQMTQSPSS LSASVGDRVT ITCRASQDVN TAVAWYQQKP GKAPKLLIYS
ASFLYSGVPS RFSGSRSGTD FTLTISSLQP EDFATYYCQQ HYTTPPTFGQ GTKVEIKRTV
AAPSVFIFPP SDEQLKSGTA SVVCLLNNFY PREAKVQWKV DNALQSGNSQ ESVTEQDSKD
STYSLSSTLT LSKADYEKHK VYACEVTHQG LSSPVTKSFN RGEC Her2-PT-LCQ05-K222R-hG1
Heavy chain: EVQLVESGGG LVQPGGSLRL SCAASGFNIK DTYIHWVRQA PGKGLEWVAR
IYPTNGYTRY ADSVKGRFTI SADTSKNTAY LQMNSLRAED TAVYYCSRWG GDGFYAMDYW
GQGTLVTVSS ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP KSCDRTHTCP
PCPAPELLGG PSVFLFPPKP KDTLMISRTP EVTCVVVDVS HEDPEVKFNW YVDGVEVHNA
KTKPREEQYN STYRVVSVLT VLHQDWLNGK EYKCKVSNKA LPAPIEKTIS KAKGQPREPQ
VYTLPPSREE MTKNQVSLTC LVKGFYPSDI AVEWESNGQP ENNYKTTPPV LDSDGSFFLY
SKLTVDKSRW QQGNVFSCSV MHEALHNHYT QKSLSLSPGK
Light chain: DIQMTQSPSS LSASVGDRVT ITCRASQDVN TAVAWYQQKP GKAPKLLIYS
ASFLYSGVPS RFSGSRSGTD FTLTISSLQP EDFATYYCQQ HYTTPPTFGQ GTKVEIKRTV
AAPSVFIFPP SDEQLKSGTA SVVCLLNNFY PREAKVQWKV DNALQSGNSQ ESVTEQDSKD
STYSLSSTLT LSKADYEKHK VYACEVTHQG LSSPVTKSFN RGECGGLLQG PP CD33-11A1-v1417-kK183C-hG1
Heavy chain: EVQLVESGGG LVQPGGSLRL SCAASGYIFT DYVTHWVRQA PGKGLEWIAY
INPYNDGTKY NERFKGRFTI SSDNAKNSLY LQMNSLRAED TAVYYCARDY RYEIYGMDYW
GQGTLVTVSS ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP KSCDKTHTCP
PCPAPELLGG PSVFLFPPKP KDTLMISRTP EVTCVVVDVS HEDPEVKFNW YVDGVEVHNA
KTKPREEQYN STYRVVSVLT VLHQDWLNGK EYKCKVSNKA LPAPIEKTIS KAKGQPREPQ
VYTLPPSREE MTKNQVSLTC LVKGFYPSDI AVEWESNGQP ENNYKTTPPV LDSDGSFFLY
SKLTVDKSRW QQGNVFSCSV MHEALHNHYT QKSLSLSPG
Light chain: DIQLTQSPSS LSASVGDRVT ITCRASSSVG YMHWYQQKPG KAPKLLIYDT
SQLASGVPSR FSGSGSGTDF TLTISSLQPE DFATYYCQLW NSNPLTFGGG TKVEIKRTVA
APSVFIFPPS DEQLKSGTAS VVCLLNNFYP REAKVQWKVD NALQSGNSQE SVTEQDSKDS
TYSLSSTLTL SCADYEKHKV YACEVTHQGL SSPVTKSFNR GEC Her2-PT-A114C-hG1
Heavy chain: EVQLVESGGG LVQPGGSLRL SCAASGFNIK DTYIHWVRQA PGKGLEWVAR
IYPTNGYTRY ADSVKGRFTI SADTSKNTAY LQMNSLRAED TAVYYCSRWG GDGFYAMDYW
GQGTLVTVSS CSTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP KSCDKTHTCP
PCPAPELLGG PSVFLFPPKP KDTLMISRTP EVTCVVVDVS HEDPEVKFNW YVDGVEVHNA
KTKPREEQYN STYRVVSVLT VLHQDWLNGK EYKCKVSNKA LPAPIEKTIS KAKGQPREPQ
VYTLPPSREE MTKNQVSLTC LVKGFYPSDI AVEWESNGQP ENNYKTTPPV LDSDGSFFLY
SKLTVDKSRW QQGNVFSCSV MHEALHNHYT QKSLSLSPGK -continued

```
Light chain: DIQMTQSPSS LSASVGDRVT ITCRASQDVN TAVAWYQQKP GKAPKLLIYS

ASFLYSGVPS RFSGSRSGTD FTLTISSLQP EDFATYYCQQ HYTTPPTFGQ GTKVEIKRTV

AAPSVFIFPP SDEQLKSGTA SVVCLLNNFY PREAKVQWKV DNALQSGNSQ ESVTEQDSKD

STYSLSSTLT LSKADYEKHK VYACEVTHQG LSSPVTKSFN RGEC
```

TABLE 1

Table of conjugation data:

| Example Number | ADC ID | Antibody | LP Number | Method | Isolated yield |
|---|---|---|---|---|---|
| 50 | CD33-11A1-v1417-H16-K222R-hG1-LP1 | CD33-11A1-v1417-H16-K222R-hG1 | LP1 | A | 48% |
| 51 | CD33-11A1-v1417-kN92S-H16-D55A-K222R-hG1-LP1 | CD33-11A1-v1417-kN92S-H16-D55A-K222R-hG1 | LP1 | B | 25% |
| 52 | Neg-8-8-H16-K222R-hG1-LP1 | Neg-8-8-H16-K222R-hG1 | LP1 | B | 45% |
| 53 | CD33-11A1-v1417-LCQ05-H16-K222R-hG1-LP1 | CD33-11A1-v1417-LCQ05-H16-K222R-hG1 | LP1 | B | 13% |
| 54 | Her2-PT-H16-K222R-hG1-LP1 | Her2-PT-H16-K222R-hG1 | LP1 | A | 43% |
| 55 | Her2-PT-A114C-hG1-LP2 | Her2-PT-A114C-hG1 | LP2 | C | 48% |
| 56 | CD33-11A1-v1417-kK183C-hG1-LP2 | CD33-11A1-v1417-kK183C-hG1 | LP2 | C | 41% |
| 57 | CD33-11A1-v1417-H16-K222R-hG1-LP3 | CD33-11A1-v1417-H16-K222R-hG1 | LP3 | A | 54% |
| 58 | CD33-11A1-v1417-H16-K222R-hG1-LP4 | CD33-11A1-v1417-H16-K222R-hG1 | LP4 | A | 63% |
| 59 | CD33-11A1-v1417-H16-K222R-hG1-LP5 | CD33-11A1-v1417-H16-K222R-hG1 | LP5 | A | 60% |
| 60 | CD33-11A1-v1417-kN92S-H16-D55A-K222R-hG1-LP5 | CD33-11A1-v1417-kN92S-H16-D55A-K222R-hG1 | LP5 | B | 29% |
| 61 | CD33-11A1-v1417-kN92S-H16-D55A-K222R-hG1-LP6 | CD33-11A1-v1417-kN92S-H16-D55A-K222R-hG1 | LP6 | B | 67% |
| 62 | Her2-PT-H16-K222R-hG1-LP6 | Her2-PT-H16-K222R-hG1 | LP6 | A | 28% |
| 63 | CD33-11A1-v1417-kN92S-H16-D55A-K222R-hG1-LP7 | CD33-11A1-v1417-kN92S-H16-D55A-K222R-hG1 | LP7 | B | 65% |
| 64 | CD33-11A1-v1417-kN92S-H16-D55A-K222R-hG1-LP8 | CD33-11A1-v1417-kN92S-H16-D55A-K222R-hG1 | LP8 | B | 44% |
| 65 | CD33-11A1-v1417-kN92S-H16-D55A-K222R-hG1-LP9 | CD33-11A1-v1417-kN92S-H16-D55A-K222R-hG1 | LP9 | B | 35% |
| 66 | CD33-11A1-v1417-H16-K222R-hG1-LP10 | CD33-11A1-v1417-H16-K222R-hG1 | LP10 | A | 6% |
| 67 | CD33-11A1-v1417-kN92S-H16-D55A-K222R-hG1-LP11 | CD33-11A1-v1417-kN92S-H16-D55A-K222R-hG1 | LP11 | B | 67% |
| 68 | CD33-11A1-v1417-kN92S-H16-D55A-K222R-hG1-LP12 | CD33-11A1-v1417-kN92S-H16-D55A-K222R-hG1 | LP12 | B | 53% |
| 69 | CD33-11A1-v1417-H16-K222R-hG1-LP13 | CD33-11A1-v1417-H16-K222R-hG1 | LP13 | A | 55% |
| 70 | CD33-11A1-v1417-kN92S-H16-D55A-K222R-hG1-LP13 | CD33-11A1-v1417-kN92S-H16-D55A-K222R-hG1 | LP13 | B | 42% |
| 71 | Neg-8-8-H16-K222R-hG1-LP13 | Neg-8-8-H16-K222R-hG1 | LP13 | B | 37% |
| 72 | CD33-11A1-v1417-LCQ05-H16-K222R-hG1-LP13 | CD33-11A1-v1417-LCQ05-H16-K222R-hG1 | LP13 | B | 12% |
| 73 | Her2-PT-H16-K222R-hG1-LP13 | Her2-PT-H16-K222R-hG1 | LP13 | A | 26% |
| 74 | CD33-11A1-v1417-H16-K222R-hG1-LP14 | CD33-11A1-v1417-H16-K222R-hG1 | LP14 | A | 60% |

TABLE 1-continued

Table of conjugation data:

| Example Number | ADC ID | Antibody | LP Number | Method | Isolated yield |
|---|---|---|---|---|---|
| 75 | CD33-11A1-v1417-LCQ05-H16-K222R-hG1-LP14 | CD33-11A1-v1417-LCQ05-H16-K222R-hG1 | LP14 | A | 63% |
| 76 | CD33-11A1-v1417-H16-K222R-hG1-LP15 | CD33-11A1-v1417-H16-K222R-hG1 | LP15 | A | 64% |
| 77 | CD33-11A1-v1417-H16-K222R-hG1-LP16 | CD33-11A1-v1417-H16-K222R-hG1 | LP16 | A | 48% |
| 78 | CD33-11A1-v1417-H16-K222R-hG1-LP17 | CD33-11A1-v1417-H16-K222R-hG1 | LP17 | A | 47% |
| 79 | CD33-11A1-v1417-kN92S-H16-D55A-K222R-hG1-LP18 | CD33-11A1-v1417-kN92S-H16-D55A-K222R-hG1 | LP18 | B | 39% |
| 80 | Her2-PT-H16-K222R-hG1-LP49 | Her2-PT-H16-K222R-hG1 | LP49 | B | 8% |
| 81 | CD33-11A1-v1417-H7C-hG1-LP19 | CD33-11A1-v1417-H7C-hG1 | LP19 | A | 53% |
| 82 | Her2-PT-H7C-K222R-hG1-LP19 | Her2-PT-H7C-K222R-hG1 | LP19 | A | 71% |
| 83 | CD33-11A1-v1417-LCQ05-H16-K222R-hG1-LP19 | CD33-11A1-v1417-LCQ05-H16-K222R-hG1 | LP19 | B | 62% |
| 84 | CD33-11A1-v1417-H16-K222R-hG1-LP19 | CD33-11A1-v1417-H16-K222R-hG1 | LP19 | A | 46% |
| 85 | CD33-11A1-v1417-kN92S-H16-D55A-K222R-hG1-LP19 | CD33-11A1-v1417-kN92S-H16-D55A-K222R-hG1 | LP19 | B | 27% |
| 86 | Neg-8-8-H16-K222R-hG1-LP19 | Neg-8-8-H16-K222R-hG1 | LP19 | B | 39% |
| 87 | Her2-PT-LCQ05-K222R-hG1-LP19 | Her2-PT-LCQ05-K222R-hG1 | LP19 | B | 28% |
| 88 | Her2-PT-H16-K222R-hG1-LP19 | Her2-PT-H16-K222R-hG1 | LP19 | A | 25% |
| 89 | CD33-11A1-v1417-kN92S-H16-D55A-K222R-hG1-(Q)_AcLysValCitPABC_LP21 | CD33-11A1-v1417-kN92S-H16-D55A-K222R-hG1 | LP21 | B | 41% |
| 90 | CD33-11A1-v1417-kN92S-H16-D55A-K222R-hG1-(Q)_AcLysValCitPABC_LP25 | CD33-11A1-v1417-kN92S-H16-D55A-K222R-hG1 | LP25 | B | 37% |
| 91 | CD33-11A1-v1417-kN92S-H16-D55A-K222R-hG1-(Q)_AcLysValCitPABC_LP26 | CD33-11A1-v1417-kN92S-H16-D55A-K222R-hG1 | LP26 | B | 5% |
| 92 | CD33-11A1-v1417-kN92S-H16-D55A-K222R-hG1-(Q)_AcLysValCitPABC_LP27 | CD33-11A1-v1417-kN92S-H16-D55A-K222R-hG1 | LP27 | B | 6% |
| 93 | CD33-11A1-v1417-kN92S-H16-D55A-K222R-hG1-(Q)_AcLysValCitPABC_LP28 | CD33-11A1-v1417-kN92S-H16-D55A-K222R-hG1 | LP28 | B | 1% |
| 94 | CD33-11A1-v1417-kN92S-H16-D55A-K222R-hG1-(Q)_AcLysValCitPABC_LP29 | CD33-11A1-v1417-kN92S-H16-D55A-K222R-hG1 | LP29 | B | 5% |
| 95 | CD33-11A1-v1417-kN92S-H16-D55A-K222R-hG1-(Q)_AcLysValCitPABC_LP33 | CD33-11A1-v1417-kN92S-H16-D55A-K222R-hG1 | LP33 | A | 64% |
| 96 | CD33-11A1-v1417-kN92S-H16-D55A-K222R-hG1-(Q)_AcLysValCitPABC_LP34 | CD33-11A1-v1417-kN92S-H16-D55A-K222R-hG1 | LP34 | A | 62% |
| 97 | CD33-11A1-v1417-kN92S-H16-D55A-K222R-hG1-(Q)_AcLysValCitPABC_LP35 | CD33-11A1-v1417-kN92S-H16-D55A-K222R-hG1 | LP35 | B | 5% |
| 98 | CD33-11A1-v1417-kN92S-H16-D55A-K222R-hG1-(Q)_AcLysValCitPABC_LP36 | CD33-11A1-v1417-kN92S-H16-D55A-K222R-hG1 | LP36 | B | 5% |
| 99 | CD33-11A1-v1417-H16-K222R-hG1-LP38 | CD33-11A1-v1417-H16-K222R-hG1 | LP38 | A | 34% |

TABLE 1-continued

Table of conjugation data:

| Example Number | ADC ID | Antibody | LP Number | Method | Isolated yield |
|---|---|---|---|---|---|
| 100 | CD33-11A1-v1417-kN92S-H16-D55A-K222R-hG1-LP39 | CD33-11A1-v1417-kN92S-H16-D55A-K222R-hG1 | LP39 | B | 42% |
| 101 | CD33-11A1-v1417-kN92S-H16-D55A-K222R-hG1-LP40 | CD33-11A1-v1417-kN92S-H16-D55A-K222R-hG1 | LP40 | B | 29% |
| 102 | CD33-11A1-v1417-kN92S-H16-D55A-K222R-hG1-LP41 | CD33-11A1-v1417-kN92S-H16-D55A-K222R-hG1 | LP41 | B | 66% |
| 103 | CD33-11A1-v1417-kN92S-H16-D55A-K222R-hG1-LP42 | CD33-11A1-v1417-kN92S-H16-D55A-K222R-hG1 | LP42 | B | 67% |
| 104 | CD33-11A1-v1417-kN92S-H16-D55A-K222R-hG1-LP43 | CD33-11A1-v1417-kN92S-H16-D55A-K222R-hG1 | LP43 | B | 69% |
| 105 | CD33-11A1-v1417-kN92S-H16-D55A-K222R-hG1-LP44 | CD33-11A1-v1417-kN92S-H16-D55A-K222R-hG1 | LP44 | B | 71% |
| 106 | CD33-11A1-v1417-kN92S-H16-D55A-K222R-hG1-LP45 | CD33-11A1-v1417-kN92S-H16-D55A-K222R-hG1 | LP45 | B | 62% |
| 107 | CD33-11A1-v1417-kN92S-H16-D55A-K222R-hG1-LP46 | CD33-11A1-v1417-kN92S-H16-D55A-K222R-hG1 | LP46 | B | 68% |
| 108 | CD33-11A1-v1417-kN92S-H16-D55A-K222R-hG1-LP47 | CD33-11A1-v1417-kN92S-H16-D55A-K222R-hG1 | LP47 | B | 60% |
| 109 | CD33-11A1-v1417-kK183C-hG1-LP48 | CD33-11A1-v1417-kK183C-hG1 | LP48 | C | NA |
| 110 | H2-PT-A114C-hG1-LP48 | Her2-PT-A114C-hG1 | LP48 | C | 30% |

TABLE 2

Table of bioanalytical data:

| E.g. # | ADC ID | MW LC | MW HC | MW (whole ADC) | LCMS DAR (mol/mol) | LCMS Observed Mass Shift from mAb | LCMS Expected Mass Shift from mAb | HIC DAR (mol/mol) | HIC Main Peak rt (min) |
|---|---|---|---|---|---|---|---|---|---|
| 50 | CD33-11A1-v1417-H16-K222R-hG1-LP1 | 23166 | 51418 | 148986 | 2 | 1922 | 1921 | 2 | 5.4 |
| 51 | CD33-11A1-v1417-kN92S-H16-D55A-K222R-hG1-LP1 | 23137 | 51312 | NA | 2 | 1924 | 1923 | 2 | 5.44 |
| 52 | Neg-8-8-H16-K222R-hG1-LP1 | 23178 | 50598 | NA | 2 | 1925 | 1923 | 2 | 5.25 |
| 53 | CD33-11A1-v1417-LCQ05-H16-K222R-hG1-LP1 | 23887 | 51356 | NA | 3 | 1924 | 1923 | | 6.59 |
| 54 | Her2-PT-H16-K222R-hG1-LP1 | NA | NA | 148828 | 1.95 | 1923 | 1923 | 2 | 6.23 |
| 55 | Her2-PT-A114C-hG1-LP2 | 23445 | 52604 | NA | 2 | 1963 | 1961.6 | 1.64 | 10.41 |
| 56 | CD33-11A1-v1417-kK183C-hG1-LP2 | 25098 | 50967 | NA | 1.6 | 1963 | 1962 | 1.4 | 9.93 |
| 57 | CD33-11A1-v1417-H16-K222R-hG1-LP3 | 23164 | 51116 | NA | 2 | 1684 | 1683 | 2 | 5.44 |
| 58 | CD33-11A1-v1417-H16-K222R-hG1-LP4 | NA | NA | 149038 | 1.83 | 1959 | 1957 | 1.9 | 5.22 |
| 59 | CD33-11A1-v1417-H16-K222R-hG1-LP5 | NA | NA | 149112 | 2 | 1996 | 2001 | 1.9 | 5.35 |
| 60 | CD33-11A1-v1417-kN92S-H16-D55A-K222R-hG1-LP5 | NA | NA | 149013 | 1.9 | 2000 | 2001 | 2 | 5.9 |
| 61 | CD33-11A1-v1417-kN92S-H16-D55A-K222R-hG1-LP6 | 23134 | 51350 | NA | 2 | 1967 | 1967 | 2 | 5.19 |
| 62 | Her2-PT-H16-K222R-hG1-LP6 | NA | NA | 148912 | 1.8 | 1953 | 1967 | 2 | 5.92 |
| 63 | CD33-11A1-v1417-kN92S-H16-D55A-K222R-hG1-LP7 | 23139 | 51244 | NA | 1.8 | 2154 | 2154 | 2 | 5.3 |
| 64 | CD33-11A1-v1417-kN92S-H16-D55A-K222R-hG1-LP8 | | | 149012 | 1.62 | 2000 | 2001 | 1.95 | 5.68 |
| 65 | CD33-11A1-v1417-kN92S-H16-D55A-K222R-hG1-LP9 | | | 148937 | 1.14 | 1955 | 1957 | | 5.76 |
| 66 | CD33-11A1-v1417-H16-K222R-hG1-LP10 | NA | NA | 149367 | 1.52 | 2085 | 2085 | 1.79 | 5.99 |
| 67 | CD33-11A1-v1417-kN92S-H16-D55A-K222R-hG1-LP11 | | | 148925 | 1.95 | 1953 | 1953 | 2 | 5.44 |

TABLE 2-continued

Table of bioanalytical data:

| E.g. # | ADC ID | MW LC | MW HC | MW (whole ADC) | LCMS DAR (mol/mol) | LCMS Observed Mass Shift from mAb | LCMS Expected Mass Shift from mAb | HIC DAR (mol/mol) | HIC Main Peak rt (min) |
|---|---|---|---|---|---|---|---|---|---|
| 68 | CD33-11A1-v1417-kN92S-H16-D55A-K222R-hG1-LP12 | NA | NA | 149005 | 1.7 | 1995 | 1997 | 2 | 5.46 |
| 69 | CD33-11A1-v1417-H16-K222R-hG1-LP13 | 23164 | 51286 | NA | 2 | 1992 | 1995 | 2 | 5.26 |
| 70 | CD33-11A1-v1417-kN92S-H16-D55A-K222R-hG1-LP13 | 23137 | 51240 | NA | 1.95 | 1993 | 1995 | 2 | 5.18 |
| 71 | Neg-8-8-H16-K222R-hG1 -LP13 | 23178 | 50740 | NA | 2 | 1996 | 1995 | 2 | 5.05 |
| 72 | CD33-11A1-v1417-LCQ05-H16-K222R-hG1-LP13 | 25477 | 51283 | NA | 4 | | 1995 | | 6.17 |
| 73 | Her2-PT-H16-K222R-hG1-LP13 | NA | NA | 148968 | 2 | 1981 | 1995 | 2 | 6 |
| 74 | CD33-11A1-v1417-H16-K222R-hG1-LP14 | 23167 | 51293 | NA | 2 | 2007 | 1977 | 2 | 5.48 |
| 75 | CD33-11A1-v1417-LCQ05-H16-K222R-hG1-LP14 | 25732 | 51292 | NA | 4 | 1968 | 1977 | 4 | 6.01 |
| 76 | CD33-11A1-v1417-H16-K222R-hG1-LP15 | NA | NA | 149094 | 2 | 1967 | 1964 | 2 | 5.24 |
| 77 | CD33-11A1-v1417-H16-K222R-hG1-LP16 | 23164 | 51282 | NA | 2 | 2088 | 2095 | NA | 4.94 |
| 78 | CD33-11A1-v1417-H16-K222R-hG1-LP17 | 23158 | 51357 | NA | 1.9 | 1935 | 1937 | 1.96 | 5.62 |
| 79 | CD33-11A1-v1417-kN92S-H16-D55A-K222R-hG1-LP18 | | | 148971 | 1.74 | 1979 | 1981 | 2 | 5.58 |
| 80 | Her2-PT-H16-K222R-hG1-LP49 | NA | NA | 149282 | 0.7 | 2140 | 2140 | NA | 5.44 |
| 81 | CD33-11A1-v1417-H7C-hG1-LP19 | 23162 | 51931 | NA | 1.5 | 1993 | 1995 | | 8.46 |
| 82 | Her2-PT-H7C-K222R-hG1-LP19 | 23438 | 53028 | NA | 1.5 | 1994 | 1995 | 1.64 | 8.33 |
| 83 | CD33-11A1-v1417-LCQ05-H16-K222R-hG1-LP19 | 23885 | 51430 | NA | 3.65 | 1995 | 1995 | 3.75 | 6.01 |
| 84 | CD33-11A1-v1417-H16-K222R-hG1-LP19 | 23166 | 51428 | NA | 2 | 1998 | 1995 | 2 | 5.31 |
| 85 | CD33-11A1-v1417-kN92S-H16-D55A-K222R-hG1-LP19 | 23137 | 51385 | NA | 2 | 1997 | 1995 | 2 | 5.26 |
| 86 | Neg-8-8-H16-K222R-hG1 -LP19 | 23178 | 50741 | NA | 2 | 1997 | 1995 | 2 | 5.03 |
| 87 | Her2-PT-LCQ05-K222R-hG1-LP19 | 26158 | 50631 | NA | 1.8 | 1997 | 1995 | 2 | 7.5 |
| 88 | Her2-PT-H16-K222R-hG1-LP19 | NA | NA | 148970 | 2 | 1982 | 1995 | 2 | 5.98 |
| 89 | CD33-11A1-v1417-kN92S-H16-D55A-K222R-hG1-(Q)_AcLysValCitPABC_LP21 | NA | NA | 148969 | 1.87 | 1964 | 1964.04 | 2 | 5.02 |
| 90 | CD33-11A1-v1417-kN92S-H16-D55A-K222R-hG1-(Q)_AcLysValCitPABC_LP25 | NA | NA | 149070 | 1.7 | 1964 | 2015.09 | 2 | 5.30 |
| 91 | CD33-11A1-v1417-kN92S-H16-D55A-K222R-hG1-(Q)_AcLysValCitPABC_LP26 | NA | NA | 149570 | 2 | 2262 | 2264.39 | 2 | 5.52 |
| 92 | CD33-11A1-v1417-kN92S-H16-D55A-K222R-hG1-(Q)_AcLysValCitPABC_LP27 | NA | NA | 149630 | 2 | 2292 | 2294.37 | 2 | 5.48 |
| 93 | CD33-11A1-v1417-kN92S-H16-D55A-K222R-hG1-(Q)_AcLysValCitPABC_LP28 | NA | NA | 149867 | 1.29 | 2412 | 2413.54 | 1.3 | 5.54 |
| 94 | CD33-11A1-v1417-kN92S-H16-D55A-K222R-hG1-(Q)_AcLysValCitPABC_LP29 | NA | NA | 149927 | 1.91 | 2440 | 2443.53 | 2 | 5.47 |
| 95 | CD33-11A1-v1417-kN92S-H16-D55A-K222R-hG1-(Q)_AcLysValCitPABC_LP33 | NA | NA | 149023 | 1.94 | 2003 | 2002.96 | 2 | 5.41 |
| 96 | CD33-11A1-v1417-kN92S-H16-D55A-K222R-hG1-(Q)_AcLysValCitPABC_LP34 | NA | NA | 148995 | 1.96 | 1989 | 1988.94 | 2 | 5.37 |
| 97 | CD33-11A1-v1417-kN92S-H16-D55A-K222R-hG1-(Q)_AcLysValCitPABC_LP35 | NA | NA | 149002 | 1.91 | 1978 | 1980.02 | 2 | 5.53 |
| 98 | CD33-11A1-v1417-kN92S-H16-D55A-K222R-hG1-(Q)_AcLysValCitPABC_LP36 | NA | NA | 149057 | 1.94 | 2006 | 2008.07 | 2 | 5.49 |
| 99 | CD33-11A1-v1417-H16-K222R-hG1-LP38 | 23166 | 51028 | NA | 2 | 1722 | 1724 | 2 | 5.2 |
| 100 | CD33-11A1-v1417-kN92S-H16-D55A-K222R-hG1-LP39 | NA | NA | 148224 | 1.88 | 1606 | 1606.45 | 2 | 5.64 |
| 101 | CD33-11A1-v1417-kN92S-H16-D55A-K222R-hG1-LP40 | NA | NA | 148081 | 1.91 | 1534 | 1534.42 | 1.85 | 5.94 |

TABLE 2-continued

Table of bioanalytical data:

| E.g. # | ADC ID | MW LC | MW HC | MW (whole ADC) | LCMS DAR (mol/mol) | LCMS Observed Mass Shift from mAb | LCMS Expected Mass Shift from mAb | HIC DAR (mol/mol) | HIC Main Peak rt (min) |
|---|---|---|---|---|---|---|---|---|---|
| 102 | CD33-11A1-v1417-kN92S-H16-D55A-K222R-hG1-LP41 | NA | NA | 148528 | 1.9 | 1757 | 1755.8 | 2 | 5.35 |
| 103 | CD33-11A1-v1417-kN92S-H16-D55A-K222R-hG1-LP42 | NA | NA | 148942 | 1.93 | 1964 | 1960 | 2 | 5.33 |
| 104 | CD33-11A1-v1417-kN92S-H16-D55A-K222R-hG1-LP43 | NA | NA | 149238 | 1.72 | 2112 | 2109 | 2 | 5.45 |
| 105 | CD33-11A1-v1417-kN92S-H16-D55A-K222R-hG1-LP44 | NA | NA | 148206 | 1.89 | 1589 | 1589.67 | 2 | 5.19 |
| 106 | CD33-11A1-v1417-kN92S-H16-D55A-K222R-hG1-LP45 | NA | NA | 149047 | 2 | 2016 | 2014 | 2 | 5.43 |
| 107 | CD33-11A1-v1417-kN92S-H16-D55A-K222R-hG1-LP46 | NA | NA | 149345 | 2 | 2165 | 2163 | 2 | 5.67 |
| 108 | CD33-11A1-v1417-kN92S-H16-D55A-K222R-hG1-LP47 | NA | NA | 149384 | 1.95 | 2183 | 2182.3 | 2 | 5.35 |
| 109 | CD33-11A1-v1417-kK183C-hG1-LP48 | 25119 | 50980 | NA | 1.9 | 1979 | 1977 | 1.8 | NA |
| 110 | Her2-PT-A114C-hG1-LP48 | 23443 | 52616 | NA | 2 | 1972 | 1975 | 1.95 | 10.87 |

In Vitro Cell Assay Procedure

Her2-Target expressing (BT474 (breast cancer), N87 (gastric cancer), MDA-MB-361-DYT2 (breast cancer)) or Her2-non-expressing (MDA-MB-468, HT29) cells, or CD33-target expressing HL60, HEL92.1.7, NB4, TF-1 or CD33-non-expressing (Raji) cells were seeded in 96-well cell culture plates for 24 hours before treatment. Cells were treated with 3-fold serially diluted antibody-drug conjugates or free compounds (i.e., no antibody conjugated to the drug) in duplicate at 10 concentrations. Cell viability was determined by CellTiter 96® AQ$_{ueous}$ One Solution Cell Proliferation MTS Assay (Promega, Madison WI) 96 hours after treatment. Relative cell viability was determined as percentage of untreated control. IC50 values were calculated using a four parameter logistic model #203 with XLfit v4.2 (IDBS, Guildford, Surry, UK). Results are shown below in Table 3 (for payloads), Table 4 (for Herceptin conjugates), and Table 5 (for CD33 conjugates).

TABLE 3

In Vitro Cytotoxicity Data (nM) for Calicheamicin Payloads

| | Average IC50 (nM) | | | | | | | |
|---|---|---|---|---|---|---|---|---|
| Identifier | N87 | MDA-MB-361-DYT2 | HT29 | HL-60 | NB4 | HEL92.1.7 | TF-1 | Raji |
| P1 | 0.007 | 0.021 | 0.003 | 0.003 | 0.003 | 0.028 | 0.071 | 0.006 |
| P3 | 0.309 | 1.749 | 0.690 | 0.149 | 0.081 | 0.371 | 1.644 | 0.378 |
| P4 | 0.086 | 0.033 | 0.094 | 0.017 | 0.011 | 0.036 | 0.184 | 0.056 |
| P6 | 1.240 | 1.352 | 1.141 | 0.568 | 0.492 | | 5.930 | 1.212 |
| P7 | 0.046 | 1.033 | 0.075 | 0.124 | 0.152 | 1.215 | >90 | 0.161 |
| P8 | 0.804 | 0.063 | 0.070 | 0.081 | | | 0.360 | 0.028 |
| P9 | 0.392 | 1.894 | 0.334 | | | | | |
| P10 | 0.031 | 0.025 | 0.030 | 0.004 | 0.003 | 0.004 | 0.029 | 0.005 |
| P11 | 0.007 | 0.008 | 0.006 | 0.002 | 0.001 | 0.003 | 0.030 | 0.002 |
| P12 | 0.640 | 4.155 | 0.687 | 0.040 | 0.005 | 0.102 | 0.245 | 0.033 |
| P13 | 0.536 | 0.982 | 0.792 | 0.044 | 0.023 | 0.039 | 0.331 | 0.022 |
| P14 | 2.734 | 15.559 | 2.216 | | | | | |
| P15 | 0.077 | 0.077 | 0.120 | | | | | |
| P16 | 0.023 | 0.045 | 0.035 | 0.024 | 0.015 | 0.071 | 0.150 | 0.077 |
| P17 | 2.376 | 0.152 | 0.501 | | | | | |
| P18 | 0.033 | 0.017 | 0.005 | 0.005 | | | 0.093 | 0.003 |
| P19 | 0.005 | 0.005 | 0.004 | | | | | |
| P20 | 0.004 | 0.005 | 0.002 | | | | | |
| P21 | 0.013 | 0.064 | 0.012 | | | | | |
| P22 | 0.015 | 0.044 | 0.009 | | | | | |
| P23 | 0.005 | 0.007 | 0.012 | | | | | |
| P26 | 0.035 | 0.017 | 0.004 | 0.002 | | | 0.036 | 0.004 |
| P27 | 0.040 | 0.003 | 0.006 | 0.004 | | | 0.020 | 0.002 |
| P29 | 0.170 | 0.025 | 0.036 | 0.025 | | | 0.466 | 0.015 |
| P30 | 0.308 | 0.049 | 0.057 | 0.049 | | | 0.112 | 0.030 |
| P31 | 0.051 | 0.032 | 0.010 | 0.011 | | | 0.084 | 0.008 |
| P32 | 0.015 | 0.013 | 0.004 | 0.003 | | | 0.038 | 0.004 |
| P33 | 1.656 | 1.502 | 0.386 | 0.205 | | | 1.093 | 0.261 |
| P34 | 0.944 | 0.923 | 1.151 | | | | | |
| P35 | 14.652 | 2.336 | 3.673 | 2.248 | | | 7.498 | 2.099 |
| P36 | 6.198 | 3.849 | 1.283 | 0.881 | | | 6.864 | 1.132 |
| P43 | 1.225 | 6.399 | 3.18 | 1.358 | 0.516 | 4.896 | 9.005 | 2.852 |
| P44 | 0.4185 | >10 | 1.264 | 0.127 | | | 1.476 | 0.171 |

TABLE 3-continued

In Vitro Cytotoxicity Data (nM) for Calicheamicin Payloads

Average IC50 (nM)

| Identifier | N87 | MDA-MB-361-DYT2 | HT29 | HL-60 | NB4 | HEL92.1.7 | TF-1 | Raji |
|---|---|---|---|---|---|---|---|---|
| P46 | 0.544 | 2.825 | 0.770 | 0.025 | 0.020 | 0.046 | 0.176 | 0.039 |
| P47 | 1.872 | 6.538 | 1.401 | 0.054 | 0.040 | 0.141 | 0.737 | 0.050 |
| P49 | 0.007 | <0.100 | 0.006 | 0.003 | | | 0.051 | 0.002 |
| P50 | 1.049 | 7.333 | 0.775 | 0.372 | 0.127 | 3.928 | 17.887 | 0.438 |

TABLE 4

In vitro Cytotoxicity Data (ng/mL) for Herceptin Conjugates

| Example Number | Identifier | Average IC50 (ng/mL) | | | | | |
|---|---|---|---|---|---|---|---|
| | | BT474 | N87 | MDA-MB-361-DYT2 | MDA-MB-453 | MDA-MB-468 | HT29 |
| 54 | Her2-PT-H16-K222R-hG1-LP1 | 122 | 0.85 | 1.63 | 10.71 | 5849 | 4.48 |
| 55 | Her2-PT-A114C-hG1-LP2 | 13.86 | 4.66 | 7.07 | | 189 | 3.58 |
| 62 | Her2-PT-H16-K222R-hG1-LP6 | 12.21 | 1.13 | 5.15 | 2.82 | 704 | 3.42 |
| 73 | Her2-PT-H16-K222R-hG1-LP13 | 11.27 | 1.14 | 3.29 | 1.84 | 637 | 4.74 |
| 80 | Her2-PT-H16-K222R-hG1-LP49 | | 2.52 | <1.52 | | | 6.64 |
| 82 | Her2-PT-H7C-K222R-hG1-LP19 | | <4.65 | 7.25 | | | 1476 |
| 87 | Her2-PT-LCQ05-K222R-hG1-LP19 | | 1.58 | 11.51 | | | 14.75 |
| 88 | Her2-PT-H16-K222R-hG1-LP19 | 13.1 | 1.23 | 9.69 | 1.48 | 932 | 8.83 |
| 110 | Her2-PT-A114C-hG1-LP48 | 29.08 | 9.71 | 64.65 | | 578 | 42.58 |

TABLE 5

In Vitro Cytotoxicity Data (ng/mL) for CD33 Conjugates

| Example Number | Identifier | Average IC50 (ng/mL) | | | | |
|---|---|---|---|---|---|---|
| | | HL-60 | NB4 | HEL92.1.7 | TF-1 | Raji |
| 50 | CD33-11A1-v1417-H16-K222R-hG1-LP1 | 0.51 | 9.14 | 5.54 | 21.11 | 714 |
| 51 | CD33-11A1-v1417-kN92S-H16-D55A-K222R-hG1-LP1 | 0.45 | 2.13 | 114 | 1212 | 570 |
| 53 | CD33-11A1-v1417-LCQ05-H16-K222R-hG1-LP1 | 0.26 | 4.69 | 8.6 | 156 | 196 |
| 56 | CD33-11A1-v1417-kK183C-hG1-LP2 | 0.55 | 0.18 | 6.68 | 9.31 | 706 |
| 57 | CD33-11A1-v1417-H16-K222R-hG1-LP3 | 161 | 96.35 | 8031 | 416 | 357 |
| 58 | CD33-11A1-v1417-H16-K222R-hG1-LP4 | 786 | 793 | 17.64 | 33.52 | 4320 |
| 59 | CD33-11A1-v1417-H16-K222R-hG1-LP5 | 2.98 | 32.4 | 4.86 | 20.44 | 5317 |
| 60 | CD33-11A1-v1417-kN92S-H16-D55A-K222R-hG1-LP5 | 0.54 | 83.44 | 0.24 | 593 | 3022 |
| 61 | CD33-11A1-v1417-kN92S-H16-D55A-K222R-hG1-LP6 | 0.27 | 1.96 | 180 | 579 | 3967 |
| 63 | CD33-11A1-v1417-kN92S-H16-D55A-K222R-hG1-LP7 | 1.84 | 1711 | 6.59 | 16.99 | 8255 |
| 64 | CD33-11A1-v1417-kN92S-H16-D55A-K222R-hG1-LP8 | 1226 | 22.38 | 0.95 | 189 | 5196 |
| 65 | CD33-11A1-v1417-kN92S-H16-D55A-K222R-hG1-LP9 | 0.83 | 22.72 | 1.87 | 75.39 | 222 |
| 66 | CD33-11A1-v1417-H16-K222R-hG1-LP10 | 1.97 | 2.16 | 66.27 | 155 | 10.72 |
| 67 | CD33-11A1-v1417-kN92S-H16-D55A-K222R-hG1-LP11 | 0.12 | 63.97 | 0.19 | 375 | 3765 |
| 68 | CD33-11A1-v1417-kN92S-H16-D55A-K222R-hG1-LP12 | 2.49 | 15.29 | 0.33 | 21.79 | 9174 |
| 69 | CD33-11A1-v1417-H16-K222R-hG1-LP13 | 0.61 | 13.55 | 1.63 | 27.57 | 3082 |
| 70 | CD33-11A1-v1417-kN92S-H16-D55A-K222R-hG1-LP13 | 0.79 | 3.42 | 1.45 | 198 | 2797 |

TABLE 5-continued

In Vitro Cytotoxicity Data (ng/mL) for CD33 Conjugates

| Example Number | Identifier | Average IC50 (ng/mL) | | | | |
|---|---|---|---|---|---|---|
| | | HL-60 | NB4 | HEL92.1.7 | TF-1 | Raji |
| 72 | CD33-11A1-v1417-LCQ05-H16-K222R-hG1-LP13 | 0.36 | 3.55 | 0.86 | 47.53 | 669 |
| 74 | CD33-11A1-v1417-H16-K222R-hG1-LP14 | 0.85 | 21.18 | 0.71 | 7.16 | 157 |
| 75 | CD33-11A1-v1417-LCQ05-H16-K222R-hG1-LP14 | 0.8 | 14.36 | <0.51 | 4.28 | 60.76 |
| 76 | CD33-11A1-v1417-H16-K222R-hG1-LP15 | 109 | 202 | 227 | 404 | 1884 |
| 77 | CD33-11A1-v1417-H16-K222R-hG1-LP16 | 4.17 | | 61.1 | 134 | >10000 |
| 78 | CD33-11A1-v1417-H16-K222R-hG1-LP17 | 0.71 | 12.36 | >10000 | 530 | 2090 |
| 79 | CD33-11A1-v1417-kN92S-H16-D55A-K222R-hG1-LP18 | 0.68 | 2.14 | 0.38 | 16.5 | 106 |
| 81 | CD33-11A1-v1417-H7C-hG1-LP19 | 0.33 | 3.56 | 1.63 | 50.18 | 3732 |
| 83 | CD33-11A1-v1417-LCQ05-H16-K222R-hG1-LP19 | 0.29 | 3.71 | 2.18 | 69.14 | 4970 |
| 84 | CD33-11A1-v1417-H16-K222R-hG1-LP19 | 0.56 | 11.76 | 22.19 | 36.77 | 4795 |
| 85 | CD33-11A1-v1417-kN92S-H16-D55A-K222R-hG1-LP19 | 0.26 | 2.78 | 39.12 | 196 | 7636 |
| 89 | CD33-11A1-v1417-kN92S-H16-D55A-K222R-hG1-(Q)_AcLysValCitPABC_LP21 | 10.58 | | | 29.45 | 618 |
| 90 | CD33-11A1-v1417-kN92S-H16-D55A-K222R-hG1-(Q)_AcLysValCitPABC_LP25 | 0.45 | | | 6.73 | 129 |
| 91 | CD33-11A1-v1417-kN92S-H16-D55A-K222R-hG1-(Q)_AcLysValCitPABC_LP26 | 2.55 | | | 60.81 | >3000 |
| 92 | CD33-11A1-v1417-kN92S-H16-D55A-K222R-hG1-(Q)_AcLysValCitPABC_LP27 | 22.67 | | | 6.29 | 2089 |
| 93 | CD33-11A1-v1417-kN92S-H16-D55A-K222R-hG1-(Q)_AcLysValCitPABC_LP28 | 2.63 | | | 31.21 | >3000 |
| 94 | CD33-11A1-v1417-kN92S-H16-D55A-K222R-hG1-(Q)_AcLysValCitPABC_LP29 | 19.33 | | | 7.91 | >3000 |
| 95 | CD33-11A1-v1417-kN92S-H16-D55A-K222R-hG1-(Q)_AcLysValCitPABC_LP33 | 10.93 | | | 7.59 | >3000 |
| 96 | CD33-11A1-v1417-kN92S-H16-D55A-K222R-hG1-(Q)_AcLysValCitPABC_LP34 | 51.01 | | | 8.96 | >3000 |
| 97 | CD33-11A1-v1417-kN92S-H16-D55A-K222R-hG1-(Q)_AcLysValCitPABC_LP35 | 0.42 | | | 7.19 | 1266 |
| 98 | CD33-11A1-v1417-kN92S-H16-D55A-K222R-hG1-(Q)_AcLysValCitPABC_LP36 | 0.44 | | | 10.91 | 1601 |
| 99 | CD33-11A1-v1417-H16-K222R-hG1-LP38 | 22.17 | 55.05 | 83.68 | 46.04 | 126 |
| 100 | CD33-11A1-v1417-kN92S-H16-D55A-K222R-hG1-LP39 | 6368 | 756 | >10000 | 8513 | 2758 |
| 101 | CD33-11A1-v1417-kN92S-H16-D55A-K222R-hG1-LP40 | 253 | 54.33 | 1171 | 4338 | 260 |
| 102 | CD33-11A1-v1417-kN92S-H16-D55A-K222R-hG1-LP41 | 112 | | | >3000 | 193 |
| 103 | CD33-11A1-v1417-kN92S-H16-D55A-K222R-hG1-LP42 | 227 | | | >3000 | 272 |
| 104 | CD33-11A1-v1417-kN92S-H16-D55A-K222R-hG1-LP43 | 12.05 | | | >3000 | 212 |
| 105 | CD33-11A1-v1417-kN92S-H16-D55A-K222R-hG1-LP44 | 178 | | | 2500 | 146 |
| 106 | CD33-11A1-v1417-kN92S-H16-D55A-K222R-hG1-LP45 | 95.87 | | | 1522 | 124 |
| 107 | CD33-11A1-v1417-kN92S-H16-D55A-K222R-hG1-LP46 | 101 | | | 1095 | 119 |

TABLE 5-continued

In Vitro Cytotoxicity Data (ng/mL) for CD33 Conjugates

| Example | | Average IC50 (ng/mL) | | | | |
|---|---|---|---|---|---|---|
| Number | Identifier | HL-60 | NB4 | HEL92.1.7 | TF-1 | Raji |
| 108 | CD33-11A1-v1417-kN92S-H16-D55A-K222R-hG1-LP47 | 24.25 | | | >3000 | 309 |
| 109 | CD33-11A1-v1417-kK183C-hG1-LP48 | 1 | 0.69 | 5.06 | 31.2 | 1340 |

Assessment of ADC Activity in Human AML In Vivo Models

The cyno-human chimeric anti CD33 antibody, 11A1, was conjugated to various linker-payloads (as per CD33 conjugates in Examples 50-110) and tested in Acute Myeloid Leukemia (AML) xenograft models. For each model described below the first dose was given on Day 0. The tumors were measured at least once a week and their volume was calculated with the formula: tumor volume $(mm^3)=0.5 \times$ (tumor width$^2$)(tumor length). The mean tumor volumes (±S.E.M.) for each treatment group were calculated having a maximum of 10 animals and a minimum of 4 animals to be included. All animal experiments were conducted in a facility accredited by the Association for Assessment of Laboratory Animal Care under Institutional Animal Care and Use Committee guidelines and appropriate animal research approval.

A. HL60 AML Xenografts

The effects of anti-CD33 ADCs were examined in immunodeficient mice on the in vivo growth of human tumors. For subcutaneous (sc) AML models, $10 \times 10^6$ HL60 cells were implanted subcutaneously in the flank of female NOD-SCID mice. When the tumors reached an average volume of 200 mm$^3$, animals were staged to ensure uniformity of the tumor size among various treatment groups. The HL60 AML sc xenograft model was dosed intravenously one time every four days for four cycles (Q4d×4) with PBS vehicle, humanized anti-CD33 ADC, and in some cases with control Neg-8.8 ADC and/or Mylotarg, administered at the doses provided in Tables 6-10.

FIG. 1 shows a graph of the data from Table 6 of the calicheamicin ADCs (examples 50, 69, and 84) dosed at 0.01, 0.05 and 0.1 mg/kg doses compared to Mylotarg dosed at 1 mg/kg and PBS vehicle.

Figure 2:
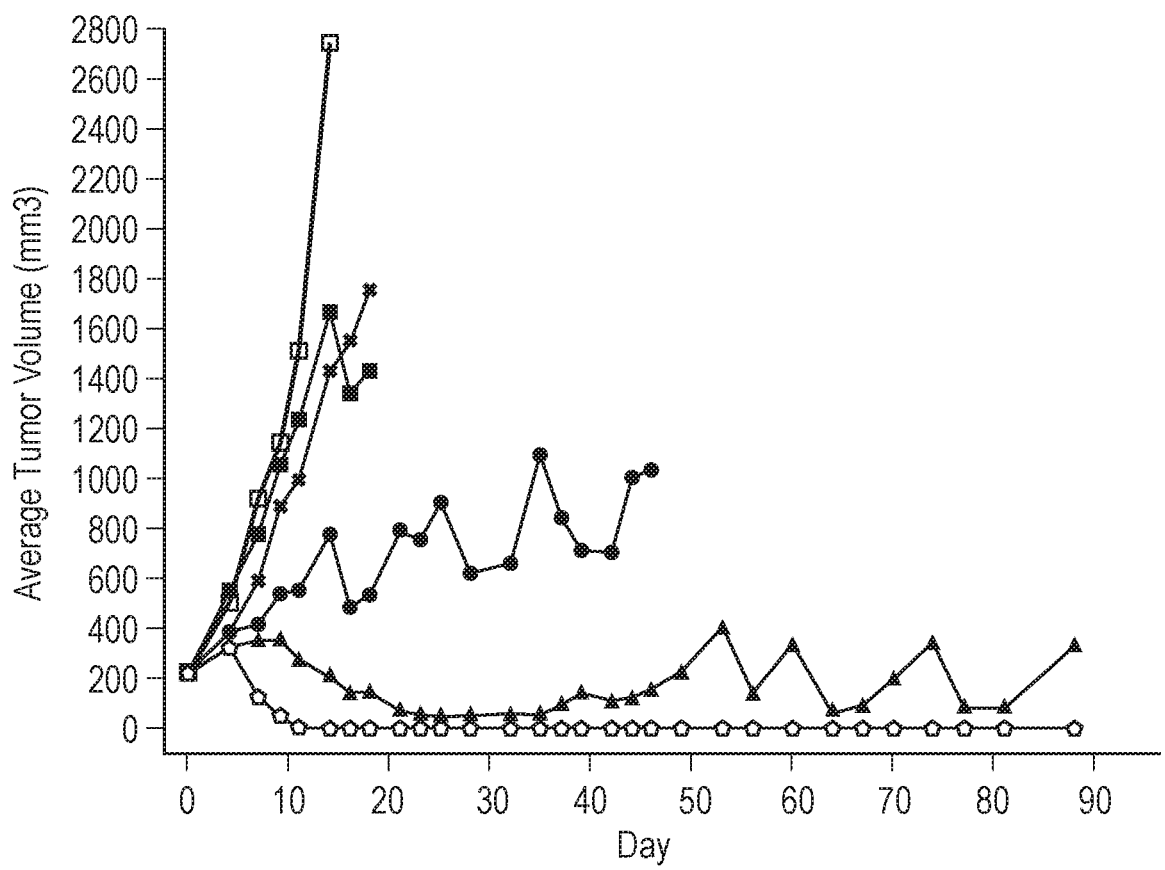
FIG. 2 shows a graph of the data from Table 7 of the anti-CD33 ADC CD33-11A1-v1417-kN92S-H16-D55A-K222R-hG1-LP19 (example 85) dosed at 0.01, 0.05 and 0.1 mg/kg, control Neg-8.8 ADC bearing the same linker payload (example 86) dosed at 0.1 mg/kg, Mylotarg dosed at 1 mg/kg, and PBS vehicle.

FIG. 2 shows a graph of the data from Table 7 of the anti-CD33 ADC CD33-11A1-v1417-kN92S-H16-D55A-K222R-hG1-LP19 (example 85) dosed at 0.01, 0.05 and 0.1 mg/kg, control Neg-8.8 ADC bearing the same linker payload (example 86) dosed at 0.1 mg/kg, Mylotarg dosed at 1 mg/kg, and PBS vehicle.

Figure 3:
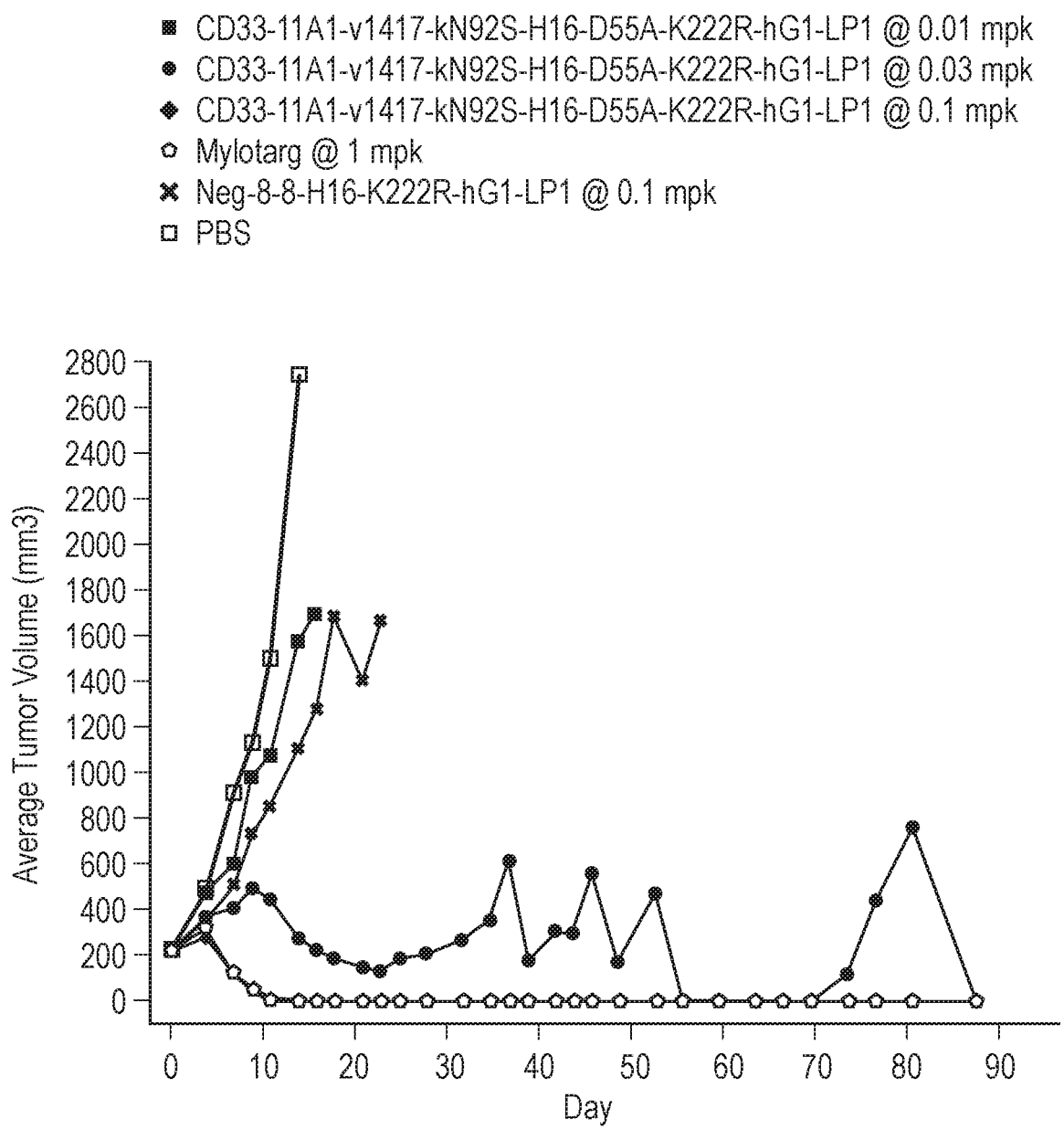
FIG. 3 shows a graph of the data from Table 8 of the anti-CD33 ADC CD33-11A1-v1417-kN92S-H16-D55A-K222R-hG1-LP1 (example 51) dosed at 0.01, 0.03 and 0.1 mg/kg, control Neg-8.8 ADC bearing the same linker payload (example 52) dosed at 0.1 mg/kg, Mylotarg dosed at 1 mg/kg, and PBS vehicle.

FIG. 3 shows a graph of the data from Table 8 of the anti-CD33 ADC CD33-11A1-v1417-kN92S-H16-D55A-K222R-hG1-LP1 (example 51) dosed at 0.01, 0.03 and 0.1 mg/kg, control Neg-8.8 ADC bearing the same linker payload (example 52) dosed at 0.1 mg/kg, Mylotarg dosed at 1 mg/kg, and PBS vehicle.

Figure 4:
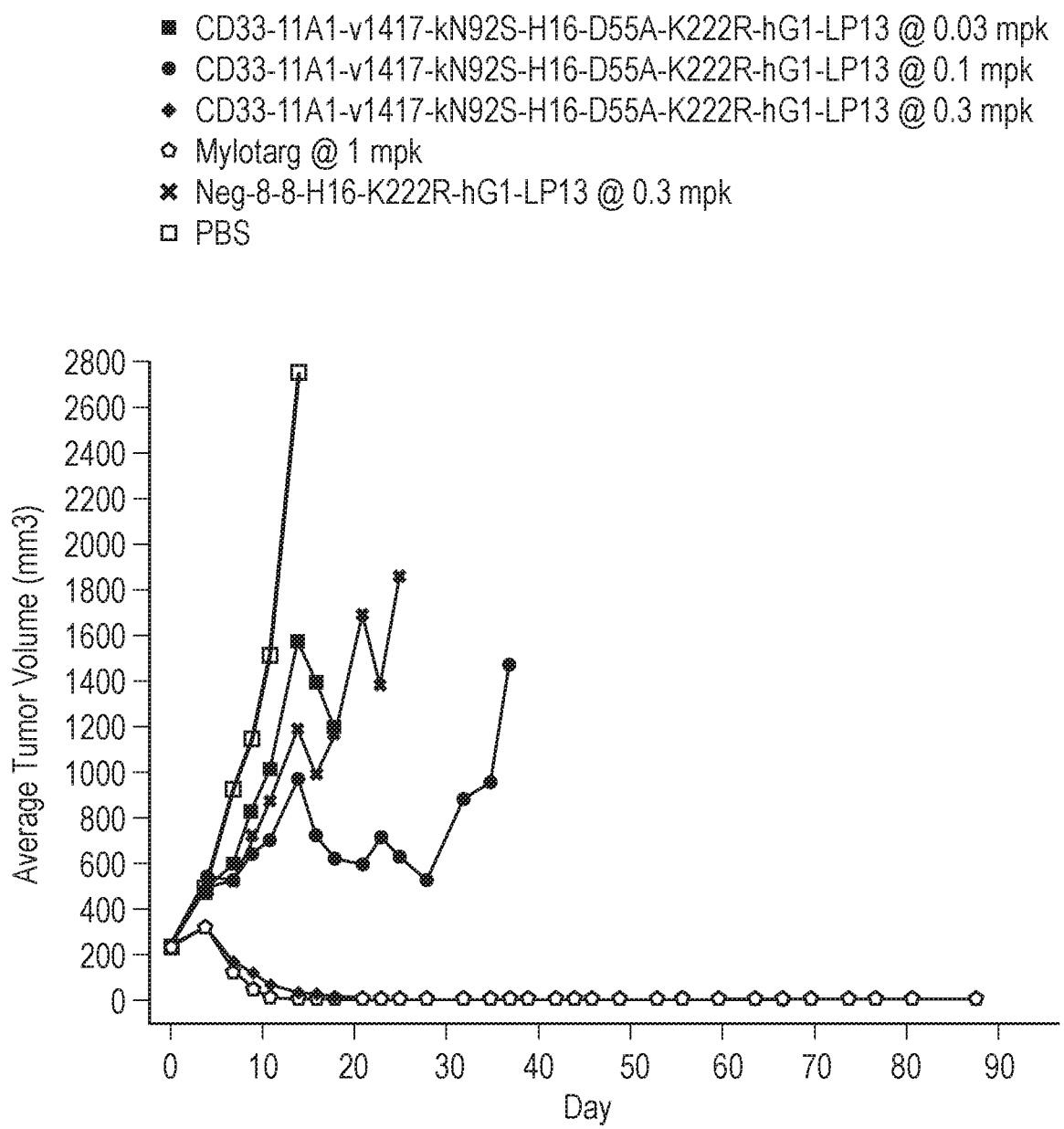
FIG. 4 shows a graph of the data from Table 9 of the anti-CD33 ADC CD33-11A1-v1417-kN92S-H16-D55A-K222R-hG1-LP13 (example 70) dosed at 0.03, 0.1 and 0.3 mg/kg, control Neg-8.8 ADC bearing the same linker payload (example 71) dosed at 0.3 mg/kg, Mylotarg dosed at 1 mg/kg, and PBS vehicle.

FIG. 4 shows a graph of the data from Table 9 of the anti-CD33 ADC CD33-11A1-v1417-kN92S-H16-D55A-K222R-hG1-LP13 (example 70) dosed at 0.03, 0.1 and 0.3 mg/kg, control Neg-8.8 ADC bearing the same linker payload (example 71) dosed at 0.3 mg/kg, Mylotarg dosed at 1 mg/kg, and PBS vehicle.

Figure 5:
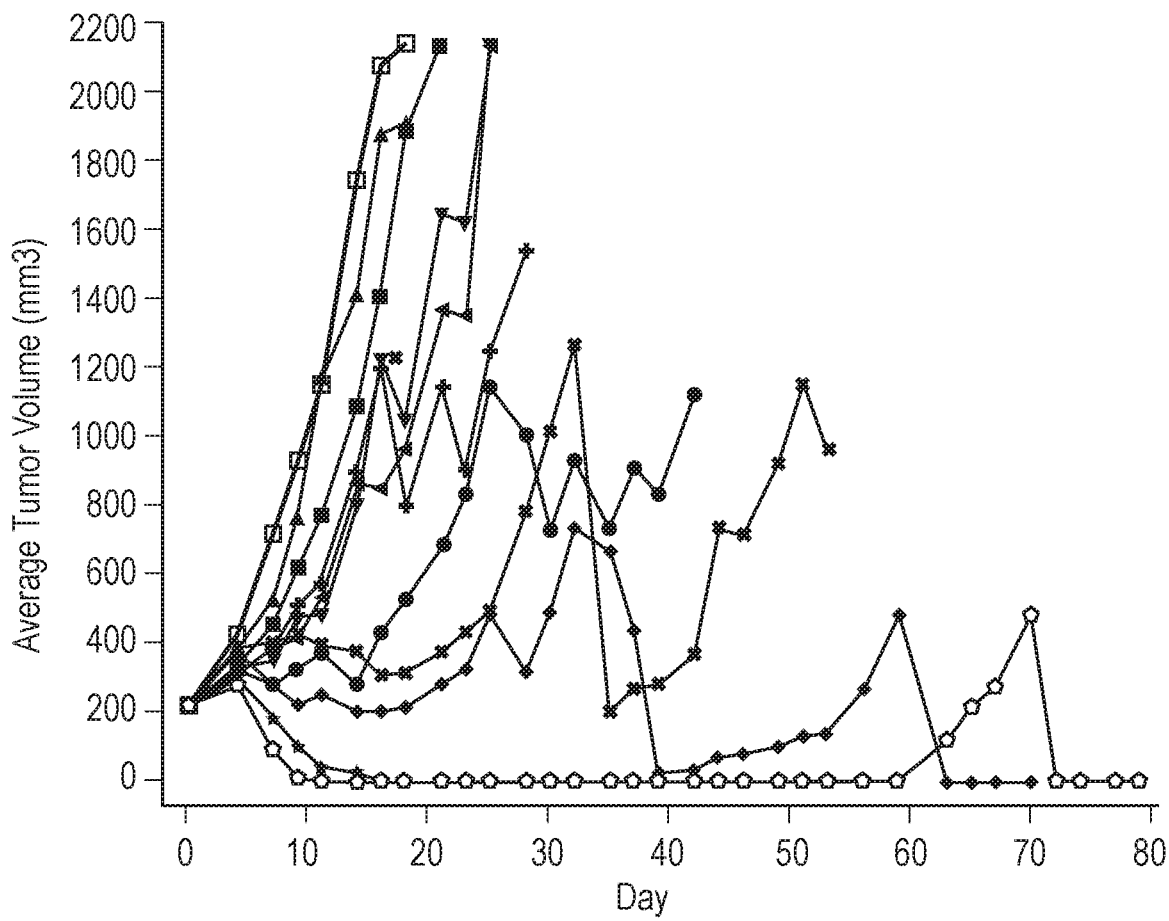
FIG. 5 shows a graph of the data from Table 10 of the anti-CD33 calicheamicin ADCs (examples 60, 61, and 67) dosed at 0.01, 0.05 and 0.1 mg/kg, Mylotarg dosed at 1 mg/kg, and PBS vehicle.

FIG. 5 shows a graph of the data from Table 10 of the anti-CD33 calicheamicin ADCs (examples 60, 61, and 67) dosed at 0.01, 0.05 and 0.1 mg/kg, Mylotarg dosed at 1 mg/kg, and PBS vehicle.

These data demonstrate that the anti-CD33 calicheamicin ADCs inhibited growth of HL60 AML xenograft tumors in a dose-dependent manner, with several examples providing complete and sustained regression of tumor growth at a fraction of the efficacious dose of Mylotarg®. Particularly efficacious examples include CD33-11A1-v1417-kN92S-H16-D55A-K222R-hG1-LP1, which provided 10/10 complete and durable responses by day 14 of the study at a dose of 0.1 mg/kg, and CD33-11A1-v1417-kN92S-H16-D55A-K222R-hG1-LP6, which provided 9/9 complete and durable responses by day 18 of the study at a dose of 0.1 mg/kg. Furthermore, these data show that anti-CD33 calicheamicin ADCs were far more efficacious than their respective control Neg8.8-ADCs (that do not recognize the CD33 antigen) at the same dose.

TABLE 6

| | HL60 AML xenografts, mean tumor volume (mm3 +/− SEM) | | | | | | |
|---|---|---|---|---|---|---|---|
| Q4dx4 Dose | PBS | CD33-11A1-v1417-H16-K222R-hG1-LP13 | | | CD33-11A1-v1417-H16-K222R-hG1-LP19 | | |
| (mg/kg) | 0.00 | 0.01 | 0.05 | 0.10 | 0.01 | 0.05 | 0.10 |
| Day-0 | 214 +/− 12 | 203 +/− 11 | 202 +/− 10 | 204 +/− 11 | 211 +/− 8 | 209 +/− 7 | 209 +/− 9 |
| Day-4 | 342 +/− 23 | 394 +/− 22 | 270 +/− 34 | 217 +/− 24 | 216 +/− 32 | 198 +/− 11 | 176 +/− 19 |
| Day-7 | 495 +/− 41 | 501 +/− 45 | 361 +/− 58 | 244 +/− 32 | 323 +/− 55 | 268 +/− 35 | 159 +/− 43 |
| Day-9 | 828 +/− 85 | 742 +/− 48 | 356 +/− 66 | 234 +/− 51 | 396 +/− 79 | 222 +/− 47 | 117 +/− 29 |
| Day-11 | 1106 +/− 75 | 930 +/− 82 | 468 +/− 90 | 214 +/− 61 | 619 +/− 144 | 271 +/− 80 | 68 +/− 28 |
| Day-14 | 1629 +/− 136 | 1465 +/− 108 | 575 +/− 136 | 198 +/− 64 | 796 +/− 198 | 323 +/− 94 | 27 +/− 24 |
| Day-16 | 2114 +/− 148 | 1941 +/− 134 | 727 +/− 206 | 193 +/− 84 | 1141 +/− 287 | 344 +/− 117 | 18 +/− 15 |
| Day-18 | 2057 +/− 156 | 2102 +/− 152 | 599 +/− 146 | 161 +/− 75 | 1097 +/− 276 | 402 +/− 140 | 16 +/− 14 |
| Day-21 | 2376 +/− 256 | 2671 +/− 161 | 725 +/− 196 | 144 +/− 70 | 1207 +/− 362 | 453 +/− 180 | 5 +/− 5 |
| Day-23 | | | 1033 +/− 302 | 237 +/− 139 | 1385 +/− 215 | 505 +/− 198 | 8 +/− 8 |
| Day-25 | | | 1064 +/− 329 | 270 +/− 170 | 1312 +/− 374 | 607 +/− 237 | 4 +/− 4 |
| Day-28 | | | 793 +/− 374 | 318 +/− 202 | 1842 +/− 304 | 576 +/− 225 | 0 +/− 0 |

TABLE 6-continued

| Day | | | | | |
|---|---|---|---|---|---|
| Day-30 | | 685 +/− 395 | 334 +/− 212 | 1914 +/− 300 | 655 +/− 253 | 0 +/− 0 |
| Day-32 | | 1204 +/− 611 | 441 +/− 273 | 2120 +/− 305 | 867 +/− 373 | 0 +/− 0 |
| Day-35 | | 312 +/− 93 | 255 +/− 164 | | 799 +/− 399 | 0 +/− 0 |
| Day-37 | | 243 +/− 63 | 323 +/− 211 | | 200 +/− 165 | 0 +/− 0 |
| Day-39 | | 258 +/− 64 | 292 +/− 199 | | 228 +/− 207 | 0 +/− 0 |
| Day-42 | | 673 +/− 200 | 559 +/− 350 | | 430 +/− 384 | 0 +/− 0 |
| Day-44 | | 814 +/− 272 | 324 +/− 159 | | 69 +/− 69 | 0 +/− 0 |
| Day-46 | | 852 +/− 397 | 380 +/− 237 | | 51 +/− 51 | 0 +/− 0 |
| Day-49 | | 1531 +/− 647 | 297 +/− 113 | | 130 +/− 81 | 0 +/− 0 |
| Day-51 | | 727 +/− 254 | 227 +/− 82 | | 200 +/− 123 | 0 +/− 0 |
| Day-53 | | 650 +/− 358 | 395 +/− 194 | | 277 +/− 203 | 0 +/− 0 |
| Day-56 | | 942 +/− 601 | 526 +/− 241 | | 636 +/− 457 | 0 +/− 0 |
| Day-58 | | 1800 +/− 744 | 680 +/− 326 | | 336 +/− 336 | 0 +/− 0 |
| Day-60 | | | 875 +/− 407 | | 643 +/− 643 | 0 +/− 0 |
| Day-64 | | | 1044 +/− 560 | | 0 +/− 0 | 0 +/− 0 |
| Day-70 | | | 238 +/− 238 | | 0 +/− 0 | 0 +/− 0 |
| Day 72 | | | 277 +/− 277 | | 0 +/− 0 | 0 +/− 0 |
| Day-74 | | | 692 +/− 692 | | 0 +/− 0 | 0 +/− 0 |

| | HL60 AML xenografts, mean tumor volume (mm3 +/− SEM) | | | |
|---|---|---|---|---|
| Q4dx4 Dose (mg/kg) | CD33-11A1-v1417-H16-K222R-hG1-LP1 | | | Mylotarg |
| | 0.01 | 0.05 | 0.10 | 1.00 |
| Day-0 | 209 +/− 8 | 210 +/− 6 | 207 +/− 14 | 211 +/− 15 |
| Day-4 | 250 +/− 10 | 245 +/− 12 | 183 +/− 19 | 261 +/− 11 |
| Day-7 | 279 +/− 18 | 131 +/− 11 | 62 +/− 14 | 153 +/− 24 |
| Day-9 | 371 +/− 39 | 117 +/− 19 | 3 +/− 3 | 94 +/− 29 |
| Day-11 | 450 +/− 57 | 45 +/− 23 | 3 +/− 3 | 36 +/− 25 |
| Day-14 | 497 +/− 50 | 11 +/− 8 | 0 +/− 0 | 21 +/− 15 |
| Day-16 | 632 +/− 102 | 6 +/− 6 | 0 +/− 0 | 9 +/− 9 |
| Day-18 | 733 +/− 99 | 4 +/− 4 | 0 +/− 0 | 3 +/− 3 |
| Day-21 | 1055 +/− 217 | 0 +/− 0 | 0 +/− 0 | 0 +/− 0 |
| Day-23 | 1032 +/− 237 | 0 +/− 0 | 0 +/− 0 | 0 +/− 0 |
| Day-25 | 1072 +/− 236 | 0 +/− 0 | 0 +/− 0 | 0 +/− 0 |
| Day-28 | 1394 +/− 215 | 0 +/− 0 | 0 +/− 0 | 0 +/− 0 |
| Day-30 | 1563 +/− 266 | 0 +/− 0 | 0 +/− 0 | 0 +/− 0 |
| Day-32 | 1813 +/− 231 | 0 +/− 0 | 0 +/− 0 | 0 +/− 0 |
| Day-35 | 2626 +/− 97 | 0 +/− 0 | 0 +/− 0 | 0 +/− 0 |
| Day-37 | | 0 +/− 0 | 0 +/− 0 | 0 +/− 0 |
| Day-39 | | 0 +/− 0 | 0 +/− 0 | 0 +/− 0 |
| Day-42 | | 0 +/− 0 | 0 +/− 0 | 0 +/− 0 |
| Day-44 | | 0 +/− 0 | 0 +/− 0 | 0 +/− 0 |
| Day-46 | | 0 +/− 0 | 0 +/− 0 | 0 +/− 0 |
| Day-49 | | 0 +/− 0 | 0 +/− 0 | 0 +/− 0 |
| Day-51 | | 0 +/− 0 | 0 +/− 0 | 0 +/− 0 |
| Day-53 | | 0 +/− 0 | 0 +/− 0 | 0 +/− 0 |
| Day-56 | | 0 +/− 0 | 0 +/− 0 | 0 +/− 0 |
| Day-58 | | 0 +/− 0 | 0 +/− 0 | 0 +/− 0 |
| Day-60 | | 0 +/− 0 | 0 +/− 0 | 0 +/− 0 |
| Day-64 | | 0 +/− 0 | 0 +/− 0 | 0 +/− 0 |
| Day-70 | | 0 +/− 0 | 0 +/− 0 | 81 +/− 81 |
| Day 72 | | 0 +/− 0 | 0 +/− 0 | 148 +/− 148 |
| Day-74 | | 0 +/− 0 | 0 +/− 0 | 233 +/− 233 |

TABLE 7

HL60 AML xenografts, mean tumor volume (mm3 +/− SEM)

| Q4dx4 Dose (mg/kg) | PBS | CD33-11A1-v1417-kN92S-H16-D55A-K222R-hG1-LP19 | | | Neg-8-8-H16-K222R-hG1-LP19 | Mylotarg |
|---|---|---|---|---|---|---|
| | 0 | 0.01 | 0.05 | 0.1 | 0.1 | 1.0 |
| Day-0 | 221 +/− 13 | 232 +/− 23 | 227 +/− 15 | 228 +/− 20 | 222 +/− 8 | 231 +/− 13 |
| Day-4 | 507 +/− 28 | 556 +/− 58 | 391 +/− 29 | 335 +/− 24 | 387 +/− 20 | 325 +/− 23 |
| Day-7 | 921 +/− 48 | 785 +/− 134 | 423 +/− 83 | 354 +/− 25 | 590 +/− 46 | 126 +/− 27 |
| Day-9 | 1144 +/− 50 | 1062 +/− 172 | 543 +/− 105 | 370 +/− 37 | 894 +/− 38 | 45 +/− 19 |
| Day-11 | 1517 +/− 107 | 1242 +/− 265 | 557 +/− 128 | 274 +/− 27 | 1003 +/− 123 | 5 +/− 5 |
| Day-14 | 2752 +/− 128 | 1670 +/− 337 | 778 +/− 204 | 214 +/− 26 | 1434 +/− 148 | 0 +/− 0 |
| Day-16 | | 1346 +/− 343 | 490 +/− 99 | 141 +/− 18 | 1560 +/− 222 | 0 +/− 0 |
| Day-18 | | 1437 +/− 390 | 540 +/− 124 | 153 +/− 26 | 1766 +/− 295 | 0 +/− 0 |
| Day-21 | | | 798 +/− 192 | 73 +/− 23 | | 0 +/− 0 |

TABLE 7-continued

HL60 AML xenografts, mean tumor volume (mm3 +/− SEM)

| Q4dx4 Dose | PBS | CD33-11A1-v1417-kN92S-H16-D55A-K222R-hG1-LP19 | | | Neg-8-8-H16-K222R-hG1 -LP19 | Mylotarg |
|---|---|---|---|---|---|---|
| (mg/kg) | 0 | 0.01 | 0.05 | 0.1 | 0.1 | 1.0 |
| Day-23 | | 753 +/− 200 | 56 +/− 24 | | | 0 +/− 0 |
| Day-25 | | 911 +/− 290 | 52 +/− 26 | | | 0 +/− 0 |
| Day-28 | | 622 +/− 127 | 55 +/− 34 | | | 0 +/− 0 |
| Day-32 | | 664 +/− 161 | 63 +/− 40 | | | 0 +/− 0 |
| Day-35 | | 1103 +/− 332 | 54 +/− 34 | | | 0 +/− 0 |
| Day-37 | | 847 +/− 314 | 99 +/− 59 | | | 0 +/− 0 |
| Day-39 | | 718 +/− 284 | 143 +/− 91 | | | 0 +/− 0 |
| Day-42 | | 710 +/− 346 | 112 +/− 73 | | | 0 +/− 0 |
| Day-44 | | 1008 +/− 352 | 123 +/− 77 | | | 0 +/− 0 |
| Day-46 | | 1035 +/− 450 | 164 +/− 117 | | | 0 +/− 0 |
| Day-49 | | | 232 +/− 175 | | | 0 +/− 0 |
| Day-53 | | | 414 +/− 288 | | | 0 +/− 0 |
| Day-56 | | | 140 +/− 115 | | | 0 +/− 0 |
| Day-60 | | | 350 +/− 296 | | | 0 +/− 0 |
| Day-64 | | | 66 +/− 66 | | | 0 +/− 0 |
| Day-67 | | | 92 +/− 92 | | | 0 +/− 0 |
| Day-70 | | | 202 +/− 202 | | | 0 +/− 0 |
| Day-74 | | | 358 +/− 325 | | | 0 +/− 0 |
| Day-77 | | | 85 +/− 85 | | | 0 +/− 0 |
| Day-81 | | | 86 +/− 86 | | | 0 +/− 0 |
| Day-88 | | | 340 +/− 340 | | | 0 +/− 0 |

TABLE 8

HL60 AML xenografts, mean tumor volume (mm3 +/− SEM)

| Q4dx4 Dose | PBS | CD33-11A1-v1417-kN92S-H16-D55A-K222R-hG1-LP1 | | | Neg-8-8-H16-K222R-hG1 -LP1 | Mylotarg |
|---|---|---|---|---|---|---|
| (mg/kg) | 0 | 0.01 | 0.03 | 0.1 | 0.1 | 1.0 |
| Day-0 | 221 +/− 13 | 235 +/− 23 | 222 +/− 14 | 227 +/− 17 | 224 +/− 15 | 231 +/− 13 |
| Day-4 | 507 +/− 28 | 482 +/− 36 | 383 +/− 48 | 292 +/− 31 | 372 +/− 27 | 325 +/− 23 |
| Day-7 | 921 +/− 48 | 608 +/− 47 | 418 +/− 72 | 134 +/− 30 | 517 +/− 46 | 126 +/− 27 |
| Day-9 | 1144 +/− 50 | 991 +/− 83 | 501 +/− 130 | 67 +/− 24 | 749 +/− 88 | 45 +/− 19 |
| Day-11 | 1517 +/− 107 | 1092 +/− 149 | 455 +/− 166 | 22 +/− 12 | 865 +/− 67 | 5 +/− 5 |
| Day-14 | 2752 +/− 128 | 1589 +/− 149 | 280 +/− 62 | 0 +/− 0 | 1122 +/− 91 | 0 +/− 0 |
| Day-16 | | 1706 +/− 140 | 236 +/− 59 | 0 +/− 0 | 1290 +/− 118 | 0 +/− 0 |
| Day-18 | | 2082 +/− 83 | 191 +/− 52 | 0 +/− 0 | 1697 +/− 127 | 0 +/− 0 |
| Day-21 | | | 155 +/− 69 | 0 +/− 0 | 1421 +/− 27 | 0 +/− 0 |
| Day-23 | | | 140 +/− 67 | 0 +/− 0 | 1683 +/− 259 | 0 +/− 0 |
| Day-25 | | | 196 +/− 105 | 0 +/− 0 | | 0 +/− 0 |
| Day-28 | | | 213 +/− 114 | 0 +/− 0 | | 0 +/− 0 |
| Day-32 | | | 276 +/− 150 | 0 +/− 0 | | 0 +/− 0 |
| Day-35 | | | 364 +/− 185 | 0 +/− 0 | | 0 +/− 0 |
| Day-37 | | | 623 +/− 312 | 0 +/− 0 | | 0 +/− 0 |
| Day-39 | | | 187 +/− 140 | 0 +/− 0 | | 0 +/− 0 |
| Day-42 | | | 317 +/− 239 | 0 +/− 0 | | 0 +/− 0 |
| Day-44 | | | 307 +/− 212 | 0 +/− 0 | | 0 +/− 0 |
| Day-46 | | | 566 +/− 384 | 0 +/− 0 | | 0 +/− 0 |
| Day-49 | | | 182 +/− 182 | 0 +/− 0 | | 0 +/− 0 |
| Day-53 | | | 478 +/− 478 | 0 +/− 0 | | 0 +/− 0 |
| Day-56 | | | 0 +/− 0 | 0 +/− 0 | | 0 +/− 0 |
| Day-60 | | | 0 +/− 0 | 0 +/− 0 | | 0 +/− 0 |
| Day-64 | | | 0 +/− 0 | 0 +/− 0 | | 0 +/− 0 |
| Day-67 | | | 0 +/− 0 | 0 +/− 0 | | 0 +/− 0 |
| Day-70 | | | 0 +/− 0 | 0 +/− 0 | | 0 +/− 0 |
| Day-74 | | | 127 +/− 127 | 0 +/− 0 | | 0 +/− 0 |
| Day-77 | | | 456 +/− 421 | 0 +/− 0 | | 0 +/− 0 |
| Day-81 | | | 773 +/− 744 | 0 +/− 0 | | 0 +/− 0 |
| Day-88 | | | 0 +/− 0 | 0 +/− 0 | | 0 +/− 0 |

TABLE 9

HL60 AML xenografts, mean tumor volume (mm3 +/− SEM)

| Q4dx4 Dose (mg/kg) | PBS 0 | CD33-11A1-v1417-kN92S-H16-D55A-K222R-hG1-LP13 | | | Neg-8-8-H16-K222R-hG1-LP13 0.3 | Mylotarg 1.0 |
|---|---|---|---|---|---|---|
| | | 0.03 | 0.1 | 0.3 | | |
| Day-0 | 221 +/− 13 | 231 +/− 20 | 230 +/− 25 | 226 +/− 15 | 231 +/− 18 | 231 +/− 13 |
| Day-4 | 507 +/− 28 | 481 +/− 43 | 539 +/− 68 | 321 +/− 40 | 481 +/− 30 | 325 +/− 23 |
| Day-7 | 921 +/− 48 | 601 +/− 49 | 530 +/− 120 | 163 +/− 82 | 511 +/− 70 | 126 +/− 27 |
| Day-9 | 1144 +/− 50 | 823 +/− 115 | 636 +/− 168 | 116 +/− 77 | 717 +/− 87 | 45 +/− 19 |
| Day-11 | 1517 +/− 107 | 1007 +/− 159 | 700 +/− 204 | 61 +/− 49 | 876 +/− 103 | 5 +/− 5 |
| Day-14 | 2752 +/− 128 | 1578 +/− 252 | 964 +/− 250 | 27 +/− 27 | 1181 +/− 170 | 0 +/− 0 |
| Day-16 | | 1389 +/− 358 | 720 +/− 230 | 20 +/− 20 | 988 +/− 105 | 0 +/− 0 |
| Day-18 | | 1192 +/− 297 | 610 +/− 190 | 17 +/− 17 | 1160 +/− 110 | 0 +/− 0 |
| Day-21 | | | 590 +/− 207 | 0 +/− 0 | 1688 +/− 173 | 0 +/− 0 |
| Day-23 | | | 714 +/− 268 | 0 +/− 0 | 1378 +/− 87 | 0 +/− 0 |
| Day-25 | | | 629 +/− 281 | 0 +/− 0 | 1864 +/− 132 | 0 +/− 0 |
| Day-28 | | | 526 +/− 175 | 0 +/− 0 | | 0 +/− 0 |
| Day-32 | | | 878 +/− 343 | 0 +/− 0 | | 0 +/− 0 |
| Day-35 | | | 951 +/− 368 | 0 +/− 0 | | 0 +/− 0 |
| Day-37 | | | 1472 +/− 570 | 0 +/− 0 | | 0 +/− 0 |
| Day-39 | | | | 0 +/− 0 | | 0 +/− 0 |
| Day-42 | | | | 0 +/− 0 | | 0 +/− 0 |
| Day-44 | | | | 0 +/− 0 | | 0 +/− 0 |
| Day-46 | | | | 0 +/− 0 | | 0 +/− 0 |
| Day-49 | | | | 0 +/− 0 | | 0 +/− 0 |
| Day-53 | | | | 0 +/− 0 | | 0 +/− 0 |
| Day-56 | | | | 0 +/− 0 | | 0 +/− 0 |
| Day-60 | | | | 0 +/− 0 | | 0 +/− 0 |
| Day-64 | | | | 0 +/− 0 | | 0 +/− 0 |
| Day-67 | | | | 0 +/− 0 | | 0 +/− 0 |
| Day-70 | | | | 0 +/− 0 | | 0 +/− 0 |
| Day-74 | | | | 0 +/− 0 | | 0 +/− 0 |
| Day-77 | | | | 0 +/− 0 | | 0 +/− 0 |
| Day-81 | | | | 0 +/− 0 | | 0 +/− 0 |
| Day-88 | | | | 0 +/− 0 | | 0 +/− 0 |

TABLE 10

HL60 AML xenografts, mean tumor volume (mm3 +/− SEM

| Q4dx4 | PBS 0 | CD33-11A1-v1417-kN92S-H16-D55A-K222R-hG1-LP5 | | | CD33-11A1-V1417-kN92S-H16-D55A-K222R-hG1-LP6 | | |
|---|---|---|---|---|---|---|---|
| | | 0.01 | 0.05 | 0.1 | 0.01 | 0.05 | 0.1 |
| Day-0 | 220 +/− 17 | 218 +/− 14 | 218 +/− 19 | 217 +/− 17 | 217 +/− 17 | 217 +/− 14 | 218 +/− 16 |
| Day-4 | 419 +/− 39 | 377 +/− 17 | 327 +/− 18 | 305 +/− 30 | 308 +/− 19 | 378 +/− 17 | 293 +/− 14 |
| Day-7 | 707 +/− 59 | 519 +/− 31 | 345 +/− 33 | 380 +/− 64 | 383 +/− 43 | 402 +/− 45 | 182 +/− 24 |
| Day-9 | 922 +/− 85 | 761 +/− 82 | 469 +/− 73 | 411 +/− 105 | 505 +/− 93 | 425 +/− 56 | 93 +/− 23 |
| Day-11 | 1146 +/− 109 | 1154 +/− 112 | 475 +/− 92 | 530 +/− 161 | 565 +/− 126 | 395 +/− 56 | 40 +/− 18 |
| Day-14 | 1725 +/− 170 | 1397 +/− 148 | 791 +/− 158 | 859 +/− 269 | 887 +/− 187 | 374 +/− 81 | 22 +/− 17 |
| Day-16 | 2060 +/− 229 | 1863 +/− 233 | 1217 +/− 247 | 838 +/− 85 | 1191 +/− 338 | 304 +/− 65 | 4 +/− 4 |
| Day-18 | 2119 +/− 176 | 1897 +/− 192 | 1033 +/− 203 | 954 +/− 132 | 794 +/− 245 | 311 +/− 73 | 0 +/− 0 |
| Day-21 | | | 1630 +/− 330 | 1357 +/− 222 | 1135 +/− 320 | 371 +/− 101 | 0 +/− 0 |
| Day-23 | | | 1605 +/− 354 | 1337 +/− 193 | 897 +/− 234 | 432 +/− 128 | 0 +/− 0 |
| Day-25 | | | 2112 +/− 469 | 2118 +/− 286 | 1234 +/− 364 | 484 +/− 141 | 0 +/− 0 |
| Day-28 | | | | | 1526 +/− 503 | 774 +/− 275 | 0 +/− 0 |
| Day-30 | | | | | | 1007 +/− 322 | 0 +/− 0 |
| Day-32 | | | | | | 1258 +/− 428 | 0 +/− 0 |
| Day-35 | | | | | | 200 +/− 77 | 0 +/− 0 |
| Day-37 | | | | | | 266 +/− 96 | 0 +/− 0 |
| Day-39 | | | | | | 281 +/− 127 | 0 +/− 0 |
| Day-42 | | | | | | 370 +/− 172 | 0 +/− 0 |
| Day-44 | | | | | | 727 +/− 394 | 0 +/− 0 |
| Day-46 | | | | | | 710 +/− 307 | 0 +/− 0 |
| Day-49 | | | | | | 914 +/− 404 | 0 +/− 0 |
| Day-51 | | | | | | 1141 +/− 579 | 0 +/− 0 |
| Day-53 | | | | | | 954 +/− 598 | 0 +/− 0 |
| Day-56 | | | | | | | 0 +/− 0 |
| Day-59 | | | | | | | 0 +/− 0 |
| Day-63 | | | | | | | 0 +/− 0 |
| Day-65 | | | | | | | 0 +/− 0 |
| Day-67 | | | | | | | 0 +/− 0 |
| Day-70 | | | | | | | 0 +/− 0 |

TABLE 10-continued

| | HL60 AML xenografts, mean tumor volume (mm3 +/− SEM | | | |
|---|---|---|---|---|
| | CD33-11A1-v1417-kN92S-H16-D55A-K222R-hG1-LP11 | | | Mylotarg |
| Q4dx4 | 0.01 | 0.05 | 0.1 | 1 |
| Day-72 | | | | 0 +/− 0 |
| Day-74 | | | | 0 +/− 0 |
| Day-77 | | | | 0 +/− 0 |
| Day-79 | | | | 0 +/− 0 |
| Day-0 | 216 +/− 22 | 214 +/− 16 | 215 +/− 24 | 216 +/− 15 |
| Day-4 | 319 +/− 17 | 316 +/− 24 | 370 +/− 41 | 278 +/− 26 |
| Day-7 | 452 +/− 43 | 277 +/− 43 | 277 +/− 90 | 90 +/− 24 |
| Day-9 | 612 +/− 71 | 321 +/− 72 | 220 +/− 100 | 12 +/− 12 |
| Day-11 | 765 +/− 107 | 366 +/− 98 | 248 +/− 136 | 0 +/− 0 |
| Day-14 | 1080 +/− 189 | 279 +/− 67 | 199 +/− 108 | 0 +/− 0 |
| Day-16 | 1392 +/− 167 | 430 +/− 140 | 203 +/− 121 | 0 +/− 0 |
| Day-18 | 1865 +/− 236 | 520 +/− 174 | 211 +/− 120 | 0 +/− 0 |
| Day-21 | 2114 +/− 325 | 677 +/− 226 | 279 +/− 175 | 0 +/− 0 |
| Day-23 | | 820 +/− 288 | 321 +/− 187 | 0 +/− 0 |
| Day-25 | | 1138 +/− 391 | 481 +/− 306 | 0 +/− 0 |
| Day-28 | | 998 +/− 491 | 309 +/− 197 | 0 +/− 0 |
| Day-30 | | 721 +/− 331 | 486 +/− 288 | 0 +/− 0 |
| Day-32 | | 920 +/− 425 | 724 +/− 399 | 0 +/− 0 |
| Day-35 | | 730 +/− 409 | 661 +/− 421 | 0 +/− 0 |
| Day-37 | | 904 +/− 384 | 430 +/− 408 | 0 +/− 0 |
| Day-39 | | 825 +/− 266 | 25 +/− 25 | 0 +/− 0 |
| Day-42 | | 1112 +/− 587 | 37 +/− 37 | 0 +/− 0 |
| Day-44 | | | 66 +/− 66 | 0 +/− 0 |
| Day-46 | | | 79 +/− 79 | 0 +/− 0 |
| Day-49 | | | 95 +/− 95 | 0 +/− 0 |
| Day-51 | | | 133 +/− 133 | 0 +/− 0 |
| Day-53 | | | 140 +/− 140 | 0 +/− 0 |
| Day-56 | | | 261 +/− 261 | 0 +/− 0 |
| Day-59 | | | 476 +/− 476 | 0 +/− 0 |
| Day-63 | | | 0 +/− 0 | 119 +/− 119 |
| Day-65 | | | 0 +/− 0 | 211 +/− 211 |
| Day-67 | | | 0 +/− 0 | 272 +/− 272 |
| Day-70 | | | 0 +/− 0 | 480 +/− 480 |
| Day-72 | | | 0 +/− 0 | 0 +/− 0 |
| Day-74 | | | 0 +/− 0 | 0 +/− 0 |
| Day-77 | | | 0 +/− 0 | 0 +/− 0 |
| Day-79 | | | 0 +/− 0 | 0 +/− 0 |

B. TF-1 AML Xenografts

The effects of anti-CD33 ADCs were examined in immunodeficient mice on the in vivo growth of human tumors. For subcutaneous (sc) AML models, $10 \times 10^6$ TF-1 cells were implanted subcutaneously in the flank of female Athymic nu/nu mice. When the tumors reached an average volume of 300 mm³, animals were staged to ensure uniformity of the tumor size among various treatment groups. The TF-1 AML sc xenograft model was dosed intravenously one time every four days for four cycles (Q4dx4) with PBS vehicle or humanized anti-CD33 ADC at the doses provided in Tables 11-13.

Figure 6:
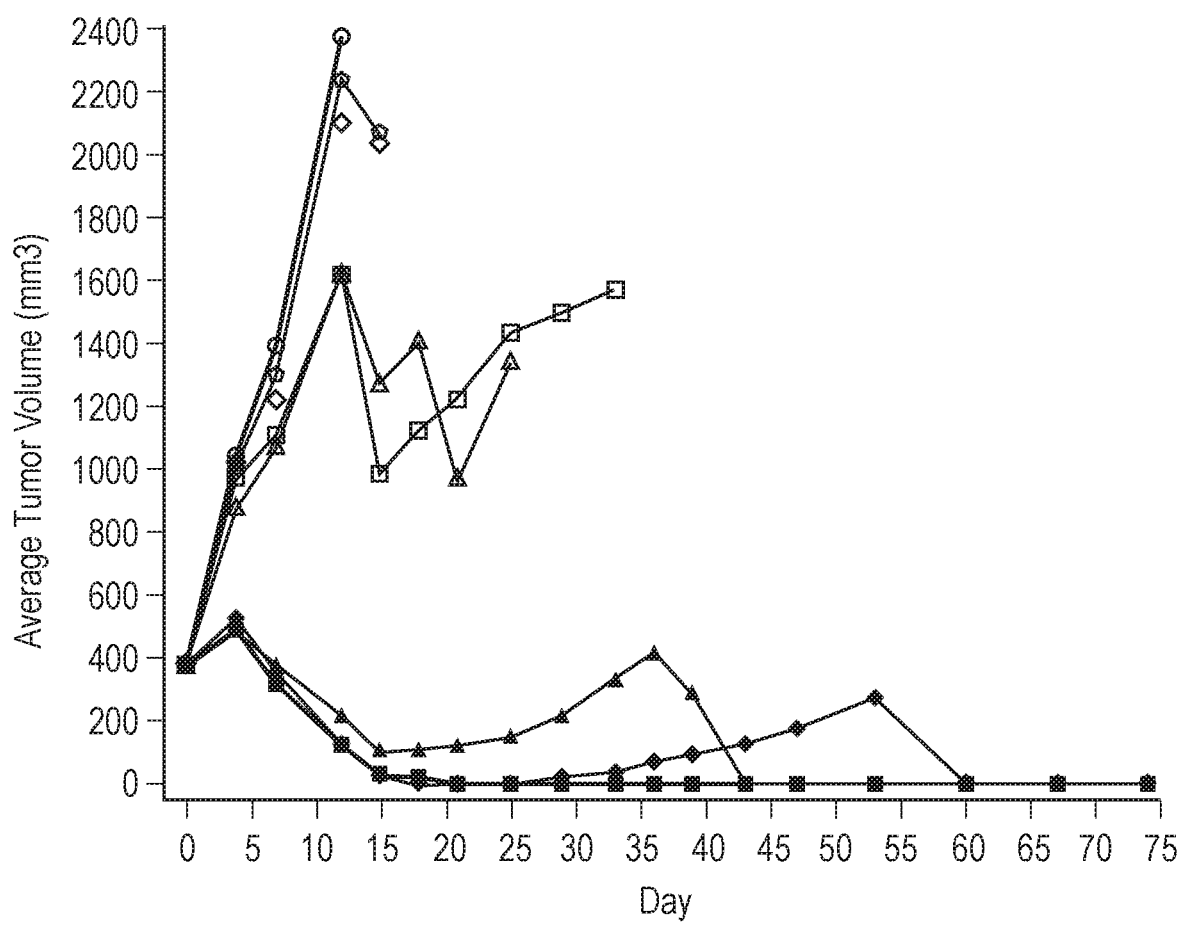
FIG. 6 shows a graph of the data from Table 11 of the anti-CD33 ADCs CD33-11A1-v1417-kN92S-H16-D55A-K222R-hG1-LP1 (example 51), CD33-11A1-v1417-kN92S-H16-D55A-K222R-hG1-LP13 (example 70), CD33-11A1-v1417-kN92S-H16-D55A-K222R-hG1-LP19 (example 85), their respective negative control ADCs (examples 52, 71, and 86, respectively), all dosed at 0.3 mg/kg, Mylotarg® dosed at 1 mg/kg, and PBS vehicle.

FIG. 6 shows a graph of the data from Table 11 of the anti-CD33 ADCs CD33-11A1-v1417-kN92S-H16-D55A-K222R-hG1-LP1 (example 51), CD33-11A1-v1417-kN92S-H16-D55A-K222R-hG1-LP13 (example 70), CD33-11A1-v1417-kN92S-H16-D55A-K222R-hG1-LP19 (example 85), their respective negative control ADCs (examples 52, 71, and 86, respectively), all dosed at 0.3 mg/kg, Mylotarg® dosed at 1 mg/kg, and PBS vehicle.

Figure 7:
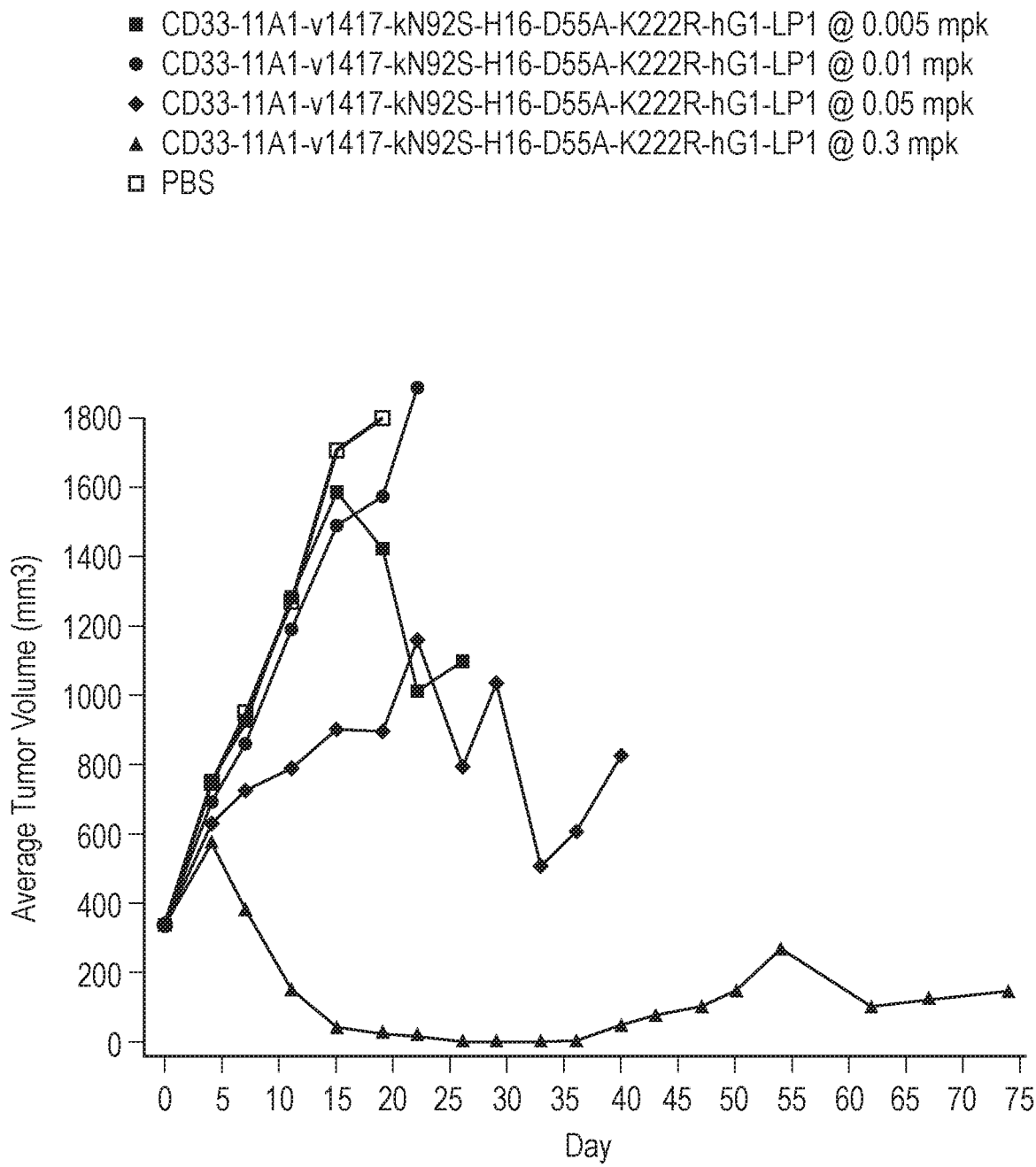
FIG. 7 shows a graph of the data from Table 12 of the anti-CD33 ADC CD33-11A1-v1417-kN92S-H16-D55A-K222R-hG1-LP1 (example 51) dosed at 0.005, 0.01, 0.05 and 0.3 mg/kg and PBS vehicle.

FIG. 7 shows a graph of the data from Table 12 of the anti-CD33 ADC CD33-11A1-v1417-kN92S-H16-D55A-K222R-hG1-LP1 (example 51) dosed at 0.005, 0.01, 0.05 and 0.3 mg/kg and PBS vehicle.

Figure 8:
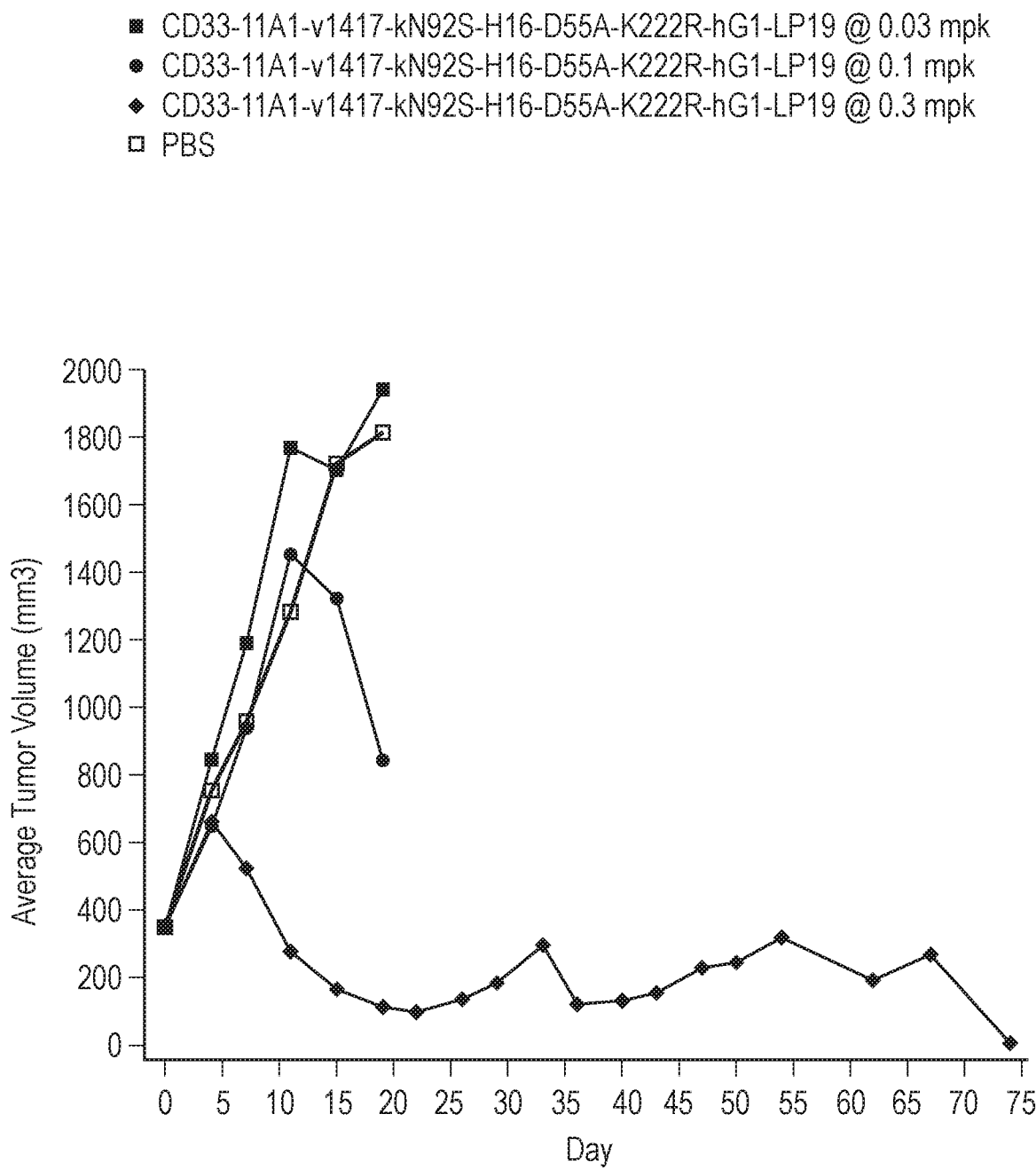
FIG. 8 shows a graph of the data from Table 13 of the anti-CD33 ADC CD33-11A1-v1417-kN92S-H16-D55A-K222R-hG1-LP19 (example 85) dosed at 0.03, 0.1, and 0.3 mg/kg and PBS vehicle.

FIG. 8 shows a graph of the data from Table 13 of the anti-CD33 ADC CD33-11A1-v1417-kN92S-H16-D55A-K222R-hG1-LP19 (example 85) dosed at 0.03, 0.1, and 0.3 mg/kg and PBS vehicle.

Figure 9:
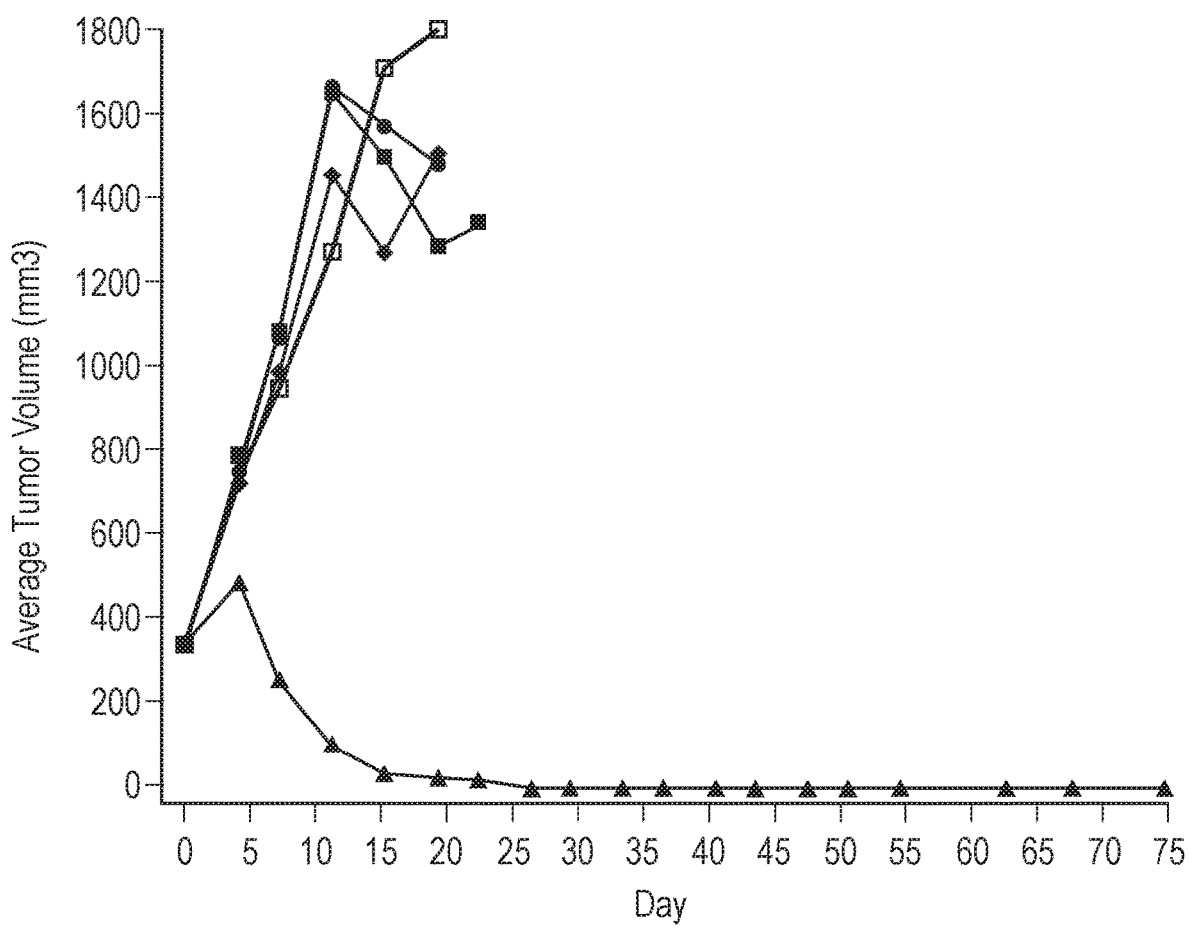
FIG. 9 shows a graph of the data from Table 14 of the anti-CD33 ADC CD33-11A1-v1417-kN92S-H16-D55A-K222R-hG1-LP13 (example 70) dosed at 0.005, 0.01, 0.05 and 0.3 mg/kg and PBS vehicle.

FIG. 9 shows a graph of the data from Table 14 of the anti-CD33 ADC CD33-11A1-v1417-kN92S-H16-D55A-K222R-hG1-LP13 (example 70) dosed at 0.005, 0.01, 0.05 and 0.3 mg/kg and PBS vehicle.

These data demonstrate that the anti-CD33 calicheamicin ADCs inhibited growth of TF-1 AML xenograft tumors in a dose-dependent manner. All three anti-CD33 calicheamicin ADCs tested, CD33-11A1-v1417-kN92S-H16-D55A-K222R-hG1-LP1, CD33-11A1-v1417-kN92S-H16-D55A-K222R-hG1-LP13, and CD33-11A1-v1417-kN92S-H16-D55A-K222R-hG1-LP19 provided strong responses when tested at 0.3 mg/kg. Two examples, CD33-11A1-v1417-kN92S-H16-D55A-K222R-hG1-LP1 and CD33-11A1-v1417-kN92S-H16-D55A-K222R-hG1-LP13, provided prolonged and complete responses in 10/10 animals when tested at 0.3 mg/kg in these studies, whereas Mylotarg® is ineffective in this assay. Furthermore, these data show that the anti-CD33 calicheamicin ADCs were far more efficacious than their respective control Neg8.8-ADCs (that do not recognize the CD33 antigen) at the same dose.

TABLE 11

| | TF-1 AML xenografts, mean tumor volume (mm³ +/− SEM) | | | | | | | |
|---|---|---|---|---|---|---|---|---|
| Q4dx4 Dose (mg/kg) | 0.0 | CD33-11A1-v1417-kN92S-H16-D55A-K222R-hG1-LP1 0.3 | Neg-8-8-H16-K222R-hG1-LP1 0.3 | CD33-11A1-v1417-kN92S-H16-D55A-K222R-hG1-LP19 0.3 | Neg-8-8-H16-K222R-hG1-LP19 0.3 | CD33-11A1-v1417-kN92S-H16-D55A-K222R-hG1-LP13 0.3 | Neg-8-8-H16-K222R-hG1-LP13 0.3 | Mylotarg 1.0 |
| 0 | 373 +/− 12 | 382 +/− 18 | 382 +/− 21 | 375 +/− 25 | 372 +/− 27 | 374 +/− 22 | 375 +/− 27 | 382 +/− 17 |
| 4 | 1046 +/− 65 | 495 +/− 63 | 977 +/− 90 | 501 +/− 77 | 883 +/− 111 | 534 +/− 59 | 1033 +/− 108 | 1004 +/− 68 |
| 7 | 1392 +/− 154 | 317 +/− 47 | 1115 +/− 124 | 385 +/− 76 | 1062 +/− 160 | 360 +/− 48 | 1233 +/− 152 | 1298 +/− 102 |
| 12 | 2374 +/− 250 | 124 +/− 24 | 1623 +/− 263 | 222 +/− 71 | 1646 +/− 290 | 137 +/− 44 | 2107 +/− 303 | 2236 +/− 225 |
| 15 | | 33 +/− 23 | 987 +/− 137 | 106 +/− 71 | 1266 +/− 283 | 25 +/− 25 | 2039 +/− 354 | 2074 +/− 357 |
| 18 | | 22 +/− 22 | 1125 +/− 176 | 111 +/− 74 | 1408 +/− 373 | 0 +/− 0 | | |
| 21 | | 0 +/− 0 | 1224 +/− 191 | 123 +/− 82 | 956 +/− 297 | 0 +/− 0 | | |
| 25 | | 0 +/− 0 | 1437 +/− 233 | 148 +/− 101 | 1348 +/− 549 | 0 +/− 0 | | |
| 29 | | 0 +/− 0 | 1499 +/− 219 | 216 +/− 147 | | 25 +/− 25 | | |
| 33 | | 0 +/− 0 | 1573 +/− 250 | 337 +/− 225 | | 41 +/− 41 | | |
| 36 | | 0 +/− 0 | | 421 +/− 283 | | 70 +/− 70 | | |
| 39 | | 0 +/− 0 | | 286 +/− 286 | | 96 +/− 96 | | |
| 43 | | 0 +/− 0 | | 0 +/− 0 | | 127 +/− 127 | | |
| 47 | | 0 +/− 0 | | 0 +/− 0 | | 178 +/− 178 | | |
| 53 | | 0 +/− 0 | | 0 +/− 0 | | 279 +/− 279 | | |
| 60 | | 0 +/− 0 | | 0 +/− 0 | | 0 +/− 0 | | |
| 67 | | 0 +/− 0 | | 0 +/− 0 | | 0 +/− 0 | | |
| 74 | | 0 +/− 0 | | 0 +/− 0 | | 0 +/− 0 | | |

TABLE 12

| | TF-1 AML xenografts, mean tumor volume (mm³ +/− SEM) | | | | |
|---|---|---|---|---|---|
| | PBS | CD33-11A1-v1417-kN92S-H16-D55A-K222R-hG1-LP1 Dose (mg/kg) | | | |
| Q4dx4 | 0 | 0.005 | 0.01 | 0.05 | 0.3 |
| Day-0 | 341 +/− 28 | 340 +/− 37 | 338 +/− 41 | 344 +/− 40 | 340 +/− 45 |
| Day-4 | 748 +/− 60 | 758 +/− 90 | 693 +/− 98 | 631 +/− 84 | 576 +/− 120 |
| Day-7 | 952 +/− 100 | 924 +/− 122 | 863 +/− 110 | 727 +/− 101 | 381 +/− 90 |
| Day-11 | 1274 +/− 186 | 1287 +/− 206 | 1194 +/− 166 | 791 +/− 177 | 150 +/− 42 |
| Day-15 | 1712 +/− 290 | 1589 +/− 295 | 1493 +/− 278 | 903 +/− 213 | 40 +/− 21 |
| Day-19 | 1802 +/− 484 | 1431 +/− 390 | 1575 +/− 262 | 895 +/− 210 | 20 +/− 20 |
| Day-22 | | 1012 +/− 328 | 1893 +/− 166 | 1163 +/− 306 | 15 +/− 15 |
| Day-26 | | 1102 +/− 366 | | 798 +/− 317 | 0 +/− 0 |
| Day-29 | | | | 1039 +/− 431 | 0 +/− 0 |
| Day-33 | | | | 503 +/− 414 | 0 +/− 0 |
| Day-36 | | | | 608 +/− 433 | 0 +/− 0 |
| Day-40 | | | | 830 +/− 616 | 47 +/− 31 |
| Day-43 | | | | | 76 +/− 57 |
| Day-47 | | | | | 101 +/− 82 |
| Day-50 | | | | | 146 +/− 126 |
| Day-54 | | | | | 269 +/− 224 |
| Day-62 | | | | | 98 +/− 98 |
| Day-67 | | | | | 121 +/− 121 |
| Day-74 | | | | | 140 +/− 140 |

TABLE 13

| | TF-1 AML xenografts, mean tumor volume (mm3 +/− SEM) | | | |
|---|---|---|---|---|
| | PBS | CD33-11A1-v1417-kN92S-H16-D55A-K222R-hG1-LP19 Dose (mg/kg) | | |
| Q4dx4 | 0 | 0.03 | 0.1 | 0.3 |
| Day-0 | 341 +/− 28 | 346 +/− 30 | 341 +/− 44 | 342 +/− 28 |
| Day-4 | 748 +/− 60 | 837 +/− 115 | 644 +/− 107 | 658 +/− 80 |
| Day-7 | 952 +/− 100 | 1180 +/− 164 | 932 +/− 177 | 516 +/− 75 |
| Day-11 | 1274 +/− 186 | 1760 +/− 274 | 1445 +/− 335 | 267 +/− 61 |

TABLE 13-continued

<table>
<tr><th colspan="5">TF-1 AML xenografts, mean tumor volume (mm3 +/− SEM)</th></tr>
<tr><th></th><th>PBS</th><th colspan="3">CD33-11A1-v1417-kN92S-H16-D55A-K222R-<br>hG1-LP19<br>Dose (mg/kg)</th></tr>
<tr><th>Q4dx4</th><th>0</th><th>0.03</th><th>0.1</th><th>0.3</th></tr>
<tr><td>Day-15</td><td>1712 +/− 290</td><td>1694 +/− 262</td><td>1311 +/− 423</td><td>160 +/− 52</td></tr>
<tr><td>Day-19</td><td>1802 +/− 484</td><td>1935 +/− 364</td><td>838 +/− 354</td><td>101 +/− 60</td></tr>
<tr><td>Day-22</td><td></td><td></td><td></td><td>91 +/− 56</td></tr>
<tr><td>Day-26</td><td></td><td></td><td></td><td>133 +/− 92</td></tr>
<tr><td>Day-29</td><td></td><td></td><td></td><td>181 +/− 136</td></tr>
<tr><td>Day-33</td><td></td><td></td><td></td><td>288 +/− 218</td></tr>
<tr><td>Day-36</td><td></td><td></td><td></td><td>118 +/− 91</td></tr>
<tr><td>Day-40</td><td></td><td></td><td></td><td>128 +/− 93</td></tr>
<tr><td>Day-43</td><td></td><td></td><td></td><td>149 +/− 106</td></tr>
<tr><td>Day-47</td><td></td><td></td><td></td><td>223 +/− 165</td></tr>
<tr><td>Day-50</td><td></td><td></td><td></td><td>237 +/− 169</td></tr>
<tr><td>Day-54</td><td></td><td></td><td></td><td>312 +/− 223</td></tr>
<tr><td>Day-62</td><td></td><td></td><td></td><td>181 +/− 181</td></tr>
<tr><td>Day-67</td><td></td><td></td><td></td><td>259 +/− 259</td></tr>
<tr><td>Day-74</td><td></td><td></td><td></td><td>0 +/− 0</td></tr>
</table>

TABLE 14

<table>
<tr><th colspan="6">TF-1 AML xenografts, mean tumor volume (mm$^3$ +/− SEM)</th></tr>
<tr><th></th><th>PBS</th><th colspan="5">CD33-11A1-v1417-kN92S-H16-D55A-K222R-hG1-LP13<br>Dose (mg/kg)</th></tr>
<tr><th>Q4dx4</th><th>0</th><th>0.005</th><th>0.01</th><th>0.05</th><th>0.3</th></tr>
<tr><td>Day-0</td><td>341 +/− 28</td><td>347 +/− 37</td><td>341 +/− 29</td><td>344 +/− 37</td><td>342 +/− 31</td></tr>
<tr><td>Day-4</td><td>748 +/− 60</td><td>795 +/− 126</td><td>753 +/− 89</td><td>728 +/− 100</td><td>488 +/− 69</td></tr>
<tr><td>Day-7</td><td>952 +/− 100</td><td>1087 +/− 148</td><td>1072 +/− 163</td><td>990 +/− 149</td><td>256 +/− 43</td></tr>
<tr><td>Day-11</td><td>1274 +/− 186</td><td>1656 +/− 274</td><td>1666 +/− 310</td><td>1462 +/− 294</td><td>103 +/− 49</td></tr>
<tr><td>Day-15</td><td>1712 +/− 290</td><td>1503 +/− 301</td><td>1572 +/− 382</td><td>1274 +/− 351</td><td>38 +/− 38</td></tr>
<tr><td>Day-19</td><td>1802 +/− 484</td><td>1291 +/− 390</td><td>1487 +/− 466</td><td>1515 +/− 535</td><td>26 +/− 26</td></tr>
<tr><td>Day-22</td><td></td><td>1348 +/− 575</td><td></td><td></td><td>21 +/− 21</td></tr>
<tr><td>Day-26</td><td></td><td></td><td></td><td></td><td>0 +/− 0</td></tr>
<tr><td>Day-29</td><td></td><td></td><td></td><td></td><td>0 +/− 0</td></tr>
<tr><td>Day-33</td><td></td><td></td><td></td><td></td><td>0 +/− 0</td></tr>
<tr><td>Day-36</td><td></td><td></td><td></td><td></td><td>0 +/− 0</td></tr>
<tr><td>Day-40</td><td></td><td></td><td></td><td></td><td>0 +/− 0</td></tr>
<tr><td>Day-43</td><td></td><td></td><td></td><td></td><td>0 +/− 0</td></tr>
<tr><td>Day-47</td><td></td><td></td><td></td><td></td><td>0 +/− 0</td></tr>
<tr><td>Day-50</td><td></td><td></td><td></td><td></td><td>0 +/− 0</td></tr>
<tr><td>Day-54</td><td></td><td></td><td></td><td></td><td>0 +/− 0</td></tr>
<tr><td>Day-62</td><td></td><td></td><td></td><td></td><td>0 +/− 0</td></tr>
<tr><td>Day-67</td><td></td><td></td><td></td><td></td><td>0 +/− 0</td></tr>
<tr><td>Day-74</td><td></td><td></td><td></td><td></td><td>0 +/− 0</td></tr>
</table>

The invention claimed is:
1. A compound of Formula (IIA):

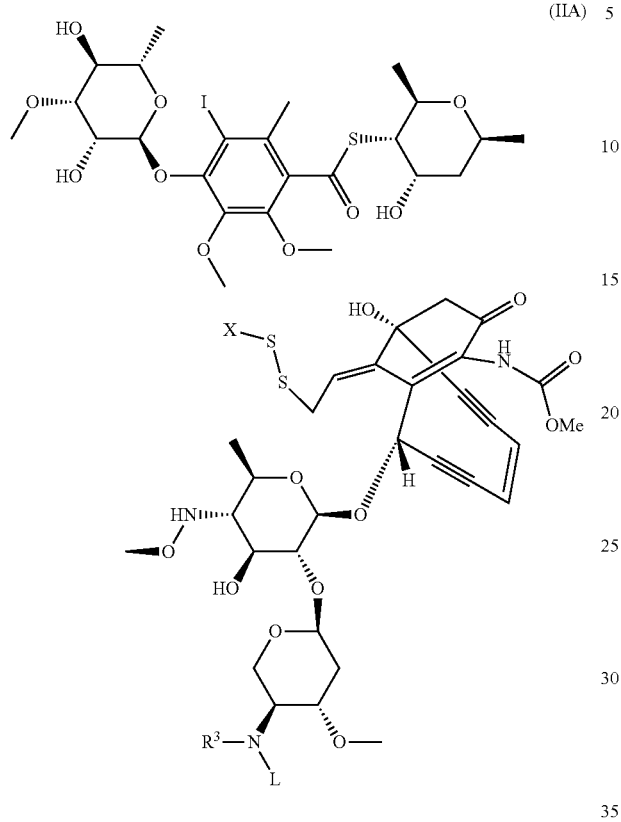

or a pharmaceutically acceptable salt thereof,
wherein:
$R^3$ is selected from the group consisting of —$CH_3$, —$CH_2CH_3$, and —$CH(CH_3)_2$;
X is selected from the group consisting of:
  (i) —$CH_3$ optionally substituted by one $R^{10}$;
  (ii) —$C_2$-$C_8$alkyl optionally substituted by one $R^{10}$;
  (iii) —($C_0$-$C_6$alkyl)-$C_3$-$C_{10}$ carbocyclyl,
    wherein said $C_3$-$C_{10}$ carbocyclyl is optionally substituted by one $R^{10}$;
  (iv) —($C_0$-$C_6$alkyl)-3 to 10 membered heterocyclyl,
    wherein said 3 to 10 membered heterocyclyl is optionally substituted by one $R^{10}$, and
    wherein said 3 to 10 membered heterocyclyl comprises one, two or three heteroatoms independently selected from the group consisting of N, O and S;
  (v) —($C_0$-$C_6$alkyl)-phenyl,
    wherein said phenyl is optionally substituted by one $R^{10}$; and
  (vi) —($C_0$-$C_6$alkyl)-5 to 10 membered heteroaryl,
    wherein said 5 to 10 membered heteroaryl is optionally substituted by one $R^{10}$, and
    wherein said 5 to 10 membered heteroaryl comprises one, two or three heteroatoms independently selected from the group consisting of N, O and S;
and which X is optionally further substituted by 1, 2, 3, 4, 5, 6, 7, or 8 G;
$R^{10}$ is —$R^{10a}$-$R^{10b}$, wherein
  $R^{10a}$ is either absent or —$(CH_2)_n$—, which $R^{10a}$ is optionally substituted by 1, 2, 3, 4, 5, 6, 7, or 8 G;
  $R^{10b}$ is selected from the group consisting of:
    (i) —OH;
    (ii) —CN;
    (iii) —$PO_3H$;
    (iv) —$CO_2H$;
    (v) —$CO_2C_1$-$C_4$alkyl,
      wherein said $C_1$-$C_4$alkyl is optionally substituted by 1, 2, 3, 4, 5, or 6 E;
    (vi) —CO—$R^{11}$;
    (vii) —NH—$R^{11}$;
    (viii) —N($C_1$-$C_4$alkyl)-$R^{11}$,
      wherein said $C_1$-$C_4$alkyl is optionally substituted by 1, 2, 3, 4, 5, or 6 E;
    (ix) —CONN—$R^{11}$;
    (x) —CON($C_1$-$C_4$alkyl)-$R^{11}$,
      wherein said $C_1$-$C_4$alkyl is optionally substituted by 1, 2, 3, 4, 5, or 6 E;
    (xi) —CONHNH—$R^{11}$;
    (xii) —CONHN($C_1$-$C_4$alkyl)-$R^{11}$,
      wherein said $C_1$-$C_4$alkyl is optionally substituted by 1, 2, 3, 4, 5, or 6 E;
    (xiii) —CON($C_1$-$C_4$alkyl)NH—$R^{11}$,
      wherein said $C_1$-$C_4$alkyl is optionally substituted by 1, 2, 3, 4, 5, or 6 E;
    (xiv) —CON($C_1$-$C_4$alkyl)N($C_1$-$C_4$alkyl)-$R^{11}$,
      wherein each said $C_1$-$C_4$alkyl is independently optionally substituted by 1, 2, 3, 4, 5, or 6 E;
    (xv) —CON($R^{11}$)$NH_2$;
    (xvi) —CON($R^{11}$)NH($C_1$-$C_4$alkyl),
      wherein said $C_1$-$C_4$alkyl is optionally substituted by 1, 2, 3, 4, 5, or 6 E;
    (xvii) —CON($R^{11}$)N($C_1$-$C_4$alkyl)$_2$,
      wherein each said $C_1$-$C_4$alkyl is independently optionally substituted by 1, 2, 3, 4, 5, or 6 E;
    (xviii) —CONHN=C($C_1$-$C_4$alkyl)-$C_6H_4$-$OC_1$-$C_4$alkyl,
      wherein each said $C_1$-$C_4$alkyl is independently optionally substituted by 1, 2, 3, 4, 5, or 6 E;
    (xix) —CON($C_1$-$C_4$alkyl)N=C($C_1$-$C_4$alkyl)-$C_6H_4$-$OC_1$-$C_4$alkyl, wherein each said $C_1$-$C_4$alkyl is independently optionally substituted by 1, 2, 3, 4, 5, or 6 E;

(xx) —N($R^{11}$)CO($C_1$-$C_4$alkyl),
wherein said $C_1$-$C_4$alkyl is optionally substituted by 1, 2, 3, 4, 5, or 6 E;

(xxi) —CH(CO$_2$H)NH—$R^{11}$;

(xxii) —CH(CO$_2$C$_1$-C$_4$alkyl)NH—$R^{11}$,
wherein said $C_1$-$C_4$alkyl is optionally substituted by 1, 2, 3, 4, 5, or 6 E;

(xxiii) —CH(NH$_2$)CO—$R^{11}$;

(xxiv) —CH(NH($C_1$-$C_4$alkyl))CO—$R^{11}$,
wherein said $C_1$-$C_4$alkyl is optionally substituted by 1, 2, 3, 4, 5, or 6 E;

(xxv) —CH(N($C_1$-$C_4$alkyl)$_2$)CO—$R^{11}$,
wherein each said $C_1$-$C_4$alkyl is independently optionally substituted by 1, 2, 3, 4, 5, or 6 E;

(xxvi) —CH(CO—$R^{11}$)NH—$R^{11}$; and (xxvii) —CH(CO—$R^{11}$)N($C_1$-$C_4$alkyl)-$R^{11}$,
wherein said $C_1$-$C_4$alkyl is optionally substituted by 1, 2, 3, 4, 5, or 6 E;

$R^{11}$ is selected from the group consisting of —$R^{11a}$-$R^{11b}$—$R^{11c}$ and —$R^{11d}$—$R^{11e}$-$R^{11f}$, wherein $R^{11a}$ is either absent, or is selected from the group consisting of,

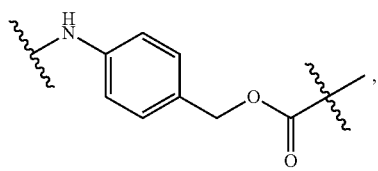

,

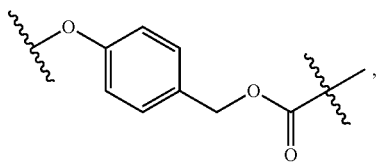

,

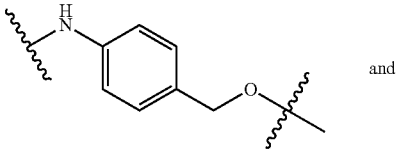

and

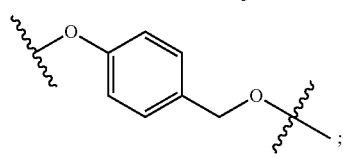

;

$R^{11b}$ is either absent, or is selected from the group consisting of

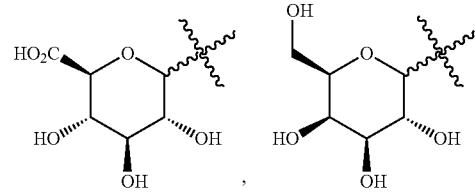

, and AA$_r$,
wherein AA is independently for each occurrence a natural amino acid or a non-natural amino acid;

$R^{11c}$ is either absent or is selected from the group consisting of —H, —$C_1$-$C_4$alkyl and -CO$C_1$-$C_4$alkyl;

$R^{11d}$ is either absent or —(CH$_2$)$_t$—,
wherein $R^{11d}$ when present is optionally substituted by 1, 2, 3, 4, 5, 6, 7, or 8 G;

$R^{11e}$ is either absent or selected from the group consisting of —O— and —NH—;

$R^{11f}$ is selected from the group consisting of $C_6$-$C_{12}$ aryl and 5 to 10 membered heteroaryl,
wherein said 5 to 10 membered heteroaryl comprises one, two or three heteroatoms independently selected from the group consisting of N, O and S, and
wherein $R^{11f}$ is optionally substituted by 1, 2, 3, 4, 5, 6, 7, or 8 G;

n is 1, 2, 3, 4, 5, or 6;
r is 1, 2, 3, 4, 5, 6, 7, 8, 9, 10, 11, 12, 13, 14, 15, 16, 17, 18, 19, or 20;
t is 1, 2, 3, 4, 5, or 6;
G is selected, independently for each occurrence, from the group consisting of —F, —Cl, —CN, —OH, —NH$_2$, —NH—$C_1$-$C_4$alkyl, —N($C_1$-$C_4$alkyl)$_2$, —NO$_2$, —CO$_2$H, —$C_1$-$C_4$alkylOH, —$C_1$-$C_4$alkylNH$_2$, —$C_1$-$C_4$alkoxy, =O, —CO$_2$$C_1$-$C_4$alkyl, —OC(O)$C_1$-$C_4$alkyl, —NHC(O)$C_1$-$C_4$alkyl, —C(O)NH$C_1$-$C_4$alkyl, and —C(O)N($C_1$-$C_4$alkyl)$_2$;

E is selected, independently for each occurrence, from the group consisting of —F, —Cl, —CN, —OH, —NH$_2$, —NHCH$_3$, —N(CH$_3$)$_2$, —NO$_2$, —CO$_2$H, —OCH$_3$, —OCF$_3$, and —CF$_3$; and L is -$L^B$-$L^A$:
wherein:
$L^A$ is selected from the group consisting of —NHR,

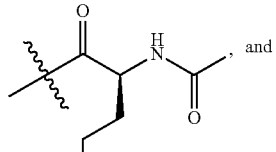

, and

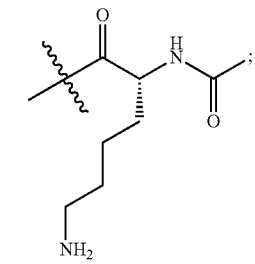

$L^B$ is —$L^{B1}$—$L^{B2}$—$L^{B3}$ wherein:
  $L^{B1}$ is absent;
  $L^{B2}$ is either absent, or is selected from the group consisting of

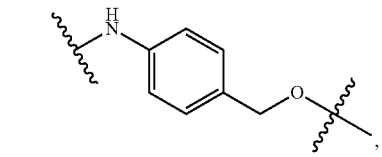,

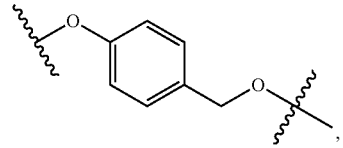,

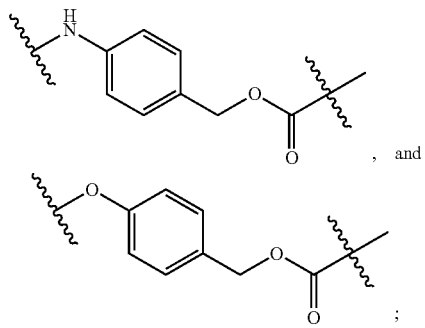, and

;

$L^{B3}$ is $AA_{0-12}$, wherein AA is independently for each occurrence a natural amino acid or a non-natural amino acid; and each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears.

2. The compound of claim 1, or a pharmaceutically acceptable salt thereof, wherein $L^A$ is selected from the group consisting of:
—$NH_2$;

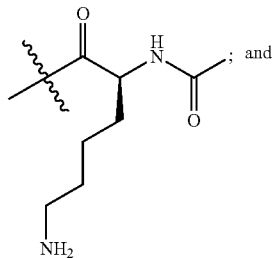; and

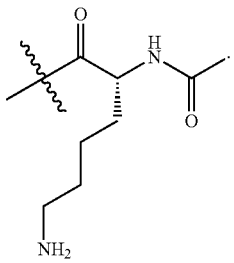

3. The compound of claim 1, or a pharmaceutically acceptable salt thereof, wherein $L^{B2}$ is absent.

4. The compound of claim 1, or a pharmaceutically acceptable salt thereof, wherein $L^{B2}$ is

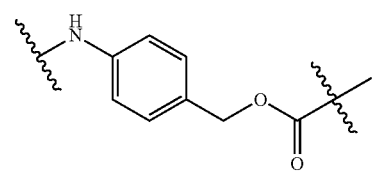.

5. The compound of claim 1, or a pharmaceutically acceptable salt thereof, wherein $L^{B3}$ is absent.

6. The compound of claim 1, or a pharmaceutically acceptable salt thereof, wherein $L^{B3}$ is $AA_2$, wherein AA is independently for each occurrence a natural amino acid or a non-natural amino acid.

7. The compound of claim 1, or a pharmaceutically acceptable salt thereof, wherein R is H.

8. The compound of claim 1, or a pharmaceutically acceptable salt thereof, wherein L is

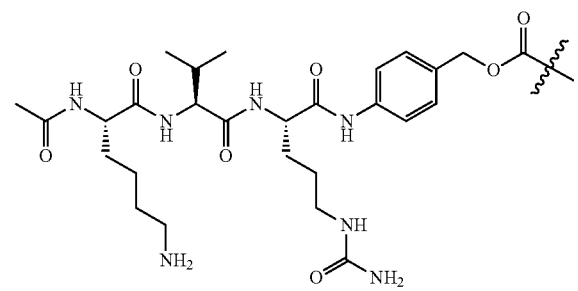

9. A compound, or a pharmaceutically acceptable salt thereof, selected from the group consisting of:
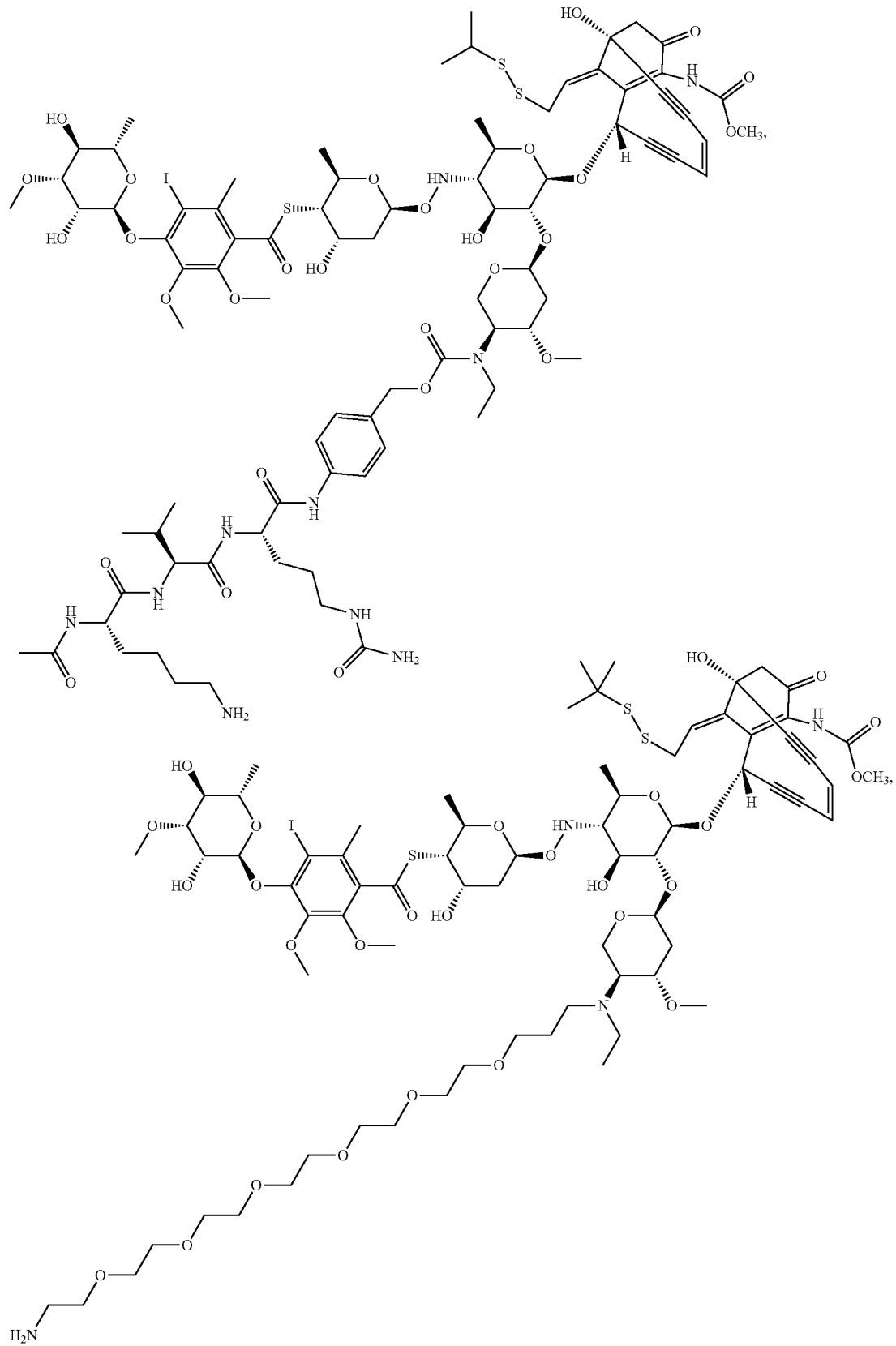

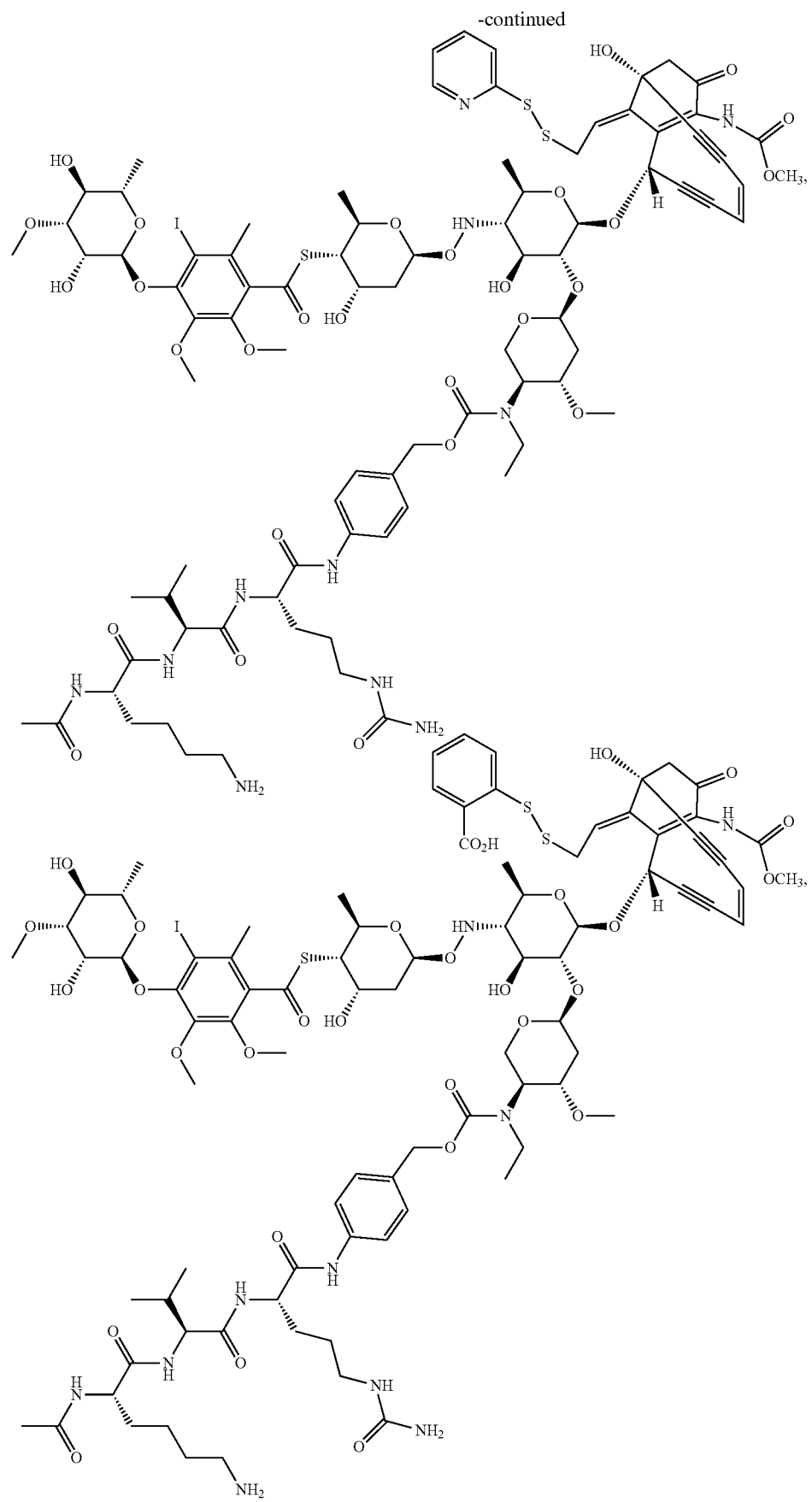

-continued
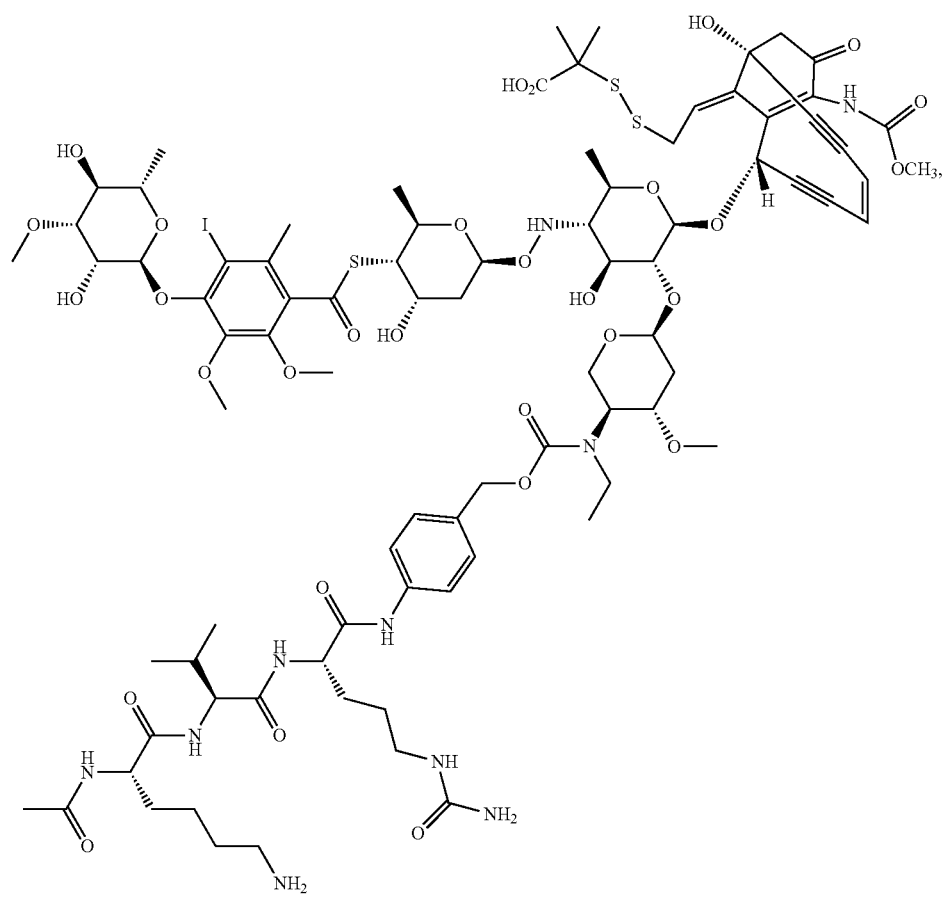

-continued
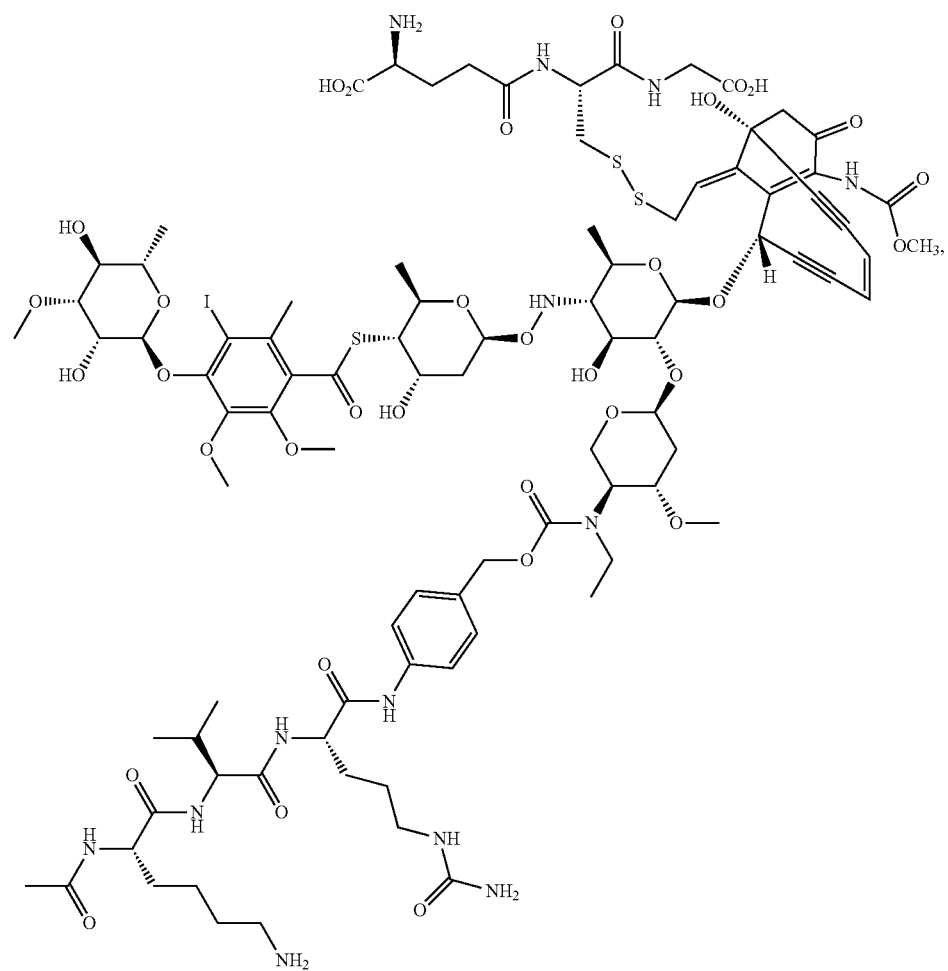

-continued
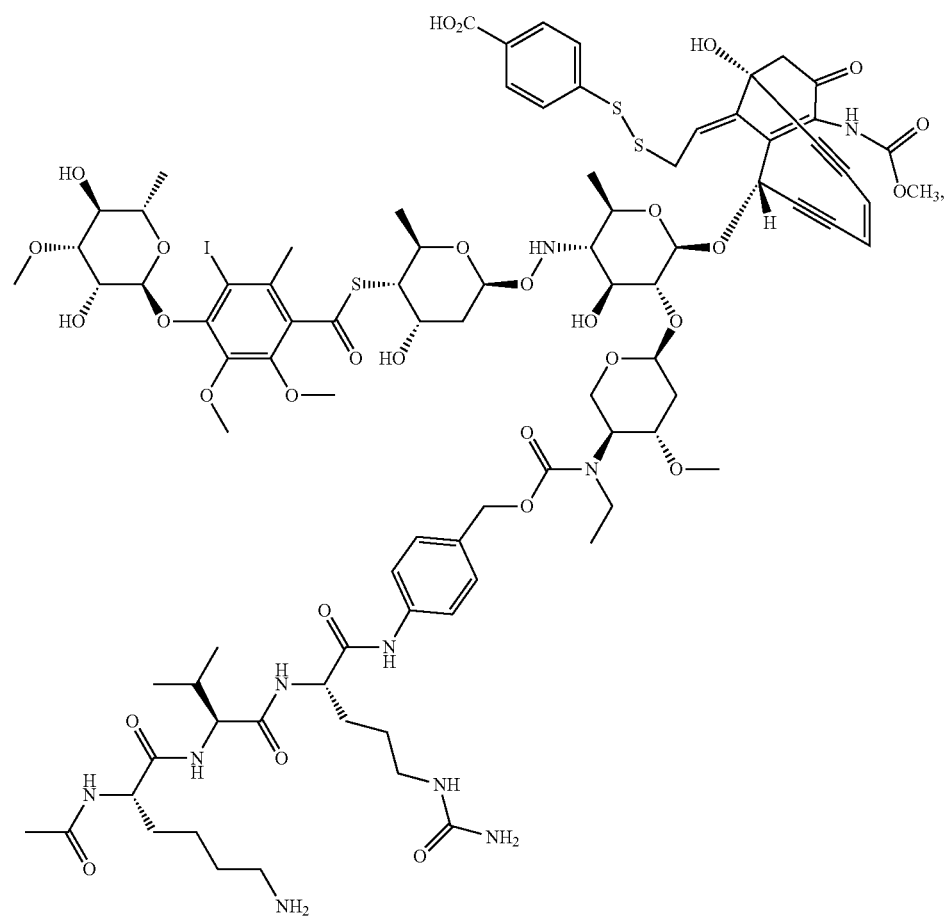

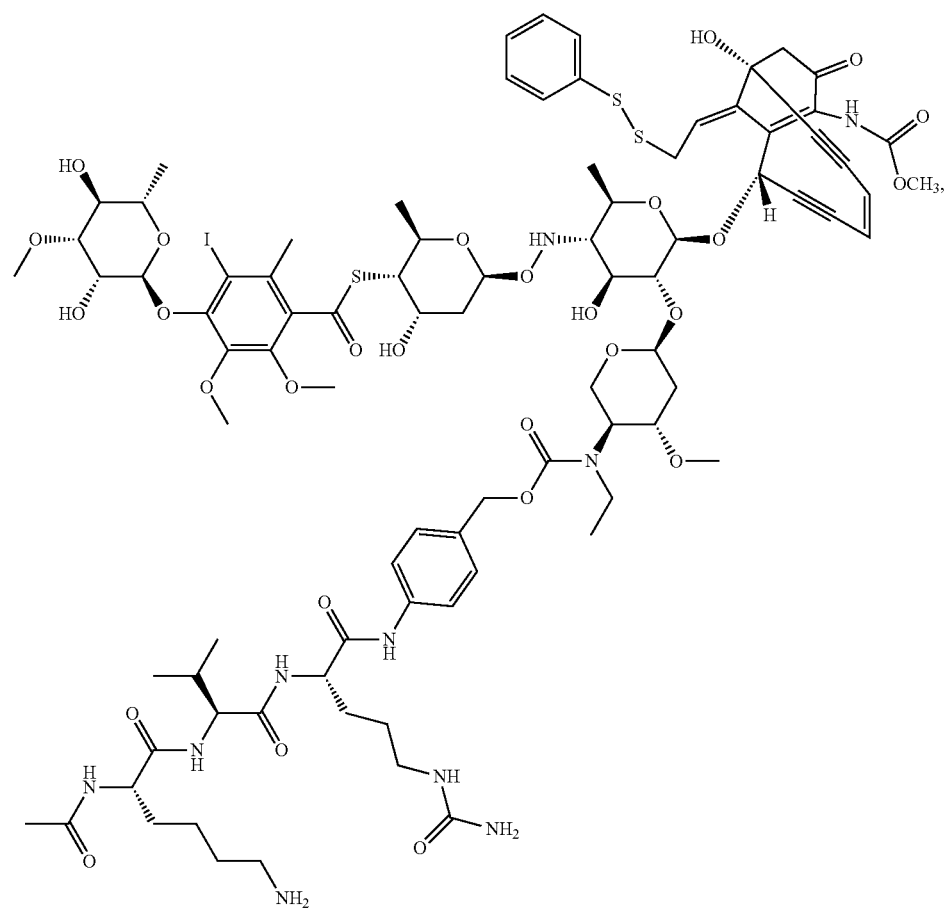

-continued
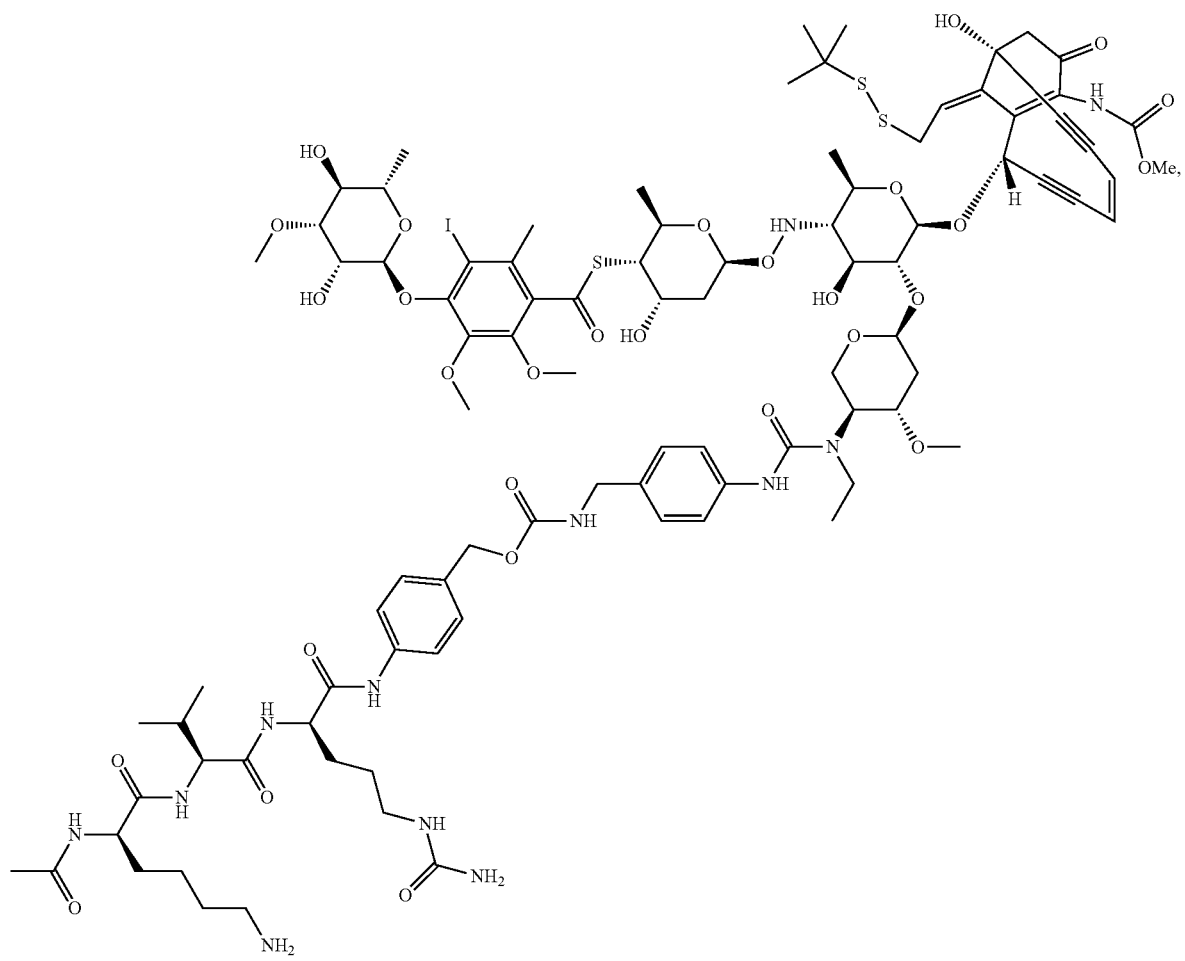

-continued
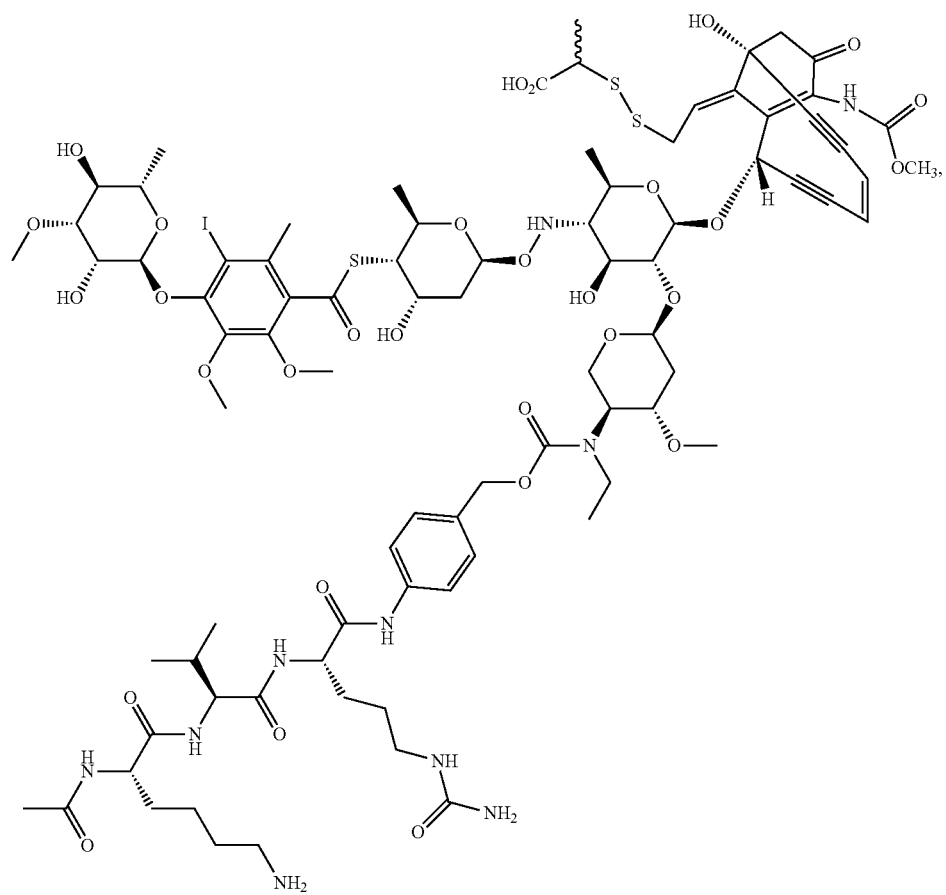

-continued
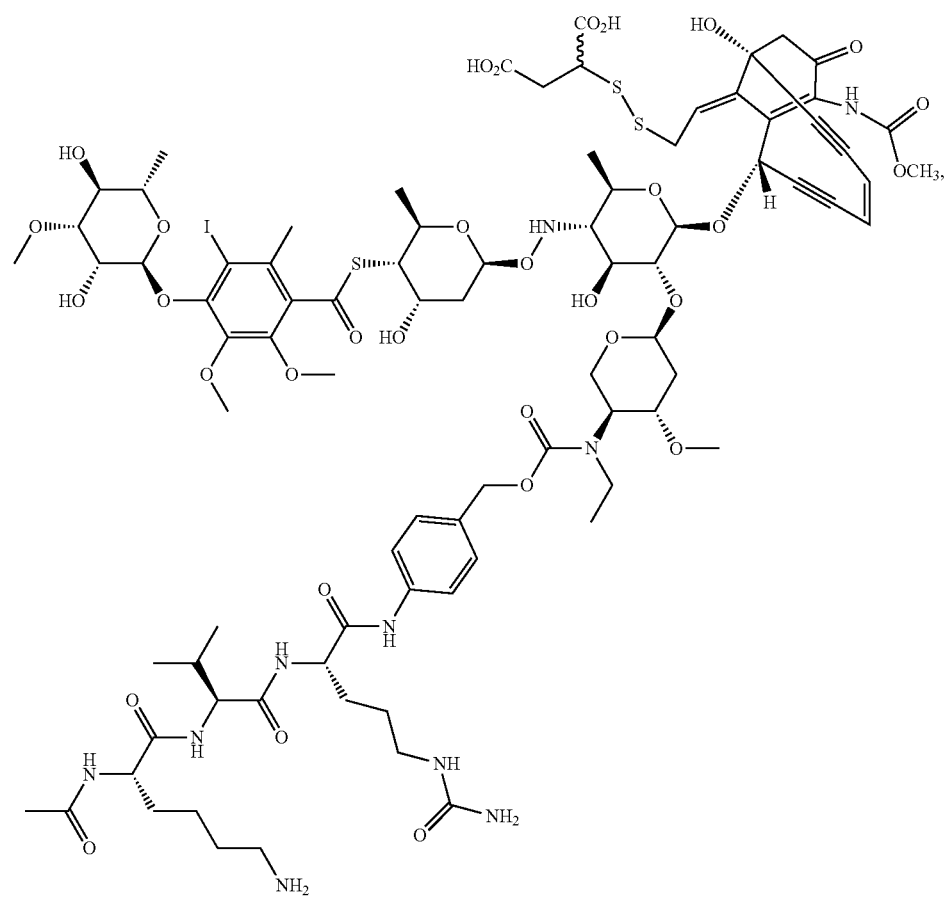

-continued
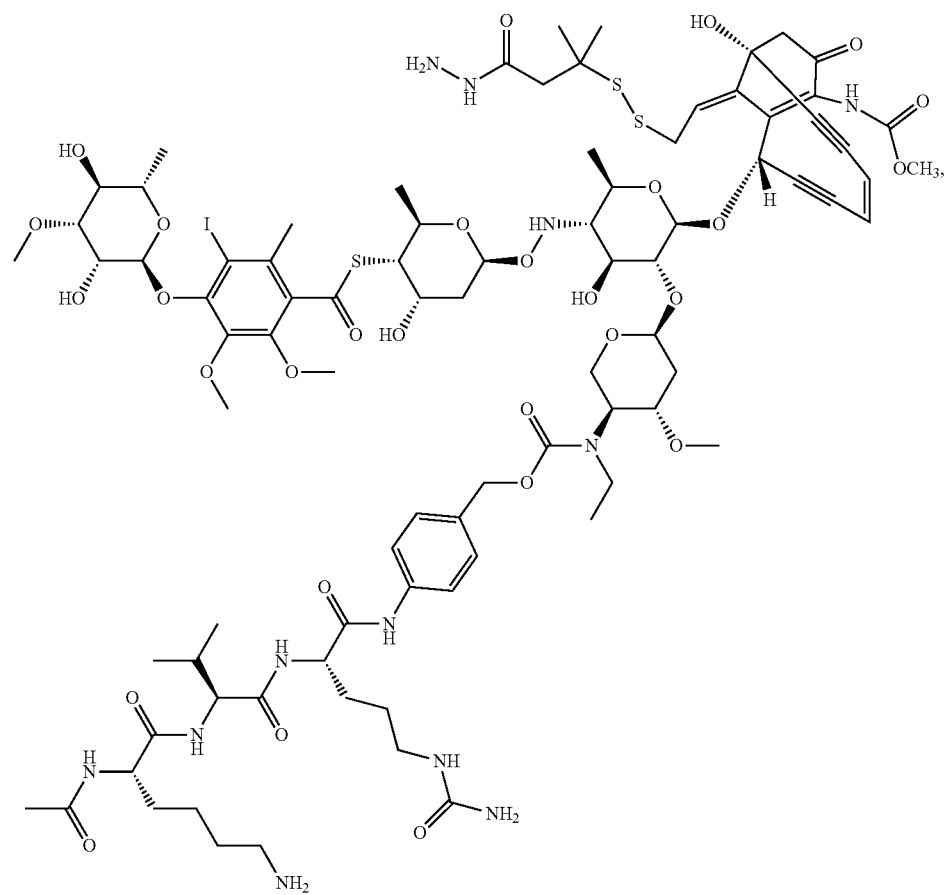

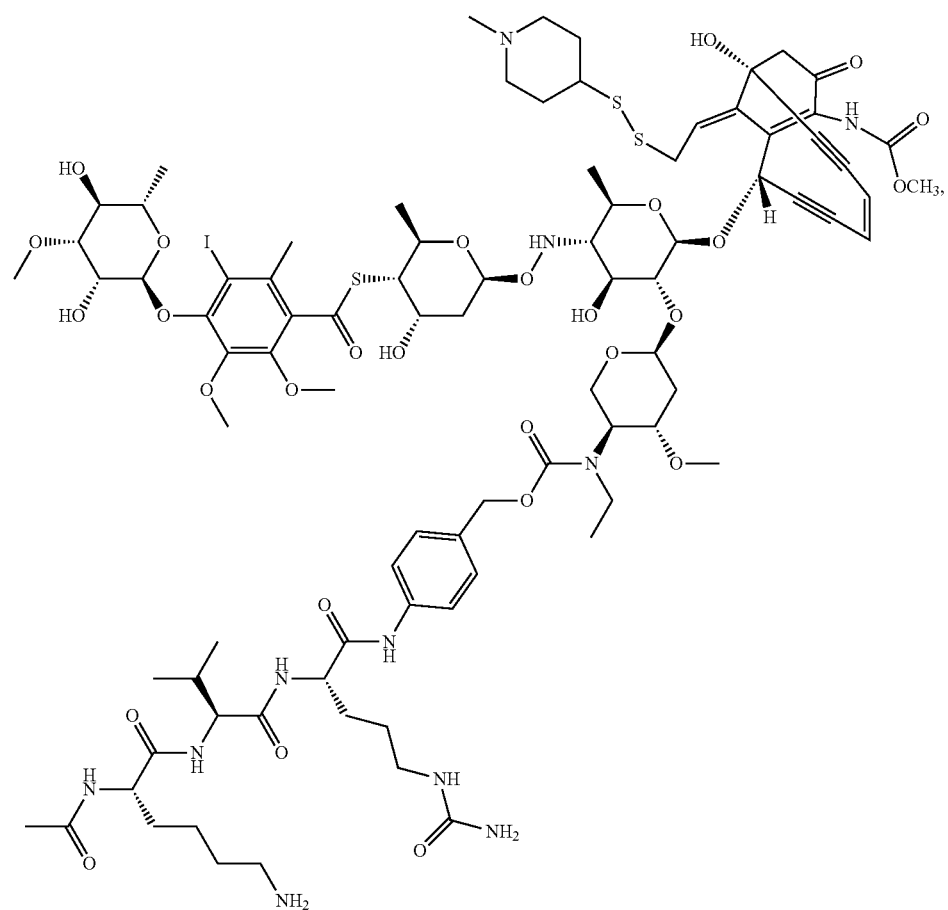

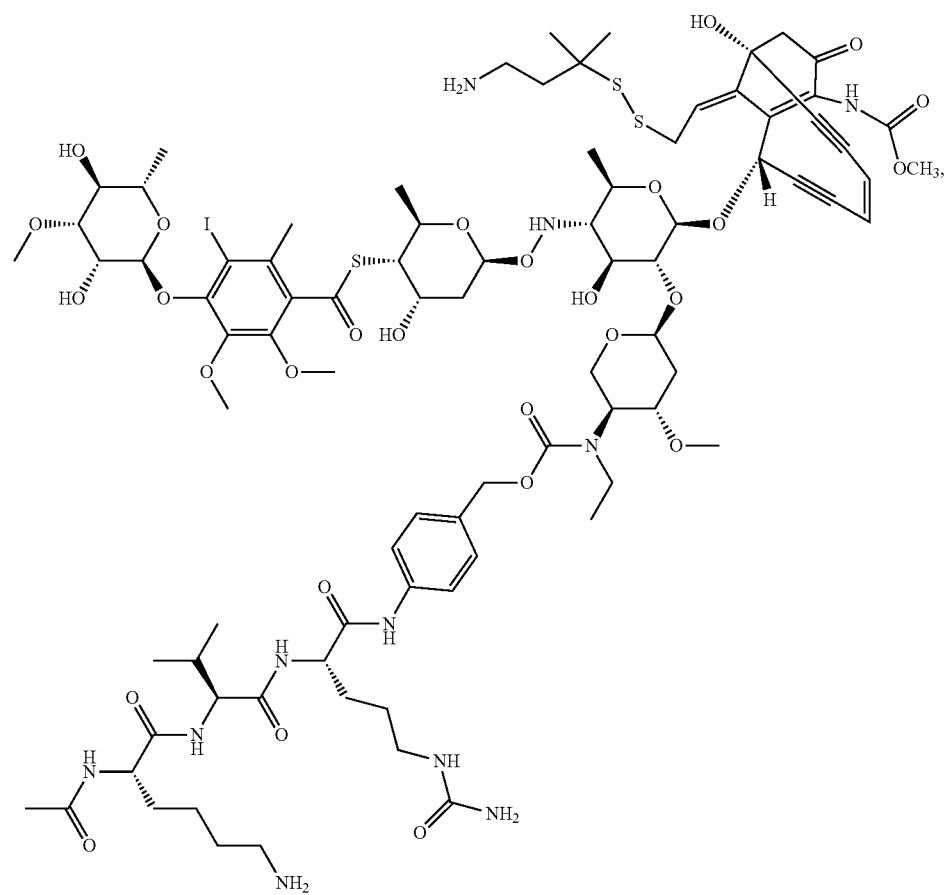

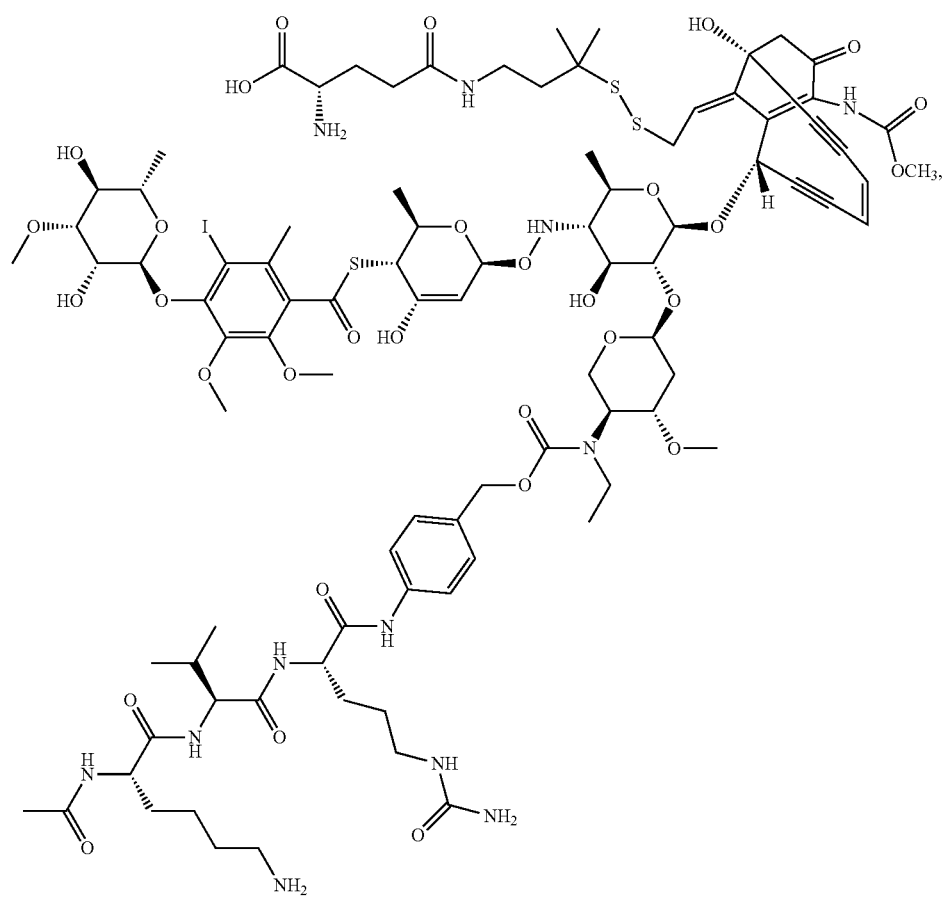

-continued
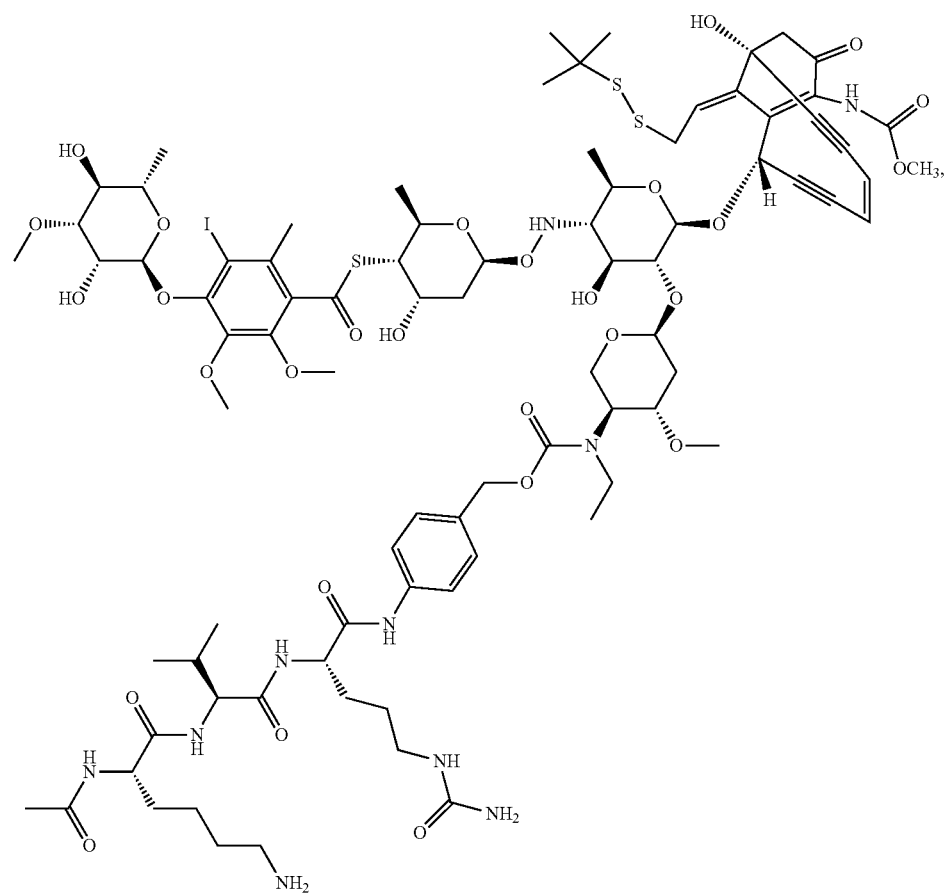

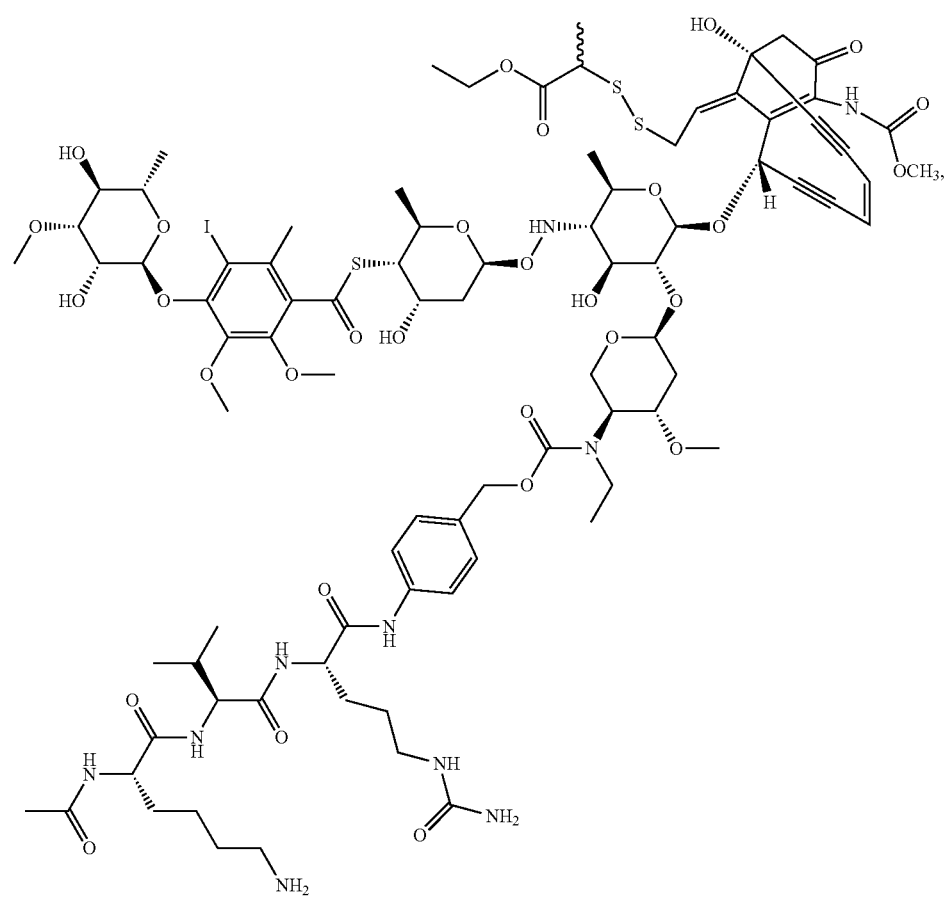

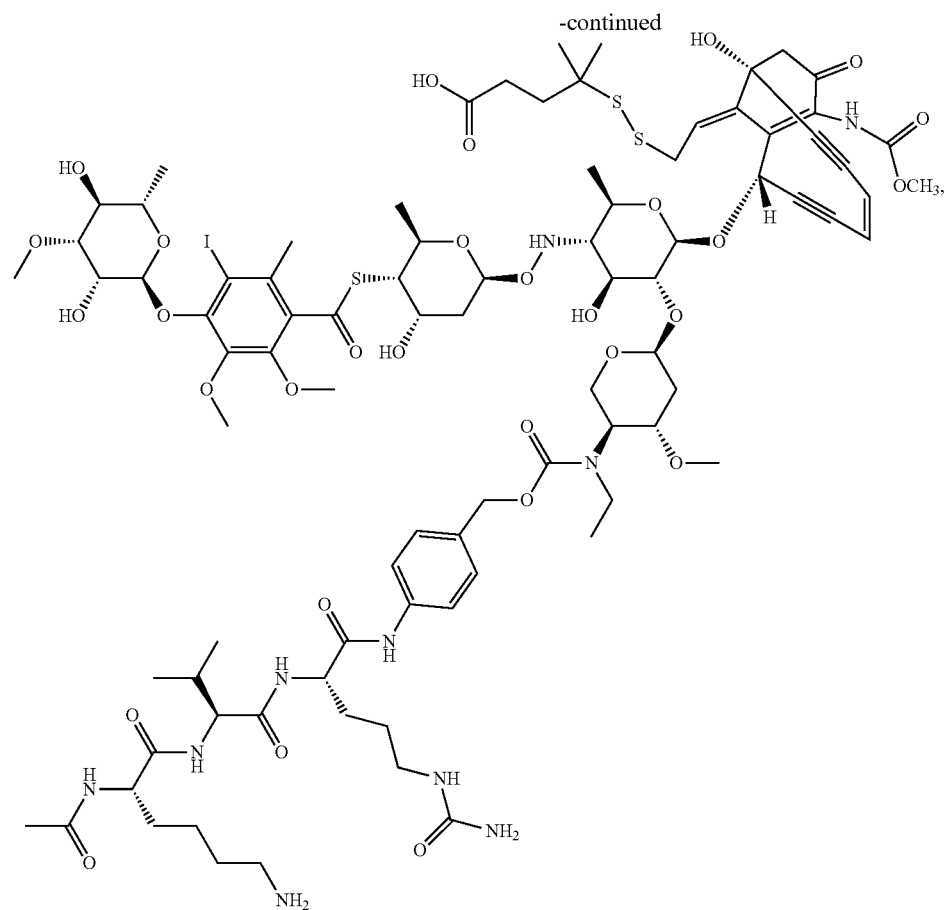
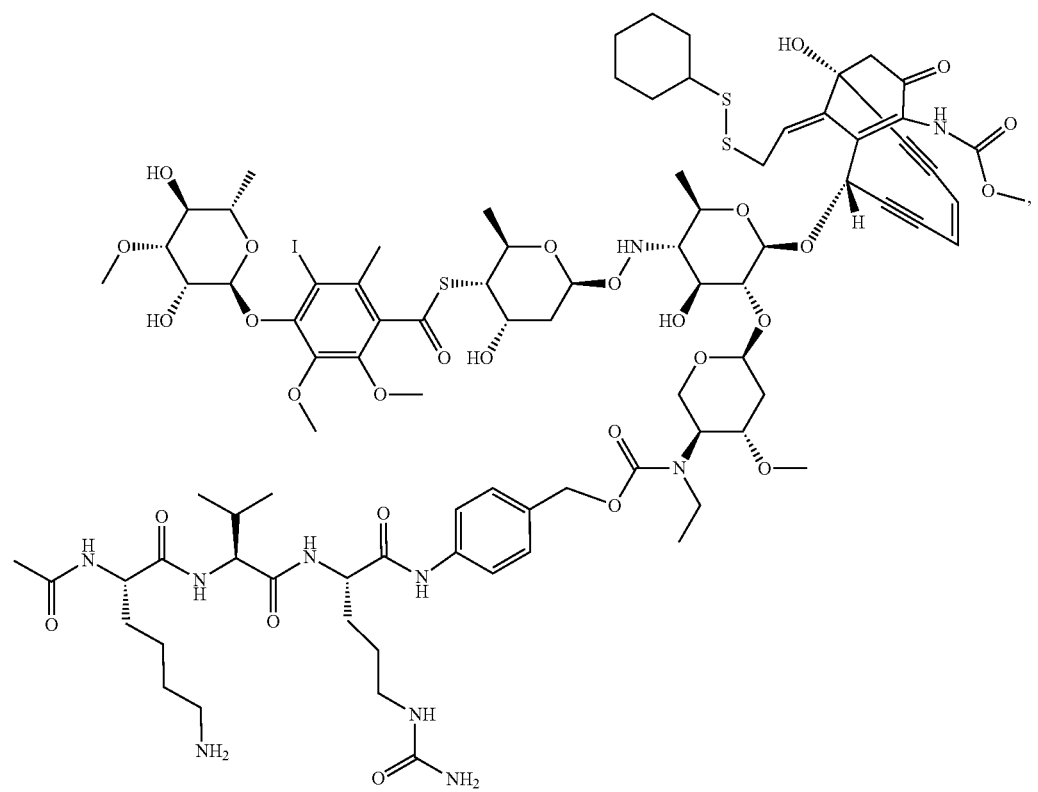

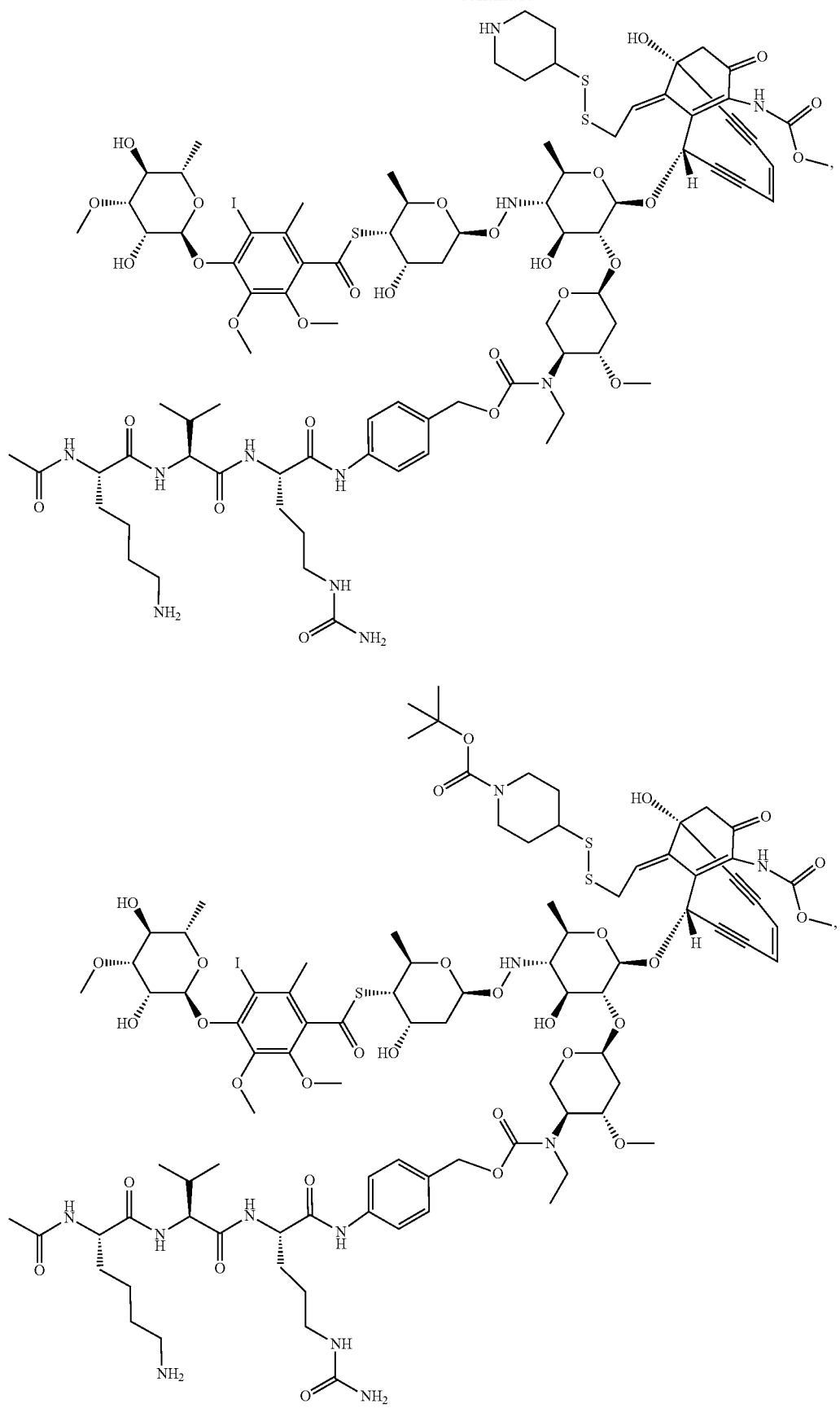

597
598
-continued
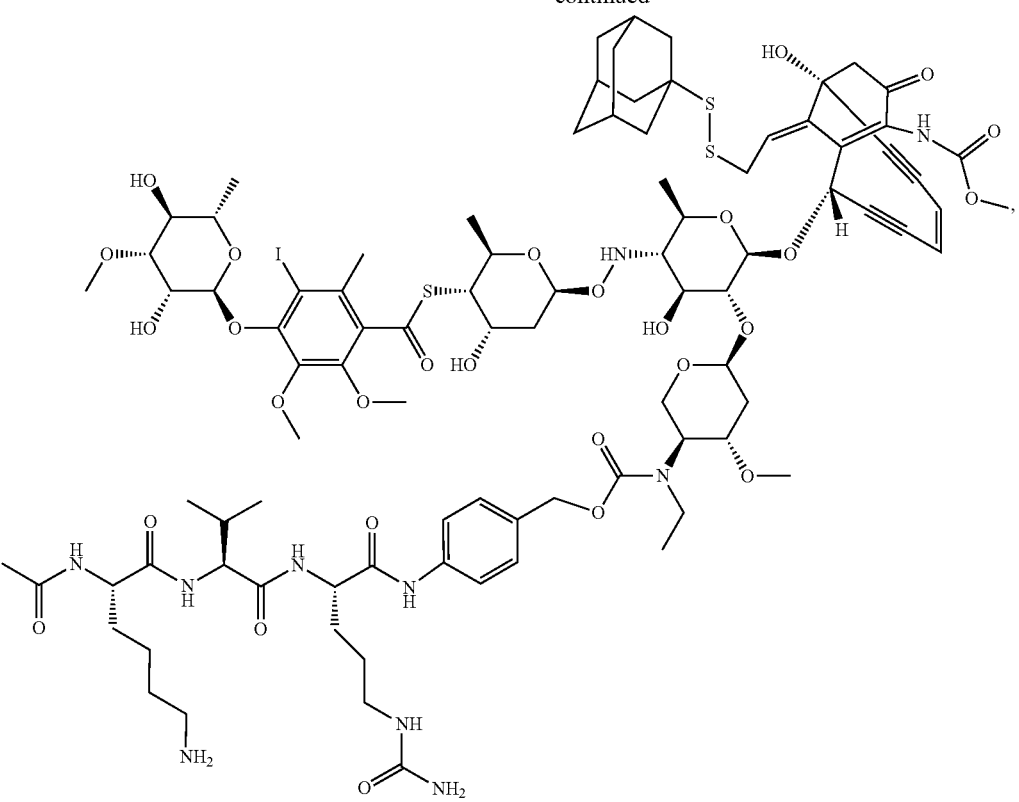
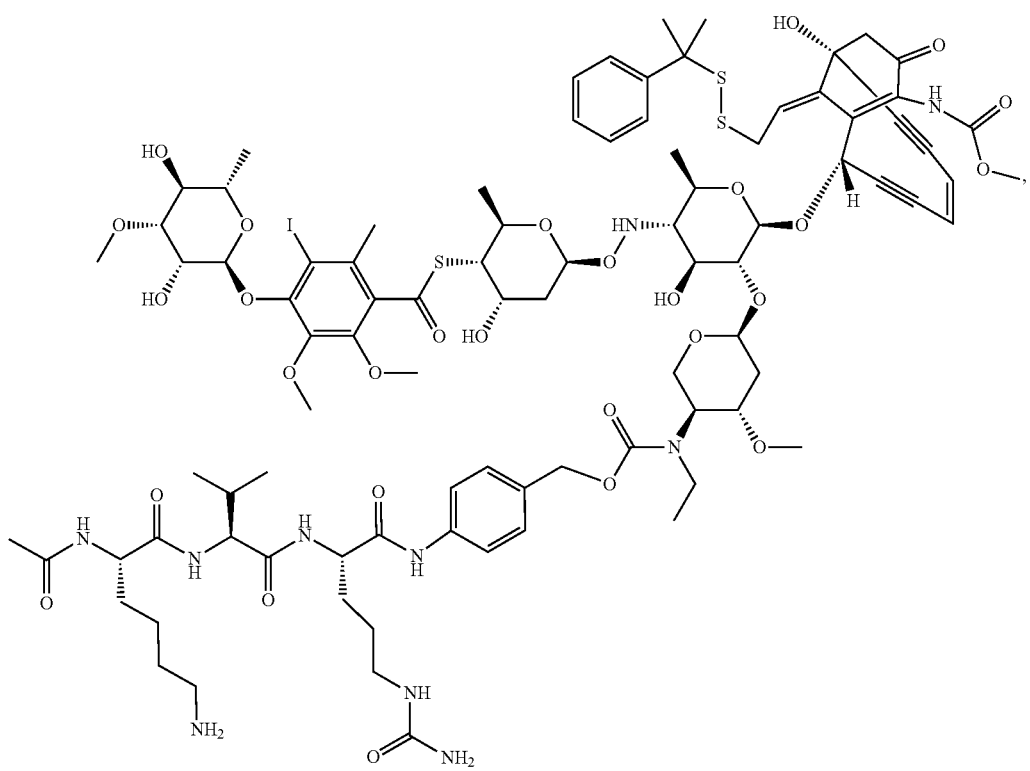

-continued
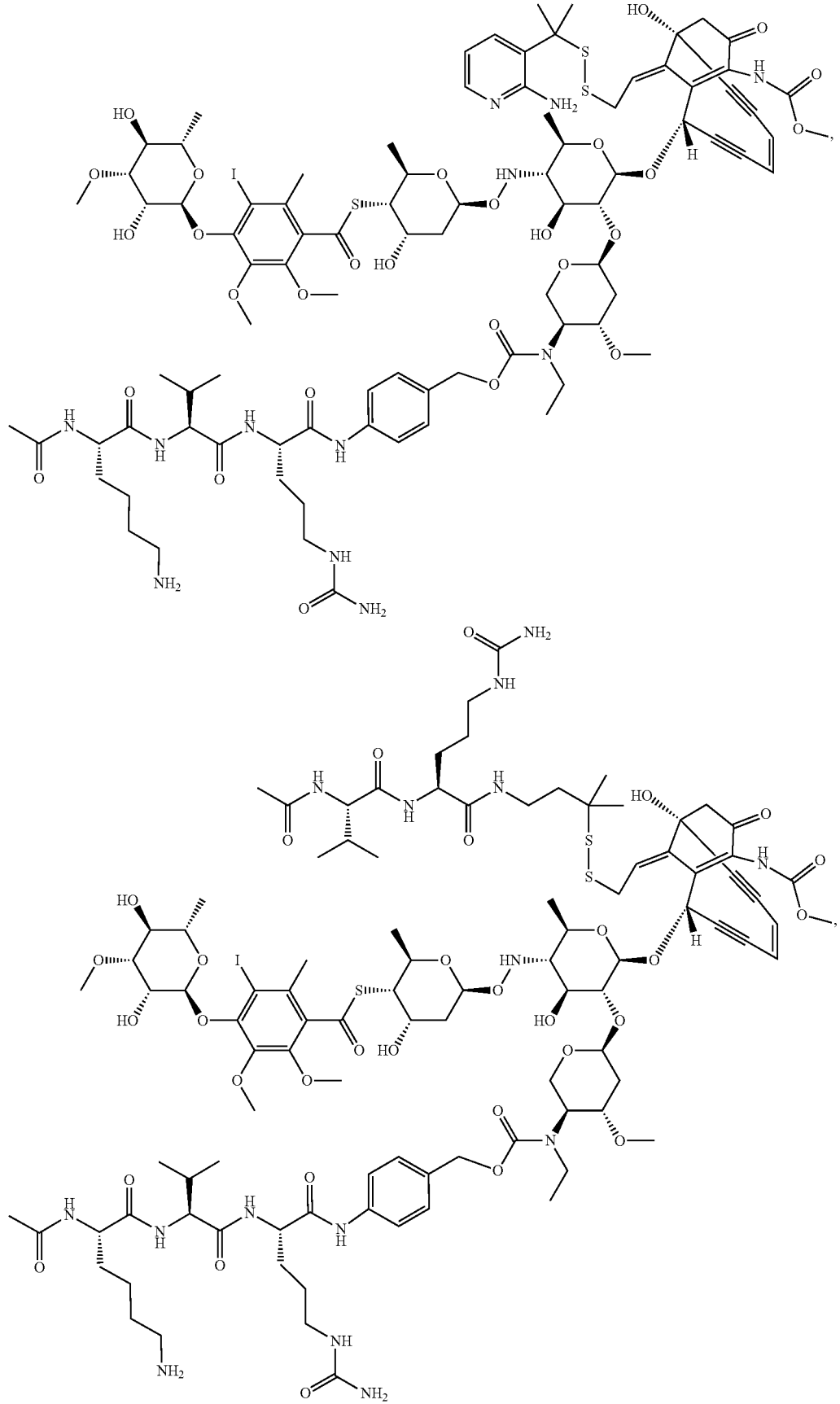

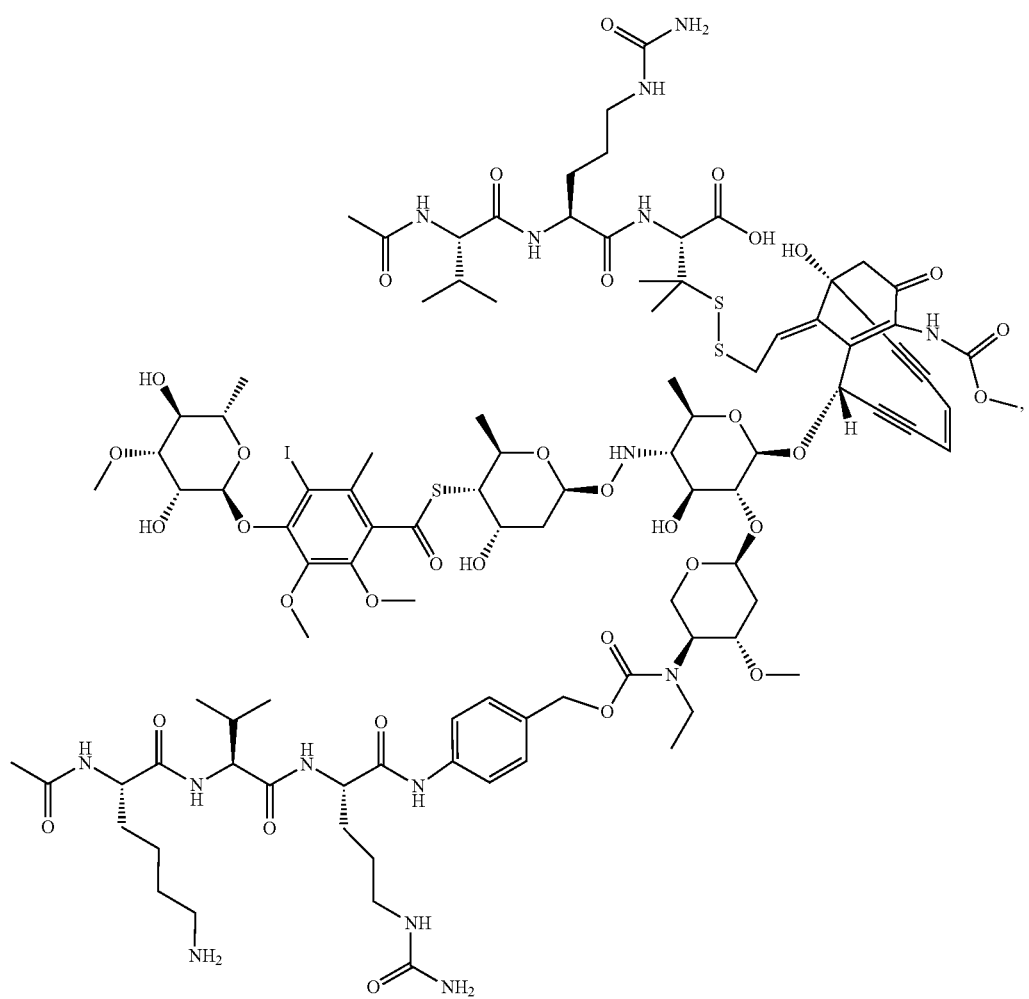

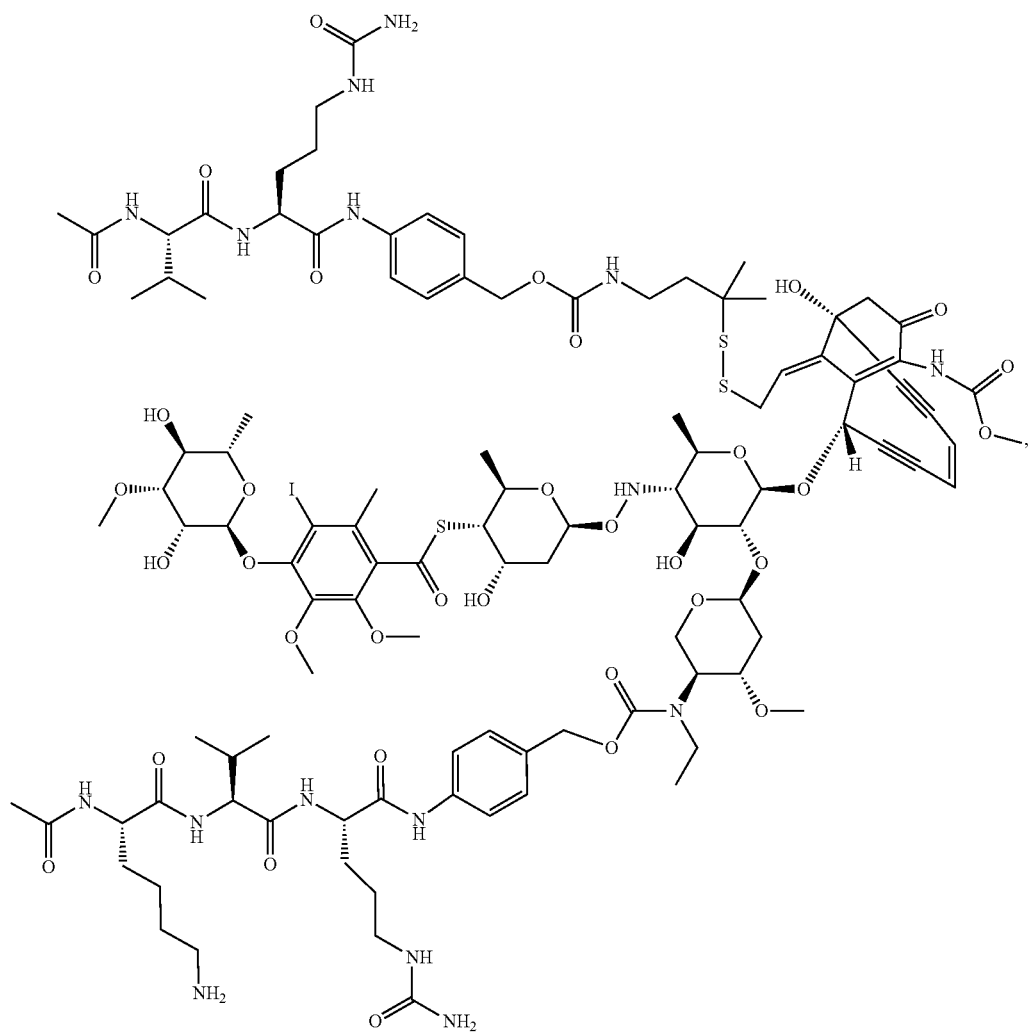

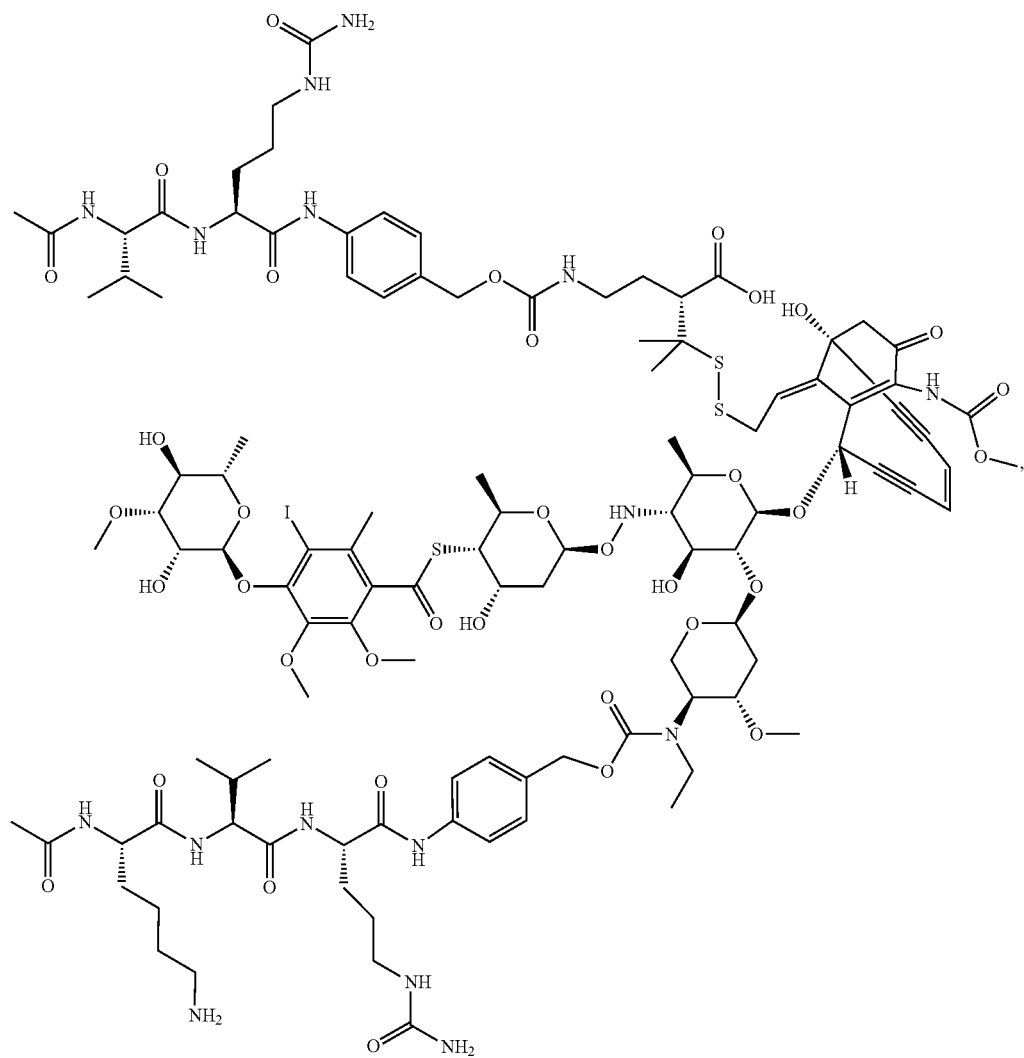

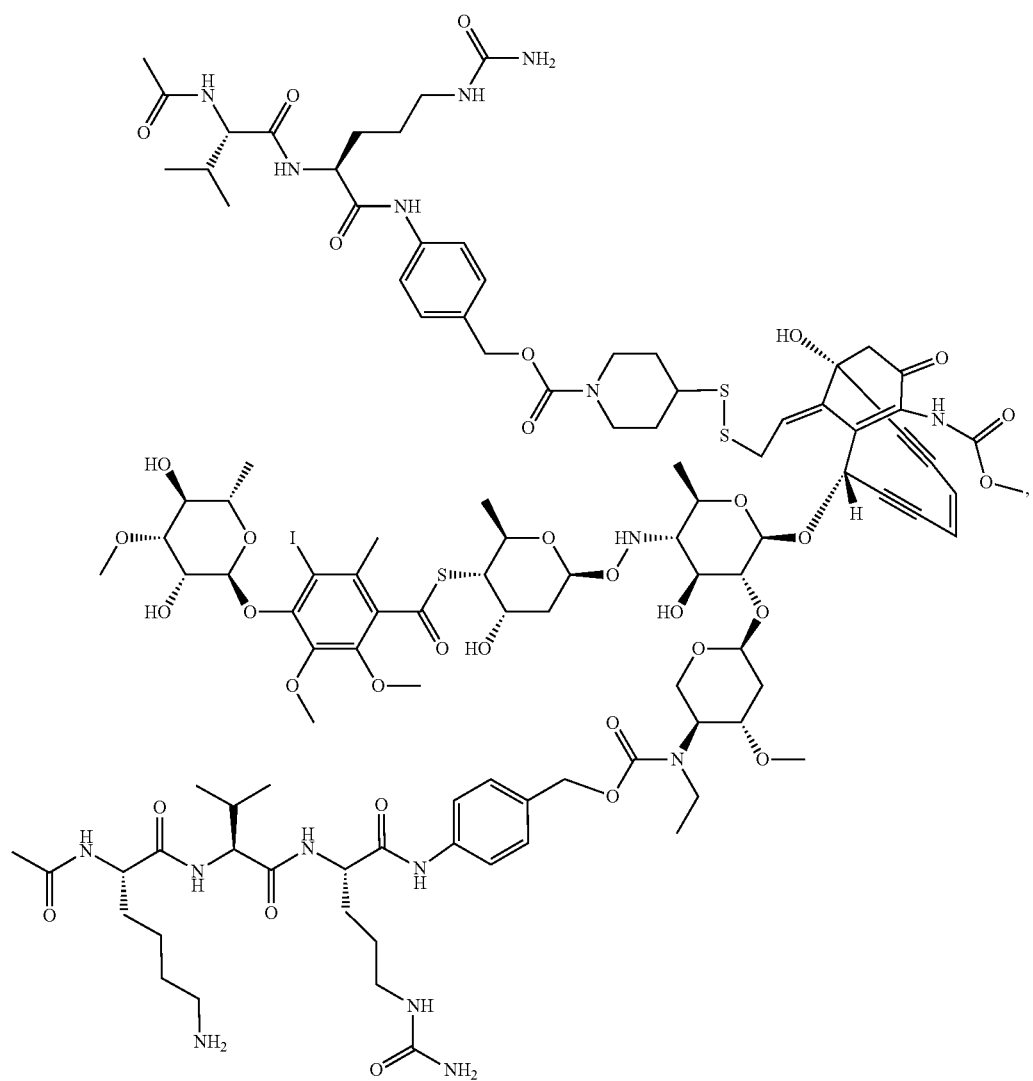

-continued
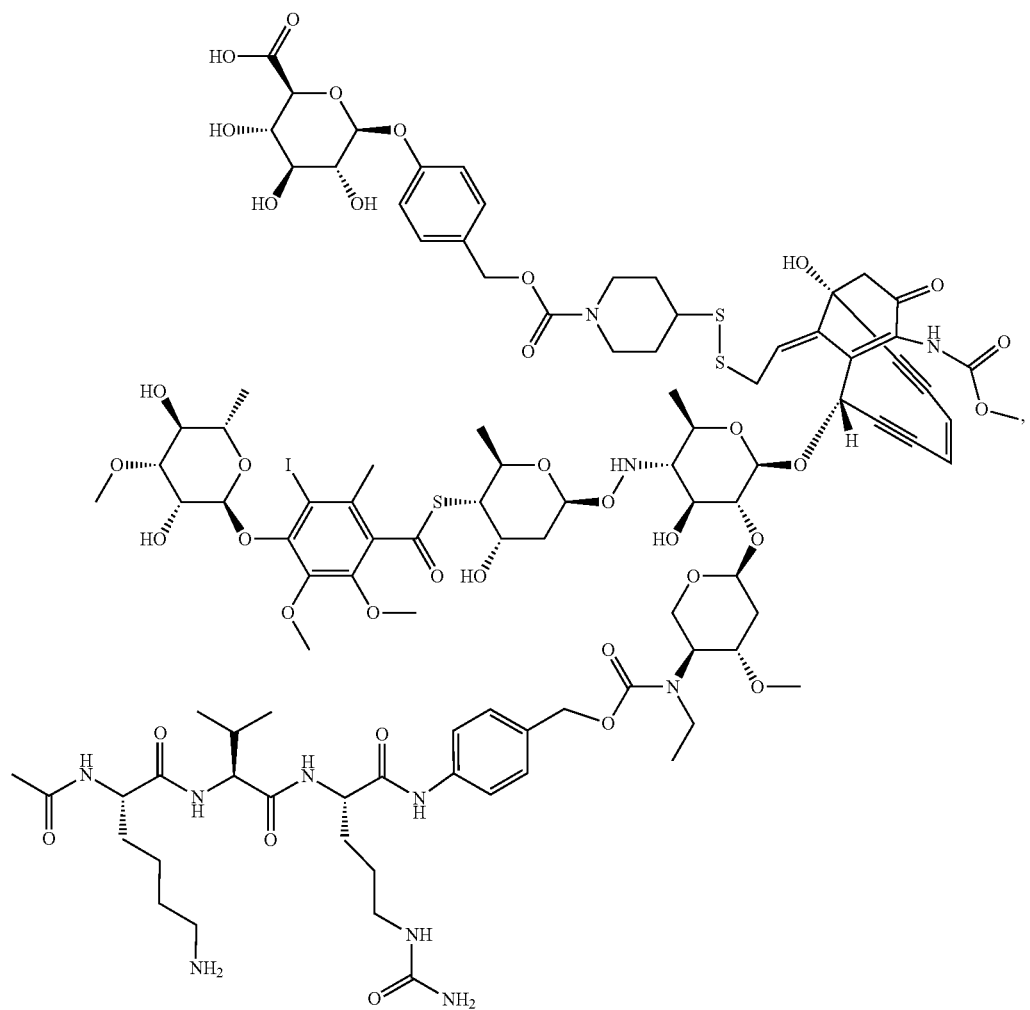

611
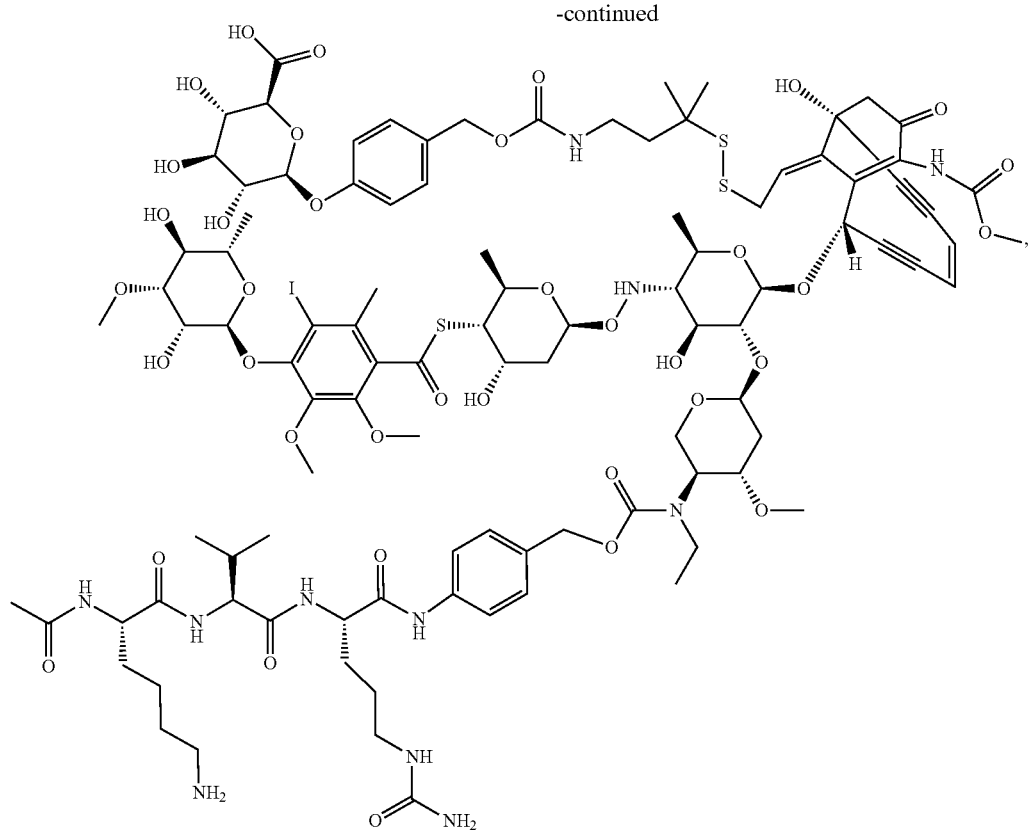
612
-continued
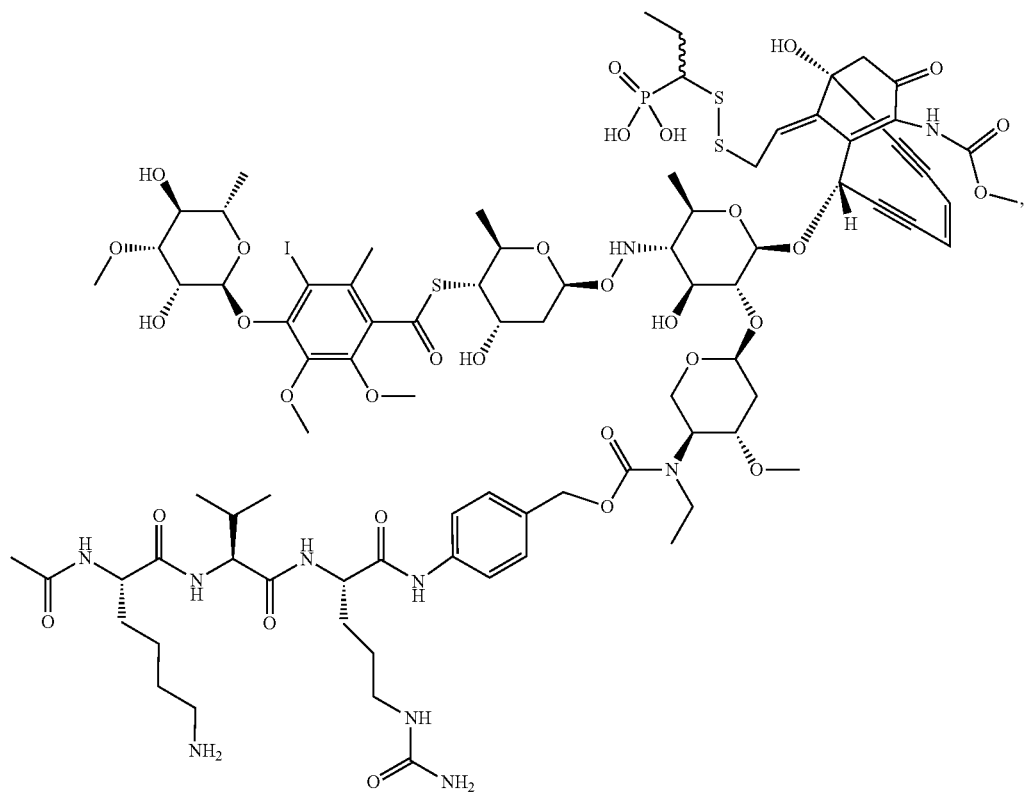

613
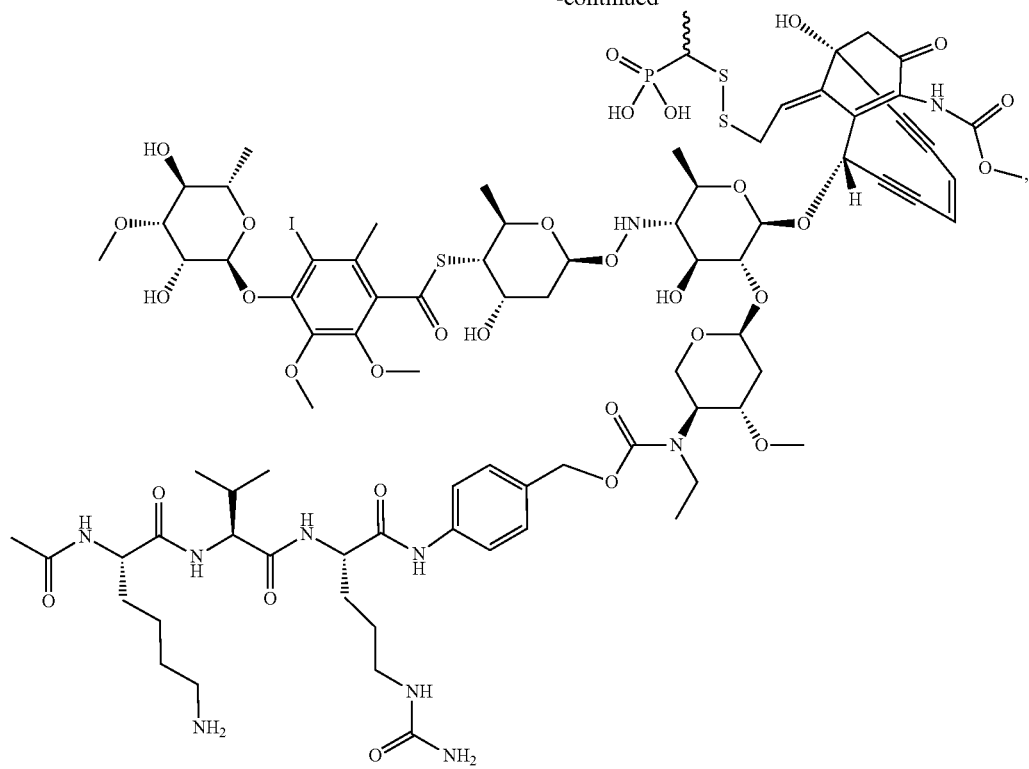
-continued
614
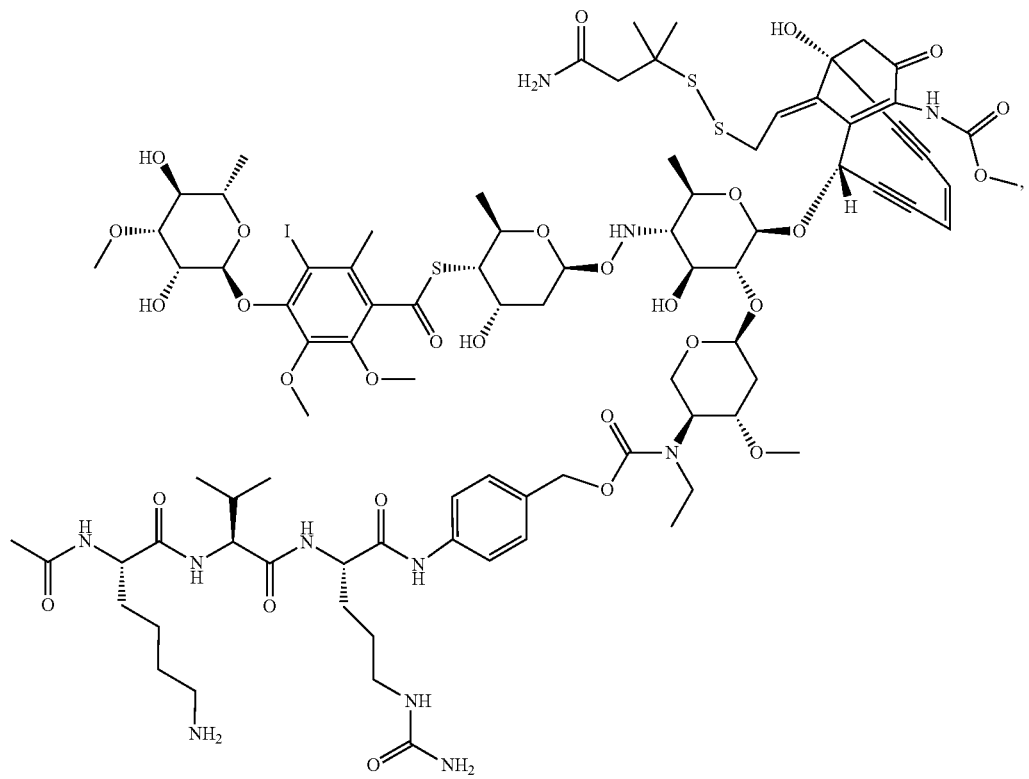

615
616
-continued
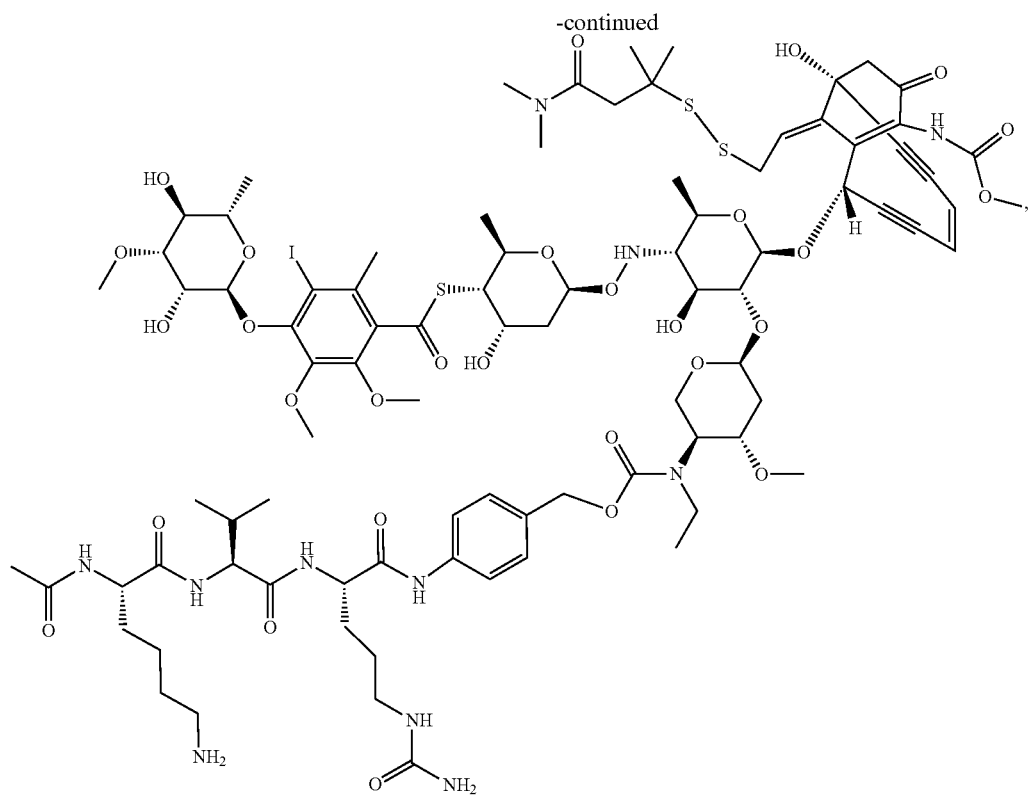
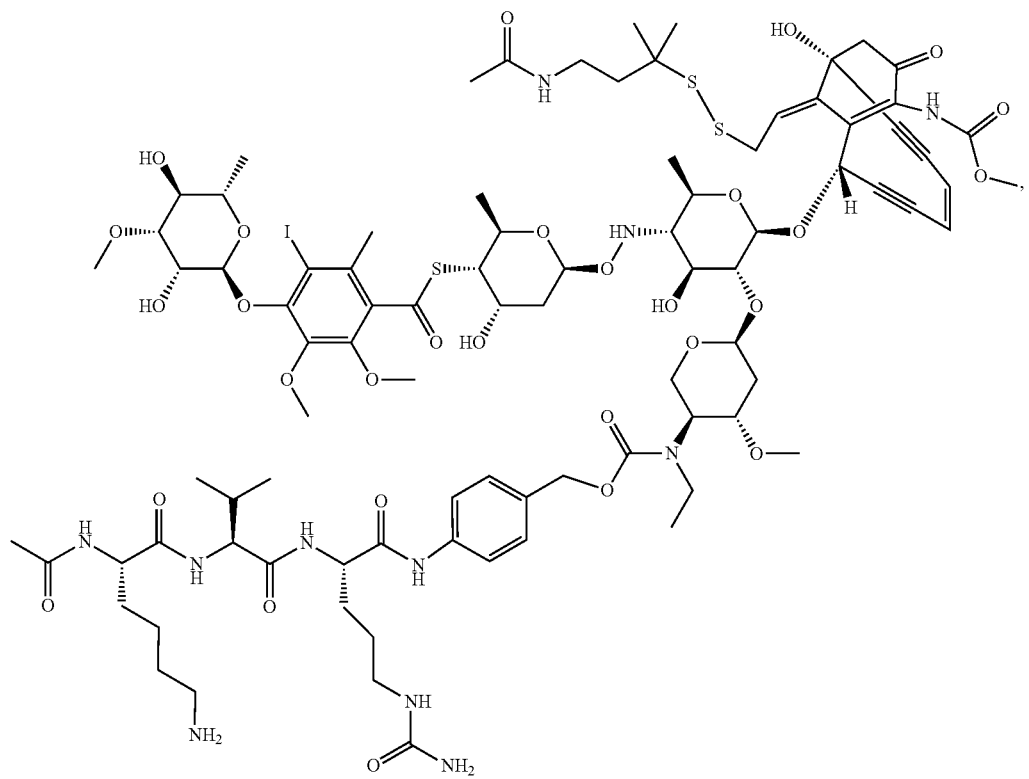

617
618
-continued
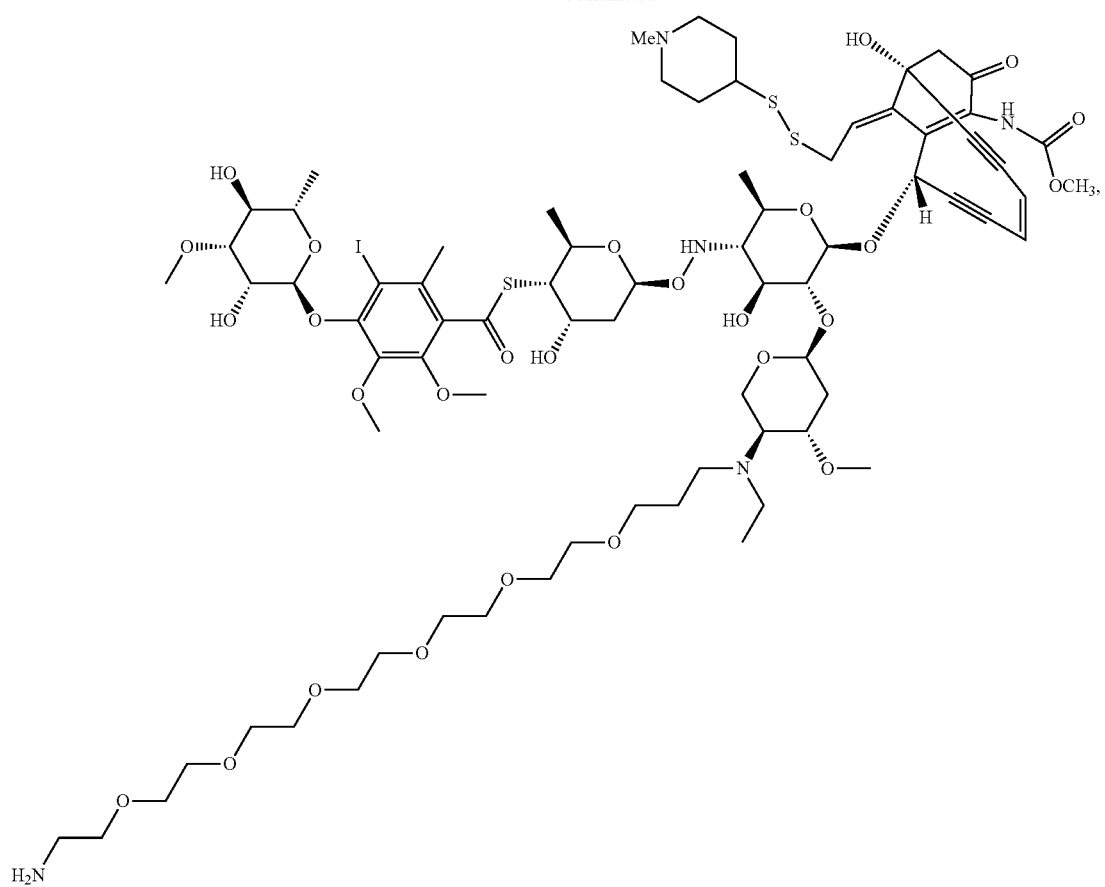
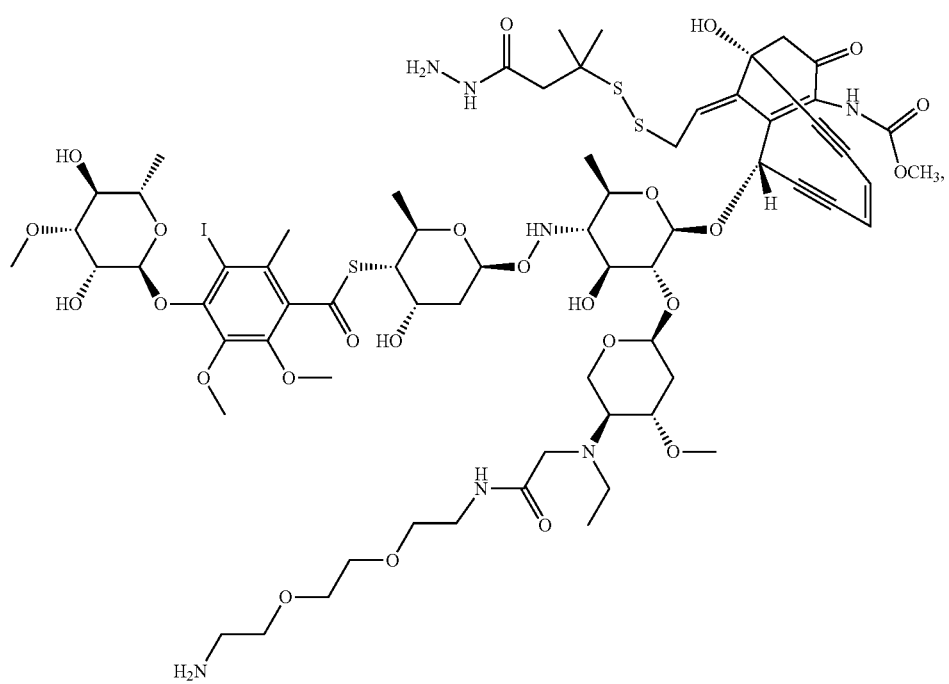

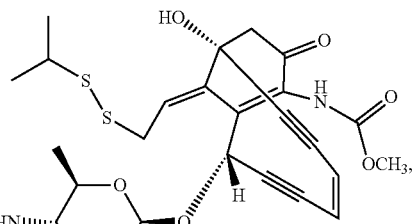
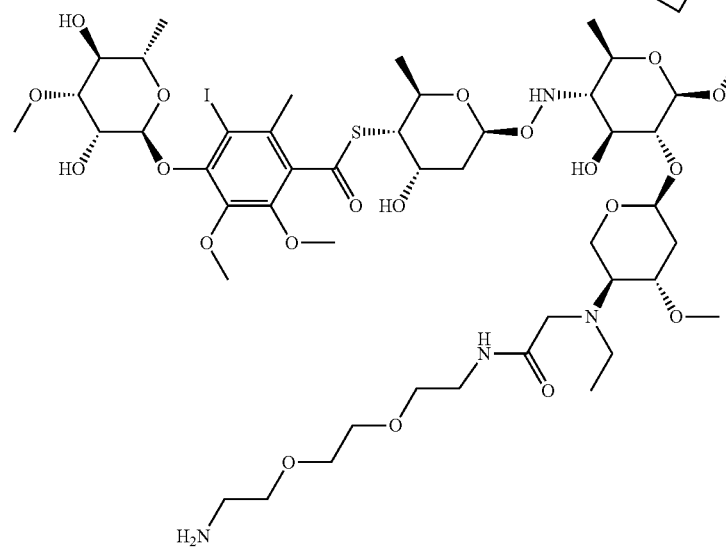
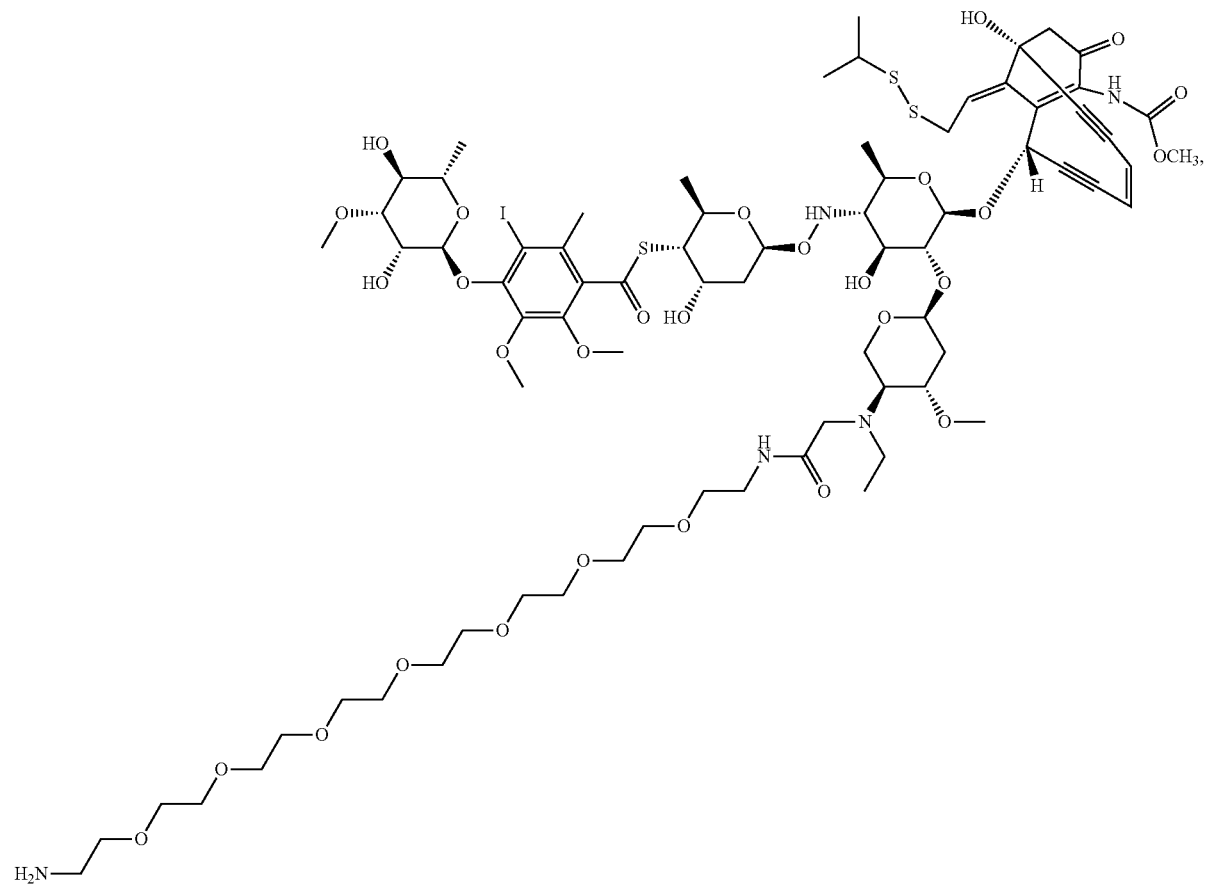

-continued
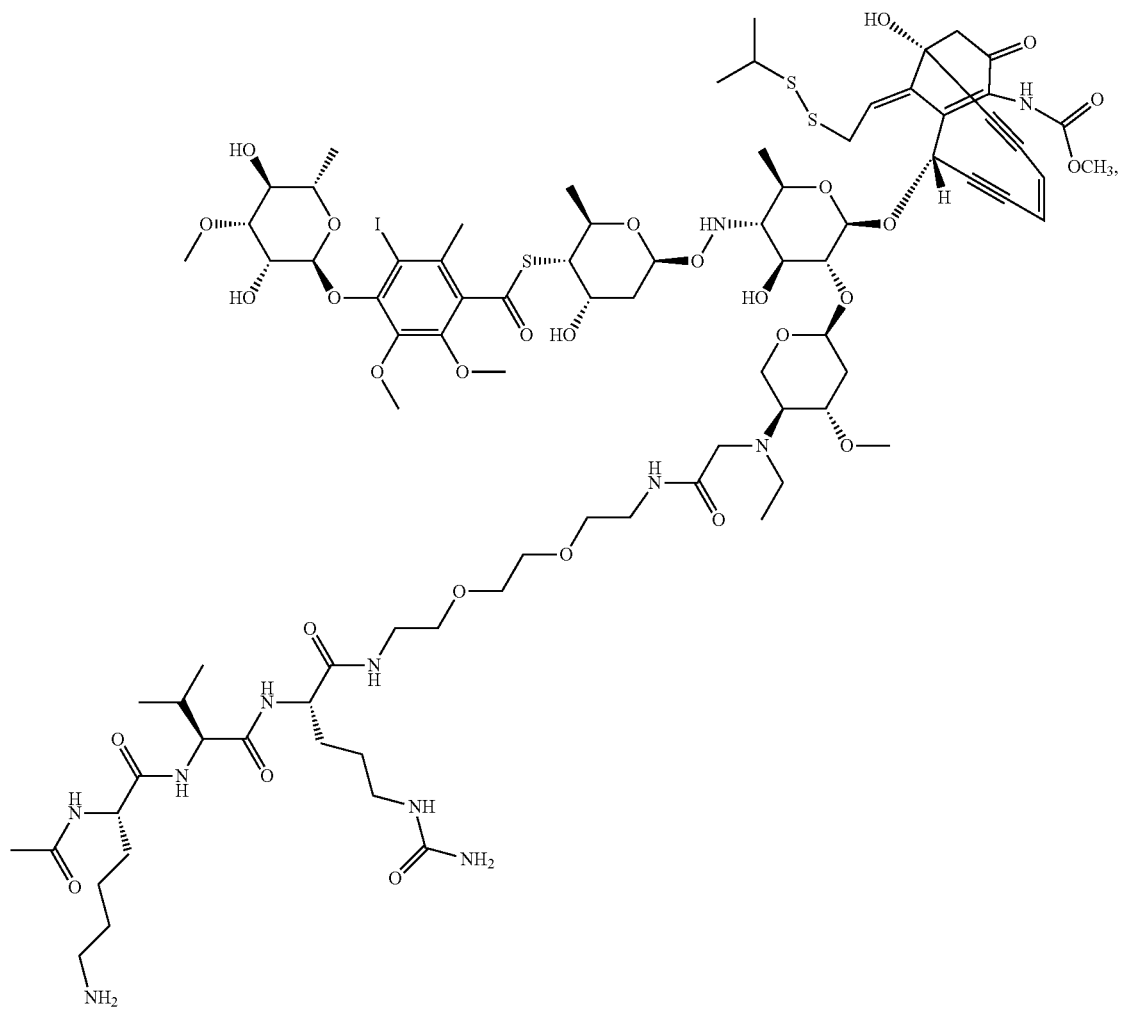 [SMILES: CCN(CC(=O)NCCOCCOCCNC(=O)[C@H](CCCNC(N)=O)NC(=O)[C@@H](NC(=O)[C@H](CCCCN)NC(C)=O)C(C)C)[C@H]1CO[C@@H](O[C@H]2[C@H](O[C@H]3C#C/C=C\C#C[C@]4(O)CC(=O)C(NC(=O)OC)=C3/C4=C\CSSC(C)C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

623 624
-continued
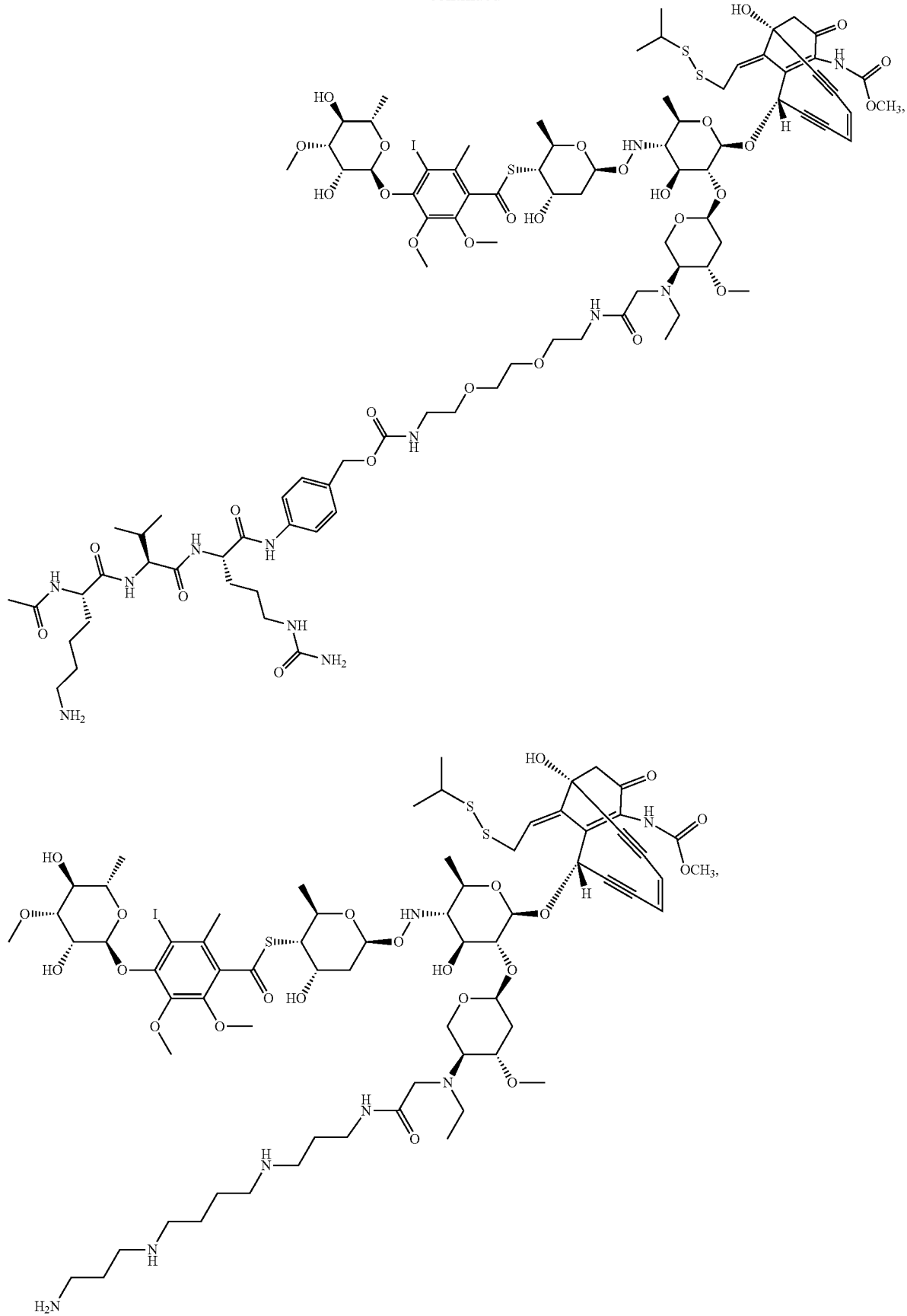

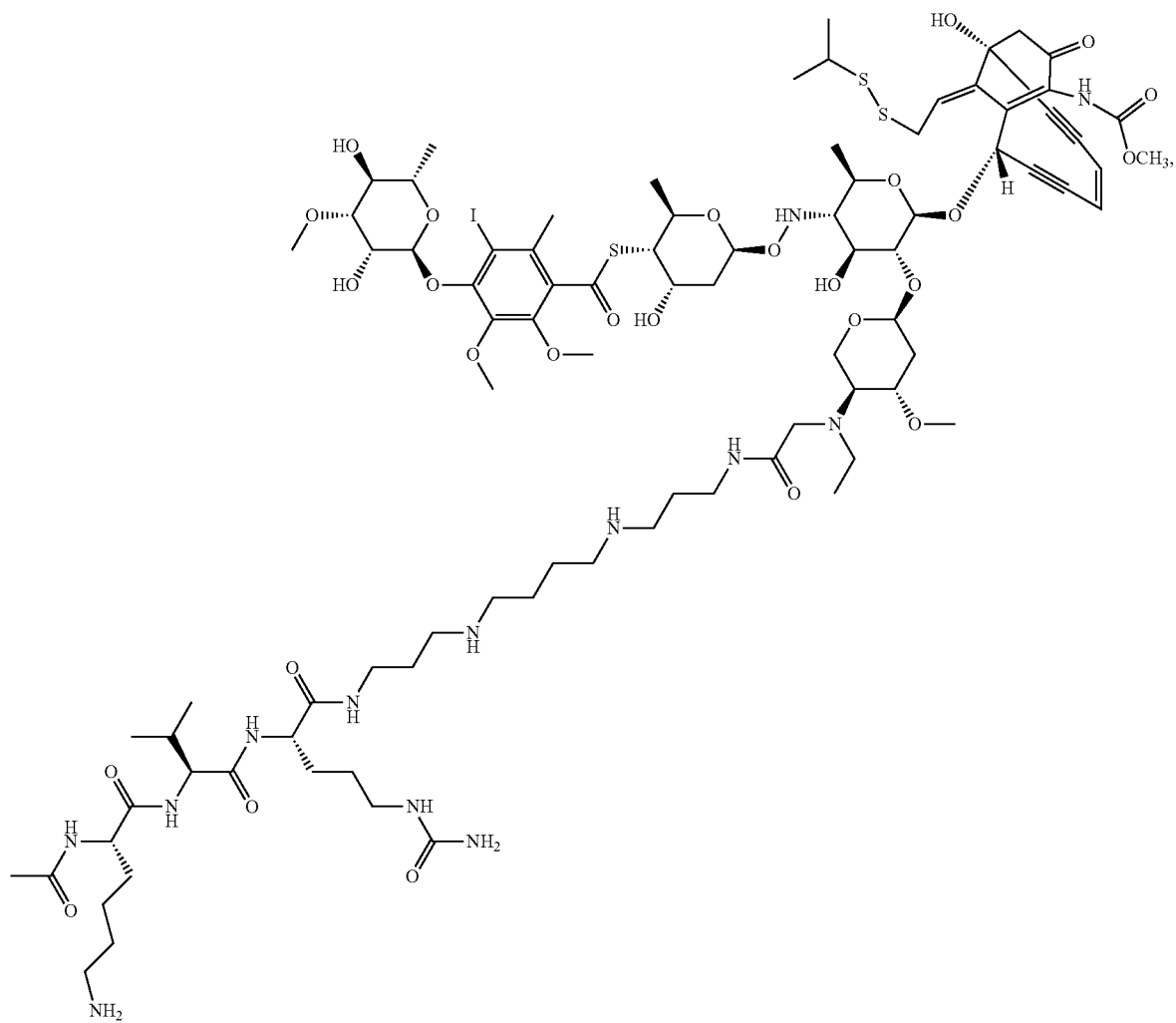

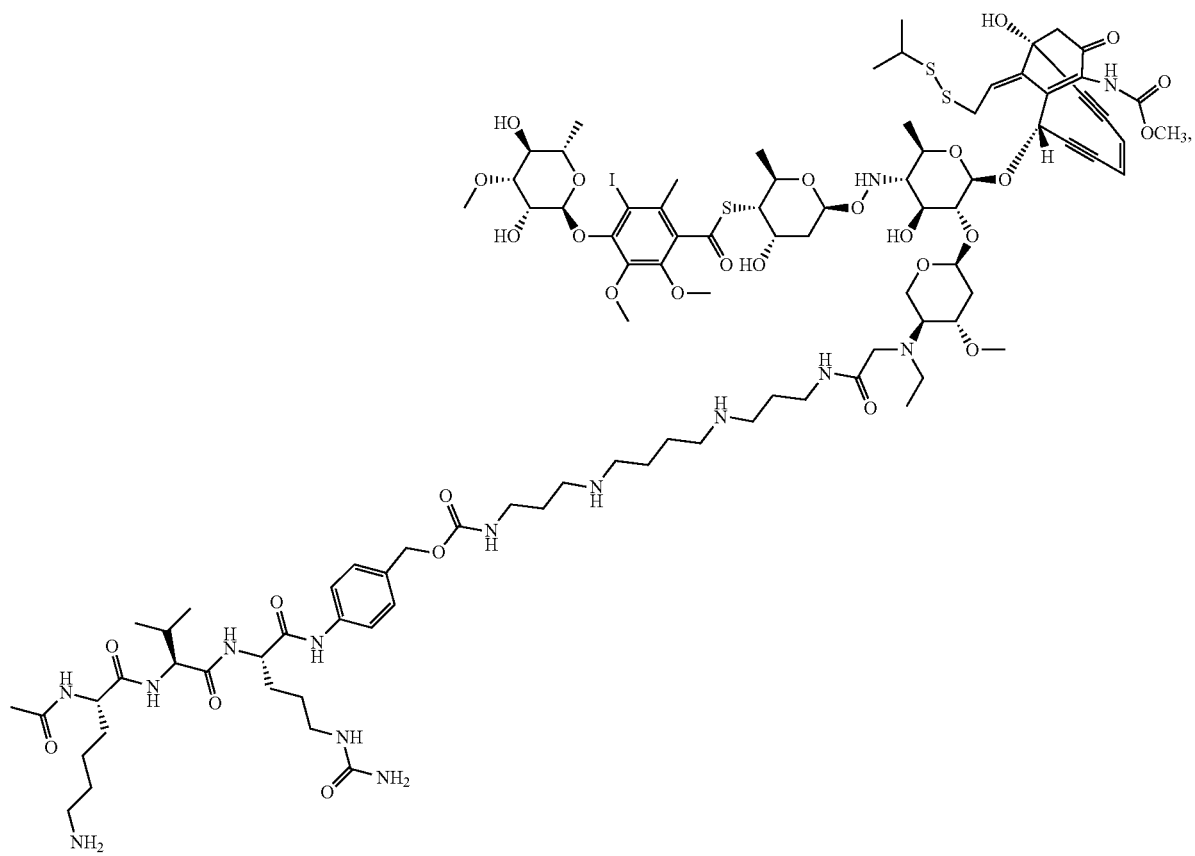 [SMILES: CCN(CC(=O)NCCCNCCCCNCCCNC(=O)OCc1ccc(NC(=O)[C@H](CCCNC(N)=O)NC(=O)[C@@H](NC(=O)[C@H](CCCCN)NC(C)=O)C(C)C)cc1)[C@H]1CO[C@@H](O[C@H]2[C@H](O[C@H]3C#C/C=C\C#C[C@]4(O)CC(=O)C(NC(=O)OC)=C3/C4=C\CSSC(C)C)O[C@H](C)[C@@H](NO[C@H]3C[C@H](O)[C@H](SC(=O)c4c(C)c(I)c(O[C@@H]5O[C@@H](C)[C@H](O)[C@@H](OC)[C@H]5O)c(OC)c4OC)[C@@H](C)O3)[C@@H]2O)C[C@@H]1OC]

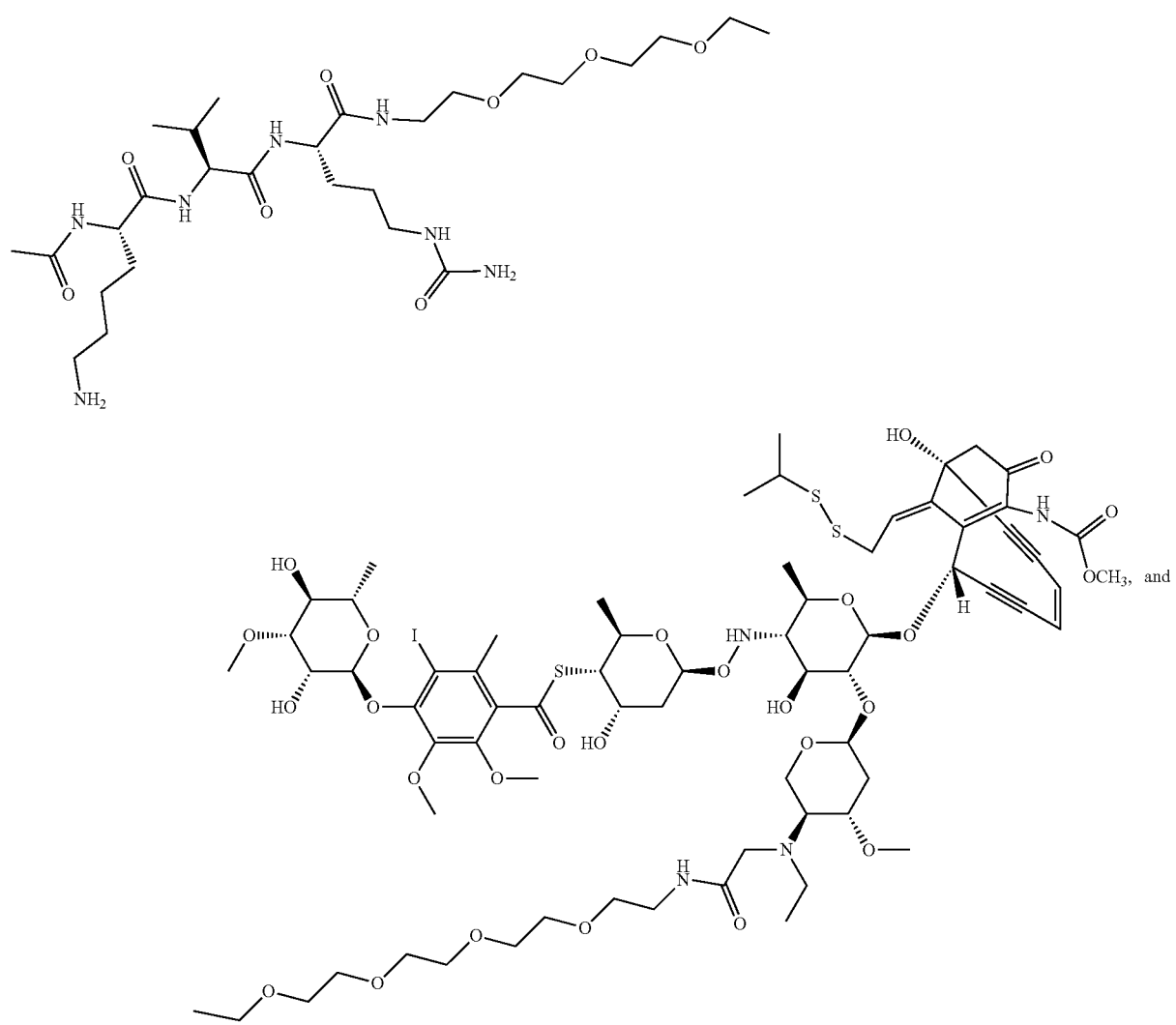

-continued
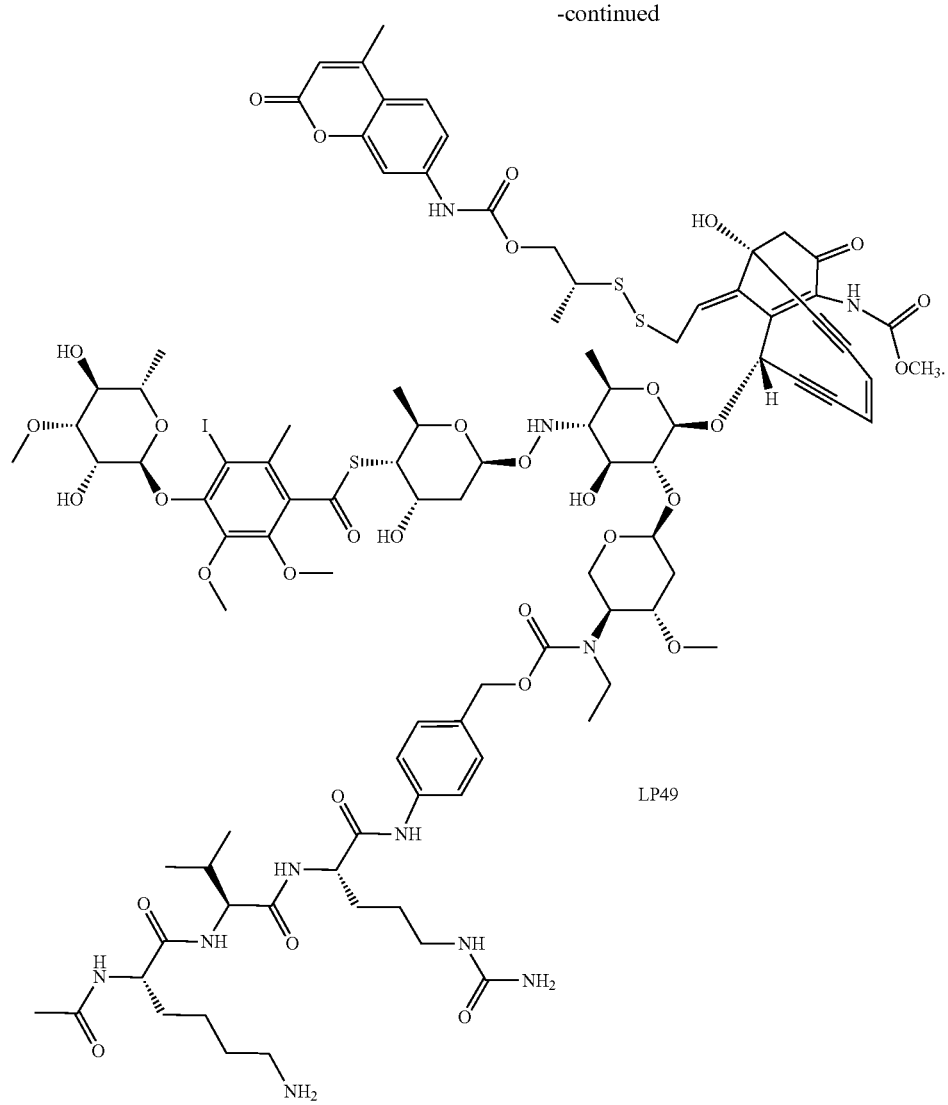
LP49
10. A pharmaceutical composition comprising an effective amount of a compound of claim 1, or a pharmaceutically acceptable salt thereof, and a pharmaceutically acceptable diluent, carrier, or excipient.
11. The compound of claim 1, or a pharmaceutically acceptable salt thereof, wherein L is:
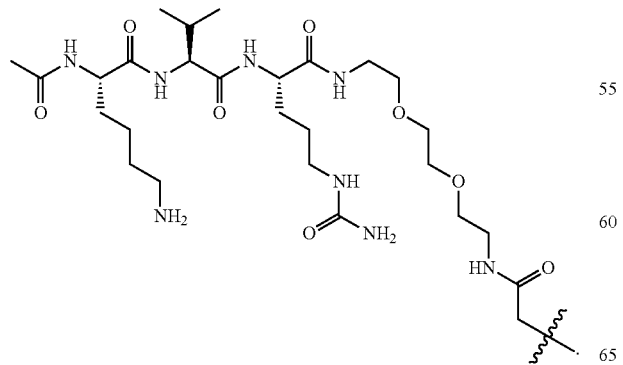

12. The compound of claim 1, or a pharmaceutically acceptable salt thereof, wherein L is:
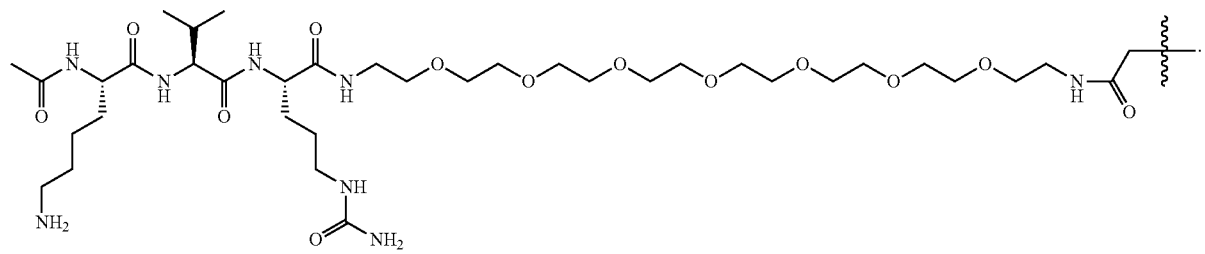
13. The compound of claim 1, or a pharmaceutically acceptable salt thereof, wherein L is:
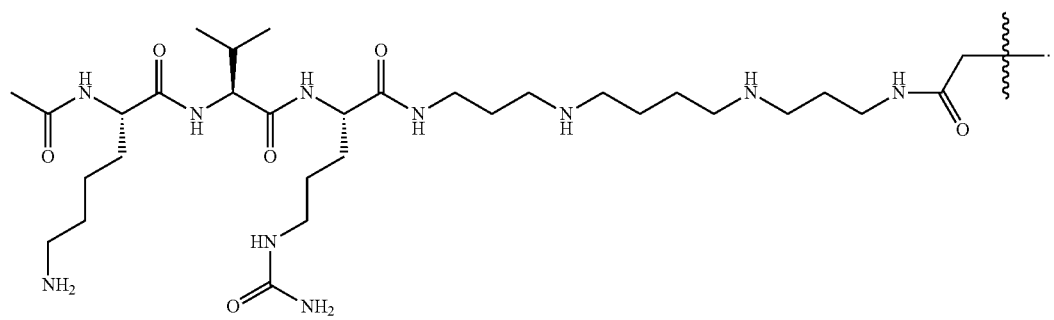
14. The compound of claim 1, or a pharmaceutically acceptable salt thereof, wherein L is:
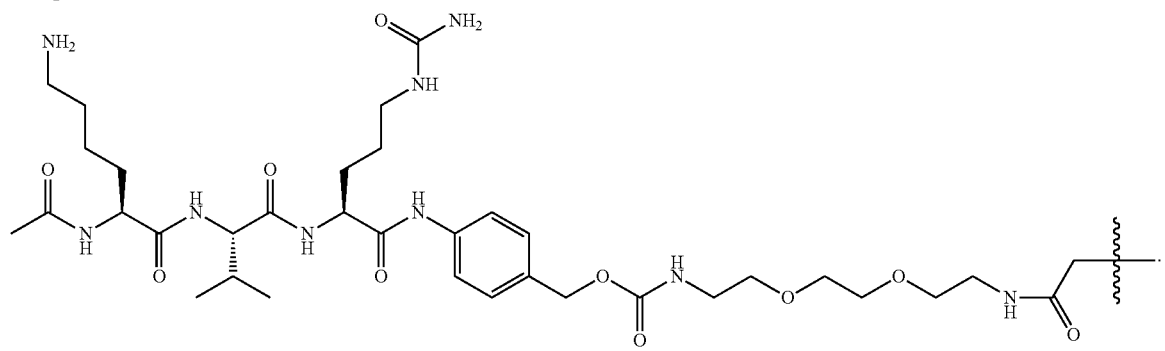
15. The compound of claim 1, or a pharmaceutically acceptable salt thereof, wherein L is:
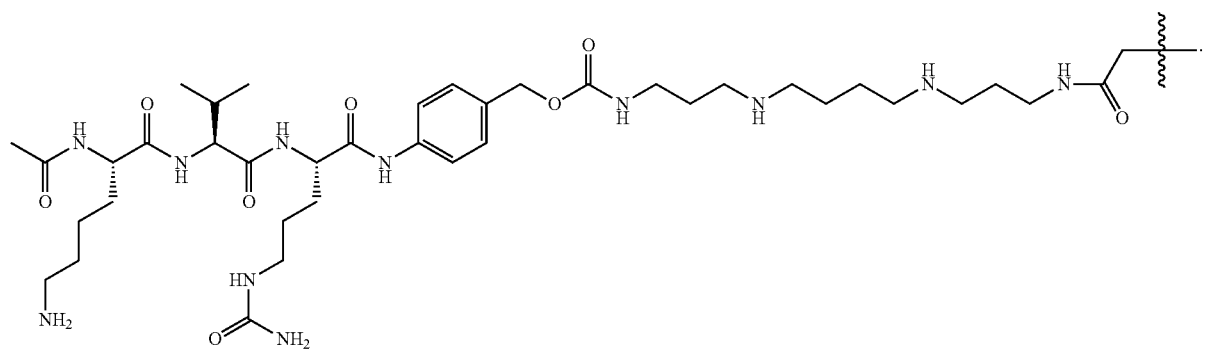

16. The compound of claim 1, or a pharmaceutically acceptable salt thereof, wherein L is:
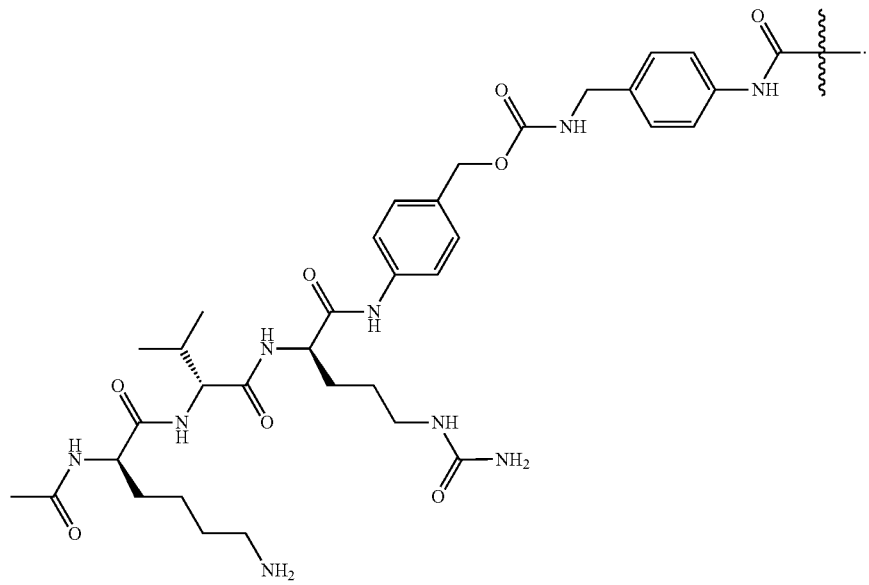

UNITED STATES PATENT AND TRADEMARK OFFICE
CERTIFICATE OF CORRECTION

| | | |
|---|---|---|
| PATENT NO. | : 11,993,625 B2 | Page 1 of 1 |
| APPLICATION NO. | : 16/477290 | |
| DATED | : May 28, 2024 | |
| INVENTOR(S) | : Ahmad et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1159 days.

Signed and Sealed this
Eighth Day of October, 2024

Katherine Kelly Vidal
*Director of the United States Patent and Trademark Office*